United States Patent
Halfon et al.

(10) Patent No.: US 11,261,189 B2
(45) Date of Patent: Mar. 1, 2022

(54) SUBSTITUTED 2,4 DIAMINO-QUINOLINE AS NEW MEDICAMENT FOR FIBROSIS, AUTOPHAGY AND CATHEPSINS B (CTSB), L (CTSL) AND D (CTSD) RELATED DISEASES

(71) Applicant: Genoscience Pharma, Marseilles (FR)

(72) Inventors: Philippe Halfon, Marseilles (FR); Firas Bassissi, Marseilles (FR); Sonia Brun, Aix en Provence (FR); Jérôme Courcambeck, Marseilles (FR); Madani Rachid, Saint-Cyr-sur-Mer (FR)

(73) Assignee: GENOSCIENCE PHARMA, Marseilles (FR)

( * ) Notice: Subject to any disclaimer, the term of this patent is extended or adjusted under 35 U.S.C. 154(b) by 0 days.

(21) Appl. No.: 16/529,072

(22) Filed: Aug. 1, 2019

(65) Prior Publication Data

US 2020/0079781 A1   Mar. 12, 2020

Related U.S. Application Data

(60) Provisional application No. 62/727,100, filed on Sep. 5, 2018.

(30) Foreign Application Priority Data

Sep. 5, 2018  (EP) .................................. 18306167

(51) Int. Cl.
*A61K 31/4709* (2006.01)
*C07D 487/04* (2006.01)
*C07D 207/02* (2006.01)
*C07D 215/02* (2006.01)

(52) U.S. Cl.
CPC ......... *C07D 487/04* (2013.01); *C07D 207/02* (2013.01); *C07D 215/02* (2013.01)

(58) Field of Classification Search
CPC ....... A61K 31/4709; A61P 43/00; A61P 25/28
USPC ............................................... 514/314, 313
See application file for complete search history.

(56) References Cited

FOREIGN PATENT DOCUMENTS

WO   WO 2016/067112 A1 *  5/2016  ............. A61K 31/47
WO   WO 2017/191599 A1 * 11/2017  ......... A61K 31/4709

OTHER PUBLICATIONS

Moles, A. et al., (2009) Cathepsins B and D drive hepatic stellate cell proliferation and promote their fibrogenic potential. Hepatology. 49, 1297-1307.
Shi, J. et al., (2017) Autophagy protein LC3 regulates the fibrosis of hypertrophic scar by controlling Bcl-xL in dermal fibroblasts. Oncotarget. 8, 93757-93770).
Wu, J. et al., (2018) Autophagy promotes fibrosis and apoptosis in the peritoneum during long-term peritoneal dialysis. J. Cell. Mol. Med. 22, 1190-1201.
Yuan, Y. et al.,(2017) Relaxin alleviates TGFβ1-induced cardiac fibrosis via inhibition of Stat3-dependent autophagy. Biochem. Biophys. Res. Commun. 493, 1601-1607.
Lin, M. et al. (2018) ASPP2 Inhibits the Profibrotic Effects of Transforming Growth Factor-β1 in Hepatic Stellate Cells by Reducing Autophagy. Dig. Dis. Sci. 63, 146-154.
Lalmanach, G. et al., (2015) Cysteine cathepsins and cystatins: From ancillary tasks to prominent status in lung diseases. Biol. Chem. 396, 111-130.
Fox, C.et al., (2016) Inhibition of lysosomal protease cathepsin D reduces renal fibrosis in murine chronic kidney disease. Sci. Rep. 6, 20101.
Wynn, T. A., and Ramalingam, T. R. (2012) Mechanisms of fibrosis: Therapeutic translation for fibrotic disease. Nat. Med. 18, 1028-1040.
Nüchel, J. et al., (2018) TGFB1 is secreted through an unconventional pathway dependent on the autophagic machinery and cytoskeletal regulators. Autophagy. 14, 465-486.

\* cited by examiner

*Primary Examiner* — Charanjit Aulakh
(74) *Attorney, Agent, or Firm* — Browdy and Neimark, PLLC

(57) ABSTRACT

2-primary amino-4-secondary amino-quinoline derivatives, their manufacture, pharmaceutical compositions comprising them and their use as medicaments are disclosed. The compounds are useful as a medicament in treating and/or decreasing the severity and/or progression and/or preventing fibrosis and/or related diseases, or for use as a medicament in treating, decreasing the severity and/or progression of and/or preventing autophagy and/or related diseases, for inhibiting autophagy flux, and for inhibiting cathepsins B (CTSB), L (CTSL) and/or D (CTSD) and/or related diseases.

36 Claims, 4 Drawing Sheets

SUBSTITUTED 2,4 DIAMINO-QUINOLINE AS NEW MEDICAMENT FOR FIBROSIS, AUTOPHAGY AND CATHEPSINS B (CTSB), L (CTSL) AND D (CTSD) RELATED DISEASES

FIELD OF THE INVENTION

The present disclosure relates to 2-primary amino-4-secondary cycloamino-quinoline compounds, their manufacture, pharmaceutical compositions comprising them and their use as medicaments. The compounds can be used to treat and/or prevent fibrosis-related diseases, and/or can be used to treat, decrease the severity or progression of, or prevent the occurrence of fibrosis in lungs, heart, kidney, guts, peritoneum membrane, eye, mucosa (mouth, vagina, uterus, and anus), ovary, prostate, liver and/or skin. The compounds can also be used to treat and/or prevent increased autophagy flux-related diseases, to inhibit cathepsins B (CTSB), L (CTSL) and/or D (CTSD), and to treat and/or prevent cathepsins B (CTSB), L (CTSL) and/or D (CTSD) related diseases.

BACKGROUND OF THE INVENTION

Fibrosis, or scar formation, is a pathological condition characterized by the excessive production and accumulation of extracellular matrix components (for example collagen), loss of tissue architecture leading to disrupted tissue function in affected organs, and organ failure in response to uncontrolled wound healing.

Fibrosis can develop in nearly every part and tissues of the body, and is an integral part of the pathophysiological mechanism underlying organ failure and death in a variety of chronic diseases. Therefore, the fibrosis can be observed in different organs such as but not limited to lungs, heart, kidney, guts, peritoneum membrane, skin, eye, mucosa (mouth, vagina, uterus, and anus), ovary, prostate and liver. Regardless of the initiating events, a feature common to all fibrotic diseases is the activation of extracellular matrix producing myofibroblasts, which are the key mediators of fibrotic tissue remodeling Wynn, T. A. & Ramalingam, T. R. *Nat. Med.* 2012 (18), 1028-1040.

Transforming growth factor β (TGF-β) has a central role in fibrogenesis by modulating the fibroblast phenotype and function, inducing myofibroblast transdifferentiation and promoting matrix accumulation. Moreover, TGF-β1 secretion depends upon autophagy-dependent pathway in different cell types (see Nüchel, J. et al. *Autophagy* 2018 (14), 465-486). Likewise, actual available literature commonly agrees that autophagy (which is the degradation of cytoplasmic proteins and organelles by their enclosure in vesicles from the endoplasmic reticulum that fuse with lysosomes) plays a major role in the development of pathological fibrosis and its inhibition is beneficial to the reduction of this phenomenon (see Ding, Y. & Choi, M. E. *Semin. Nephrol.* 2014 (34), 62-71; Mallat, A. et al. *BioMed Res. Int.* 2014, 869390; Thoen, L. F. R., Guimardes, E. L. & Grunsven, L. A. van. 2012 (8), 126-128; Song, Y. et al. *BioMed Res. Int.* 2014, 436242). Moreover, the cathepsin protein family (lysosome proteases) plays also a key role in the pathologic fibrosis development and in the autophagy process. In the same way as autophagy inhibition, inhibiting cathepsins (B, L and/or D) is suggested to have a beneficial effect on the reduction of the deleterious effects of pathologic fibrosis. (see Canbay, A. et al. *J. Clin. Invest.* 2003 (112), 152-159; Fox, C. et al. *Sci. Rep.* 2016 (6), 20101; Moles, A. et al *Hepatology* 2009 (49), 1297-1307; Manchanda, M. et al. *Clin. Transl. Gastroenterol.* 2017 (8), e99).

Autophagy is a lysosome-based physiological process, which in basal conditions occurs at low levels to continuously degrade unwanted cytoplasmic constituents and generate substrates for energy production. During oxidative stress, hypoxia or nutritional starvation, its level raises to allow cell survival. Autophagy represents therefore a major hub involved in cellular homeostasis. It also plays a pivotal role in differentiation of many lineages, including adipocytes, erythrocytes and lymphocytes, and tissue remodelling. Under specific environmental conditions, however, autophagy can also mediate cell death and it is mechanistically important to distinguish autophagic cell death, which refers to cell death "by" autophagy from cell death "with" autophagy. Thus, recent studies suggest that autophagy and apoptosis processes are closely nested and share cross-talk between signal transduction elements. It has been shown in particular that certain autophagy-related (ATG) proteins play dual roles in autophagy and apoptosis regulation. This is the case of ATG5 and its binding partner ATG12, BCL-2 interacting myosin moesin-like coiled-coil protein 1 (BECLIN1/beclin-1), the mammalian ortholog of yeast Atg6/vacuolar protein sorting (Vps)-30 that acts during the formation of autophagosomes by interacting with the class III PI3K pathway, and microtubule-associated-protein light chain 3 (MAP1LC3/LC3) a mammalian ortholog of yeast Atg8, for example. Other forms of cell death are also interconnected with autophagy, such as necrosis, necroptosis (regulated Fas-dependent, caspase-independent non-apoptotic cell death), and pyroptosis (caspase-1-dependent cell death).

Three main types of autophagy have been identified and can be distinguished by both their physiological functions and the mechanisms they use to deliver cytoplasmic cargo to lysosomes. They are macroautophagy, microautophagy and chaperone-mediated autophagy (CMA). In fact, many more forms of autophagy have been described. Mention can be made, for example, of aggrephagy (for aggregated proteins), mitophagy (for mitochondria), ribophagy (for ribosomes), pexophagy (for peroxisomes), reticulophagy (for the endoplasmic reticulum, ER), and xenophagy (for pathogens). Thus, we now realize that while originally viewed as a nonselective (random) cytoplasmic degradation system, autophagy actually participates in a highly selective and tightly regulated process of substrate delivery.

Macroautophagy (commonly referred as "autophagy", which can in some cases create confusion in the literature) remains the major autophagic process through its ability to massively entrap macromolecules and entire organelles. The latter are captured into double-membrane autophagosomes where they are degraded. It therefore represents an alternative mechanism of proteasomal degradation, which rather treats short-lived intracellular proteins, although a cross-talk that is being increasingly understood, has been described to occur between the ubiquitin-proteasome system (UPS) and macroautophagy. The fusion of autophagosomes with lysosomes leads to the formation of autolysosomes in which absorbed cellular constituents, which include lipid droplets and protein aggregates, are degraded by lysosomal glycosidases, proteases, lipases and sulfatases. Concerning the chaperone-mediated autophagy process (CMA), proteins containing a specific peptide motif biochemically related to KFERQ are recognized by the HSPA5/HSC70 chaperone protein prior being internalized and degraded in lysosomes. By contrast, in microautophagy, cytosolic components are directly taken up by invaginations of the lysosomal membrane.

Dysfunctional autophagy has been associated with wide ranges of human diseases such as, neurodegenerative disease, heart disease, diabetes or bacterial infection.

Macroautophagy (autophagy) is an important mechanism for targeting cellular components including proteins, protein aggregates, misfolded proteins, and damaged cellular organelles for degradation in lysosomes. This catabolic, cellular self-digestion process is induced in response to starvation or a wide variety of biological stresses, causing the formation of double membrane vesicles called autophagosomes that surround proteins and organelles. Then, autophagosomes fuse with lysosomes to form an autophagolysosome where the autophagosome and their cargo are degraded that allows to recycle the contents and to maintain cellular homeostasis. This lysosome-mediated cellular self-digestion serves to recycle intracellular nutrients to sustain cell metabolism during starvation and to eliminate damaged proteins and organelles that accumulate during stress. Although elimination of individual proteins occurs by the ubiquitin-mediated proteasome degradation pathway, the autophagy pathway can eliminate protein aggregates and organelles. Thus, autophagy complements and overlaps with proteasome function to prevent the accumulation of damaged cellular components during starvation and stress. Through these functions, autophagy is an essential cellular stress response that maintains protein and organelle quality control, protects the genome from damage, and sustains cell and mammalian viability.

Autophagy is controlled by ATG proteins, initially identified in yeast, for which there are mammalian homologues. ATG proteins are comprised of kinases, proteases, and two ubiquitin-like conjugation systems that likely function in concert with a host of unknown cellular proteins to control autophagosome formation, cargo recognition, engulfment, and trafficking to lysosomes. Autophagy dysfunction is a major contributor to diseases including, but not limited to, neurodegeneration, and liver disease. Many human neurodegenerative diseases are associated with aberrant mutant and/or polyubiquitinated protein accumulation and excessive neuronal cell death.

The importance of autophagy in cellular garbage disposal is clear, since autophagy is the only identified mechanism for the turnover of large cellular sub-structures, such as organelles and protein aggregates. How organelles are recognized and directed to autophagosomes for degradation can involve organelle-specific processes, such as mitophagy and ER-phagy (endoplasmic reticulum-phagy) that can mitigate oxidative stress emanating from dysfunctional organelles. Damaged proteins that accumulate during stress can be refolded, ubiquitinated, and degraded by the proteasome pathway, or aggregated and degraded by autophagy. To direct damaged or unfolded proteins to the autophagy pathway, p62 binds to polyubiquitinated proteins, forming protein aggregates by oligomerization, and to Atg8/LC3 on the autophagosome membrane to target aggregates to autophagosomes for degradation. Protein aggregation can be a protective mechanism to limit cellular exposure to toxic proteins through sequestration, as well as an efficient packaging and delivery mechanism that collects and directs damaged proteins to autophagosomes. Thus, the inability to dispose of p62 aggregates through autophagy appears to be toxic to normal tissues.

The ATG6/BECN1-Vps34-ATG8/LC3 complex regulates autophagosome formation. LC3 cleavage, lipidation, and membrane translocation are frequently utilized to monitor autophagy induction. The mechanism by which starvation and stress activate autophagy is controlled in part through the PI-3 kinase pathway via the protein kinase mTOR. Growth factor and nutrient availability promote mTOR activation that suppresses autophagy, whereas starvation and mTOR inactivation stimulate autophagy. While there are other mechanisms to regulate autophagy, mTOR provides a link between nutrient and growth factor availability, growth control, autophagy, and metabolism.

Autophagy plays an essential role in maintaining protein quality control, while defective autophagy is involved in the development of diseases including, but not limited to neurodegenerative disorders, autoimmune disorders, cardiovascular disorders, metabolic disorders, hamartoma syndrome, genetic muscle disorders, and myopathies.

Autophagy is a normal physiological process that plays a pivotal role for cell survival, differentiation, development, and homeostasis. Selective or not, canonical or noncanonical, autophagy processes are considerably more complex than originally thought. Depending on favourable or unfavourable cell environment conditions, the autophagy machinery will promote both cell survival and cell death, thus maintaining a decisive balance between manufacture of cellular components and breakdown of damaged or superfluous organelles and other cellular constituents, for example. Autophagy displays complex, stilldebated, interwoven links with several other degradative pathways, such as apoptosis and proteasome-mediated systems. Among its many cellular regulatory functions that have been experimentally proven or that are anticipated, autophagy decisively controls immunity and inflammation, and any impaired autophagy signalling can potentially lead to autoimmunerelated diseases.

The multifactorial and polymorphic nature of most autoimmune diseases dramatically complicates their diagnosis and the treatment that can be applied to mitigate the symptoms. Except in very rare cases, the treatments are largely palliative and do not target the cause of illness. Although immense progress has been made over the last decades leading to patients' survival rates that have considerably augmented, innovative therapeutic solutions are still awaiting that would combine efficacy, selectivity—and thus less secondary effects and reliability. Without adapted treatment, the quality-of-life can be relatively poor in autoimmune patients and decreases as the disease evolves (fatigue, pain, fever associated to specific symptoms). Unfortunately, the medications required to minimize symptoms and slow-down inflammatory syndrome (i.e. corticosteroids, immunosuppressive drugs and tumor necrosis factor (TNF-α) blockers used for long-term periods) induce an alteration of the whole immune system leading to intestinal bleeding, kidney failure, increased blood pressure, insomnia, depression, psychosis, osteoporosis, muscle loss, and diabetes, not to mention overwhelming repetitive infection episodes. In certain autoimmune diseases such as those affecting the central nervous system, or in anti-phospholipid syndrome that can be associated to systemic lupus erythematosus (SLE), the therapeutic solutions are limited, not specific, and unfortunately sometimes inefficient. Intense research is currently ongoing to develop novel immunomodulatory strategies based on molecular targets that are engaged in deregulated autoimmune processes and can be specifically re-orientated. In this context, a better knowledge of cellular and molecular mechanisms that underline autoimmune responses and most particularly the homeostasis and regulation of autoimmune cells is central.

Under the term autoimmune diseases, there are more than eighty illnesses caused by autoimmunity, including, e.g. Crohn's disease/CD; primary biliary cirrhosis, myasthenia gravis, immune thrombocytopenic purpura, rheumatoid arthritis, neuropsychiatric systemic lupus erythematosus, ocular myasthenia gravis, psoriatic arthritis. Also some individuals can have more than one autoimmune disorder at the same time, which complicates the task of follow-up and treatment, and makes each case unique. However, there is no known prevention for most autoimmune disorders, and in general there is no specific treatment.

A large number of autoimmune diseases are recognized. They are characterized as "organ-specific" when they are restricted to certain organs such as thyroid (e.g. Graves' disease, autoimmune thyroiditis, Hashimoto's disease), pancreas (e.g. type 1 diabetes in which insulin-producing beta cells are destroyed) and muscles (myasthenia gravis) or involve a particular tissue in different places (e.g. Goodpasture's disease, which affects the basement membrane in the lung and kidney). In contrast, they are classified as "systemic" when they implicate a variety of organs and tissues in the whole body. The most emblematic representative of the large family of systemic autoimmune diseases is systemic lupus erythematosus (SLE) in which heart, joints, skin, lungs, blood vessels, liver, kidneys, and nervous system can be affected. In fact, between these two commonly described families, there is no sharp delineation. For example, scleroderma, also known as systemic sclerosis, which is a chronic systemic autoimmune disease characterized by hardening of the skin, also affects blood vessels, muscles, and internal organs in severe forms.

Innate immune responses importantly influence the adaptive immunity in the induction and regulation of autoimmune diseases. In innate immunity, autophagy works at different levels, notably by controlling activation and release of certain cytokines and chemokines (Deretic, V. J. Immunol. 2012 (189), 15-20; Deretic, V. et al. Nat. Rev. Immunol 2013 (13), 722-737; Gros, F. and Muller S. Br J. Pharmacol. 2014 (171), 4337-4359; Jones, S. et al. Immunol. Cell Biol. 2013 (91), 250-258; Saitoh, T. and Akira, S. J. Cell. Biol. 2010 (189), 925-935). Autophagy would activate the secretion of TNFα, interleukin (IL)-6, IL-8 and type I interferon (IFN) while it controls the production of IL-1α and β (the latter by regulating inflammasome activation and by targeting pro-He-If for degradation), IL-18 and type I IFN. In turn, some secreted cytokines influence autophagy. Thus, T helper type 1 (Th1) and pro-inflammatory cytokines such as IFN-γ (via immunity-related GTPase family M, IRGM), TNFα, IL-1α, and β, IL-23, reactive oxygen species (ROS) and engagement of some TLRs (mechanisms that are still poorly understood) induce autophagy. TWEAK (the TNF-like weak inducer of apoptosis, in C2C12 myotubes), IL-2 in CD4+ T cells, IL-6 in peripheral blood mononuclear cells (PBMCs) and TGF-β in hepatocarcinoma cell lines also promote autophagy. Conversely, Th2 and regulatory cytokines such as IL-4, IL-13 and IL-10, via an effect on STAT-3 or -6 pathways and the serine/threonine-protein kinase (AKT) pathway were found to activate mammalian target of rapamycin (mTOR), which inhibits the serine/threonine protein kinase ULK1 and therefore autophagosome formation. Via its effect on cytokine secretion, particularly in antigen-presenting cells (APCs), autophagy represents a pivotal regulator of immune responses.

Although not yet recognized to such a level of crucial importance in current text books, autophagy in fact exerts profound effects on different aspects of adaptive immunity. It is a major player in thymic selection of T cells, affecting also T cell homeostasis, repertoire and polarization, survival of B cells, immune tolerance, and antigen presentation.

The discovery that autophagy is a key regulatory element for delivering self-antigens to major histocompatibility complex II (MHCII) molecules has been a critical turning point. It was established classically that MHC I molecules presented peptides from intracellular source proteins to T cells while MHCII molecules presented antigenic peptides from exogenous and membrane proteins. The overall picture of T cell activation by MHCII peptide was thus considerably reconsidered and new nexus between immune response and cellular stress, cell metabolism, cell nutrient and cell environment were suggested and analyzed further.

Anaphase-promoting complexes (APCs) that are less proteolytically active than other cells such as macrophages, cleavage by lysosomal cysteine proteases (generally known as cathepsins) of particles and proteins that finally reach autolysosomes give rise to protein fragments, which will constitute the major source of peptides for MHCII molecules. Lysosomes and autolysosomes have a pH of 4-4.5, which is optimum for cathepsins proteolytic activity. Thus, and of importance in the context of autoimmunity, MHCII molecules can bind peptides generated from endogenous antigens that are generated by lysosomal proteolysis. Such endogeneous antigens can be from membranous, cytoplasmic (including vesicle components) or nuclear origin and can have trafficked into the endo-lysosomal network via several forms of autophagy for subsequent processing and presentation by MHCII molecules to promote CD4+ T cells priming.

In the many examples of antigens that have been examined so far, stability was found to be a determining factor that influences antigen presentation. Furthermore because the cleavage via cathepsin proteins can liberate epitopes but also destroy some others, cathepsins regulation is even more strategic for defining the final panel of antigenic peptides that are delivered. Finally, another important role of endolysosomal proteases in antigen presentation lies to their influence on TLR-receptor signaling. Initially claimed while observing the effect of chloroquine (CQ) on TLR9 signaling, it was demonstrated later that endo-lysosomal proteases also activate endosomal TLRs 3, 7, and 8 and that the mode of action was not the one proposed firstly. In fact, whether for TLR9 or for endosomal TLRs, endolysosomal proteases would act by converting the receptor from a non-signaling full-length form to a shorter form deleted from an N-terminal region. Although the precise mechanisms that are behind this effect, notably considering the specific proteases that are involved, are still a continuing matter of studies debates, it remains that such an effect can be strategic as TLR-signaling is central for dendritic cell (DC) maturation that dictates protease activity and consequently influences the quality of peptides that are presented onto MHCII molecules. These data highlight the importance of TLRs in autophagy processes in conjunction with both innate and adaptive immunity.

The close relationships between autophagy and immunity explain that any deregulation of autophagy machinery can affect various aspects of immune responses and lead to autoimmunity development.

Enhanced autophagy, allowing survival of self-reactive lymphocytes, can promote autoimmunity. Moreover, autophagy, which produces autoantigens through intracellular protein digestion, can participate in the initiation or maintenance of autoimmunity. In addition to single nucleotide polymorphisms (SNPs) and susceptibility genes, it is known that expression of some genes related to autophagy process is modified during autoimmunity. In rheumatoid arthritis (RA), it has been shown that both ATG7 and BECLIN-1 gene expression is increased in osteoclasts from patients. Atg7 expression was also found to be increased by pro-inflammatory cytokine TNF-α, a critical element for the pathogenesis through the regulation of synovial inflammation. Other studies have similarly demonstrated that in autoimmune demyelination syndrome and in multiple sclerosis (MS), ATG5 gene expression is also significantly elevated compared to healthy controls.

Therefore, the role of autophagy in autoimmune diseases is crucial. In rheumatoid arthritis (RA) autophagy appears to be activated in osteoclasts and regulates osteoclasts differentiation. This increased autophagic process, also found in rheumatoid arthritis synovial fibroblast compared to osteoarthritis synovial fibroblast correlates with a reduced apoptosis level in rheumatoid arthritis synovial tissues. In rheumatoid arthritis, the activation of autophagy induced by overproduced TFN-α leads to the reduction of apoptosis in joints and more importantly causes the survival of synovial fibroblasts, which are responsible for the pathology. This again highlights the dual effect of autophagy, which is cytoprotective when it eliminates misfolded or too abundant cellular components, but autophagy excess can become deleterious and generate negative effects. Furthermore, number of recent findings underlined the pivotal role of macroautophagy in the control of muscle mass, and misregulation of autophagy has been described in myopathies and muscular dystrophies.

Decrypting the molecular and cellular mechanisms leading to Immune tolerance breaking and evolution toward autoimmune disease remains a vast area of investigations in the scientific and clinical community. Nowadays, no universal signature can be identified, and clues are largely lacking regarding the reasons of their tropism as well as on the elements triggering their initiation and maintenance. Relatively little is also known regarding the events governing the successive periods of flares and remission occurring in certain autoimmune diseases such as lupus erythematosus.

Thus, there exists in the art an ongoing need for therapeutic interventions to treat and prevent autoimmune diseases. In particular, there exists a need for therapeutic interventions that target key cellular processes involved in the initiation and persistence of autoimmune diseases, e.g. the autophagic process, which is involved in the establishment and maintenance of immune tolerance and the proper effectiveness of the immune system, which has particular importance in autoimmunity. Accordingly, there is a need to provide therapeutic interventions capable of advantageously modulating the autophagic processes as a means for treating, preventing and/or ameliorating the symptoms of autoimmune disorders.

A large number of chemicals have been found to either promote or inhibit autophagy and some of these compounds have been widely used to dissect the mechanisms underlying autophagy. Most popular autophagy inducers include mTOR kinase inhibitors (e.g. rapamycin and torin 1 and commonly used autophagy inhibitors include chloroquine (CQ), 3-methyladenine, wortmannin and bafilomycin. Although chloroquine (CQ) or hydroxychloroquine (HCQ) offers great promises in autoimmune diseases therapy, CQ induces ocular toxicities and damages the renal system and functions. Moreover, it is uncertain whether the tolerated doses of HCQ or CQ can be reached in human to effectively inhibit autophagy in clinic. Also, most of the available autophagy inhibitors, like CQ and HCQ lack either specificity or potency.

Thus, potent and specific inhibitors of the autophagy survival pathway are needed in order to provide a novel and powerful approach to treat diseases in subject where autophagy must be inhibited.

SUMMARY OF THE INVENTION

In one embodiment, the invention relates to novel compounds which inhibit the autophagy flux, and/or the inhibition of cathepsins B (CTSB), L (CTSL) and/or D (CTSD). These compounds include those in Formula (III): 5-3 (HCl salt (5-2), 6-3 (HCl salt 6-4), 7-1 (HCl salt 7-2), 8-2 (HCl salt 8-3), 9-1 (HCl salt 9-2), 10-2 (HCl salt 10-3), 11-1 (HCl salt 11-2), 12-4 (HCl salt 12-5), 13-1 (HCl salt 13-2), Formula (I): 14-5, 15-1 ((HCl salt 15-2), 16-6, 17-1 (HCl salt 17-2), 18-3, (HCl salt 18-4), and Formula (III): 19-1 (HCl salt 19-2), 20-1 (HCl salt 20-2), 21-2, 22-1 (HCl salt 22-2), and 23-2 (HCl salt 23-3), as shown below:
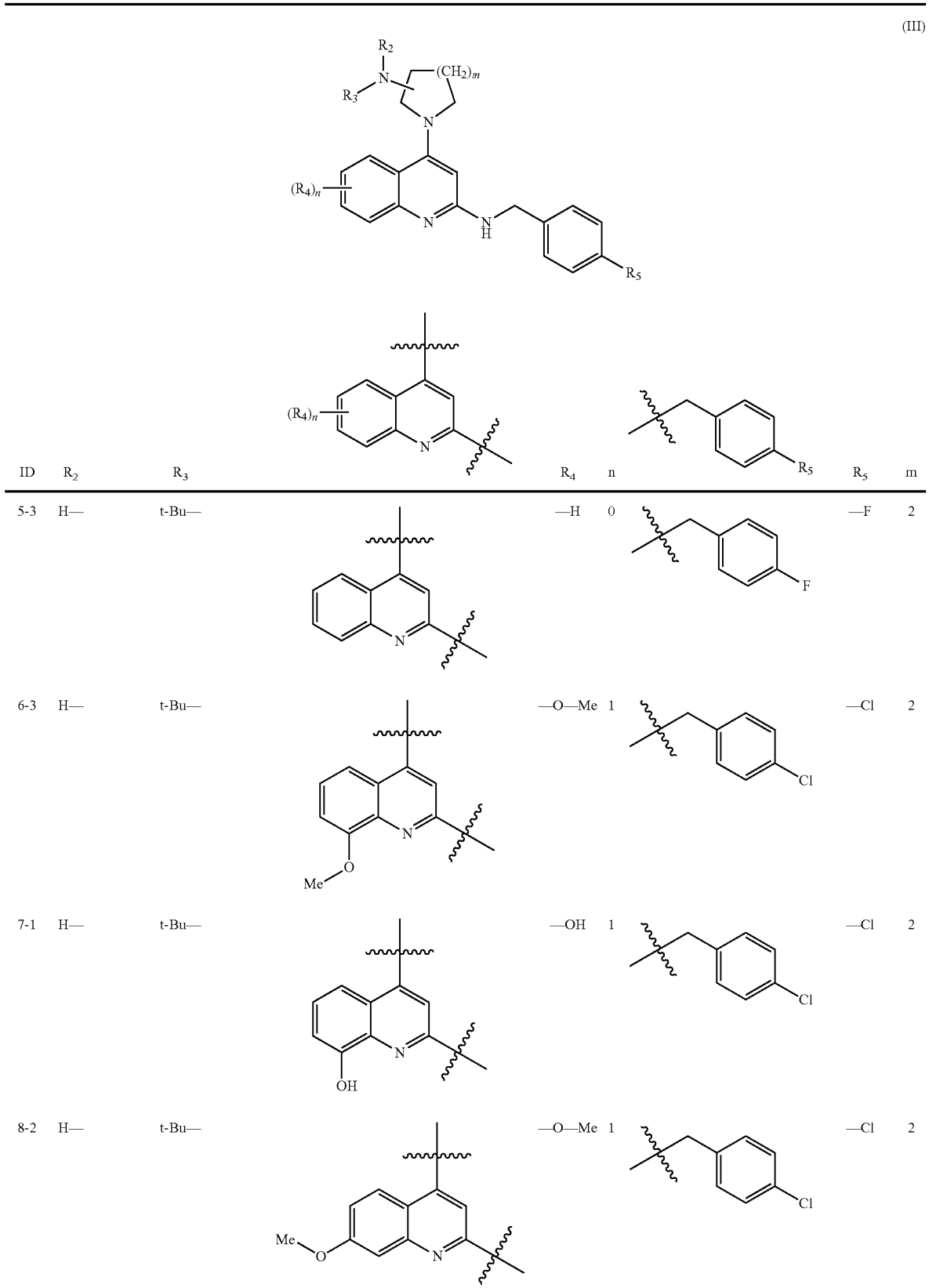

-continued
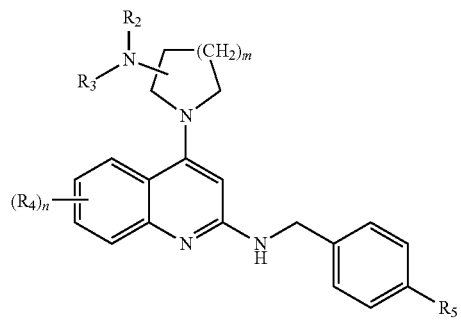
(III)
| ID | $R_2$ | $R_3$ | 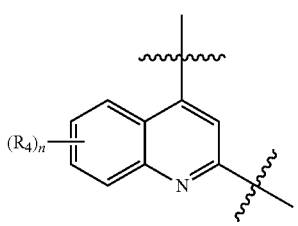 | $R_4$ | n | 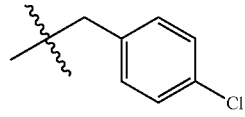 $R_5$ | $R_5$ | m |
|---|---|---|---|---|---|---|---|---|
| 9-1 | H— | t-Bu— | 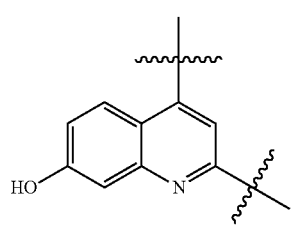 | —OH | 1 | 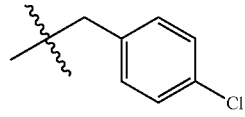 | —Cl | 2 |
| 10-2 | H— | t-Bu— | 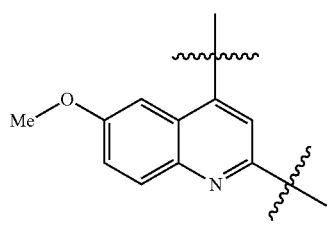 [SMILES: *c1cc(*)c2cc(OC)ccc2n1] | —O—Me | 1 | 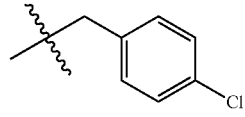 | —Cl | 2 |
| 11-1 | H— | t-Bu— | 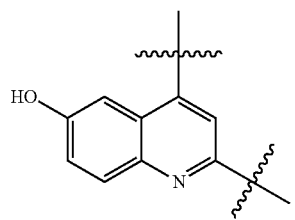 | —OH | 1 | 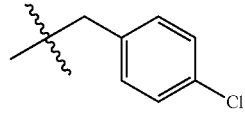 [SMILES: *Cc1ccc(Cl)cc1] | —Cl | 2 |
| 12-4 | H— | t-Bu— | 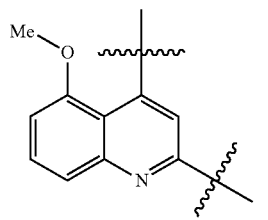 | —O—Me | 1 | 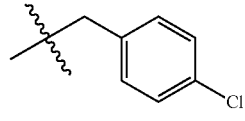 [SMILES: *Cc1ccc(Cl)cc1] | —Cl | 2 |

-continued
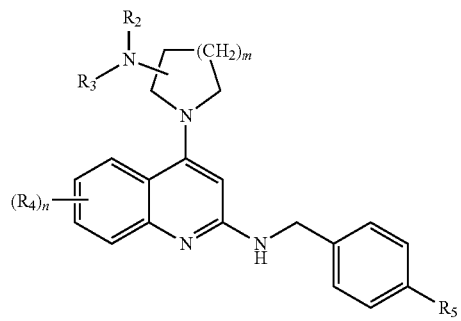
(III)
| ID | R$_2$ | R$_3$ | 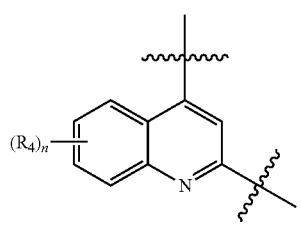 | R$_4$ | n | 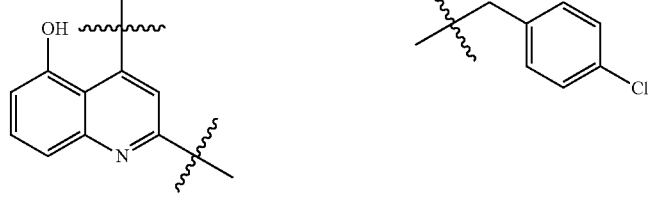 R$_5$ | R$_5$ | m |
|---|---|---|---|---|---|---|---|---|
| 13-1 | H— | t-Bu— | 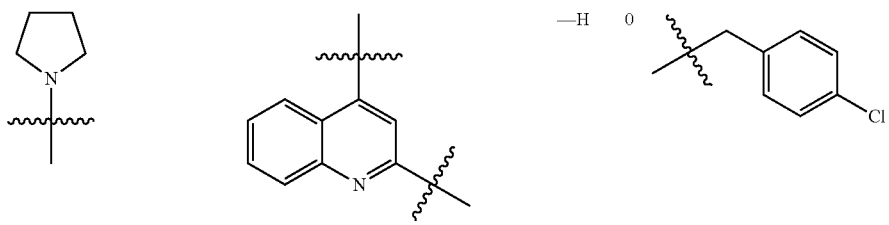 | —OH | 1 | 4-Cl-benzyl | —Cl | 2 |
| 19-1 | | pyrrolidine | quinoline | —H | 0 | 4-Cl-benzyl | —Cl | 2 |
| 20-1 | H— | Me-N-piperidine | 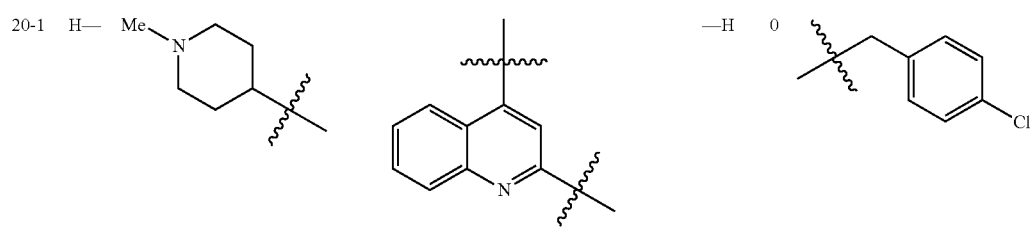 | —H | 0 | 4-Cl-benzyl | —Cl | 2 |

-continued
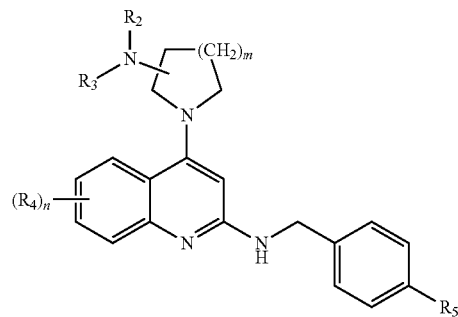
(III)
| ID | R₂ | R₃ | 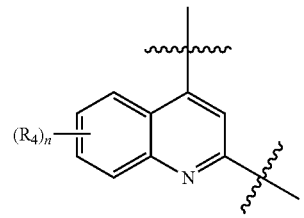 | R₄ | n | 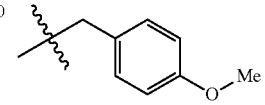 | R₅ | m |
|---|---|---|---|---|---|---|---|---|
| 21-2 | H— | t-Bu— | 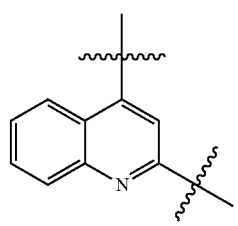 [SMILES: *c1cc(*)c2ccccc2n1] | —H | 0 | 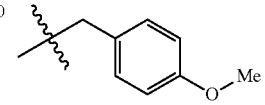 | —O—Me | 2 |
| 22-1 | H— | t-Bu— | 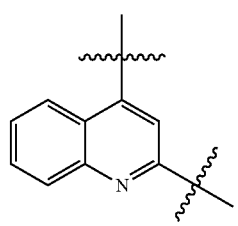 [SMILES: *c1cc(*)c2ccccc2n1] | —H | 0 | 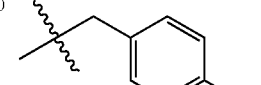 | —OH | 2 |
| 23-1 | H— | t-Bu— | 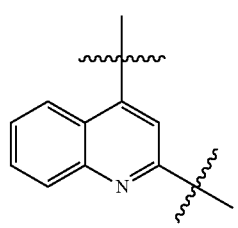 [SMILES: *c1cc(*)c2ccccc2n1] | —H | 0 |  | —H | 2 | as well as their pharmaceutically acceptable salts, hydrates, solvates, prodrugs, polymorphs, tautomers, isotopic variants, and stereoisomers thereof.
Within general Formula I, novel compounds described herein include the following:
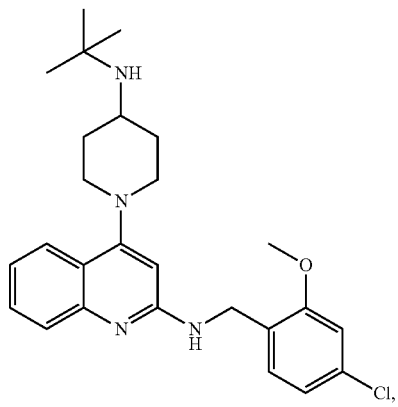
(I-n)
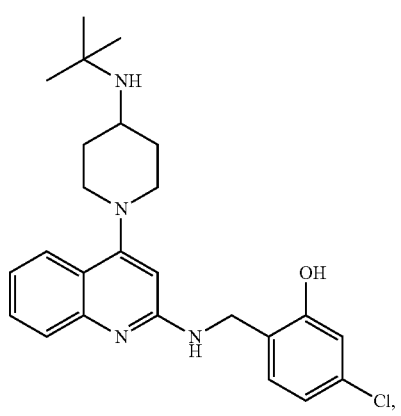
(I-o)
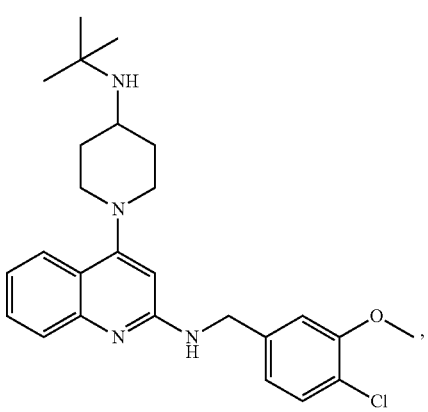
(I-p)
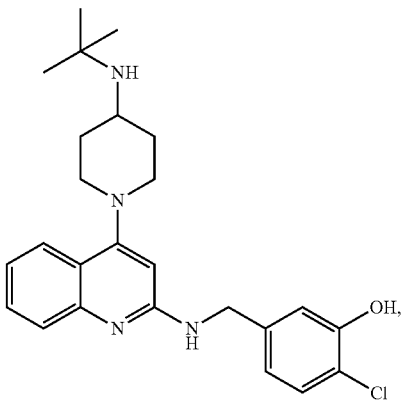
(I-q)
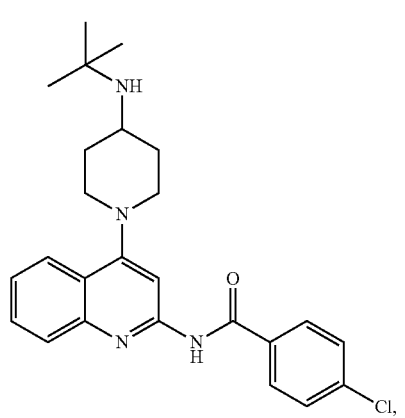
(I-r)
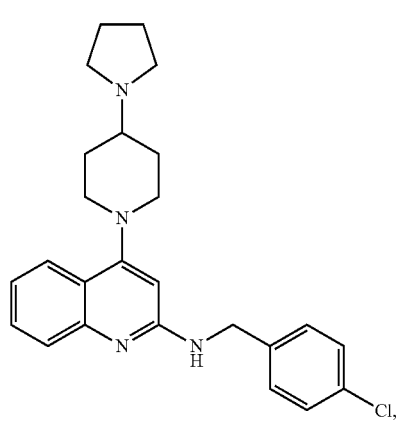
(I-s)

(I-t)

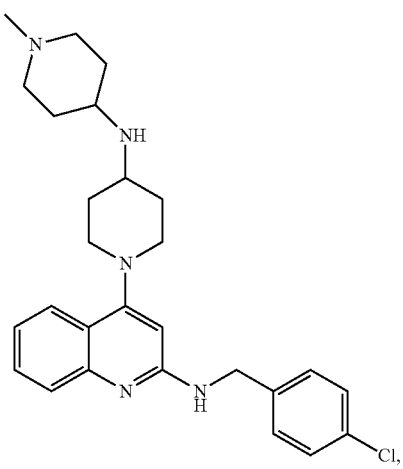

(I-u)

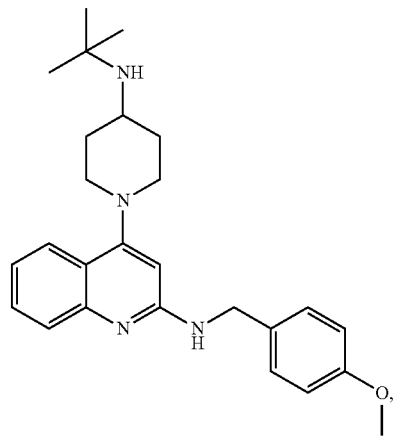

(I-v)

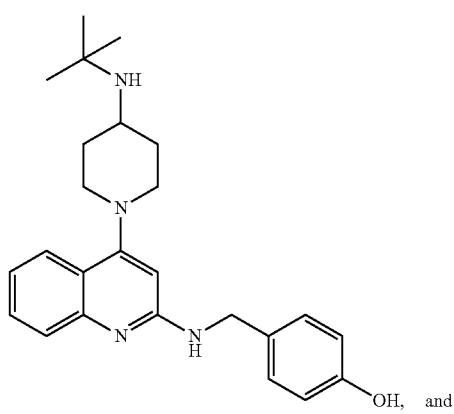
OH, and (I-w)

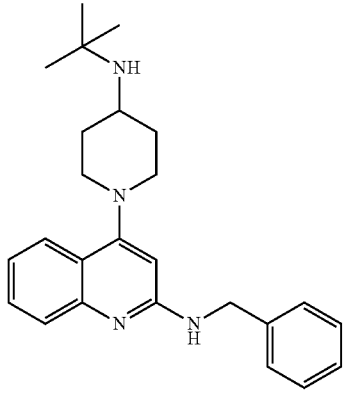

as well as their pharmaceutically acceptable salts, hydrates, solvates, prodrugs, polymorphs, tautomers, isotopic variants, and stereoisomers thereof.

In another embodiment, the invention relates to methods of inhibiting autophagy flux by administering a 2-primary amino-4-secondary cycloamino-quinoline compound, for example, a compound of Formulas I, II, III, IV or V as described herein, to a patient in need of treatment thereof.

In a further embodiment, the invention relates to methods of inhibiting cathepsins B (CTSB), L (CTSL) and/or D (CTSD), and, in doing so, treating, preventing, or reducing the severity and/or progression of a disorder mediated by these cathepsins.

Furthermore, the compounds described herein modulate the autophagy cellular processes, as shown in different cell lines: HepG2 (hepatocellular carcinoma cell line), Huh-7 (hepatocellular carcinoma cell line) and RBE (cholangiocarcinoma cell line), and the results showed inhibiting the autophagy cellular process.

Therefore, the compounds described herein reduce the outcomes of pathological fibrosis as described herein.

To validate these hypotheses, as shown in the working example, the in vitro antifibrotic activity was evaluated based on the capacity of the compounds to inhibit the phenotypic transformation of the quiescent fibroblast (human primary cells or cell lines) into pro-fibrogenic myofibroblasts. This effect was achieved by activating the quiescent fibroblast or primary cells with TGF-β to induce a differentiation into myofibroblasts which express some pro-fibrotic markers such as α-Smooth Muscle Actin (α-SMA).

Finally, the results and hypothesis obtained from previous in vitro data (not shown) were confirmed and validated in vivo, using a diethylnitrosamine (DEN) rat liver fibrosis animal model.

The antifibrotic activity confirmed in vivo in a rat liver fibrosis model, together with the in vitro activity of the compounds as autophagy and cathepsins inhibitors, demonstrates that the compounds of Formulas I, II, III, IV or V as described herein have antifibrotic activity in other fibrotic tissues and organs, such as skin, lungs, heart, kidney, guts, peritoneum membrane, skin, eye, mucosa (mouth, vagina, uterus, and anus), ovary, prostate, nervous system, and liver, and can be used to treat fibrosis-related diseases in these organs.

Several of the compounds described herein, as well as their syntheses, particularly those of Examples 1, 2, 3 and 4, were disclosed in WO2016067112, the contents of which we incorporated by reference, though not for use in treating fibrosis-related diseases. Therefore, the compounds disclosed herein can be used as drug in treating, decreasing the severity and/or progression of, and/or preventing fibrosis-related diseases.

Therefore, in one embodiment, the invention relates to treating, reducing the severity and/or progression of, and/or preventing fibrosis-related diseases.

In a another embodiment, the invention relates to methods for inhibiting the autophagy flux and treating, decreasing the severity and/or progression of, and/or preventing increased autophagy flux-related diseases.

In yet another embodiment, the invention relates to treating conditions in which modulation of cathepsin activity, particularly cathepsin B, D and/or L, is therapeutically useful. This embodiment is based, in part, on the discovery of novel cysteine protease inhibitors that are substantially selective for inhibiting the function or activity of cathepsin B, and/or cathepsin L and on the discovery of novel aspartyl protease inhibitors that are substantially selective for inhibiting the function or activity of cathepsin D.

A skilled artisan will appreciate that inhibiting cathepsin activity can be accomplished using any method known in the art. Examples of methods to inhibit cathepsin activity include, but are not limited to, decreasing the severity and/or progression of the expression of an endogenous cathepsin gene, decreasing the severity and/or progression expression of cathepsin mRNA, and inhibiting activity of cathepsin protein. A cathepsin inhibitor can therefore be a compound or composition that decreases expression of a cathepsin gene, a compound or composition that decreases cathepsin mRNA half-life, stability and/or expression, or a compound or composition that inhibits cathepsin protein function. A cathepsin inhibitor can be any type of compound, including but not limited to, a polypeptide, a nucleic acid, an aptamer, a peptidomimetic, and a small molecule, or combinations thereof.

Cathepsin inhibition can be accomplished either directly or indirectly. For example, a cathepsin can be directly inhibited by compounds or compositions that directly interact with cathepsin protein, such as antibodies or soluble cathepsin receptors. Alternatively, cathepsin can be inhibited indirectly by compounds or compositions that inhibit cathepsin receptors, cathepsin downstream effectors, upstream regulators which up-regulate cathepsin expression or by increasing the pH of subcellular organelle wherein cathepsins are concentrated such as, but not limited to, lysosome organelle.

Decreasing the severity and/or progression expression of an endogenous cathepsin gene includes providing a specific inhibitor of cathepsin gene expression. Decreasing the severity and/or progression expression of cathepsin mRNA or cathepsin protein includes decreasing the severity and/or progression the half-life or stability of cathepsin mRNA or decreasing the severity and/or progression expression of cathepsin mRNA. Methods of decreasing the severity and/or progression expression of cathepsin include, but are not limited to, methods that use an siRNA, a microRNA, an antibody, a soluble receptor, an antisense nucleic acid, a ribozyme, an expression vector encoding a transdominant negative mutant, a peptide, a small molecule, other specific inhibitors of cathepsin gene, mRNA, and protein expression, and combinations thereof.

The name cathepsin, which is derived from the ancient Greek kathepsein (kata-"down" and hepsein "boil"), was proposed for the protease that was active in a slightly acidic environment. Later, the name cathepsin was introduced for the serine proteases cathepsins A and G, the aspartic proteases cathepsins D and E, and the lysosomal cysteine cathepsins proteases.

Cathepsins cysteine protease are members of the papain proteins family and are an important enzymatic class in medicinal research fields. In this cysteine proteases family, there are eleven cathepsin enzymes known as: Cathepsins B, C, F, H, K, L O, S, V, W and X. They have unique reactive-site properties and an irregular tissue-specific expression pattern. Lysosomal cathepsins require a reducing the severity and/or progression and slightly acidic environment, such as found in the lysosomes, in order to be optimally active. Such specificities explain in part, why cathepsins are found in the highest concentration in cellular acidic environment such as lysosomes, where the cathepsins concentration increase up to 1 mM. Therefore, cysteine cathepsins were initially considered as intracellular enzymes, responsible for the non-specific, bulk proteolysis in the acidic environment of the endosomal/lysosomal compartment, where they degrade intracellular and extracellular proteins. However, cathepsins can equally be released from the lysosomes into the extracellular medium. Cysteine cathepsins play an important role in degradation and processing of protein in lysosomes which are involved in hydrolyzing the precursor peptide of some zymogen or hormone to active form, or activating other proteolytic enzymes system. In addition, cathepsins are also involved in MHC class II expression. Over expression of cysteine cathepsins proteases has been implicated in certain inflammatory diseases, in osteoporosis and rheumatoid arthritis among other diseases and can result in severe diseases. A number of infections agents (bacteria, viruses and protozoa) also use either host or their own cysteine proteases for infectivity, virulence and/or replication processes and targeting these cysteine proteases is a popular strategy for anti-infective pharmaceutical efforts.

The view of cysteine cathepsins as lysosomal proteases is changing as there is now clear evidence of their localization in other cellular compartments. Besides being involved in protein turnover, they build an important part of the endosomal antigen presentation. Together with the growing number of non-endosomal roles of cysteine cathepsins is growing also the knowledge of their involvement in diseases such as rheumatoid arthritis, among others. Finally, cysteine cathepsins are important regulators and signaling molecules, therefore aberrant activities of cathepsins such as increasing enzyme expression, enhancing activation or unusual localization can be involved in key steps of pathological events.

Cathepsins B and L have been investigated extensively, due to their implication in numerous human diseases. Thereby, cathepsin B activity is implicated in such disease states such as rheumatoid arthritis, osteoarthritis, Alzheimer's Disease (AD), *Pneumocystisis carinii*, acute pancreatitis, inflammatory respiratory disease, liver fibrosis, bone and joint disorders (e.g. osteoporosis). Cathepsin inhibitors as drug candidates for treating various diseases in the pharmaceutical pipeline include treating liver fibrosis while cathepsin K inhibitors have also the target of much research owing to its key role in bone resorption and its implication in osteoporosis.

Rheumatoid arthritis is characterized by chronic synovial joint inflammation and the infiltration of an activated CD4+ T cell and APC, such as dendritic cells and macrophages. It involves a progressive destruction of the articular cartilage, eventually leading to a loss of joint function. In addition to metalloproteases, such as collagenases and aggrecanases, lysosomal cysteine cathepsins B and L have been identified in synovial fluids of rheumatoird arthritis patients. Furthermore, the cathepsin B and L were also involved in bone degradation.

Cathepsin B is in humans encoded by the CTSB gene. Cathepsin B belongs to the lysosomal cysteine proteases of the papain family and plays an important role in intracellular proteolysis. Cathepsin B is synthesized on the rough endoplasmic reticulum as a preproenzyme with a signal peptide of 17 amino acids. Procathepsin B of 43/46 kDa is then transported to the Golgi apparatus and where active cathepsin B is formed. Mature cathepsin B is composed of a heavy chain of 25-26 kDa and a light chain of 5 kDa, which are linked by a dimer of disulfide. Cathepsin B is a lysosomal cysteine protease with both endopeptidase and exopeptidase activity that can play a role in protein turnover and is typically associated with the lysosomes involved in autophagy and immune response. Cathepsin B is unique among the cathepsins because it has two conformations, exopeptidase (carboxydipeptidase activity) and endopeptidase activities, due to the presence of around 20 amino (Ile105-Thr125) acid insertion termed "occluding loop". When cathepsin B acts as exopeptidase, the occluding loop that is no covalently linked to the body of the enzyme by two salt bridges (Asp22-His110 and Asp224-Arg116) blocks the active site cleft at the end of the primed site of the substrates. This event leaves only space for two amino acid residues of the substrate C-terminal of the scissile bond in the P1' and P2' positions. Additionally, the occluding loop provides two His residues (His110 and His111) that bind the substrate's C-terminal carboxylate which enables the exopeptidase activity. Exopeptidase activity has a pH optimum around 5 which is suitable for the lysosomal compartments.

Cathepsin B functions in intracellular protein catabolism and in certain situations can also be involved in other physiological processes, such as processing of antigens in the immune response, hormone activation and bone turnover. Cathepsin B can enhance the activity of other protease, including matrix metalloproteinase, urokinase (serine protease urokinase plasminogen activator) and cathepsin D. Therefore, cathepsin B has an essential position for the proteolysis of extracellular matrix components, intercellular communication disruption, and reduced protease inhibitor expression. There is also some evidences that cathepsin B is implicated in the pathology of chronic inflammatory diseases of airways and joints and pancreatitis.

Cathepsin B acts also as β-secretase in the regulated pathway and is the major source of secreted extracellular Aβ (Amyloid beta peptide). Aβ forms aggregates which are widely believed to be the key neurotoxic agents in Alzheimer's disease. These aggregates ultimately results in the insoluble deposits and dense neuritic plaques that are pathological characteristics of Alzheimer's disease. Hence, selective inhibitors of cathepsin B can be used to treat and/or prevent Alzheimer's disease.

Cathepsin B is also associated with fibrotic diseases, such as hepatitis B and C associated liver fibrosis, all types of steatosis (including non-alcoholic steatohepatitis) and alcohol-associated steatohepatitis, non-alcoholic fatty liver disease, forms of pulmonary fibrosis including idiopathic pulmonary fibrosis, pathological diagnosis of interstitial pneumonia following lung biopsy, renal fibrosis, cardiac fibrosis, retinal angiogenesis, retinal fibrosis, retinal gliosis, scleroderma, systemic sclerosis and keloids and other forms of scarring.

Cathepsin L is an important lysosomal endopeptidase enzyme which is involved in the initiation of protein degradation. Cathepsin L is a member of the Peptidase C1 family (a member of the papain-like family of cysteine proteinases), which play an important role in diverse processes including normal lysosome mediated protein turnover, antigen processing, bone resorption, protein processing and apoptosis. Cathepsin L has a major function in intracellular lysosomal proteolysis and in the degradation of the extracellular matrix. Cathepsin L also has been implicated in regulatory events relating among others to diabetes, immunological responses, degradation of the articular cartilage matrix, and other pathological processes including osteoporosis, myofibril necrosis in myopathies, myocardial ischemia, rheumatoid arthritis, atherosclerosis, renal disease, viral infection and pulmonary emphysema. Pulmonary emphysema develops because of progressive loss or derangement of lung elastin through a process mediated by elastinolytic enzymes (including cathepsins B, H, K, L, and S) derived from alveolar macrophages. By proteolytic activity, Cathepsin L inactivates secretory leucoprotease inhibitor (SLPI), alpha1-antitrypsin and two major protease inhibitors of the respiratory tract, moreover the epithelial lining fluid of the lungs of emphysema patients had increased cathepsin L activity, which led together that cathepsin L can play a major role in the progression of pulmonary emphysema. Furthermore, inhibition of cathepsin L has also been shown to block the entry processes of some enveloped viruses such as severe acute respiratory syndrome coronavirus (SARS-CoV), Ebola virus (EBOV), Hendra virus (HeV) and Nipah virus (NiV) virus infections. The enveloped viruses critically require cathepsin L for their glycoprotein processing and cleavage to allow for virus fusion and entry into the host cells. Cathepsin L is equally involved in metabolic syndrome as it controls adipogenesis and peripheral glucose tolerance. In renal disease Cathepsin L regulates podocyte function by proteolytically processing dynamin and thereby proteinuria. Cathepsin L is equally involved in tissue remodeling, extracellular matrix degradation, the generation of active neuropeptides and has some roles in antigen presentation in thymic epithelial cells. Cathepsin L takes part equally to the production of hormonal peptides such as ACTH, β-endorphin and α-MSH.

Cathepsin D is involved in lysosomal biogenesis and protein targeting, and can also be involved in antigen processing and presentation of peptide fragments. Cathepsin D has been linked to numerous diseases including Alzheimer's disease, connective tissue disease and muscular dystrophy. Cathepsin D (CTSD) is a soluble lysosomal aspartic endopeptidase coded by the CTSD gene and synthesized in the rough endoplasmic reticulum as pre-proCTSD. After removal of signal peptide, the proCTSD is targeted to endosomes to form an active, 48-kDa, single-chain intermediate, and then to the lysosomes to form the fully active mature protease, composed of a 34-kDa heavy chain and a 14-kDa light chain. Besides cathepsin D, the well-known aspartyl proteases also include the HIV aspartyl protease, renin, pepsin A and C, BACE, plasmepsins or aspartyl haemoglobinases. No endogenous inhibitors of CTSD are known and natural inhibitors, called pepstatins, are synthesized by *Streptomyces* bacteria, but not by eukaryotic animal cells. The mature CTSD is predominantly active at pH below 5, found in the lysosomes. However, CTSD is the only proteolytic enzyme whose expression, in different tissues, is regulated in response to growth factors, cytokines, and vitamins.

Cathepsin D is normally involved in the degradation of intracellular or phagocytized proteins and therefore plays an important role in protein metabolism, in protein catabolism and in antigen processing.

Cathepsin D is equally associated with degenerative changes in the brain, such as Alzheimer's disease. Hence, cathepsin D is associated with the cleavage of the amyloid-beta precursor protein (AβPP). The proteolysis of the amyloid-beta precursor protein allows to release the amyloid-beta protein, which result in the formation of hard and insoluble plaques in the brain and appears to be responsible for the development of Alzheimer's disease. Increased cathepsin D levels have also been found in the cerebrospinal fluid of Alzheimer's patients 7 associated with a high proteolytic activity of cathepsin D. Furthermore, a significant increase in cathepsin D activity is measured in biopsies from Huntington's disease patients.

Cathepsin D plays equally an essential role at some levels in the development of arthrosis. Thus, increased mRNA levels of Cathepsin D are measured in the joint cartilage of the hip joint head with arthrosis compared to standard hip. Cathepsin D also appears to play a role in mucolipidosis. Cathepsin D is the most widespread proteinase in the chondrocytes and its proteolytic activity is equally well established in synovium from osteoarthrosis patients, in synovectomy tissue of patients with rheumatoid arthritis or in cartilage of patients with arthrosis. In the case of arthrosis, a reduction in the pH occurs in regions of the cartilage at an acidic level wherein the proteolytic activity of Cathepsin D is optimal. This reduction in the pH is of crucial importance for understanding of catabolic processes in the cartilage. In the case of arthrosis, a direct correlation is thus also found between a low pH in the joint tissue and the severity and progress of the disease. At a pH of 5.5, autodigestion of the cartilage occurs. This cartilage digestion can be inhibited in explant cultures by peptatin or ritonavir, this suggests an essential role, or even a key role of Cathepsin D in arthrosis, since pepstatin inhibits aspartyl proteases, with the BACE-1 exception, and only Cathepsin D and BACE-1 aspartyl proteases have been identified in the cartilage tissue.

Therefore, it is an object of the invention to provide compounds which act as inhibitors of cathepsins B (CTSB), L (CTSL) and/or D (CTSD), and their use in methods for treating and/or preventing cathepsins B (CTSB), L (CTSL) and/or D (CTSD) related diseases.

It is a further object of the present disclosure to provide compounds which act to treating, decreasing the severity and/or progression of and/or preventing fibrosis-related diseases.

It is another object of the present disclosure to provide compounds which act as inhibitors of the autophagy flux and treating, decreasing the severity and/or progression of and/or preventing increased autophagy flux related diseases.

Therefore, a preferred embodiment of the present disclosure relates to inhibiting cathepsins B (CTSB), L (CTSL) and/or D (CTSD) and for treating and/or preventing cathepsins B (CTSB), L (CTSL) and/or D (CTSD) related diseases using the compound described herein.

A still further embodiment of the present disclosure relates to treating, decreasing the severity and/or progression of and/or preventing fibrosis-related diseases using the compounds described herein.

Another embodiment of the present disclosure relates to inhibiting the autophagy flux and treating, decreasing the severity and/or progression of and/or preventing increased autophagy flux related diseases.

Another embodiment of the present disclosure relates to inhibiting cathepsins B (CTSB), L (CTSL) and/or D (CTSD) and for treating or preventing cathepsins B (CTSB), L (CTSL) and/or D (CTSD) related diseases.

Methods for treating and/or preventing fibrosis-related diseases and/or diseases related to inhibiting the autophagy flux and/or diseases related to inhibiting cathepsins B (CTSB), L (CTSL) and/or D (CTSD) are also disclosed.

Pharmaceutical compositions comprising a therapeutically effective amount of compounds, alone or in combination with each other and/or with other active agents and/or pharmaceutically acceptable adjuvant, diluent or carrier, are also disclosed, as is the use of the compounds in therapy.

BRIEF DESCRIPTION OF THE FIGURES

The above and other characteristics and advantages of the embodiments described herein will be more readily apparent through the following examples, and with reference to the appended drawings, wherein.

DETAILED DESCRIPTION

Figure 1:
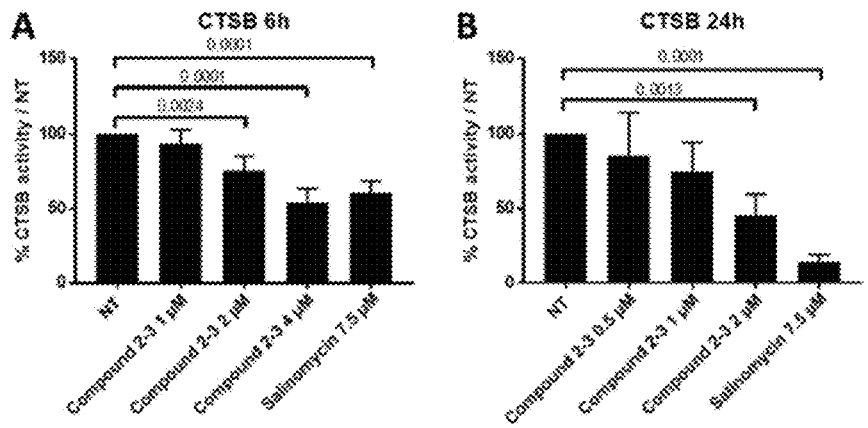
FIG. 1: describes the effect of compound 2-3 on cathepsin B (CTSB) activity (Mean±SD) after 6 hours and 24 hours of HepG2 cell line treatment.

In one embodiment, the present disclosure is based on the discovery that the compounds of Formulas (I), (II), (III), (IV) or (V) can be used to treat and/or prevent fibrosis and related diseases, to inhibit, treat, decrease the severity of, and/or prevent autophagy flux and related diseases, and/or inhibit cathepsins B (CTSB), L (CTSL) and/or D (CTSD), and thus treat or prevent diseases related to these cathepsins, in a subject, particularly in mammals, are also disclosed.

Methods for preparing the compounds, and intermediates for their preparation, are also disclosed.

Pharmaceutical compositions comprising a compound as described herein, and their uses as a medicament for treating or preventing fibrosis disorders and related diseases, for inhibiting, treating, decreasing the severity and/or progression the severity of, and/or preventing autophagy flux and related diseases, and/or for inhibiting cathepsins B (CTSB), L (CTSL) and/or D (CTSD), and thus treating or preventing diseases related to these cathepsins, in a subject, particularly in mammals.

According to the present text and invention and unless otherwise indicated whenever the term or expression defined hereinafter appears in the text it implies the definition given below and must be understood as such:

"as defined herein" or "as defined herein above" or "as defined above" or "as defined" means that the term or expression that precedes this expression first takes the definition given below; these expressions refer to the broadest definition for each group as well as each substituents which can be present in each embodiment as described below in the specification or in the broadest claims.

"i.e." is a abbreviation of the Latin expression id est, which translates to "that is." It is used to introduce a rephrasing or elaboration on something that has already been stated.

"e.g." is an abbreviation of the Latin expression "exempli gratia", meaning "for the sake of example" or more colloquially, "for example." This term is used to introduce examples of something that has already been stated.

"eq.", as well know in chemistry, is the abbreviation of "equivalent" that is the amount of a substance that reacts with (or is equivalent to) an arbitrary amount of another substance in a given chemical reaction.

The expression "optionally substituted" means not substituted or substituted with one or more substituents simultaneously or independently chosen from a halogen atom as defined herein; an hydroxyl; a cyano; an azido; a -nitro; a carboxyl; a —$CF_3$; —a —(CO)—$R_8$; a —(CO)—O—$R_8$; a —(CO)—$NR_{12}$OH; a —(CO)—$NR_8$OH; a —(CO)—$NR_{12}R_{13}$; a —(CO)—$NR_8R_{8'}$; a —O—(CO)—$R_8$; a —O—(CO)—$NR_{12}R_{13}$; a —O—(CO)—$NR_8R_{8'}$; a —$NR_{12}$—(CO)—$R_8$; a —$NR_8$—(CO)—$R_{8'}$; a —$NR_{12}$—(CO)—$NR_8$; a —$NR_8$—(CO)—$OR_{8'}$; a —O—(CO)—$OR_8$; a —$NR_{12}$—(CO)—$NR_{12}R_{13}$; a —$NR_8$—(CO)—$NR_8R_{8'}$; a —(O—$CH_2CH_2$—)$_p$—$NR_{12}$; a —(O—$CH_2CH_2$—)$_p$—$NR_8$; a —(O—$CH_2CH_2$—)$_p$—$NR_{12}R_{13}$; a —(O—$CH_2CH_2$—)$_p$—$NR_8R_{8'}$; a —($NR_{12}$—$CH_2CH_2$—)$_p$—$NR_{13}$; a —($NR_8$—$CH_2CH_2$—)$_p$—$OR_{8'}$; a —$NR_{12}$—($CH_2CH_2$—)$_p$—$NR_{12}R_{13}$; a —$NR_8$—($CH_2CH_2$—)$_p$—$NR_8R_{8'}$, a —$NR_{12}$—($C_2$-$C_8$)-alkyl-$NR_{12}R_{13}$; a —$NR_8$—($C_2$-$C_8$)-alkyl-$NR_8R_{8'}$; a —$NR_{12}$—($C_2$-$C_8$)-alkyl-$OR_{13}$; a —$NR_8$—($C_2$-$C_8$)-alkyl-$OR_{8'}$; a —$SO_2$—$R_8$; a —$NR_{12}$—$SO_2$—$R_8$; a —$NR_8$—$SO_2$—$R_{8'}$; a —$SO_2$—$NR_{12}R_{13}$; a —$SO_2$—$NR_8R_{8'}$; a —$NR_{12}SO_2$—$NR_{12}R_{13}$; a —$NR_8SO_2$—$NR_8R_{8'}$; a —$NR_{12}R_{13}$; a —$NR_8R_{8'}$; a —$OR_8$; an optionally substituted alkyl as defined herein, preferably said optionally substituted alkyl being substituted by one or more halogen atom(s) as defined herein; by one or more hydroxyl, by one or more alkoxy as defined herein, or by one or more —$NR_8R_{8'}$ and combination thereof; an optionally substituted fluoroalkyl as defined herein; an optionally substituted alkenyl as defined herein, preferably said optionally substituted alkenyl being substituted by one or more halogen atom(s) as defined herein; by one or more hydroxyl, by one or more alkoxy as defined herein, or by one or more —$NR_8R_{8'}$ and combination thereof; an optionally substituted alkynyl as defined herein, preferably said optionally substituted alkynyl being substituted by one or more halogen atom(s) as defined herein; by one or more hydroxyl, by one or more alkoxy as defined herein, or by one or more —$NR_8R_{8'}$ and combination thereof, an optionally substituted cycloalkyl as defined herein, preferably said optionally substituted cycloalkyl being substituted by one or more halogen atom(s) as defined herein; by one or more hydroxyl, by one or more alkoxy as defined herein, or by one or more —$NR_8R_{8'}$ and combination thereof, an optionally substituted a cycloalkenyl as defined herein, preferably said optionally substituted cycloalkenyl being substituted by one or more halogen atom(s) as defined herein; by one or more hydroxyl, by one or more alkoxy as defined herein, or by one or more —$NR_8R_{8'}$ and combination thereof, an optionally substituted a cycloalkynyl as defined herein, preferably said optionally substituted cycloalkynyl being substituted by one or more halogen atom(s) as defined herein, by one or more hydroxyl, by one or more alkoxy as defined herein, or by one or more —$NR_8R_{8'}$ and combination thereof; an optionally substituted fluoroalkyl as defined herein; an optionally substituted alkoxy as defined herein; with p being an equal integer which can have any one of the values 1, 2, 3, 4 or 5, preferably 1, 2, 3 or 4, more preferably 1, 2 or 3, still more preferably 1 or 2; wherein $R_{12}$, $R_{13}$, $R_8$ and $R_{8'}$ are as described in general Formula (I).

The expressions "halogen", "halogen atom", "halogens" or "halogen atoms" everywhere it appears mean an or more atom(s) that can be chosen from fluorine (F), chlorine (Cl), bromine (Br), iodine (I), astatine (At), and tennessine (Ts), preferably a fluorine, a chlorine or a bromine and more preferably a fluorine or a chlorine.

The expressions, "compound of the invention", "compounds of the present disclosure" and "compounds described herein", are meant to embrace compounds of general Formulas (I), (II), (III), (IV) or (V) as hereinafter described, which expression includes the pharmaceutically acceptable salts, the hydrates, the solvates, the prodrugs, the isotopic variants, the tautomers, the stereoisomers and the polymorphs thereof, where the context so permits. Unless otherwise indicated the use of the term "compound(s)" alone must be understood as compound(s) of general Formulas (I), (II), (III), (IV) or (V), their pharmaceutically acceptable salts, their hydrates, their solvates, their prodrugs, their isotopic variants, their tautomers, their stereoisomers and their polymorphs.

Similarly, reference to intermediates, whether or not they themselves are claimed, is meant to embrace their salts, solvates, hydrates, tautomers, and isotopic variants where the context so permits. For the sake of clarity, particular instances when the context so permits are sometimes indicated in the text, but these instances are purely illustrative and it is not intended to exclude other instances as defined when the context so permits.

$C_1$-$C_x$ includes $C_1$-$C_2$, $C_1$-$C_3$ . . . $C_1$-$C_x$, wherein x is an equal integer, whatever the structure of the molecule, linear or branched. By way of example only, "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the $C_1$-$C_4$ alkyl group is selected from among methyl, ethyl, propyl, iso-propyl, n-butyl, iso-butyl, sec-butyl, and t-butyl. Whenever it appears herein, a numerical range such as "1 to 10" refers to each integer in the given range; e.g., "1 to 10 carbon atoms" means that the group can have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms, whatever the structure of the molecule, linear or branched. The term "alkyl", alone or in combination with other groups, refers to a branched or linear chain monovalent saturated aliphatic hydrocarbon radical of 1 to 20 carbon atoms ($C_1$-$C_{20}$ carbon atoms), preferably 1 to 16 carbon atoms ($C_1$-$C_{16}$ carbon atoms), more preferably lower alkyl of 1 to 10 carbon atoms ($C_1$-$C_{10}$ carbon atoms). Alkyl groups can be optionally substituted as defined herein.

The term "lower alkyl", alone or in combination, signifies a linear or branched-chain alkyl group with 1 to 10 carbon atoms ("$C_1$-$C_{10}$-alkyl"), preferably a linear or branched-chain alkyl group with 1 to 5 carbon atoms ("$C_1$-$C_5$-alkyl"), and particularly preferred a linear or branched-chain alkyl group with 1 to 3 carbon atoms ("$C_1$-$C_3$-alkyl"). Lower alkyl groups can be optionally substituted as defined herein. Non-limiting examples of linear and branched lower alkyl groups are methyl, ethyl, n-propyl, isopropyl, n-butyl, isobutyl, sec-butyl, tert-butyl, the isomeric pentyls, the isomeric hexyls, the isomeric heptyls, the isomeric octyls, the isomeric nonyls, the isomeric decanyls, preferably methyl and ethyl and propyl and isopropyl and tert-butyl and isobutyl and sec-butyl and the isomeric pentyls and most preferred methyl and ethyl and n-propyl and isopropyl, and n-butyl and tert-butyl.

The term "alkenyl" signifies a linear or branched chain hydrocarbon residue comprising an olefinic bond

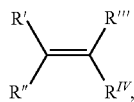

wherein R', R'', R''' and $R^{IV}$ refer to the remaining portions of the alkenyl group, which can be the same or different. The R', R'', R''' and $R^{IV}$ portion of the alkenyl moiety can be branched, linear chain, or cyclic. Alkenyl groups can have 2 to 10 carbon atoms ("$C_2$-$C_{10}$-alkenyl"), preferably 2 to 5 carbon atoms ("$C_2$-$C_5$-alkenyl"), particularly preferred 2 to 4 carbon atoms ("$C_2$-$C_4$-alkenyl"). The alkenyl moiety can be branched, linear chain, or cyclic (in which case, it would also be known as a "cycloalkenyl" group). The alkenyl group can also be a "lower alkenyl" having 2 to 6 carbon atoms including all isomeric forms (cis, trans, Z, E). Alkenyl groups can be optionally substituted as defined herein. Non-limiting examples of lower alkenyl groups are ethenyl, 1-propenyl, 2-propenyl, 1-butenyl, 2-butenyl, isobutenyl, 1-pentenyl, 2-pentenyl, 3-pentenyl, 3-penten-2-yl, 3-penten-4-yl isopentenyl, 1-hexenyl, 2-hexenyl, 3-hexenyl, 4-hexenyl, isohexenyl. Preferred examples are ethenyl, 1-propenyl, 2-propenyl, 2-butenyl, 2-buten-2-yl and isopentenyl.

The term "alkynyl" signifies a linear or branched chain hydrocarbon residue comprising an alkyne bond where two carbon atoms form a triple bond R'—C≡C—R'', wherein R' and R'' refer to the remaining portions of the alkynyl group, which can be the same or different. The R' and R'' portion of the alkynyl moiety can be branched, linear chain, or cyclic. Alkynyl groups can have 2 to 10 carbon atoms ("$C_2$-$C_{10}$-alkynyl"), preferably 2 to 5 carbon atoms ("$C_2$-$C_5$-alkynyl"), particularly preferred 2 to 4 carbon atoms ("$C_2$-$C_4$-alkynyl"). Alkynyl groups can be optionally substituted as defined herein. Non limiting examples of alkynyl groups are, ethynyl, 1-propynyl, 2-propynyl, 1-butynyl, 3-butynyl, 4-butynyl, but-2-yn-1-yl, 1-pentynyl, pent-2-yn-1-yl, pent-3-yn-1-yl, pent-4-yn-1-yl, pent-2-yn-3-yl. Preferred examples are propyn-1-yl, propyn-3-yl, butyn-1-yl, butyn-3yl, butyn-4-yl, but-2-yn-1-yl. The alkynyl group can also be a "lower alkynyl" having 2 to 6 carbon atoms ("$C_2$-$C_6$-alkynyl").

The term "ring" refers to any covalently closed structure. Rings include, for example, carbocycles (e.g. aryls and cycloalkyls), heterocycles (e.g. heteroaryls and non-aromatic heterocycles), aromatics (e.g. aryls and heteroaryls), and non-aromatics (e.g. cycloalkyls and non-aromatic heterocycles). Rings can be monocyclic or polycyclic. Rings can be optionally substituted.

The term "ring system" refers to one, or more than one ring.

The term "membered ring" can embrace any cyclic structure. The term "membered" is meant to denote the number of skeletal atoms that constitute the ring. Thus, for example, cyclohexyl, pyridine, benzene, pyran and thiopyran are 6-membered rings and cyclopentyl, pyrrole, furan, and thiophene are 5-membered rings.

The term "fused" refers to structures in which two or more rings share one or more bonds. Illustrative examples of fused systems include the following moieties:

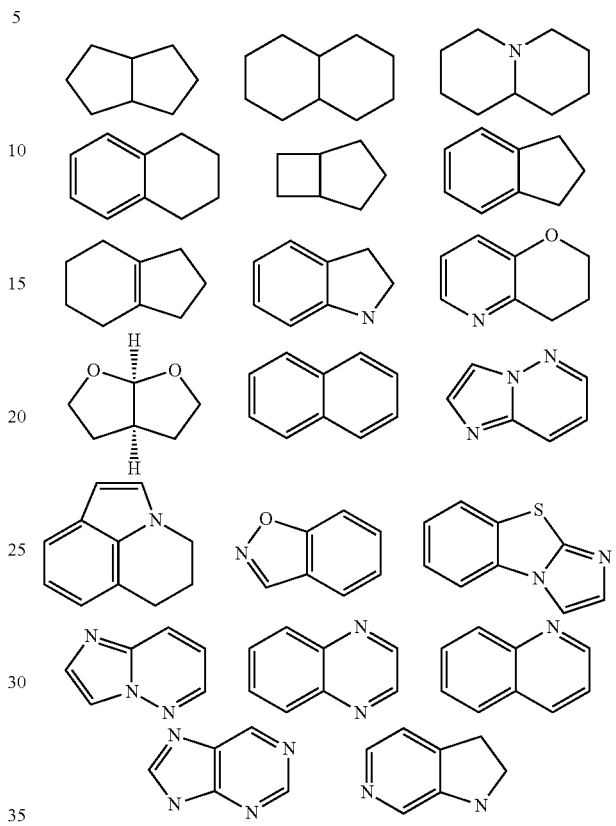

The term "cycloalkyl" denotes to a monocyclic or polycyclic radical that contains only carbon and hydrogen, being saturated rings and containing from 3 to 12 carbon atoms "$C_3$-$C_{12}$-cycloalkyl", such as cyclopropyl, cyclobutyl, cyclopentyl, cyclohexyl, cycloheptyl, cyclooctyl, cyclononyl or cyclodecane. Cycloalkyl groups include groups having from 3 to 12 ring atoms "$C_3$-$C_{12}$-cycloalkyl", preferably from 3 to 8 ring atoms "$C_3$-$C_8$-cycloalkyl" and more preferably from 3 to 7 ring atoms "$C_3$-$C_7$-cycloalkyl" and still more preferably from 3 to 6 ring atoms "$C_3$-$C_6$-cycloalkyl". Depending on the structure, a cycloalkyl group can contain an adjacent and substituting cycloalkenyl and/or alkenyl group. Cycloalkyl groups can be optionally substituted as defined herein. Illustrative examples of cycloalkyl groups include the following moieties:

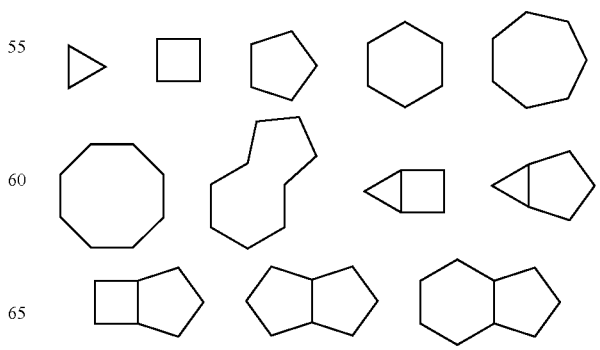

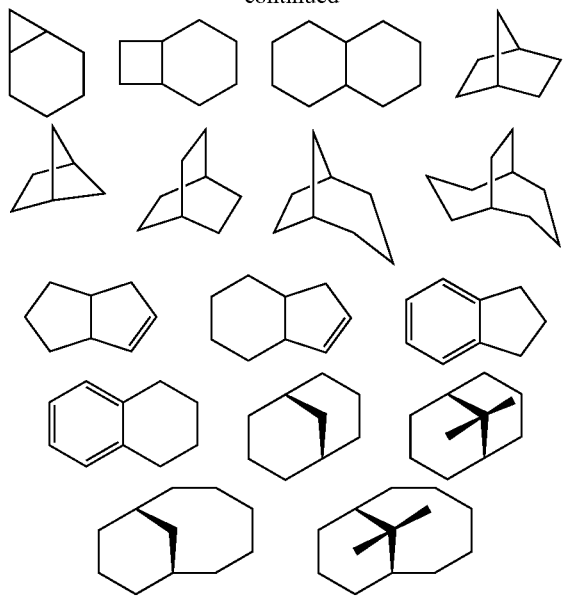

and the like. Preferred cycloalkyls are cyclopropyl, cyclobutyl, cyclopentyl and cyclohexyl.

The terms "heterocyclic group", "non-aromatic heterocycle", "heterocycloalkyl", "heterocyclyl" or "heteroalicyclic" signify a fully saturated or unsaturated but not fully unsaturated, being a 3 to 9 membered monocyclic groups, preferably from 3 to 7 membered monocyclic groups and more preferably from 3 to 6 membered monocyclic groups or fused heterocyclic ring systems comprising from 5 to 16 atoms, preferably from 5 to 14 atoms, and more preferably from 5 to 10 atoms and still more preferably from 5 to 9 which have at least one heteroatom, said heteroatom being, when more than one, simultaneously or independently chosen from oxygen atom, nitrogen atom or sulfur atom. Each ring of the heterocyclic group can have at least one heteroatom, said heteroatom being, when more than one, simultaneously or independently chosen from nitrogen atoms, oxygen atoms and/or sulphur atoms. "Heterocycloalkyl" can be optionally substituted as defined herein. Covalent binding to a "heterocycloalkyl" can be at a heteroatom or via a carbon atom. In certain embodiments, non-aromatic heterocycles contain one or more carbonyl or thiocarbonyl groups such as, for example, oxo- and thio-containing groups. Heterocyclic groups can be optionally substituted as defined herein. Examples of heterocycloalkyls include, but are not limited to, lactams, lactones, cyclic imides, cyclic thioimides, cyclic carbamates, cyclic urea, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, 1,3-oxathiolane and N-oxides thereof for amino heterocycle. Illustrative examples of heterocycloalkyl groups, also referred to as non-aromatic heterocycles, include:

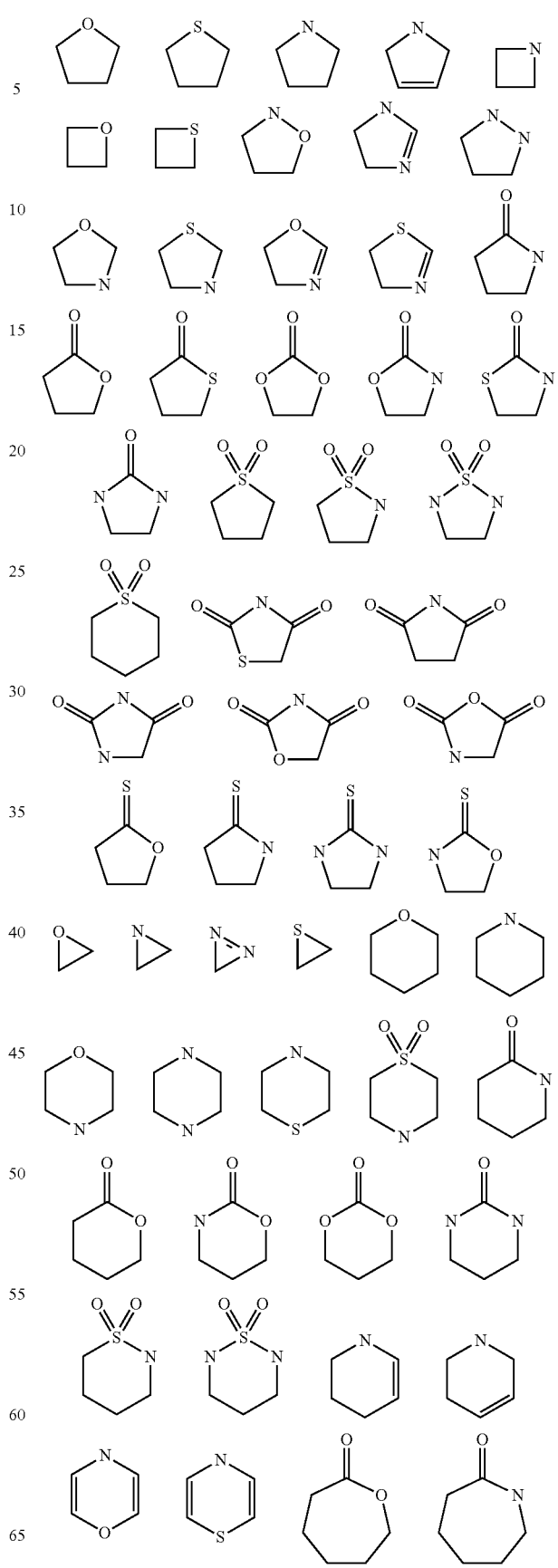

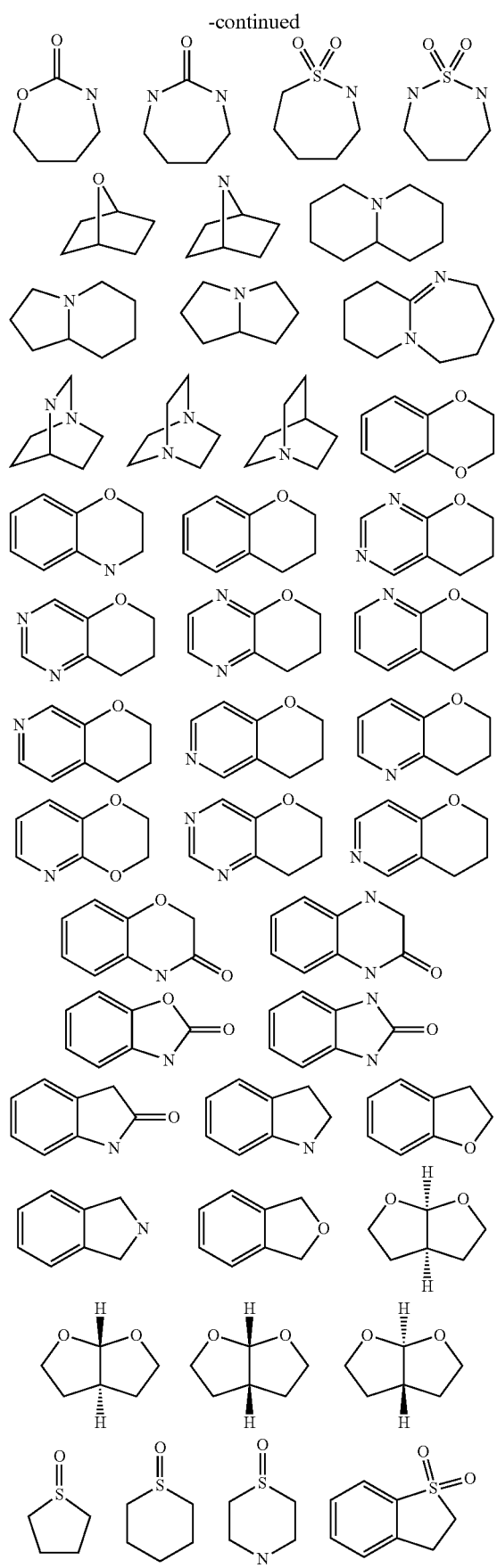
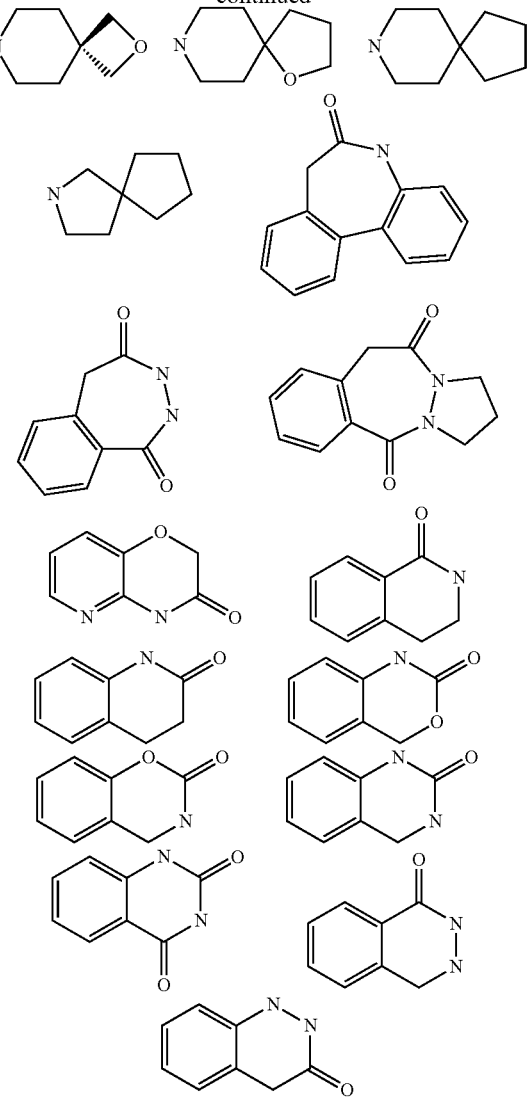

and the like.

The term "heterocyclic group", also includes all ring forms of the carbohydrates, including but not limited to the monosaccharides, the disaccharides and the oligosaccharides. Preferred heterocyclic groups are pyrrolidine, piperidine, piperazine, tetrahydrofuran, bis-tetrahydrofuran, morpholine, tetrahydropyran, thiomorpholine, glucuronic acid and the like. Heterocyclic groups can be optionally substituted as defined herein.

The term "ring system substituents" means being optionally substituted with one or more substituents independently chosen from a halogen atom as defined herein, an alkyl linear or branched as defined herein substituted or not by one or more halogen atom(s) as defined herein, a fluoroalkyl as defined herein, an alkenyl linear or branched as defined herein substituted or not by one or more halogen atom(s), an alkynyl linear or branched as defined herein substituted or not by one or more halogen atom(s) as defined herein, a cycloalkyl as defined herein substituted or not by one or more halogen atom(s) as defined herein, a cycloalkenyl as defined herein substituted or not by one or more halogen atom(s) as defined herein, a cycloalkynyl as defined herein substituted or not by one or more halogen atom(s) as defined herein, an alkoxy as defined herein, a hydroxyl, a cyano, a nitro, an azido, a carboxyl.

The term "cycloalkenyl" means a non-aromatic mono or multicyclic ring system comprising about 3 to about 12 carbon atoms, preferably about 5 to about 10 carbon atoms, and more preferably about 5 to about 7 carbon atoms, and still more preferably about 5 to about 6 carbon atoms which contains at least one carbon-carbon double bond C=C. The cycloalkenyl can be optionally substituted with one or more "ring system substituents" which can be the same or different, and are as defined above. Non-limiting examples of monocyclic cycloalkenyls include cyclopentenyl, cyclohexenyl, cyclohepta-1,3-dienyl, and the like. Non-limiting example of a suitable multicyclic cycloalkenyl is for example norbornylenyl, and the like. Cycloalkenyl groups can be optionally substituted as defined herein.

The term "cycloalkynyl" means a non-aromatic mono or multicyclic ring system comprising about 8 to about 12 carbon atoms, preferably about 8 to about 10 carbon atoms which contains at least one carbon-carbon triple bond (C≡C). The cycloalkynyl can be optionally substituted with one or more "ring system substituents" which can be the same or different, and are as defined above. Non-limiting examples of monocyclic cycloalkynyls include cyclooctynyl, cyclononynyl, cyclodecynyl and the like. Cycloalkynyl groups can be optionally substituted as defined herein.

The terms "haloalkyl," "haloalkenyl," "haloalkynyl" and "haloalkoxy" include alkyl, alkenyl, alkynyl and alkoxy structures as defined herein in which at least one hydrogen is replaced with a halogen atom as defined herein. In certain embodiments in which two or more hydrogen atoms are replaced with halogen atoms, the halogen atoms are all the same as one another. In other embodiments in which two or more hydrogen atoms are replaced with halogen atoms, the halogen atoms are all the same or not all the same as one another.

The term "fluoroalkyl," as used herein, refers to linear or branched-chain alkyl group as defined herein in which at least one hydrogen is replaced with a fluorine atom. Examples of fluoroalkyl groups include, but are not limited to —CH$_2$F, —CHF$_2$, —CF$_3$, —CH$_2$CF$_3$, —CF$_2$CF$_3$, —CF$_2$CH$_3$, —CH$_2$CH$_2$CF$_3$, —CH(CF$_3$)$_2$, —CF$_2$CH(CH$_3$)$_2$ and the like. The "fluoroalkyl" can be optionally substituted as defined herein.

The term "carboxyl" means the group —CO$_2$H.
The term "carbonyl" means the group

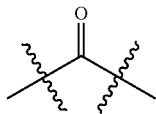 [SMILES: *C(*)=O]

corresponding to an organic functional group or radical occurring in aldehydes, ketones, carboxylic acids, esters, and their derivatives, wherein

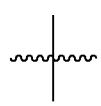

materialized the bound between the carbonyl and the skeleton of the compound.

The terms "bond" or "single bond" refers to a chemical bond between two atoms, or two moieties when the atoms joined by the bond are considered to be part of larger substructure.

An "alkoxy" group refers to a —O(C$_1$-C$_{10}$ alkyl) group, —O(cycloalkyl) group, —O(heterocyclyl) group, wherein "C$_1$-C$_{10}$ alkyl", "C$_1$-C$_{10}$ cycloalkyl" and "heterocyclyl" is as defined above. The term "lower alkoxy" refers to the group R'—O—, wherein R' is lower alkyl and the term "lower alkyl" has the previously given significance. Alkoxy groups can be optionally substituted as defined herein. Non limiting examples of lower alkoxy groups are methoxy, ethoxy, n-propoxy, isopropoxy, n-butoxy, isobutoxy, sec-butoxy and tert-butoxy, n-pentoxy, n-hexyloxy, preferably methoxy and ethoxy and isopropoxy and tert-butoxy most preferred methoxy and ethoxy. Illustrative examples of "alkoxy" group includes, but not limited to, the following alkoxy molecular systems:

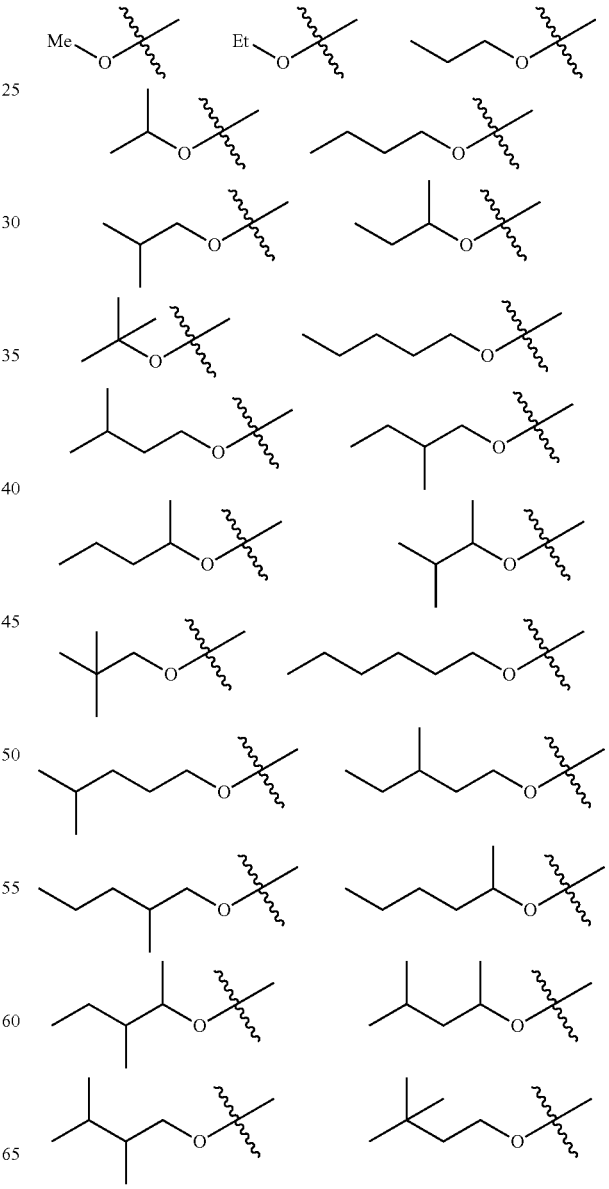

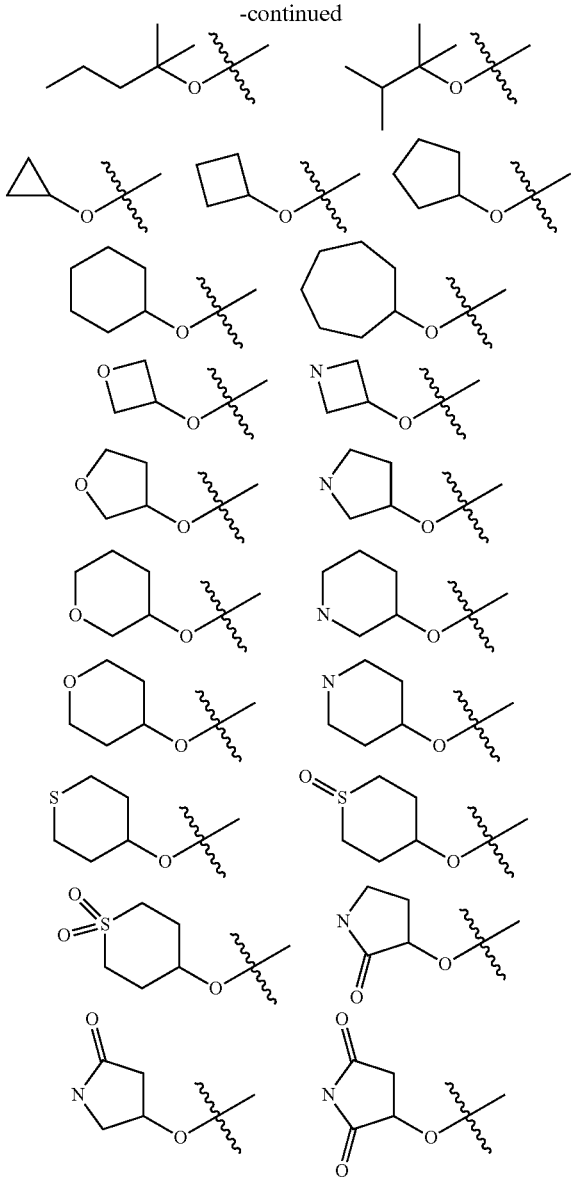

wherein

materialized the bound between the substituent and the skeleton of the compound.

The term "heteroatom" refers to an atom other than carbon or hydrogen. Heteroatoms are typically independently selected from among oxygen (O), sulfur (S), nitrogen (N), silicon (Si), boron (B) and phosphorus (P), but are not limited to these atoms. In embodiments in which two or more heteroatoms are present, the two or more heteroatoms can all be the same as one another, or some or all of the two or more heteroatoms can each be different from the others.

The term "thiol" as used herein refers to the group of formula —SH.

The term "hydroxyl" as used herein refers to the group of formula —OH.

The term "cyano" refers to a group of formula —C≡N.

The term "cyanoalkyl" means an ($C_1$-$C_{10}$-alkyl) radical, as defined herein, substituted with at least one cyano group of formula —C≡N.

The term "azido" refers to the radical —$N_3$ of formula —N=N=N.

The term "nitro" refers to the radical of formula —$NO_2$.

The term "amino" refers to the group —$NH_2$.

The terms "or not further substituted" or "optionally or not further substituted" means that the referenced group that can be an "optionally substituted" group can be substituted with one or more additional group(s), said additional groups being individually and independently chosen, and can be identical or different.

The terms "moiety", "chemical moiety", "group" and "chemical group", as used herein refer to a specific segment or functional group of a molecule. Chemical moieties are often recognized chemical entities embedded in or appended to a molecule.

The term "aromatic" refers to a planar ring having a delocalized π-electron system containing 4n+2π electrons, where n is an integer being chosen in the positive natural number including from 0 (n∈$N^0$). Aromatic rings can be formed from five, six, seven, eight, nine, or more than nine atoms. Aromatics can be optionally substituted as defined herein. The term "aromatic" includes both carbocyclic aryl (e.g. phenyl) and heterocyclic aryl (or "heteroaryl" or "heteroaromatic") groups (e.g. pyridine, thiazole). The term includes monocyclic or fused-ring polycyclic groups (i.e. rings which share adjacent pairs of carbon atoms, e.g. quinoline, quinazoline, benzoxazole).

The term "aryl" refers to an aromatic ring wherein each of the atoms forming the ring is a carbon atom. Aryl rings can contain five, six, seven, eight, nine, or more than nine carbon atoms, preferably from 5 to 16 carbon atoms, more preferably from 5 to 12 carbon atoms, and still more preferably from 5 to 10 carbon atoms and mean any stable monocyclic, bicyclic and tricyclic ring systems wherein at least one ring is aromatic. Aryl groups can be optionally substituted as defined herein. Examples of aryl groups include, but are not limited to phenyl, naphthalenyl, phenanthrenyl, anthracenyl, fluorenyl, biphenyl, and indenyl. Depending on the structure, an aryl group can be a monoradical or a diradical in which case it would be known as an arylene group. Examples of arylene groups include, but are not limited to, benzene-1,3-diyl, benzene-1,4-diyl, naphthalene-2,7-diyl, naphthalene-2,6-diyl, naphthalene-1,4-diyl naphthalene-1,5-diyl, acenaphthene-diyl, phenanthren-3,8-diyl, fluoranthene-diyl, 3-methylbenzene-1,4-diyl and the like. Illustrative examples of "aryl" group includes, but not limited to, the following aryl molecular systems:

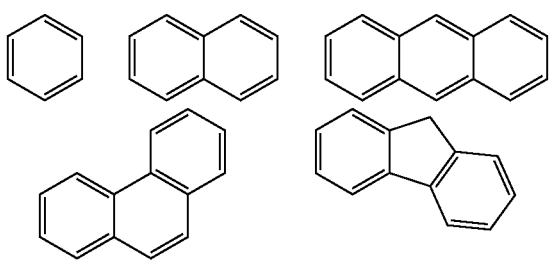

The terms "heteroaryl" or "heteroaromatic" in general refers to an aromatic molecular system from 5 to 8 membered ring, preferably from 5 to 6 membered ring which comprises at least one heteroatom, said heteroatom being, when more than one, simultaneously or independently selected from nitrogen (N), oxygen (O) and/or Sulphur (S) and comprising from 1 to 7 carbon atoms. Examples, but not limited to, of such heteroaryl comprising a single-ring heteroaryl group are: pyridyl, pyrazinyl, pyrimidinyl, pyridazinyl, 2-oxo-1,2-dihydropyridinyl, oxadiazolyl, isoxazolyl, thiadiazolyl, triazolyl, tetrazolyl pyrazolyl, imidazolyl, thiophenyl, furanyl, oxazolyl, isothiazolyl, and thiazolyl. The term "heteroaryl" further refers to bicyclic or tricyclic aromatic or partly unsaturated groups comprising two 5- or 6-membered rings, in which one or more rings can contain one, two, three or four atoms independently chosen from nitrogen (N), oxygen (O) or sulphur (S), such as quinolinyl, isoquinolinyl, cinnolinyl, pyrazolyl, imidazolyl, thiazolyl, thiophenyl, furanyl, oxazolyl, isothiazolyl, pyrazolo[1,5-a]pyridyl, imidazo[1,2-a] pyridyl, quinoxalinyl, quinazolyl, benzothiazolyl, benzotriazolyl, 1H-benzo[d]imidazole, benzo[d]isoxazolyl, benzo[d]isothiazolyl, benzo[c]isoxazolyl, benzo[c]isothiazolyl, indolyl, isoindolinyl, 6,7-dihydro-5H-pyrrolo[3,4-b]pyridinyl, 2,3-dihydro-1H-pyrrolo[3,4-c]pyridinyl, 6,7-dihydro-5H-pyrrolo[3,4-d]pyrimidinyl, purinyl, indazolyl, indolizinyl, imidazo[1,2-a]pyridinyl, imidazo[1,5-a]pyridinyl, imidazo[1,5-a]pyrazinyl, imidazo[1,2-a]pyrazinyl, 1H-imidazo[4,5-b]pyrazinyl, pyrazolo[1,5-a]pyridinyl, pyrrolo[1,2-a]pyrimidinyl, pyrrolo[1,2-a]pyrazinyl, pyrrolo[1,2-c]pyrimidinyl, oxazolo[4,5-b]pyridinyl, oxazolo[4,5-c]pyridinyl, oxazolo[5,4-c]pyridinyl, oxazolo[5,4-b]pyridinyl, thiazolo[4,5-b]pyridinyl, thiazolo[4,5-c]pyridinyl, thiazolo[5,4-c]pyridinyl, thiazolo[5,4-b]pyridinyl, oxazolo[5,4-d]pyrimidinyl, oxazolo[4,5-d]pyrimidinyl, thiazolo[5,4-d]pyrimidinyl, thiazolo[4,5-d]pyrimidinyl, oxazolo[4,5-b]pyrazinyl, thiazolo[4,5-b]pyrazinyl, isoxazolo[4,5-b]pyrazinyl, isothiazolo[4,5-b]pyrazinyl, isoxazolo[4,5-d]pyrimidinyl, isothiazolo[4,5-d]pyrimidinyl, is oxazolo[5,4-d]pyrimidinyl, isothiazolo[5,4-d]pyrimidinyl, isoxazolo[5,4-b]pyridinyl, isothiazolo[5,4-c]pyridinyl, isoxazolo[5,4-c]pyridinyl, isothiazolo[4,5-c]pyridinyl, isoxazolo[4,5-c]pyridinyl, isoxazolo[4,5-b]pyridinyl, isoxazolo[4,3-d]pyrimidinyl, isthiazolo[4,3-d]pyrimidinyl, isoxazolo[3,4-d]pyrimidinyl, isothiazolo[3,4-d]pyrimidinyl, pyrido[2,3-d]pyrimidinyl, pyrido[3,4-d]pyrimidinyl, pyrido[4,3-d]pyrimidinyl, pyrido[3,2-d]pyrimidinyl, pyrido[2,3-b]pyrazinyl, pyrido[3,4-b]pyrazinyl, [1,2,3]triazolo[4,5-b]pyridinyl, [1,2,3]triazolo[4,5-c]pyridinyl, 3H-[1,2,3]triazolo[4,5-d]pyrimidinyl. The terms "heteroaryl" or, alternatively, "heteroaromatic" refers to an aryl group that includes one or more ring and one or more heteroatoms independently selected from nitrogen (N), oxygen (O) and sulfur (S). An N-containing "heteroaryl" or "heteroaromatic" moiety refers to an aromatic group in which at least one of the skeletal atoms of the ring is a nitrogen atom (N). Heteroaryl groups can be optionally substituted as defined herein.

The terms "heteroaryl" or, alternatively, "heteroaromatic" also refers equally to fused heteroaryl systems wherein two or more rings share one or more bonds comprising from 7 to 16 ring atoms, preferably from 8 to 13 ring atoms, more preferably from 8 to 10 ring atoms comprising 1, 2, 3, 4 or 5 heteroatoms simultaneously or independently selected from nitrogen (N), oxygen (O) and sulfur (S) and comprising at least one carbon atom (C), provided that the fused rings do not include adjacent oxygen (O) and/or sulfur (S) atoms. Said "heteroaryl" can be optionally substituted as defined herein. Covalent binding to a heteroaryl can be at a heteroatom or via a carbon atom. N-oxides of the ring nitrogens are also included, as well as heteroaryls wherein a ring nitrogen is substituted by an optionally substituted alkyl group to form a quaternary amine. Preferred heteroaryl groups are pyridyl, pyrimidyl, thiozolyl, isothiazolyl, oxazolyl, isoxazolyl, quinazolinyl, pyrazinyl and N-oxides thereof and the like. All positional isomers are contemplated (e.g. pyridin-2-yl, pyridin-3-yl, pyridin-4-yl, pyridin-5-yl, pyridin-6-yl, pyrimidin-2-yl, pyrimidin-4-yl, pyrimidin-5-yl and pyrimidin-6-yl). Heteroaryl groups can be optionally substituted as defined herein. Illustrative examples of "heteroaryl" or "heteroaromatic" groups include, but not limited to, the following heteroaryl molecular systems:

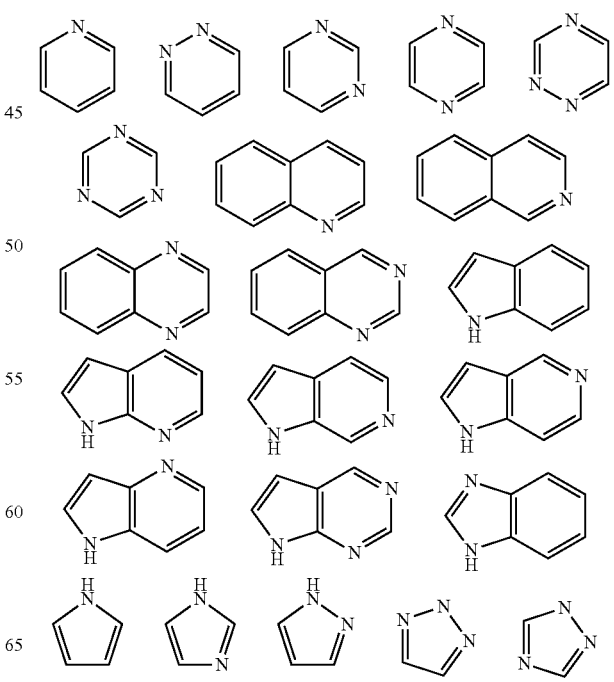

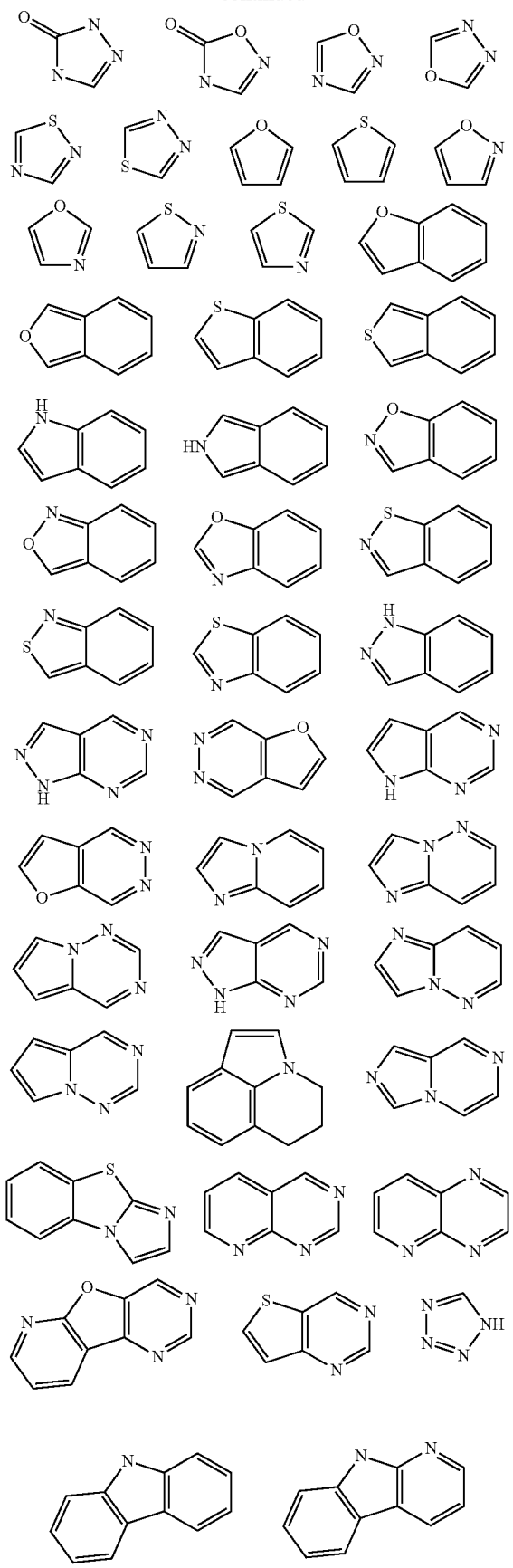
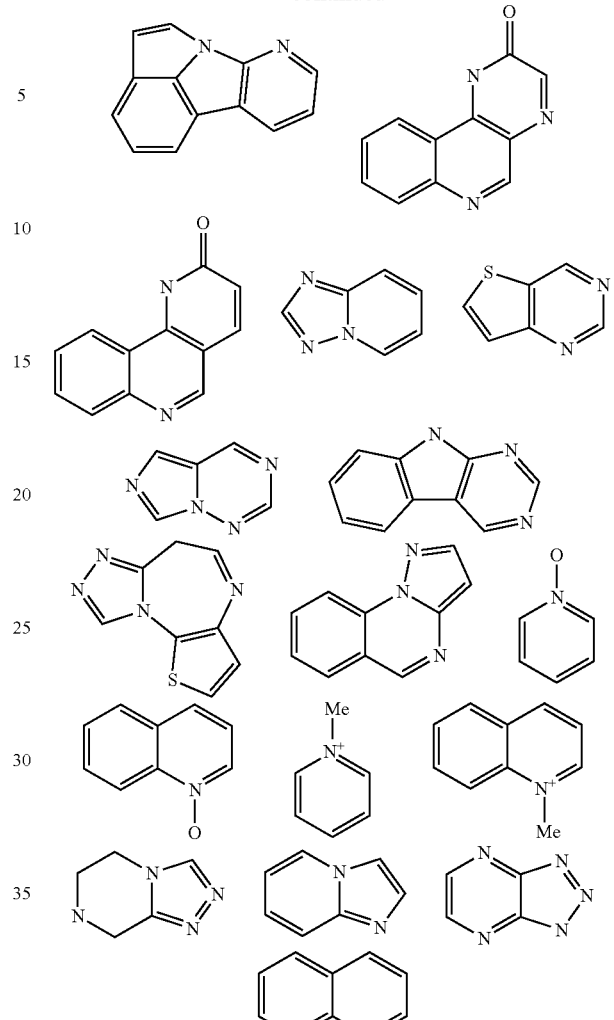

The term benzyl refers to the group of formula

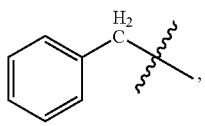 [SMILES: *Cc1ccccc1], wherein

materialized the bound between the benzyl and the skeleton of the compound. The benzyl group can be optionally substituted as defined herein.

The term "heterospirocyclic" refers to a spirocyclic structure containing 3 to 8 carbon (C) atoms and 1 or 2 heteroatoms as defined herein, preferably simultaneously or independently selected from nitrogen (N), oxygen (O) and sulfur (S), provided that the heteroatoms can be or not adjacent. The heterospirocyclic group can be optionally substituted as defined herein.

The term "isotopic variant" refers to a presently disclosed compound including pharmaceutical salts, hydrates, solvates and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, sulfur, fluorine, chlorine, bromine and iodine, such as $^{2}H$, $^{3}H$, $^{13}C$, $^{14}C$, $^{15}N$, $^{18}O$, $^{17}O$, $^{18}F$, $^{31}P$, $^{32}P$, $^{35}S$, $^{36}Cl$, $^{82}Br$, $^{123}I$, $^{124}I$, $^{125}I$, $^{129}I$ and $^{131}I$ respectively. Isotopic variants of the presently disclosed compounds can be useful in drug and/or substrate tissue distribution assays. Tritiated ($^{3}H$) and carbon-14 ($^{14}C$) labeled compounds are particularly preferred for their ease of preparation and detectability. Further, substitution with heavier isotopes such as deuterium ($^{2}H$) can afford certain therapeutic advantages resulting from greater metabolic stability, for example increased in vivo half-life or reduced dosage requirements and, hence, can be preferred in some circumstances. Isotopic variants of the compounds described herein, including pharmaceutical salts, esters, solvates, hydrates, and prodrugs thereof, can be prepared by any means known in the art. Further, substitution of normally abundant hydrogen ($^{1}H$) with heavier isotopes such as deuterium can afford certain therapeutic advantages, e.g., resulting from improved absorption, distribution, metabolism and/or excretion (ADME) properties, creating drugs with improved efficacy, safety, and/or tolerability. Benefits can also be obtained from replacement of normally abundant $^{12}C$ with $^{13}C$.

The terms "protected," "protecting group" and "protective group" refer to the presence of a moiety (i.e., the protecting group) that prevents or blocks chemical reaction of a particular chemically reactive functional group in a molecule under certain chemical reaction conditions. The protecting group will vary depending upon the type of chemically reactive group being protected as well as the reaction conditions to be employed and the presence of additional reactive or protecting groups in the molecule, if any. Protecting groups known in the art can be found in Kocienski, P. PROTECTING GROUP 3$^{rd}$ ed., Georg Thieme Verlag (2003) or Greene, T. W., Wuts, P. G. M. PROTECTIVE GROUPS IN ORGANIC SYNTHESIS, 4$^{st}$ ed., John Wiley & Sons, Inc., New York, N.Y. (2006).

The terms "pharmaceutically acceptable salts" refers to those salts which retain the biological effectiveness and properties of the free bases or free acids, which are not biologically or otherwise undesirable. The pharmaceutically acceptable salts have no persistent detrimental effect on the general health of the subject being treated or does not abrogate the biological activity or properties of the compound, and is relatively nontoxic, i.e., the material, formulation, composition or ingredient can be administered to an subject without causing undesirable biological effects or interacting in a deleterious manner with any of the components of the composition in which it is contained. The salts are formed with inorganic acids such as hydrochloric acid, hydrobromic acid, sulfuric acid, nitric acid, phosphoric acid and the like, preferably hydrochloric acid, sulfuric acid and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, glutaric acid, cinnamic acid, mandelic acid, malic acid, methanesulfonic acid, ethanesulfonic acid, p-toluenesulfonic acid, benzenesulfonic acid, N-acetylcystein and the like. In addition, these salts can be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, pyrrolidine, piperidine, morpholine, N-(2-hydroethyl)pyrrolidine, lysine, arginine, glycine, N-ethylpiperidine, polyamine resins and the like. The compounds of Formulas (I), (II), (III), (IV) or (V) can also be present in the form of zwitterions. Lists of suitable salts can be found, e.g., in "Remington's Pharmaceutical Sciences", 22$^{th}$ ed., Allen Loyd V. Jr., (2012); and in "Handbook of Pharmaceutical Salts: Properties, Selection, and Use" 2$^{nd}$ ed. by Stahl and Wermuth (Wiley-VCH, Weinheim, Germany, 2011). Particularly preferred pharmaceutically acceptable salts of a compound of Formulas (I), (II), (III), (IV) or (V) are the hydrochloride salts.

The compounds of Formulas (I), (II), (III), (IV) or (V) can also be solvated, e.g. hydrated. The solvation can be effectuated in the course of the manufacturing process or can take place e.g. as a consequence of hygroscopic properties of an initially anhydrous compound of formula A or B (hydration). The term "pharmaceutically acceptable salts" also includes physiologically acceptable solvates. Wherein, the term "solvate" means a compound described herein described herein, that further includes a stoichiometric or non-stoichiometric amount of a pharmaceutically acceptable solvent bound by non-covalent intermolecular forces. In some embodiments solvates can be formed during the process of crystallization with solvents such as water, ethanol, isopropanol, acetonitrile, acetone, methyl ethyl ketone, ethyl acetate, isopropyl acetate, dioxane, tetrahydrofuran, methyltetrahydrofuran, iso-propanol, acetone, methylbutylketone, cyclohexane, heptane, 1-butanol, 2-butanol, methylcyclohexane, propyl acetate, butyl acetate, methyl acetate, isobutyl acetate, 1-pentanol, 1-propanol, tert-butylmethyl ether, acetic acid or methanol and the like. Non-limitative examples of solvates include hydrates that can be formed when the solvent is water, and alcoholates that can be formed when the solvent is alcohol. In some embodiments, the compound is a single polymorph. In some other embodiments, the compound is a mixture of polymorph. In other embodiments, the compound is in crystalline form. In still other embodiments, the compound is in amorphous form.

The term "hydrate" means a compound described herein, that further includes a stoichiometric or non-stoichiometric amount of water bound by non-covalent intermolecular forces. The hydrates include but are not limited to hemihydrate, monohydrate, dihydrate, trihydrate and the like. Hydrates of the compounds described herein and of pharmaceutically acceptable salts thereof can be prepared by contacting these compounds or their pharmaceutically acceptable salts with water under suitable conditions to produce the hydrate of choice.

The term "solvate" means a compound described herein, that further includes a stoichiometric or non-stoichiometric amount of solvent bound by non-covalent intermolecular forces. In some embodiments solvates can be formed during the process of crystallization with solvents such as water, ethanol, iso-propanol and the like. Non-limitative examples of solvates include hydrates that can be formed when the solvent is water, and alcoholates that can be formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran, methyltetrahydrofuran, ethanol, acetonitrile, iso-propanol, acetone, methylethylketone, methylbutylketone, cyclohexane, heptane, 1-butanol, 2-butanol, methylcyclohexane, ethyl acetate, propyl acetate, butyl acetate, methyl acetate, isopropyl acetate, isobutyl acetate, 1-pentanol, 1-propanol, tert-butylmethyl ether, acetic acid or methanol. In addition, the compounds provided herein can exist in unsolvated as well as solvated forms. In general, the solvated forms are considered equivalent to the unsolvated forms for the purposes of the compounds and uses thereof provided herein.

The term "isomers" refers to compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. All stereoisomers of the compounds of Formulas (I), (II), (III), (IV) or (V) (for example, those which can exist due to asymmetric carbons on various substituents), enantiomeric forms and diastereomeric forms, are contemplated within the scope of this invention, either in a mixture, or in pure or substantially pure form. The compounds described herein can have asymmetric centers at any of the carbon atoms. Consequently, they can exist in the form of their racemates, in the form of the pure enantiomers and/or diastereomers or in the form of mixtures of these enantiomers and/or diastereomers. The mixtures can have any desired mixing ratio of the stereoisomers. Thus, for example, the compounds described herein which have one or more centers of chirality and which occur as racemates or as diastereomer mixtures can be fractionated by methods known per se into their optical pure isomers, i.e. enantiomers or diastereomers. The chiral centers of the compounds can have the S or R configuration as defined by the IUPAC 1974 Recommendations and can be designated by the symbols "(+)", "(−)", "R" or "S". The separation of the compounds described herein that can be present in racemate or diastereomer mixtures can take place by column separation on chiral or nonchiral phases, by fractional crystallization, or by recrystallization from an optionally optically active solvent or with use of an optically active acid or base or by derivatization with an optically active reagent such as, for example, an optically active alcohol, an optically active amine, an optically active acid and subsequent elimination of the radical. The resolution methods well known to those skilled in the art include equally kinetic resolution techniques using stereoselective chemical or enzymatic reagents. The stereoselective syntheses are chemical or enzymatic reaction in which a single reactant forms an unequal mixture of stereoisomers during the creation of a new stereocenter or during the transformation of a pre-existing one, which are well known to those skilled in the art. Stereoselective syntheses encompass both enantio- and diastereoselective transformations and can involve the use of chiral auxiliaries, reagents or catalysts. In some instances, the compounds described herein can possess one or more double bonds wherein each double bond exists in the E (trans) or Z (cis) configuration, or combinations thereof. Compounds described herein can contain a carbocyclic or heterocyclic ring and therefore, exist as geometric isomers resulting from the arrangement of the substituents around the ring(s) such as cyclopropane, cyclobutane, cyclopentane, cyclohexane, cycloheptane, tetrahydrofuran, tetrahydro-2H-pyran, 1,4-dioxane and the like. The arrangement of the substituent around a carbocyclic or heterocyclic ring are designated as being in the "Z" or "E" configuration wherein the terms "Z" and "E" are used in accordance with the IUPAC standards nomenclature. Unless otherwise specified, structures depicting carbocyclic or heterocyclic rings encompass both "Z" and "E" isomers. Substituents around a carbocyclic or heterocyclic rings can also be referred to as "cis" or "trans", wherein the term "cis" represents substituents on the same side of the plane of the ring and the term "trans" represents substituents on opposite sides of the plane of the ring. Mixtures of compounds wherein the substituents are disposed on both the same and the opposite sides of the plane of the ring are designated "cis/trans". Illustrative examples of "R", "S", "E", "Z", "cis", "trans" isomers are depicted below:

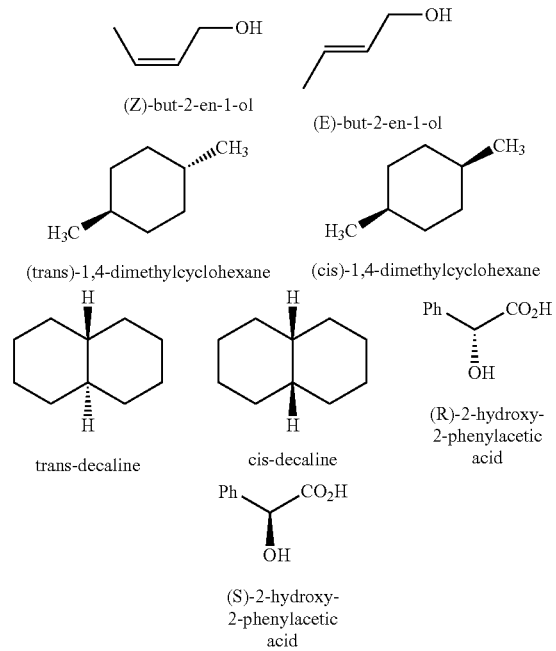

Any formula, compound, moiety or chemical illustration with unsatisfied valences in the present specification and/or claims herein is assumed to have sufficient hydrogen atom(s) to satisfy the valences.

The terms "subject" or "patient" or "individual" are used interchangeably. As used herein, the terms "subject" and "subjects" refer to an animal (e.g. birds, reptiles, and mammals), preferably a mammal including a non-primate (e.g. a camel, donkey, zebra, cow, pig, horse, goat, sheep, cat, dog, rat, and mouse) and a primate (e.g. a monkey, chimpanzee, and a human). Mammals are any member of the Mammalian class, including but not limited to humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the methods and compositions provided herein, the subject is a mammal. In preferred embodiments, the subject is a human.

The terms "therapies" and "therapy" can refer to any protocol(s), method(s), compositions, formulations, and/or agent(s) that can be used to treat, prevent, manage, or ameliorate (or reduce or decrease) the severity, symptoms and/or progression of a disease, including viral or bacterial infections or symptoms associated therewith, fibrosis, radiation, etc. In certain embodiments, the terms "therapies" and "therapy" refer to biological therapy, supportive therapy, and/or other therapies useful in treating managing, preventing, or ameliorating the different diseases known to one of skill in the art.

The term "autophagy flux" refers to a measure of autophagic degradation activity in cellular environment (in vitro) and/or in a subject (in vivo) and/or in a specific organ of a subject and/or in a organ subpart of a subject.

The term "liver function" refers to a normal function of the liver, including but not limited to a synthetic function, including, but not limited to, synthesis of proteins such as serum proteins (e.g. albumin, clotting factors, alkaline phosphatase, aminotransferases e.g. alanine transaminase or aspartate transaminase or 5'-nuclesidase or γ-glutaminyl-transpeptidase, etc); synthesis of bilirubin, synthesis of cholesterol, synthesis of bile acids; liver metabolic function, including but not limited to carbohydrate metabolism, lipid metabolism; detoxification of exogenous molecules (e.g. drugs and toxics); a hemodynamic function, including splanchnic and portal hemodynamics; and the like.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and can be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of 0.1 mg to 5 g, preferably from about 0.1 mg to 1 g, more preferably from 0.5 mg to 500 mg, and most preferably from about 1 mg to 300 mg, should be appropriate, although the upper limit can be exceeded when indicated. The daily dosage can be administered as a single dose or in divided doses, or for parenteral administration, it can be given as continuous infusion.

The terms "administer", "administering", "administration", and the like, as used herein, refer to the methods that can be used to enable delivery of compounds or compositions to the desired site of biological action. These methods include, but are not limited to oral routes, intraduodenal routes, parenteral injection (including intravenous, subcutaneous, intraperitoneal, intramuscular, intravascular, intraarticular, intra-synovial, intra-arterial or infusion), topical, spray, nasal, inhalation, buccal, vaginal, rectal administration, subdermal, trans-mucosal, ophthalmic preparation, intraperitoneal, or via an implanted reservoir. Those of skill in the art are familiar with administration techniques that can be employed with the compounds and methods described herein. In preferred embodiments, the compounds and compositions described herein are administered orally and by parenteral injection and more preferably administered orally.

The terms "co-administration", "administered in combination with" and their grammatical equivalents or the like, as used herein, are meant to encompass administration of the selected therapeutic agents to a single individual, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the individual at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, compounds described herein and the other agent(s) are admixed in the composition.

The terms "active ingredient", "active substance" or "active agent" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" can be an optically active isomer of a compound described herein.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount can differ from one individual to another. An appropriate "effective" amount in any individual case can be determined using techniques, such as a dose escalation study or pharmacokinetic study.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, uses thereof in the compositions described herein are contemplated. Supplementary active compounds can also be incorporated into the compositions. These compositions can be prepared by applying known techniques in the art as described in *Ansel's Pharmaceutical Dosage Forms and Drug Delivery Systems* (Tenth Edition) 2014, Edited by Loyd Allen, Howard C. Ansel, published by Wolters Kluwer Health and *Remington: The Science and Practice of Pharmacy* (Twenty-second Edition) 2012, Edited by Loyd V. Allen, Published by Pharmaceutical Press, each of which is incorporated herein by reference.

The term "pharmaceutical composition", as used herein, refers to a biologically active compound, optionally mixed with at least one pharmaceutically acceptable chemical component, such as, those not limited to carriers, stabilizers, diluents, dispersing agents, suspending agents, thickening agents, excipients and the like which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions described herein encompass any composition made by admixing a compound described herein and a pharmaceutically acceptable carrier.

The terms "pharmaceutical combination", "administering an additional therapy", "administering an additional therapeutic agent" and the like, as used herein, refer to a pharmaceutical therapy resulting from the mixing or combining of more than one active ingredient and includes both fixed and non-fixed combinations of the active ingredients. The term "fixed combination" means that at least one of the compounds described herein, and at least one co-agent, are both administered to an individual simultaneously in the form of a single entity or dosage. The term "non-fixed combination" means that at least one of the compounds described herein, and at least one co-agent, are administered to an individual as separate entities either simultaneously, concurrently or sequentially with variable intervening time limits, wherein such administration provides effective levels of the two or more compounds in the body of the individual. These also apply to cocktail therapies, e.g. the administration of three or more active ingredients.

The terms "inhibiting", "inhibition" and/or "retardation" are intended to refer for the purposes of the present disclosure to as follows: "partial or complete inhibiting, inhibition and/or retardation". In this case, it is within the specialist knowledge of the average person skilled in the art to measure and determine such inhibiting, inhibition, and/or retardation by means of the usual methods of measurement and determination. Thus, a partial inhibiting, inhibition and/or retardation, for example, can be measured and determined in relation to a complete inhibiting, inhibition and/or retardation.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing the severity and/or progression a subject's risk of acquiring a disorder, disease, or condition.

The terms "treat," "treatment," and "treating" refer in the context of administration of a therapy(ies) to a subject to treat a disease refer to one, two, three, four, five or more of the following effects resulting from the administration of a therapy or a combination of therapies: (i) the reduction or amelioration of the severity of a disease and/or a symptom associated therewith; (ii) the reduction in the duration of a disease and/or a symptom associated therewith; (iii) the regression of a disease and/or a symptom associated therewith; (iv) the reduction of the titer of a pathogen; (v) the reduction in organ failure associated with a disease; (vi) the reduction in hospitalization of a subject; (vii) the reduction in hospitalization length; (viii) the increase in the survival of a subject; (ix) the elimination of an infection; (x) inhibiting the progression of an infection and/or a symptom associated therewith; (xi) preventing the spread of a virus or bacteria from a cell, tissue or subject to another cell, tissue or subject; and/or (xii) the enhancement or improvement the therapeutic effect of another therapy. Also, a therapeutic benefit is achieved with the eradication or amelioration of one or more of the physiological symptoms associated with the underlying disorder such that an improvement is observed in the individual, notwithstanding that the individual is still be afflicted with the underlying disorder. For prophylactic benefit, the compositions are administered to an individual at risk of developing a particular disease, or to an individual reporting one or more of the physiological symptoms of a disease, even though a diagnosis of this disease has not been made.

The term "radiation therapy", "radiotherapeutic treatment" or "radiotherapy" is a term commonly used in the art to refer to multiple types of radiation therapy including internal and external radiation therapy, radioimmunotherapy, and the use of various types of radiation including X-rays, gamma rays, alpha particles, beta particles, photons, electrons, neutrons, radioisotopes, and other forms of ionizing radiation. Preferably, the radiotherapy involves the use of X-rays.

The terms "fibrosis" and "organ fibrosis" refer the development in an organ of fibrous connective tissue as a reparative response to injury or damage. Fibrosis can refer to the connective tissue deposition that occurs as part of normal healing or to the excess tissue deposition that occurs as a pathological process. When fibrosis occurs in response to injury, the term "scarring" is used. Fibrosis is a consequence of local chronic inflammation and is characterized by abnormal deposition of extracellular matrix proteins (ECM) producted by activated myofibroblasts. Some of the main types of fibrosis that occur in the body are:

pulmonary fibrosis that refers to a number of conditions that cause interstitial lung damage, followed by fibrosis and eventually loss of lung elasticity. Pulmonary fibrosis can occur as a secondary condition in various other diseases, but in many cases the underlying cause is not clear and in such cases the term idiopathic pulmonary fibrosis is used.

liver fibrosis which lead at the end stage to liver cirrhosis. The liver cirrhosis refers to the scar tissue and nodules that replace liver tissue and disrupt liver function. The condition is usually caused by alcoholism, diabetes, fatty liver disease, cirrhosis and non cirrhosis portal hypertension, infection with viral hepatitis (including hepatitis B virus, hepatitis delta or hepatitis C virus), autoimmune hepatitis, biliary obstruction, iron overload (hemochromatosis), nonalcoholic fatty liver disease which includes nonalcoholic fatty liver disease (NAFLD) and nonalcoholic steatohepatitis (NASH), alpha-1 antitrypsin deficiency, Wilson disease, primary biliary cirrhosis, primary sclerosing cholangitis, Budd-Chiari syndrome, heart failure, portal vein thrombosis, veno-occlusive disease of the liver, congenital hepatitis fibrosis.

cardiac fibrosis which occurs after heart injury. Areas of the heart that have become damaged due to myocardial infarction can undergo fibrosis. Cardiac fibrosis can affect the valves in the heart as well as the muscle, which becomes stiff and less compliant. This can increase the risk of heart failure.

skin fibrosis which refers to scar tissue that forms on the skin in response to injury is referred to as a keloid.

scleroderma or systemic sclerosis which is an autoimmune disease of the connective tissue that primarily affects the skin but can also involve other organs such as the kidneys, heart and lungs.

intestinal fibrosis is a common complication of in inflammatory bowel disease (IBD) and can occur in both ulcerative colitis (UC) and Crohn's disease (CD), but is much more prevalent in Chrohn's disease.

eye fibrosis refers to the response of the eye tissue to injury. The injury can occur as a result of a mechanical wound or various metabolic malfunctions, including responses to inflammation, ischemia, and degenerative disease. The local response to such injuries includes infiltration by inflammatory cells, neovascularization, altered vascular permeability, proliferation of fibroblasts and fibroblast-like cells, modification of the extracellular matrix and ultimately some sort of resolution of the damaged tissue. Eye fibrosis includes macular fibrosis, premacular fibrosis, retinal fibrosis, retinopathy, diabetic retinopathy, Diabetic Macular Edema, Proliferative Diabetic Retinopathy, fibrosis of the extraocular muscles, fibrovascular scarring, retina gliosis, Subretinal fibrosis, Epiretinal fibrosis.

renal fibrosis or kidney fibrosis is the inevitable consequence of an excessive accumulation of extracellular matrix that occurs in virtually every type of chronic kidney disease. Renal or kidney fibrosis refers to tubulointerstitial renal fibrosis, glomerulosclerosis, glomerular injury, diabetic nephropathy.

"Viral infection" as used herein refers to infection by a viral pathogen wherein there is clinical evidence of the infection based on symptoms or based on the demonstration of the presence of the viral pathogen in a biological sample from the subject.

A "non-viral infection" as used herein refers to infection by non-viral pathogen, such as bacteria, fungus, protozoan or parasite, wherein there is clinical evidence of the non-viral infection based on symptoms or based on the demonstration of the presence of the non-viral pathogen in a biological sample from the subject.

The term "infectivity", as used herein, describes the ability of an organism to enter, survive and multiply in the host, while the "infectiousness" of a disease indicates the comparative ease with which the disease is transmitted to other hosts.

The term "infection," as used herein, refers to a detrimental colonization of a host organism by a foreign species, including a bacterium, a virus, a fungus, a protozoan, or a parasite. In an infection, the infecting organism seeks to utilize the host's resources to multiply, usually at the expense of the host. The infecting organism, or pathogen, interferes with the normal functioning of the host. The host's response to infection is mounted by the humoral and cellular components of the host's immune system. An "occult infection" is one which presents no symptoms.

A "pathogen" or "infectious agent," used synonymously herein, refers to any disease-causing virus, bacteria, fungi, protozoa, or parasite that infects and causes disease in an animal or plant.

The phrase "treating a viral infection," or the phrase "treating an individual infected with a pathogen, specifically a virus," as used herein, encompasses alleviating, reducing the severity and/or progression, the frequency, and/or duration of, or eliminating one or more symptoms of the viral infection.

A "medium", as used herein, refers to as solution, a bodily fluid, a cell or a tissue, either in vitro or in vivo.

In order to manipulate the oxidative metabolism of the compound by way of the primary kinetic isotope effect, deuterium ($^2H$) can also be incorporated into a compound of Formula (I). The primary kinetic isotope effect is a change in the rate of a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity a saddle-point region along the coordinate of a multi-product reaction, the product distribution ratios can be altered substantially. For example, if deuterium is bonded to a carbon atom in a non-exchangeable position (e.g. covalently linked to an aryl ring, wherein said aryl ring is for example a phenyl or a naphtyl, a further example is the benzylic hydrogen atoms: Ph-$CH_2$—), rate differences of $k_M/k_D$=2-7 are typical. If this rate difference is successfully applied to a compound of the Formula (I) that is susceptible to oxidation or cytochrome metabolism, the profile of this compound in vivo can thereby be drastically modified and results in improved pharmacokinetic properties. When discovering and developing therapeutic agents, the person skilled in the art attempts to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn allows the rational design of deutared compounds of the Formulas (I), (II), (III), (IV) or (V) with improved stability through resistance to such oxidative metabolism. Significant improvements in the pharmacokinetic profiles of the compounds of the Formulas (I), (II), (III), (IV) or (V) are thereby obtained and can be expressed quantitatively in terms of increases in the in vivo half-life (T/2), concentration at maximum therapeutic effect ($C_{max}$), area under the dose response curve (AUC), and F; and in terms of reduced clearance, dose and costs of materials. The following is intended to illustrate the above definition: a compound of the Formulas (I), (II), (III), (IV) or (V) which has multiple potential sites of attack for oxidative metabolism, for example benzylic hydrogen atoms (e.g. Ph-$CH_2$—) and hydrogen atoms bonded on a carbon atom in alpha position to a nitrogen atom (e.g. N—$CH_2$—), is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent to which the improvement in resistance to oxidative metabolism has improved. In this way, it is determined that the half-life of the parent compound can be extended by up to 100% as the result of deuterium-hydrogen exchange of this type. The replacement of the hydrogen by deuterium in a compound of the Formulas (I), (II), (III), (IV) or (V) can also be used to achieve a favorable modification of the metabolite spectrum of the starting compound in order to diminish or eliminate undesired toxic metabolites. For example, if a toxic metabolite arises through oxidative carbon-hydrogen bond cleavage (C—H), it can reasonably be assumed that the deuterated analogue will greatly diminish or eliminate production of the undesired metabolite, even if the particular oxidation is not a rate-determining step.

The term "hyperaesthesis" relates to pain syndrome. Pain is a complex sensory perception which, as an acute event, has the character of a warning and control signal, but as chronic pain has lost this and in this case (as chronic pain syndrome) should be regarded and treated as an independent syndrome. Hyperalgesia is the term used in medicine for excessive sensitivity to pain and reaction to a stimulus which is usually painful. Stimuli which can trigger pain are, for example, pressure, heat, cold or inflammation. Hyperalgesia is a form of hyperaesthesia, the generic term for excessive sensitivity to a stimulus. Allodynia is the term used in medicine for the sensation of pain which is triggered by stimuli which do not usually cause pain.

The term "prodrug" means a compound that undergoes conversion to the compound described herein within a biological system. A prodrug is a chemical derivative inactive or less active than the drug itself. After administration and diffusion in the body, the prodrug derivative undergoes one or more metabolic processes that release the active drug. The conversion of the prodrug to the drug is generally carry out under the control of enzymatic processes (usually by metabolic means, e.g. hydrolysis, reduction or oxidation) and less frequently by classical chemical reactions during its diffusion in the body. The linkage between the carrier and the drug can be an, but not limited to, ester, amide, carbonate, carbamate, imine, acetal, ether (e.g. glucoro conjugation), oxydizable function and molecular system, reducible function and reducible molecular system, photoactivated function and photoactivated molecular system. For example, an ester prodrug of a compound containing a hydroxyl group can be convertible by hydrolysis in vivo to the parent molecule. Suitable esters of the compounds described herein containing a hydroxyl group, are for example acetates, citrates, lactates, tartrates, malonates, oxalates, salicylates, propionates, succinates, fumarates, maleates, methylene-bis-β-hydroxynaphthoates, gestisates, isethionates, di-p-toluoyltartrates, methanesulphonates, ethanesulphonates, benzenesulphonates, p-toluenesulphonates, cyclohexylsulphamates and quinates. As another example an ester prodrug of the compound described herein containing a carboxy group can be convertible by hydrolysis in vivo to the parent molecule (Examples of ester prodrugs are described by Leinweber, F. J. Drug Metab. Res. 1987 (18), 379-439; incorporated herein by reference). Similarly, an acyl prodrug of a compound containing an amino group can be convertible by hydrolysis in vivo to the parent molecule (examples of prodrugs for these and other functional groups, including amine, alcohol are described in *Prodrugs: Challenges and Rewards* (Parts 1 and 2); Ed V. Stella, R. Borchardt et al., Springer, 2007, and *Prodrugs and Targeted Delivery: Towards Better ADME Properties* Ed. J. Rautio, Seies Ed. R. Mannhold, H. Kubinyl, G. Folkers. Wiley-VCH 2011, each of which is incorporated herein by reference). A prodrug carrier system is generally used in order to increase water or lipid solubility, reduce toxicity, increase chemical and biological stability of a sensitive compound, increase the circulating time in the body ($T_{1/2}$), increase the total drug exposure (AUC) and organ distribution (PK-PD profiling) and site specific targeting.

The term "composition", as in pharmaceutical composition, for the purposes of this invention is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions described herein encompass any composition made by admixing a compound described herein and a pharmaceutically acceptable carrier.

As used herein, "$IC_{50}$" or "$EC_{50}$" refers to a dosage, concentration or amount of a particular test compound that elicits a dose-dependent response at 50% of maximal expression of a particular response that is induced, provoked or potentiated by the particular test compound.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

It is to be understood that the phraseology and terminology used herein is for the purpose of description and should not be regarded as limiting. The use of "including", "comprising", or "having" and variations thereof herein is meant to encompass the items listed thereafter and equivalents thereof as well as additional items.

In some instances, the compounds described herein or pharmaceutically acceptable salts or prodrugs thereof can be present in various polymorphic forms and certain modifications can moreover be metastable. All these polymorphic forms of the compounds are to be regarded as belonging to the invention. As used herein, the term "polymorph" means solid crystalline forms of a compound described herein. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Polymorphs typically exhibit different differential scanning calorimetry profile (DSC), melting points, IR spectra and X-ray powder diffraction patterns, which can be used for identification. Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it. Those skilled from the art will appreciate that different polymorphs can be produced, for example by changing or adjusting the reaction conditions or reagents, used in making the compound. For example, changes in temperature, pressure, solvent or mixture of solvents can result in polymorphs. In addition, on polymorph can spontaneously convert to another polymorph under certain conditions. The invention includes all such polymorphs.

It is further known that chemical substances are converted in the body into metabolites which can where appropriate likewise elicit the desired biological effect in some circumstances even in more pronounced form. Any biologically active compound that was converted in vivo by metabolism from any of the compounds described herein is a metabolite within the scope and spirit of the invention. As used herein, the term "metabolite", refers to a derivative of a compound which is formed when the compound is metabolized.

The term "active metabolite," as used herein, refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes can produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups.

The methods and compositions described herein are not limited to the particular methodology, protocols, cell lines, constructs, and reagents described herein and as such can vary. It is also to be understood that the terminology used herein is for the purpose of describing particular embodiments only, and is not intended to limit the scope of the methods and compositions described herein, which will be limited only by the appended claims.

All publications and patents mentioned herein are incorporated herein by reference in their entirety for the purpose of describing and disclosing, for example, the constructs and methodologies that are described in the publications, which might be used in connection with the methods, compositions and compounds described herein. The publications discussed herein are provided solely for their disclosure prior to the filing date of the present application. Nothing herein is to be construed as an admission that the inventors described herein are not entitled to antedate such disclosure by virtue of prior invention or for any other reason.

Definitions of standard chemistry terms can be found in reference works, including Carey and Sundberg "ADVANCED ORGANIC CHEMISTRY 5$^{th}$ ed." Vols. A (2008) and B (2010), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treating patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification.

The expression "simultaneously or independently" is used herein to indicate that a variable is applied in any one instance without regard to the presence or absence of a variable having that same or a different definition within the same compound. Thus, for instance, in a compound in which a substituent Xi appears twice and is defined as "simultaneously or independently group G1 or group G2", both Xi can be G1 (simultaneously), both Xi can be G2 (simultaneously), or one Xi can be G1 and the other G2 (independently).

In the present text "inhibition of expression" means inhibition of the synthesis of nucleic acids (RNA and/or DNA) coding the corresponding proteins, for example cathepsins B (CTSB), L (CTSL) and/or D (CTSD), and inhibition of the translation of the nucleic acids to the corresponding proteins, as well as inhibition of the catalytic or signaling activity of the proteins theirself.

Described herein can be compounds of Formula (I), pharmaceutically acceptable salts, hydrates, solvates, prodrugs, polymorphs, tautomers, isotopic variants, and stereoisomers thereof.

Therefore the present disclosure provides compound of Formula (I)

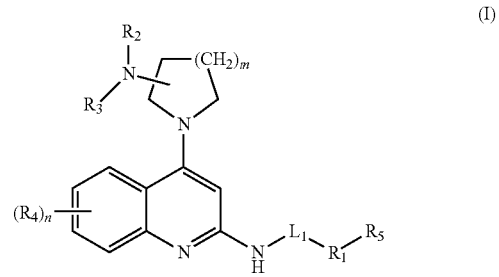

(I)

wherein $L_1$ can be chosen from a single bond; an optionally substituted alkyl as defined herein, said optionally substituted alkyl being or not further substituted by at least one $R_6$ as defined herein; an optionally substituted cycloalkyl as defined herein; an optionally substituted alkenyl as defined herein; an optionally substituted cycloalkenyl as defined herein; an optionally substituted alkynyl as defined herein; an optionally substituted cycloalkynyl as defined herein; a —C=O; a —SO; a —SO$_2$; a —(C=O)—NR$_8$; a —(C=O)—O; a —(C=O)—O-alkyl; a —SO$_2$—NR$_8$; a —NR$_8$.

$R_1$ can be chosen from an optionally substituted aryl as defined herein, said optionally substituted aryl being or not further substituted by at least one $R_9$ as defined herein; or an optionally substituted heteroaryl as defined herein, said optionally substituted heteroaryl being or not further substituted by at least one $R_9$ as defined herein.

$R_2$ and $R_3$ can be simultaneously or independently chosen from a hydrogen atom; a —(CO)—R$_7$; a —(CO)—O—R$_7$; a —(CO)—NR$_8$R$_8$; a —(CO)—NR$_{12}$R$_{13}$; a —SO$_2$—R$_7$; a —SO$_2$—NR$_8$R$_8$; a —SO$_2$—NR$_{12}$R$_{13}$; an optionally substituted alkyl as defined herein, preferably said optionally substituted alkyl being substituted with at least one —NR$_8$R$_8$; an optionally substituted cycloalkyl as defined herein, preferably said optionally substituted cycloalkyl being substituted with at least one —NR$_8$R$_8$; an optionally substituted alkenyl as defined herein; an optionally substituted alkynyl as defined herein; an optionally substituted cycloalkenyl as defined herein; an optionally substituted cycloalkynyl as defined herein; an optionally substituted aryl as defined herein; an optionally substituted benzyl as defined herein; an optionally substituted heteroaryl as defined herein; an optionally substituted heterocyclyl group as defined herein; or $R_2$ and $R_3$ can be linked together with the nitrogen atom to which they are covalently linked to form an optionally substituted heterocyclyl group as defined herein.

$R_2'$ can be chosen from a hydrogen atom; an optionally substituted alkyl as defined herein; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted heterocyclyl group as defined herein.

$R_4$ can be, alone or simultaneously or independently when n>1, chosen from a hydrogen atom; a halogen atom as defined herein; an optionally substituted alkyl as defined herein, preferably said optionally substituted alkyl being substituted by one or more halogen atom(s) as defined herein, by one or more hydroxyl, by one or more alkoxy as defined herein, or by one or more —$NR_8R_{8'}$ or combination thereof; an optionally substituted fluoroalkyl as defined herein; an optionally substituted alkenyl as defined herein; an optionally substituted alkynyl as defined herein; a optionally substituted cycloalkyl as defined herein; a optionally substituted cycloalkenyl as defined herein; a optionally substituted cycloalkynyl as defined herein; an optionally substituted alkoxy as defined herein; a hydroxyl; a nitro; an azido; a cyano; a —$NR_{12}R_{13}$; a —$NR_8R_{8'}$; a —O—($R_7$); a —(CO)—$R_7$; a —(CO)—O—$R_7$; a —(CO)—$NR_{12}OH$; a —(CO)—$NR_8OH$; a —(CO)—$NR_{12}R_{13}$; a —(CO)—$NR_8R_{8'}$; a —O—(CO)—$R_7$; a —O—(CO)—$NR_{12}R_{13}$; a —O—(CO)—$NR_8R_{8'}$; a —$NR_{12}$—(CO)—$R_7$; a —$NR_8$—(CO)—$R_7$; a —$NR_{12}$—(CO)—$NR_7$; a —$NR_8$—(CO)—$OR_7$; a O—(CO)—$OR_7$; a —$NR_{12}$—(CO)—$NR_{12}R_{13}$; a —$NR_8$—(CO)—$NR_8R_{8'}$; a —(O—$CH_2CH_2$—)$_p$—$NR_{12}$; a —(O—$CH_2CH_2$—)$_p$—$OR_7$; a (O—$CH_2CH_2$—)$_p$—$NR_{12}R_{13}$; a (O—$CH_2CH_2$—)$_p$—$NR_8R_{8'}$; a —$NR_{12}$(—$CH_2CH_2$—O)$_p$—$R_{13}$; a $NR_8$(—$CH_2CH_2$—O)$_p$—$R_7$; a —$SO_2$—$R_7$; a —$NR_{12}$—$SO_2$—$R_7$; a —$NR_8$—$SO_2$—$R_7$; a —$SO_2$—$NR_{12}R_{13}$; a —$SO_2$—$NR_8R_{8'}$; a —$NR_{12}$—$SO_2$—$NR_{12}R_{13}$; a —$NR_8$—$SO_2$—$NR_8R_{8'}$; a —$NR_{12}$—($C_2$-$C_8$)-alkyl-$NR_{12}R_{13}$; a —$NR_8$—($C_2$-$C_8$)-alkyl-$NR_8R_{8'}$; a —$NR_{12}$—($C_2$-$C_8$)-alkyl-$OR_{13}$; a —$NR_8$—($C_2$-$C_8$)-alkyl-$OR_7$; an optionally substituted aryl as defined herein; an optionally substituted benzyl as defined herein; an optionally substituted heteroaryl as defined herein; an optionally substituted heterocyclyl group as defined herein.

$R_5$ can be selected from a hydrogen atom; a halogen atom as defined herein; a hydroxyl; an optionally substituted alkoxy as defined herein; a —$NR_2'R_{10}$; a —O—$R_{10}$; a nitro; an azido; a cyano; a —$NR_{12}R_{13}$; a —$NR_8R_{8'}$; a —(CO)—$R_7$; a —(CO)—O—$R_7$; a —(CO)—$NR_{12}OH$; a (CO)—$NR_8OH$; a —(CO)—$NR_{12}R_{13}$; a —(CO)—$NR_8R_{8'}$; a —O—(CO)—$R_7$; a —O—(CO)—$NR_{12}R_{13}$; a —O—(CO)—$NR_8R_{8'}$; a —$NR_{12}$—(CO)—$R_7$; a —$NR_8$—(CO)—$R_7$; a —$NR_{12}$—(CO)—$OR_7$; a —$NR_8$—(CO)—$OR_7$; a —O—(CO)—$OR_7$; a —$NR_{12}$—(CO)—$NR_{12}R_{13}$; a —$NR_8$—(CO)—$NR_8R_{8'}$; a —$SO_2$—$R_7$; a —$NR_{12}$—$SO_2$—$R_7$; a —$NR_8$—$SO_2$—$R_7$; a —$SO_2$—$NR_{12}R_{13}$; a —$SO_2$—$NR_8R_{8'}$; a —$NR_{12}$—$SO_2$—$NR_{12}R_{13}$; a —$NR_8$—$SO_2$—$NR_8R_{8'}$; a —$NR_{12}$—($C_2$-$C_{10}$)-alkyl-$NR_{12}R_{13}$; a —$NR_8$—($C_2$-$C_{10}$)-alkyl-$NR_8R_{8'}$; a —$NR_{12}$($C_2$-$C_{10}$)-alkyl-$NR_{13}$; a —$NR_8$—($C_2$-$C_{10}$)-alkyl-$OR_7$; a $OR_7$; a —(O—$CH_2CH_2$)$_p$—$NR_{12}$; a (O—$CH_2CH_2$)$_p$—$OR_7$; a —(O—$CH_2CH_2$)$_p$—$NR_{12}R_{13}$; a (O—$CH_2CH_2$)$_p$—$NR_8R_{8'}$; a —$NR_{12}$(—$CH_2CH_2$—O)$_p$—$R_{13}$; a —$NR_8$(—$CH_2CH_2$—O)$_p$—$R_7$; an optionally substituted alkyl as defined herein, preferably said optionally substituted alkyl being substituted with one or more —$NR_{12}R_{13}$, one or more halogen atom(s) as defined herein, one or more hydroxyl, one or more alkoxy as defined herein, one or more azido, one or more nitro, one or more cyano, one or more carboxyl and combination thereof, and/or said optionally substituted alkyl being or not further substituted with one or more —$NR_{12}R_{13}$; an optionally substituted fluoroalkyl as defined herein; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted alkoxy as defined herein; an optionally substituted aryl as defined herein; an optionally substituted benzyl as defined herein; an optionally substituted heteroaryl as defined herein; an optionally substituted heterocyclyl group as defined herein.

$R_6$ can be simultaneously or independently chosen from a hydrogen atom; an optionally substituted alkyl as defined herein; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted aryl as defined herein; an optionally substituted heteroaryl as defined herein; an optionally substituted heterocyclyl group as defined herein; an optionally substituted alkoxy as defined herein.

$R_7$ can be chosen from a hydrogen atom; an optionally substituted alkyl as defined herein; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted aryl as defined herein; an optionally substituted benzyl as defined herein; an optionally substituted heteroaryl as defined herein; an optionally substituted heterocyclyl group as defined herein.

$R_8$ and $R_{8'}$ can be simultaneously or independently chosen from a hydrogen atom; an optionally substituted alkyl as defined herein; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted heterocyclyl group as defined herein; an optionally substituted aryl as defined herein; an optionally substituted benzyl as defined herein; an optionally substituted heteroaryl as defined herein or $R_8$ and $R_{8'}$ can be linked together with the nitrogen atom to which they are covalently linked to form an optionally substituted heterocyclyl group as defined herein.

$R_9$ can be simultaneously or independently chosen from a hydrogen atom; a halogen atom as defined herein; a hydroxyl; an optionally substituted alkoxy as defined herein; a —$NR_2'R_{10}$; a —O—$R_{10}$; a nitro; an azido; a cyano; a —$NR_{12}R_{13}$; a —$NR_8R_{8'}$; a —(CO)—$R_7$; a —(CO)—O—$R_7$; a —(CO)—$NR_{12}OH$; a —(CO)—$NR_8OH$; a —(CO)—$NR_{12}R_{13}$; a —(CO)—$NR_8R_{8'}$; a —O—(CO)—$R_7$; a —O—(CO)—$NR_{12}R_{13}$; a —O—(CO)—$NR_8R_{8'}$; a —$NR_{12}$—(CO)—$R_7$; a —$NR_8$—(CO)—$R_7$; a —$NR_{12}$—(CO)—$NR_7$; a —$NR_8$—(CO)—$OR_7$; a —O—(CO)—$OR_7$; a —$NR_{12}$—(CO)—$NR_{12}R_{13}$; a —$NR_8$—(CO)—$NR_8R_{8'}$; a —$SO_2$—$R_7$; a —$NR_{12}$—$SO_2$—$R_7$; a —$NR_8$—$SO_2$—$R_7$; a —$SO_2$—$NR_{12}R_{13}$; a —$SO_2$—$NR_8R_{8'}$; a —$NR_{12}$—$SO_2$—$NR_{12}R_{13}$; a —$NR_8$—$SO_2$—$NR_8R_{8'}$; a —$NR_{12}$—($C_2$-$C_{10}$)-alkyl-$NR_{12}R_{13}$; a —$NR_8$—($C_2$-$C_{10}$)-alkyl-$NR_8R_{8'}$; a —$NR_{12}$—($C_2$-$C_{10}$)-alkyl-$NR_{13}$; a —$NR_8$—($C_2$-$C_{10}$)-alkyl-$OR_7$; a —$OR_7$; a —(O—$CH_2CH_2$)$_p$—$NR_{12}$; a —(O—$CH_2CH_2$)$_p$—$NR_7$; a —(O—$CH_2CH_2$)$_p$—$NR_{12}R_{13}$; a —(O—$CH_2CH_2$)$_p$—$NR_8R_{8'}$; a —$NR_{12}$(—$CH_2CH_2$—O)$_p$—$R_{13}$; a —$NR_8$(—$CH_2CH_2$—O)$_p$—$R_7$; an optionally substituted alkyl as defined herein, preferably said optionally substituted alkyl being substituted with one or more $NR_{12}R_{13}$, one or more halogen atom(s) as defined herein, one or more hydroxyl, one or more alkoxy as defined herein, one or more azido, one or more nitro, one or more cyano, one or more carboxyl and combination thereof, and/or said optionally substituted alkyl being or not further substituted with one or more $NR_{12}R_{13}$; an optionally substituted fluoroalkyl as defined herein; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted alkoxy as defined herein; an optionally substituted aryl as defined herein; an optionally substituted benzyl as defined herein; an optionally substituted heteroaryl as defined herein; an optionally substituted heterocyclyl group as defined herein.

$R_{10}$ can be chosen from a hydrogen atom; an optionally substituted aryl as defined herein, said optionally substituted aryl being or not further substituted by one or more $R_{11}$; an optionally substituted benzyl as defined herein, said optionally substituted benzyl being or not further substituted by one or more $R_{11}$; an optionally substituted heteroaryl as defined herein, said optionally substituted heteroaryl being or not further substituted by one or more $R_{11}$; an optionally substituted heterocyclyl group as defined herein, said optionally substituted heterocyclyl group being or not further substituted by one or more $R_{11}$.

$R_{11}$ can be simultaneously or independently chosen from a hydrogen atom; a halogen atom as defined herein; an optionally substituted alkoxy as defined herein; a hydroxyl; a nitro; a cyano; an azido; a —$NR_{12}R_{13}$; a —$NR_8R_{8'}$; a —O-(148); a —(CO)—$R_8$; a —(CO)—O—$R_8$; a —(CO)—$NR_{12}OH$; a —(CO)—$NR_8OH$; a —(CO)—$NR_{12}R_{13}$; a —(CO)—$NR_8R_{8'}$; a —O—(CO)—$R_8$; a —O—(CO)—$NR_{12}R_{13}$; a —O—(CO)—$NR_8R_{8'}$; a —$NR_{12}$—(CO)—$R_8$; a —$NR_8$—(CO)—$R_{8'}$; a —$NR_{12}$—(CO)—$NR_8$; a —$NR_8$—(CO)—$OR_{8'}$; a —O—(CO)—$OR_8$; a —$NR_{12}$—(CO)—$NR_{12}R_{13}$; a —$NR_8$—(CO)—$NR_8R_{8'}$; a —(O—$CH_2CH_2$)$_p$—$OR_{12}$; a —(O—$CH_2CH_2$)$_p$—$NR_8$; a —(O—$CH_2CH_2$)$_p$—$NR_{12}R_{13}$; a —(O—$CH_2CH_2$)$_p$—$NR_8R_{8'}$; a —$NR_{12}$(—$CH_2CH_2$—O)$_p$—$R_{13}$; a —$NR_8$(—$CH_2CH_2$—O)$_p$—$R_{8'}$; a —$SO_2$—$R_8$; a —$NR_{12}$—$SO_2$—$R_8$; a —$NR_8$—$SO_2$—$R_{8'}$; a —$SO_2$—$NR_{12}R_{13}$; a —$SO_2$—$NR_8R_{8'}$; a —$NR_{12}$—$SO_2$—$NR_{12}R_{13}$; a —$NR_8$—$SO_2$—$NR_8R_{8'}$; a —$NR_{12}$—($C_2$-$C_8$)-alkyl-$NR_{12}R_{13}$; a —$NR_8$—($C_2$-$C_8$)-alkyl-$NR_8R_{8'}$; a —$NR_{12}$—($C_2$-$C_8$)-alkyl-$OR_{13}$; a —$NR_8$—($C_2$-$C_8$)-alkyl-$OR_{8'}$; an optionally substituted alkyl as defined herein, preferably said optionally substituted alkyl being substituted by one or more halogen atom(s) as defined herein, by one or more hydroxyl, by one or more alkoxy as defined herein, or by one or more —$NR_8R_{8'}$ and combination thereof; an optionally substituted fluoroalkyl as defined herein; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted aryl as defined herein; an optionally substituted benzyl as defined herein; an optionally substituted heteroaryl as defined herein; an optionally substituted heterocyclyl group as defined herein.

$R_{12}$ and $R_{13}$ can be simultaneously or independently chosen from a hydrogen atom; a —(CO)—$R_7$; a —(CO)—O—$R_7$; a —(CO)—$NR_8OH$; a —(CO)—$NR_8R_{8'}$; a —$SO_2$—$R_7$; a —$SO_2$—$NR_8R_{8'}$; an optionally substituted alkyl as defined herein, preferably said optionally substituted alkyl being substituted with at least one —$NR_8R_{8'}$; an optionally substituted cycloalkyl as defined herein, preferably said optionally substituted cycloalkyl being substituted with at least one —$NR_8R_{8'}$; an optionally substituted alkenyl as defined herein; an optionally substituted alkynyl as defined herein; an optionally substituted cycloalkenyl as defined herein; an optionally substituted cycloalkynyl as defined herein; an optionally substituted aryl as defined herein; an optionally substituted benzyl as defined herein; an optionally substituted heteroaryl as defined herein; an optionally substituted heterocyclyl group as defined herein; or $R_{12}$ and $R_{13}$ can be linked together with the nitrogen atom to which they are covalently linked to form an optionally substituted heterocyclyl group as defined herein.

n can represent an equal integer which can have any one of the values 0, 1, 2, 3 or 4, preferably 0, 1, 2 or 3, more preferably 0, 1 or 2 still more preferably 0 or 1.

m can represent an equal integer which can have any one of the values 1, 2 or 3 preferably 1 or 2, more preferably 2.

p can represent an equal integer which can have any one of the values 1, 2, 3, 4 or 5, preferably 1, 2, 3 or 4, more preferably 1, 2 or 3, still more preferably 1 or 2.

The compounds also include any pharmaceutically acceptable salt, hydrates, solvate, prodrugs, polymorphs, tautomers, isotopic variants, isomers, stereoisomers or mixtures of stereoisomers thereof.

In various embodiments, the compounds are used as a medicament to treat, decrease the severity and/or progression of, and/or prevent fibrosis and/or related diseases, to treat, decrease the severity and/or progression of and/or prevent autophagy and/or related diseases, to inhibit the autophagy flux, and to inhibit cathepsins B (CTSB), L (CTSL) and/or D (CTSD) and/or related diseases. It is not intended that the compounds be used to treat cancer.

Other preferred embodiments of the invention are presented hereafter, any combination of two or more of these embodiments being considered within the scope of the present disclosure. At each time the preferred embodiment of the compound concerns a particular compound for use as a medicament for treating and/or decreasing the severity and/or progression of and/or preventing fibrosis and/or related diseases, of the autophagy and/or related diseases, and for inhibiting the autophagy flux, and for inhibiting cathepsins B (CTSB), L (CTSL) and/or D (CTSD) and/or related diseases.

A preferred embodiment provides a compound of Formula (I), wherein $L_1$ can be a single bond; a carbonyl as defined herein; an optionally substituted alkyl as defined herein, said optionally substituted alkyl being or not further substituted by at least one $R_6$ as defined herein; or an optionally substituted cycloalkyl as defined herein; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

A further preferred embodiment provides a compound of Formula (I), wherein $L_1$ can be a single bond; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a carbonyl as defined herein; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

A further preferred embodiment provides a compound of Formula (I), wherein $L_1$ can be an optionally substituted alkyl as defined herein, said optionally substituted alkyl being or not further substituted by at least one $R_6$ as defined herein; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

A further preferred embodiment provides a compound of Formula (I), wherein $L_1$ can be an optionally substituted alkyl as defined herein; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

A further preferred embodiment provides a compound of Formula (I), wherein $L_1$ can be an optionally substituted cycloalkyl as defined herein; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

A further preferred embodiment provides a compound of Formula (I), wherein $L_1$ can be an alkyl as defined herein; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

A further preferred embodiment provides a compound of Formula (I), wherein $L_1$ can be a methylene ($-CH_2-$); it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

A further preferred embodiment provides a compound of formula (I), wherein $L_1$ can be an optionally substituted alkyl, said optionally substituted alkyl being or not further substituted with at least one $R_6$.

A further preferred embodiment provides a compound of formula (I), wherein $L_1$ can be an alkyl, said alkyl being or not further substituted with at least one $R_6$.

Yet, another preferred embodiment provides a compound of Formula (I), wherein $R_1$ can be an optionally substituted heteroaryl as defined herein; it being understood that $L_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Disclosed herein in yet another preferred embodiment provides a compound of Formula (I), wherein $R_1$ can be an optionally substituted aryl, as defined herein; it being understood that $L_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, a further preferred embodiment provides a compound of Formula (I), wherein when $R_1$ is an optionally substituted aryl, said optionally substituted aryl can be preferably an optionally substituted napthyl or optionally substituted phenyl, and more preferably an optionally substituted phenyl; it being understood that $L_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I). Yet, a further preferred embodiment provides a compound of Formula (I), wherein when $R_1$ is an optionally substituted aryl, said optionally substituted aryl can be preferably an optionally substituted 3-methylbenzene-1,4-diyl; it being understood that $L_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein when $R_1$ is an optionally substituted aryl, said optionally substituted aryl can be preferably an optionally substituted phenyl; it being understood that $L_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

A further preferred embodiment provides a compound of formula (I), wherein $R_1$ can be an optionally substituted aryl, said optionally substituted aryl being or not further substituted with at least one $R_9$.

A further preferred embodiment provides a compound of formula (I), wherein $R_1$ can be an aryl, said aryl being or not further substituted with at least one $R_9$.

A further preferred embodiment provides a compound of formula (I), wherein $R_2$ can be a hydrogen.

A further preferred embodiment provides a compound of formula (I), wherein $R_3$ can be an optionally substituted alkyl, an optionally substituted cycloalkyl, or an optionally substituted heterocyclyl.

A further preferred embodiment provides a compound of formula (I), wherein $R_3$ can be an alkyl, cycloalkyl, or heterocyclyl. Another preferred embodiment provides a compound of Formula (I), wherein $R_2$ and $R_3$ can be simultaneously or independently chosen from a hydrogen atom; an optionally substituted alkyl as defined herein; an optionally substituted cycloalkyl as defined herein; an optionally substituted aryl as defined herein; an optionally substituted heteroaryl as defined herein; an optionally substituted heterocyclyl group as defined herein; or $R_2$ and $R_3$ can be linked together with the nitrogen atom to which they are covalently linked to form an optionally substituted heterocyclyl group as defined herein; it being understood that $L_1$, $R_1$, $R_{2'}$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_2$ and $R_3$ can be simultaneously or independently chosen from a hydrogen atom; an optionally substituted alkyl as defined herein; an optionally substituted cycloalkyl as defined herein; an optionally substituted heterocyclyl group as defined herein; or $R_2$ and $R_3$ can be linked together with the nitrogen atom to which they are covalently linked to form an optionally substituted heterocyclyl group as defined herein; it being understood that $L_1$, $R_1$, $R_{2'}$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

A further preferred embodiment provides a compound of Formula (I), wherein $R_2$ and $R_3$ are simultaneously or independently chosen from a hydrogen atom or an optionally substituted alkyl as defined herein; it being understood that $L_1$, $R_1$, $R_{2'}$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

A further preferred embodiment provides a compound of Formula (I), wherein $R_2$ and $R_3$ are simultaneously or independently chosen from a hydrogen atom or an optionally substituted cycloalkyl as defined herein; it being understood that $L_1$, $R_1$, $R_{2'}$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

A further preferred embodiment provides a compound of Formula (I), wherein $R_2$ and $R_3$ are simultaneously or independently chosen from a hydrogen atom or an optionally substituted heterocyclyl group as defined herein; it being understood that $L_1$, $R_1$, $R_{2'}$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

A further preferred embodiment provides a compound of Formula (I), wherein $R_2$ and $R_3$ are linked together with the nitrogen atom to which they are covalently linked to form a heterocyclyl group as defined herein; it being understood that $L_1$, $R_1$, $R_{2'}$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

A further preferred embodiment provides a compound of Formula (I), wherein $R_2$ and $R_3$ are simultaneously or independently chosen from a hydrogen atom and a tert-butyl; it being understood that $L_1$, $R_1$, $R_{2'}$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

A further preferred embodiment provides a compound of Formula (I), wherein $R_2$ and $R_3$ are simultaneously or independently chosen from a hydrogen atom or a 1-methylpiperidin-4-yl; it being understood that $L_1$, $R_1$, $R_{2'}$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

A further preferred embodiment provides a compound of Formula (I), wherein $R_2$ and $R_3$ are linked together with the nitrogen atom to which they are covalently linked to form a pyrrolidin-1-yl; it being understood that $L_1$, $R_1$, $R_{2'}$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

A further preferred embodiment provides a compound of formula (I), wherein $R_2$ and $R_3$ can be linked together with nitrogen to which they are covalently linked to form an optionally substituted heterocyclyl.

A further preferred embodiment provides a compound of formula (I), wherein $R_2$ and $R_3$ can be linked together with nitrogen to which they are covalently linked to form a heterocyclyl.

Yet, another preferred embodiment provides a compound of Formula (IV), wherein $R_4$ can be, alone or simultaneously or independently when n>1, chosen from a hydrogen atom; a halogen atom as defined herein; —$NR_8R_{8'}$; an optionally substituted alkyl as defined herein, preferably said optionally substituted alkyl being substituted by one or more halogen atom(s) as defined herein, by one or more hydroxyl, by one or more alkoxy as defined herein, by one or more —$NR_8R_{8'}$ and combination thereof; an optionally substituted alkenyl as defined herein; an optionally substituted alkynyl as defined herein; an optionally substituted cycloalkyl as defined herein, preferably said optionally substituted cycloalkyl being substituted by one or more halogen atom(s) as defined herein, by one or more hydroxyl, by one or more alkoxy as defined herein, by one or more —$NR_8R_{8'}$ and combination thereof; an optionally substituted cycloalkenyl as defined herein; an optionally substituted cycloalkynyl as defined herein; an optionally substituted alkoxy as defined herein; a hydroxyl; a nitro; a cyano; an azido; a carboxyl; a —$NR_{12}R_{13}$, wherein, $R_{12}$ and $R_{13}$ can be simultaneously or independently chosen from a hydrogen atom, an optionally substituted alkyl as defined herein, preferably said optionally substituted alkyl being substituted by one or more —$NR_8R_{8'}$, an optionally substituted alkenyl as defined herein, an optionally substituted alkynyl as defined herein, an optionally substituted cycloalkenyl as defined herein, an optionally substituted cycloalkynyl as defined herein, an optionally substituted cycloalkyl as defined herein, preferably said optionally substituted cycloalkyl being substituted by one or more —$NR_8R_{8'}$, an optionally substituted aryl as defined herein, an optionally substituted benzyl as defined herein, an optionally substituted heteroaryl as defined herein, an optionally substituted heterocyclyl group as defined herein, or $R_{12}$ and $R_{13}$ can be linked together with the nitrogen atom to which they are covalently linked to form a heterocyclyl group as defined herein; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, a further preferred embodiment provides a compound of Formula (I), wherein $R_4$ can be, alone or simultaneously or independently when n>1, chosen from a hydrogen atom; or a —$NR_{12}R_{13}$ wherein $R_{12}$ and $R_{13}$ can be simultaneously or independently chosen from a hydrogen atom, an optionally substituted alkyl, preferably said optionally substituted alkyl being substituted by one or more —$NR_8R_{8'}$, an optionally substituted alkenyl as defined herein, an optionally substituted alkynyl as defined herein, an optionally substituted cycloalkenyl as defined herein, an optionally substituted cycloalkynyl as defined herein, an optionally substituted cycloalkyl as defined herein, preferably said optionally substituted cycloalkyl being substituted by one or more —$NR_8R_{8'}$, an optionally substituted aryl as defined herein, an optionally substituted benzyl, an optionally substituted heteroaryl as defined herein, an optionally substituted heterocyclyl group as defined herein, or $R_{12}$ and $R_{13}$ can be linked together with the nitrogen atom to which they are covalently linked to form a heterocyclyl group as defined herein; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, a further preferred embodiment provides a compound of Formula (I), wherein $R_4$ can be, alone or simultaneously or independently when n>1, chosen from a hydrogen atom; or a —$NR_{12}R_{13}$ wherein $R_{12}$ and $R_{13}$ can be simultaneously or independently chosen from a hydrogen atom, an optionally substituted alkyl as defined herein, an optionally substituted cycloalkyl as defined herein, an optionally substituted aryl as defined herein, an optionally substituted benzyl as defined herein, an optionally substituted heteroaryl as defined herein, an optionally substituted heterocyclyl as defined herein, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_4$ can be, alone or simultaneously or independently when n>1, chosen from a hydrogen atom; or a —$NR_{12}R_{13}$ wherein $R_{12}$ and $R_{13}$ can be simultaneously or independently chosen from a hydrogen atom, an optionally substituted alkyl as defined herein, an optionally substituted cycloalkyl as defined herein, an optionally substituted aryl as defined herein, an optionally substituted heteroaryl as defined herein, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_4$ can be, alone or simultaneously or independently when n>1, chosen from a hydrogen atom; or a —$NR_{12}R_{13}$ wherein $R_{12}$ and $R_{13}$ can be simultaneously or independently chosen from a hydrogen atom, an optionally substituted alkyl as defined herein, an optionally substituted cycloalkyl as defined herein, an optionally substituted heteroaryl as defined herein, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_4$ can be, alone or simultaneously or independently when n>1, chosen from a hydrogen atom; or a —$NR_{12}R_{13}$ wherein $R_{12}$ and $R_{13}$ can be simultaneously or independently chosen from a hydrogen atom, an optionally substituted alkyl as defined herein, an optionally substituted cycloalkyl as defined herein, an optionally substituted pyrimidin, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_4$ can be, alone or simultaneously or independently when n>1, chosen from a hydrogen atom; or a —$NR_{12}R_{13}$ wherein $R_{12}$ and $R_{13}$ can be simultaneously or independently chosen from a hydrogen atom, an optionally substituted benzyl as defined herein, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_4$ can be, alone or simultaneously or independently when n>1, chosen from a hydrogen atom; or a —$NR_{12}R_{13}$ wherein $R_{12}$ and $R_{13}$ can be simultaneously or independently chosen from a hydrogen atom, an optionally substituted aryl as defined herein, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_4$ can be, alone or simultaneously or independently when n>1, chosen from a hydrogen atom; or a —$NR_{12}R_{13}$ wherein $R_{12}$ and $R_{13}$ can be simultaneously or independently chosen from a hydrogen atom, an optionally substituted heteroaryl as defined herein, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_4$ can be, alone or simultaneously or independently when n>1, chosen from a hydrogen atom; or a —$NR_{12}R_{13}$ wherein $R_{12}$ and $R_{13}$ can be simultaneously or independently chosen from a hydrogen atom, a methyl, a cyclopropyl, an optionally substituted pyrimidin-2-yl, an optionally substituted pyrimidin-4-yl, an optionally substituted pyrimidin-5-yl, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_4$ can be, alone or simultaneously or independently when n>1, chosen from a hydrogen atom; or a —$NR_{12}R_{13}$ wherein $R_{12}$ and $R_{13}$ can be simultaneously or independently chosen from a hydrogen atom, a methyl, a cyclopropyl, a pyrimidin-2-yl, a pyrimidin-4-yl, a pyrimidin-5-yl, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_4$ can be, alone or simultaneously or independently when n>1, chosen from a hydrogen atom; or a —$NR_{12}R_{13}$ wherein $R_{12}$ and $R_{13}$ can be simultaneously or independently chosen from a hydrogen atom, an optionally substituted pyrimidin-2-yl, an optionally substituted pyrimidin-4-yl, an optionally substituted pyrimidin-5-yl, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, a further preferred embodiment provides a compound of Formula (I), wherein $R_4$ can be, alone or simultaneously or independently when n>1, chosen from a hydrogen atom; or a —$NR_{12}R_{13}$ wherein $R_{12}$ and $R_{13}$ can be simultaneously or independently chosen from a hydrogen atom, an optionally substituted alkyl as defined herein, an optionally substituted cycloalkyl as defined herein, an optionally substituted heterocyclyl group as defined herein, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

A further preferred embodiment provides a compound of Formula (I), wherein $R_4$ can be, alone or simultaneously or independently when n>1, chosen from, a hydrogen atom; or a —$NR_{12}R_{13}$ wherein $R_{12}$ and $R_{13}$ can be linked together with the nitrogen atom to which they are covalently linked to form an optionally heterocyclyl group as defined herein, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

In yet another preferred embodiment provides a compound of Formula (I), wherein $R_4$ can be, alone or simultaneously or independently when n>1, chosen from a hydrogen atom; or —(CO)—$NR_{12}R_{13}$ wherein $R_{12}$ and $R_{13}$ can be simultaneously or independently chosen from a hydrogen atom, an optionally substituted alkyl as defined herein, an optionally substituted cycloalkyl as defined herein, an optionally substituted aryl as defined herein, an optionally substituted heteroaryl as defined herein, an optionally substituted heterocyclyl group, or $R_{12}$ and $R_{13}$ can be linked together with the nitrogen atom to which they are covalently linked to form an optionally heterocyclyl group as defined herein, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_4$ can be, alone or simultaneously or independently when n>1, chosen from a hydrogen atom; or —(CO)—$NR_{12}R_{13}$ wherein $R_{12}$ and $R_{13}$ can be simultaneously or independently chosen from a hydrogen atom, an optionally substituted alkyl as defined herein, an optionally substituted cycloalkyl as defined herein, an optionally substituted heterocyclyl group as defined herein, or $R_{12}$ and $R_{13}$ can be linked together with the nitrogen atom to which they are covalently linked to form an optionally heterocyclyl group as defined herein, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_4$ can be, alone or simultaneously or independently when n>1, chosen from a hydrogen atom; or —(CO)—$NR_{12}R_{13}$ wherein $R_{12}$ and $R_{13}$ can be simultaneously or independently chosen from a hydrogen atom, or an optionally substituted benzyl as defined herein, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_4$ can be, alone or simultaneously or independently when n>1, chosen from a hydrogen atom; or —(CO)—$NR_{12}R_{13}$ wherein $R_{12}$ and $R_{13}$ can be simultaneously or independently chosen from a hydrogen atom, or an optionally substituted aryl as defined herein, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_4$ can be, alone or simultaneously or independently when n>1, chosen from a hydrogen atom; or —(CO)—$NR_{12}R_{13}$ wherein $R_{12}$ and $R_{13}$ can be simultaneously or independently chosen from a hydrogen atom, or an optionally substituted heteroaryl as defined herein, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_4$ can be, alone or simultaneously or independently when n>1, chosen from a hydrogen atom; or —(CO)—$NR_{12}R_{13}$ wherein $R_{12}$ and $R_{13}$ can be simultaneously or independently chosen from a hydrogen atom, or an optionally substituted alkyl as defined herein, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_4$ can be, alone or simultaneously or independently when n>1, chosen from a hydrogen atom; or —(CO)—$NR_{12}R_{13}$ wherein $R_{12}$ and $R_{13}$ can be simultaneously or independently chosen from a hydrogen atom, an optionally substituted heterocyclyl group as defined herein, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_4$ can be, alone or simultaneously or independently when n>1, chosen from a hydrogen atom; or —(CO)—$NR_{12}R_{13}$ wherein $R_{12}$ and $R_{13}$ can be linked together with the nitrogen atom to which they are covalently linked to form an optionally heterocyclyl group as defined herein, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_4$ can be, alone or simultaneously or independently when n>1, chosen from a hydrogen atom; or —(CO)—$NR_{12}R_{13}$ wherein $R_{12}$ and $R_{13}$ can be simultaneously or independently chosen from a hydrogen atom, a methyl, an ethyl, an isopropyl, a tert-butyl, a cyclopropyl, a cyclobutyl, a cyclopentyl, a cyclohexyl, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, m, n and p have the same definitions as those given previously with Formula (I).

Another preferred embodiment provides a compound of Formula (I), wherein $R_4$ can be, alone or simultaneously or independently when n>1, chosen from a hydrogen atom; a halogen atom as defined herein; an optionally substituted alkyl as defined herein; an optionally substituted alkenyl as defined herein; an optionally substituted alkynyl as defined herein; an optionally substituted cycloalkyl as defined herein; an optionally substituted alkoxy as defined herein; a hydroxyl; a cyano; an azido; a carboxyl; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_4$ can be, alone or simultaneously or independently when n>1, chosen from a hydrogen atom; a halogen atom as defined herein; an optionally substituted alkyl as defined herein; an optionally substituted alkoxy as defined herein; a hydroxyl; a cyano; a carboxyl; an azido; $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_4$ can be, alone or simultaneously or independently when n>1, chosen from a hydrogen atom; a halogen atom as defined herein; an optionally substituted alkyl as defined herein; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_4$ can be, alone or simultaneously or independently when n>1, chosen from a hydrogen atom; a halogen atom as defined herein; an optionally substituted alkyl as defined herein; an optionally substituted alkoxy as defined herein; a hydroxyl; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_4$ can be, alone or simultaneously or independently when n>1, chosen from a hydrogen atom; an optionally substituted alkyl as defined herein; an optionally substituted alkoxy as defined herein; a hydroxyl; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_4$ can be, alone or simultaneously or independently when n>1, chosen from a hydrogen atom; an optionally substituted alkoxy as defined herein; a hydroxyl; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_4$ can be, alone or simultaneously or independently when n>1, chosen from a hydrogen atom; an optionally substituted alkoxy as defined herein; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_4$ can be, alone or simultaneously or independently when n>1, chosen from a hydrogen atom; a hydroxyl; a methoxy; a ethoxy; a isopropoxy; a tert-butoxy; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_4$ can be, alone or simultaneously or independently when n>1, chosen from a hydrogen atom; a methoxy; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_4$ can be, alone or simultaneously or independently when n>1, chosen from a hydrogen atom; a halogen atom as defined herein; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_4$ can be, alone or simultaneously or independently when n>1, chosen from a hydrogen atom, a fluorine, a chlorine; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, m, n and p have the same definitions as those given previously with Formula (I).

Another preferred embodiment provides a compound of Formula (I), wherein $R_4$ can be, alone or simultaneously or independently when n>1, chosen from a hydrogen atom; a hydroxyl; a methoxy, it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_4$ can be, alone or simultaneously or independently when n>1, chosen from a hydrogen atom; a hydroxyl; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_4$ can be, alone or simultaneously or independently when n>1, chosen from a hydrogen atom; an optionally substituted alkyl as defined herein; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_4$ can be, alone or simultaneously or independently when n>1, chosen from a hydrogen atom; an optionally substituted alkyl said optionally substituted alkyl being preferably substituted by one or more halogen atom(s), as defined herein; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_4$ can be, alone or simultaneously or independently when n>1, chosen from a hydrogen atom; an optionally substituted fluoroalkyl as defined herein; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_4$ can be, alone or simultaneously or independently when n>1, chosen from a hydrogen atom; an unsubstituted alkyl as defined herein; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_4$ can be, alone or simultaneously or independently when n>1, chosen from a hydrogen atom; a methyl; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_4$ can be, alone or simultaneously or independently when n>1, chosen from a hydrogen atom; a cyano; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_4$ can be, alone or simultaneously or independently when n>1, chosen from a hydrogen atom; a —$CF_3$; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_4$ is a hydrogen atom; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, a further preferred embodiment provides a compound of Formula (I), wherein $R_4$ can be, alone or simultaneously or independently when n>1, chosen from a hydrogen atom; a —(O—$CH_2CH_2$—)$_p$—$OR_{12}$; a —(O—$CH_2CH_2$—)$_p$—$NR_{12}R_{13}$; —$NR_{12}$—($CH_2CH_2$—O)$_p$—$R_{13}$; a —$NR_{12}$—($C_2$-$C_8$)-alkyl-$NR_{12}R_{13}$; a —$NR_{12}$—($C_2$-$C_8$)-alkyl-$OR_{13}$; it being understood that $L_1$, $R_1$, $R_2$, $R_{2'}$, $R_3$, $R_8$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, a further preferred embodiment provides a compound of Formula (I), wherein $R_4$ can be, alone or simultaneously or independently when n>1, chosen from a hydrogen atom; a —(O—$CH_2CH_2$—)$_p$—$NR_8$; a —(O—$CH_2CH_2$—)$_p$—$NR_8R_{8'}$; —$NR_8$—($CH_2CH_2$—O)$_p$—$R_{8'}$; a —$NR_8$—($C_2$-$C_8$)-alkyl-$NR_8R_{8'}$; a —$NR_8$—($C_2$-$C_8$)-alkyl-$OR_{8'}$; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, a further preferred embodiment provides a compound of Formula (I), wherein $R_4$ can be, alone or simultaneously or independently when n>1, chosen from a hydrogen atom; a —(O—$CH_2CH_2$—)$_p$—$NR_8$; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, a further preferred embodiment provides a compound of Formula (I), wherein $R_4$ can be, alone or simultaneously or independently when n>1, chosen from a hydrogen atom; a —(O—$CH_2CH_2$—)$_p$—$NR_8R_{8'}$; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, a further preferred embodiment provides a compound of Formula (I), wherein $R_4$ can be a hydrogen atom, a —$NR_8$—($CH_2CH_2$—O)$_p$—$R_{8'}$; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, a further preferred embodiment provides a compound of Formula (I), wherein $R_4$ can be, alone or simultaneously or independently when n>1, chosen from a hydrogen atom; a —$NR_8$—($C_2$-$C_8$)-alkyl-$NR_8R_{8'}$; it being understood that $L_1$, $R_1$, $R_2$, $R_{2'}$, $R_3$, $R_5$, $R_6$, $R_7$, $R_8$, $R_{8'}$, $R_9$, $R_{10}$, Rut, $R_{12}$, $R_{13}$, m, n and p have the same definitions as those given previously with Formula (I).

Yet, a further preferred embodiment provides a compound of Formula (I), wherein $R_4$ can be, alone or simultaneously or independently when n>1, chosen from a hydrogen atom; a —$NR_8$—($C_2$-$C_8$)-alkyl-$NR_{8'}$; it being understood that $L_1$, $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

A further preferred embodiment provides a compound of formula (I), wherein $R_4$ can be a hydrogen, a hydroxyl, or a methoxy.

Yet, a further preferred embodiment provides a compound of Formula (I), wherein when $R_5$ is —$NR_2R_{10}$ then $R_2'$ can be chosen from a hydrogen atom; an optionally substituted alkyl as defined herein; an optionally substituted cycloalkyl as defined herein; an optionally substituted heterocyclyl group as defined herein; it being understood that $L_1$, $R_1$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein when $R_5$ is —$NR_2R_{10}$ then $R_2'$ can be chosen from a hydrogen atom; an optionally substituted alkyl as defined herein; an optionally substituted cycloalkyl as defined herein; it being understood that $L_1$, $R_1$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein when $R_5$ is $-NR_2 \cdot R_{10}$ then $R_2'$ is a hydrogen atom; it being understood that $L_1$, $R_1$, $R_2$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein when $R_5$ is $-NR_2 \cdot R_{10}$ then $R_2'$ is an optionally substituted alkyl as defined herein; it being understood that $L_1$, $R_1$, $R_2$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein when $R_5$ is $-NR_2 \cdot R_{10}$ then $R_2'$ is an optionally substituted cycloalkyl as defined herein; it being understood that $L_1$, $R_1$, $R_2$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein when $R_5$ is $-NR_2 \cdot R_{10}$ then $R_2'$ is an optionally substituted heterocyclyl group as defined herein; it being understood that $L_1$, $R_1$, $R_2$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein when $R_5$ is $-NR_2 \cdot R_{10}$ then $R_2'$ can be chosen from a hydrogen atom; a methyl; a cyclopropyl; it being understood that $L_1$, $R_1$, $R_2$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein when $R_5$ is $-NR_2 \cdot R_{10}$ then $R_2'$ is a methyl; it being understood that $L_1$, $R_1$, $R_2$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein when $R_5$ is $-NR_2 \cdot R_{10}$ then $R_2'$ is a cyclopropyl; it being understood that $L_1$, $R_1$, $R_2$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet another preferred embodiment provides a compound of Formula (I), wherein $R_5$ can be a hydrogen atom; a halogen atom as defined herein; an optionally substituted alkyl as defined herein, preferably said optionally substituted alkyl being substituted by one or more halogen atom(s) as defined herein; an optionally substituted cycloalkyl as defined herein; an optionally substituted alkoxy as defined herein; a hydroxyl; a cyano; an azido; a $-NR_8R_{8'}$; a $-(CO)-O-R_7$; a $-(CO)-NR_{12}R_{13}$; an optionally substituted aryl as defined herein; an optionally substituted heteroaryl as defined herein; an optionally substituted heterocyclyl group as defined herein; a $-NR_2'R_{10}$; a $-O-R_{10}$; it being understood that $L_1$, $R_1$, $R_2$, $R_2'$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ can be a hydrogen atom; a halogen atom as defined herein; an optionally substituted alkyl as defined herein, preferably said optionally substituted alkyl being substituted by one or more halogen atom(s); an optionally substituted alkoxy as defined herein; a hydroxyl; a $-(CO)-O-R_7$; a $-(CO)-NR_{12}R_{13}$; an optionally substituted heteroaryl as defined herein; an optionally substituted heterocyclyl group as defined herein; a $-NR_2'R_{10}$; a $-O-R_{10}$; it being understood that $L_1$, $R_1$, $R_2$, $R_2'$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $R_5$ can be a hydrogen atom; a halogen atom as defined herein; an optionally substituted alkyl as defined herein, preferably said optionally substituted alkyl being substituted by one or more halogen atom(s); an optionally substituted alkoxy as defined herein; a hydroxyl; a $-NR_8R_{8'}$; a $-(CO)-O-R_7$; a $-(CO)-NR_{12}R_{13}$; it being understood that $L_1$, $R_1$, $R_2$, $R_2'$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $R_5$ can be a hydrogen atom; a halogen atom as defined herein; an optionally substituted alkyl as defined herein, preferably said optionally substituted alkyl being substituted by one or more halogen atom(s), as defined herein; an optionally substituted alkyl as defined herein; it being understood that $L_1$, $R_1$, $R_2$, $R_2'$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ can be a hydrogen atom; a halogen atom as defined herein; an optionally substituted alkyl as defined herein, preferably said optionally substituted alkyl being substituted by one or more halogen atom(s) as defined herein; it being understood that $L_1$, $R_1$, $R_2$, $R_2'$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ can be an optionally substituted alkyl as defined herein, preferably said optionally substituted alkyl being substituted by one or more halogen atom(s) as defined herein; it being understood that $L_1$, $R_1$, $R_2$, $R_2'$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ can be an optionally substituted fluoroalkyl as defined herein; it being understood that $L_1$, $R_1$, $R_2$, $R_2'$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $R_5$ can be an optionally substituted alkyl as defined herein; it being understood that $L_1$, $R_1$, $R_2$, $R_2'$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $R_5$ can be an unsubstituted alkyl as defined herein.

Yet, another preferred embodiment provides a compound of Formula (I), wherein $R_5$ is a $-(CO)-O-R_7$; it being understood that $L_1$, $R_1$, $R_2$, $R_2'$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $R_5$ is a $-(CO)-O-R_7$, wherein $R_7$ is an optionally substituted alkyl as defined herein; it being understood that $L_1$, $R_1$, $R_2$, $R_2'$, $R_3$, $R_4$, $R_6$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ is a $-CO_2H$; it being understood that $L_1$, $R_1$, $R_2$, $R_2'$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $R_5$ is a —(CO)—$NR_{12}R_{13}$, wherein $R_{12}$ and $R_{13}$ can be simultaneously or independently chosen from a hydrogen atom, an optionally substituted alkyl as defined herein, an optionally substituted cycloalkyl as defined herein, an optionally substituted aryl as defined herein, an optionally substituted heteroaryl as defined herein, an optionally substituted benzyl, an optionally substituted heterocyclyl group as defined herein, or $R_{12}$ and $R_{13}$ can be linked together with the nitrogen atom to which they are covalently linked to form an optionally heterocyclyl group as defined herein; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_5$ is a —(CO)—$NR_{12}R_{13}$, wherein $R_{12}$ and $R_{13}$ can be simultaneously or independently chosen from a hydrogen atom, an optionally substituted alkyl as defined herein, an optionally substituted cycloalkyl as defined herein, an optionally substituted heterocyclyl group as defined herein, or Rig and $R_{13}$ can be linked together with the nitrogen atom to which they are covalently linked to form an optionally heterocyclyl group as defined herein, it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_5$ is a —(CO)—$NR_{12}R_{13}$, wherein $R_{12}$ and $R_{13}$ can be simultaneously or independently chosen from a hydrogen atom, an optionally substituted alkyl as defined herein, an optionally substituted cycloalkyl as defined herein, an optionally substituted heterocyclyl group as defined herein, it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, m, n and p have the same definitions as those given previously with Formula (I).

Yet, another preferred embodiment provides a compound of Formula (I), wherein $R_5$ is a —(CO)—$NR_{12}R_{13}$, wherein $R_{12}$ and $R_{13}$ can be simultaneously or independently chosen from a hydrogen atom, an optionally substituted alkyl as defined herein, an optionally substituted cycloalkyl as defined herein, it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, m, n and p have the same definitions as those given previously with Formula (I).

Another preferred embodiment provides a compound of Formula (I), wherein $R_5$ is a —(CO)—$NR_{12}R_{13}$, wherein $R_{12}$ and $R_{13}$ can be simultaneously or independently chosen from a hydrogen atom or an optionally substituted alkyl as defined herein; it being understood $L_1$, $R_1$, $R_2$, $R_{2'}$, $R_3$, $R_4$, $R_6$, $R_7$, $R_8$, $R_{8'}$, $R_9$, $R_{10}$, $R_{11}$, m, n and p have the same definitions as those given previously with Formula (I).

Another preferred embodiment provides a compound of Formula (I), wherein $R_5$ is a —(CO)—$NR_{12}R_{13}$, wherein $R_{12}$ and $R_{13}$ can be simultaneously or independently chosen from a hydrogen atom or an optionally substituted benzyl as defined herein; it being understood $L_1$, $R_1$, $R_2$, $R_{2'}$, $R_3$, $R_4$, $R_6$, $R_7$, $R_8$, $R_{8'}$, $R_9$, $R_{10}$, $R_{11}$, m, n and p have the same definitions as those given previously with Formula (I).

Another preferred embodiment provides a compound of Formula (I), wherein $R_5$ is a —(CO)—$NR_{12}R_{13}$, wherein $R_{12}$ and $R_{13}$ can be simultaneously or independently chosen from a hydrogen atom or an optionally substituted aryl as defined herein; it being understood $L_1$, $R_1$, $R_2$, $R_{2'}$, $R_3$, $R_4$, $R_6$, $R_7$, $R_8$, $R_{8'}$, $R_9$, $R_{10}$, $R_{11}$, m, n and p have the same definitions as those given previously with Formula (I).

Another preferred embodiment provides a compound of Formula (I), wherein $R_5$ is a —(CO)—$NR_{12}R_{13}$, wherein $R_{12}$ and $R_{13}$ can be simultaneously or independently chosen from a hydrogen atom or an optionally substituted heteroaryl as defined herein; it being understood $L_1$, $R_1$, $R_2$, $R_{2'}$, $R_3$, $R_4$, $R_6$, $R_7$, $R_8$, $R_{8'}$, $R_9$, $R_{10}$, $R_{11}$, m, n and p have the same definitions as those given previously with Formula (I).

Another preferred embodiment provides a compound of Formula (I), wherein $R_5$ is a —(CO)—$NR_{12}R_{13}$, wherein $R_{12}$ and $R_{13}$ can be simultaneously or independently chosen from a hydrogen atom or an optionally substituted cycloalkyl as defined herein; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, m, n and p have the same definitions as those given previously with Formula (I).

Another preferred embodiment provides a compound of Formula (I), wherein $R_5$ is a —(CO)—$NR_{12}R_{13}$, wherein $R_{12}$ and $R_{13}$ can be simultaneously or independently chosen from a hydrogen atom or a heterocyclyl group as defined herein; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, m, n and p have the same definitions as those given previously with Formula (I).

Another preferred embodiment provides a compound of Formula (I), wherein $R_5$ is a —(CO—$NR_{12}R_{13}$, wherein $R_{12}$ and $R_{13}$ are linked together with the nitrogen atom to which they are covalently linked to form an optionally heterocyclyl group as defined herein; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, m, n and p have the same definitions as those given previously with Formula (I).

Another preferred embodiment provides a compound of Formula (I), wherein $R_5$ is a —(CO)—$NR_{12}R_{13}$, wherein $R_{12}$ and $R_{13}$ can be simultaneously or independently chosen from a hydrogen atom, a methyl, a ethyl, a isopropyl, a tert-butyl, a cyclopropyl, a cyclobutyl, a cyclopentyl, a cyclohexyl, it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, m, n and p have the same definitions as those given previously with Formula (I).

Another preferred embodiment provides a compound of Formula (I), wherein $R_5$ is a —$CF_3$; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $R_5$ is a cyano; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $R_5$ is a hydroxyl; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $R_5$ is an azido; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $R_5$ is a methyl; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $R_5$ is a hydrogen atom; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $R_5$ is an optionally substituted alkoxy as defined herein; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ is a methoxy; an ethoxy; an isopropoxy; a tert-butoxy; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $R_5$ is a hydroxyl, methoxy; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $R_5$ is a methoxy; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ can be an optionally substituted aryl as defined herein; an optionally substituted heteroaryl as defined herein; it being understood $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ is an optionally substituted aryl as defined herein; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ is an optionally substituted heteroaryl as defined herein; it being understood $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ can be a hydrogen atom; a halogen atom as defined herein; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ is a halogen atom as defined herein; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ is a chlorine; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ is a fluorine; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ is a —$NR_8R_{8'}$; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ is a —$NR_8R_{8'}$; wherein $R_5$ and $R_{8'}$ can be simultaneously or independently chosen from a hydrogen atom, an optionally substituted alkyl, an optionally substituted heterocyclyl as defined herein, an optionally substituted aryl as defined herein, an optionally substituted heteroaryl as defined herein, an optionally substituted benzyl as defined herein or $R_8$ and $R_{8'}$ are linked together with the nitrogen atom to which they are covalently linked to form an optionally substituted heterocyclyl group as defined herein; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ is a —$NR_8R_{8'}$; wherein $R_5$ and $R_8$, can be simultaneously or independently chosen from a hydrogen atom, an optionally substituted aryl as defined herein; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ is a —$NR_8R_{8'}$; wherein $R_5$ and $R_{8'}$ can be simultaneously or independently chosen from a hydrogen atom, an optionally substituted heteroaryl as defined herein; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ is a —$NR_8R_{8'}$; wherein $R_5$ and $R_{8'}$ can be simultaneously or independently chosen from a hydrogen atom, an optionally substituted benzyl as defined herein; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ is an optionally substituted heterocyclyl group as defined herein; it being understood $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, a further preferred embodiment provides a compound of Formula (I), wherein $R_5$ can be a hydrogen atom, a —(O—$CH_2CH_2$—)$_p$—$OR_{12}$; a —(O—$CH_2CH_2$—)$_p$—$NR_{12}R_{13}$; a —$NR_{12}$—($CH_2CH_2$—O)$_p$—$R_{13}$; a —$NR_{12}$—($C_2$-$C_{10}$)-alkyl-$NR_{12}R_{13}$; a —$NR_{12}$—($C_2$-$C_{10}$)-alkyl-$OR_{13}$; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, a further preferred embodiment provides a compound of Formula (I), wherein $R_5$ can be a hydrogen atom, a —(O—$CH_2CH_2$—)$_p$—ORB; a —(O—$CH_2CH_2$—)$_p$—$NR_8R_{8'}$; a —$NR_8$—($CH_2CH_2$—O)$_p$—$R_{8'}$; a —$NR_8$—($C_2$-$C_{10}$)-alkyl-$NR_8R_{8'}$; a —$NR_8$—($C_2$-$C_{10}$)-alkyl-$OR_{8'}$; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, a further preferred embodiment provides a compound of Formula (I), wherein $R_5$ can be a —(O—$CH_2CH_2$—)$_p$—$NR_8$; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, a further preferred embodiment provides a compound of Formula (I), wherein $R_5$ can be a hydrogen atom, a —(O—$CH_2CH_2$—)$_p$—$NR_8R_{8'}$; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, a further preferred embodiment provides a compound of Formula (I), wherein $R_5$ can be a hydrogen atom, a —$NR_8$—($CH_2CH_2$—O)$_p$—$R_{8'}$; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, a further preferred embodiment provides a compound of Formula (I), wherein $R_5$ can be a hydrogen atom, a —$NR_8$—($C_2$-$C_{10}$)-alkyl-$NR_8R_{8'}$; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, a further preferred embodiment provides a compound of Formula (I), wherein $R_5$ can be a hydrogen atom, a —$NR_8$—($C_2$-$C_{10}$)-alkyl-$OR_{8'}$; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ can be a hydrogen atom; a —$NR_2'R_{10}$; a —O—$R_{10}$; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ can be a hydrogen atom; a —O—$R_{10}$; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $R_5$ can be a hydrogen atom; a —$NR_2'R_{10}$; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Disclosed herein in a preferred embodiment is a compound of Formula (I), wherein $R_5$ is —$NR_2'R_{10}$; it being understood $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

A preferred embodiment provides a compound of Formula (I), wherein $R_5$ is —$NR_2'R_{10}$ wherein $R_2'$ can be a hydrogen atom, an optionally substituted alkyl as defined herein, an optionally substituted cycloalkyl as defined herein; and wherein $R_{10}$ can be an optionally substituted heteroaryl as defined herein, said optionally substituted heteroaryl being or not further substituted by one or more $R_{11}$, an optionally substituted aryl group as defined herein, said optionally substituted aryl group being or not further substituted by one or more $R_{11}$, an optionally substituted heterocyclyl group as defined herein, said optionally substituted heterocyclyl group being or not further substituted by one or more $R_{11}$; it being understood that $L_1$, $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

A preferred embodiment provides a compound of Formula (I), wherein $R_5$ is —$NR_2'R_{10}$ wherein $R_2'$ can be a hydrogen atom, an optionally substituted alkyl as defined herein, an optionally substituted cycloalkyl as defined herein; and wherein $R_{10}$ can be an optionally substituted heteroaryl as defined herein, said optionally substituted heteroaryl being or not further substituted by one or more $R_{11}$, an optionally substituted heterocyclyl group as defined herein, said optionally substituted heterocyclyl group being or not further substituted by one or more $R_{11}$; it being understood that $L_1$, $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

A preferred embodiment provides a compound of Formula (I), wherein $R_5$ is —$NR_2'R_{10}$ wherein $R_2'$ can be a hydrogen atom, an optionally substituted alkyl as defined herein, an optionally substituted cycloalkyl as defined herein; and wherein $R_{10}$ can be an optionally substituted aryl as defined herein, said optionally substituted aryl being or not further substituted by one or more $R_{11}$; it being understood that $L_1$, $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

A further preferred embodiment of the present disclosure provides a compound of Formula (I), wherein $R_5$ is —$NR_2'R_{10}$, wherein $R_2'$ can be a hydrogen atom; or a methyl or a cyclopropyl; and wherein $R_{10}$ can be an optionally substituted heteroaryl as defined herein, said optionally substituted heteroaryl being or not further substituted by one or more $R_{11}$; an optionally substituted heterocyclyl group as defined herein, said optionally substituted heterocyclyl group being or not further substituted by one or more $R_{11}$; it being understood that $L_1$, $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

In a further preferred embodiment the invention provide a compound of Formula (I), wherein $R_5$ is —$NR_2'R_{10}$, wherein $R_2'$ can be a hydrogen atom; or a methyl; or a cyclopropyl; and wherein $R_{10}$ is an optionally substituted aryl as defined herein, said optionally substituted aryl being or not further substituted by one or more $R_{11}$; it being understood that $L_1$, $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

In a further preferred embodiment the invention provide a compound of Formula (I), wherein $R_5$ is —$NR_2'R_{10}$, wherein $R_2'$ can be a hydrogen atom; or a methyl; or a cyclopropyl; and wherein $R_{10}$ is an optionally substituted phenyl, said optionally substituted phenyl being or not further substituted by one or more $R_{11}$; it being understood that $L_1$, $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

A further preferred embodiment the invention provide a compound of Formula (I), wherein $R_5$ can be —$NR_2'R_{10}$, wherein $R_2'$ can be a hydrogen atom; or a methyl; or a cyclopropyl; and wherein $R_{10}$ is an optionally substituted heteroaryl as defined herein, said optionally substituted heteroaryl being or not further substituted by one or more $R_{11}$; it being understood that $L_1$, $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

A further preferred embodiment of the invention provides a compound of Formula (I), wherein $R_5$ is —$NR_2'R_{10}$, wherein $R_2'$ can be a hydrogen atom, or a methyl; or a cyclopropyl; and wherein $R_{10}$ can be an optionally substituted pyrimidin-2-yl; or an optionally substituted pyrimidin-4-yl; or an optionally substituted pyrimidin-5-yl, said optionally substituted pyrimidin-2-yl; optionally substituted pyrimidin-4-yl; optionally substituted pyrimidin-5-yl being or not further substituted by one or more $R_{11}$; it being understood that $L_1$, $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

A further preferred embodiment of the invention provides a compound of Formula (I), wherein $R_5$ is —$NR_2'R_{10}$, wherein $R_2'$ is a hydrogen atom; and wherein $R_{10}$ is an optionally substituted heteroaryl as defined herein, said optionally substituted heteroaryl being or not further substituted by one or more $R_{11}$; it being understood that $L_1$, $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

A further preferred embodiment of the invention provides a compound of Formula (I), wherein $R_5$ is —$NR_2'R_{10}$, wherein $R_2'$ is a methyl; and wherein $R_{10}$ is an optionally substituted heteroaryl as defined herein, said optionally substituted heteroaryl being or not further substituted by one or more $R_{11}$; it being understood that $L_1$, $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

A further preferred embodiment of the invention provides a compound of Formula (I), wherein $R_5$ is-$NR_2'R_{10}$, wherein $R_2'$ is a cyclopropyl; and wherein $R_{10}$ is an optionally substituted heteroaryl as defined herein, said optionally substituted heteroaryl being or not further substituted by one or more $R_{11}$; it being understood that $L_1$, $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

A further preferred embodiment of the invention provides a compound of Formula (I), wherein $R_5$ is —$NR_2'R_{10}$, wherein $R_2'$ is a methyl; and wherein $R_{10}$ can be an optionally substituted pyrimidin-2-yl; an optionally substituted pyrimidin-4-yl; an optionally substituted pyrimidin-5-yl, said optionally substituted pyrimidin-2-yl; optionally substituted pyrimidin-4-yl; optionally substituted pyrimidin-5-yl being or not further substituted by one or more $R_{11}$; it being understood that $L_1$, $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

A further preferred embodiment of the invention provides a compound of Formula (I), wherein $R_5$ is —$NR_2'R_{10}$, wherein $R_2'$ is a cyclopropyl; and wherein $R_{10}$ can be an optionally substituted pyrimidin-2-yl; an optionally substituted pyrimidin-4-yl; an optionally substituted pyrimidin-5-yl, said optionally substituted pyrimidin-2-yl; optionally substituted pyrimidin-4-yl; optionally substituted pyrimidin-5-yl being or not further substituted by one or more $R_{11}$; it being understood that $L_1$, $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

A further preferred embodiment of the invention provides a compound of Formula (I), wherein $R_5$ is —$NR_2'R_{10}$, wherein $R_2'$ is a hydrogen atom; and wherein $R_{10}$ can be an optionally substituted pyrimidin-2-yl; an optionally substituted pyrimidin-4-yl; an optionally substituted pyrimidin-5-yl, said optionally substituted pyrimidin-2-yl; optionally substituted pyrimidin-4-yl; optionally substituted pyrimidin-5-yl being or not further substituted or not by one or more $R_{11}$; it being understood that $L_1$, $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

A further preferred embodiment of the invention provides a compound of Formula (I), wherein $R_5$ is —$NR_2'R_{10}$, wherein $R_2'$ is a hydrogen atom; and wherein $R_{10}$ can be an optionally substituted pyrimidin-2-yl; said optionally substituted pyrimidin-2-yl being or not further substituted by one or more $R_{11}$; it being understood that $L_1$, $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

A further preferred embodiment of the invention provides a compound of Formula (I), wherein $R_5$ is —$NR_2'R_{10}$, wherein $R_2'$ is a hydrogen atom; and wherein $R_{10}$ is a pyrimidin-2-yl; said pyrimidin-2-yl being or not further substituted by one or more $R_{11}$; it being understood that $L_1$, $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

Yet, another preferred embodiment provides a compound of Formula (I), wherein when $R_5$ is —$NR_2'R_{10}$ or —$OR_{10}$ then $R_{10}$ can be an optionally substituted heteroaryl as defined herein, said optionally substituted heteroaryl being or not further substituted by one or more $R_{11}$; an optionally substituted heterocyclyl group as defined herein, said optionally substituted heterocyclyl group being or not further substituted by one or more $R_{11}$; it being understood that $L_1$, $R_1$, $R_2$, $R_{2'}$, $R_3$, $R_4$, $R_5$, $R_6$, $R_7$, $R_8$, $R_{8'}$, $R_9$, $R_{11}$, $R_{12}$, $R_{13}$, m, n and p have the same definitions as those given previously with Formula (I).

Yet, another preferred embodiment provides a compound of Formula (I), wherein when $R_5$ is —$NR_2'R_{10}$ or —$OR_{10}$ then $R_{10}$ can be an optionally substituted heteroaryl as defined herein, said optionally substituted heteroaryl being or not further substituted by one or more $R_{11}$; it being understood that $L_1$, $R_1$, $R_2$, $R_{2'}$, $R_3$, $R_4$, $R_5$, $R_6$, $R_7$, $R_8$, $R_{8'}$, $R_9$, $R_{11}$, $R_{12}$, $R_{13}$, m, n and p have the same definitions as those given previously with Formula (I).

Yet, another preferred embodiment provides a compound of Formula (I), wherein when $R_5$ is —$NR_2'R_{10}$ or —$OR_{10}$ then $R_{10}$ can be an optionally substituted aryl as defined herein, said optionally substituted aryl being or not further substituted by one or more $R_{11}$; it being understood that $L_1$, $R_1$, $R_2$, $R_{2'}$, $R_3$, $R_4$, $R_5$, $R_6$, $R_7$, $R_8$, $R_{8'}$, $R_9$, $R_{11}$, $R_{12}$, $R_{13}$, m, n and p have the same definitions as those given previously with Formula (I).

A further preferred embodiment provides a compound of Formula (I), wherein when $R_5$ is —$NR_2'R_{10}$ or —$OR_{10}$ then $R_{10}$ can be an optionally substituted pyrimidin-2-yl; an optionally substituted pyrimidin-4-yl; an optionally substituted pyrimidin-5-yl; it being understood that $L_1$, $R_1$, $R_2$, $R_{2'}$, $R_3$, $R_4$, $R_5$, $R_6$, $R_7$, $R_8$, $R_{8'}$, $R_9$, $R_{11}$, $R_{12}$, $R_{13}$, m, n and p have the same definitions as those given previously with Formula (I).

A further preferred embodiment provides a compound of Formula (I), wherein when $R_5$ is —$NR_2'R_{10}$ or —$OR_{10}$ then $R_{10}$ can be a pyrimidin-2-yl; pyrimidin-4-yl; pyrimidin-5-yl; it being understood that $L_1$, $R_1$, $R_2$, $R_{2'}$, $R_3$, $R_4$, $R_5$, $R_6$, $R_7$, $R_8$, $R_{8'}$, $R_9$, $R_{11}$, $R_{12}$, $R_{13}$, m, n and p have the same definitions as those given previously with Formula (I).

A further preferred embodiment provides a compound of Formula (I), wherein when $R_5$ is —$NR_2'R_{10}$ or —$OR_{10}$ then $R_{10}$ is an optionally substituted pyrimidin-2-yl; it being understood $L_1$, $R_1$, $R_2$, $R_{2'}$, $R_3$, $R_4$, $R_5$, $R_6$, $R_7$, $R_8$, $R_{8'}$, $R_9$, $R_{11}$, $R_{12}$, $R_{13}$, m, n and p have the same definitions as those given previously with Formula (I).

A further preferred embodiment provides a compound of Formula (I), wherein when $R_5$ is —$NR_2'R_{10}$ or —$OR_{10}$ then $R_{10}$ is a pyrimidin-2-yl; it being understood that $L_1$, $R_1$, $R_2$, $R_{2'}$, $R_3$, $R_4$, $R_5$, $R_6$, $R_7$, $R_8$, $R_{8'}$, $R_9$, $R_{11}$, $R_{12}$, $R_{13}$, m, n and p have the same definitions as those given previously with Formula (I).

A further preferred embodiment provides a compound of formula (I), wherein $R_{10}$ can be an optionally substituted heterocyclyl, an optionally substituted aryl, or an optionally substituted heteraryl, said optionally substituted heterocyclyl, optionally substituted aryl, or optionally substituted heteraryl, being or not further substituted with at least one $R_{11}$.

A further preferred embodiment provides a compound of formula (I), wherein $R_{10}$ can be a heterocyclyl, an aryl, or a heteraryl, said heterocyclyl, aryl, or heteraryl, being or not further substituted with at least one $R_{11}$.

Yet, another preferred embodiment provides a compound of Formula (I), wherein $R_{11}$ can be an optionally substituted aryl as defined herein; an optionally substituted heteroaryl as defined herein; an optionally substituted heterocyclyl group as defined herein; it being understood that $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I).

Yet, another preferred embodiment provides a compound of Formula (I), wherein $R_{11}$ is an optionally substituted aryl as defined herein; it being understood that $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I).

Yet, another preferred embodiment provides a compound of Formula (I), wherein $R_{11}$ is an optionally substituted heteroaryl as defined herein it being understood that $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I).

Yet, another preferred embodiment provides a compound of Formula (I), wherein $R_{11}$ is an optionally substituted heterocyclyl group as defined herein; it being understood that $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I).

A further preferred embodiment provides a compound of Formula (I), wherein $R_{11}$ can be an optionally substituted pyridin-2-yl; an optionally substituted pyridin-3-yl; an optionally substituted pyridin-4-yl; it being understood $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I).

A further preferred embodiment provides a compound of Formula (I), wherein $R_{11}$ can be a pyridin-2-yl; a pyridin-3-yl; a pyridin-4-yl; it being understood $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I).

A further preferred embodiment provides a compound of Formula (I), wherein $R_{11}$ is an optionally substituted pyridin-3-yl; it being understood that $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I).

A further preferred embodiment provides a compound of Formula (I), wherein $R_{11}$ is a pyridin-3-yl; it being understood that $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I).

Yet, a further preferred embodiment provides a compound of Formula (I), wherein $R_{11}$ can be chosen from a hydrogen atom; a —(O—CH$_2$CH$_2$—)$_p$—OR$_8$; a —(O—CH$_2$CH$_2$—)$_p$—NR$_8$R$_{8'}$; a —NR$_8$(—CH$_2$CH$_2$—O)$_p$—R$_{8'}$; a —NR$_8$—(C$_2$-C$_8$)-alkyl-NR$_8$R$_{8'}$; a —NR$_8$—(C$_2$-C$_8$)-alkyl-OR$_{8'}$; it being understood that $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I).

In another preferred embodiment, a compound according to Formula (I) can be provided wherein $R_{11}$ can be chosen from a hydrogen atom; a halogen atom as defined herein; an optionally substituted alkyl as defined herein, said substituted alkyl being preferably substituted by one or more halogen atom(s); an optionally substituted alkoxy as defined herein; a hydroxyl; it being understood that $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I).

In another preferred embodiment, a compound according to Formula (I) can be provided wherein $R_{11}$ can be chosen from a hydrogen atom; a fluorine; a chlorine; a methyl; a —CF$_3$; a cyano; an azido; a hydroxyl; a methoxy; an ethoxy; an isopropoxy; a tert-butoxy; it being understood that $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I).

In another preferred embodiment, a compound according to Formula (I) can be provided wherein $R_{11}$ can be chosen from a hydrogen atom; a fluorine; a chlorine; a methyl; a hydroxyl; a methoxy; it being understood that $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I).

In another preferred embodiment, a compound according to Formula (I) can be provided wherein $R_{11}$ can be chosen from a hydrogen atom; a fluorine; a chlorine; it being understood that $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I).

In another preferred embodiment, a compound according to Formula (I) can be provided wherein $R_{11}$ can be chosen from a hydrogen atom; an optionally substituted alkoxy as defined herein; it being understood that $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I).

In another preferred embodiment, a compound according to Formula (I) can be provided wherein $R_{11}$ can be chosen from a hydrogen atom; a hydroxyl, a methoxy, an ethoxy, an isopropoxy; a tert-butoxy; it being understood that $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I). In another preferred embodiment, a compound according to Formula (I) can be provided wherein $R_{11}$ can be chosen from a hydrogen atom; a hydroxyl, a methoxy; it being understood that $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I).

In another preferred embodiment, a compound according to Formula (I) can be provided wherein $R_{11}$ can be a hydroxyl; it being understood that $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I). In another preferred embodiment, a compound according to Formula (I) can be provided wherein $R_{11}$ can be a methoxy; it being understood that $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I).

A further preferred embodiment provides a compound of formula (I), wherein m can be 1.

A further preferred embodiment provides a compound of formula (I), wherein m can be 2.

Yet, another preferred embodiment provides a compound of Formula (I), wherein $L_1$ can be a single bond; a carbonyl; an optionally substituted alkyl as defined herein; an optionally substituted alkenyl as defined herein; an optionally substituted alkynyl as defined herein; and $R_1$ is an optionally substituted aryl as defined herein; it being understood that $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $L_1$ can be a single bond; a carbonyl; an optionally substituted alkyl as defined herein; and $R_1$ is an optionally substituted aryl as defined herein; it being understood that $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $L_1$ can be a single bond; an optionally substituted alkyl as defined herein; and $R_1$ is an optionally substituted heteroaryl as defined herein; it being understood that $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $L_1$ can be a single bond; an optionally substituted alkyl as defined herein; and $R_1$ is an optionally substituted aryl as defined herein; it being understood that $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_1$ is an optionally substituted heteroaryl as defined herein; it being understood that $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $L_1$ can be a single bond a carbonyl; a methylene (—$CH_2$—); and $R_1$ is an optionally substituted aryl as defined herein; it being understood that $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_1$ can be an optionally substituted phenyl or an optionally substituted 3-methylbenzene-1,4-diyl; it being understood that $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a single bond; and $R_1$ can be an optionally substituted phenyl or an optionally substituted 3-methylbenzene-1,4-diyl; it being understood that $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a carbonyl; and $R_1$ is an optionally substituted phenyl; it being understood that $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is an optionally substituted alkyl as defined herein; and $R_1$ is an optionally substituted phenyl; it being understood that $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a methylene (—$CH_2$—); and $R_1$ is an optionally substituted phenyl; it being understood that $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a methylene (—$CH_2$—); and $R_1$ is an optionally substituted heteroaryl as defined herein; it being understood that $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $L_1$ can be a single bond; a carbonyl; an optionally substituted alkyl as defined herein; an optionally substituted alkenyl as defined herein; an optionally substituted alkynyl as defined herein; and $R_1$ is an optionally substituted aryl and $R_5$ is a halogen atom as defined herein; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_1$ is an optionally substituted aryl and $R_5$ is a halogen atom as defined herein; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_1$ is an optionally substituted aryl as defined herein and $R_5$ is a fluorine or a chlorine; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_1$ is an optionally substituted phenyl and $R_5$ can be a fluorine or a chlorine; it being understood $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_1$ is an optionally substituted phenyl and $R_5$ is a chlorine; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bound; a carbonyl; a methylene (—$CH_2$—); and $R_1$ is an optionally substituted phenyl and $R_5$ is a fluorine; it being understood $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $L_1$ can be a single bond; a carbonyl; an optionally substituted alkyl as defined herein; and $R_1$ is an optionally substituted aryl as defined herein and $R_5$ is an optionally substituted alkoxy as defined herein; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a methylene (—$CH_2$—); and $R_1$ is an optionally substituted aryl as defined herein and $R_5$ is an optionally substituted alkoxy as defined herein; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a methylene (—$CH_2$—); and $R_1$ is an optionally substituted phenyl and $R_5$ is an optionally substituted alkoxy as defined herein; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a single bond; and $R_1$ is an optionally substituted aryl as defined herein and $R_5$ is an optionally substituted alkoxy as defined herein; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a single bond; and $R_1$ is an optionally substituted phenyl and $R_5$ is an optionally substituted alkoxy as defined herein; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a carbonyl; and $R_1$ is an optionally substituted aryl as defined herein and $R_5$ is an optionally substituted alkoxy as defined herein; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a carbonyl; and $R_1$ is an optionally substituted phenyl and $R_5$ is an optionally substituted alkoxy as defined herein; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_1$ is an optionally substituted aryl as defined herein and $R_5$ can be a hydroxyl; a methoxy; an ethoxy; an isopropoxy; a tert-butoxy; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a methylene (—$CH_2$—); and $R_1$ is an optionally substituted aryl as defined herein and $R_5$ is a methoxy; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a methylene (—$CH_2$—); and $R_1$ is an optionally substituted phenyl and $R_5$ is a hydroxyl; a methoxy; an ethoxy; an isopropoxy; a tert-butoxy; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a methylene (—$CH_2$—); and $R_1$ is an optionally substituted phenyl and $R_5$ is a hydroxyl; a methoxy; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a methylene (—$CH_2$—); and $R_1$ is an optionally substituted phenyl and $R_5$ is a methoxy; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a single bond; and $R_1$ is an optionally substituted phenyl and $R_5$ is a methoxy; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a carbonyl; and $R_1$ is an optionally substituted phenyl and $R_5$ is a methoxy; it being understood that $R_2$, $R_{2'}$, $R_3$, $R_4$, $R_6$, $R_7$, $R_8$, $R_{8'}$, $R_9$, $R_{10}$, $R_{11}$ 1, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_1$ is an optionally substituted aryl as defined herein and $R_5$ is a hydroxyl; it being understood $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a methylene (—$CH_2$—); and $R_1$ is an optionally substituted aryl as defined herein and $R_5$ is a hydroxyl; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a methylene (—$CH_2$—); and $R_1$ is an optionally substituted phenyl and $R_5$ is a hydroxyl; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a carbonyl; and $R_1$ is an optionally substituted aryl as defined herein and $R_5$ is a hydroxyl; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a carbonyl; and $R_1$ is an optionally substituted phenyl and $R_5$ is a hydroxyl; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a single bond; and $R_1$ is an optionally substituted aryl as defined herein and $R_5$ is a hydroxyl; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a single bond; and $R_1$ is an optionally substituted phenyl and $R_5$ is a hydroxyl; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_1$ is an optionally substituted aryl as defined herein and $R_5$ is an optionally substituted fluoroalkyl as defined herein; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_1$ is an optionally substituted phenyl as defined herein and $R_5$ is an optionally substituted fluoroalkyl as defined herein; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; and $R_1$ is an optionally substituted phenyl as defined herein and $R_5$ is an optionally substituted fluoroalkyl as defined herein; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a carbonyl; and $R_1$ is an optionally substituted phenyl as defined herein and $R_5$ is an optionally substituted fluoroalkyl as defined herein; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a methylene (—$CH_2$—); and $R_1$ is an optionally substituted phenyl as defined herein and $R_5$ is an optionally substituted fluoroalkyl as defined herein; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_1$ is an optionally substituted aryl as defined herein and $R_5$ is a —$CF_3$; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_1$ is an optionally substituted phenyl as defined herein and $R_5$ is a —$CF_3$; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; and $R_1$ is an optionally substituted phenyl as defined herein and $R_5$ is a —$CF_3$; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a carbonyl; and $R_1$ is an optionally substituted phenyl as defined herein and $R_5$ is a —$CF_3$; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a methylene (—$CH_2$—); and $R_1$ is an optionally substituted phenyl as defined herein and $R_5$ is a —$CF_3$; it being understood that $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $L_1$ can be a single bond; a carbonyl; an optionally substituted alkyl as defined herein; an optionally substituted alkenyl as defined herein; an optionally substituted alkynyl as defined herein; and $R_2$ and $R_3$ can be independently or simultaneously chosen from a hydrogen atom, an optionally substituted alkyl as defined herein, an optionally substituted cycloalkyl as defined herein, an optionally substituted heterocyclyl group as defined herein, or $R_2$ and $R_3$ are linked together with the nitrogen atom to which they are covalently linked to form an optionally substituted heterocyclyl group as defined herein; it being understood that $R_1$, $R_{2'}$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_2$ and $R_3$ can be simultaneously or independently chosen from a hydrogen atom; an optionally substituted alkyl as defined herein; or an optionally substituted cycloalkyl as defined herein it being understood that $R_1$, $R_{2'}$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_2$ and $R_3$ can be simultaneously or independently chosen from a hydrogen atom; an optionally substituted alkyl as defined herein; it being understood that $R_1$, $R_{2'}$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_2$ and $R_3$ can be simultaneously or independently chosen from a hydrogen atom; an optionally substituted cycloalkyl as defined herein; it being understood that $R_1$, $R_{2'}$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_2$ and $R_3$ can be simultaneously or independently chosen from a hydrogen atom; or an optionally substituted heterocyclyl group as defined herein; it being understood that $R_1$, $R_{2'}$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_2$ and $R_3$ are linked together with the nitrogen atom to which they are covalently linked to form an optionally substituted heterocyclyl group as defined herein; it being understood that $R_1$, $R_{2'}$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a methylene (—$CH_2$—); and $R_2$ and $R_3$ can be simultaneously or independently chosen from a hydrogen atom; or an optionally substituted heterocyclyl group as defined herein; it being understood that $R_1$, $R_{2'}$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a methylene (—$CH_2$—); and $R_2$ and $R_3$ can be simultaneously or independently chosen from a hydrogen atom; or an optionally substituted alkyl as defined herein; it being understood that $R_1$, $R_{2'}$, $R_4$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a methylene (—$CH_2$—); and $R_2$ and $R_3$ can be simultaneously or independently chosen from a hydrogen atom; or an optionally substituted cycloalkyl as defined herein; it being understood that $R_1$, $R_{2'}$, $R_4$, $R_5$, $R_6$, $R_7$, $R_8$, $R_8'$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a methylene (—$CH_2$—); and $R_2$ and $R_3$ can be linked together with the nitrogen atom to which they are covalently linked to form an optionally substituted heterocyclyl group as defined herein; it being understood that $R_1$, $R_2'$, $R_4$, $R_5$, $R_6$, $R_7$, $R_8$, $R_8'$, $R_9$, $R_{10}$, $R_{11}$, $R_{12}$, $R_{13}$, m, n and p have the same definitions as those given previously with Formula (I).

In another preferred embodiment provides a compound of Formula (I), wherein $L_1$ can be a single bond; a carbonyl; a methylene (—$CH_2$—); and $R_2$ and $R_3$ can be simultaneously or independently chosen from a hydrogen atom or a tert-butyl; it being understood that $R_1$, $R_2'$, $R_4$, $R_5$, $R_6$, $R_7$, $R_8$, $R_8'$, $R_9$, $R_{10}$, $R_{11}$, $R_{12}$, $R_{13}$, m, n and p have the same definitions as those given previously with Formula (I).

In another preferred embodiment provides a compound of Formula (I), wherein $L_1$ is a methylene (—$CH_2$—); and $R_2$ and $R_3$ can be simultaneously or independently chosen from a hydrogen atom or a tert-butyl; it being understood that $R_1$, $R_2'$, $R_4$, $R_5$, $R_6$, $R_7$, $R_8$, $R_8'$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_2$ and $R_3$ can be simultaneously or independently chosen from a hydrogen atom or a 1-methylpiperidin-4-yl; it being understood that $R_1$, $R_2'$, $R_4$, $R_5$, $R_6$, $R_7$, $R_8$, $R_8'$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a methylene (—$CH_2$—); and $R_2$ and $R_3$ can be simultaneously or independently chosen from a hydrogen atom or a 1-methylpiperidin-4-yl; it being understood that $R_1$, $R_2'$, $R_4$, $R_5$, $R_6$, $R_7$, $R_8$, $R_8'$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_2$ and $R_3$ are linked together with the nitrogen atom to which they are covalently linked to form a pyrrolidin-1-yl; it being understood that $R_1$, $R_2'$, $R_4$, $R_5$, $R_6$, $R_7$, $R_8$, $R_8'$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a methylene (—$CH_2$—); and $R_2$ and $R_3$ are linked together with the nitrogen atom to which they are covalently linked to form a pyrrolidin-1-yl; it being understood that $R_1$, $R_2'$, $R_4$, $R_5$, $R_6$, $R_7$, $R_8$, $R_8'$, $R_9$, $R_{10}$, $R_{11}$, $R_{12}$, $R_{13}$, m, n and p have the same definitions as those given previously with Formula (I).

Yet, in another preferred embodiment provides a compound of Formula (I), wherein $L_1$ can be a single bond, a carbonyl, a methylene (—$CH_2$—); and $R_4$ can be a hydrogen atom; a halogen atom as defined herein; an optionally substituted alkyl as defined herein, preferably said an optionally substituted alkyl being substituted by one or more halogen atom as defined herein; an optionally substituted alkoxy as defined herein; a hydroxyl; a carboxyl; a cyano; an azido; a —$CF_3$; a —$NR_{12}R_{13}$; a —$COOR_7$; a —(CO)—$NR_{12}R_{13}$; it being understood that $R_1$, $R_2$, $R_2'$, $R_3$, $R_5$, $R_6$, $R_7$, $R_8$, $R_8'$, $R_9$, $R_{10}$, $R_{11}$, $R_{12}$, $R_{13}$, m, n and p have the same definitions as those given previously with Formula (I).

Yet, in another preferred embodiment provides a compound of Formula (I), wherein $L_1$ can be a single bond; a carbonyl; a methylene (—$CH_2$—); and $R_4$ can be a hydrogen atom; a halogen atom as defined herein; an optionally substituted alkyl as defined herein; an optionally substituted alkoxy as defined herein; a hydroxyl; a carboxyl; a cyano; an azido; a —$CF_3$; a —$NR_8R_8'$; a —$COOR_7$; a —(CO)—$NR_8R_8'$; it being understood that $R_1$, $R_2$, $R_2'$, $R_3$, $R_5$, $R_6$, $R_7$, $R_8$, $R_8'$, $R_9$, $R_{10}$, $R_{11}$, $R_{12}$, $R_{13}$, m, n and p have the same definitions as those given previously with Formula (I).

Yet, in another preferred embodiment provides a compound of Formula (I), wherein $L_1$ can be a single bond; a carbonyl; a methylene (—$CH_2$—); and $R_4$ can be a hydrogen atom; a halogen atom as defined herein; an optionally substituted alkyl as defined herein; an optionally substituted alkoxy as defined herein; a hydroxyl; a carboxyl; a cyano; an azido; a —$CF_3$; —$NR_8R_8'$; a —(CO)—$NR_8R_8'$; it being understood that $R_1$, $R_2$, $R_2'$, $R_3$, $R_5$, $R_6$, $R_7$, $R_8$, $R_8'$, $R_9$, $R_{10}$, $R_{11}$, $R_{12}$, $R_{13}$, m, n and p have the same definitions as those given previously with Formula (I).

Yet, in another preferred embodiment provides a compound of Formula (I), wherein $L_1$ can be a single bond; a carbonyl; a methylene (—$CH_2$—); and $R_4$ can be a hydrogen atom; a halogen atom as defined herein; an optionally substituted alkyl as defined herein; an optionally substituted alkoxy as defined herein; a hydroxyl; a carboxyl; a cyano; an azido; a —$CF_3$; it being understood that $R_1$, $R_2$, $R_2'$, $R_3$, $R_5$, $R_6$, $R_7$, $R_8$, $R_8'$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_4$ is an optionally substituted fluoroalkyl as defined herein; it being understood that $R_1$, $R_2$, $R_2'$, $R_3$, $R_5$, $R_6$, $R_7$, $R_8$, $R_8'$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_4$ is a —$CF_3$; it being understood that $R_1$, $R_2$, $R_2'$, $R_3$, $R_5$, $R_6$, $R_7$, $R_8$, $R_8'$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_4$ is a methyl; it being understood that $R_1$, $R_2$, $R_2'$, $R_3$, $R_5$, $R_6$, $R_7$, $R_8$, $R_8'$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_4$ is a hydrogen atom; it being understood that $R_1$, $R_2$, $R_2'$, $R_3$, $R_5$, $R_6$, $R_7$, $R_8$, $R_8'$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_4$ is an optionally substituted alkoxy as defined herein; it being understood that $R_1$, $R_2$, $R_2'$, $R_3$, $R_5$, $R_6$, $R_7$, $R_8$, $R_8'$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_4$ can be a hydroxyl; a methoxy; an ethoxy; an isopropoxy; a tert-butoxy; it being understood that $R_1$, $R_2$, $R_2'$, $R_3$, $R_5$, $R_6$, $R_7$, $R_8$, $R_8'$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_4$ is a methoxy; it being understood that $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and $R_4$ is a hydroxyl; it being understood that $R_1$, $R_2$, $R_{2'}$, $R_3$, $R_5$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, a further preferred embodiment provides a compound of Formula (I), wherein $L_1$ can be a single bond; a carbonyl; a methylene (—$CH_2$—); and wherein $R_5$ can be a hydrogen atom; a halogen atom as defined herein; an optionally substituted alkyl as defined herein, preferably said optionally substituted alkyl being substituted by one or more halogen atom as defined herein; an optionally substituted alkoxy as defined herein; a hydroxyl; a carboxyl; a cyano; an azido; a —$CF_3$; —$NR_8R_{8'}$, a $C_{00147}$; a —(CO)—$NR_{12}R_{13}$; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, a further preferred embodiment provides a compound of Formula (I), wherein $L_1$ can be a single bond; a carbonyl; a methylene (—$CH_2$—); and wherein $R_5$ can be a hydrogen atom; a halogen atom as defined herein; an optionally substituted alkyl as defined herein; an optionally substituted alkoxy as defined herein; a hydroxyl; a carboxyl; a cyano; an azido; a —$CF_3$; a —$NR_8R_{8'}$; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is a hydrogen atom; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is a methyl; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is a fluorine or a chlorine; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a methylene (—$CH_2$—); and wherein $R_5$ is a fluorine or a chlorine; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a single bond; and wherein $R_5$ is a fluorine or a chlorine; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a carbonyl; and wherein $R_5$ is a fluorine or a chlorine; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is a chlorine; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is a fluorine; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a single bond; and wherein $R_5$ is a chlorine; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a single bond; and wherein $R_5$ is a fluorine; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a carbonyl; and wherein $R_5$ is a chlorine; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a carbonyl; and wherein $R_5$ is a fluorine; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a methylene (—$CH_2$—); and wherein $R_5$ is a chlorine; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a methylene (—$CH_2$—); and wherein $R_5$ is a fluorine; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $L_1$ can be a single bond; a carbonyl; a methylene (—$CH_2$—); and wherein $R_5$ is an optionally substituted alkoxy as defined herein; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Yet, another preferred embodiment provides a compound of Formula (I), wherein $L_1$ can be a single bond; a carbonyl; a methylene (—$CH_2$—); and wherein $R_5$ is a hydroxyl; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a single bond; and wherein $R_5$ is a hydroxyl; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a carbonyl; and wherein $R_5$ is a hydroxyl; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a methylene (—$CH_2$—); and wherein $R_5$ is a hydroxyl; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ can be a methoxy, an ethoxy, an isopropoxy; a tert-butoxy; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a methylene (—$CH_2$—); and wherein $R_5$ is a methoxy; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a bond; and wherein $R_5$ is a methoxy; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ is a carbonyl; and wherein $R_5$ is a methoxy; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is an optionally substituted fluoroalkyl as defined herein, it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a methylene (—$CH_2$—); and wherein $R_5$ is an optionally substituted fluoroalkyl as defined herein, it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is a —$CF_3$ it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is a cyano it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is an azido it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is an optionally substituted heteroaryl as defined herein; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is an optionally substituted aryl as defined herein; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is an optionally substituted phenyl; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is a —$NR_8R_{8'}$; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ can be a —$NR_9'R_{10}$; or a —O—$R_{10}$; it being understood that $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is a —O—$R_{10}$ and wherein $R_{10}$ is an optionally substituted aryl as defined herein, said optionally substituted aryl being or not further substituted by at least one $R_{11}$; it being understood that $R_1$, $R_2$, $R_{2'}$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is a —O—$R_{10}$ and wherein $R_{10}$ is an optionally substituted phenyl, said optionally substituted phenyl being or not further substituted by at least one $R_{11}$; it being understood that $R_1$, $R_2$, $R_{2'}$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is a —O—$R_{10}$ and wherein $R_{10}$ is an optionally substituted heteroaryl as defined herein, said optionally substituted heteroaryl being or not further substituted by at least one $R_{11}$; it being understood that $R_1$, $R_2$, $R_{2'}$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

Another preferred embodiment provides a compound of Formula (I), wherein $L_1$ is a single bond; and wherein $R_5$ is —$OR_{10}$; wherein $R_{10}$ is an optionally heteroaryl as defined herein, said optionally substituted heteroaryl being or not further substituted by at least one $R_{11}$; it being understood that $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

Another preferred embodiment provides a compound of Formula (I), wherein $L_1$ is a single bond; and wherein $R_5$ is —$OR_{10}$; wherein $R_{10}$ is an optionally aryl as defined herein, said optionally substituted aryl being or not further substituted by at least one $R_{11}$; it being understood that $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is a —$NR_2'R_{10}$, wherein $R_2'$ can be a hydrogen atom; a methyl; a cyclopropyl and wherein $R_{10}$ is an optionally substituted aryl as defined herein, said optionally substituted aryl being or not further substituted by at least one $R_{11}$; it being understood that $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is a —$NR_2'R_{10}$; wherein $R_2'$ can be a hydrogen atom; a methyl; a cyclopropyl and wherein $R_{10}$ is an optionally substituted phenyl, said optionally substituted phenyl being or not further substituted by at least one $R_{11}$; it being understood that $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is a —$NR_2'R_{10}$, wherein $R_2'$ can be a hydrogen atom; a methyl; a cyclopropyl and wherein $R_{10}$ is an optionally substituted heteroaryl as defined herein, said optionally substituted heteroaryl being or not further substituted by at least one $R_{11}$; it being understood that $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is a —$NR_2'R_{10}$, wherein $R_2'$ is a hydrogen atom and wherein $R_{10}$ is an optionally substituted aryl as defined herein, said optionally substituted aryl being or not further substituted by at least one $R_{11}$; it being understood that $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is a —$NR_2'R_{10}$, wherein $R_2'$ is a hydrogen atom and wherein $R_{10}$ is an optionally substituted heteroaryl as defined herein, said optionally substituted heteroaryl being or not further substituted by at least one $R_{11}$; it being understood that $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

Another preferred embodiment provides a compound of Formula (I), wherein $L_1$ is a single bond; and wherein $R_5$ is —$NR_2'R_{10}$; wherein $R_2'$ can be a hydrogen atom; a methyl; a cyclopropyl; and wherein $R_{10}$ is an optionally heteroaryl as defined herein, said optionally substituted heteroaryl being or not further substituted by at least one $R_{11}$; it being understood that $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

Another preferred embodiment provides a compound of Formula (I), wherein $L_1$ is a single bond; and wherein $R_5$ is —$NR_2'R_{10}$; wherein $R_2'$ is a hydrogen atom; and wherein $R_{10}$ is an optionally heteroaryl as defined herein, said optionally substituted heteroaryl being or not further substituted by at least one $R_{11}$; it being understood that $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

Another preferred embodiment provides a compound of Formula (I), wherein $L_1$ can be a single bond; a carbonyl; a methylene (—$CH_2$—); and wherein $R_5$ is a —$NR_2'R_{10}$; wherein $R_2'$ is a hydrogen atom; and wherein $R_{10}$ can be an optionally substituted pyrimidin-2-yl, an optionally substituted pyrimidin-4-yl, an optionally substituted pyrimidin-5-yl, said optionally substituted pyrimidin-2-yl; optionally substituted pyrimidin-4-yl; optionally substituted pyrimidin-5-yl being or not further substituted by at least one $R_{11}$; it being understood that $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

Another preferred embodiment provides a compound of Formula (I), wherein $L_1$ is a single bond; and wherein $R_5$ is a —$NR_2'R_{10}$, wherein $R_2'$ is a hydrogen atom; and wherein $R_{10}$ can be an optionally substituted pyrimidin-2-yl, an optionally substituted pyrimidin-4-yl, an optionally substituted pyrimidin-5-yl said optionally substituted pyrimidin-2-yl; optionally substituted pyrimidin-4-yl; optionally substituted pyrimidin-5-yl being or not further substituted by at least one $R_{11}$; it being understood that $R_1$, $R_2$, $R_3$, $R_4$, $R_6$, $R_7$, $R_8$, $R_{8'}$, $R_9$, $R_{11}$, $R_{12}$, $R_{13}$, m, n and p have the same definitions as those given previously with Formula (I).

Another preferred embodiment provides a compound of Formula (I), wherein $L_1$ is a single bond; and wherein when $R_5$ is —$NR_2'R_{10}$ or —$OR_{10}$ then $R_{10}$ can be an optionally substituted heteroaryl as defined herein, said optionally substituted heteroaryl being or not further substituted by at least one $R_{11}$; it being understood that $R_1$, $R_2$, $R_{2'}$, $R_3$, $R_4$, $R_5$, $R_6$, $R_7$, $R_8$, $R_{8'}$, $R_9$, $R_{11}$, $R_{12}$, $R_{13}$, m, n and p have the same definitions as those given previously with Formula (I).

Another preferred embodiment provides a compound of Formula (I), wherein $L_1$ is a single bond; and wherein when $R_5$ is —$NR_2'R_{10}$ or —$OR_{10}$ then $R_{10}$ can be an optionally substituted pyrimidin-2-yl; an optionally substituted pyrimidin-4-yl; an optionally substituted pyrimidin-5-yl, said optionally substituted pyrimidin-2-yl; optionally substituted pyrimidin-4-yl; optionally substituted pyrimidin-5-yl being or not further substituted by at least one $R_{11}$; it being understood that $R_1$, $R_2$, $R_{2'}$, $R_3$, $R_4$, $R_5$, $R_6$, $R_7$, $R_8$, $R_{8'}$, $R_9$, $R_{11}$, $R_{12}$, $R_{13}$, m, n and p have the same definitions as those given previously with Formula (I).

Another preferred embodiment provides a compound of Formula (I), wherein $L_1$ is a single bond; and wherein $R_{11}$ can be an optionally aryl as defined herein; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I).

Another preferred embodiment provides a compound of Formula (I), wherein $L_1$ is a single bond; and wherein $R_{11}$ can be an optionally heteroaryl as defined herein; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I).

Another preferred embodiment provides a compound of Formula (I), wherein $L_1$ is a single bond; and wherein $R_{11}$ can be an optionally substituted pyridin-2-yl; an optionally substituted pyridin-3-yl or an optionally substituted pyridin-4-yl; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{12}$, $R_{13}$, m, n and p have the same definitions as those given previously with Formula (I).

Another preferred embodiments provides a compound of Formula (I), wherein n can take any one of the values 0, 1, 2, 3 or 4, preferably 0, 1, 2 or 3, more preferably 0, 1 or 2, still more preferably 0 or 1 and m can be 1 or 2, preferably 2; it being understood that $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

Another preferred embodiments provides a compound of Formula (I), wherein n can take any one of the values 0, 1, 2, 3 or 4, preferably 0, 1, 2 or 3, more preferably 0, 1 or 2, still more preferably 0 or 1 and m is 1; it being understood that $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

Another preferred embodiments provides a compound of Formula (I), wherein n can take any one of the values 0, 1, 2, 3 or 4, preferably 0, 1, 2 or 3, more preferably 0, 1 or 2, still more preferably 0 or 1 and m is 2; it being understood that $L_1$, $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

Yet, another preferred embodiment provides a compound of Formula (I), wherein $L_1$ is a single bond; and wherein n can take any one of the values 0, 1, 2, 3, preferably 0, 1, 2 or 3, more preferably 0, 1 or 2, still more preferably 0 or 1 and m is 1; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

Yet, another preferred embodiment provides a compound of Formula (I), wherein $L_1$ is a single bond; and wherein n can take any one of the values 0, 1, 2, 3 or preferably 0, 1, 2 or 3, more preferably 0, 1 or 2, still more preferably 0 or 1 and m is 2; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

Yet, another preferred embodiment provides a compound of Formula (I), wherein $L_1$ is a carbonyl and wherein n can take any one of the values 0, 1, 2, 3 or 4 preferably 0, 1, 2 or 3, more preferably 0, 1 or 2, still more preferably 0 or 1 and m is 1; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

Yet, another preferred embodiment provides a compound of Formula (I), wherein $L_1$ is a carbonyl and wherein n can take any one of the values 0, 1, 2, 3 or 4 preferably 0, 1, 2 or 3, more preferably 0, 1 or 2, still more preferably 0 or 1 and m is 2; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

Yet, another preferred embodiment provides a compound of Formula (I), wherein $L_1$ is a methylene (—$CH_2$—) and wherein n can take any one of the values 0, 1, 2, 3 or 4, preferably 0, 1, 2 or 3, more preferably 0, 1 or 2, still more preferably 0 or 1 and m is 1; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

Yet, another preferred embodiment provides a compound of Formula (I), wherein $L_1$ is a methylene (—$CH_2$—) and wherein n can take any one of the values 0, 1, 2, 3 or 4, preferably 0, 1, 2 or 3, more preferably 0, 1 or 2, still more preferably 0 or 1 and m is 2; it being understood that $R_1$, $R_2$, $R_{2'}$, $R_3$, $R_4$, $R_5$, $R_6$, $R_7$, $R_8$, $R_{8'}$, $R_{10}$, $R_{11}$, $R_{12}$, $R_{13}$ and p have the same definitions as those given previously with Formula (I).

Yet, another preferred embodiment provides a compound of Formula (I), wherein $L_1$ is a methylene (—$CH_2$—) and $R_1$ is an optionally substituted aryl as defined herein and wherein n can take any one of the values 0, 1, 2, 3 or 4, preferably 0, 1, 2 or 3, more preferably 0, 1 or 2, still more preferably 0 or 1 and m is 1; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

Yet, another preferred embodiment provides a compound of Formula (I), wherein $L_1$ is a methylene (—$CH_2$—) and $R_1$ is an optionally substituted aryl as defined herein and wherein n can take any one of the values 0, 1, 2, 3 or 4, preferably 0, 1, 2 or 3, more preferably 0, 1 or 2, still more preferably 0 or 1 and m is 2; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

Yet, another preferred embodiment provides a compound of Formula (I), wherein $L_1$ is a methylene (—$CH_2$—) and $R_1$ is an optionally substituted aryl as defined herein and $R_5$ is a halogen atoms as defined herein and wherein n can take any one of the values 0, 1, 2, 3 or 4, preferably 0, 1, 2 or 3, more preferably 0, 1 or 2, still more preferably 0 or 1 and m is 1; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

Yet, another preferred embodiment provides a compound of Formula (I), wherein $L_1$ is a methylene (—$CH_2$—) and $R_1$ is an optionally substituted aryl as defined herein and $R_5$ is a halogen atoms as defined herein and wherein n can take any one of the values 0, 1, 2, 3 or 4, preferably 0, 1, 2 or 3, more preferably 0, 1 or 2, still more preferably 0 or 1 and m is 2; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

Yet, another preferred embodiment provides a compound of Formula (I), wherein $L_1$ is a methylene (—$CH_2$—) and $R_1$ is an optionally substituted aryl as defined herein and $R_5$ is a fluorine atom and wherein n can take any one of the values 0, 1, 2, 3 or 4, preferably 0, 1, 2 or 3, more preferably 0, 1 or 2, still more preferably 0 or 1 and m is 1; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

Yet, another preferred embodiment provides a compound of Formula (I), wherein $L_1$ is a methylene (—$CH_2$—) and $R_1$ is an optionally substituted aryl as defined herein and $R_5$ is a fluorine atom and wherein n can take any one of the values 0, 1, 2, 3 or 4, preferably 0, 1, 2 or 3, more preferably 0, 1 or 2, still more preferably 0 or 1 and m is 2; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

Yet, another preferred embodiment provides a compound of Formula (I), wherein $L_1$ is a methylene (—$CH_2$—) and $R_1$ is an optionally substituted aryl as defined herein and $R_5$ is a chlorine atom and wherein n can take any one of the values 0, 1, 2, 3 or 4, preferably 0, 1, 2 or 3, more preferably 0, 1 or 2, still more preferably 0 or 1 and m is 1; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

Yet, another preferred embodiment provides a compound of Formula (I), wherein $L_1$ is a methylene (—$CH_2$—) and $R_1$ is an optionally substituted aryl as defined herein and $R_5$ is a chlorine atom and wherein n can take any one of the values 0, 1, 2, 3 or 4, preferably 0, 1, 2 or 3, more preferably 0, 1 or 2, still more preferably 0 or 1 and m is 2; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

Yet, another preferred embodiment provides a compound of Formula (I), wherein $L_1$ is a methylene (—CH$_2$—) and $R_1$ is an optionally substituted aryl as defined herein and $R_5$ is a hydroxyl and wherein n can take any one of the values 0, 1, 2, 3 or 4, preferably 0, 1, 2 or 3, more preferably 0, 1 or 2, still more preferably 0 or 1 and m is 1; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

Yet, another preferred embodiment provides a compound of Formula (I), wherein $L_1$ is a methylene (—CH$_2$—) and $R_1$ is an optionally substituted aryl as defined herein and $R_5$ is a hydroxyl and wherein n can take any one of the values 0, 1, 2, 3 or 4, preferably 0, 1, 2 or 3, more preferably 0, 1 or 2, still more preferably 0 or 1 and m is 2; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

Yet, another preferred embodiment provides a compound of Formula (I), wherein $L_1$ is a methylene (—CH$_2$—) and $R_1$ is an optionally substituted aryl as defined herein and $R_5$ is an alkoxy as defined herein and wherein n can take any one of the values 0, 1, 2, 3 or 4, preferably 0, 1, 2 or 3, more preferably 0, 1 or 2, still more preferably 0 or 1 and m is 1; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

Yet, another preferred embodiment provides a compound of Formula (I), wherein $L_1$ is a methylene (—CH$_2$—) and $R_1$ is an optionally substituted aryl as defined herein and $R_5$ is an alkoxy as defined herein and wherein n can take any one of the values 0, 1, 2, 3 or 4, preferably 0, 1, 2 or 3, more preferably 0, 1 or 2, still more preferably 0 or 1 and m is 2; it being understood that $R_1$, $R_2$, $R_{2'}$, $R_3$, $R_4$, $R_5$, $R_6$, $R_7$, $R_8$, $R_{8'}$, $R_9$, $R_{10}$, $R_{11}$, $R_{12}$, $R_{13}$ and p have the same definitions as those given previously with Formula (I).

In some specific embodiments, the invention provides a compound chosen from:

2-(4-chlorophenylamino)-4-(4-tert-butylaminopiperidin-1-yl)-quinoline (1-5) of formula (I-a)

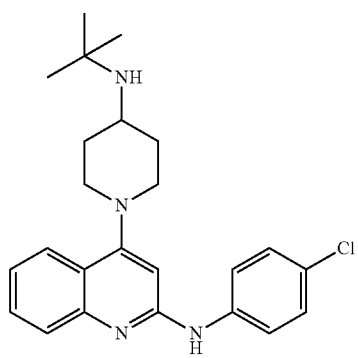

2-(4-chlorobenzylamino)-4-(4-tert-butylaminopiperidin-1-yl)-quinoline (2-2) of formula (I-b)

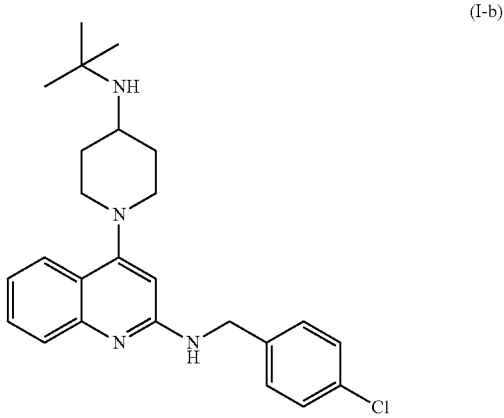 [SMILES: CC(C)(C)NC1CCN(c2cc(NCc3ccc(Cl)cc3)nc3ccccc23)CC1]

2-[3-methyl-4-(pyrimidin-2-ylamino)phenylamino]-4-(4-tert-butylaminopiperidin-1-yl)-quinoline (3-4) of formula (I-c)

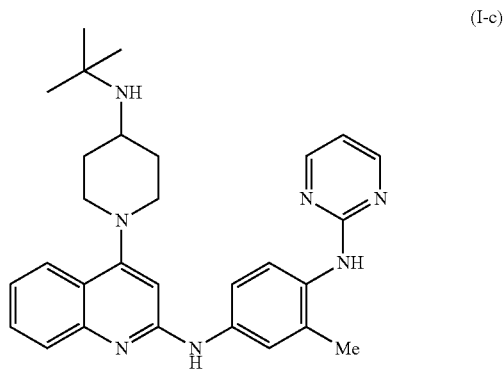 [SMILES: Cc1cc(Nc2cc(N3CCC(NC(C)(C)C)CC3)c3ccccc3n2)ccc1Nc1ncccn1]

2-{4-[4-(pyridin-3-yl)-2-pyrimidinamino]-3-methyl-phenylamino}-4-(4-tert-butylaminopiperidin-1-yl)-quinoline (4-2) of formula (I-d)

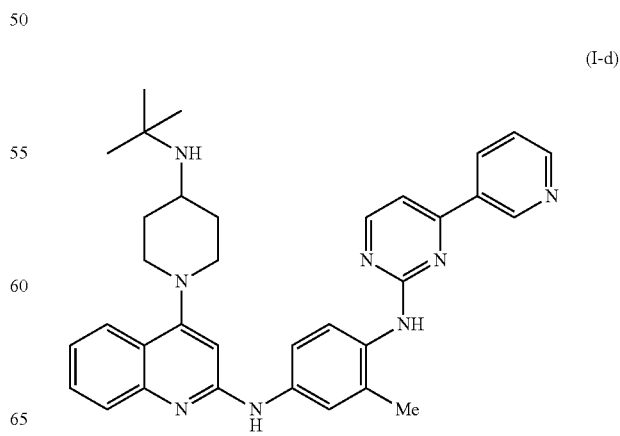

| 101 | 102 |
|---|---|
| 2-(4-fluorobenzylamino)-4-(4-tert-butylaminopiperidin-1-yl)-quinoline (5-3) of formula (I-e) | 2-(4-chlorobenzylamino)-4-(4-tert-butylaminopiperidin-1-yl)-'7-methoxyquinoline (8-2) of formula (I-h) |

(I-e)

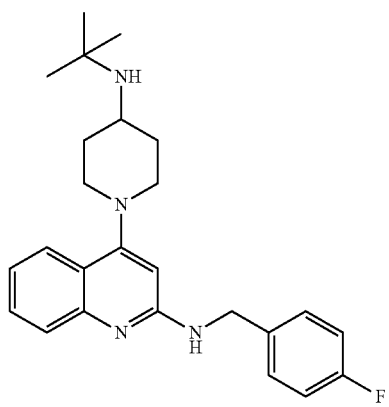

(I-h)

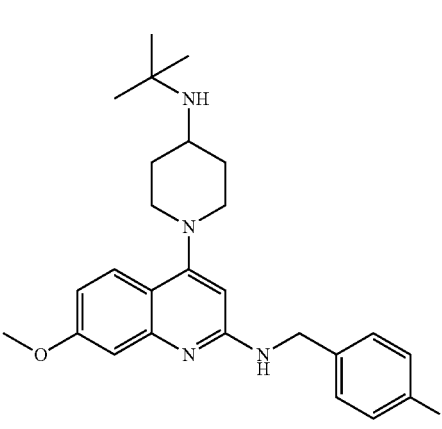

2-(4-chlorobenzylamino)-4-(4-tert-butylaminopiperidin-1-yl)-8-methoxyquinoline (6-3) of formula (I-f)

2-(4-chlorobenzylamino)-4-(4-tert-butylaminopiperidin-1-yl)-'7-hydroxyquinoline (9-1) of formula (I-i)

(I-f)

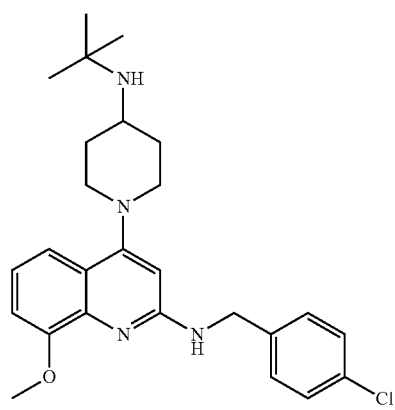

(I-i)

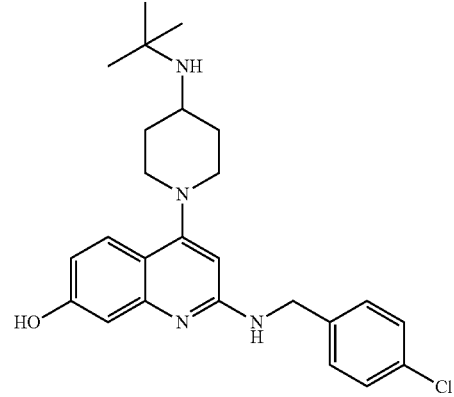

2-(4-chlorobenzylamino)-4-(4-tert-butylaminopiperidin-1-yl)-8-hydroxyquinoline (7-1) of formula (I-g)

2-(4-chlorobenzylamino)-4-(4-tert-butylaminopiperidin-1-yl)-6-methoxyquinoline (10-2) of formula (I-j)

(I-g)

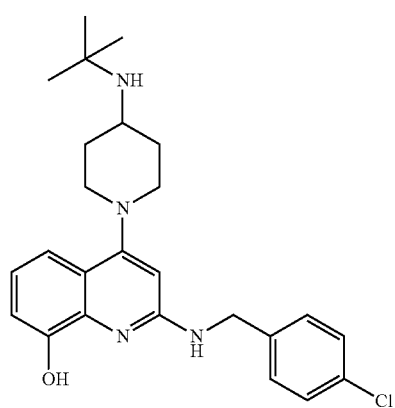

(I-j)

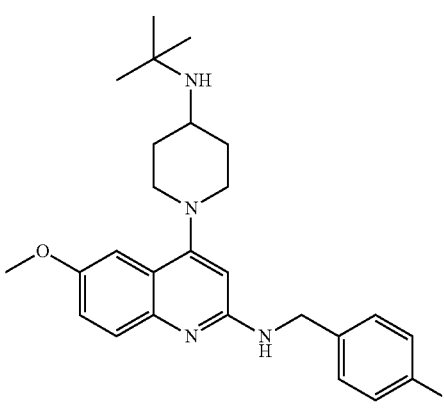

2-(4-chlorobenzylamino)-4-(4-tert-butylaminopiperidin-1-yl)-6-hydroxyquinoline (11-1) of formula (I-k)

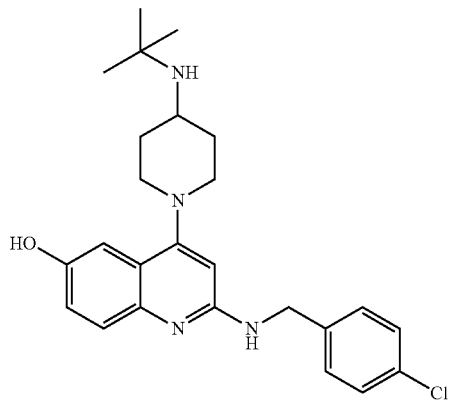
(I-k)

2-(4-chlorobenzylamino)-4-(4-tert-butylaminopiperidin-1-yl)-5-methoxyquinoline (12-4) of formula (I-l)

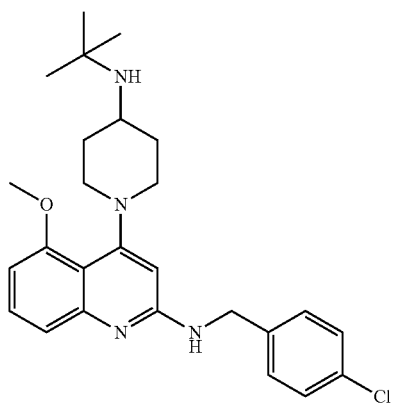
(I-l)

2-(4-chlorobenzylamino)-4-(4-tert-butylaminopiperidin-1-yl)-5-hydroxyquinoline (13-1) of formula (I-m)

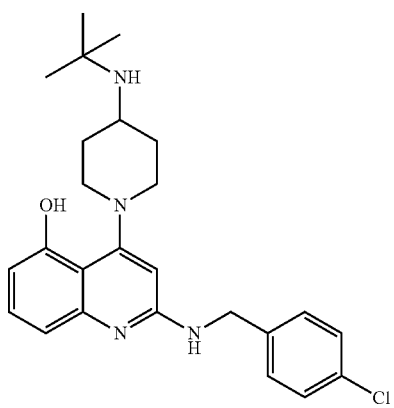
(I-m)

2-(2-methoxy-4-chlorobenzylamino)-4-(4-tert-butylaminopiperidin-1-yl)quinoline (14-5) of formula (I-n)

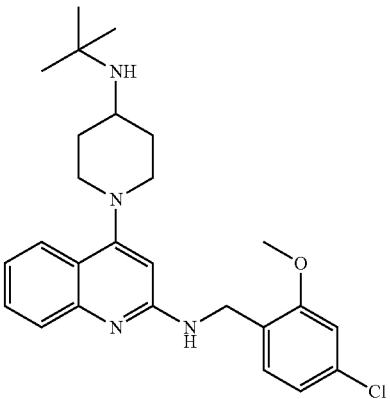
(I-n)

2-(2-hydroxy-4-chlorobenzylamino)-4-(4-tert-butylaminopiperidin-1-yl)quinoline (15-1) of formula (I-o)

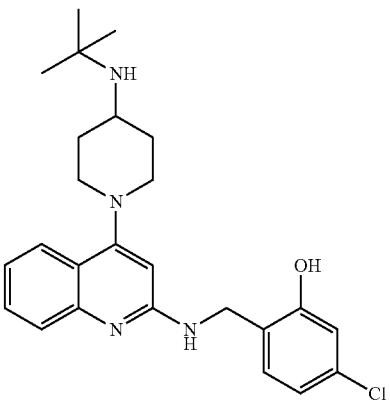
(I-o)

2-(3-methoxy-4-chlorobenzylamino)-4-(4-tert-butylaminopiperidin-1-yl)quinoline (16-6) of formula (I-p)

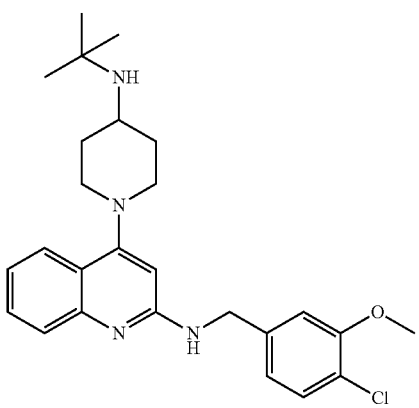
(I-p)

105

2-(3-hydroxy-4-chlorobenzylamino)-4-(4-tert-butylaminopiperidin-1-yl)quinoline (17-1) of formula (I-q)

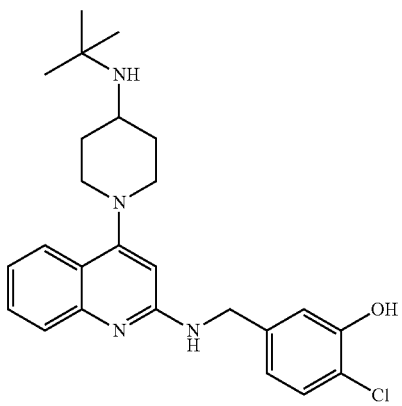

(I-q)

2-(4-chlorobenzamido)-4-(4-tert-butylaminopiperidin-1-yl)quinoline (18-3) of formula (I-r)

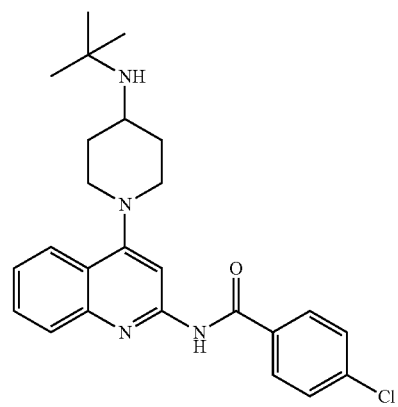

(I-r)

2-(4-chlorobenzylamino)-4-[4-(pyrrolidin-1-yl)piperidin-1-yl]quinoline (19-1) of formula (I-s)

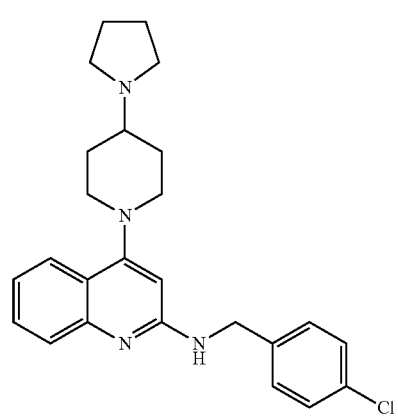

(I-s)

106

2-(4-chlorobenzylamino)-4-{4-[(1-methylpiperidin-4-yl)amino]piperidin-1-yl}quinoline (20-1) of formula (I-t)

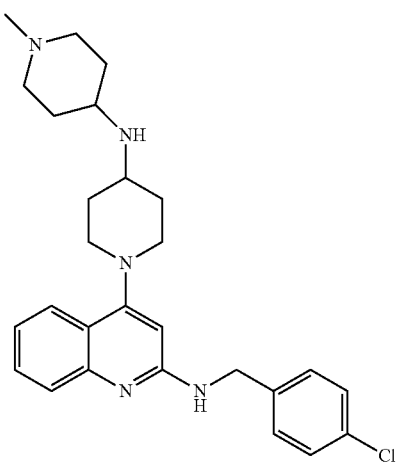

(I-t)

2-(4-methoxybenzylamino)-4-(4-tert-butylaminopiperidin-1-yl)quinoline (21-2) of formula (I-u)

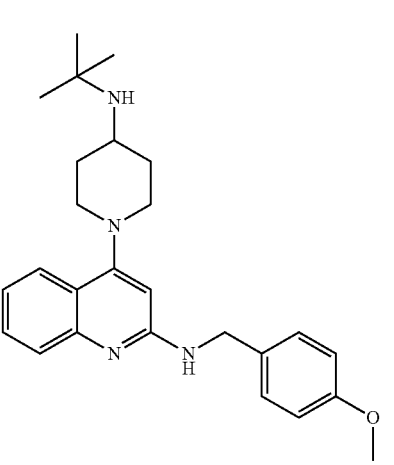

(I-u)

2-(4-hydroxybenzylamino)-4-(4-tert-butylaminopiperidin-1-yl)quinoline (22-1) of formula (I-v)

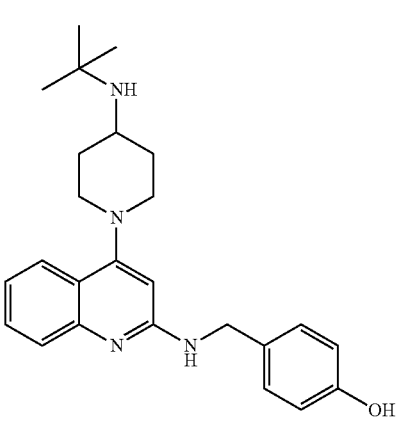

(I-v)

2-benzylamino-4-(4-tert-butylaminopiperidin-1-yl)quinoline (23-2) of formula (I-w)

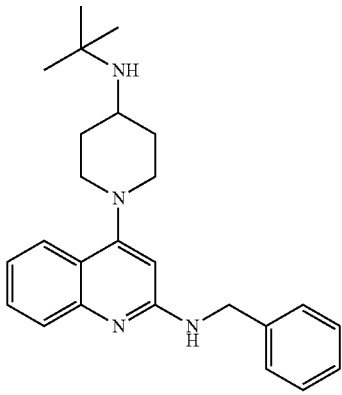

and any pharmaceutically acceptable salt, hydrates, solvate, prodrugs, polymorphs, tautomers, isotopic variants, isomers, stereoisomers or mixtures of stereoisomers thereof.

In some other specific embodiments, the invention provides a compound chosen from:
2-(4-chlorophenylamino)-4-(4-tert-butylaminopiperidin-1-yl)-quinoline hydrochloride salt (1-6),
2-(4-chlorobenzylamino)-4-(4-tert-butylaminopiperidin-1-yl)-quinoline hydrochloride salt (2-3),
2-[3-methyl-4-(pyrimidin-2-ylamino)phenylamino]-4-(4-tert-butylaminopiperidin-1-yl)-quinoline hydrochloride salt (3-5),
2-{4-[4-(pyridin-3-yl)-2-pyrimidinamino]-3-methyl-phenylamino}-4-(4-tert-butylaminopiperidin-1-yl)-quinoline hydrochloride salt (4-3),
2-(4-fluorobenzylamino)-4-(4-tert-butylaminopiperidin-1-yl)-quinoline hydrochloride salt (5-2),
2-(4-chlorobenzylamino)-4-(4-tert-butylaminopiperidin-1-yl)-8-methoxyquinoline hydrochloride salt (6-4),
2-(4-chlorobenzylamino)-4-(4-tert-butylaminopiperidin-1-yl)-8-hydroxyquinoline hydrochloride salt (7-2),
2-(4-chlorobenzylamino)-4-(4-tert-butylaminopiperidin-1-yl)-7-methoxyquinoline hydrochloride salt (8-3),
2-(4-chlorobenzylamino)-4-(4-tert-butylaminopiperidin-1-yl)-7-hydroxyquinoline hydrochloride salt (9-2),
2-(4-chlorobenzylamino)-4-(4-tert-butylaminopiperidin-1-yl)-6-methoxyquinoline hydrochloride salt (10-3),
2-(4-chlorobenzylamino)-4-(4-tert-butylaminopiperidin-1-yl)-6-hydroxyquinoline hydrochloride salt (11-2),
2-(4-chlorobenzylamino)-4-(4-tert-butylaminopiperidin-1-yl)-5-methoxyquinoline hydrochloride salt (12-5),
2-(4-chlorobenzylamino)-4-(4-tert-butylaminopiperidin-1-yl)-5-hydroxyquinoline hydrochloride salt (13-2),
2-(2-methoxy-4-chlorobenzylamino)-4-(4-tert-butylaminopiperidin-1-yl)quinoline (14-5),
2-(2-hydroxy-4-chlorobenzylamino)-4-(4-tert-butylaminopiperidin-1-yl)quinoline hydrochloride salt (15-2),
2-(3-methoxy-4-chlorobenzylamino)-4-(4-tert-butylaminopiperidin-1-yl)quinoline (16-6)
2-(3-hydroxy-4-chlorobenzylamino)-4-(4-tert-butylaminopiperidin-1-yl)quinoline hydrochloride salt (17-2),
2-(4-chlorobenz amido)-4-(4-tert-butylaminopiperidin-1-yl)quinoline hydrochloride salt (18-4),
2-(4-chlorobenzylamino)-4-[4-(pyrrolidin-1-yl)piperidin-1-yl]quinoline hydrochloride salt (19-2),
2-(4-chlorobenzylamino)-4-{4-[(1-methylpiperidin-4-yl)amino]piperidin-1-yl}quinoline hydrochloride salt (20-2),
2-(4-methoxybenzylamino)-4-(4-tert-butylaminopiperidin-1-yl)quinoline hydrochloride salt (21-2)
2-(4-hydroxybenzylamino)-4-(4-tert-butylaminopiperidin-1-yl)quinoline hydrochloride salt (22-2),
2-benzylamino-4-(4-tert-butylaminopiperidin-1-yl)quinoline hydrochloride salt (23-3),
and any pharmaceutically acceptable salt, hydrates, solvate, prodrugs, polymorphs, tautomers, isotopic variants, isomers, stereoisomers or mixtures of stereoisomers thereof, for use as a medicament to treat, decrease the severity and/or progression of, and/or prevent fibrosis and/or related diseases, or for use as a medicament to treat and/or decrease the severity and/or progression of and/or prevent autophagy and/or related diseases and for inhibiting the autophagy flux, or for use in inhibiting cathepsins B (CTSB), L (CTSL) and/or D (CTSD) and/or related diseases; with the proviso that said compounds are not to be used for treating any forms of cancers.

In a preferred embodiment, a compound of Formula (II) can be provided:

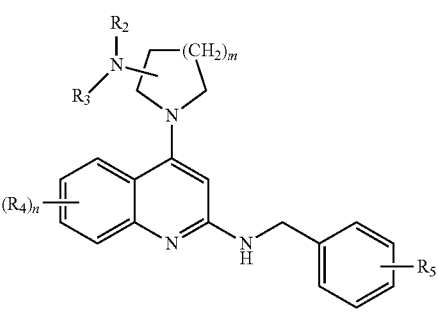

wherein,
$R_2$ and $R_3$ can be simultaneously or independently chosen from a hydrogen atom; a —(CO)—$R_7$; a —(CO)—O—$R_7$; a (CO)—$NR_8OH$; a —(CO)—$NR_8R_{8'}$; a —$SO_2$—$R_7$; a —$SO_2$—$NR_8R_{8'}$; an optionally substituted alkyl as defined herein, preferably said optionally substituted alkyl being substituted with one or more —$NR_8R_{8'}$; an optionally substituted cycloalkyl as defined herein, preferably said optionally substituted cycloalkyl being substituted with one or more —$NR_8R_{8'}$; an optionally substituted alkenyl as defined herein; an optionally substituted alkynyl as defined herein; an optionally substituted cycloalkenyl as defined herein; an optionally substituted cycloalkynyl as defined herein; an optionally substituted aryl as defined herein; an optionally substituted benzyl as defined herein; an optionally substituted heteroaryl as defined herein; an optionally substituted heterocyclyl group as defined herein; or $R_2$ and $R_3$ can be linked together with the nitrogen atom to which they are covalently linked to form an optionally substituted heterocyclyl group as defined herein;

$R_4$ can be, alone or simultaneously or independently when n>1, chosen from a hydrogen atom; a halogen atom as defined herein; an optionally substituted alkyl as defined herein, preferably said optionally substituted alkyl being substituted by one or more halogen atom(s) as defined herein, by one or more hydroxyl, by one or more alkoxy as defined herein, by one or more —$NR_8R_{8'}$, or a combination thereof; an optionally substituted fluoroalkyl as defined herein; an optionally substituted alkenyl as defined herein;

an optionally substituted alkynyl as defined herein; an optionally substituted cycloalkyl as defined herein; an optionally substituted cycloalkenyl as defined herein; an optionally substituted cycloalkynyl as defined herein; an optionally substituted alkoxy as defined herein; a hydroxyl; a nitro; an azido; a cyano; a —$NR_{12}R_{13}$; a —$NR_8R_{8'}$; a —O—($R_7$); a —(CO)—$R_7$; a —(CO)—O—$R_7$; a —(CO)—$NR_{12}OH$; a —(CO)—$NR_8OH$; a —(CO)—$NR_{12}R_{13}$; a —(CO)—$NR_8R_{8'}$; a —O—(CO)—$R_7$; a —O—(CO)—$NR_{12}R_{13}$; a —O—(CO)—$NR_8R_{8'}$; a —$NR_{12}$—(CO)—$R_7$; a —$NR_8$—(CO)—$R_7$; a —$NR_{12}$—(CO)—$NR_7$; a —$NR_8$(CO)—$OR_7$; a —O—(CO)—$NR_7$; a —$NR_{12}$—(CO)—$NR_{12}R_{13}$; a —$NR_8$—(CO)—$NR_8R_{8'}$; a —(O—$CH_2CH_2$)$_p$—$NR_{12}$; a (O—$CH_2CH_2$)$_p$—$NR_7$; a —(O—$CH_2CH_2$)$_p$—$NR_{12}R_{13}$; a —(O—$CH_2CH_2$)$_p$—$NR_8R_{8'}$; a —$NR_{12}$(—$CH_2CH_2$—O)$_p$—$R_{13}$; a —$NR_8$(—$CH_2CH_2$—O)$_p$—$R_7$; a —$SO_2$—$R_7$; a —$NR_{12}$—$SO_2$—$R_7$; a —$NR_8$—$SO_2$—$R_7$; a —$SO_2$—$NR_{12}R_{13}$; a —$SO_2$—$NR_8R_{8'}$; a —$NR_{12}$—$SO_2$—$NR_{12}R_{13}$; a —$NR_8$—$SO_2$—$NR_8R_{8'}$; a —$NR_{12}$—($C_2$-$C_8$)-alkyl-$NR_{12}R_{13}$; a —$NR_8$—($C_2$-$C_8$)-alkyl-$NR_8R_{8'}$; a —$NR_{12}$—($C_2$-$C_8$)-alkyl-$OR_{12}$; a —$NR_8$—($C_2$-$C_8$)-alkyl-$NR_7$; an optionally substituted aryl as defined herein; an optionally substituted benzyl as defined herein; an optionally substituted heteroaryl as defined herein; an optionally substituted heterocyclyl group as defined herein;

$R_5$ can be selected from a hydrogen atom; a halogen atom as defined herein; a hydroxyl; a nitro; an azido; a cyano; a —$NR_{12}R_{13}$; a —$NR_8R_{8'}$; a —O—($R_7$); a —(CO)—$R_7$; a —(CO)—O—$R_7$; a —(CO)—$NR_{12}OH$; a —(CO)—$NR_8OH$; a —(CO)—$NR_{12}R_{13}$; a —(CO)—$NR_8R_{8'}$; a —O—(CO)—$R_7$; a —$NR_{12}$—(CO)—$R_7$; a —$NR_8$—(CO)—$R_7$; a —O—(CO)—$NR_{12}$; a —O—(CO)—$NR_8$; a —$NR_{12}$—(CO)—$OR_7$; a —$NR_8$—(CO)—$OR_7$; a —O—(CO)—$OR_7$; a —$NR_{12}$—(CO)—$NR_{12}R_{13}$; a —$NR_8$—(CO)—$NR_{8'}$; a —$NR_{12}$—$SO_2$—$R_7$; a —$NR_8$—$SO_2$—$R_7$; a —$SO_2$—$NR_{12}R_{13}$; a —$SO_2$—$NR_8R_{8'}$; a —$NR_{12}$—$SO_2$—$NR_{12}R_{13}$; a —$NR_8$—$SO_2$—$NR_8R_{8'}$; a —$NR_{12}$—($C_2$-$C_{10}$)-alkyl-$NR_{12}R_{13}$; a —$NR_8$—($C_2$-$C_{10}$)-alkyl-$NR_8R_{8'}$; a —$NR_{12}$—($C_2$-$C_{10}$)-alkyl-$OR_{13}$; a —$NR_8$—($C_2$-$C_{10}$)-alkyl-$OR_7$; a —(O—$CH_2CH_2$)$_p$—$NR_{12}$; a —(O—$CH_2CH_2$)$_p$—$OR_7$; a —(O—$CH_2CH_2$)$_p$—$NR_{12}R_{13}$; a —(O—$CH_2CH_2$)$_p$—$NR_8R_{8'}$; a —$NR_{12}$(—$CH_2CH_2$—O)$_p$—$R_{13}$; a —$NR_8$(—$CH_2CH_2$—O)$_p$—$R_7$; an optionally substituted alkyl as defined herein, preferably said optionally substituted alkyl being substituted with, one or more halogen atom(s) as defined herein, one or more hydroxyl, one or more alkoxy as defined herein, one or more azido, one or more nitro, one or more cyano, one or more carboxyl, and a combination thereof; and/or said optionally substituted alkyl being or not further substituted with one or more —$NR_{12}R_{13}$; an optionally substituted fluoroalkyl as defined herein; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted alkoxy as defined herein; an optionally substituted heterocyclyl group as defined herein.

$R_7$ is chosen from a hydrogen atom; optionally substituted alkyl as defined herein, preferably said optionally substituted alkyl being substituted by one or more —$NR_8R_{8'}$; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted aryl as defined herein; an optionally substituted benzyl as defined herein; an optionally substituted heteroaryl as defined herein; an optionally substituted heterocyclyl group as defined herein.

$R_8$ and $R_{8'}$ can be independently chosen from a hydrogen atom; an optionally substituted alkyl as defined herein; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted heterocyclyl group as defined herein; an optionally substituted aryl as defined herein; an optionally substituted benzyl as defined herein; an optionally substituted heteroaryl as defined herein or $R_8$ and $R_{8'}$ can be linked together with the nitrogen atom to which they are covalently linked to form an optionally substituted heterocyclyl group as defined herein.

$R_{12}$ and $R_{13}$ can be simultaneously or independently chosen from a hydrogen atom; a —(CO)—$R_7$; a —(CO)—O—$R_7$; a —(CO)—$NR_8OH$; a —(CO)—$NR_8R_{8'}$; a —$SO_2$—$R_7$; a —$SO_2$—$NR_8R_{8'}$; an optionally substituted alkyl as defined herein, preferably said optionally substituted alkyl being substituted with at least one —$NR_8R_{8'}$; an optionally substituted cycloalkyl as defined herein, preferably said optionally substituted cycloalkyl being substituted with at least one —$NR_8R_{8'}$; an optionally substituted alkenyl as defined herein; an optionally substituted alkynyl as defined herein; an optionally substituted cycloalkenyl as defined herein; an optionally substituted cycloalkynyl as defined herein; an optionally substituted aryl as defined herein; an optionally substituted benzyl as defined herein; an optionally substituted heteroaryl as defined herein; an optionally substituted heterocyclyl group as defined herein; or $R_{12}$ and $R_{13}$ can be linked together with the nitrogen atom to which they are covalently linked to form an optionally substituted heterocyclyl group as defined herein.

n can represent an equal integer which can have any one of the values 0, 1, 2, 3 or 4, preferably 0, 1, 2 or 3, more preferably 0, 1 or 2 still more preferably 0 or 1.

m can represent an equal integer which can have any one of the values 1, 2 or 3 preferably 1 or 2, more preferably 2.

p can represent an equal integer which can have any one of the values 1, 2, 3, 4 or 5, preferably 1, 2, 3 or 4, more preferably 1, 2 or 3 still more preferably 1 or 2.

and any pharmaceutically acceptable salt, hydrates, solvate, prodrugs, polymorphs, tautomers, isotopic variants, isomers, stereoisomers or mixtures of stereoisomers thereof, for use as a medicament to treat, decrease the severity and/or progression of, and/or prevent fibrosis and/or related diseases, or for use as a medicament to treat, decrease the severity and/or progression of, and/or prevent autophagy and/or related diseases and to inhibit autophagy flux, or for use in inhibiting cathepsins B (CTSB), L (CTSL) and/or D (CTSD) and/or related diseases; with the proviso that said compounds are not intended to be used for treating any forms of cancers.

In a preferred embodiment, a compound according to Formula (II) can be provided, wherein $R_2$ and $R_3$ can be simultaneously or independently chosen from a hydrogen atom; an optionally substituted alkyl as defined herein; an optionally substituted alkenyl as defined herein; an optionally substituted alkynyl as defined herein; an optionally substituted cycloalkyl as defined herein; an optionally substituted aryl as defined herein; an optionally substituted benzyl as defined herein; an optionally substituted heteroaryl as defined herein; an optionally substituted heterocyclyl group as defined herein; or $R_2$ and $R_3$ can be linked together with the nitrogen atom to which they are covalently linked to form an optionally substituted heterocyclyl group as defined herein; it being understood that $R_4$, $R_5$, $R_7$, $R_8$, $R_{8'}$, $R_{12}$, $R_{13}$, m, n and p have the same definitions as those given previously with Formula (II).

In a further preferred embodiment, a compound according to Formula (II) can be provided, wherein $R_2$ and $R_3$ can be simultaneously or independently chosen from a hydrogen atom; an optionally substituted alkyl as defined herein; an optionally substituted cycloalkyl as defined herein; an optionally heterocyclyl group as defined herein; or $R_2$ and $R_3$ can be linked together with the nitrogen atom to which they are covalently linked to form an optionally substituted forming a heterocyclyl group as defined herein; it being understood that $R_4$, $R_5$, $R_7$, $R_8$, $R_{8'}$, $R_{12}$, $R_{13}$, m, n and p have the same definitions as those given previously with Formula (II).

In also a preferred embodiment, a compound according to Formula (II) can be provided, wherein $R_2$ and $R_3$ can be simultaneously or independently chosen from a hydrogen atom; an optionally substituted alkyl as defined herein; an optionally substituted cycloalkyl as defined herein; or $R_2$ and $R_3$ can be linked together with the nitrogen atom to which they are covalently linked to form an optionally substituted heterocyclyl group as defined herein; it being understood that $R_4$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided, wherein $R_2$ and $R_3$ can be simultaneously or independently chosen from a hydrogen atom; an optionally substituted alkyl as defined herein; an optionally substituted cycloalkyl as defined herein; it being understood that $R_4$, $R_5$, $R_7$, $R_8$, $R_{8'}$, $R_{12}$, $R_{13}$, m, n and p have the same definitions as those given previously with Formula (II).

In a further preferred embodiment, a compound according to Formula (II) can be provided, wherein $R_2$ and $R_3$ can be simultaneously or independently chosen from a hydrogen atom; an optionally substituted alkyl as defined herein; it being understood that $R_4$, $R_5$, $R_7$, $R_8$, $R_{8'}$, $R_{12}$, $R_{13}$, m, n and p have the same definitions as those given previously with Formula (II).

In a further preferred embodiment, a compound according to Formula (II) can be provided, wherein $R_2$ and $R_3$ can be simultaneously or independently chosen from a hydrogen atom; an optionally substituted cycloalkyl as defined herein; it being understood that $R_4$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided, wherein $R_2$ and $R_3$ can be simultaneously or independently chosen from a hydrogen atom; an optionally substituted heterocyclyl group as defined herein; it being understood that $R_4$, $R_5$, $R_7$, $R_8$, $R_{8'}$, $R_{12}$, $R_{13}$, m, n and p have the same definitions as those given previously with Formula (II).

In a further preferred embodiment, a compound according to Formula (II) can be provided, wherein $R_2$ and $R_3$ are linked together with the nitrogen atom to which they are covalently linked to form an optionally substituted a heterocyclyl group as defined herein; it being understood that $R_4$, $R_5$, $R_7$, $R_8$, $R_{8'}$, $R_{12}$, $R_{13}$, m, n and p have the same definitions as those given previously with Formula (II).

A further preferred embodiment provides a compound of Formula (II), wherein $R_2$ and $R_3$ can be simultaneously or independently chosen from a hydrogen atom and a 1-methylpiperidin-4-yl; it being understood that $R_4$, $R_5$, $R_7$, $R_8$, $R_{8'}$, $R_{12}$, $R_{13}$, m, n and p have the same definitions as those given previously with Formula (II).

A further preferred embodiment provides a compound of Formula (II), wherein $R_2$ and $R_3$ are linked together with the nitrogen atom to which they are covalently linked to form a pyrrolidin-1-yl; it being understood that $R_4$, $R_5$, $R_7$, $R_8$, $R_{8'}$, $R_{12}$, $R_{13}$, m, n and p have the same definitions as those given previously with Formula (II).

A further preferred embodiment provides a compound of Formula (II), wherein $R_2$ and $R_3$ can be simultaneously or independently chosen from a hydrogen atom and a tert-butyl; it being understood that $R_4$, $R_5$, $R_7$, $R_8$, $R_{8'}$, $R_{12}$, $R_{13}$, m, n and p have the same definitions as those given previously with Formula (II).

Yet, in another preferred embodiment, a compound according to Formula (II) can be provided, wherein $R_4$ can be, alone or simultaneously or independently when n>1, chosen from a hydrogen atom; a halogen atom as defined herein; an optionally substituted alkyl as defined herein, preferably said optionally substituted alkyl being substituted by one or more halogen atom(s) as defined herein, one or more hydroxyl, one or more —$NR_8R_{8'}$ and combinations thereof; an optionally substituted alkyl as defined herein; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted alkoxy as defined herein; a nitro; a cyano; an azido; a carboxyl, a —$NR_{12}R_{13}$; a —(CO)—$NR_{12}R_{13}$; it being understood that $R_2$, $R_3$, $R_5$, $R_7$, $R_8$, $R_{8'}$, $R_{12}$, $R_{13}$, m, n and p have the same definitions as those given previously with Formula (II).

In Another preferred embodiment, a compound according to Formula (II) can be provided wherein $R_4$ can be, alone or simultaneously or independently when n>1, chosen from a hydrogen atom; a halogen atom as defined herein; an optionally substituted alkyl as defined herein, preferably said optionally substituted alkyl being substituted by one or more halogen atom(s) as defined herein; an optionally substituted alkoxy as defined herein; a hydroxyl; a cyano; an azido; a carboxyl, a —$NR_{12}R_{13}$; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ can be, alone or simultaneously or independently when n>1, chosen from a hydrogen atom; a halogen atom as defined herein; an optionally substituted alkyl as defined herein; an optionally substituted alkoxy as defined herein; a hydroxyl; a cyano; an azido; a —$CF_3$; a carboxyl, a —$NR_{12}R_{13}$; it being understood that $R_2$, $R_3$, $R_5$, $R_7$, $R_8$, $R_{8'}$, $R_{12}$, $R_{13}$, m, n and p have the same definitions as those given previously with Formula (II).

Yet, a further preferred embodiment provides a compound of Formula (II), wherein $R_4$, can be, alone or simultaneously or independently when n>1, chosen from a hydrogen atom; a —$NR_{12}R_{13}$ wherein, $R_{12}$ and $R_{13}$ can be simultaneously or independently chosen from a hydrogen atom, an optionally substituted alkyl as defined herein, preferably said optionally substituted alkyl being substituted with one or more —$NR_8R_{8'}$, an optionally substituted alkenyl as defined herein, an optionally substituted alkynyl as defined herein, an optionally substituted cycloalkyl as defined herein, an optionally substituted cycloalkenyl as defined herein, an optionally substituted cycloalkynyl as defined herein, an optionally substituted cycloalkyl as defined herein, preferably said optionally substituted cycloalkyl being substituted with one or more —$NR_8R_{8'}$, an optionally substituted aryl as defined herein, an optionally substituted benzyl as defined herein, an optionally substituted heteroaryl as defined herein, an optionally substituted heterocyclyl group as defined herein; or $R_{12}$ and $R_{13}$ can be linked together with the nitrogen atom to which they are covalently linked to form a heterocyclyl group as defined herein; it being understood that $R_2$, $R_3$, $R_5$, $R_7$, $R_8$, $R_{8'}$, m, n and p have the same definitions as those given previously with Formula (II).

Yet, a further preferred embodiment provides a compound of Formula (II), wherein $R_4$ can be, alone or simultaneously or independently when n>1, chosen a hydrogen atom; a —$NR_{12}R_{13}$ wherein, $R_{12}$ and $R_{13}$ can be simultaneously or independently chosen from a hydrogen atom, an optionally substituted alkyl as defined herein, an optionally substituted cycloalkyl as defined herein, an optionally substituted aryl as defined herein; an optionally substituted benzyl as defined herein; an optionally substituted heteroaryl as defined herein; an optionally substituted heterocyclyl group as defined herein; it being understood that $R_2$, $R_3$, $R_5$, $R_7$, $R_8$, $R_{8'}$, m, n and p have the same definitions as those given previously with Formula (II).

Yet, another preferred embodiment provides a compound of Formula (II), wherein $R_4$ can be, alone or simultaneously or independently when n>1, chosen from a hydrogen atom; a —$NR_{12}R_{13}$ wherein, $R_{12}$ and $R_{13}$ can be simultaneously or independently chosen from a hydrogen atom, an optionally substituted alkyl as defined herein, an optionally substituted cycloalkyl as defined herein, an optionally substituted aryl as defined herein, an optionally substituted heteroaryl as defined herein; it being understood that $R_2$, $R_3$, $R_5$, $R_7$, $R_8$, $R_{8'}$, m, n and p have the same definitions as those given previously with Formula (II).

Yet, another preferred embodiment provides a compound of Formula (II), wherein $R_4$ can be, alone or simultaneously or independently when n>1, chosen from a hydrogen atom; a —$NR_{12}R_{13}$ wherein, $R_{12}$ and $R_{13}$ can be simultaneously or independently chosen from a hydrogen atom, an optionally substituted aryl as defined herein; it being understood that $R_2$, $R_3$, $R_5$, $R_7$, $R_8$, $R_{8'}$, m, n and p have the same definitions as those given previously with Formula (II).

Yet, another preferred embodiment provides a compound of Formula (II), wherein $R_4$ can be, alone or simultaneously or independently when n>1, chosen from a hydrogen atom; a —$NR_{12}R_{13}$ wherein, $R_{12}$ and $R_{13}$ can be simultaneously or independently chosen from a hydrogen atom, an optionally substituted heteroaryl as defined herein; it being understood that $R_2$, $R_3$, $R_5$, $R_7$, $R_8$, $R_{8'}$, m, n and p have the same definitions as those given previously with Formula (II).

Yet, a further preferred embodiment provides a compound of Formula (II), wherein $R_4$ can be, alone or simultaneously or independently when n>1, chosen from a hydrogen atom; a —$NR_{12}R_{13}$ wherein, $R_{12}$ and $R_{13}$ can be simultaneously or independently chosen from a hydrogen atom, an optionally substituted benzyl group as defined herein; it being understood that $R_2$, $R_3$, $R_5$, $R_7$, $R_8$, $R_{8'}$, m, n and p have the same definitions as those given previously with Formula (II).

Yet, another preferred embodiment provides a compound of Formula (II), wherein $R_4$ can be, alone or simultaneously or independently when n>1, chosen from a hydrogen atom; a —$NR_{12}R_{13}$ wherein, $R_{12}$ and $R_{13}$ can be simultaneously or independently chosen from a hydrogen atom, an optionally substituted alkyl, an optionally substituted heteroaryl as defined herein; it being understood that $R_2$, $R_3$, $R_5$, $R_7$, $R_8$, $R_{8'}$, m, n and p have the same definitions as those given previously with Formula (II).

Yet, another preferred embodiment provides a compound of Formula (II), wherein $R_4$ can be, alone or simultaneously or independently when n>1, chosen from a hydrogen atom; a —$NR_{12}R_{13}$ wherein, $R_{12}$ and $R_{13}$ can be simultaneously or independently chosen from a hydrogen atom, an optionally substituted alkyl as defined herein, an optionally substituted cycloalkyl as defined herein, an optionally substituted pyrimidin; it being understood that $R_2$, $R_3$, $R_5$, $R_7$, $R_8$, $R_{8'}$, m, n and p have the same definitions as those given previously with Formula (II).

Yet, another preferred embodiment provides a compound of Formula (II), wherein $R_4$ can be, alone or simultaneously or independently when n>1, chosen from a hydrogen atom; a —$NR_{12}R_{13}$ wherein, $R_{12}$ and $R_{13}$ can be simultaneously or independently chosen from a hydrogen atom, a methyl, a cyclopropyl, an optionally substituted pyrimidin-2-yl, an optionally substituted pyrimidin-4-yl, an optionally substituted pyrimidin-5-yl; it being understood that $R_2$, $R_3$, $R_5$, $R_7$, $R_8$, $R_{8'}$, m, n and p have the same definitions as those given previously with Formula (II).

Yet, another preferred embodiment provides a compound of Formula (II), wherein $R_4$ can be, alone or simultaneously or independently when n>1, chosen from a hydrogen atom; a —$NR_{12}R_{13}$ wherein, $R_{12}$ and $R_{13}$ can be simultaneously or independently chosen from a hydrogen atom, a methyl, a cyclopropyl, a pyrimidin-2-yl, a pyrimidin-4-yl, a pyrimidin-5-yl; it being understood that $R_2$, $R_3$, $R_5$, $R_7$, $R_8$, $R_{8'}$, m, n and p have the same definitions as those given previously with Formula (II).

Yet, another preferred embodiment provides a compound of Formula (II), wherein $R_4$ can be, alone or simultaneously or independently when n>1, chosen from a hydrogen atom; a —$NR_{12}R_{13}$ wherein, $R_{12}$ and $R_{13}$ can be simultaneously or independently chosen from a hydrogen atom, an optionally substituted pyrimidin-2-yl, an optionally substituted pyrimidin-4-yl, an optionally substituted pyrimidin-5-yl; it being understood that $R_2$, $R_3$, $R_5$, $R_7$, $R_8$, $R_{8'}$, m, n and p have the same definitions as those given previously with Formula (II).

Yet, a further preferred embodiment provides a compound of Formula (II), wherein $R_4$ can be, alone or simultaneously or independently when n>1, chosen from a hydrogen atom; a —$NR_{12}R_{13}$ wherein, $R_{12}$ and $R_{13}$ can be simultaneously or independently chosen from a hydrogen atom, an optionally substituted alkyl as defined herein, an optionally substituted cycloalkyl as defined herein, an optionally substituted heterocyclyl group as defined herein; it being understood that $R_2$, $R_3$, $R_5$, $R_7$, $R_8$, $R_{8'}$, m, n and p have the same definitions as those given previously with Formula (II).

Yet, a further preferred embodiment provides a compound of Formula (II), wherein $R_4$ can be, alone or simultaneously or independently when n>1, chosen from a hydrogen atom; a —$NR_{12}R_{13}$ wherein, $R_{12}$ and $R_{13}$ can be simultaneously or independently chosen from a hydrogen atom, an optionally substituted heterocyclyl group as defined herein; it being understood that $R_2$, $R_3$, $R_5$, $R_7$, $R_8$, $R_{8'}$, m, n and p have the same definitions as those given previously with Formula (II).

Yet, a further preferred embodiment provides a compound of Formula (II), wherein $R_4$ can be, alone or simultaneously or independently when n>1, chosen from a hydrogen atom; a —$NR_{12}R_{13}$ wherein, $R_{12}$ and $R_{13}$ can be simultaneously or independently chosen from a hydrogen atom, an optionally substituted heterocyclyl group as defined herein; or $R_{12}$ and $R_{13}$ can be linked together with the nitrogen atom to which they are covalently linked to form a heterocyclyl group as defined herein; it being understood that $R_2$, $R_3$, $R_5$, $R_7$, $R_8$, $R_{8'}$, m, n and p have the same definitions as those given previously with Formula (II).

Yet, a further preferred embodiment provides a compound of Formula (II), wherein $R_4$ can be, alone or simultaneously or independently when n>1, chosen from a hydrogen atom, a —$NR_{12}R_{13}$ wherein, $R_{12}$ and $R_{13}$ can be linked together with the nitrogen atom to which they are covalently linked to form a heterocyclyl group as defined herein; it being understood that $R_2$, $R_3$, $R_5$, $R_7$, $R_8$, $R_{8'}$, m, n and p have the same definitions as those given previously with Formula (II).

In yet another preferred embodiment provides a compound of Formula (II), wherein $R_4$ can be, alone or simultaneously or independently when n>1, chosen from a hydrogen atom; —(CO) $NR_{12}R_{13}$ wherein, $R_{12}$ and $R_{13}$ can be simultaneously or independently chosen from a hydrogen atom, an optionally substituted alkyl as defined herein, an optionally substituted cycloalkyl as defined herein, an optionally substituted aryl as defined herein, an optionally substituted heteroaryl as defined herein, an optionally substituted benzyl as defined herein, an optionally substituted heterocyclyl group as defined herein; or $R_{12}$ and $R_{13}$ can be linked together with the nitrogen atom to which they are covalently linked to form an optionally heterocyclyl group as defined herein; it being understood that $R_2$, $R_3$, $R_5$, $R_7$, $R_8$, $R_{8'}$, m, n and p have the same definitions as those given previously with Formula (II).

Yet, another preferred embodiment provides a compound of Formula (II), wherein $R_4$ can be, alone or simultaneously or independently when n>1, chosen from a hydrogen atom; —(CO) $NR_{12}R_{13}$ wherein, $R_{12}$ and $R_{13}$ can be simultaneously or independently chosen from a hydrogen atom, an optionally substituted alkyl as defined herein, an optionally substituted cycloalkyl as defined herein, an optionally substituted heterocyclyl group as defined herein; or $R_{12}$ and $R_{13}$ can be linked together with the nitrogen atom to which they are covalently linked to form an optionally heterocyclyl group as defined herein; it being understood that $R_2$, $R_3$, $R_5$, $R_7$, $R_8$, $R_{8'}$, m, n and p have the same definitions as those given previously with Formula (II).

Yet, another preferred embodiment provides a compound of Formula (II), wherein $R_4$ can be, alone or simultaneously or independently when n>1, chosen from a hydrogen atom; —(CO)—$NR_{12}R_{13}$ wherein, $R_{12}$ and $R_{13}$ can be simultaneously or independently chosen from a hydrogen atom, an optionally substituted alkyl as defined herein, an optionally substituted cycloalkyl as defined herein, an optionally substituted heterocyclyl group as defined herein; it being understood that $R_2$, $R_3$, $R_5$, $R_7$, $R_8$, $R_{8'}$, m, n and p have the same definitions as those given previously with Formula (II).

Yet, another preferred embodiment provides a compound of Formula (II), wherein $R_4$ can be, alone or simultaneously or independently when n>1, chosen from a hydrogen atom; —(CO)—$NR_{12}R_{13}$ wherein, $R_{12}$ and $R_{13}$ can be simultaneously or independently chosen from a hydrogen atom, an optionally substituted alkyl as defined herein, an optionally substituted cycloalkyl as defined herein; it being understood that $R_2$, $R_3$, $R_5$, $R_7$, $R_8$, $R_{8'}$, have the same definitions as those given previously with Formula (II).

Yet, another preferred embodiment provides a compound of Formula (II), wherein $R_4$ can be, alone or simultaneously or independently when n>1, chosen from a hydrogen atom; —(CO)—$NR_{12}R_{13}$ wherein, $R_{12}$ and $R_{13}$ are linked together with the nitrogen atom to which they are covalently linked to form an optionally heterocyclyl group as defined herein; it being understood that $R_2$, $R_3$, $R_5$, $R_7$, $R_8$, $R_{8'}$, m, n and p have the same definitions as those given previously with Formula (II).

Yet, another preferred embodiment provides a compound of Formula (II), wherein $R_4$ can be, alone or simultaneously or independently when n>1, chosen from a hydrogen atom; —(CO)—$NR_{12}R_{13}$ wherein, $R_{12}$ and $R_{13}$ can be simultaneously or independently chosen from a hydrogen atom, an optionally substituted aryl as defined herein, it being understood that $R_2$, $R_3$, $R_5$, $R_7$, $R_8$, $R_{8'}$, m, n and p have the same definitions as those given previously with Formula (II).

Yet, another preferred embodiment provides a compound of Formula (II), wherein $R_4$ can be, alone or simultaneously or independently when n>1, chosen from a hydrogen atom; —(CO)—$NR_{12}R_{13}$ wherein, $R_{12}$ and $R_{13}$ can be simultaneously or independently chosen from a hydrogen atom, an optionally substituted heteroaryl as defined herein, it being understood that $R_2$, $R_3$, $R_5$, $R_7$, $R_8$, $R_{8'}$, m, n and p have the same definitions as those given previously with Formula (II).

Yet, another preferred embodiment provides a compound of Formula (II), wherein $R_4$ can be, alone or simultaneously or independently when n>1, chosen from a hydrogen atom; —(CO)—$NR_{12}R_{13}$ wherein, $R_{12}$ and $R_{13}$ can be simultaneously or independently chosen from a hydrogen atom, an optionally substituted benzyl as defined herein, it being understood that $R_2$, $R_3$, $R_5$, $R_7$, $R_8$, $R_{8'}$, m, n and p have the same definitions as those given previously with Formula (II).

Yet, another preferred embodiment provides a compound of Formula (II), wherein $R_4$ can be, alone or simultaneously or independently when n>1, chosen from a hydrogen atom; —(CO)—$NR_{12}R_{13}$ wherein, $R_{12}$ and $R_{13}$ can be simultaneously or independently chosen from a hydrogen atom, an optionally substituted alkyl as defined herein, it being understood that $R_2$, $R_3$, $R_5$, $R_7$, $R_8$, $R_{8'}$, m, n and p have the same definitions as those given previously with Formula (II).

Yet, another preferred embodiment provides a compound of Formula (II), wherein $R_4$ can be, alone or simultaneously or independently when n>1, chosen from a hydrogen atom; —(CO)—$NR_{12}R_{13}$ wherein, $R_{12}$ and $R_{13}$ can be simultaneously or independently chosen from a hydrogen atom; a methyl; an ethyl; an isopropyl; a tert-butyl; a cyclopropyl; a cyclobutyl; a cyclopentyl; a cyclohexyl; it being understood that $R_2$, $R_3$, $R_5$, $R_7$, $R_8$, $R_{8'}$, m, n and p have the same definitions as those given previously with Formula (II).

Yet, another preferred embodiment provides a compound of Formula (II), wherein $R_4$ can be, alone or simultaneously or independently when n>1, chosen from a hydrogen atom; an optionally substituted alkyl as defined herein; an optionally substituted cycloalkyl as defined herein; an optionally substituted aryl as defined herein; an optionally substituted heteroaryl as defined herein; a —$NR_8R_{8'}$; it being understood that $R_2$, $R_3$, $R_5$, $R_7$, $R_8$, $R_{8'}$, $R_{12}$, $R_{13}$, m, n and p have the same definitions as those given previously with Formula (II).

Yet, another preferred embodiment provides a compound of Formula (II), wherein $R_4$ can be, alone or simultaneously or independently when n>1, chosen from a hydrogen atom; an optionally substituted alkyl as defined herein; it being understood that $R_2$, $R_3$, $R_5$, $R_7$, $R_8$, $R_{8'}$, $R_{12}$, $R_{13}$, m, n and p have the same definitions as those given previously with Formula (II).

Yet, another preferred embodiment provides a compound of Formula (II), wherein $R_4$ can be, alone or simultaneously or independently when n>1, chosen from a hydrogen atom;

an optionally substituted cycloalkyl as defined herein; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ can be, alone or simultaneously or independently when n>1, chosen from a hydrogen atom; a halogen atom as defined herein; an optionally substituted alkyl as defined herein, preferably said optionally substituted alkyl being substituted by one or more halogen atom(s); an optionally substituted alkoxy as defined herein; a hydroxyl; a cyano; an azido; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ can be, alone or simultaneously or independently when n>1, chosen from a hydrogen atom; a halogen atom as defined herein an optionally substituted alkyl as defined herein, preferably said optionally substituted alkyl being substituted by one or more halogen atom(s); an optionally substituted alkoxy as defined herein; a hydroxyl; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ can be, alone or simultaneously or independently when n>1, chosen from a hydrogen atom or a halogen atom as defined herein, said halogen atom being preferably a fluorine, a chlorine or a bromine, more preferably a fluorine or a chlorine; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ can be, alone or simultaneously or independently when n>1, chosen from a hydrogen atom; a fluorine; a chlorine; a methyl; a —$CF_3$; a cyano; an azido; an optionally substituted alkoxy; a hydroxyl; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ can be, alone or simultaneously or independently when n>1, chosen from a hydrogen atom; a fluorine; a chlorine; a methyl; a —$CF_3$; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ can be, alone or simultaneously or independently when n>1, chosen from a hydrogen atom; a fluorine; a chlorine; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ can be, alone or simultaneously or independently when n>1, chosen from a hydrogen atom; an optionally substituted fluoroalkyl; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ can be, alone or simultaneously or independently when n>1, chosen from a hydrogen atom; a —$CF_3$; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ can be, alone or simultaneously or independently when n>1, chosen from a hydrogen atom; a cyano; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ can be, alone or simultaneously or independently when n>1, chosen from a hydrogen atom; a hydroxyl; an optionally substituted alkoxy as defined herein; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ can be, alone or simultaneously or independently when n>1, chosen from a hydrogen atom or an optionally substituted alkoxy as defined herein; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ can be, alone or simultaneously or independently when n>1, chosen from a hydrogen atom or a hydroxyl; or a methoxy, or an ethoxy, or an isopropoxy; or a tert-butoxy; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ can be, alone or simultaneously or independently when n>1, chosen from a hydrogen atom or a methoxy; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ can be, alone or simultaneously or independently when n>1, chosen from a hydrogen atom or a hydroxyl; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ can be, alone or simultaneously or independently when n>1, chosen from a hydrogen atom or an azido; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ is a hydrogen atom; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ is a methyl; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ is a halogen atom as defined herein; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ is an optionally substituted alkoxy as defined herein; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ is a hydroxyl; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ is a methoxy; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ is a —$CF_3$; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ is a cyano; it being understood that $R_2$, $R_3$, $R_5$, $R_7$, $R_8$, $R_{8'}$, $R_{12}$, $R_{13}$, m, n and p have the same definitions as those given previously with Formula (II).

Yet, a further preferred embodiment provides a compound of Formula (II), wherein $R_4$ can be, alone or simultaneously or independently when n>1, chosen from a hydrogen atom, a —(O—$CH_2CH_2$—)$_p$—$OR_{12}$; a —(O—$CH_2CH_2$—)$_p$—$NR_{12}R_{13}$; a —$NR_{12}$—($CH_2CH_2$—O)$_p$—$R_{13}$; a —$NR_{12}$—($C_2$-$C_8$)-alkyl-$NR_{12}R_{13}$; a —$NR_{12}$—($C_2$-$C_8$)-alkyl-$OR_{13}$; it being understood that $R_2$, $R_3$, $R_5$, $R_7$, $R_8$, $R_{8'}$, $R_{12}$, $R_{13}$, m, n and p have the same definitions as those given previously with Formula (II).

Yet, a further preferred embodiment provides a compound of Formula (II), wherein $R_4$ can be, alone or simultaneously or independently when n>1, chosen from a hydrogen atom, a —(O—$CH_2CH_2$—)$_p$—$NR_8$; a —(O—$CH_2CH_2$—)$_p$—$NR_8R_{8'}$; a —$NR_8$—($CH_2CH_2$—O)$_p$—$R_{8'}$; a —$NR_8$—($C_2$-$C_8$)-alkyl-$NR_8R_{8'}$; a —$NR_8$—($C_2$-$C_8$)-alkyl-$OR_{8'}$; it being understood that $R_2$, $R_3$, $R_5$, $R_7$, $R_8$, $R_{8'}$, $R_{12}$, $R_{13}$, m, n and p have the same definitions as those given previously with Formula (II).

Yet, a further preferred embodiment provides a compound of Formula (II), wherein $R_4$ can be, alone or simultaneously or independently when n>1, chosen from a hydrogen atom, a —(O—$CH_2CH_2$—)$_p$—$OR_8$; it being understood that $R_2$, $R_3$, $R_5$, $R_7$, $R_8$, $R_{8'}$, $R_{12}$, $R_{13}$, m, n and p have the same definitions as those given previously with Formula (II).

Yet, a further preferred embodiment provides a compound of Formula (II), wherein $R_4$ can be, alone or simultaneously or independently when n>1, chosen from a hydrogen atom, a —(O—$CH_2CH_2$—)$_p$—$NR_8R_{8'}$; it being understood that $R_2$, $R_3$, $R_5$, $R_7$, $R_8$, $R_{8'}$, $R_{12}$, $R_{13}$, m, n and p have the same definitions as those given previously with Formula (II).

Yet, a further preferred embodiment provides a compound of Formula (II), wherein $R_4$ can be, alone or simultaneously or independently when n>1, chosen from a hydrogen atom, a —$NR_8$—($CH_2CH_2$—O)$_p$—$R_{8'}$; it being understood that $R_2$, $R_3$, $R_5$, $R_7$, $R_8$, $R_{8'}$, $R_{12}$, $R_{13}$, m, n and p have the same definitions as those given previously with Formula (II).

Yet, a further preferred embodiment provides a compound of Formula (II), wherein $R_4$ can be, alone or simultaneously or independently when n>1, chosen from a hydrogen atom, a —$NR_8$—($C_2$-$C_8$)-alkyl-$NR_8R_{8'}$; it being understood that $R_2$, $R_3$, $R_5$, $R_7$, $R_8$, $R_{8'}$, $R_{12}$, $R_{13}$, m, n and p have the same definitions as those given previously with Formula (II).

Yet, a further preferred embodiment provides a compound of Formula (II), wherein $R_4$ can be, alone or simultaneously or independently when n>1, chosen from a hydrogen atom, a —$NR_8$—($C_2$-$C_8$)-alkyl-$OR_{8'}$; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment, a compound according to Formula (II) can be provided wherein $R_4$ can be, alone or simultaneously or independently when n>1, chosen from a hydrogen atom or a —$NR_8R_{8'}$; it being understood that $R_2$, $R_3$, $R_5$, $R_7$, $R_8$, $R_{8'}$, $R_{12}$, $R_{13}$, m, n and p have the same definitions as those given previously with Formula (II).

In another preferred embodiment provides a compound of Formula (II), can be provided wherein $R_4$ can be, alone or simultaneously or independently when n>1, chosen from a hydrogen atom; —$NR_8R_{8'}$, wherein $R_5$ and $R_{8'}$ can be simultaneously or independently chosen from a hydrogen atom, an optionally substituted alkyl as defined herein, an optionally substituted cycloalkyl as defined herein; it being understood that $R_2$, $R_3$, $R_5$, $R_7$, $R_{12}$, $R_{13}$, m, n and p have the same definitions as those given previously with Formula (II).

In another preferred embodiment, a compound according to Formula (II) can be provided wherein $R_4$ can be, alone or simultaneously or independently when n>1, chosen from a hydrogen atom or a —$NR_8R_{8'}$; wherein $R_5$ and $R_{8'}$ are linked together with the nitrogen atom to which they are covalently linked to form an optionally heterocyclyl group as defined herein it being understood that $R_2$, $R_3$, $R_5$, $R_7$, $R_{12}$, $R_{13}$, m, n and p have the same definitions as those given previously with Formula (II).

In another preferred embodiment provides a compound of Formula (II), can be provided wherein $R_4$ can be, alone or simultaneously or independently when n>1, chosen from a hydrogen atom; —$NR_8R_{8'}$, wherein $R_5$ and $R_8$, can be simultaneously or independently chosen from a hydrogen atom, an optionally substituted aryl as defined herein, an optionally substituted cycloalkyl as defined herein; it being understood that $R_2$, $R_3$, $R_5$, $R_7$, $R_{12}$, $R_{13}$, m, n and p have the same definitions as those given previously with Formula (II).

In another preferred embodiment provides a compound of Formula (II), can be provided wherein $R_4$ can be, alone or simultaneously or independently when n>1, chosen from a hydrogen atom; —$NR_8R_{8'}$, wherein $R_5$ and $R_8$, can be simultaneously or independently chosen from a hydrogen atom, an optionally substituted heteroaryl as defined herein, an optionally substituted cycloalkyl as defined herein; it being understood that $R_2$, $R_3$, $R_5$, $R_7$, $R_{12}$, $R_{13}$, m, n and p have the same definitions as those given previously with Formula (II).

In another preferred embodiment provides a compound of Formula (II), can be provided wherein $R_4$ can be, alone or simultaneously or independently when n>1, chosen from a hydrogen atom; —$NR_8R_{8'}$, wherein $R_5$ and $R_8$, can be simultaneously or independently chosen from a hydrogen atom, an optionally substituted benzyl as defined herein, an optionally substituted cycloalkyl as defined herein; it being understood that $R_2$, $R_3$, $R_5$, $R_7$, $R_{12}$, $R_{13}$, m, n and p have the same definitions as those given previously with Formula (II).

In yet a further preferred embodiment, a compound according to Formula (II) can be provided, wherein $R_5$ can be chosen from a hydrogen atom; an optionally substituted alkoxy as defined herein; a hydroxyl; a halogen atom as defined herein; a methyl; it being understood that $R_2$, $R_3$, $R_4$, $R_7$, $R_8$, $R_{8'}$, $R_{12}$, $R_{13}$, m, n and p have the same definitions as those given previously with Formula (II).

Yet another preferred embodiment provides a compound of Formula (II), wherein $R_5$ can be a hydrogen atom; a halogen atom as defined herein; an optionally substituted alkyl as defined herein, preferably said optionally substituted alkyl being substituted by one or more halogen atom(s) as defined herein; an optionally substituted cycloalkyl as defined herein; an optionally substituted alkoxy as defined herein; a hydroxyl; a cyano; an azido; a —NR$_8$R$_{8'}$; a —(CO)—O—R$_7$; a —(CO)—NR$_{12}$R$_{13}$; an optionally substituted heterocyclyl group as defined herein; it being understood that R$_2$, R$_3$, R$_4$, R$_7$, R$_8$, R$_{8'}$, R$_{12}$, R$_{13}$, m, n and p have the same definitions as those given previously with Formula (II).

Yet another preferred embodiment provides a compound of Formula (II), wherein R$_5$ can be a hydrogen atom; a halogen atom as defined herein; an optionally substituted alkyl as defined herein, preferably said optionally substituted alkyl being substituted by one or more halogen atom(s); an optionally substituted alkoxy as defined herein; a hydroxyl; a cyano; an azido; a —NR$_8$R$_{8'}$; a —(CO)—O—R$_7$; a —(CO)—NR$_{12}$R$_{13}$; it being understood that R$_2$, R$_3$, R$_4$, R$_7$, R$_8$, R$_{8'}$, R$_{12}$, R$_{13}$, m, n and p have the same definitions as those given previously with Formula (II).

Yet another preferred embodiment provides a compound of Formula (II), wherein R$_5$ can be a hydrogen atom; a halogen atom as defined herein; an optionally substituted alkyl as defined herein, preferably said optionally substituted alkyl being substituted by one or more halogen atom(s); an optionally substituted alkoxy as defined herein; a hydroxyl; a cyano; an azido; a —NR$_8$R$_{8'}$; it being understood that R$_2$, R$_3$, R$_4$, R$_7$, R$_8$, R$_{8'}$, R$_{12}$, R$_{13}$, m, n and p have the same definitions as those given previously with Formula (II).

In a further preferred embodiment, a compound according to Formula (II) can be provided, wherein R$_5$ can be selected from a hydrogen atom; a methoxy; an ethoxy; an iso-propoxy; a tert-butoxy; a hydroxyl; a fluorine; a chlorine; a cyano; an azido; a —CF$_3$; a methyl; it being understood that R$_2$, R$_3$, R$_4$, R$_7$, R$_8$, R$_{8'}$, R$_{12}$, R$_{13}$, m, n and p have the same definitions as those given previously with Formula (II).

In a further preferred embodiment, a compound according to Formula (II) can be provided, wherein R$_5$ can be selected from a hydrogen atom; a methoxy; an ethoxy; an iso-propoxy; a tert-butoxy; a hydroxyl; a fluorine; a chlorine; it being understood that R$_2$, R$_3$, R$_4$, R$_7$, R$_8$, R$_{8'}$, R$_{12}$, R$_{13}$, m, n and p have the same definitions as those given previously with Formula (II).

In a further preferred embodiment, a compound according to Formula (II) can be provided, wherein R$_5$ is a hydrogen atom; it being understood that R$_2$, R$_3$, R$_4$, R$_7$, R$_8$, R$_{8'}$, R$_{12}$, R$_{13}$, m, n and p have the same definitions as those given previously with Formula (II).

In a further preferred embodiment, a compound according to Formula (II) can be provided, wherein R$_5$ is an optionally substituted alkoxy as defined herein; it being understood that R$_2$, R$_3$, R$_4$, R$_7$, R$_8$, R$_{8'}$, R$_{12}$, R$_{13}$, m, n and p have the same definitions as those given previously with Formula (II).

In a further preferred embodiment, a compound according to Formula (II) can be provided, wherein R$_5$ is an optionally substituted fluoroalkyl as defined herein; it being understood that R$_2$, R$_3$, R$_4$, R$_7$, R$_8$, R$_{8'}$, R$_{12}$, R$_{13}$, m, n and p have the same definitions as those given previously with Formula (II).

In a further preferred embodiment, a compound according to Formula (II) can be provided, wherein R$_5$ is a methoxy; it being understood that R$_2$, R$_3$, R$_4$, R$_7$, R$_8$, R$_{8'}$, R$_{12}$, R$_{13}$, m, n and p have the same definitions as those given previously with Formula (II).

In a further preferred embodiment, a compound according to Formula (II) can be provided, wherein R$_5$ is an ethoxy; it being understood that R$_2$, R$_3$, R$_4$, R$_7$, R$_8$, R$_{8'}$, R$_{12}$, R$_{13}$, m, n and p have the same definitions as those given previously with Formula (II).

In a further preferred embodiment, a compound according to Formula (II) can be provided, wherein R$_5$ is an iso-propoxy; it being understood that R$_2$, R$_3$, R$_4$, R$_7$, R$_8$, R$_{8'}$, R$_{12}$, R$_{13}$, m, n and p have the same definitions as those given previously with Formula (II).

In a further preferred embodiment, a compound according to Formula (II) can be provided, wherein R$_5$ is a tert-butoxy; it being understood that R$_2$, R$_3$, R$_4$, R$_7$, R$_8$, R$_{8'}$, R$_{12}$, R$_{13}$, m, n and p have the same definitions as those given previously with Formula (II).

In a further preferred embodiment, a compound according to Formula (II) can be provided, wherein R$_5$ is a hydroxyl; it being understood that R$_2$, R$_3$, R$_4$, R$_7$, R$_8$, R$_{8'}$, R$_{12}$, R$_{13}$, m, n and p have the same definitions as those given previously with Formula (II).

In a further preferred embodiment, a compound according to Formula (II) can be provided, wherein R$_5$ is a fluorine; it being understood that R$_2$, R$_3$, R$_4$, R$_7$, R$_8$, R$_{8'}$, R$_{12}$, R$_{13}$, m, n and p have the same definitions as those given previously with Formula (II).

In a further preferred embodiment, a compound according to Formula (II) can be provided, wherein R$_5$ is a chlorine; it being understood that R$_2$, R$_3$, R$_4$, R$_7$, R$_8$, R$_{8'}$, R$_{12}$, R$_{13}$, m, n and p have the same definitions as those given previously with Formula (II).

In a further preferred embodiment, a compound according to Formula (II) can be provided, wherein R$_5$ is a —CF$_3$; it being understood that R$_2$, R$_3$, R$_4$, R$_7$, R$_8$, R$_{8'}$, R$_{12}$, R$_{13}$, m, n and p have the same definitions as those given previously with Formula (II).

In a further preferred embodiment, a compound according to Formula (II) can be provided, wherein R$_5$ is a cyano; it being understood that R$_2$, R$_3$, R$_4$, R$_7$, R$_8$, R$_{8'}$, R$_{12}$, R$_{13}$, m, n and p have the same definitions as those given previously with Formula (II).

In a further preferred embodiment, a compound according to Formula (II) can be provided, wherein R$_5$ is an azido; it being understood that R$_2$, R$_3$, R$_4$, R$_7$, R$_8$, R$_{8'}$, R$_{12}$, R$_{13}$, m, n and p have the same definitions as those given previously with Formula (II).

In a further preferred embodiment, a compound according to Formula (II) can be provided, wherein R$_5$ is a methyl; it being understood that R$_2$, R$_3$, R$_4$, R$_7$, R$_8$, R$_{8'}$, R$_{12}$, R$_{13}$, m, n and p have the same definitions as those given previously with Formula (II).

In a further preferred embodiment, a compound according to Formula (II) can be provided, wherein R$_5$ is a hydrogen atom; it being understood that R$_2$, R$_3$, R$_4$, R$_7$, R$_8$, R$_{8'}$, R$_{12}$, R$_{13}$, m, n and p have the same definitions as those given previously with Formula (II).

Yet, a further preferred embodiment provides a compound of Formula (II), wherein R$_5$ can be chosen from a hydrogen atom; a —(O—CH$_2$CH$_2$—)$_p$—NR$_{12}$; a —(O—CH$_2$CH$_2$—)$_p$—NR$_{12}$R$_{13}$; a —NR$_{12}$—(CH$_2$CH$_2$—O)$_p$—R$_{13}$; a —NR$_{12}$—(C$_2$-C$_{10}$)-alkyl-NR$_{12}$R$_{13}$; a —NR$_{12}$—(C$_2$-C$_{10}$)-alkyl-OR$_{13}$; it being understood that R$_2$, R$_3$, R$_4$, R$_7$, R$_8$, R$_{8'}$, R$_{12}$, R$_{13}$, m, n and p have the same definitions as those given previously with Formula (II).

Yet, a further preferred embodiment provides a compound of Formula (II), wherein R$_5$ can be chosen from a hydrogen atom; a —(O—CH$_2$CH$_2$—)$_p$—NR$_8$; a —(O—CH$_2$CH$_2$—)$_p$—NR$_8$R$_{8'}$; a —NR$_8$—(CH$_2$CH$_2$—O)$_p$—R$_8$; a —NR$_8$—(C$_2$-C$_{10}$)-alkyl-NR$_8$R$_{8'}$; a —NR$_8$—(C$_2$-C$_{10}$)-alkyl- $OR_{8'}$; it being understood that $R_2$, $R_3$, $R_4$, $R_7$, $R_8$, $R_{8'}$, $R_{12}$, $R_{13}$, m, n and p have the same definitions as those given previously with Formula (II).

Yet, a further preferred embodiment provides a compound of Formula (II), wherein $R_5$ can be a —(O—CH$_2$CH$_2$—)$_p$—NR$_8$; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (II).

Yet, a further preferred embodiment provides a compound of Formula (II), wherein $R_5$ can be a hydrogen atom, a —(O—CH$_2$CH$_2$—)$_p$—NR$_8$R$_{8'}$; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (II).

Yet, a further preferred embodiment provides a compound of Formula (II), wherein $R_5$ can be a hydrogen atom, a —NR$_8$—(CH$_2$CH$_2$—O)$_p$—R$_{8'}$; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (II).

Yet, a further preferred embodiment provides a compound of Formula (II), wherein $R_5$ can be a hydrogen atom, a —NR$_8$—(C$_2$-C$_{10}$)-alkyl-NR$_8$R$_{8'}$; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (II).

Yet, a further preferred embodiment provides a compound of Formula (II), wherein $R_5$ can be a hydrogen atom, a —NR$_8$—(C$_2$-C$_{10}$)-alkyl-OR$_{8'}$; it being understood that $L_1$, $R_1$, $R_2$, $R_{2'}$, $R_3$, $R_4$, $R_6$, $R_7$, $R_8$, $R_{8'}$, $R_9$, $R_{10}$, $R_{11}$, $R_{12}$, $R_{13}$, m, n and p have the same definitions as those given previously with Formula (II).

In yet another preferred embodiment provides a compound of Formula (II), wherein $R_5$ can be chosen from a hydrogen atom; —(CO)—NR$_{12}$R$_{13}$, wherein $R_{12}$ and $R_{13}$ can be simultaneously or independently chosen from a hydrogen atom, an optionally substituted alkyl as defined herein, an optionally substituted cycloalkyl as defined herein, an optionally substituted aryl as defined herein, an optionally substituted benzyl group as defined herein; an optionally substituted heteroaryl as defined herein, an optionally substituted heterocyclyl group as defined herein; or $R_{12}$ and $R_{13}$ can be linked together with the nitrogen atom to which they are covalently linked to form an optionally heterocyclyl group as defined herein; it being understood that $R_2$, $R_3$, $R_4$, $R_7$, $R_8$, $R_{8'}$, m, n and p have the same definitions as those given previously with Formula (II).

Yet, another preferred embodiment provides a compound of Formula (II), wherein $R_5$ can be chosen from a hydrogen atom; —(CO)—NR$_{12}$R$_{13}$, wherein $R_{12}$ and $R_{13}$ can be simultaneously or independently chosen from a hydrogen atom, an optionally substituted alkyl as defined herein, an optionally substituted cycloalkyl as defined herein, an optionally substituted heterocyclyl group as defined herein; or $R_{12}$ and $R_{13}$ can be linked together with the nitrogen atom to which they are covalently linked to form an optionally heterocyclyl group as defined herein; it being understood that $R_2$, $R_3$, $R_4$, $R_7$, $R_8$, $R_{8'}$, m, n and p have the same definitions as those given previously with Formula (II).

Yet, another preferred embodiment provides a compound of Formula (II), wherein $R_5$ can be chosen from a hydrogen atom; —(CO)—NR$_{12}$R$_{13}$, wherein $R_{12}$ and $R_{13}$ can be simultaneously or independently chosen from a hydrogen atom, an optionally substituted alkyl as defined herein, an optionally substituted cycloalkyl as defined herein, an optionally substituted heterocyclyl group as defined herein; it being understood that $R_2$, $R_3$, $R_4$, $R_7$, $R_8$, $R_{8'}$, m, n and p have the same definitions as those given previously with Formula (II).

Yet, another preferred embodiment provides a compound of Formula (II), wherein $R_5$ can be chosen from a hydrogen atom; —(CO)—NR$_{12}$R$_{13}$, wherein $R_{12}$ and $R_{13}$ can be simultaneously or independently chosen from a hydrogen atom, an optionally substituted alkyl as defined herein, an optionally substituted cycloalkyl as defined herein; it being understood that $R_2$, $R_3$, $R_4$, $R_7$, $R_8$, $R_{8'}$, m, n and p have the same definitions as those given previously with Formula (II).

Another preferred embodiment provides a compound of Formula (II), wherein $R_5$ is a —(CO)—NR$_{12}$R$_{13}$, wherein $R_{12}$ and $R_{13}$ can be simultaneously or independently chosen from a hydrogen atom and an optionally substituted alkyl as defined herein; it being understood that $R_2$, $R_3$, $R_4$, $R_7$, $R_8$, $R_{8'}$, m, n and p have the same definitions as those given previously with Formula (II).

Another preferred embodiment provides a compound of Formula (II), wherein $R_5$ is —(CO)—NR$_{12}$R$_{13}$, wherein $R_{12}$ and $R_{13}$ can be simultaneously or independently chosen from a hydrogen atom and an optionally substituted cycloalkyl as defined herein; it being understood that $R_2$, $R_3$, $R_4$, $R_7$, $R_8$, $R_{8'}$, m, n and p have the same definitions as those given previously with Formula (II).

Another preferred embodiment provides a compound of Formula (II), wherein $R_5$ is a —(CO)—NR$_{12}$R$_{13}$, wherein $R_{12}$ and $R_{13}$ can be simultaneously or independently chosen from a hydrogen atom and a heterocyclyl group as defined herein; it being understood that $R_2$, $R_3$, $R_4$, $R_7$, $R_8$, $R_{8'}$, m, n and p have the same definitions as those given previously with Formula (II).

Another preferred embodiment provides a compound of Formula (II), wherein $R_5$ is a —(CO)—NR$_{12}$R$_{13}$, wherein $R_{12}$ and $R_{13}$ can be simultaneously or independently chosen from a hydrogen atom and an optionally substituted aryl as defined herein; it being understood that $R_2$, $R_3$, $R_4$, $R_7$, $R_8$, $R_{8'}$, m, n and p have the same definitions as those given previously with Formula (II).

Another preferred embodiment provides a compound of Formula (II), wherein $R_5$ is a —(CO)—NR$_{12}$R$_{13}$, wherein $R_{12}$ and $R_{13}$ can be simultaneously or independently chosen from a hydrogen atom and an optionally substituted heteroaryl as defined herein; it being understood that $R_2$, $R_3$, $R_4$, $R_7$, $R_8$, $R_{8'}$, m, n and p have the same definitions as those given previously with Formula (II).

Another preferred embodiment provides a compound of Formula (II), wherein $R_5$ is a —(CO)—NR$_{12}$R$_{13}$, wherein $R_{12}$ and $R_{13}$ can be simultaneously or independently chosen from a hydrogen atom and an optionally substituted benzyl as defined herein; it being understood that $R_2$, $R_3$, $R_4$, $R_7$, $R_8$, $R_{8'}$, m, n and p have the same definitions as those given previously with Formula (II).

Another preferred embodiment provides a compound of Formula (II), wherein $R_5$ is —(CO)—NR$_{12}$R$_{13}$, wherein $R_{12}$ and $R_{13}$ are linked together with the nitrogen atom to which they are covalently linked to form an optionally substituted heterocyclyl group as defined herein; it being understood that $R_2$, $R_3$, $R_4$, $R_7$, $R_8$, $R_{8'}$, m, n and p have the same definitions as those given previously with Formula (II).

Another preferred embodiment provides a compound of Formula (II), wherein $R_5$ is a —(CO)—NR$_{12}$R$_{13}$, wherein $R_{12}$ and $R_{13}$ can be simultaneously or independently chosen from a hydrogen atom; a methyl; a ethyl; a isopropyl; a tert-butyl; a cyclopropyl; a cyclobutyl; a cyclopentyl; a cyclohexyl; it being understood that $R_2$, $R_3$, $R_4$, $R_7$, $R_8$, $R_{8'}$, m, n and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m can be 1 or 2; it being understood that $R_2$, $R_3$, $R_4$, $R_5$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; it being understood that $R_2$, $R_3$, $R_4$, $R_5$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; it being understood that $R_2$, $R_3$, $R_4$, $R_5$, $R_7$, $R_8$, $R_{8'}$, $R_{12}$, $R_{13}$ and p have the same definitions as those given previously with Formula (II).

In yet a preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a heterocyclyl group as defined herein; it being understood that $R_4$, $R_5$, $R_7$, $R_8$, $R_{8'}$, $R_{12}$, $R_{13}$ and p the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a heterocyclyl group as defined herein; it being understood that $R_4$, $R_5$, $R_7$, $R_8$, $R_{8'}$, $R_{12}$, $R_{13}$ and p have the same definitions as those given previously with Formula (II).

In yet a preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a 1-methylpiperidin-4-yl; it being understood that $R_4$, $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m can be 2; and $R_2$ is a hydrogen atom and $R_3$ is a 1-methylpiperidin-4-yl; it being understood that $R_4$, $R_5$, $R_7$, $R_8$, $R_{8'}$, $R_{12}$, $R_{13}$ and p have the same definitions as those given previously with Formula (II).

In yet a preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ and $R_3$ are linked together with the nitrogen atom to which they are covalently linked to form a heterocyclyl group as defined herein; it being understood that $R_4$, $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ and $R_3$ are linked together with the nitrogen atom to which they are covalently linked to form a heterocyclyl group as defined herein; it being understood that $R_4$, $R_5$, $R_7$, $R_8$, $R_{8'}$, $R_{12}$, $R_{13}$ and p have the same definitions as those given previously with Formula (II).

In yet a preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ and $R_3$ are linked together with the nitrogen atom to which they are covalently linked to form a pyrrolidin-1-yl; it being understood that $R_4$, $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ and $R_3$ are linked together with the nitrogen atom to which they are covalently linked to form a pyrrolidin-1-yl; it being understood that $R_4$, $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1 or 2; and $R_2$ is a hydrogen atom and $R_3$ is an optionally substituted alkyl as defined herein; it being understood that $R_4$, $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m can be 1; and $R_2$ is a hydrogen atom and $R_3$ is an optionally substituted alkyl as defined herein; it being understood that $R_4$, $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m can be 2; and $R_2$ is a hydrogen atom and $R_3$ is an optionally substituted alkyl as defined herein; it being understood that $R_4$, $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m can be 1; and $R_2$ is a hydrogen atom and $R_3$ is an optionally substituted cycloalkyl as defined herein; it being understood that $R_4$, $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is an optionally substituted cycloalkyl as defined herein; it being understood that $R_4$, $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; it being understood that $R_4$, $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; it being understood that $R_4$, $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ is an optionally substituted alkyl as defined herein; it being understood that $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ is an optionally substituted alkyl as defined herein; it being understood that $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ is a hydrogen atom; it being understood that $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ is a hydrogen atom; it being understood that $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ is a methyl; it being understood that $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ is a methyl; it being understood that $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ is a —$CF_3$; it being understood that $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ is a —$CF_3$; it being understood that $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ is a cyano; it being understood that $R_5$, $R_7$, $R_8$, $R_{8'}$, $R_{12}$ and $R_{13}$, $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ is a cyano; it being understood that $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ can be a methoxy, an ethoxy, an isopropoxy, a tert-butoxy; it being understood that $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ can be a methoxy, an ethoxy, an isopropoxy, a tert-butoxy; it being understood that $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ can be a halogen atoms as defined herein; it being understood that $R_8$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ can be a halogen atoms as defined herein; it being understood that $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ is a hydroxyl; it being understood that $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ is a hydroxyl; it being understood that $R_5$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is hydrogen atom and $R_3$ is a 1-methylpiperidin-4-yl; and $R_5$ can be a chlorine; it being understood that $R_4$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a 1-methylpiperidin-4-yl; and $R_5$ is a chlorine; it being understood that $R_4$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is hydrogen atom and $R_3$ is a 1-methylpiperidin-4-yl; and $R_5$ can be a fluorine; it being understood that $R_4$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a 1-methylpiperidin-4-yl; and $R_5$ is a fluorine; it being understood that $R_4$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ and $R_3$ are linked together with the nitrogen atom to which they are covalently linked to form a pyrrolidin-1-yl; and $R_5$ is a chlorine; it being understood that $R_4$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ and $R_3$ are linked together with the nitrogen atom to which they are covalently linked to form a pyrrolidin-1-yl; and $R_5$ is a chlorine; it being understood that $R_4$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ and $R_3$ are linked together with the nitrogen atom to which they are covalently linked to form a pyrrolidin-1-yl; and $R_5$ is a fluorine; it being understood that $R_4$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ and $R_3$ are linked together with the nitrogen atom to which they are covalently linked to form a pyrrolidin-1-yl; and $R_5$ is a fluorine; it being understood that $R_4$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_5$ is a halogen atom as define herein; it being understood that $R_4$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_5$ is a halogen atom as define herein; it being understood that $R_4$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_5$ is a fluorine; it being understood that $R_4$, $R_7$, $R_8$, $R_{8'}$, $R_{12}$, $R_{13}$ and p have the same definitions as those given previously with Formula (II).

In yet a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_5$ is a fluorine; it being understood that $R_4$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_5$ is a chlorine; it being understood that $R_4$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_5$ is a chlorine; it being understood that $R_4$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_5$ is a —$CF_3$; it being understood that $R_4$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_5$ is a —$CF_3$; it being understood that $R_4$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_5$ is a cyano; it being understood that $R_4$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_5$ is a cyano; it being understood that $R_4$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_5$ is an azido; it being understood that $R_4$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_5$ is an azido; it being understood that $R_4$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_5$ is a methyl; it being understood that $R_4$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_5$ is a methyl; it being understood that $R_4$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_5$ is an optionally substituted alkoxy as defined herein; it being understood that $R_4$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_5$ is an optionally substituted alkoxy; it being understood that $R_4$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is tert-butyl; and $R_5$ can be a methoxy, an ethoxy, an isopropoxy, a tert-butoxy; it being understood that $R_4$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_5$ can be a methoxy, an ethoxy, an isopropoxy; a tert-butoxy; it being understood that $R_4$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_5$ is a methoxy; it being understood that $R_4$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m can be 2; and $R_2$ is a hydrogen atom; and $R_3$ is a tert-butyl; and $R_5$ is a methoxy; it being understood that $R_4$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_5$ is a hydroxyl; it being understood that $R_4$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_5$ is a hydroxyl; it being understood that $R_4$, $R_7$, $R_8$, $R_{8'}$, $R_{12}$, $R_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 1;

and R$_2$ is a hydrogen atom; and R$_3$ is a tert-butyl; and R$_5$ is a hydrogen atom; it being understood that R$_4$, R$_7$, R$_8$, R$_{8'}$, R$_{12}$, R$_{13}$ and p have the same definitions as those given previously with Formula (II).

In a further preferred embodiment, a compound according to Formula (II) can be provided, wherein n can take any one of the values 0, 1, 2, 3 or 4, preferably 0, 1, 2 or 3, more preferably 0, 1 or 2, still more preferably 0 or 1 and m is 2; and R$_2$ is a hydrogen atom; and R$_3$ is a tert-butyl; and R$_5$ is a hydrogen atom; it being understood that R$_4$, R$_7$, R$_8$, R$_{8'}$, R$_{12}$, R$_{13}$ and p have the same definitions as those given previously with Formula (II).

The present disclosure also provides in a preferred embodiment a compound of Formula (III) having the structure:

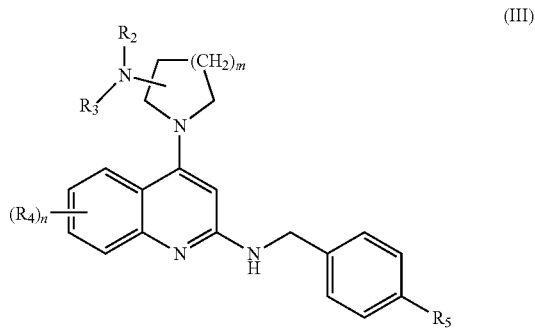

(III)

wherein,

R$_2$ and R$_3$ can be simultaneously or independently chosen from a hydrogen atom; a —(CO)—R$_7$; a —(CO)—O—R$_7$; a —(CO)—NR$_8$OH; a —(CO)—NR$_8$R$_{8'}$; a —SO$_2$—R$_7$; a —SO$_2$—NR$_8$R$_{8'}$; an optionally substituted alkyl as defined herein, preferably said optionally substituted alkyl being substituted with one or more —NR$_8$R$_{8'}$; an optionally substituted cycloalkyl as defined herein, preferably said optionally substituted cycloalkyl being substituted with one or more —NR$_8$R$_{8'}$; an optionally substituted alkenyl as defined herein; an optionally substituted alkynyl as defined herein; an optionally substituted cycloalkenyl as defined herein; an optionally substituted cycloalkynyl as defined herein; an optionally substituted aryl as defined herein; an optionally substituted benzyl as defined herein; an optionally substituted heteroaryl as defined herein; an optionally substituted heterocyclyl group as defined herein; or R$_2$ and R$_3$ can be linked together with the nitrogen atom to which they are covalently linked to form an optionally substituted heterocyclyl group as defined herein;

R$_4$ can be, alone or simultaneously or independently when n>1, chosen from a hydrogen atom; a halogen atom as defined herein; an optionally substituted alkyl as defined herein, preferably said optionally substituted alkyl being substituted by one or more halogen atom(s) as defined herein, by one or more hydroxyl, by one or more alkoxy as defined herein, by one or more —NR$_8$R$_{8'}$ and combination thereof; an optionally substituted fluoroalkyl as defined herein; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted alkoxy as defined herein; a hydroxyl; a nitro; an azido; a cyano; a —NR$_{12}$R$_{13}$; a —NR$_8$R$_{8'}$; a —O—(R$_7$); a —(CO)—R$_7$; a —(CO)—O—R$_7$; a —(CO)—NR$_{12}$OH; a —(CO)—NR$_8$OH; a —(CO)—NR$_{12}$R$_{13}$; a —(CO)—NR$_8$R$_{8'}$; a —O—(CO)—R$_7$; a —O—(CO)—NR$_{12}$R$_{13}$; a —O—(CO)—NR$_8$R$_{8'}$; a —NR$_{12}$—(CO)—R$_7$; a —NR$_8$—(CO)—R$_7$; a —NR$_{12}$—(CO)—OR$_7$; a —NR$_8$—(CO)—OR$_7$; a O—(CO)—OR$_7$; a —NR$_{12}$—(CO)—NR$_{12}$R$_{13}$; a —NR$_8$—(CO)—NR$_8$R$_{8'}$; a —(O—CH$_2$CH$_2$)$_p$—OR$_{12}$; a —(O—CH$_2$CH$_2$)$_p$—NR$_7$; a —(O—CH$_2$CH$_2$)$_p$—NR$_{12}$R$_{13}$; a —(O—CH$_2$CH$_2$)$_p$—NR$_8$R$_{8'}$; a —NR$_{12}$(—CH$_2$CH$_2$—O)$_p$—R$_{13}$; a —NR$_8$(—CH$_2$CH$_2$—O)$_p$—R$_7$; a —SO$_2$—R$_7$; a —NR$_{12}$—SO$_2$—R$_7$; a —NR$_8$—SO$_2$—R$_7$; a —SO$_2$—NR$_{12}$R$_{13}$; a —SO$_2$—NR$_8$R$_{8'}$; a —NR$_{12}$—SO$_2$—NR$_{12}$R$_{13}$; a —NR$_8$—SO$_2$—NR$_8$R$_{8'}$; a —NR$_{12}$—(C$_2$-C$_8$)-alkyl-NR$_{12}$R$_{13}$; a —NR$_8$—(C$_2$-C$_8$)-alkyl-NR$_8$R$_{8'}$; a —NR$_{12}$—(C$_2$-C$_8$)-alkyl-OR$_{13}$; a —NR$_8$—(C$_2$-C$_8$)-alkyl-NR$_7$; an optionally substituted aryl as defined herein; an optionally substituted benzyl as defined herein; an optionally substituted heteroaryl as defined herein; an optionally substituted heterocyclyl group as defined herein;

R$_5$ can be selected from a hydrogen atom; a fluorine; a chlorine; a CF$_3$; a methyl; a hydroxyl; an optionally substituted alkoxy; a cyano; an azido; a carboxyl;

R$_7$ can be chosen from a hydrogen atom; an optionally substituted alkyl as defined herein, preferably said optionally substituted alkyl being substituted by one or more —NR$_8$R$_{8'}$; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted aryl as defined herein; an optionally substituted benzyl as defined herein; an optionally substituted heteroaryl as defined herein; an optionally substituted heterocyclyl group as defined herein;

R$_8$ and R$_{8'}$ can be simultaneously or independently chosen from a hydrogen atom; an optionally substituted alkyl as defined herein; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted heterocyclyl group as defined herein; an optionally substituted aryl as defined herein; an optionally substituted benzyl as defined herein; an optionally substituted heteroaryl as defined herein; or R$_8$ and R$_{8'}$ can be linked together with the nitrogen atom to which they are covalently linked to form an optionally substituted heterocyclyl group as defined herein;

R$_{12}$ and R$_{13}$ can be simultaneously or independently chosen from a hydrogen atom; a —(CO)—R$_7$; a —(CO)—O—R$_7$; a —(CO)—NR$_8$OH; a —(CO)—NR$_8$R$_{8'}$; a —SO$_2$—R$_7$; a —SO$_2$—NR$_8$R$_{8'}$; an optionally substituted alkyl as defined herein, preferably said optionally substituted alkyl being substituted with at least one —NR$_8$R$_{8'}$; an optionally substituted cycloalkyl as defined herein, preferably said optionally substituted cycloalkyl being substituted with at least one —NR$_8$R$_{8'}$; an optionally substituted alkenyl as defined herein; an optionally substituted alkynyl as defined herein; an optionally substituted cycloalkenyl as defined herein; an optionally substituted cycloalkynyl as defined herein; an optionally substituted aryl as defined herein; an optionally substituted benzyl as defined herein; an optionally substituted heteroaryl as defined herein; an optionally substituted heterocyclyl group as defined herein; or R$_{12}$ and R$_{13}$ can be linked together with the nitrogen atom to which they are covalently linked to form an optionally substituted heterocyclyl group as defined herein;

n can represent an equal integer which can have any one of the values 0, 1, 2, 3 or 4, preferably 0, 1, 2 or 3, more preferably 0, 1 or 2 still more preferably 0 or 1.

m can represent an equal integer which can have any one of the values 1, 2 or 3 preferably 1 or 2, more preferably 2.

p can represent an equal integer which can have any one of the values 1, 2, 3, 4 or 5, preferably 1, 2, 3 or 4, more preferably 1, 2 or 3 still more preferably 1 or 2.

and any pharmaceutically acceptable salt, hydrates, solvate, prodrugs, polymorphs, tautomers, isotopic variants, isomers, stereoisomers or mixtures of stereoisomers thereof, for use as a medicament to treat, decrease the severity and/or progression of, and/or prevent fibrosis and/or related diseases, or for use as a medicament to treat, decrease the severity and/or progression of, and/or prevent autophagy and/or related diseases and to inhibit autophagy flux, or for use in inhibiting cathepsins B (CTSB), L (CTSL) and/or D (CTSD) and/or related diseases; with the proviso that said compounds are not intended to be used for treating any forms of cancers.

In a preferred embodiment, a compound according to Formula (III) can be provided, wherein $R_2$ and $R_3$ can be simultaneously or independently chosen from a hydrogen atom; an optionally substituted alkyl as defined herein; an optionally substituted alkenyl as defined herein; an optionally substituted alkynyl as defined herein; an optionally substituted cycloalkyl as defined herein; an optionally substituted aryl as defined herein; an optionally substituted benzyl as defined herein; an optionally substituted heteroaryl as defined herein; an optionally substituted heterocyclyl group as defined herein; or $R_2$ and $R_3$ are linked together with the nitrogen atom to which they are covalently linked to form an optionally heterocyclyl group as defined herein; it being understood that $R_7$, $R_8$, $R_{8'}$, $R_{12}$, $R_{13}$, m, n and p have the same definitions as those given previously with Formula (III).

In a further preferred embodiment, a compound according to Formula (III) can be provided, wherein $R_2$ and $R_3$ can be simultaneously or independently chosen from a hydrogen atom; an optionally substituted alkyl as defined herein; an optionally substituted cycloalkyl as defined herein; an optionally substituted heterocyclyl group as defined herein; or $R_2$ and $R_3$ are linked together with the nitrogen atom to which they are covalently linked to form an optionally substituted heterocyclyl group as defined herein; it being understood that $R_4$, $R_5$, $R_7$, $R_8$, $R_{8'}$, $R_{12}$, $R_{13}$, m, n and p have the same definitions as those given previously with Formula (III).

In also a preferred embodiment, a compound according to Formula (III) can be provided, wherein $R_2$ and $R_3$ can be simultaneously or independently chosen from a hydrogen atom; an optionally substituted alkyl as defined herein; an optionally substituted cycloalkyl as defined herein; or $R_2$ and $R_3$ are linked together with the nitrogen atom to which they are covalently linked to form an optionally substituted heterocyclyl group as defined herein; it being understood that $R_4$, $R_5$, $R_7$, $R_8$, $R_{8'}$, $R_{12}$, $R_{13}$, m, n and p have the same definitions as those given previously with Formula (III).

In another preferred embodiment, a compound according to Formula (III) can be provided, wherein $R_2$ and $R_3$ can be simultaneously or independently chosen from a hydrogen; an optionally substituted alkyl as defined herein; an optionally substituted cycloalkyl as defined herein; an optionally substituted aryl as defined herein; an optionally substituted heteroaryl as defined herein; it being understood that $R_4$, $R_5$, $R_7$, $R_8$, $R_{8'}$, $R_{12}$, $R_{13}$, m, n and p have the same definitions as those given previously with Formula (III).

In another preferred embodiment, a compound according to Formula (III) can be provided, wherein $R_2$ and $R_3$ can be simultaneously or independently chosen from a hydrogen; an optionally substituted alkyl as defined herein; an optionally substituted cycloalkyl as defined herein; it being understood that $R_4$, $R_5$, $R_7$, $R_8$, $R_{8'}$, $R_{12}$, $R_{13}$, m, n and p have the same definitions as those given previously with Formula (III).

In a further preferred embodiment, a compound according to Formula (III) can be provided, wherein $R_2$ and $R_3$ can be simultaneously or independently chosen from a hydrogen atom; an optionally substituted alkyl as defined herein; it being understood that $R_4$, $R_5$, $R_7$, $R_8$, $R_{8'}$, $R_{12}$, $R_{13}$, m, n and p have the same definitions as those given previously with Formula (III).

In a further preferred embodiment, a compound according to Formula (III) can be provided, wherein $R_2$ and $R_3$ can be simultaneously or independently chosen from a hydrogen atom; an optionally substituted cycloalkyl as defined herein; it being understood that $R_4$, $R_5$, $R_7$, $R_8$, $R_{8'}$, $R_{12}$, $R_{13}$, m, n and p have the same definitions as those given previously with Formula (III).

In another preferred embodiment, a compound according to Formula (III) can be provided, wherein $R_2$ and $R_3$ can be simultaneously or independently chosen from a hydrogen atom; an optionally substituted heterocyclyl group as defined herein; it being understood that $R_4$, $R_5$, $R_7$, $R_8$, $R_{8'}$, $R_{12}$, $R_{13}$, m, n and p have the same definitions as those given previously with Formula (III).

In another preferred embodiment, a compound according to Formula (III) can be provided, wherein $R_2$ and $R_3$ can be simultaneously or independently chosen from a hydrogen atom; a 1-methylpiperidin-4-yl; it being understood that $R_4$, $R_5$, $R_7$, $R_8$, $R_{8'}$, $R_{12}$, $R_{13}$, m, n and p have the same definitions as those given previously with Formula (III).

In another preferred embodiment, a compound according to Formula (III) can be provided, wherein $R_2$ and $R_3$ can be simultaneously or independently chosen from a hydrogen atom; a tert-butyl; it being understood that $R_4$, $R_5$, $R_7$, $R_8$, $R_{8'}$, $R_{12}$, $R_{13}$, m, n and p have the same definitions as those given previously with Formula (III).

In another preferred embodiment, a compound according to Formula (III) can be provided, wherein $R_2$ and $R_3$ are linked together with the nitrogen atom to which they are covalently linked to form an optionally substituted heterocyclyl group as defined herein; it being understood that $R_4$, $R_5$, $R_7$, $R_8$, $R_{8'}$, $R_{12}$, $R_{13}$, m, n and p have the same definitions as those given previously with Formula (III).

In another preferred embodiment, a compound according to Formula (III) can be provided, wherein $R_2$ and $R_3$ are linked together with the nitrogen atom to which they are covalently linked to form a pyrrolidin-1-yl; it being understood that $R_4$, $R_5$, $R_7$, $R_8$, $R_{8'}$, $R_{12}$, $R_{13}$, m, n and p have the same definitions as those given previously with Formula (III).

Yet, in another preferred embodiment, a compound according to Formula (III) can be provided, wherein $R_4$ can be, alone or simultaneously or independently when n>1, chosen from a hydrogen atom; a halogen atom as defined herein; an optionally substituted alkyl as defined herein, preferably said optionally substituted alkyl being substituted by one or more halogen atom(s) as defined herein, by one or more hydroxyl, by one or more alkoxy, by one or more a —$NR_8R_{8'}$, and combination thereof; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted alkoxy as defined herein; a hydroxyl; a nitro; a cyano; an azido; a carboxyl, a —$NR_{12}R_{13}$. it being understood that $R_2$, $R_3$, $R_5$, $R_7$, $R_8$, $R_{8'}$, $R_{12}$, $R_{13}$, m, n and p have the same definitions as those given previously with Formula (III).

In another preferred embodiment, a compound according to Formula (III) can be provided wherein $R_4$ can be, alone or simultaneously or independently when n>1, chosen from a hydrogen atom; a halogen atom as defined herein; an optionally substituted alkyl as defined herein, preferably said optionally substituted alkyl being substituted by one or more halogen atom(s); an optionally substituted alkoxy as defined herein; a hydroxyl; a cyano; an azido; a carboxyl; a —$NR_{12}R_{13}$; it being understood that $R_2$, $R_3$, $R_5$, $R_7$, $R_8$, $R_{8'}$, $R_{12}$, $R_{13}$, m, n and p have the same definitions as those given previously with Formula (III).

Yet, another preferred embodiment provides a compound of Formula (III), wherein $R_4$ can be, alone or simultaneously or independently when n>1, chosen from a hydrogen atom; a —$NR_{12}R_{13}$, wherein $R_{12}$ and $R_{13}$ can be simultaneously or independently chosen from a hydrogen atom, an optionally substituted alkyl as defined herein, an optionally substituted cycloalkyl as defined herein, an optionally substituted heterocyclyl group as defined herein, an optionally substituted aryl as defined herein, an optionally substituted heteroaryl as defined herein, an optionally substituted benzyl as defined herein, or $R_{12}$ and $R_{13}$ can be linked together with the nitrogen atom to which they are covalently linked to form an optionally heterocyclyl group as defined herein; it being understood that $R_2$, $R_3$, $R_5$, $R_7$, $R_8$, $R_{8'}$, m, n and p have the same definitions as those given previously with Formula (III).

Yet, another preferred embodiment provides a compound of Formula (III), wherein $R_4$ can be, alone or simultaneously or independently when n>1, chosen from a hydrogen atom; a —$NR_{12}R_{13}$, wherein $R_{12}$ and $R_{13}$ can be simultaneously or independently chosen from a hydrogen atom, an optionally substituted aryl as defined herein; it being understood that $R_2$, $R_3$, $R_5$, $R_7$, $R_8$, $R_{8'}$, m, n and p have the same definitions as those given previously with Formula (III).

Yet, another preferred embodiment provides a compound of Formula (III), wherein $R_4$ can be, alone or simultaneously or independently when n>1, chosen from a hydrogen atom; a —$NR_{12}R_{13}$, wherein $R_{12}$ and $R_{13}$ can be simultaneously or independently chosen from a hydrogen atom, an optionally substituted heteroaryl as defined herein; it being understood that $R_2$, $R_3$, $R_5$, $R_7$, $R_8$, $R_{8'}$, m, n and p have the same definitions as those given previously with Formula (III).

Yet, another preferred embodiment provides a compound of Formula (III), wherein $R_4$ can be, alone or simultaneously or independently when n>1, chosen from a hydrogen atom; a —$NR_{12}R_{13}$, wherein $R_{12}$ and $R_{13}$ can be simultaneously or independently chosen from a hydrogen atom, an optionally substituted benzyl as defined herein; it being understood that $R_2$, $R_3$, $R_5$, $R_7$, $R_8$, $R_{8'}$, m, n and p have the same definitions as those given previously with Formula (III).

Yet, another preferred embodiment provides a compound of Formula (III), wherein $R_4$ can be, alone or simultaneously or independently when n>1, chosen from a hydrogen atom; a —$NR_{12}R_{13}$ wherein, $R_{12}$ and $R_{13}$ can be simultaneously or independently chosen from a hydrogen atom, an optionally substituted alkyl as defined herein, an optionally substituted cycloalkyl as defined herein; it being understood that $R_2$, $R_3$, $R_5$, $R_7$, $R_8$, $R_{8'}$, m, n and p have the same definitions as those given previously with Formula (III).

Yet, another preferred embodiment provides a compound of Formula (III), wherein $R_4$ can be, alone or simultaneously or independently when n>1, chosen from a hydrogen atom; a —$NR_{12}R_{13}$ wherein, $R_{12}$ and $R_{13}$ can be simultaneously or independently chosen from a hydrogen atom, an optionally substituted alkyl as defined herein, an optionally substituted cycloalkyl as defined herein, an optionally substituted pyrimidin; it being understood that $R_2$, $R_3$, $R_5$, $R_7$, $R_8$, $R_{8'}$, m, n and p have the same definitions as those given previously with Formula (III).

Yet, another preferred embodiment provides a compound of Formula (III), wherein $R_4$ can be, alone or simultaneously or independently when n>1, chosen from a hydrogen atom; a —$NR_{12}R_{13}$ wherein, $R_{12}$ and $R_{13}$ can be simultaneously or independently chosen from a hydrogen atom, an optionally substituted alkyl as defined herein, an optionally substituted cycloalkyl as defined herein, an optionally substituted pyrimidin-2-yl, an optionally substituted pyrimidin-4-yl, an optionally substituted pyrimidin-5-yl; it being understood that $R_2$, $R_3$, $R_5$, $R_7$, $R_8$, $R_{8'}$, m, n and p have the same definitions as those given previously with Formula (III).

Yet, another preferred embodiment provides a compound of Formula (III), wherein $R_4$ can be, alone or simultaneously or independently when n>1, chosen from a hydrogen atom; a —$NR_{12}R_{13}$ wherein, $R_{12}$ and $R_{13}$ can be simultaneously or independently chosen from a hydrogen atom, a methyl, a cyclopropyl, an optionally substituted pyrimidin-2-yl, an optionally substituted pyrimidin-4-yl, an optionally substituted pyrimidin-5-yl; it being understood that $R_2$, $R_3$, $R_5$, $R_7$, $R_8$, $R_{8'}$, m, n and p have the same definitions as those given previously with Formula (III).

Yet, another preferred embodiment provides a compound of Formula (III), wherein $R_4$ can be, alone or simultaneously or independently when n>1, chosen from a hydrogen atom; a —$NR_{12}R_{13}$ wherein, $R_{12}$ and $R_{13}$ can be simultaneously or independently chosen from a hydrogen atom, an optionally substituted pyrimidin-2-yl, an optionally substituted pyrimidin-4-yl, an optionally substituted pyrimidin-5-yl; it being understood that $R_2$, $R_3$, $R_5$, $R_7$, $R_8$, $R_{8'}$, m, n and p have the same definitions as those given previously with Formula (III).

Yet, a further preferred embodiment provides a compound of Formula (III), wherein $R_4$ can be, alone or simultaneously or independently when n>1, chosen from a hydrogen atom; a —$NR_{12}R_{13}$ wherein, $R_{12}$ and $R_{13}$ can be simultaneously or independently chosen from a hydrogen atom, an optionally substituted alkyl as defined herein, an optionally substituted cycloalkyl as defined herein, an optionally substituted heterocyclyl group as defined herein; it being understood that $R_2$, $R_3$, $R_5$, $R_7$, $R_8$, $R_{8'}$, m, n and p have the same definitions as those given previously with Formula (III).

A further preferred embodiment provides a compound of Formula (III), wherein $R_4$ can be, alone or simultaneously or independently when n>1, chosen from a hydrogen atom; a —$NR_{12}R_{13}$ wherein, $R_{12}$ and $R_{13}$ are linked together with the nitrogen atom to which they are covalently linked to form an optionally heterocyclyl group as defined herein; it being understood that $R_2$, $R_3$, $R_5$, $R_7$, $R_8$, $R_{8'}$, m, n and p have the same definitions as those given previously with Formula (III).

In yet another preferred embodiment provides a compound of Formula (III), wherein $R_4$ can be, alone or simultaneously or independently when n>1, chosen from a hydrogen atom; —(CO)—$NR_{12}R_{13}$, wherein $R_{12}$ and $R_{13}$ can be simultaneously or independently chosen from a hydrogen atom, an optionally substituted alkyl as defined herein, an optionally substituted cycloalkyl as defined herein, an optionally substituted aryl as defined herein, an optionally substituted benzyl as defined herein; an optionally substituted heteroaryl as defined herein, an optionally substituted heterocyclyl group as defined herein; or $R_{12}$ and $R_{13}$ can be linked together with the nitrogen atom to which they are covalently linked to form an optionally heterocyclyl group as defined herein; it being understood that $R_2$, $R_3$, $R_5$, $R_7$, $R_8$, $R_{8'}$, m, n and p have the same definitions as those given previously with Formula (III).

Yet, another preferred embodiment provides a compound of Formula (III), wherein $R_4$ can be, alone or simultaneously or independently when n>1, chosen from a hydrogen atom; —(CO) $NR_{12}R_{13}$ wherein, $R_{12}$ and $R_{13}$ can be simultaneously or independently chosen from a hydrogen atom, an optionally substituted alkyl as defined herein, an optionally substituted cycloalkyl as defined herein, an optionally substituted heterocyclyl group as defined herein; or $R_{12}$ and $R_{13}$ are linked together with the nitrogen atom to which they are covalently linked to form an optionally heterocyclyl group as defined herein; it being understood that $R_2$, $R_3$, $R_5$, $R_7$, $R_8$, $R_{8'}$, m, n and p have the same definitions as those given previously with Formula (III).

Yet, another preferred embodiment provides a compound of Formula (III), wherein $R_4$ can be, alone or simultaneously or independently when n>1, chosen from a hydrogen atom; —(CO)—$NR_{12}R_{13}$ wherein, $R_{12}$ and $R_{13}$ can be simultaneously or independently chosen from a hydrogen atom, an optionally substituted alkyl as defined herein, an optionally substituted cycloalkyl as defined herein; it being understood that $R_2$, $R_3$, $R_5$, $R_7$, $R_8$, $R_{8'}$, m, n and p have the same definitions as those given previously with Formula (III).

Yet, another preferred embodiment provides a compound of Formula (III), wherein $R_4$ can be, alone or simultaneously or independently when n>1, chosen from a hydrogen atom; —(CO)—$NR_{12}R_{13}$ wherein, $R_{12}$ and $R_{13}$ can be simultaneously or independently chosen from a hydrogen atom, an optionally substituted alkyl as defined herein; it being understood that $R_2$, $R_3$, $R_5$, $R_7$, $R_8$, $R_{8'}$, m, n and p have the same definitions as those given previously with Formula (III).

Yet, another preferred embodiment provides a compound of Formula (III), wherein $R_4$ can be, alone or simultaneously or independently when n>1, chosen from a hydrogen atom; —(CO)—$NR_{12}R_{13}$ wherein, $R_{12}$ and $R_{13}$ can be simultaneously or independently chosen from a hydrogen atom, an optionally substituted cycloalkyl as defined herein; it being understood that $R_2$, $R_3$, $R_5$, $R_7$, $R_8$, $R_{8'}$, m, n and p have the same definitions as those given previously with Formula (III).

Yet, another preferred embodiment provides a compound of Formula (III), wherein $R_4$ can be, alone or simultaneously or independently when n>1, chosen from a hydrogen atom; —(CO)—$NR_{12}R_{13}$ wherein, $R_{12}$ and $R_{13}$ can be simultaneously or independently chosen from a hydrogen atom, an optionally substituted heterocyclyl group as defined herein; it being understood that $R_2$, $R_3$, $R_5$, $R_7$, $R_8$, $R_{8'}$, m, n and p have the same definitions as those given previously with Formula (III).

Yet, another preferred embodiment provides a compound of Formula (III), wherein $R_4$ can be, alone or simultaneously or independently when n>1, chosen from a hydrogen atom; —(CO)—$NR_{12}R_{13}$ wherein, $R_{12}$ and $R_{13}$ can be simultaneously or independently chosen from a hydrogen atom, an optionally substituted aryl as defined herein; it being understood that $R_2$, $R_3$, $R_5$, $R_7$, $R_8$, $R_{8'}$, m, n and p have the same definitions as those given previously with Formula (III).

Yet, another preferred embodiment provides a compound of Formula (III), wherein $R_4$ can be, alone or simultaneously or independently when n>1, chosen from a hydrogen atom; —(CO)—$NR_{12}R_{13}$ wherein, $R_{12}$ and $R_{13}$ can be simultaneously or independently chosen from a hydrogen atom, an optionally substituted heteroaryl as defined herein; it being understood that $R_2$, $R_3$, $R_5$, $R_7$, $R_8$, $R_{8'}$, m, n and p have the same definitions as those given previously with Formula (III).

Yet, another preferred embodiment provides a compound of Formula (III), wherein $R_4$ can be, alone or simultaneously or independently when n>1, chosen from a hydrogen atom; —(CO)—$NR_{12}R_{13}$ wherein, $R_{12}$ and $R_{13}$ can be simultaneously or independently chosen from a hydrogen atom, an optionally substituted benzyl as defined herein; it being understood that $R_2$, $R_3$, $R_5$, $R_7$, $R_8$, $R_{8'}$, m, n and p have the same definitions as those given previously with Formula (III).

Yet, another preferred embodiment provides a compound of Formula (III), wherein $R_4$ can be, alone or simultaneously or independently when n>1, chosen from a hydrogen atom; —(CO)—$NR_{12}R_{13}$ wherein, $R_{12}$ and $R_{13}$ are linked together with the nitrogen atom to which they are covalently linked to form an optionally substituted heterocyclyl group as defined herein; it being understood that $R_2$, $R_3$, $R_5$, $R_7$, $R_8$, $R_{8'}$, m, n and p have the same definitions as those given previously with Formula (III).

Yet, another preferred embodiment provides a compound of Formula (III), wherein $R_4$ can be, alone or simultaneously or independently when n>1, chosen from a hydrogen atom; —(CO)—$NR_{12}R_{13}$ wherein, $R_{12}$ and $R_{13}$ can be simultaneously or independently chosen from a hydrogen atom, a methyl, an ethyl, an isopropyl, a tert-butyl, a cyclopropyl, a cyclobutyl, a cyclopentyl, a cyclohexyl, it being understood that $R_2$, $R_3$, $R_5$, $R_7$, $R_8$, $R_{8'}$, m, n and p have the same definitions as those given previously with Formula (III).

In another preferred embodiment, a compound according to Formula (III) can be provided wherein $R_4$ can be, alone or simultaneously or independently when n>1, chosen from a hydrogen atom; a halogen atom as defined herein; an optionally substituted alkyl as defined herein, preferably said optionally substituted alkyl being substituted by one or more halogen atom(s) as defined herein; an optionally substituted alkoxy as defined herein; a hydroxyl; it being understood that $R_2$, $R_3$, $R_5$, $R_7$, $R_8$, $R_{8'}$, $R_{12}$, $R_{13}$, m, n and p have the same definitions as those given previously with Formula (III).

In another preferred embodiment, a compound according to Formula (III) can be provided wherein $R_4$ can be, alone or simultaneously or independently when n>1, chosen from a hydrogen atom; a halogen atom as defined herein; it being understood that $R_2$, $R_3$, $R_5$, $R_7$, $R_8$, $R_{8'}$, $R_{12}$, $R_{13}$, m, n and p have the same definitions as those given previously with Formula (III).

In another preferred embodiment, a compound according to Formula (III) can be provided wherein $R_4$ can be, alone or simultaneously or independently when n>1, chosen from a hydrogen atom; a fluorine; a chlorine; a methyl; an optionally substituted alkoxy as defined herein; an hydroxyl; a —$CF_3$; a cyano; an azido; a carboxyl; it being understood that $R_2$, $R_3$, $R_5$, $R_7$, $R_8$, $R_{8'}$, $R_{12}$, $R_{13}$, m, n and p have the same definitions as those given previously with Formula (III).

In another preferred embodiment, a compound according to Formula (III) can be provided wherein $R_4$ can be, alone or simultaneously or independently when n>1, chosen from a hydrogen atom; a fluorine; a chlorine; a methyl; it being understood that $R_2$, $R_3$, $R_5$, $R_7$, $R_8$, $R_{8'}$, $R_{12}$, $R_{13}$, m, n and p have the same definitions as those given previously with Formula (III).

In another preferred embodiment, a compound according to Formula (III) can be provided wherein $R_4$ can be, alone or simultaneously or independently when n>1, chosen from a hydrogen atom; a fluorine; a chlorine; it being understood that $R_2$, $R_3$, $R_5$, $R_7$, $R_8$, $R_{8'}$, $R_{12}$, $R_{13}$, m, n and p have the same definitions as those given previously with Formula (III).

In another preferred embodiment, a compound according to Formula (III) can be provided wherein $R_4$ can be, alone or simultaneously or independently when n>1, chosen from a hydrogen atom; an optionally substituted alkoxy; it being understood that $R_2$, $R_3$, $R_5$, $R_7$, $R_8$, $R_{8'}$, $R_{12}$, $R_{13}$, m, n and p have the same definitions as those given previously with Formula (III).

In another preferred embodiment, a compound according to Formula (III) can be provided wherein $R_4$ can be, alone or simultaneously or independently when n>1, chosen from a hydrogen atom; a methoxy; an ethoxy; an isopropoxy; a tert-butoxy; it being understood that $R_2$, $R_3$, $R_5$, $R_7$, $R_8$, $R_{8'}$, $R_{12}$, $R_{13}$, m, n and p have the same definitions as those given previously with Formula (III).

In another preferred embodiment, a compound according to Formula (III) can be provided wherein $R_4$ can be, alone or simultaneously or independently when n>1, chosen from a hydrogen atom; a methoxy; it being understood that $R_2$, $R_3$, $R_5$, $R_7$, $R_8$, $R_{8'}$, $R_{12}$, $R_{13}$, m, n and p have the same definitions as those given previously with Formula (III).

In another preferred embodiment, a compound according to Formula (III) can be provided wherein $R_4$ can be, alone or simultaneously or independently when n>1, chosen from a hydrogen atom; a hydroxyl; it being understood that $R_2$, $R_3$, $R_5$, $R_7$, $R_8$, $R_{8'}$, $R_{12}$, $R_{13}$, m, n and p have the same definitions as those given previously with Formula (III).

In another preferred embodiment, a compound according to Formula (III) can be provided wherein $R_4$ can be, alone or simultaneously or independently when n>1, chosen from a hydrogen atom; an optionally substituted fluoroalkyl as defined herein; it being understood that $R_2$, $R_3$, $R_5$, $R_7$, $R_8$, $R_{8'}$, $R_{12}$, $R_{13}$, m, n and p have the same definitions as those given previously with Formula (III).

In another preferred embodiment, a compound according to Formula (III) can be provided wherein $R_4$ is a hydrogen atom; it being understood that $R_2$, $R_3$, $R_5$, $R_7$, $R_8$, $R_{8'}$, $R_{12}$, $R_{13}$, m, n and p have the same definitions as those given previously with Formula (III).

Yet, a further preferred embodiment provides a compound of Formula (III), wherein $R_4$ can be, alone or simultaneously or independently when n>1, chosen from a hydrogen atom; a —(O—CH$_2$CH$_2$—)$_p$—OR$_{12}$; a —(O—CH$_2$CH$_2$—)$_p$—NR$_{12}$R$_{13}$; a —NR$_{12}$—(CH$_2$CH$_2$—O)$_p$—R$_{13}$; a —NR$_{12}$—(C$_2$-C$_8$)-alkyl-NR$_{12}$R$_{13}$; a —NR$_{12}$—(C$_2$-C$_8$)-alkyl-OR$_{13}$; it being understood that $R_2$, $R_3$, $R_5$, $R_7$, $R_8$, $R_{8'}$, $R_{12}$, $R_{13}$, m, n and p have the same definitions as those given previously with Formula (III).

Yet, a further preferred embodiment provides a compound of Formula (III), wherein $R_4$ can be, alone or simultaneously or independently when n>1, chosen from a hydrogen atom; a —(O—CH$_2$CH$_2$—)$_p$—NR$_8$; a —(O—CH$_2$CH$_2$—)$_p$—NR$_8$R$_{8'}$; a —NR$_8$—(CH$_2$CH$_2$—O)$_p$—R$_{8'}$; a —NR$_8$—(C$_2$-C$_8$)-alkyl-NR$_8$R$_{8'}$; a —NR$_8$—(C$_2$-C$_8$)-alkyl-OR$_{8'}$; it being understood that $R_2$, $R_3$, $R_5$, $R_7$, $R_8$, $R_{8'}$, $R_{12}$, $R_{13}$, m, n and p have the same definitions as those given previously with Formula (III).

Yet, a further preferred embodiment provides a compound of Formula (III), wherein $R_4$ can be, alone or simultaneously or independently when n>1, chosen from a hydrogen atom; a —(O—CH$_2$CH$_2$—)$_p$—NR$_8$; it being understood that $R_2$, $R_3$, $R_5$, $R_7$, $R_8$, $R_{8'}$, $R_{12}$, $R_{13}$, m, n and p have the same definitions as those given previously with Formula (III).

Yet, a further preferred embodiment provides a compound of Formula (III), wherein $R_4$ can be, alone or simultaneously or independently when n>1, chosen from a hydrogen atom; a —(O—CH$_2$CH$_2$—)$_p$—NR$_8$R$_{8'}$; it being understood that $R_2$, $R_3$, $R_5$, $R_7$, $R_8$, $R_{8'}$, $R_{12}$, $R_{13}$, m, n and p have the same definitions as those given previously with Formula (III).

Yet, a further preferred embodiment provides a compound of Formula (III), wherein $R_4$ can be, alone or simultaneously or independently when n>1, chosen from a hydrogen atom; a —NR$_8$—(CH$_2$CH$_2$—O)$_p$—R$_{8'}$; it being understood that $R_2$, $R_3$, $R_5$, $R_7$, $R_8$, $R_{8'}$, $R_{12}$, $R_{13}$, m, n and p have the same definitions as those given previously with Formula (III).

Yet, a further preferred embodiment provides a compound of Formula (III), wherein $R_4$ can be, alone or simultaneously or independently when n>1, chosen from a hydrogen atom; a —NR$_8$—(C$_2$-C$_8$)-alkyl-NR$_8$R$_{8'}$; it being understood that $R_2$, $R_3$, $R_5$, $R_7$, $R_8$, $R_{8'}$, $R_{12}$, $R_{13}$, m, n and p have the same definitions as those given previously with Formula (III).

Yet, a further preferred embodiment provides a compound of Formula (III), wherein $R_4$ can be, alone or simultaneously or independently when n>1, chosen from a hydrogen atom; a —NR$_8$—(C$_2$-C$_8$)-alkyl-NR$_{8'}$; it being understood that $R_2$, $R_3$, $R_5$, $R_7$, $R_8$, $R_{8'}$, $R_{12}$, $R_{13}$, m, n and p have the same definitions as those given previously with Formula (III).

In yet a further preferred embodiment, a compound according to Formula (III) can be provided, wherein $R_5$ can be chosen from a hydrogen atom; an optionally substituted alkoxy as defined herein; a hydroxyl; a halogen atom as defined herein; a methyl; a —CF$_3$; it being understood that $R_2$, $R_3$, $R_4$, $R_7$, $R_8$, $R_{8'}$, $R_{12}$, $R_{13}$, m, n and p have the same definitions as those given previously with Formula (III).

In yet a further preferred embodiment, a compound according to Formula (III) can be provided, wherein $R_5$ can be chosen from a hydrogen atom; an optionally substituted alkoxy as defined herein; a hydroxyl; a halogen atom as defined herein; a methyl; it being understood that $R_2$, $R_3$, $R_4$, $R_7$, $R_8$, $R_{8'}$, $R_{12}$, $R_{13}$, m, n and p have the same definitions as those given previously with Formula (III).

In a further preferred embodiment, a compound according to Formula (III) can be provided, wherein $R_5$ can be chosen from a hydrogen atom; a fluorine; a chlorine; a hydroxyl; an optionally substituted alkoxy as defined herein; it being understood that $R_2$, $R_3$, $R_4$, $R_7$, $R_8$, $R_{8'}$, $R_{12}$, $R_{13}$, m, n and p have the same definitions as those given previously with Formula (III).

In a further preferred embodiment, a compound according to Formula (III) can be provided, wherein $R_5$ is a hydrogen atom; it being understood that $R_2$, $R_3$, $R_4$, $R_7$, $R_8$, $R_{8'}$, $R_{12}$, $R_{13}$, m, n and p have the same definitions as those given previously with Formula (III).

In a further preferred embodiment, a compound according to Formula (III) can be provided, wherein $R_5$ can be an optionally substituted alkoxy as defined herein; it being understood that $R_2$, $R_3$, $R_4$, $R_7$, $R_8$, $R_{8'}$, $R_{12}$, $R_{13}$, m, n and p have the same definitions as those given previously with Formula (III).

In a further preferred embodiment, a compound according to Formula (III) can be provided, wherein $R_5$ can be chosen from a methoxy, an ethoxy, an isopropoxy; a tert-butoxy; it being understood $R_2$, $R_3$, $R_4$, $R_7$, $R_8$, $R_{8'}$, $R_{12}$, $R_{13}$, m, n and p have the same definitions as those given previously with Formula (III).

In a further preferred embodiment, a compound according to Formula (III) can be provided, wherein $R_5$ is a methoxy; it being understood that $R_2$, $R_3$, $R_4$, $R_7$, $R_8$, $R_{8'}$, $R_{12}$, $R_{13}$, m, n and p have the same definitions as those given previously with Formula (III).

In a further preferred embodiment, a compound according to Formula (III) can be provided, wherein $R_5$ is a hydroxyl; it being understood that $R_2$, $R_3$, $R_4$, $R_7$, $R_8$, $R_{8'}$, $R_{12}$, $R_{13}$, m, n and p have the same definitions as those given previously with Formula (III).

In a further preferred embodiment, a compound according to Formula (III) can be provided, wherein $R_5$ is a fluorine; it being understood that $R_2$, $R_3$, $R_4$, $R_7$, $R_8$, $R_{8'}$, $R_{12}$, $R_{13}$, m, n and p have the same definitions as those given previously with Formula (III).

In a further preferred embodiment, a compound according to Formula (III) can be provided, wherein $R_5$ is a chlorine; it being understood that $R_2$, $R_3$, $R_4$, $R_7$, $R_8$, $R_{8'}$, $R_{12}$, $R_{13}$, m, n and p have the same definitions as those given previously with Formula (III).

In a further preferred embodiment, a compound according to Formula (III) can be provided, wherein $R_5$ is a $-CF_3$; it being understood that $R_2$, $R_3$, $R_4$, $R_7$, $R_8$, $R_{8'}$, $R_{12}$, $R_{13}$, m, n and p have the same definitions as those given previously with Formula (III).

In a further preferred embodiment, a compound according to Formula (III) can be provided, wherein $R_5$ is a methyl; it being understood that $R_2$, $R_3$, $R_4$, $R_7$, $R_8$, $R_{8'}$, $R_{12}$, $R_{13}$, m, n and p have the same definitions as those given previously with Formula (III).

In a further preferred embodiment, a compound according to Formula (III) can be provided, wherein $R_5$ is a cyano; it being understood that $R_2$, $R_3$, $R_4$, $R_7$, $R_8$, $R_{8'}$, $R_{12}$, $R_{13}$, m, n and p have the same definitions as those given previously with Formula (III).

In a further preferred embodiment, a compound according to Formula (III) can be provided, wherein $R_5$ is an azido; it being understood that $R_2$, $R_3$, $R_4$, $R_7$, $R_8$, $R_{8'}$, $R_{12}$, $R_{13}$, m, n and p have the same definitions as those given previously with Formula (III).

In a further preferred embodiment, a compound according to Formula (III) can be provided, wherein $R_5$ is a carboxyl; it being understood that $R_2$, $R_3$, $R_4$, $R_7$, $R_8$, $R_{8'}$, $R_{12}$, $R_{13}$, m, n and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m can be 1 or 2, preferably 2; it being understood that $R_2$, $R_3$, $R_4$, $R_5$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; it being understood that $R_2$, $R_3$, $R_4$, $R_5$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; it being understood that $R_2$, $R_3$, $R_4$, $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ is a hydrogen atom and $R_3$ is a heterocyclyl group as defined herein; it being understood that $R_4$, $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ is a hydrogen atom and $R_3$ is a heterocyclyl group as defined herein; it being understood that $R_4$, $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ is a hydrogen atom and $R_3$ is a 1-methylpiperidin-4-yl; it being understood that $R_4$, $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ is a hydrogen atom and $R_3$ is a 1-methylpiperidin-4-yl; it being understood that $R_4$, $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4 preferably 0, 1, 2 or 3, more preferably 0, 1 or 2, still more preferably 0 or 1; and m is 1; and $R_2$ and $R_3$ are linked together with the nitrogen atom to which they are covalently linked to form a heterocyclyl group as defined herein; it being understood that $R_4$, $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4 preferably 0, 1, 2 or 3, more preferably 0, 1 or 2, still more preferably 0 or 1; and m is 2; and $R_2$ and $R_3$ are linked together with the nitrogen atom to which they are covalently linked to form a heterocyclyl group; it being understood that $R_4$, $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4 preferably 0, 1, 2 or 3, more preferably 0, 1 or 2, still more preferably 0 or 1; and m is 1; and $R_2$ and $R_3$ is linked together with the nitrogen atom to which they are covalently linked to form a pyrrolidin-1-yl; it being understood that $R_4$, $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4 preferably 0, 1, 2 or 3, more preferably 0, 1 or 2, still more preferably 0 or 1; and m is 2; and $R_2$ and $R_3$ are linked together with the nitrogen atom to which they are covalently linked to form a pyrrolidin-1-yl; it being understood that $R_4$, $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ is a hydrogen atom and $R_3$ is an optionally substituted alkyl as defined herein; it being understood that $R_4$, $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ is a hydrogen atom and $R_3$ is an optionally substituted alkyl as defined herein; it being understood that $R_4$, $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m can be 1; and $R_2$ is a hydrogen atom and $R_3$ is an optionally substituted cycloalkyl as defined herein; it being understood that $R_4$, $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ is a hydrogen atom and $R_3$ is an optionally substituted cycloalkyl as defined herein; it being understood that $R_4$, $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, 0, 1, 2 or 3, more preferably 0, 1 or 2, still more preferably 0 or 1; and m can be 1; and $R_2$ can be a hydrogen atom and $R_3$ can be a tert-butyl; it being understood that $R_4$, $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ is a hydrogen atom and $R_3$ is a tert-butyl; it being understood that $R_4$, $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ is an optionally substituted alkyl as defined herein; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ is an optionally substituted alkyl as defined herein; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ is a hydrogen atom; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ is a hydrogen atom; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ is a methyl; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ is a methyl; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ is a —$CF_3$; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ is a —$CF_3$; it being understood $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ is a cyano; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ is a cyano; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ is an optionally substituted alkoxy as defined herein; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ is an optionally substituted alkoxy as defined herein; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ can be a methoxy, an ethoxy, an isopropoxy, a tert-butoxy; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ can be a methoxy, an ethoxy, an isopropoxy, a tert-butoxy; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ is a methoxy; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ is a methoxy; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ can be a halogen atoms as defined herein; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ can be a halogen atoms as defined herein; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ can be a chlorine; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ can be a chlorine; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ can be a fluorine; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ can be a fluorine; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom; and $R_3$ is a tert-butyl; and $R_4$ is a hydroxyl; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom; and $R_3$ is a tert-butyl; and $R_4$ is a hydroxyl; it being understood that $R_5$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ is a hydrogen atom and $R_3$ is a 1-methylpiperidin-4-yl; and $R_5$ is a chlorine; it being understood that $R_4$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ is a hydrogen atom and $R_3$ is a 1-methylpiperidin-4-yl; and $R_5$ is a chlorine; it being understood that $R_4$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ is a hydrogen atom and $R_3$ is a 1-methylpiperidin-4-yl; and $R_5$ is a fluorine; it being understood that $R_4$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ is a hydrogen atom and $R_3$ is a 1-methylpiperidin-4-yl; and $R_5$ is a fluorine; it being understood that $R_4$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ is a hydrogen atom and $R_3$ is a 1-methylpiperidin-4-yl; and $R_5$ is an optionally substituted alkoxy as defined herein; it being understood that $R_4$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ is a hydrogen atom and $R_3$ is a 1-methylpiperidin-4-yl; and $R_5$ is an optionally substituted alkoxy as defined herein; it being understood that $R_4$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ is a hydrogen atom and $R_3$ is a 1-methylpiperidin-4-yl; and $R_5$ is a hydroxyl; it being understood that $R_4$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ is a hydrogen atom and $R_3$ is a 1-methylpiperidin-4-yl; and $R_5$ is a hydroxyl; it being understood that $R_4$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ and $R_3$ are linked together with the nitrogen atom to which they are covalently linked to form a pyrrolidin-1-yl; and $R_5$ is a chlorine; it being understood that $R_4$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2 and $R_2$ and $R_3$ are linked together with the nitrogen atom to which they are covalently linked to form a pyrrolidin-1-yl; and $R_5$ is a chlorine it being understood that $R_4$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ and $R_3$ are linked together with the nitrogen atom to which they are covalently linked to form a pyrrolidin-1-yl; and $R_5$ is a fluorine; it being understood that $R_4$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ and $R_3$ are linked together with the nitrogen atom to which they are covalently linked to form a pyrrolidin-1-yl; and $R_5$ is a fluorine; it being understood that $R_4$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ and $R_3$ are linked together with the nitrogen atom to which they are covalently linked to form a pyrrolidin-1-yl; and $R_5$ is an optionally substituted alkoxy as defined herein; it being understood that $R_4$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2 and $R_2$ and $R_3$ are linked together with the nitrogen atom to which they are covalently linked to form a pyrrolidin-1-yl; and $R_5$ is an optionally substituted alkoxy as defined herein; it being understood that $R_4$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ and $R_3$ are linked together with the nitrogen atom to which they are covalently linked to form a pyrrolidin-1-yl; and $R_5$ is a hydroxyl; it being understood that $R_4$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ and $R_3$ are linked together with the nitrogen atom to which they are covalently linked to form a pyrrolidin-1-yl; and $R_5$ is a hydroxyl; it being understood that $R_4$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ is a hydrogen atom; and $R_3$ is a tert-butyl; and $R_5$ is a fluorine; it being understood that $R_4$, $R_7$, $R_8$, $R_{8'}$, $R_{12}$, $R_{13}$ and p have the same definitions as those given previously with Formula (III).

In yet a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ is a hydrogen atom; and $R_3$ is a tert-butyl; and $R_5$ is a fluorine; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ is a hydrogen atom; and $R_3$ is a tert-butyl; and $R_5$ is a chlorine; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, is 1, 2 or 3, more preferably 0, 1 or 2, still more preferably 0 or 1; and $_2$m is 2; and $R_2$ is a hydrogen atom; and $R_3$ is a tert-butyl; and $R_5$ is a chlorine; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ is a hydrogen atom; and $R_3$ is a tert-butyl; and $R_5$ is an azido; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ is a hydrogen atom; and $R_3$ is a tert-butyl; and $R_5$ is an azido; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ is a hydrogen atom; and $R_3$ is a tert-butyl; and $R_5$ is a —$CF_3$; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ is a hydrogen atom; and $R_3$ is a tert-butyl; and $R_5$ is a —$CF_3$; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ is a hydrogen atom; and $R_3$ is a tert-butyl; and $R_5$ is a methyl; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ is a hydrogen atom; and $R_3$ is a tert-butyl; and $R_5$ is a methyl; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ is a hydrogen atom; and $R_3$ is a tert-butyl; and $R_5$ is a cyano; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ is a hydrogen atom; and $R_3$ is a tert-butyl; and $R_5$ is a cyano; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ is a hydrogen atom; and $R_3$ is a tert-butyl; and $R_5$ is an optionally substituted alkoxy as defined herein; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ is a hydrogen atom; and $R_3$ is a tert-butyl; and $R_5$ is an alkoxy as defined herein; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ is a hydrogen atom; and $R_3$ is a tert-butyl; and $R_5$ can be chosen from a methoxy, an ethoxy, an isopropoxy; a tert-butoxy; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ is a hydrogen atom; and $R_3$ is a tert-butyl; and $R_5$ can be chosen from a methoxy, an ethoxy, an isopropoxy; a tert-butoxy; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ is a hydrogen atom; and $R_3$ is a tert-butyl; and $R_5$ is a methoxy; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2;

and $R_2$ is a hydrogen atom; and $R_3$ is a tert-butyl; and $R_5$ is a methoxy; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ is a hydrogen atom; and $R_3$ is a tert-butyl; and $R_5$ is a hydroxyl; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ is a hydrogen atom; and $R_3$ is a tert-butyl; and $R_5$ is a hydroxyl; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 1; and $R_2$ is a hydrogen atom; and $R_3$ is a tert-butyl; and $R_5$ is a hydrogen atom; it being understood that $R_4$, $R_7$, $R_8$, $R_{8'}$, $R_{12}$, $R_{13}$ and p have the same definitions as those given previously with Formula (III).

In a further preferred embodiment, a compound according to Formula (III) can be provided, wherein n can take any one of the values 0, 1, 2, 3 or 4, preferably 0, 1, 2 or 3, more preferably 0, 1 or 2, still more preferably 0 or 1; and m is 2; and $R_2$ is a hydrogen atom; and $R_3$ is a tert-butyl; and $R_5$ is a hydrogen atom; it being understood that $R_4$, $R_7$, $R_8$, $R_{8'}$, $R_{12}$, $R_{13}$ and p have the same definitions as those given previously with Formula (III).

The present disclosure also provides in a preferred embodiment a compound of Formula (IV) having the structure:

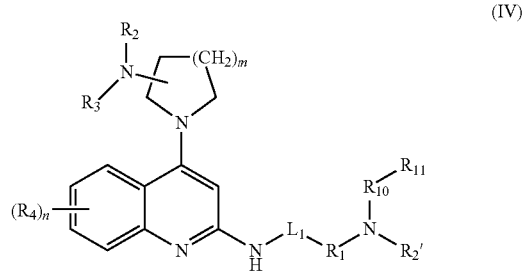

(IV)

wherein, $L_1$ can be chosen from a single bond; an optionally substituted alkyl as defined herein; a carbonyl.

$R_1$ can be chosen from an optionally substituted aryl as defined herein; an optionally substituted heteroaryl as defined herein.

$R_2$ and $R_3$ can be simultaneously or independently chosen from a hydrogen; an optionally substituted alkyl as defined herein, preferably said optionally substituted alkyl being substituted with one or more —$NR_8R_{8'}$; an optionally substituted alkenyl as defined herein; an optionally substituted alkynyl as defined herein; an optionally substituted cycloalkyl as defined herein, preferably said optionally substituted cycloalkyl being substituted with one or more —$NR_8R_{8'}$; an optionally substituted cycloalkenyl as defined herein; an optionally substituted cycloalkynyl as defined herein; a —(CO)—$R_7$; a —(CO)—O—$R_7$; a —(CO)—$NR_8OH$; a —(CO)—$NR_8R_{8'}$; a —$SO_2$—$R_7$; a —$SO_2$—$NR_8R_{8'}$; an optionally substituted aryl as defined herein; an optionally substituted benzyl as defined herein; an optionally substituted heteroaryl as defined herein; an optionally substituted heterocyclyl group as defined herein; or $R_2$ and $R_3$ can be linked together with the nitrogen atom to which they are covalently linked to form an optionally substituted heterocyclyl group as defined herein.

$R_2'$ can be chosen from a hydrogen atom; an optionally substituted alkyl as defined herein; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted heterocyclyl group as defined herein.

$R_4$ can be, alone or simultaneously or independently when n>1, chosen from a hydrogen atom; a halogen atom as defined herein; an optionally substituted alkyl as defined herein, preferably said optionally substituted alkyl being substituted by one or more halogen atom(s) as defined herein, by one or more hydroxyl, by one or more alkoxy as defined herein, by one or more —$NR_8R_{8'}$ and combination thereof; an optionally substituted fluoroalkyl as defined herein; an optionally substituted alkenyl as defined herein; an optionally substituted alkynyl as defined herein; a optionally substituted cycloalkyl as defined herein; a optionally substituted cycloalkenyl as defined herein; an optionally substituted cycloalkynyl as defined herein; an optionally substituted alkoxy as defined herein; a hydroxyl as defined herein; a nitro; an azido; a cyano; a —$NR_{12}R_{13}$; a —$NR_8R_{8'}$; a —O—($R_7$); a —(CO)—$R_7$; a —(CO)—O—$R_7$; a —(CO)—$NR_{12}OH$; a —(CO)—$NR_8OH$; a —(CO)—$NR_{12}R_{13}$; a —(CO)—$NR_8R_{8'}$; a —O—(CO)—$R_7$; a —O—(CO)—$NR_{12}R_{13}$; a —O—(CO)—$NR_8R_{8'}$; a —$NR_{12}$—(CO)—$R_7$; a —$NR_8$—(CO)—$R_7$; a —$NR_{12}$—(CO)—$OR_7$; a —$NR_8$—(CO)—$OR_7$; a O—(CO)—$OR_7$; a —$NR_{12}$—(CO)—$NR_{12}R_{13}$; a —$NR_8$—(CO)—$NR_8R_{8'}$; a —(O—$CH_2CH_2$)$_p$—$NR_{12}$; a —(O—$CH_2CH_2$)$_p$—$OR_7$; a —(O—$CH_2CH_2$)$_p$—$NR_{12}R_{13}$; a —(O—$CH_2CH_2$)$_p$—$NR_8R_{8'}$; a —$NR_{12}$—($CH_2CH_2$—O)$_p$—$R_{13}$; a —$NR_8$—($CH_2CH_2$—O)$_p$—$R_7$; a —$SO_2$—$R_7$; a —$NR_{12}$—$SO_2$—$R_7$; a —$NR_8$—$SO_2$—$R_7$; a —$SO_2$—$NR_{12}R_{13}$; a —$SO_2$—$NR_8R_{8'}$; a —$NR_{12}$—$SO_2$—$NR_{12}R_{13}$; a —$NR_8$—$SO_2$—$NR_8R_{8'}$; a —$NR_{12}$—($C_2$-$C_8$)-alkyl-$NR_{12}R_{13}$; a —$NR_8$—($C_2$-$C_8$)-alkyl-$NR_8R_{8'}$; a —$NR_{12}$—($C_2$-$C_8$)-alkyl-$OR_{13}$; a —$NR_8$—($C_2$-$C_8$)-alkyl-$OR_7$; an optionally substituted aryl as defined herein; an optionally substituted benzyl as defined herein; an optionally substituted heteroaryl as defined herein; an optionally substituted heterocyclyl group as defined herein.

$R_8$ and $R_{8'}$ can be simultaneously or independently chosen from a hydrogen atom; an optionally substituted alkyl as defined herein; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted heterocyclyl group as defined herein; an optionally substituted aryl as defined herein; an optionally substituted benzyl as defined herein; an optionally substituted heteroaryl as defined herein; or $R_8$ and $R_{8'}$ can be linked together with the nitrogen atom to which they are covalently linked to form an optionally substituted heterocyclyl group as defined herein.

$R_{10}$ can be chosen from an optionally substituted aryl as defined herein; an optionally substituted heteroaryl as defined herein.

$R_{11}$ can be chosen from a hydrogen atom; a halogen atom as defined herein; an optionally substituted alkoxy as defined herein; a hydroxyl; a nitro; a cyano; an azido; a —$NR_{12}R_{13}$; a —$NR_8R_{8'}$; a —O-(148); a —(CO)—$R_8$; a —(CO)—O—$R_8$; a —(CO)—$NR_{12}$OH; a —(CO)—$NR_8$OH; a —(CO)—$NR_{12}R_{13}$; a —(CO)—$NR_8R_{8'}$; a —O—(CO)—$R_8$; a —O—(CO)—$NR_{12}R_{13}$; a —O—(CO)—$NR_8R_{8'}$; a $NR_{12}$—(CO)—$R_{13}$; a —$NR_8$—(CO)—$R_{8'}$; a —$NR_{12}$—(CO)—$OR_{13}$; a —$NR_8$—(CO)—$OR_{8'}$; a O—(CO)—$OR_8$; a —$NR_{12}$—(CO)—$NR_{12}R_{13}$; a —$NR_8$—(CO)—$NR_8R_{8'}$; a —(O—$CH_2CH_2$)$_p$—$NR_{12}$; a —(O—$CH_2CH_2$)$_p$—$NR_8$; a —(O—$CH_2CH_2$)$_p$—$NR_{12}R_{13}$; a —(O—$CH_2CH_2$)$_p$—$NR_8R_{8'}$; a —$NR_{12}$—($CH_2CH_2$—O)$_p$—$R_{13}$; a —$NR_8$—($CH_2CH_2$—O)$_p$—$R_{8'}$; a —$SO_2$—$R_8$; a $NR_{12}$—$SO_2$—$R_{13}$; a —$NR_8$—$SO_2$—$R_{8'}$; a —$SO_2$—$NR_{12}R_{13}$; a —$SO_2$—$NR_8R_{8'}$; a —$NR_{12}$—$SO_2$—$NR_{12}R_{13}$; a —$NR_8$—$SO_2$—$NR_8R_{8'}$; a —$NR_{12}$—($C_2$-$C_8$)-alkyl-$NR_{12}R_{13}$; a —$NR_8$—($C_2$-$C_8$)-alkyl-$NR_8R_{8'}$; a —$NR_{12}$—($C_2$-$C_8$)-alkyl-$OR_{13}$; a —$NR_8$—($C_2$-$C_8$)-alkyl-$OR_{8'}$; an optionally substituted alkyl as defined herein, preferably said optionally substituted alkyl being substituted by one or more halogen atom(s), by one or more hydroxyl, by one or more alkoxy as defined herein, or by one or more $NR_8R_{8'}$ and combination thereof; an optionally substituted fluoroalkyl as defined herein; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted aryl as defined herein; an optionally substituted benzyl as defined herein; an optionally substituted heteroaryl as defined herein; an optionally substituted heterocyclyl group as defined herein.

$R_{12}$ and $R_{13}$ can be simultaneously or independently chosen from a hydrogen atom; a —(CO)—$R_7$; a —(CO)—O—$R_7$; a —(CO)—$NR_8$OH; a —(CO)—$NR_8R_{8'}$; a —$SO_2$—$R_7$; a —$SO_2$—$NR_8R_{8'}$; an optionally substituted alkyl as defined herein, preferably said optionally substituted alkyl being substituted with at least one —$NR_8R_{8'}$; an optionally substituted cycloalkyl as defined herein, preferably said optionally substituted cycloalkyl being substituted with at least one —$NR_8R_{8'}$; an optionally substituted alkenyl as defined herein; an optionally substituted alkynyl as defined herein; an optionally substituted cycloalkenyl as defined herein; an optionally substituted cycloalkynyl as defined herein; an optionally substituted aryl as defined herein; an optionally substituted benzyl as defined herein; an optionally substituted heteroaryl as defined herein; an optionally substituted heterocyclyl group as defined herein; or $R_2$ and $R_3$ can be linked together with the nitrogen atom to which they are covalently linked to form an optionally substituted heterocyclyl group as defined herein.

n can represent an equal integer which can have any one of the values 0, 1, 2, 3 or 4, preferably 0, 1, 2 or 3, more preferably 0, 1 or 2 still more preferably 0 or 1.

m can represent an equal integer which can have any one of the values 1, 2 or 3 preferably 1 or 2, more preferably 2.

p can represent an equal integer which can have any one of the values 1, 2, 3, 4 or 5, preferably 1, 2, 3 or 4, more preferably 1, 2 or 3 still more preferably 1 or 2.

and any pharmaceutically acceptable salt, hydrates, solvate, prodrugs, polymorphs, tautomers, isotopic variants, isomers, stereoisomers or mixtures of stereoisomers thereof, for use as a medicament to treat, decrease the severity and/or progression of, and/or prevent fibrosis and/or related diseases, or for use as a medicament to treat, decrease the severity and/or progression of, and/or prevent autophagy and/or related diseases and to inhibit autophagy flux, or for use in inhibiting cathepsins B (CTSB), L (CTSL) and/or D (CTSD) and/or related diseases; with the proviso that said compounds are not intended to be used for treating any forms of cancers.

In a further preferred embodiment, the invention provides a compound of Formula (IV), wherein $L_1$ is a bond; it being understood that $R_1$, $R_2$, $R_{2'}$, $R_3$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In a further preferred embodiment, the invention provides a compound of Formula (IV), wherein $L_1$ is an optionally substituted alkyl as defined herein; it being understood that $R_1$, $R_2$, $R_{2'}$, $R_3$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

Yet, a further preferred embodiment, the invention provides a compound of Formula (IV), wherein $L_1$ is a methylene (—$CH_2$—); it being understood that $R_1$, $R_2$, $R_{2'}$, $R_3$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In a further preferred embodiment, the invention provides a compound of Formula (IV), wherein $L_1$ is a carbonyl; it being understood that $R_1$, $R_2$, $R_{2'}$, $R_3$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

Yet in a further preferred embodiment, the invention provides compound of Formula (IV) wherein $R_1$ is an optionally substituted heteroaryl as defined herein; it being understood that $L_1$, $R_2$, $R_{2'}$, $R_3$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

Yet in a further preferred embodiment, the invention provides compound of Formula (IV) wherein $R_1$ is an optionally substituted aryl as defined herein; it being understood that $L_1$, $R_2$, $R_{2'}$, $R_3$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In a further preferred embodiment, the invention provides compound of Formula (IV) wherein $R_1$ is an optionally substituted phenyl; it being understood $L_1$, $R_2$, $R_{2'}$, $R_3$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

Yet in a further preferred embodiment, the invention provides compound of Formula (IV) wherein $R_1$ is an 3-methylbenzene-1,4-diyl; it being understood that $L_1$, $R_2$, $R_{2'}$, $R_3$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

Yet, a further preferred embodiment, a compound according to Formula (IV) can be provided, wherein $R_2$ and $R_3$ can be simultaneously or independently chosen from a hydrogen atom; an optionally substituted alkyl as defined herein; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted heterocyclyl group as defined herein; or $R_2$ and $R_3$ can be linked together with the nitrogen atom to which they are covalently linked to form an optionally substituted heterocyclyl group as defined herein; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In a further preferred embodiment, a compound according to Formula (IV) can be provided, wherein $R_2$ and $R_3$ can be simultaneously or independently chosen from a hydrogen atom; an optionally substituted alkyl as defined herein; an optionally substituted cycloalkyl as defined herein; an optionally substituted heterocyclyl group as defined herein; or $R_2$ and $R_3$ can be linked together with the nitrogen atom to which they are covalently linked to form an optionally substituted heterocyclyl group as defined herein; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In also a preferred embodiment, a compound according to Formula (IV) can be provided, wherein $R_2$ and $R_3$ can be simultaneously or independently chosen from a hydrogen atom; an optionally substituted alkyl as defined herein; an optionally substituted cycloalkyl as defined herein; or $R_2$ and $R_3$ can be linked together with the nitrogen atom to which they are covalently linked to form an optionally substituted heterocyclyl group as defined herein; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided, wherein $R_2$ and $R_3$ can be simultaneously or independently chosen from a hydrogen atom; an optionally substituted alkyl as defined herein; an optionally substituted cycloalkyl as defined herein; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided, wherein $R_2$ and $R_3$ can be simultaneously or independently chosen from a hydrogen atom; and an optionally substituted heterocyclyl group as defined herein; it being understood that $L_1$, $R_1$, $R_2$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided, wherein $R_2$ and $R_3$ can be simultaneously or independently chosen from a hydrogen atom; and an optionally substituted alkyl as defined herein; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided, wherein $R_2$ and $R_3$ can be simultaneously or independently chosen from a hydrogen atom; 1-methylpiperidin-4-yl; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In also a preferred embodiment, a compound according to Formula (IV) can be provided, wherein $R_2$ and $R_3$ can be linked together with the nitrogen atom to which they are covalently linked to form an optionally substituted heterocyclyl group as defined herein; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided, wherein $R_2$ and $R_3$ are linked together with the nitrogen atom to which they are covalently linked to form a pyrrolidin-1-yl; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided, wherein $R_2$ and $R_3$ can be simultaneously or independently chosen from a hydrogen atom; and an optionally substituted cycloalkyl as defined herein; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided, wherein $R_2$ and $R_3$ can be simultaneously or independently chosen from a hydrogen atom; a tert-butyl; it being understood $L_1$, $R_1$, $R_{2'}$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided wherein $R_4$ can be, alone or simultaneously or independently when n>1, chosen from a hydrogen atom; a halogen atom as defined herein; an optionally substituted alkyl as defined herein, preferably said optionally substituted alkyl being preferentially substituted by one or more halogen atom(s) as defined herein, one or more hydroxyl, one or more alkoxy as defined herein, one or more —$NR_8R_{8'}$ and combination thereof; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted alkoxy as defined herein; a hydroxyl; a nitro; a cyano; an azido; a carboxyl; a —$NR_8R_{8'}$; a —(CO)—$NR_{12}R_{13}$; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided wherein $R_4$ can be, alone or simultaneously or independently when n>1, chosen from a hydrogen atom; a halogen atom as defined herein, an optionally substituted alkyl as defined herein, preferably said optionally substituted alkyl being preferentially substituted by one or more halogen atom(s); an optionally substituted alkyl as defined herein; an optionally substituted alkoxy as defined herein; a hydroxyl; a cyano; a carboxyl; an azido; a —$NR_8R_{8'}$; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided wherein $R_4$ can be, alone or simultaneously or independently when n>1, chosen from a hydrogen atom; a halogen atom as defined herein; an optionally substituted alkyl as defined herein, preferably said optionally substituted alkyl being preferably substituted by one or more halogen atom(s); an optionally substituted alkyl as defined herein; an optionally substituted alkoxy as defined herein; a hydroxyl; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided wherein $R_4$ can be, alone or simultaneously or independently when n>1, chosen from a hydrogen atom; a halogen atom as defined herein; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided wherein $R_4$ can be, alone or simultaneously or independently when n>1, chosen from a hydrogen atom; a fluorine; a chlorine; a methyl; a —$CF_3$; a hydroxyl; a methoxy; an ethoxy; an isopropoxy; a tert-butoxy; a cyano; a carboxyl; an azido; a —$NR_8R_{8'}$; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided wherein $R_4$ can be, alone or simultaneously or independently when n>1, chosen from a hydrogen atom; a fluorine; a chlorine; a methyl; a cyano; a hydroxyl; a methoxy; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided wherein $R_4$ can be, alone or simultaneously or independently when n>1, chosen from a hydrogen atom; a fluorine; a chlorine; a methyl; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided wherein $R_4$ can be, alone or simultaneously or independently when n>1, chosen from a hydrogen atom; a fluorine; a chlorine; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided wherein $R_4$ can be, alone or simultaneously or independently when n>1, chosen from a hydrogen atom; an optionally substituted fluoroalkyl; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided wherein $R_4$ can be, alone or simultaneously or independently when n>1, chosen from a hydrogen atom; a methyl; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided wherein $R_4$ can be, alone or simultaneously or independently when n>1, chosen from a hydrogen atom; an optionally substituted alkoxy as defined herein; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided wherein $R_4$ can be, alone or simultaneously or independently when n>1, chosen from a hydrogen atom; a hydroxyl; a methoxy; an ethoxy; an isopropoxy; a tert-butoxy; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided wherein $R_4$ can be, alone or simultaneously or independently when n>1, chosen from a hydrogen atom; a hydroxyl; a methoxy; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided wherein $R_4$ can be, alone or simultaneously or independently when n>1, chosen from a hydrogen atom; a methoxy; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided wherein $R_4$ can be, alone or simultaneously or independently when n>1, chosen from a hydrogen atom; a hydroxyl; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

In another preferred embodiment, a compound according to Formula (IV) can be provided wherein $R_4$ is a hydrogen atom; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

Yet, a further preferred embodiment provides a compound of Formula (IV), wherein $R_4$ can be, alone or simultaneously or independently when n>1, chosen from a hydrogen atom; a —(O—$CH_2CH_2$—)$_p$—$NR_{12}$; a —(O—$CH_2CH_2$—)$_p$—$NR_{12}R_{13}$; a —$NR_{12}$(—$CH_2CH_2$—O)$_p$—$R_{13}$; a —$NR_{12}$—($C_2$-$C_8$)-alkyl-$NR_{12}R_{13}$; a —$NR_{12}$—($C_2$-$C_8$)-alkyl-$OR_{13}$; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

Yet, a further preferred embodiment provides a compound of Formula (IV), wherein $R_4$ can be, alone or simultaneously or independently when n>1, chosen from a hydrogen atom; a —(O—$CH_2CH_2$—)$_p$—$NR_8$; a —(O—$CH_2CH_2$—)$_p$—$NR_8R_{8'}$; a —$NR_8$(—$CH_2CH_2$—O)$_p$—$R_{8'}$; a —$NR_8$—($C_2$-$C_8$)-alkyl-$NR_8R_{8'}$; a —$NR_8$—($C_2$-$C_8$)-alkyl-$OR_{8'}$; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

Yet, a further preferred embodiment provides a compound of Formula (IV), wherein $R_4$ can be, alone or simultaneously or independently when n>1, chosen from a hydrogen atom; a —(O—$CH_2CH_2$—)$_p$—$NR_8$; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

Yet, a further preferred embodiment provides a compound of Formula (IV), wherein $R_4$ can be, alone or simultaneously or independently when n>1, chosen from a hydrogen atom; a —(O—$CH_2CH_2$—)$_p$—$NR_8R_{8'}$; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

Yet, a further preferred embodiment provides a compound of Formula (IV), wherein $R_4$ can be, alone or simultaneously or independently when n>1, chosen from a hydrogen atom; a —$NR_{12}$(—$CH_2CH_2$—O)$_p$—$R_{13}$; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

Yet, a further preferred embodiment provides a compound of Formula (IV), wherein $R_4$ can be, alone or simultaneously or independently when n>1, chosen from a hydrogen atom; a —$NR_8$—($C_2$-$C_8$)-alkyl-$NR_8R_{8'}$; it being understood that $L_1$, $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (IV).

Yet, a further preferred embodiment provides a compound of Formula (IV), wherein $R_4$ can be, alone or simultaneously or independently when n>1, chosen from a hydrogen atom; a —NR$_8$—(C$_2$-C$_8$)-alkyl-OR$_{8'}$; it being understood that L$_1$, R$_1$, R$_2$, R$_{2'}$, R$_3$, R$_5$, R$_7$, R$_8$, R$_{8'}$, R$_{10}$, R$_{11}$, R$_{12}$, R$_{13}$, m, n and p have the same definitions as those given previously with Formula (IV).

In yet another preferred embodiment provides a compound of Formula (IV), wherein R$_4$ can be, alone or simultaneously or independently when n>1, chosen from a hydrogen atom; —(CO)—NR$_{12}$R$_{13}$, wherein R$_{12}$ and R$_{13}$ can be simultaneously or independently chosen from a hydrogen atom, an optionally substituted alkyl as defined herein, an optionally substituted cycloalkyl as defined herein, an optionally substituted heterocyclyl group as defined herein, an optionally substituted aryl as defined herein, an optionally substituted heteroaryl as defined herein; an optionally substituted benzyl as defined herein; or R$_{12}$ and R$_{13}$ can be linked together with the nitrogen atom to which they are covalently linked to form an optionally heterocyclyl group as defined herein; it being understood that L$_1$, R$_1$, R$_2$, R$_{2'}$, R$_3$, R$_5$, R$_7$, R$_8$, R$_{8'}$, R$_{10}$, R$_{11}$, m, n and p have the same definitions as those given previously with Formula (IV).

In yet another preferred embodiment provides a compound of Formula (IV), wherein R$_4$ can be, alone or simultaneously or independently when n>1, chosen from a hydrogen atom; —(CO)—NR$_{12}$R$_{13}$, wherein R$_{12}$ and R$_{13}$ can be simultaneously or independently chosen from a hydrogen atom, an optionally substituted alkyl as defined herein, an optionally substituted cycloalkyl as defined herein, an optionally substituted heterocyclyl group as defined herein, or R$_{12}$ and R$_{13}$ can be linked together with the nitrogen atom to which they are covalently linked to form an optionally heterocyclyl group as defined herein; it being understood that L$_1$, R$_1$, R$_2$, R$_{2'}$, R$_3$, R$_5$, R$_7$, R$_8$, R$_{8'}$, R$_{10}$, R$_{11}$, m, n and p have the same definitions as those given previously with Formula (IV).

Yet, another preferred embodiment provides a compound of Formula (IV), wherein R$_4$ can be, alone or simultaneously or independently when n>1, chosen from a hydrogen atom; —(CO)—NR$_{12}$R$_{13}$, wherein R$_{12}$ and R$_{13}$ can be simultaneously or independently chosen from a hydrogen atom, an optionally substituted alkyl as defined herein, an optionally substituted cycloalkyl as defined herein, an optionally substituted heterocyclyl group as defined herein, it being understood that L$_1$, R$_1$, R$_2$, R$_{2'}$, R$_3$, R$_5$, R$_7$, R$_8$, R$_{8'}$, R$_{10}$, R$_{11}$, m, n and p have the same definitions as those given previously with Formula (IV).

Yet, another preferred embodiment provides a compound of Formula (IV), wherein R$_4$ can be, alone or simultaneously or independently when n>1, chosen from a hydrogen atom; —(CO)—NR$_{12}$R$_{13}$, wherein R$_{12}$ and R$_{13}$ can be simultaneously or independently chosen from a hydrogen atom, an optionally substituted alkyl as defined herein, an optionally substituted cycloalkyl as defined herein, it being understood that L$_1$, R$_1$, R$_2$, R$_{2'}$, R$_3$, R$_5$, R$_7$, R$_8$, R$_{8'}$, R$_{10}$, R$_{11}$, m, n and p have the same definitions as those given previously with Formula (IV).

Yet, another preferred embodiment provides a compound of Formula (IV), wherein R$_4$ can be, alone or simultaneously or independently when n>1, chosen from a hydrogen atom; —(CO)—NR$_{12}$R$_{13}$, wherein R$_{12}$ and R$_{13}$ can be simultaneously or independently chosen from a hydrogen atom, an optionally substituted alkyl as defined herein; it being understood that L$_1$, R$_1$, R$_2$, R$_{2'}$, R$_3$, R$_5$, R$_7$, R$_8$, R$_{8'}$, R$_{10}$, R$_{11}$, m, n and p have the same definitions as those given previously with Formula (IV).

Yet, another preferred embodiment provides a compound of Formula (IV), wherein R$_4$ can be, alone or simultaneously or independently when n>1, chosen from a hydrogen atom; —(CO)—NR$_{12}$R$_{13}$, wherein R$_{12}$ and R$_{13}$ can be simultaneously or independently chosen from a hydrogen atom, an optionally substituted cycloalkyl as defined herein, it being understood that L$_1$, R$_1$, R$_2$, R$_{2'}$, R$_3$, R$_5$, R$_7$, R$_8$, R$_{8'}$, R$_{10}$, R$_{11}$, m, n and p have the same definitions as those given previously with Formula (IV).

Yet, another preferred embodiment provides a compound of Formula (IV), wherein R$_4$ can be, alone or simultaneously or independently when n>1, chosen from a hydrogen atom; —(CO)—NR$_{12}$R$_{13}$, wherein R$_{12}$ and R$_{13}$ can be simultaneously or independently chosen from a hydrogen atom, an optionally substituted heterocyclyl group as defined herein; it being understood that L$_1$, R$_1$, R$_2$, R$_{2'}$, R$_3$, R$_5$, R$_7$, R$_8$, R$_{8'}$, R$_{10}$, R$_{11}$, m, n and p have the same definitions as those given previously with Formula (IV).

Yet, another preferred embodiment provides a compound of Formula (IV), wherein R$_4$ can be, alone or simultaneously or independently when n>1, chosen from a hydrogen atom; —(CO)—NR$_{12}$R$_{13}$, wherein R$_{12}$ and R$_{13}$ can be simultaneously or independently chosen from a hydrogen atom, an optionally substituted aryl as defined herein, it being understood that L$_1$, R$_1$, R$_2$, R$_{2'}$, R$_3$, R$_5$, R$_7$, R$_8$, R$_{8'}$, R$_{10}$, R$_{11}$, m, n and p have the same definitions as those given previously with Formula (IV).

Yet, another preferred embodiment provides a compound of Formula (IV), wherein R$_4$ can be, alone or simultaneously or independently when n>1, chosen from a hydrogen atom; —(CO)—NR$_{12}$R$_{13}$, wherein R$_{12}$ and R$_{13}$ can be simultaneously or independently chosen from a hydrogen atom, an optionally substituted heteroaryl as defined herein, it being understood that L$_1$, R$_1$, R$_2$, R$_{2'}$, R$_3$, R$_5$, R$_7$, R$_8$, R$_{8'}$, R$_{10}$, R$_{11}$, m, n and p have the same definitions as those given previously with Formula (IV).

Yet, another preferred embodiment provides a compound of Formula (IV), wherein R$_4$ can be, alone or simultaneously or independently when n>1, chosen from a hydrogen atom; —(CO)—NR$_{12}$R$_{13}$, wherein R$_{12}$ and R$_{13}$ can be simultaneously or independently chosen from a hydrogen atom, an optionally substituted benzyl as defined herein, it being understood that L$_1$, R$_1$, R$_2$, R$_{2'}$, R$_3$, R$_5$, R$_7$, R$_8$, R$_{8'}$, R$_{10}$, R$_{11}$, m, n and p have the same definitions as those given previously with Formula (IV).

Yet, another preferred embodiment provides a compound of Formula (IV), wherein R$_4$ can be, alone or simultaneously or independently when n>1, chosen from a hydrogen atom; —(CO)—NR$_{12}$R$_{13}$, wherein R$_{12}$ and R$_{13}$ can be linked together with the nitrogen atom to which they are covalently linked to form an optionally substituted heterocyclyl group; it being understood that L$_1$, R$_1$, R$_2$, R$_{2'}$, R$_3$, R$_5$, R$_7$, R$_8$, R$_{8'}$, R$_{10}$, R$_{11}$, m, n and p have the same definitions as those given previously with Formula (IV).

Yet, another preferred embodiment provides a compound of Formula (IV), wherein R$_4$ can be, alone or simultaneously or independently when n>1, chosen from a hydrogen atom; —(CO)—NR$_{12}$R$_{13}$, wherein R$_{12}$ and R$_{13}$ can be simultaneously or independently chosen from a hydrogen atom, a methyl, an ethyl, an isopropyl, a tert-butyl, a cyclopropyl, a cyclobutyl, a cyclopentyl, a cyclohexyl; it being understood that L$_1$, R$_1$, R$_2$, R$_{2'}$, R$_3$, R$_5$, R$_7$, R$_8$, R$_{8'}$, R$_{10}$, R$_{11}$, m, n and p have the same definitions as those given previously with Formula (IV).

Yet, another preferred embodiment provides a compound of Formula (IV), wherein R$_4$ can be, alone or simultaneously or independently when n>1, chosen from a hydrogen atom; —NR$_8$R$_{8'}$; it being understood that L$_1$, R$_1$, R$_2$, R$_{2'}$, R$_3$, R$_5$, $R_7$, $R_8$, $R_{8'}$, $R_{10}$, $R_{11}$, $R_{12}$, $R_{13}$, m, n and p have the same definitions as those given previously with Formula (IV).

In a further preferred embodiment, the invention provides a compound of Formula (IV), wherein $R_2'$ can be chosen from a hydrogen atom; an optionally substituted alkyl as defined herein; an optionally substituted cycloalkyl as defined herein; an optionally substituted heterocyclyl group as defined herein it being understood that $L_1$, $R_1$, $R_2$, $R_3$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In a further preferred embodiment, the invention provides a compound of Formula (IV), wherein $R_2'$ can be chosen from a hydrogen atom; an optionally substituted cycloalkyl as defined herein; it being understood that $L_1$, $R_1$, $R_2$, $R_3$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In a further preferred embodiment, the invention provides a compound of Formula (IV), wherein $R_2'$ can be chosen from a hydrogen atom; an optionally substituted heterocyclyl group as defined herein; it being understood that $L_1$, $R_1$, $R_2$, $R_3$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In some further preferred embodiment, the invention provides a compound of Formula (IV), wherein $R_2'$ can be can be chosen from a hydrogen atom; an optionally substituted alkyl as defined herein; it being understood that $L_1$, $R_1$, $R_2$, $R_3$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In yet a further preferred embodiment, the invention provides a compound of Formula (IV), wherein $R_2'$ can be can be chosen from a hydrogen atom; a methyl; a cyclopropyl; it being understood that $L_1$, $R_1$, $R_2$, $R_3$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In a further preferred embodiment, the invention provides a compound of Formula (IV), wherein $R_2'$ is a hydrogen atom; it being understood that $L_1$, $R_1$, $R_2$, $R_3$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In a further preferred embodiment, the invention provides a compound of Formula (IV), wherein $R_2'$ is a methyl; it being understood $L_1$, $R_1$, $R_2$, $R_3$, $R_4$, $R_5$, $R_7$, $R_8$, $R_{8'}$, $R_{10}$, $R_{11}$, $R_{12}$, $R_{13}$, m, n and p have the same definitions as those given previously with Formula (IV).

In yet a further preferred embodiment, the invention provides a compound of Formula (IV), wherein $R_{10}$ is an optionally substituted aryl as defined herein; it being understood that $L_1$, $R_1$, $R_2$, $R_{2'}$, $R_3$, $R_4$, $R_5$, $R_7$, $R_8$, $R_{8'}$, $R_{11}$, $R_{12}$, $R_{13}$, m, n and p have the same definitions as those given previously with Formula (IV).

In a further preferred embodiment, the invention provides a compound of Formula (IV), wherein $R_{10}$ is an optionally substituted phenyl; it being understood that $L_1$, $R_1$, $R_2$, $R_{2'}$, $R_3$, $R_4$, $R_5$, $R_7$, $R_8$, $R_{8'}$, $R_{11}$, $R_{12}$, $R_{13}$, m, n and p have the same definitions as those given previously with Formula (IV).

In yet a further preferred embodiment, the invention provides a compound of Formula (IV), wherein $R_{10}$ is an optionally substituted heteroaryl as defined herein; it being understood that $L_1$, $R_1$, $R_2$, $R_{2'}$, $R_3$, $R_4$, $R_5$, $R_7$, $R_8$, $R_{8'}$, $R_{11}$, $R_{12}$, $R_{13}$, m, n and p have the same definitions as those given previously with Formula (IV).

In another preferred embodiment, the invention provides a compound of Formula (IV), wherein $R_{10}$ can be chosen from an optionally substituted pyrimidin-2-yl; an optionally substituted pyrimidin-4-yl; an optionally substituted pyrimidin-5-yl; it being understood that $L_1$, $R_1$, $R_2$, $R_{2'}$, $R_3$, $R_4$, $R_5$, $R_7$, $R_8$, $R_{8'}$, $R_{11}$, $R_{12}$, $R_{13}$, m, n and p have the same definitions as those given previously with Formula (IV).

In another preferred embodiment, the invention provides a compound of Formula (IV), wherein $R_{10}$ is an optionally substituted pyrimidin-2-yl; it being understood that $L_1$, $R_1$, $R_2$, $R_{2'}$, $R_3$, $R_4$, $R_5$, $R_7$, $R_8$, $R_{8'}$, $R_{11}$, $R_{12}$, $R_{13}$, m, n and p have the same definitions as those given previously with Formula (IV).

In another preferred embodiment, the invention provides a compound of Formula (IV), wherein $R_{10}$ is a pyrimidin-2-yl; it being understood that $L_1$, $R_1$, $R_2$, $R_{2'}$, $R_3$, $R_4$, $R_5$, $R_7$, $R_8$, $R_{8'}$, $R_{11}$, $R_{12}$, $R_{13}$, m, n and p have the same definitions as those given previously with Formula (IV).

In yet a further preferred embodiment, the invention provides a compound of Formula (IV), wherein $R_{11}$ is can be chosen from a hydrogen atom; an optionally substituted aryl as defined herein; an optionally substituted heteroaryl as defined herein; an optionally substituted heterocyclyl group as defined herein; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

In a further preferred embodiment, the invention provides a compound of Formula (IV), wherein $R_{11}$ is optionally substituted aryl as defined herein; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

In a further preferred embodiment, the invention provides a compound of Formula (IV), wherein $R_{11}$ is an optionally substituted phenyl; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

In a further preferred embodiment, the invention provides a compound of Formula (IV), wherein $R_{11}$ is an optionally substituted heteroaryl as defined herein; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

In yet a further preferred embodiment, the invention provides a compound of Formula (IV), wherein $R_{11}$ is an optionally substituted heterocyclyl group as defined herein; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

In a further preferred embodiment, the invention provides a compound of Formula (IV), wherein $R_{11}$ can be chosen from an optionally substituted pyridin-2-yl; an optionally substituted pyridin-3-yl; an optionally substituted pyridin-4-yl; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

In a further preferred embodiment, the invention provides a compound of Formula (IV), wherein $R_{11}$ is an optionally substituted pyridin-3-yl; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

In a further preferred embodiment, the invention provides a compound of Formula (IV), wherein $R_{11}$ is a pyridin-3-yl; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

Yet, a further preferred embodiment provides a compound of Formula (IV), wherein $R_{11}$ can be chosen from a hydrogen atom; a $-(O-CH_2CH_2-)_p-OR_8$; a $-(O-CH_2CH_2-)_p-NR_8R_{8'}$; a $-NR_8(-CH_2CH_2-O)_p-R_{8'}$; a $-NR_8-(C_2-C_8)$-alkyl-$NR_8R_{8'}$; a $-NR_8-(C_2-C_8)$-alkyl-$OR_{8'}$; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

Yet, a further preferred embodiment provides a compound of Formula (IV), wherein $R_{11}$ can be chosen from a hydrogen atom; a $-(O-CH_2CH_2-)_p-ORB$; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

Yet, a further preferred embodiment provides a compound of Formula (IV), wherein $R_{11}$ can be chosen from a hydrogen atom; a $-(O-CH_2CH_2-)_p-NR_8R_{8'}$; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

Yet, a further preferred embodiment provides a compound of Formula (IV), wherein $R_{11}$ can be chosen from a hydrogen atom; a $-NR_8(-CH_2CH_2-O)_p-R_{8'}$; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

Yet, a further preferred embodiment provides a compound of Formula (IV), wherein $R_{11}$ can be chosen from a hydrogen atom; a $-NR_8-(C_2-C_8)$-alkyl-$NR_8R_{8'}$; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

Yet, a further preferred embodiment provides a compound of Formula (IV), wherein $R_{11}$ can be chosen from a hydrogen atom; a $-NR_8-(C_2-C_8)$-alkyl-$OR_{8'}$; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

In another preferred embodiment, a compound according to Formula (IV) can be provided wherein $R_{11}$ can be chosen from a hydrogen atom; a halogen atom as defined herein; an optionally substituted alkyl as defined herein, preferably said substituted alkyl being substituted by one or more halogen atom(s) as defined herein; an optionally substituted alkyl as defined herein; an alkoxy as defined herein; a hydroxyl; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

In another preferred embodiment, a compound according to Formula (IV) can be provided wherein $R_{11}$ can be chosen from a hydrogen atom; a halogen atom as defined herein; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

In another preferred embodiment, a compound according to Formula (IV) can be provided wherein $R_{11}$ can be chosen from a hydrogen atom; a fluorine; a chlorine; a methyl; a $-CF_3$; a hydroxyl; a methoxy; an ethoxy; an isopropoxy; a tert-butoxy; a cyano; an azido; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

In another preferred embodiment, a compound according to Formula (IV) can be provided wherein $R_{11}$ can be chosen from a hydrogen atom; a fluorine; a chlorine; a methyl; a hydroxyl; a methoxy; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

In another preferred embodiment, a compound according to Formula (IV) can be provided wherein $R_{11}$ can be chosen from a hydrogen atom; a fluorine; a chlorine; a methyl; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

In another preferred embodiment, a compound according to Formula (IV) can be provided wherein $R_{11}$ can be chosen from a hydrogen atom; a fluorine; a chlorine; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

In another preferred embodiment, a compound according to Formula (IV) can be provided wherein $R_{11}$ can be chosen from a hydrogen atom; an optionally substituted alkoxy; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, have the same definitions as those given previously with Formula (IV).

In another preferred embodiment, a compound according to Formula (IV) can be provided wherein $R_{11}$ can be chosen from a hydrogen atom; a hydroxyl, a methoxy, an ethoxy, an isopropoxy; a tert-butoxy; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

In another preferred embodiment, a compound according to Formula (IV) can be provided wherein $R_{11}$ can be chosen from a hydrogen atom; a hydroxyl; a methoxy; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

In another preferred embodiment, a compound according to Formula (IV) can be provided wherein $R_{11}$ is a hydroxyl; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

In another preferred embodiment, a compound according to Formula (IV) can be provided wherein $R_{11}$ is a methoxy; it being understood that $L_1$, $R_1$, $R_2$, $R_{2'}$, $R_3$, $R_4$, $R_5$, $R_7$, $R_8$, $R_{8'}$, $R_{10}$, $R_{12}$, $R_{13}$, m, n and p have the same definitions as those given previously with Formula (IV).

In another preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m can be 1 or 2, preferably 2; it being understood that $L_1$, $R_1$, $R_2$, $R_{2'}$, $R_3$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In another preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; it being understood that $L_1$, $R_1$, $R_2$, $R_{2'}$, $R_3$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In another preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; it being understood that $L_1$, $R_1$, $R_2$, $R_{2'}$, $R_3$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is an optionally substituted alkyl as defined herein; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is an optionally substituted alkyl as defined herein; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is an optionally substituted cycloalkyl as defined herein; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is an optionally substituted cycloalkyl as defined herein; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is an optionally substituted heterocyclyl group as defined herein; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is an optionally substituted heterocyclyl group as defined herein; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ and $R_3$ are linked together with the nitrogen atom to which they are covalently linked to form a heterocyclyl group as defined herein; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ and $R_3$ are linked together with the nitrogen atom to which they are covalently linked to form a heterocyclyl group as defined herein; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ and $R_3$ are linked together with the nitrogen atom to which they are covalently linked to form a pyrrolidin-1-yl; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ and $R_3$ are linked together with the nitrogen atom to which they are covalently linked to form a pyrrolidin-1-yl; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a 1-methylpiperidin-4-yl; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a 1-methylpiperidin-4-yl; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; it being understood that $L_1$, $R_1$, $R_{2'}$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_1$ is an optionally substituted aryl as defined herein; it being understood that $L_1$, $R_{2'}$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_1$ is an optionally substituted aryl as defined herein; it being understood that $L_1$, $R_{2'}$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_1$ is an optionally substituted phenyl; it being understood that $L_1$, $R_{2'}$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or l and m is 2; and $R_2$ is a hydrogen atom and $R_3$ is a tert-butyl; and $R_1$ is an optionally substituted phenyl; it being understood that $L_1$, $R_{2'}$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_1$ is a 3-methylbenzene-1,4-diyl; it being understood that $L_1$, $R_2$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or l and m is 2; and $R_2$ is a hydrogen atom and $R_3$ is a tert-butyl; and $R_1$ is a 3-methylbenzene-1,4-diyl; it being understood that $L_1$, $R_2$, $R_4$, $R_5$, $R_7$, $R_8$, $R_{8'}$, $R_{10}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ is an optionally substituted aryl as defined herein; it being understood that $L_1$, $R_1$, $R_{2'}$, $R_4$, $R_7$, $R_8$, $R_{8'}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ is an optionally substituted aryl as defined herein; it being understood that $L_1$, $R_1$, $R_2$, $R_4$, $R_5$, $R_7$, $R_8$, $R_{8'}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ is an optionally substituted phenyl; it being understood that $L_1$, $R_1$, $R_{2'}$, $R_4$, $R_5$, $R_7$, $R_8$, $R_{8'}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ is an optionally substituted phenyl; it being understood that $L_1$, $R_1$, $R_{2'}$, $R_4$, $R_5$, $R_7$, $R_8$, $R_{8'}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ is an optionally substituted heteroaryl as defined herein; it being understood that $L_1$, $R_1$, $R_{2'}$, $R_4$, $R_5$, $R_7$, $R_8$, $R_{8'}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ is an optionally substituted heteroaryl as defined herein; it being understood that $L_1$, $R_1$, $R_2$, $R_4$, $R_5$, $R_7$, $R_8$, $R_{8'}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ can be chosen from an optionally substituted pyrimidin-2-yl; an optionally substituted pyrimidin-4-yl; an optionally substituted pyrimidin-5-yl; it being understood that $L_1$, $R_1$, $R_{2'}$, $R_4$, $R_5$, $R_7$, $R_8$, $R_{8'}$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ can be chosen from an optionally substituted pyrimidin-2-yl; an optionally substituted pyrimidin-4-yl; an optionally substituted pyrimidin-5-yl; it being understood that $L_1$, $R_1$, $R_{2'}$, $R_4$, $R_5$, $R_7$, $R_8$, $R_{8'}$, $R_{11}$, $R_{12}$, $R_{13}$ and p have the same definitions as those given previously with Formula (IV).

In yet a further preferred embodiment, the invention provides a compound of Formula (IV), wherein n can take any one of the 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ is an optionally substituted pyrimidin-2-yl; it being understood that $L_1$, $R_1$, $R_{2'}$, $R_4$, $R_5$, $R_7$, $R_8$, $R_{8'}$, $R_{11}$, $R_{12}$, $R_{13}$ and p have the same definitions as those given previously with Formula (IV).

In yet a further preferred embodiment, the invention provides a compound of Formula (IV), wherein n can take any one of the 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ is an optionally substituted pyrimidin-2-yl; it being understood that $L_1$, $R_1$, $R_2'$, $R_4$, $R_5$, $R_7$, $R_8$, $R_8'$, $R_{11}$, $R_{12}$, $R_{13}$ and p have the same definitions as those given previously with Formula (IV).

In yet a further preferred embodiment, the invention provides a compound of Formula (IV), wherein n can take any one of the 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ is a pyrimidin-2-yl; it being understood that $L_1$, $R_1$, $R_2'$, $R_4$, $R_5$, $R_7$, $R_8$, $R_8'$, $R_{11}$, $R_{12}$, $R_{13}$ and p have the same definitions as those given previously with Formula (IV).

In yet a further preferred embodiment, the invention provides a compound of Formula (IV), wherein n can take any one of the 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ is a pyrimidin-2-yl; it being understood that $L_1$, $R_1$, $R_2'$, $R_4$, $R_5$, $R_7$, $R_8$, $R_8'$, $R_{11}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{11}$ is an optionally substituted aryl as defined herein; it being understood that $L_1$, $R_1$, $R_2'$, $R_4$, $R_5$, $R_7$, $R_8$, $R_8'$, $R_{10}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{11}$ is an optionally substituted aryl as defined herein; it being understood that $L_1$, $R_1$, $R_2'$, $R_4$, $R_5$, $R_7$, $R_8$, $R_8'$, $R_{10}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{11}$ is an optionally substituted phenyl; it being understood that $L_1$, $R_1$, $R_2'$, $R_4$, $R_5$, $R_7$, $R_8$, $R_8'$, $R_{10}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{11}$ is an optionally substituted phenyl; it being understood that $L_1$, $R_1$, $R_2'$, $R_4$, $R_5$, $R_7$, $R_8$, $R_8'$, $R_{10}$, $R_{12}$, $R_{13}$ and p have the same definitions as those given previously with Formula (IV).

In yet a preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{11}$ is an optionally substituted heteroaryl as defined herein; it being understood that $L_1$, $R_1$, $R_2'$, $R_4$, $R_5$, $R_7$, $R_8$, $R_8'$, $R_{10}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{11}$ is an optionally substituted heteroaryl as defined herein; it being understood that $L_1$, $R_1$, $R_2'$, $R_4$, $R_5$, $R_7$, $R_8$, $R_8'$, $R_{10}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{11}$ can be chosen from an optionally substituted pyridin-2-yl, or an optionally substituted pyridin-3-yl, or an optionally substituted pyridin-4-yl; it being understood that $L_1$, $R_1$, $R_2'$, $R_4$, $R_5$, $R_7$, $R_8$, $R_8'$, $R_{10}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ can be a hydrogen atom and $R_3$ is a tert-butyl; and $R_{11}$ can be chosen from an optionally substituted pyridin-2-yl, or an optionally substituted pyridin-3-yl, or an optionally substituted pyridin-4-yl; it being understood that $L_1$, $R_1$, $R_2'$, $R_4$, $R_5$, $R_7$, $R_8$, $R_8'$, $R_{10}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{11}$ is an optionally substituted pyridin-3-yl; it being understood that $L_1$, $R_1$, $R_2'$, $R_4$, $R_5$, $R_7$, $R_8$, $R_8'$, $R_{10}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{11}$ is an optionally substituted pyridin-3-yl; it being understood that $L_1$, $R_1$, $R_2'$, $R_4$, $R_5$, $R_7$, $R_8$, $R_8'$, $R_{10}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{11}$ is a pyridin-3-yl; it being understood that $L_1$, $R_1$, $R_2'$, $R_4$, $R_5$, $R_7$, $R_8$, $R_8'$, $R_{10}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{11}$ is a pyridin-3-yl; it being understood that $L_1$, $R_1$, $R_2'$, $R_4$, $R_5$, $R_7$, $R_8$, $R_8'$, $R_{10}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ can be an optionally substituted heteroaryl as defined herein; and $R_{11}$ can be an optionally substituted heteroaryl as defined herein; it being understood that $R_4$, $R_7$, $R_8$, $R_{8'}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ can be an optionally substituted heteroaryl as defined herein; and $R_{11}$ can be an optionally substituted heteroaryl as defined herein; it being understood that $R_4$, $R_7$, $R_8$, $R_{8'}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ can be chosen from an optionally substituted pyrimidin-2-yl, an optionally substituted pyrimidin-4-yl, or an optionally substituted pyrimidin-5-yl; and $R_{11}$ can be chosen from an optionally substituted pyridin-2-yl, an optionally substituted pyridin-3-yl, or an optionally substituted pyridin-4-yl; it being understood that $L_1$, $R_1$, $R_{2'}$, $R_4$, $R_5$, $R_7$, $R_8$, $R_{8'}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ can be chosen from an optionally substituted pyrimidin-2-yl, an optionally substituted pyrimidin-4-yl, or an optionally substituted pyrimidin-5-yl; and $R_{11}$ can be chosen from an optionally substituted pyridin-2-yl, an optionally substituted pyridin-3-yl, or an optionally substituted pyridin-4-yl; it being understood that $L_1$, $R_1$, $R_{2'}$, $R_4$, $R_5$, $R_7$, $R_8$, $R_{8'}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ is an optionally substituted pyrimidin-2-yl, and $R_{11}$ can be chosen from an optionally substituted pyridin-2-yl, an optionally substituted pyridin-3-yl, or an optionally substituted pyridin-4-yl; it being understood that $L_1$, $R_1$, $R_{2'}$, $R_4$, $R_5$, $R_7$, $R_8$, $R_{8'}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ is an optionally substituted pyrimidin-2-yl, and $R_{11}$ can be chosen from an optionally substituted pyridin-2-yl, an optionally substituted pyridin-3-yl, or an optionally substituted pyridin-4-yl; it being understood that $L_1$, $R_1$, $R_{2'}$, $R_4$, $R_5$, $R_7$, $R_8$, $R_{8'}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ can be an optionally substituted pyrimidin-2-yl, an optionally substituted pyrimidin-4-yl, or an optionally substituted pyrimidin-5-yl; and $R_{11}$ is an optionally substituted pyridin-2-yl; it being understood that $L_1$, $R_1$, $R_{2'}$, $R_4$, $R_5$, $R_7$, $R_8$, $R_{8'}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ can be chosen from an optionally substituted pyrimidin-2-yl, an optionally substituted pyrimidin-4-yl, or an optionally substituted pyrimidin-5-yl; and $R_{11}$ is an optionally substituted pyridin-2-yl; it being understood that $L_1$, $R_1$, $R_{2'}$, $R_4$, $R_5$, $R_7$, $R_8$, $R_{8'}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ can be chosen from an optionally substituted pyrimidin-2-yl, an optionally substituted pyrimidin-4-yl, or an optionally substituted pyrimidin-5-yl; and $R_{11}$ is an optionally substituted pyridin-3-yl; it being understood that $L_1$, $R_1$, $R_{2'}$, $R_4$, $R_5$, $R_7$, $R_8$, $R_{8'}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ can be chosen from an optionally substituted pyrimidin-2-yl, an optionally substituted pyrimidin-4-yl, or an optionally substituted pyrimidin-5-yl; and $R_{11}$ is an optionally substituted pyridin-3-yl; it being understood that $L_1$, $R_1$, $R_{2'}$, $R_4$, $R_5$, $R_7$, $R_8$, $R_{8'}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ can be chosen from an optionally substituted pyrimidin-2-yl, an optionally substituted pyrimidin-4-yl, or an optionally substituted pyrimidin-5-yl; and $R_{11}$ is an optionally substituted pyridin-4-yl; it being understood that $L_1$, $R_1$, $R_{2'}$, $R_4$, $R_5$, $R_7$, $R_8$, $R_{8'}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ can be chosen from an optionally substituted pyrimidin-2-yl, an optionally substituted pyrimidin-4-yl, or an optionally substituted pyrimidin-5-yl; and $R_{11}$ is an optionally substituted pyridin-4-yl; it being understood that $L_1$, $R_1$, $R_{2'}$, $R_4$, $R_5$, $R_7$, $R_8$, $R_{8'}$, $R_{12}$, $R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ can be chosen from an optionally substituted pyrimidin- 2-yl, an optionally substituted pyrimidin-4-yl, or an optionally substituted pyrimidin-5-yl; and $R_{11}$ can be chosen from a pyridin-2-yl, a pyridin-3-yl, or a pyridin-4-yl; it being understood that $L_1, R_1, R_{2'}, R_4, R_5, R_7, R_8, R_{8'}, R_{12}, R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ can be chosen from an optionally substituted pyrimidin-2-yl, an optionally substituted pyrimidin-4-yl, or an optionally substituted pyrimidin-5-yl; and $R_{11}$ can be chosen from a pyridin-2-yl, a pyridin-3-yl, or a pyridin-4-yl; it being understood that $L_1, R_1, R_{2'}, R_4, R_5, R_7, R_8, R_{8'}, R_{12}, R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ can be chosen from a pyrimidin-2-yl, a pyrimidin-4-yl, or a pyrimidin-5-yl; and $R_{11}$ can be chosen from a pyridin-2-yl, a pyridin-3-yl, or a pyridin-4-yl; it being understood that $L_1, R_1, R_{2'}, R_4, R_5, R_7, R_8, R_{8'}, R_{12}, R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ can be chosen from a pyrimidin-2-yl, a pyrimidin-4-yl, or a pyrimidin-5-yl; and $R_{11}$ can be chosen from a pyridin-2-yl, a pyridin-3-yl, or a pyridin-4-yl; it being understood that $L_1, R_1, R_{2'}, R_4, R_5, R_7, R_8, R_{8'}, R_{12}, R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ is an optionally substituted pyrimidin-2-yl and $R_{11}$ is an optionally substituted pyridin-3-yl; it being understood that $L_1, R_1, R_{2'}, R_4, R_5, R_7, R_8, R_{8'}, R_{12}, R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ is an optionally substituted pyrimidin-2-yl and $R_{11}$ is an optionally substituted pyridin-3-yl; it being understood that $L_1, R_1, R_{2'}, R_4, R_5, R_7, R_8, R_{8'}, R_{12}, R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ is pyrimidin-2-yl and $R_{11}$ is a pyridin-3-yl; it being understood that $L_1, R_1, R_{2'}, R_4, R_5, R_7, R_8, R_{8'}, R_{12}, R_{13}$ and p have the same definitions as those given previously with Formula (IV).

In yet a further preferred embodiment, the invention provides a compound of Formula (IV), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ is a pyrimidin-2-yl and $R_{11}$ is a pyridin-3-yl; it being understood that $L_1, R_1, R_{2'}, R_4, R_5, R_7, R_8, R_{8'}, R_{12}, R_{13}$ and p have the same definitions as those given previously with Formula (IV).

The present disclosure also provides in a preferred embodiment a compound of Formula (V) having the structure:

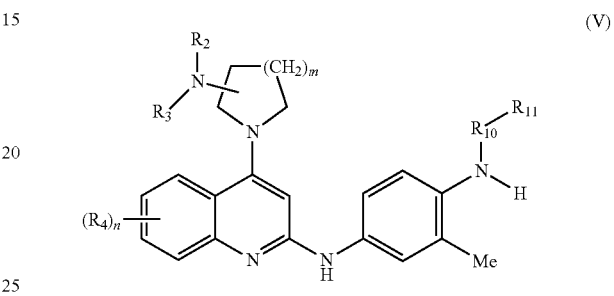

wherein $R_2$ and $R_3$ can be simultaneously or independently chosen from a hydrogen; an optionally substituted alkyl as defined herein, preferably said optionally substituted alkyl being substituted with one or more —$NR_8R_{8'}$; an optionally substituted alkenyl as defined herein; an optionally substituted alkynyl as defined herein; an optionally substituted cycloalkyl as defined herein, preferably said optionally substituted cycloalkyl being substituted with one or more —$NR_8R_{8'}$; an optionally substituted cycloalkenyl as defined herein; an optionally substituted cycloalkynyl as defined herein; a —(CO)—$R_7$; a —(CO)—O—$R_7$; a —(CO)—$NR_8OH$; a —(CO)—$NR_8R_{8'}$; a —$SO_2$—$R_7$; a —$SO_2$—$NR_8R_{8'}$; an optionally substituted aryl as defined herein; an optionally substituted benzyl as defined herein; an optionally substituted heteroaryl as defined herein; an optionally substituted heterocyclyl group as defined herein; or $R_2$ and $R_3$ can be linked together with the nitrogen atom to which they are covalently linked to form an optionally substituted heterocyclyl group as defined herein.

$R_4$ can be, alone or simultaneously or independently when n>1, chosen from a hydrogen atom; a halogen atom as defined herein; an optionally substituted alkyl as defined herein, preferably said optionally substituted alkyl being substituted by one or more halogen atom(s) as defined herein, by one or more hydroxyl, by one or more alkoxy as defined herein, by one or more —$NR_8R_{8'}$ and combination thereof; an optionally substituted fluoroalkyl as defined herein; an optionally substituted alkenyl as defined herein; an optionally substituted alkynyl as defined herein; a optionally substituted cycloalkyl as defined herein; a optionally substituted cycloalkenyl as defined herein; a optionally substituted cycloalkynyl as defined herein; an optionally substituted alkoxy as defined herein; a hydroxyl; a nitro; an azido; a cyano; a —$NR_{12}R_{13}$; a —$NR_8R_{8'}$; a —O—($R_7$); a —(CO)—$R_7$; a —(CO)—O—$R_7$; a —(CO)—$NR_{12}OH$; a —(CO)—$NR_8OH$; a —(CO)—$NR_{12}R_{13}$; a —(CO)—$NR_8R_{8'}$; a —O—(CO)—$R_7$; a —O—(CO)—$NR_{12}R_{13}$; a —O—(CO)—$NR_8R_{8'}$; a —$NR_{12}$—(CO)—$R_7$; a —$NR_8$—(CO)—$R_7$; a —$NR_{12}$—(CO)—$OR_7$; a —$NR_8$—(CO)—$OR_7$; a O—(CO)—$OR_7$; a —$NR_{12}$—(CO)—$NR_{12}R_{13}$; a —$NR_8$—(CO)—$NR_8R_{8'}$; a —(O—$CH_2CH_2$)$_p$—$OR_{12}$; a —(O—$CH_2CH_2$)$_p$—$OR_7$; a —(O—$CH_2CH_2$)$_p$—$NR_{12}R_{13}$; a —(O—$CH_2CH_2$)$_p$—$NR_8R_{8'}$; —$NR_{12}$—($CH_2CH_2$—O)$_p$—$R_{13}$; —$NR_8$—($CH_2CH_2$—O)$_p$—$R_7$; a —$SO_2$—$R_7$; a —$NR_{12}$—$SO_2$—$R_7$; a —$NR_8$—$SO_2$—$R_7$; a —$SO_2$—$NR_{12}R_{13}$; a —$SO_2$—$NR_8R_{8'}$; a —$NR_{12}$—$SO_2$—$NR_{12}R_{13}$; a —$NR_8$—$SO_2$—$NR_8R_{8'}$; a —$NR_{12}$—($C_2$-$C_8$)-alkyl-$NR_{12}R_{13}$; a —$NR_8$—($C_2$-$C_8$)-alkyl-$NR_8R_{8'}$; a —$NR_{12}$—($C_2$-$C_8$)-alkyl-$OR_{13}$; a —$NR_8$—($C_2$-$C_8$)-alkyl-$OR_7$; an optionally substituted aryl as defined herein; an optionally substituted benzyl as defined herein; an optionally substituted heteroaryl as defined herein; an optionally substituted heterocyclyl group as defined herein.

$R_7$ is chosen from a hydrogen atom; optionally substituted alkyl as defined herein, preferably said optionally substituted alkyl being substituted by one or more —$NR_8R_{8'}$; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted aryl as defined herein; an optionally substituted benzyl as defined herein; an optionally substituted heteroaryl as defined herein; an optionally substituted heterocyclyl group as defined herein.

$R_8$ and $R_{8'}$ can be simultaneously or independently chosen from a hydrogen atom; an optionally substituted alkyl as defined herein; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted heterocyclyl group as defined herein; an optionally substituted aryl as defined herein; an optionally substituted benzyl as defined herein; an optionally substituted heteroaryl as defined herein; or $R_8$ and $R_{8'}$ can be linked together with the nitrogen atom to which they are covalently linked to form an optionally substituted heterocyclyl group as defined herein.

$R_{10}$ can be chosen from an optionally substituted aryl as defined herein; an optionally substituted heteroaryl as defined herein.

$R_{11}$ can be chosen from a hydrogen atom; a halogen atom as defined herein; an optionally substituted alkoxy as defined herein; a hydroxyl as defined herein; a nitro; a cyano; an azido; a —$NR_{12}R_{13}$; a —$NR_8R_{8'}$; a —O—($R_8$); a —(CO)—$R_8$; a —(CO)—O—$R_8$; a —(CO)—$NR_{12}$OH; a —(CO)—$NR_8$OH; a —(CO)—$NR_{12}R_{13}$; a —(CO)—$NR_8R_{8'}$; a —O—(CO)—$R_8$; a —O—(CO)—$NR_{12}R_{13}$; a —O—(CO)—$NR_8R_{8'}$; a —$NR_{12}$—(CO)—$R_8$; a —$NR_8$—(CO)—$R_{8'}$; a —$NR_{12}$—(CO)—$NR_{13}$; a —$NR_8$—(CO)—$NR_{8'}$; a O—(CO)—$NR_8$; a —$NR_{12}$—(CO)—$NR_{12}R_{13}$; a —$NR_8$—(CO)—$NR_8R_{8'}$; a —(O—$CH_2CH_2$—)$_p$—$NR_{12}$; a —(O—$CH_2CH_2$—)$_p$—$OR_8$; a —(O—$CH_2CH_2$—)$_p$—$NR_{12}R_{13}$; a —(O—$CH_2CH_2$—)$_p$—$NR_8R_{8'}$; —$NR_{12}$—($CH_2CH_2$—O)$_p$—$R_{13}$; —$NR_8$—($CH_2CH_2$—O)$_p$—$R_{8'}$; a —$SO_2$—$R_8$; a —$NR_{12}$—$SO_2$—$R_8$; a —$NR_8$—$SO_2$—$R_{8'}$; a —$SO_2$—$NR_{12}R_{13}$; a —$SO_2$—$NR_8R_{8'}$; —$NR_{12}$—$SO_2$—$NR_{12}R_{13}$; —$NR_8$—$SO_2$—$NR_8R_{8'}$; a —$NR_{12}$—($C_2$-$C_8$)-alkyl-$NR_{12}R_{13}$; a —$NR_8$—($C_2$-$C_8$)-alkyl-$NR_8R_{8'}$; a —$NR_{12}$—($C_2$-$C_8$)-alkyl-$NR_{13}$; a —$NR_8$—($C_2$-$C_8$)-alkyl-$OR_{8'}$; an optionally substituted alkyl as defined herein, preferably said optionally substituted alkyl being substituted by one or more halogen atom(s) as defined herein, by one or more hydroxyl, by one or more alkoxy as defined herein, or by one or more $NR_8R_{8'}$ and combination thereof; an optionally substituted fluoroalkyl as defined herein; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted aryl as defined herein; an optionally substituted benzyl as defined herein; an optionally substituted heteroaryl as defined herein; an optionally substituted heterocyclyl group as defined herein.

$R_{12}$ and $R_{13}$ can be simultaneously or independently chosen from a hydrogen atom; a —(CO)—$R_7$; a —(CO)—O—$R_7$; a —(CO)—$NR_8$OH; a —(CO)—$NR_8R_{8'}$; a —$SO_2$—$R_7$; a —$SO_2$—$NR_8R_{8'}$; an optionally substituted alkyl as defined herein, preferably said optionally substituted alkyl being substituted with at least one —$NR_8R_{8'}$; an optionally substituted cycloalkyl as defined herein, preferably said optionally substituted cycloalkyl being substituted with at least one —$NR_8R_{8'}$; an optionally substituted alkenyl as defined herein; an optionally substituted alkynyl as defined herein; an optionally substituted cycloalkenyl as defined herein; an optionally substituted cycloalkynyl as defined herein; an optionally substituted aryl as defined herein; an optionally substituted benzyl as defined herein; an optionally substituted heteroaryl as defined herein; an optionally substituted heterocyclyl group as defined herein; or $R_{12}$ and $R_{13}$ can be linked together with the nitrogen atom to which they are covalently linked to form an optionally substituted heterocyclyl group as defined herein.

n can represent an equal integer which can have any one of the values 0, 1, 2, 3 or 4, preferably 0, 1, 2 or 3, more preferably 0, 1 or 2 still more preferably 0 or 1.

m can represent an equal integer which can have any one of the values 1, 2 or 3 preferably 1 or 2, more preferably 2.

p can represent an equal integer which can have any one of the values 1, 2, 3, 4 or 5, preferably 1, 2, 3 or 4, more preferably 1, 2 or 3 still more preferably 1 or 2.

and any pharmaceutically acceptable salt, hydrates, solvate, prodrugs, polymorphs, tautomers, isotopic variants, isomers, stereoisomers or mixtures of stereoisomers thereof, for use as a medicament to treat, decrease the severity and/or progression of, and/or prevent fibrosis and/or related diseases, or for use as a medicament treat, decrease the severity and/or progression of, and/or prevent autophagy and/or related diseases, and to inhibit autophagy flux, or for use in inhibiting cathepsins B (CTSB), L (CTSL) and/or D (CTSD) and/or related diseases; with the proviso that said compounds are not to be used for treating any forms of cancers.

In a preferred embodiment, a compound according to Formula (V) can be provided, wherein $R_2$ and $R_3$ can be simultaneously or independently chosen from a hydrogen atom; an optionally substituted alkyl as defined herein; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted heterocyclyl group as defined herein; or $R_2$ and $R_3$ can be linked together with the nitrogen atom to which they are covalently linked to form an optionally substituted heterocyclyl group as defined herein; it being understood that $R_4$, $R_7$, $R_8$, $R_{8'}$, $R_{10}$, $R_{11}$, $R_{12}$, $R_{13}$, m, n and p' have the same definitions as those given previously with Formula (V).

In a further preferred embodiment, a compound according to Formula (V) can be provided, wherein $R_2$ and $R_3$ can be simultaneously or independently chosen from a hydrogen atom; an optionally substituted alkyl as defined herein; an optionally substituted cycloalkyl as defined herein; an optionally substituted heterocyclyl group as defined herein; or $R_2$ and $R_3$ can be linked together with the nitrogen atom to which they are covalently linked to form an optionally substituted heterocyclyl group as defined herein; it being understood that $R_4$, $R_7$, $R_8$, $R_{8'}$, $R_{10}$, $R_{11}$, $R_{12}$, $R_{13}$, m, n and p' have the same definitions as those given previously with Formula (V).

In also a preferred embodiment, a compound according to Formula (V) can be provided, wherein $R_2$ and $R_3$ can be simultaneously or independently chosen from a hydrogen atom; an optionally substituted alkyl as defined herein; an optionally substituted cycloalkyl as defined herein; or $R_2$ and $R_3$ can be linked together with the nitrogen atom to which they are covalently linked to form an optionally substituted heterocyclyl group as defined herein; it being understood that $R_4$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided, wherein $R_2$ and $R_3$ can be simultaneously or independently chosen from a hydrogen atom; an optionally substituted alkyl as defined herein; an optionally substituted cycloalkyl as defined herein; it being understood that $R_4$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided, wherein $R_2$ and $R_3$ can be simultaneously or independently chosen from a hydrogen atom; an optionally heterocyclyl group as defined herein; it being understood that $R_4$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided, wherein $R_2$ and $R_3$ can be simultaneously or independently chosen from a hydrogen atom; an optionally substituted alkyl as defined herein; it being understood that $R_4$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided, wherein $R_2$ and $R_3$ can be can be linked together with the nitrogen atom to which they are covalently linked to form a heterocyclyl group as defined herein; it being understood that $R_4$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided, wherein $R_2$ and $R_3$ can be can be linked together with the nitrogen atom to which they are covalently linked to form a pyrrolidin-1-yl; it being understood that $R_4$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided, wherein $R_2$ and $R_3$ can be simultaneously or independently chosen from a hydrogen atom; a 1-methylpiperidin-4-yl; it being understood that $R_4$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided, wherein $R_2$ and $R_3$ can be simultaneously or independently chosen from a hydrogen; a tert-butyl; it being understood that $R_4$, $R_7$, $R_8$, $R_{8'}$, $R_{10}$, $R_{11}$, $R_{12}$, $R_{13}$, m, n and p' have the same definitions as those given previously with Formula (V).

Yet, in another preferred embodiment, a compound according to Formula (V) can be provided, wherein $R_4$ can be, alone or simultaneously or independently when n>1 chosen from a hydrogen atom; a halogen atom as defined herein; an optionally alkyl as defined herein, preferably said optionally substituted alkyl being substituted by one or more halogen atom(s) as defined herein, one or more hydroxyl as defined herein, one or more alkoxy as defined herein, one or more —$NR_8R_{8'}$ and combination thereof; an optionally substituted alkenyl as defined herein; an optionally substituted alkynyl as defined herein; an optionally substituted cycloalkyl as defined herein; an optionally substituted cycloalkenyl as defined herein; an optionally substituted cycloalkynyl as defined herein; an optionally substituted alkoxy as defined herein; a hydroxyl; a nitro; a cyano; an azido; a carboxyl, a —$NR_8R_{8'}$; a —(CO)—$NR_2R_3$; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided wherein $R_4$ can be, alone or simultaneously or independently when n>1 chosen from a hydrogen atom; a halogen atom as defined herein; an optionally substituted alkyl as defined herein, preferably said optionally substituted alkyl being substituted by one or more halogen atom(s) as defined herein; an optionally substituted alkoxy as defined herein; a hydroxyl; a cyano; a carboxyl, an azido a —$NR_8R_{8'}$; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided wherein $R_4$ can be, alone or simultaneously or independently when n>1 chosen from a hydrogen atom; a halogen atom as defined herein; an optionally substituted alkyl as defined herein, preferably said substituted alkyl being substituted by one or more halogen atom(s) as defined herein; an optionally substituted alkoxy as defined herein; a hydroxyl; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided wherein $R_4$ can be, alone or simultaneously or independently when n>1 chosen from a hydrogen atom; a halogen atom as defined herein; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided wherein $R_4$ can be, alone or simultaneously or independently when n>1 chosen from a hydrogen atom; a fluorine; a chlorine; a methyl; a —$CF_3$; an azido; a cyano; a hydroxyl; a methoxy; an ethoxy; an isopropoxy; a tert-butoxy; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided wherein $R_4$ can be, alone or simultaneously or independently when n>1 chosen from a hydrogen atom; a fluorine; a chlorine; a methyl; a hydroxyl; a methoxy; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided wherein $R_4$ can be, alone or simultaneously or independently when n>1 chosen from a hydrogen atom; a fluorine; a chlorine; a methyl; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided wherein $R_4$ can be, alone or simultaneously or independently when n>1 chosen from a hydrogen atom; a fluorine; a chlorine; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided, wherein $R_4$ can be, alone or simultaneously or independently when n>1 chosen from a hydrogen or a methyl; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided wherein $R_4$ can be, alone or simultaneously or independently when n>1 chosen from a hydrogen atom; an optionally substituted alkoxy as defined herein; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided wherein $R_4$ can be, alone or simultaneously or independently when n>1 chosen from a hydrogen atom; a hydroxyl, a methoxy, an ethoxy, an isopropoxy; a tert-butoxy; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided wherein $R_4$ can be, alone or simultaneously or independently when n>1 chosen from a hydrogen atom; a hydroxyl, a methoxy; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided wherein $R_4$ can be, alone or simultaneously or independently when n>1 chosen from a hydrogen atom; a methoxy; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided wherein $R_4$ can be, alone or simultaneously or independently when n>1 chosen from a hydrogen atom; an optionally substituted fluoroalkyl; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided wherein $R_4$ can be, alone or simultaneously or independently when n>1 chosen from a hydrogen atom; a —$CF_3$; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

Yet, another preferred embodiment provides a compound of Formula (V), wherein $R_4$ can be, alone or simultaneously or independently when n>1, chosen from a hydrogen atom; —$NR_8R_{8'}$; it being understood that $R_1$, $R_2$, $R_{2'}$, $R_3$, $R_5$, $R_7$, $R_8$, $R_{8'}$, $R_{10}$, $R_{11}$, $R_{12}$, $R_{13}$, m, n and p have the same definitions as those given previously with Formula (V).

In another preferred embodiment, a compound according to Formula (V) can be provided wherein $R_4$ can be, alone or simultaneously or independently when n>1 chosen from a hydrogen atom; a hydroxyl; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

In another preferred embodiment, a compound according to Formula (V) can be provided wherein $R_4$ is a hydrogen atom; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

Yet, a further preferred embodiment provides a compound of Formula (V), wherein $R_4$ can be, alone or simultaneously or independently when n>1 chosen from a hydrogen; a —(O—$CH_2CH_2$—)$_p$—$OR_{12}$; a —(O—$CH_2CH_2$—)$_p$—$NR_{12}R_{13}$; a —$NR_{12}$—($CH_2CH_2$—O)$_p$—$R_{13}$; a —$NR_{12}$—($C_2$-$C_8$)-alkyl-$NR_{12}R_{13}$; a —$NR_{12}$—($C_2$-$C_8$)-alkyl-$OR_{13}$; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

Yet, a further preferred embodiment provides a compound of Formula (V), wherein $R_4$ can be, alone or simultaneously or independently when n>1 chosen from a hydrogen; a —(O—$CH_2CH_2$—)$_p$—$NR_8$; a —(O—$CH_2CH_2$—)$_p$—$NR_8R_{8'}$; a —$NR_8$—($CH_2CH_2$—O)$_p$—$R_8$; a —$NR_8$—($C_2$-$C_8$)-alkyl-$NR_8R_{8'}$; a —$NR_8$—($C_2$-$C_8$)-alkyl-$OR_8$; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

Yet, a further preferred embodiment provides a compound of Formula (V), wherein $R_4$ can be, alone or simultaneously or independently when n>1 chosen from a hydrogen; a —(O—$CH_2CH_2$—)$_p$—$OR_8$; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

Yet, a further preferred embodiment provides a compound of Formula (V), wherein $R_4$ can be, alone or simultaneously or independently when n>1 chosen from a hydrogen; a —(O—$CH_2CH_2$—)$_p$—$NR_8R_{8'}$; it being understood that $R_2$, $R_3$, $R_7$, $R_8$, $R_{8'}$, $R_{10}$, $R_{11}$, $R_{12}$, $R_{13}$, m, n and p have the same definitions as those given previously with Formula (V).

Yet, a further preferred embodiment provides a compound of Formula (V), wherein $R_4$ can be, alone or simultaneously or independently when n>1 chosen from a hydrogen; a —$NR_{12}$—($CH_2CH_2$—O)$_p$—$R_{13}$; it being understood that $R_2$, $R_3$, $R_7$, $R_8$, $R_{8'}$, $R_{10}$, $R_{11}$, $R_{12}$, $R_{13}$, m, n and p have the same definitions as those given previously with Formula (V).

Yet, a further preferred embodiment provides a compound of Formula (V), wherein $R_4$ can be, alone or simultaneously or independently when n>1 chosen from a hydrogen; a —$NR_8$—($C_2$-$C_8$)-alkyl-$NR_8R_{8'}$; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

Yet, a further preferred embodiment provides a compound of Formula (V), wherein $R_4$ can be, alone or simultaneously or independently when n>1 chosen from a hydrogen; a —$NR_8$—($C_2$-$C_8$)-alkyl-$OR_8$; it being understood that $R_2$, $R_3$, $R_7$, $R_8$, $R_{8'}$, $R_{10}$, $R_{11}$, $R_{12}$, $R_{13}$, m, n and p' have the same definitions as those given previously with Formula (V).

In yet another preferred embodiment provides a compound of Formula (V), wherein $R_4$ can be, alone or simultaneously or independently when n>1 chosen from a hydrogen atom; —(CO)—$NR_{12}R_{13}$, wherein $R_{12}$ and $R_{13}$ can be simultaneously or independently chosen from a hydrogen atom; an optionally substituted alkyl as defined herein; an optionally substituted cycloalkyl as defined herein; an optionally substituted heterocyclyl group as defined herein; an optionally substituted aryl as defined herein; an optionally substituted heteroaryl as defined herein; or $R_{12}$ and $R_{13}$ can be linked together with the nitrogen atom to which they are covalently linked to form an optionally heterocyclyl group as defined herein; it being understood that $R_2$, $R_3$, $R_7$, $R_8$, $R_{8'}$, $R_{10}$, $R_{11}$, m, n and p' have the same definitions as those given previously with Formula (V).

In yet another preferred embodiment provides a compound of Formula (V), wherein $R_4$ can be, alone or simultaneously or independently when n>1 chosen from a hydrogen atom; —(CO)—$NR_{12}R_{13}$, wherein $R_{12}$ and $R_{13}$ can be simultaneously or independently chosen from a hydrogen atom, an optionally substituted alkyl as defined herein, an optionally substituted cycloalkyl as defined herein, an optionally substituted heterocyclyl group as defined herein, or $R_{12}$ and $R_{13}$ can be linked together with the nitrogen atom to which they are covalently linked to form an optionally heterocyclyl group as defined herein; it being understood that $R_2$, $R_3$, $R_7$, $R_8$, $R_{8'}$, $R_{10}$, $R_{11}$, m, n and p' have the same definitions as those given previously with Formula (V).

Yet, another preferred embodiment provides a compound of Formula (V), wherein $R_4$ can be, alone or simultaneously or independently when n>1 chosen from a hydrogen atom; —(CO)—$NR_{12}R_{13}$, wherein $R_{12}$ and $R_{13}$ can be simultaneously or independently chosen from a hydrogen atom, an optionally substituted alkyl as defined herein, an optionally substituted cycloalkyl as defined herein, an optionally substituted heterocyclyl group as defined herein, it being understood that $R_2$, $R_3$, $R_7$, $R_8$, $R_{8'}$, $R_{10}$, $R_{11}$, m, n and p' have the same definitions as those given previously with Formula (V).

Yet, another preferred embodiment provides a compound of Formula (V), wherein $R_4$ can be, alone or simultaneously or independently when n>1 chosen from a hydrogen atom; —(CO)—$NR_{12}R_{13}$, wherein $R_{12}$ and $R_{13}$ can be simultaneously or independently chosen from a hydrogen atom, an optionally substituted alkyl as defined herein, an optionally substituted cycloalkyl as defined herein; it being understood that $R_2$, $R_3$, $R_7$, $R_8$, $R_{8'}$, $R_{10}$, $R_{11}$, m, n and p' have the same definitions as those given previously with Formula (V).

Yet, another preferred embodiment provides a compound of Formula (V), wherein $R_4$ can be, alone or simultaneously or independently when n>1 chosen from a hydrogen atom; —(CO)—$NR_{12}R_{13}$, wherein $R_{12}$ and $R_{13}$ can be simultaneously or independently chosen from a hydrogen atom, an optionally substituted alkyl as defined herein; it being understood that $R_2$, $R_3$, $R_7$, $R_8$, $R_{8'}$, $R_{10}$, $R_{11}$, m, n and p' have the same definitions as those given previously with Formula (V).

Yet, another preferred embodiment provides a compound of Formula (V), wherein $R_4$ can be, alone or simultaneously or independently when n>1 chosen from a hydrogen atom; —(CO)—$NR_{12}R_{13}$, wherein $R_{12}$ and $R_{13}$ can be simultaneously or independently chosen from a hydrogen atom, an optionally substituted cycloalkyl as defined herein; it being understood that $R_2$, $R_3$, $R_7$, $R_8$, $R_{8'}$, $R_{10}$, $R_{11}$, m, n and p' have the same definitions as those given previously with Formula (V).

Yet, another preferred embodiment provides a compound of Formula (V), wherein $R_4$ can be, alone or simultaneously or independently when n>1 chosen from a hydrogen atom; —(CO)—$NR_{12}R_{13}$, wherein $R_{12}$ and $R_{13}$ can be simultaneously or independently chosen from a hydrogen atom, an optionally substituted heterocyclyl group as defined herein, it being understood that $R_2$, $R_3$, $R_7$, $R_8$, $R_{8'}$, $R_{10}$, $R_{11}$, m, n and p' have the same definitions as those given previously with Formula (V).

Yet, another preferred embodiment provides a compound of Formula (V), wherein $R_4$ can be, alone or simultaneously or independently when n>1 chosen from a hydrogen atom; —(CO)—$NR_{12}R_{13}$, wherein $R_{12}$ and $R_{13}$ can be simultaneously or independently chosen from a hydrogen atom, an optionally substituted aryl as defined herein, it being understood that $R_2$, $R_3$, $R_7$, $R_8$, $R_{8'}$, $R_{10}$, $R_{11}$, m, n and p' have the same definitions as those given previously with Formula (V).

Yet, another preferred embodiment provides a compound of Formula (V), wherein $R_4$ can be, alone or simultaneously or independently when n>1 chosen from a hydrogen atom; —(CO)—$NR_{12}R_{13}$, wherein $R_{12}$ and $R_{13}$ can be simultaneously or independently chosen from a hydrogen atom, an optionally substituted benzyl as defined herein, it being understood that $R_2$, $R_3$, $R_7$, $R_8$, $R_{8'}$, $R_{10}$, $R_{11}$, m, n and p' have the same definitions as those given previously with Formula (V).

Yet, another preferred embodiment provides a compound of Formula (V), wherein $R_4$ can be, alone or simultaneously or independently when n>1 chosen from a hydrogen atom; —(CO)—$NR_{12}R_{13}$, wherein $R_{12}$ and $R_{13}$ can be simultaneously or independently chosen from a hydrogen atom, an optionally substituted heteroaryl as defined herein, it being understood that $R_2$, $R_3$, $R_7$, $R_8$, $R_{8'}$, $R_{10}$, $R_{11}$, m, n and p' have the same definitions as those given previously with Formula (V).

Yet, another preferred embodiment provides a compound of Formula (V), wherein $R_4$ can be, alone or simultaneously or independently when n>1 chosen from a hydrogen atom; —(CO)—$NR_{12}R_{13}$, wherein $R_{12}$ and $R_{13}$ can be linked together with the nitrogen atom to which they are covalently linked to form an optionally substituted heterocyclyl group as defined herein; it being understood that $R_2$, $R_3$, $R_7$, $R_8$, $R_{8'}$, $R_{10}$, $R_{11}$, m, n and p' have the same definitions as those given previously with Formula (V).

Yet, another preferred embodiment provides a compound of Formula (V), wherein $R_4$ can be, alone or simultaneously or independently when n>1 chosen from a hydrogen atom; —(CO)—$NR_{12}R_{13}$, wherein $R_{12}$ and $R_{13}$ can be simultaneously or independently chosen from a hydrogen atom, methyl, an ethyl, an isopropyl, a tert-butyl, a cyclopropyl, a cyclobutyl, a cyclopentyl, a cyclohexyl; it being understood that $R_2$, $R_3$, $R_7$, $R_8$, $R_{8'}$, $R_{10}$, $R_{11}$, m, n and p' have the same definitions as those given previously with Formula (V).

In a further preferred embodiment, the invention provides a compound according to Formula (V), wherein $R_{10}$ is chosen from an optionally substituted aryl as defined herein; it being understood that $R_2$, $R_3$, $R_4$, $R_7$, $R_8$, $R_{8'}$, $R_{11}$, $R_{12}$, $R_{13}$, m, n and p' have the same definitions as those given previously with Formula (V).

In a further preferred embodiment, the invention provides a compound according to Formula (V), wherein $R_{10}$ is chosen from an optionally substituted phenyl; it being understood that $R_2$, $R_3$, $R_4$, $R_7$, $R_8$, $R_{8'}$, $R_{11}$, $R_{12}$, $R_{13}$, m, n and p' have the same definitions as those given previously with Formula (V).

In a further preferred embodiment, the invention provides a compound according to Formula (V), wherein $R_{10}$ is chosen from an optionally substituted heteroaryl ring as defined herein; it being understood that $R_2$, $R_3$, $R_4$, $R_7$, $R_8$, $R_{8'}$, $R_{11}$, $R_{12}$, $R_{13}$, m, n and p' have the same definitions as those given previously with Formula (V).

In another preferred embodiment, the invention provides a compound of Formula (V), wherein $R_{10}$ can be chosen from an optionally substituted pyrimidin-2-yl; an optionally substituted pyrimidin-4-yl; an optionally substituted pyrimidin-5-yl; it being understood that $R_2$, $R_3$, $R_4$, $R_7$, $R_8$, $R_{8'}$, $R_{11}$, $R_{12}$, $R_{13}$, m, n and p' have the same definitions as those given previously with Formula (V).

In another preferred embodiment, the invention provides a compound of Formula (V), wherein $R_{10}$ is an optionally substituted pyrimidin-2-yl; it being understood that $R_2$, $R_3$, $R_4$, $R_7$, $R_8$, $R_{8'}$, $R_{11}$, $R_{12}$, $R_{13}$, m, n and p' have the same definitions as those given previously with Formula (V).

In another preferred embodiment, the invention provides a compound of Formula (V), wherein $R_{10}$ is a pyrimidin-2-yl; it being understood that $R_2$, $R_3$, $R_4$, $R_7$, $R_8$, $R_{8'}$, $R_{11}$, $R_{12}$, $R_{13}$, m, n and p' have the same definitions as those given previously with Formula (V).

Yet, in a further preferred embodiment, the invention provides a compound of Formula (V), wherein $R_{11}$ can be chosen from a hydrogen atom; an optionally substituted aryl as defined herein; an optionally substituted heteroaryl as defined herein; an optionally substituted heterocyclyl group as defined herein; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

In a further preferred embodiment, the invention provides a compound according to Formula (V), wherein $R_{11}$ is an optionally substituted aryl as defined herein; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

In a further preferred embodiment, the invention provides a compound according to Formula (V), wherein $R_{11}$ is an optionally substituted phenyl; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

In a further preferred embodiment, the invention provides a compound according to Formula (V), wherein $R_{11}$ is an optionally substituted heteroaryl as defined herein; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

In yet a further preferred embodiment, the invention provides a compound of Formula (V), wherein $R_{11}$ is an optionally substituted heterocyclyl group as defined herein; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

In a further preferred embodiment, the invention provides a compound of Formula (V), wherein $R_{11}$ can be chosen from an optionally substituted pyridin-2-yl, an optionally substituted pyridin-3-yl, or an optionally substituted pyridin-4-yl; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

In a further preferred embodiment, the invention provides a compound of Formula (V), wherein $R_{11}$ is an optionally substituted pyridin-3-yl; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

In a further preferred embodiment, the invention provides a compound of Formula (V), wherein $R_{11}$ is a pyridin-3-yl; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

Yet, a further preferred embodiment provides a compound of Formula (V), wherein $R_{11}$ can be chosen from a hydrogen atom; a —(O—CH$_2$CH$_2$—)$_p$—NR$_8$; a —(O—CH$_2$CH$_2$—)$_p$—NR$_8$R$_{8'}$; —NR$_8$—(CH$_2$CH$_2$—O)$_p$—R$_{8'}$; a —NR$_8$—(C$_2$-C$_8$)-alkyl-NR$_8$R$_{8'}$; a —NR$_8$—(C$_2$-C$_8$)-alkyl-OR$_{8'}$; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

In, a further preferred embodiment provides a compound of Formula (V), wherein $R_{11}$ can be chosen from a hydrogen atom; a —(O—CH$_2$CH$_2$—)$_p$—NR$_8$; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

Yet, a further preferred embodiment provides a compound of Formula (V), wherein $R_{11}$ can be chosen from a hydrogen atom; a —(O—CH$_2$CH$_2$—)$_p$—NR$_8$R$_{8'}$; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

Yet, a further preferred embodiment provides a compound of Formula (V), wherein $R_{11}$ can be chosen from a hydrogen atom; a —NR$_8$—(CH$_2$CH$_2$—O)$_p$—R$_{8'}$; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

Yet, a further preferred embodiment provides a compound of Formula (V), wherein $R_{11}$ can be chosen from a hydrogen atom; a —NR$_8$—(C$_2$-C$_8$)-alkyl-NR$_8$R$_{8'}$; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

Yet, a further preferred embodiment provides a compound of Formula (V), wherein $R_{11}$ can be chosen from a hydrogen atom; a —NR$_8$—(C$_2$-C$_8$)-alkyl-OR$_{8'}$; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

In another preferred embodiment, a compound according to Formula (V) can be provided wherein $R_{11}$ can be chosen from a hydrogen atom; a halogen atom as defined herein; an optionally substituted alkyl as defined herein, preferably said substituted alkyl being substituted by one or more halogen atom(s) as defined herein; an optionally substituted alkoxy as defined herein; a hydroxyl; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

In another preferred embodiment, a compound according to Formula (V) can be provided wherein $R_{11}$ can be chosen from a hydrogen atom; a halogen atom as defined herein; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

In another preferred embodiment, a compound according to Formula (V) can be provided wherein $R_{11}$ can be chosen from a hydrogen atom; a fluorine; a chlorine; a methyl; a —CF$_3$; a cyano; an azido; a hydroxyl; a methoxy; an ethoxy; an isopropoxy; a tert-butoxy; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

In another preferred embodiment, a compound according to Formula (V) can be provided wherein $R_{11}$ can be chosen from a hydrogen atom; a fluorine; a chlorine; a methyl; a hydroxyl; a methoxy; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

In another preferred embodiment, a compound according to Formula (V) can be provided wherein $R_{11}$ can be chosen from a hydrogen atom; a fluorine; a chlorine; a methyl; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

In another preferred embodiment, a compound according to Formula (V) can be provided wherein $R_{11}$ can be chosen from a hydrogen atom; a fluorine; a chlorine; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

In another preferred embodiment, a compound according to Formula (V) can be provided wherein $R_{11}$ can be chosen from a hydrogen atom; an optionally substituted alkoxy as defined herein; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

In another preferred embodiment, a compound according to Formula (V) can be provided wherein $R_{11}$ can be chosen from a hydrogen atom; a hydroxyl, a methoxy, an ethoxy, an isopropoxy; a tert-butoxy; it being understood that $R_2$, $R_3$, $R_4$, $R_7$, $R_8$, $R_{8'}$, $R_{10}$, $R_{12}$, $R_{13}$, m, n and p have the same definitions as those given previously with Formula (V).

In another preferred embodiment, a compound according to Formula (V) can be provided wherein $R_{11}$ can be chosen from a hydrogen atom; a hydroxyl, a methoxy; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

In another preferred embodiment, a compound according to Formula (V) can be provided wherein $R_{11}$ can be chosen from a hydrogen atom; an optionally substituted fluoroalkyl as defined herein; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

In another preferred embodiment, a compound according to Formula (V) can be provided wherein $R_{11}$ can be chosen from a hydrogen atom; a —$CF_3$; it being understood that $R_2$, $R_3$, $R_4$, $R_7$, $R_8$, $R_{8'}$, $R_{10}$, $R_{12}$, $R_{13}$, m, n and p' have the same definitions as those given previously with Formula (V).

In yet a further preferred embodiment, the invention provides a compound according to Formula (V), wherein n can take any one of the values 0, 1, 2, 3 or 4, preferably 0, 1, 2 or 3, more preferably 0, 1 or 2, still more preferably 0 or 1 and m can take any one of the values 1 or 2, preferably 2; it being understood that $R_2$, $R_3$, $R_4$, $R_7$, $R_8$, $R_{8'}$, $R_{10}$, $R_{11}$, $R_{12}$, $R_{13}$ and p have the same definitions as those given previously with Formula (V).

In yet another preferred embodiment, the invention provides a compound according to Formula (V), wherein n can take any one of the values 0, 1, 2, 3 or 4, preferably 0, 1, 2 or 3, more preferably 0, 1 or 2, still more preferably 0 or 1 and m is 2; it being understood that $R_2$, $R_3$, $R_4$, $R_7$, $R_8$, $R_{8'}$, $R_{10}$, $R_{11}$, $R_{12}$, $R_{13}$ and p have the same definitions as those given previously with Formula (V).

In yet another preferred embodiment, the invention provides a compound according to Formula (V), wherein n can take any one of the values 0, 1, 2, 3 or 4, preferably 0, 1, 2 or 3, more preferably 0, 1 or 2, still more preferably 0 or 1 and m is 1; it being understood that $R_2$, $R_3$, $R_4$, $R_7$, $R_8$, $R_{8'}$, $R_{10}$, $R_{11}$, $R_{12}$, $R_{13}$ and p have the same definitions as those given previously with Formula (V).

In yet another preferred embodiment, the invention provides a compound according to Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is an optionally substituted alkyl as defined herein; it being understood that $R_4$, $R_7$, $R_8$, $R_{8'}$, $R_{10}$, $R_{11}$, $R_{12}$, $R_{13}$ and p have the same definitions as those given previously with Formula (V).

In yet another preferred embodiment, the invention provides a compound according to Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is an optionally substituted alkyl as defined herein; it being understood that $R_4$, $R_7$, $R_8$, $R_{8'}$, $R_{10}$, $R_{11}$, $R_{12}$, $R_{13}$ and p have the same definitions as those given previously with Formula (V).

In yet another preferred embodiment, the invention provides a compound according to Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is an optionally substituted cycloalkyl as defined herein; it being understood that $R_4$, $R_7$, $R_8$, $R_{8'}$, $R_{10}$, $R_{11}$, $R_{12}$, $R_{13}$ and p have the same definitions as those given previously with Formula (V).

In yet another preferred embodiment, the invention provides a compound according to Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is an optionally substituted cycloalkyl as defined herein; it being understood that $R_4$, $R_7$, $R_8$, $R_{8'}$, $R_{10}$, $R_{11}$, $R_{12}$, $R_{13}$ and p have the same definitions as those given previously with Formula (V).

In yet another preferred embodiment, the invention provides a compound according to Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is an optionally substituted heterocyclyl group as defined herein; it being understood that $R_4$, $R_7$, $R_8$, $R_{8'}$, $R_{10}$, $R_{11}$, $R_{12}$, $R_{13}$ and p have the same definitions as those given previously with Formula (V).

In yet another preferred embodiment, the invention provides a compound according to Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is an optionally substituted heterocyclyl group as defined herein; it being understood that $R_4$, $R_7$, $R_8$, $R_{8'}$, $R_{10}$, $R_{11}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ and $R_3$ can be linked together with the nitrogen atom to which they are covalently linked to form a heterocyclyl group as defined herein; it being understood that $R_4$, $R_7$, $R_8$, $R_{8'}$, $R_{10}$, $R_{11}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ and $R_3$ can be linked together with the nitrogen atom to which they are covalently linked to form a heterocyclyl group; it being understood that $R_4$, $R_7$, $R_8$, $R_{8'}$, $R_{10}$, $R_{11}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ and $R_3$ can be linked together with the nitrogen atom to which they are covalently linked to form a pyrrolidin-1-yl; it being understood that $R_4$, $R_7$, $R_8$, $R_{8'}$, $R_{10}$, $R_{11}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ and $R_3$ can be linked together with the nitrogen atom to which they are covalently linked to form a pyrrolidin-1-yl; it being understood that $R_4$, $R_7$, $R_8$, $R_8'$, $R_{10}$, $R_{11}$, $R_{12}$, $R_{13}$ and p have the same definitions as those given previously with Formula (V).

In yet another preferred embodiment, the invention provides a compound according to Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a 1-methylpiperidin-4-yl; it being understood that $R_4$, $R_7$, $R_8$, $R_8'$, $R_{10}$, $R_{11}$, $R_{12}$, $R_{13}$ and p have the same definitions as those given previously with Formula (V).

In yet another preferred embodiment, the invention provides a compound according to Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a 1-methylpiperidin-4-yl; it being understood that $R_4$, $R_7$, $R_8$, $R_8'$, $R_{10}$, $R_{11}$, $R_{12}$, $R_{13}$ and p have the same definitions as those given previously with Formula (V).

In yet another preferred embodiment, the invention provides a compound according to Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; it being understood that $R_4$, $R_7$, $R_8$, $R_8'$, $R_{10}$, $R_{11}$, $R_{12}$, $R_{13}$ and p have the same definitions as those given previously with Formula (V).

In yet another preferred embodiment, the invention provides a compound according to Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; it being understood that $R_4$, $R_7$, $R_8$, $R_8'$, $R_{10}$, $R_{11}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ is an optionally substituted aryl as defined herein; it being understood that $R_4$, $R_7$, $R_8$, $R_8'$, $R_{11}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ is an optionally substituted aryl as defined herein; it being understood that $R_4$, $R_7$, $R_8$, $R_8'$, $R_{11}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ is an optionally substituted phenyl; it being understood that $R_4$, $R_7$, $R_8$, $R_8'$, $R_{11}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ is an optionally substituted phenyl; it being understood that $R_4$, $R_7$, $R_8$, $R_8'$, $R_{11}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ is an optionally substituted heteroaryl as defined herein; it being understood that $R_4$, $R_7$, $R_8$, $R_8'$, $R_{11}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ is an optionally substituted heteroaryl as defined herein; it being understood that $R_4$, $R_7$, $R_8$, $R_8'$, $R_{11}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ can be chosen from an optionally substituted pyrimidin-2-yl, an optionally substituted pyrimidin-4-yl, or an optionally substituted pyrimidin-5-yl; it being understood that $R_4$, $R_7$, $R_8$, $R_8'$, $R_{11}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ can be chosen from an optionally substituted pyrimidin-2-yl, an optionally substituted pyrimidin-4-yl, or an optionally substituted pyrimidin-5-yl; it being understood that $R_4$, $R_7$, $R_8$, $R_8'$, $R_{11}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ is an optionally substituted pyrimidin-2-yl; it being understood that $R_4$, $R_7$, $R_8$, $R_8'$, $R_{11}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ is an optionally substituted pyrimidin-2-yl; it being understood that $R_4$, $R_7$, $R_8$, $R_8'$, $R_{11}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ is a pyrimidin-2-yl; it being understood that $R_4$, $R_7$, $R_8$, $R_{8'}$, $R_{11}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ is a pyrimidin-2-yl; it being understood that $R_4$, $R_7$, $R_8$, $R_{8'}$, $R_{11}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{11}$ is an optionally substituted aryl as defined herein; it being understood that $R_4$, $R_7$, $R_8$, $R_{8'}$, $R_{10}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{11}$ is an optionally substituted aryl as defined herein; it being understood that $R_4$, $R_7$, $R_8$, $R_{8'}$, $R_{10}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{11}$ is an optionally substituted phenyl; it being understood that $R_4$, $R_7$, $R_8$, $R_{8'}$, $R_{10}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{11}$ is an optionally substituted phenyl; it being understood that $R_4$, $R_7$, $R_8$, $R_{8'}$, $R_{10}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{11}$ is an optionally substituted heteroaryl as defined herein; it being understood that $R_4$, $R_7$, $R_8$, $R_{8'}$, $R_{10}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{11}$ is an optionally substituted heteroaryl as defined herein; it being understood that $R_4$, $R_7$, $R_8$, $R_{8'}$, $R_{10}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{11}$ can be chosen from an optionally substituted pyridin-2-yl, an optionally substituted pyridin-3-yl, or an optionally substituted pyridin-4-yl; it being understood that $R_4$, $R_7$, $R_8$, $R_{8'}$, $R_{10}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{11}$ can be chosen from an optionally substituted pyridin-2-yl, an optionally substituted pyridin-3-yl, or an optionally substituted pyridin-4-yl; it being understood that $R_4$, $R_7$, $R_8$, $R_{8'}$, $R_{10}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{11}$ is an optionally substituted pyridin-3-yl; it being understood that $R_4$, $R_7$, $R_8$, $R_{8'}$, $R_{10}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{11}$ is an optionally substituted pyridin-3-yl; it being understood that $R_4$, $R_7$, $R_8$, $R_{8'}$, $R_{10}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{11}$ is a pyridin-3-yl; it being understood that $R_4$, $R_7$, $R_8$, $R_{8'}$, $R_{10}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{11}$ is a pyridin-3-yl; it being understood that $R_4$, $R_7$, $R_8$, $R_{8'}$, $R_{10}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ can be an optionally substituted heteroaryl as defined herein; and $R_{11}$ can be an optionally substituted heteroaryl as defined herein; it being understood that $R_4$, $R_7$, $R_8$, $R_{8'}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ can be an optionally substituted heteroaryl as defined herein; and $R_{11}$ can be an optionally substituted heteroaryl as defined herein; it being understood that $R_4$, $R_7$, $R_8$, $R_{8'}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ can be chosen from an optionally substituted pyrimidin-2-yl, an optionally substituted pyrimidin-4-yl, or an optionally substituted pyrimidin-5-yl; and $R_{11}$ can be chosen from an optionally substituted pyridin-2-yl, an optionally substituted pyridin-3-yl, or an optionally substituted pyridin-4-yl; it being understood that $R_4$, $R_7$, $R_8$, $R_{8'}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ can be chosen from an optionally substituted pyrimidin-2-yl, an optionally substituted pyrimidin-4-yl, or an optionally substituted pyrimidin-5-yl; and $R_{11}$ can be chosen from an optionally substituted pyridin-2-yl, an optionally substituted pyridin-3-yl, or an optionally substituted pyridin-4-yl; it being understood that $R_4$, $R_7$, $R_8$, $R_{8'}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ is an optionally substituted pyrimidin-2-yl, and $R_{11}$ can be chosen from an optionally substituted pyridin-2-yl, an optionally substituted pyridin-3-yl, or an optionally substituted pyridin-4-yl; it being understood that $R_4$, $R_7$, $R_8$, $R_{8'}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is value 2; and $R_2$ is a hydrogen atom and $R_3$ is a tert-butyl; and $R_{10}$ is an optionally substituted pyrimidin-2-yl, and $R_{11}$ can be chosen from an optionally substituted pyridin-2-yl, an optionally substituted pyridin-3-yl, or an optionally substituted pyridin-4-yl; it being understood that $R_4$, $R_7$, $R_8$, $R_{8'}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ can be an optionally substituted pyrimidin-2-yl, an optionally substituted pyrimidin-4-yl, an optionally substituted pyrimidin-5-yl; and $R_{11}$ is an optionally substituted pyridin-2-yl; it being understood that $R_4$, $R_7$, $R_8$, $R_{8'}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ can be chosen from an optionally substituted pyrimidin-2-yl, an optionally substituted pyrimidin-4-yl, or an optionally substituted pyrimidin-5-yl; and $R_{11}$ is an optionally substituted pyridin-2-yl; it being understood that $R_4$, $R_7$, $R_8$, $R_{8'}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ can be chosen from an optionally substituted pyrimidin-2-yl, an optionally substituted pyrimidin-4-yl, or an optionally substituted pyrimidin-5-yl; and $R_{11}$ is an optionally substituted pyridin-3-yl; it being understood that $R_4$, $R_7$, $R_8$, $R_{8'}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ can be chosen from an optionally substituted pyrimidin-2-yl, an optionally substituted pyrimidin-4-yl, or an optionally substituted pyrimidin-5-yl; and $R_{11}$ is an optionally substituted pyridin-3-yl; it being understood that $R_4$, $R_7$, $R_8$, $R_{8'}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ can be chosen from an optionally substituted pyrimidin-2-yl, an optionally substituted pyrimidin-4-yl, or an optionally substituted pyrimidin-5-yl; and $R_{11}$ is an optionally substituted pyridin-4-yl; it being understood that $R_4$, $R_7$, $R_8$, $R_{8'}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ is can be an optionally substituted pyrimidin-2-yl, an optionally substituted pyrimidin-4-yl, or an optionally substituted pyrimidin-5-yl; and $R_{11}$ is an optionally substituted pyridin-4-yl; it being understood that $R_4$, $R_7$, $R_8$, $R_{8'}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ can be chosen from an optionally substituted pyrimidin-2-yl, an optionally substituted pyrimidin-4-yl, or an optionally substituted pyrimidin-5-yl; and $R_{11}$ can be chosen from a pyridin-2-yl, a pyridin-3-yl, or a pyridin-4-yl; it being understood that $R_4$, $R_7$, $R_8$, $R_{8'}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ can be chosen from an optionally substituted pyrimidin- 2-yl, an optionally substituted pyrimidin-4-yl, or an optionally substituted pyrimidin-5-yl; and $R_{11}$ can be chosen from a pyridin-2-yl, a pyridin-3-yl, or a pyridin-4-yl; it being understood that $R_4$, $R_7$, $R_8$, $R_{8'}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m can take the value 1; and $R_2$ is a hydrogen atom and $R_3$ is a tert-butyl; and $R_{10}$ can be chosen from a pyrimidin-2-yl, a pyrimidin-4-yl, or a pyrimidin-5-yl; and $R_{11}$ can be chosen from a pyridin-2-yl, a pyridin-3-yl, or a pyridin-4-yl; it being understood that $R_4$, $R_7$, $R_8$, $R_{8'}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ can be a pyrimidin-2-yl, a pyrimidin-4-yl, a pyrimidin-5-yl; and $R_{11}$ can be a pyridin-2-yl, a pyridin-3-yl, a pyridin-4-yl; it being understood that $R_4$, $R_7$, $R_8$, $R_{8'}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ is an optionally substituted pyrimidin-2-yl and $R_{11}$ is an optionally substituted pyridin-3-yl; it being understood that $R_4$, $R_7$, $R_8$, $R_{8'}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ is an optionally substituted pyrimidin-2-yl and $R_{11}$ is an optionally substituted pyridin-3-yl; it being understood that $R_4$, $R_7$, $R_8$, $R_{8'}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 1; and $R_2$ is a hydrogen atom and $R_3$ is a tert-butyl; and $R_{10}$ is a pyrimidin-2-yl and $R_{11}$ is a pyridin-3-yl; it being understood that $R_4$, $R_7$, $R_8$, $R_{8'}$, $R_{12}$, $R_{13}$ and p have the same definitions as those given previously with Formula (V).

In yet a further preferred embodiment, the invention provides a compound of Formula (V), wherein n can take any one of the values 0, 1, 2, 3 or 4, preferably 0, 1, 2 or 3, more preferably 0, 1 or 2, still more preferably 0 or 1 and m is 2; and $R_2$ is a hydrogen atom and $R_3$ is a tert-butyl; and $R_{10}$ is a pyrimidin-2-yl and $R_{11}$ is a pyridin-3-yl; it being understood that $R_4$, $R_7$, $R_8$, $R_{8'}$, $R_{12}$, $R_{13}$ and p have the same definitions as those given previously with Formula (V).

Any combination of two or more of the embodiments described herein is considered within the scope of the present disclosure.

Representative compounds of general Formula (I) according to the present disclosure include, but are not limited to the compounds of general Formula (II) which are shown in Table 1 below:

TABLE 1

Representative compound of general Formula (II)

| ID | $R_2$ | $R_3$ | | $R_4$ | n | | $R_5$ | m |
|---|---|---|---|---|---|---|---|---|
| 2-2 | H— | t-Bu— | | —H | 0 | | —Cl | 2 |

TABLE 1-continued
Representative compound of general Formula (II)
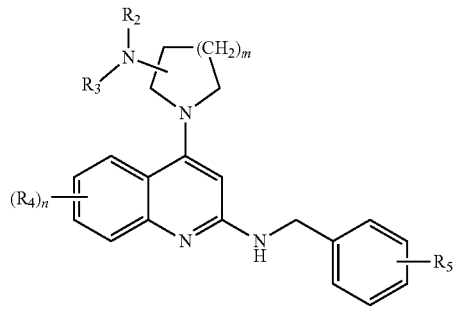
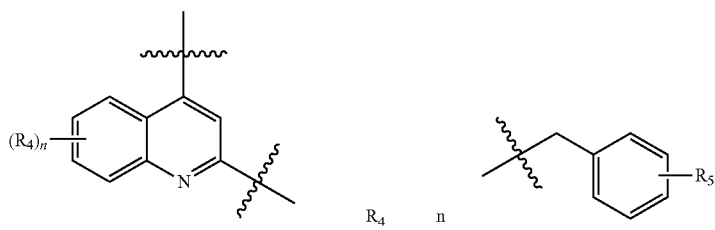
| ID | R₂ | R₃ | R₄ | n | R₅ | m |
|---|---|---|---|---|---|---|
| 5-3 | H— | t-Bu— | —H | 0 | —F | 2 |
| 6-3 | H— | t-Bu— | —O—Me | 1 | —Cl | 2 |
| 7-1 | H— | t-Bu— | —OH | 1 | —Cl | 2 |
| 8-2 | H— | t-Bu— | —O—Me | 1 | —Cl | 2 |

TABLE 1-continued
Representative compound of general Formula (II)
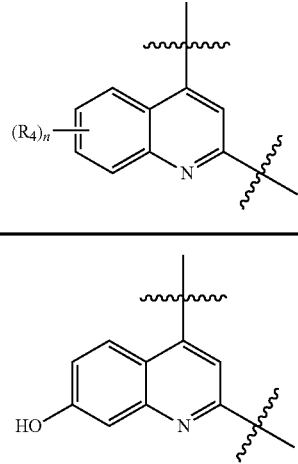
(II)
| ID | R₂ | R₃ | (quinoline) | R₄ | n | (benzyl) | R₅ | m |
|---|---|---|---|---|---|---|---|---|
| 9-1 | H— | t-Bu— | 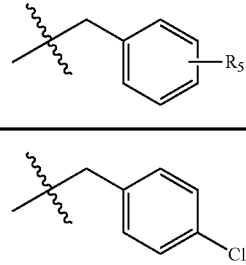 | —OH | 1 | 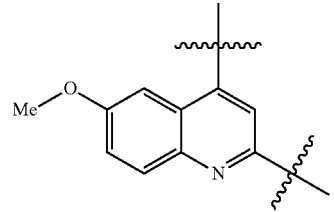 [SMILES: *c1cc(*)c2cc(OC)ccc2n1] | —Cl | 2 |
| 10-2 | H— | t-Bu— | 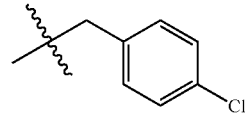 [SMILES: *Cc1ccc(Cl)cc1] | —O—Me | 1 | 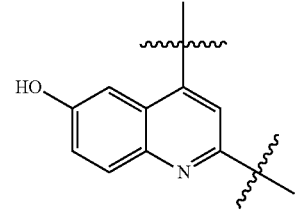 | —Cl | 2 |
| 11-1 | H— | t-Bu— | 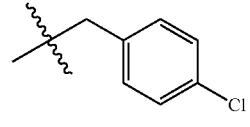 [SMILES: *Cc1ccc(Cl)cc1] | —OH | 1 | 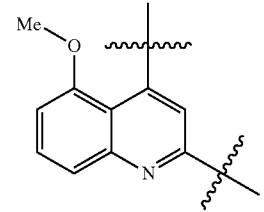 [SMILES: *c1cc(*)c2c(OC)cccc2n1] | —Cl | 2 |
| 12-4 | H— | t-Bu— | 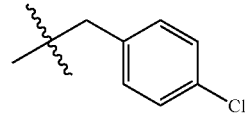 [SMILES: *Cc1ccc(Cl)cc1] | —O—Me | 1 | | —Cl | 2 |

TABLE 1-continued
Representative compound of general Formula (II)
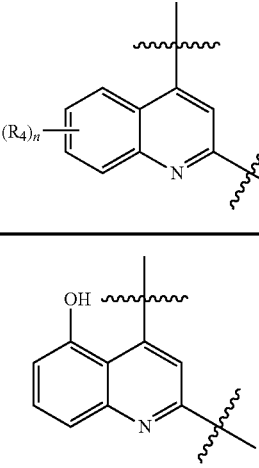
(II)
| ID | R₂ | R₃ | | R₄ | n | | R₅ | m |
|---|---|---|---|---|---|---|---|---|
| 13-1 | H— | t-Bu— | 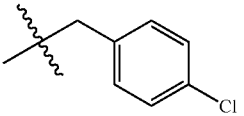 [SMILES: *Cc1ccc(Cl)cc1] | —OH | 1 | 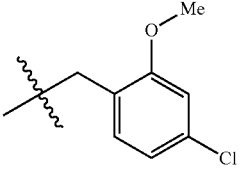 [SMILES: *Cc1ccc(Cl)cc1OC] | —Cl | 2 |
| 14-5 | H— | t-Bu— | 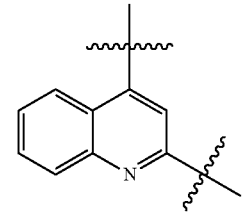 [SMILES: *c1cc(*)c2ccccc2n1] | —H | 0 |  | —Cl | 2 |
| 15-1 | H— | t-Bu— | 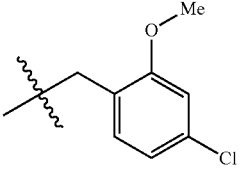 [SMILES: *Cc1ccc(Cl)cc1OC] | —H | 0 | 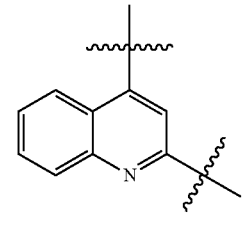 [SMILES: *c1cc(*)c2ccccc2n1] | —Cl | 2 |
| 16-6 | H— | t-Bu— |  | —H | 0 | 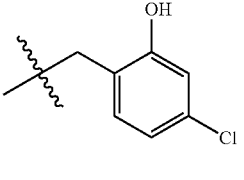 [SMILES: *Cc1ccc(Cl)cc1O] | —Cl | 2 |

TABLE 1-continued
Representative compound of general Formula (II)
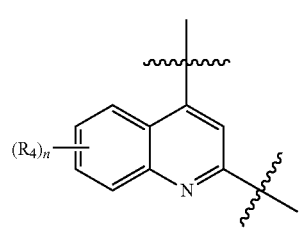
| ID | R$_2$ | R$_3$ | | R$_4$ | n | | R$_5$ | m |
|---|---|---|---|---|---|---|---|---|
| 17-1 | H— | t-Bu— | 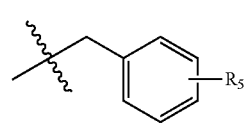 | —H | 0 | 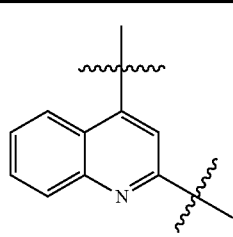 | —Cl | 2 |
| 19-1 | 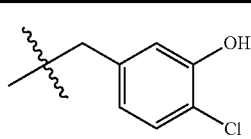 | | 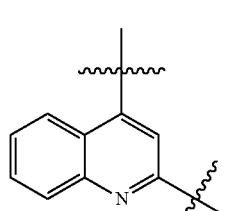 | —H | 0 | 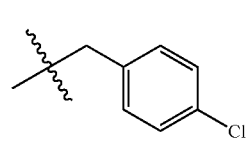 [SMILES: *Cc1ccc(Cl)cc1] | —Cl | 2 |
| 20-1 | H— | Me | 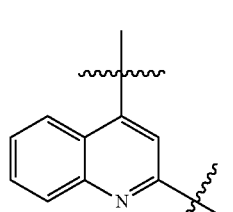 | —H | 0 | 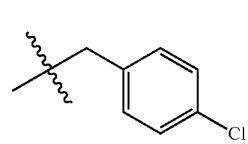 [SMILES: *Cc1ccc(Cl)cc1] | —Cl | 2 |

TABLE 1-continued
Representative compound of general Formula (II)
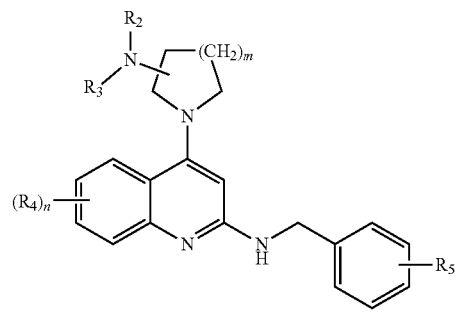
| ID | R$_2$ | R$_3$ | R$_4$ | n | R$_5$ | m |
|---|---|---|---|---|---|---|
| 21-2 | H— | t-Bu— | —H | 0 | —O—Me | 2 |
| 22-1 | H— | t-Bu— | —H | 0 | —OH | 2 |
| 23-2 | H— | t-Bu— | —H | 0 | —H | 2 |
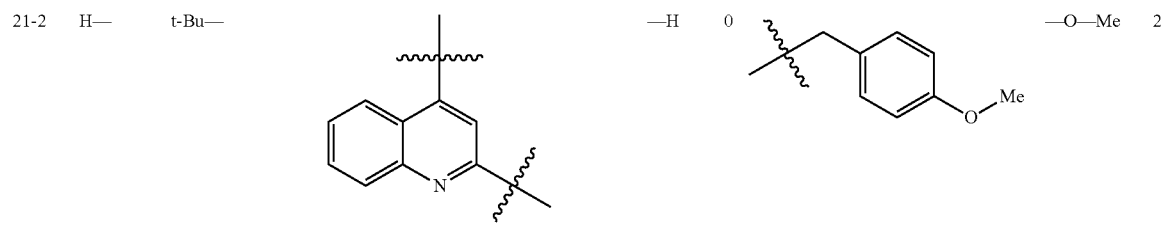
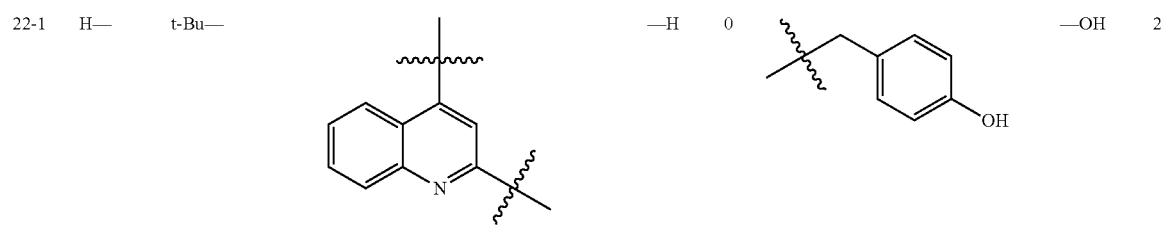
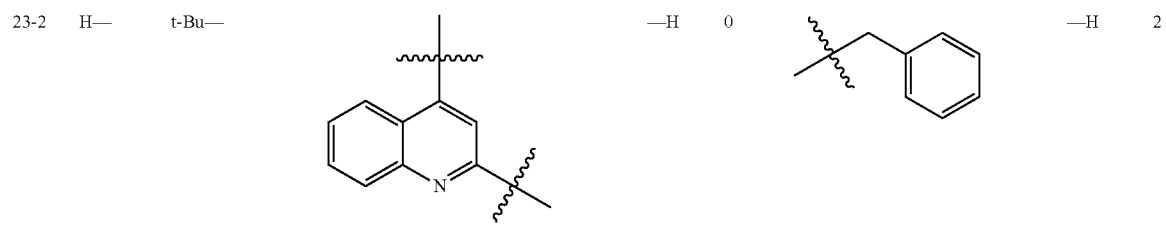

Representative compounds of general Formula (I) according to the present disclosure include, but can be not limited to the compounds of general Formula (III) which can be shown in Table 2 below.
TABLE 2
Representative compound of general Formula (III)
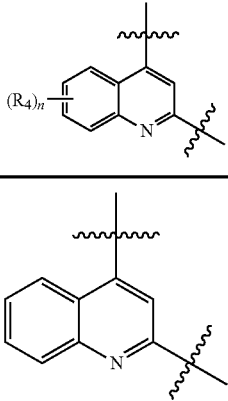
III
| ID | R₂ | R₃ | | R₄ | n | | R₅ | m |
|----|----|----|---|----|---|---|----|----|
| 2-2 | H— | t-Bu— | 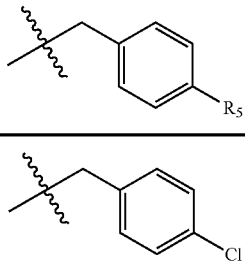 | —H | 0 | 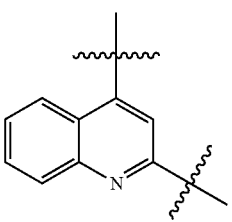 [SMILES: *c1cc(*)c2ccccc2n1] | —Cl | 2 |
| 5-3 | H— | t-Bu— | 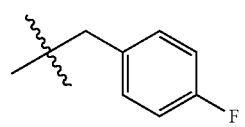 [SMILES: *Cc1ccc(F)cc1] | —H | 0 | 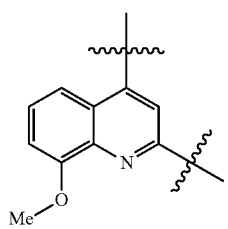 [SMILES: *c1cc(*)c2cccc(OC)c2n1] | —F | 2 |
| 6-3 | H— | t-Bu— | 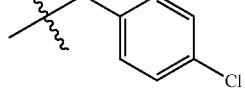 | —O—Me | 1 | 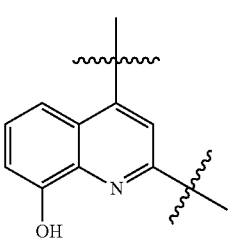 [SMILES: *c1cc(*)c2cccc(O)c2n1] | —Cl | 2 |
| 7-1 | H— | t-Bu— | 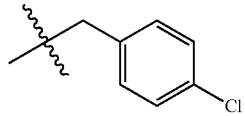 [SMILES: *Cc1ccc(Cl)cc1] | —OH | 1 | | —Cl | 2 |

TABLE 2-continued

Representative compound of general Formula (III)

| ID | R₂ | R₃ | R₄ (quinoline) | R₄ | n | R₅ (benzyl) | R₅ | m |
|---|---|---|---|---|---|---|---|---|
| 8-2 | H— | t-Bu— | 7-MeO-quinoline | —O—Me | 1 | 4-Cl-benzyl | —Cl | 2 |
| 9-1 | H— | t-Bu— | 7-HO-quinoline | —OH | 1 | 4-Cl-benzyl | —Cl | 2 |
| 10-2 | H— | t-Bu— | 6-MeO-quinoline | —O—Me | 1 | 4-Cl-benzyl | —Cl | 2 |
| 11-1 | H— | t-Bu— | 6-HO-quinoline | —OH | 1 | 4-Cl-benzyl | —Cl | 2 |
| 12-4 | H— | t-Bu— | 5-MeO-quinoline | —O—Me | 1 | 4-Cl-benzyl | —Cl | 2 |

TABLE 2-continued
Representative compound of general Formula (III)
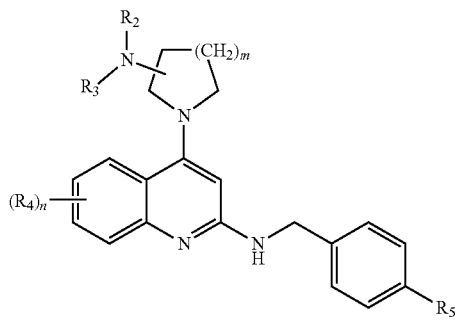
| ID | $R_2$ | $R_3$ | | $R_4$ | n | | $R_5$ | m |
|---|---|---|---|---|---|---|---|---|
| 13-1 | H— | t-Bu— | 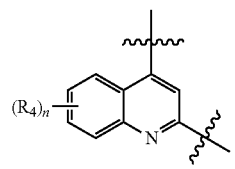 | —OH | 1 | 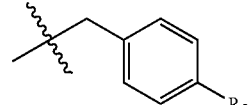 | —Cl | 2 |
| 19-1 | 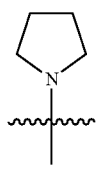 | | 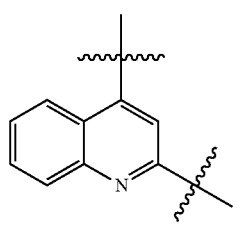 [SMILES: *c1cc(*)c2ccccc2n1] | —H | 0 | 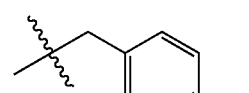 | —Cl | 2 |
| 20-1 | H— | Me | 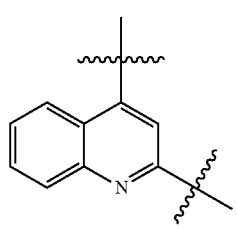 [SMILES: *c1cc(*)c2ccccc2n1] | —H | 0 | 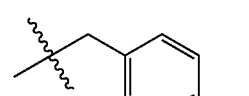 | —Cl | 2 |

TABLE 2-continued
Representative compound of general Formula (III)
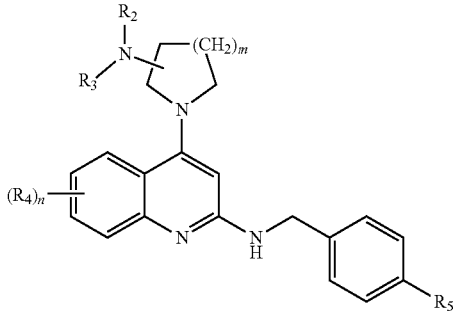
| ID | R$_2$ | R$_3$ | R$_4$ structure | R$_4$ | n | R$_5$ structure | R$_5$ | m |
|---|---|---|---|---|---|---|---|---|
| 21-2 | H— | t-Bu— |  | —H | 0 | 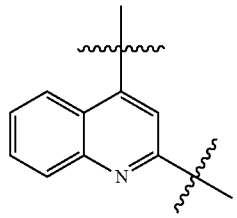 [SMILES: *c1cc(*)c2ccccc2n1] | —O—Me | 2 |
| 22-1 | H— | t-Bu— | 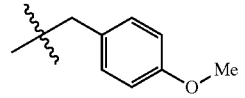 [SMILES: *Cc1ccc(OC)cc1] | —H | 0 | 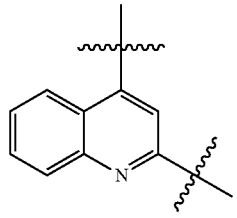 [SMILES: *c1cc(*)c2ccccc2n1] | —OH | 2 |
| 23-1 | H— | t-Bu— | 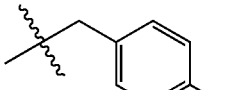 | —H | 0 | 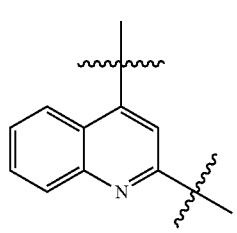 [SMILES: *c1cc(*)c2ccccc2n1] | —H | 2 |

Representative compounds of general Formula (I) according to the present disclosure include, but are not limited to the compounds of general Formula (IV) which are shown in Table 3 below.

Representative compounds of general Formula (I) according to the present disclosure include, but are not limited to the compounds of general Formula (V) which are shown in Table 4 below.

TABLE 3

Representative compound of general Formula (IV)

(IV)

| ID | L₁ | R₁ | R₂ | R₃ | (structure) |
|---|---|---|---|---|---|
| 3-4 | a bond | (phenyl with Me) | —H | t-Bu— | (quinoline) |
| 4-2 | a bond | (phenyl with Me) | —H | t-Bu— | (quinoline) |

| ID | R₄ | n | R₂' | R₁₀ | R₁₁ | m |
|---|---|---|---|---|---|---|
| 3-4 | —H | 0 | —H | (pyrimidine with R₁₁) | —H | 2 |
| 4-2 | —H | 0 | —H | (pyrimidine with R₁₁) | (pyridine with R₁₀) | 2 |

TABLE 4

Representative compound of general Formula (V)

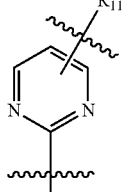

| ID | $R_2$ | $R_3$ | | $R_4$ | n | $R_{10}$ | $R_{11}$ | m |
|---|---|---|---|---|---|---|---|---|
| 3-4 | H— | t-Bu— | | —H | 0 | | —H | 2 |
| 4-2 | H— | t-Bu— | | —H | 0 | | | 2 |

Methods of Treatment

Advantageously, the compounds exhibit a strong anti-fibrotic effect and decrease the extracellular matrix deposition in vivo. This strong anti-fibrotic effect and decrease in extracellular matrix deposition was easily demonstrated by in vitro assays and in vivo in rat model. The compounds generally have an efficacy value in vivo by oral dosage of less than about 30 mg/kg, and even less than about 15 mg/kg. Moreover, the compounds show a high bioavailability in mice and rat animal models after oral administration (92% and 67%, respectively).

Due to their surprisingly strong anti-fibrotic effect and decrease in the extracellular matrix (collagens) deposition effects observed in vivo, the compounds described herein can be advantageously administered at lower doses compared to other less potent anti-fibrotic drugs of the prior art (e.g. Sorafenib in liver fibrosis) while still achieving equivalent or even superior desired biological effects. In addition, such a dose reduction can advantageously lead to less or even no medicinal adverse effects. Moreover, the highly anti-fibrotic effects of the compounds described herein can translate into a decrease of undesired side effects on its own regardless of the dose applied.

The compounds are therefore effective against organ fibrosis-related diseases which can avoid or delay an organ failure in a subject. The compounds can also improve the regression of an organ fibrosis, and increase the survivability of a patient suffering of an organ fibrosis-related disease.

In each of the various treatment methods described in detail below, where the term "compound" is used, it is intended that the compound is a compound of Formulas (I), (II), (III), (IV), or (V), or a pharmaceutically acceptable salt, hydrate, solvate, or prodrug thereof, or an isotopic variant, tautomer, or stereoisomer thereof.

In one embodiment, the compound can be used to treat or prevent a disease or condition associated with fibrosis in a subject, particularly in a mammal, preferably a human.

The compounds can be used to treat or prevent organ fibrosis-related diseases, chronic and non-chronic disorders and medical conditions. Representative fibrotic diseases include, but are not limited to, fibrotic skin, lung, liver, kidney, heart, muscular, prostate, peritoneum membrane, nervous system, and eye disorders.

In some embodiments, the compounds can be used to treat a disease or condition, whether or not associated with fibrosis, selected from the group consisting of scleroderma, lung diseases and conditions, such as pulmonary fibrosis including idiopathic pulmonary fibrosis (IPF), nonidiopathic pulmonary fibrosis interstitial pneumonias, interstitial lung disease (ILD), idiopathic interstitial lung disease, pulmonary hypertension, chronic obstructive pulmonary disease (COPD) or sarcoidosis; heart diseases and conditions, such as heart failure due to ischaemic heart disease, valvular heart disease and hypertensive heart disease, diabetic cardiomyopathy and hypertension; liver diseases and conditions, such as cirrhosis of the liver, hemochromatosis, liver cirrhosis, hepatitis B virus infection, hepatitis C virus infection, hepatitis delta virus infection, Wilson's disease, alpha-1-antitrypsin deficiency, primary biliary cirrhosis, primary sclerosing chlolangitis, biliary obstruction, autoimmune hepatitis, drug induced hepatitis, fibrosis of the liver, Non-alcoholic fatty liver disease (NAFLD) and Non-alcoholic steatohepatitis (NASH), focal fatty liver, alcoholism, diabetes, fatty liver disease, cirrhosis and non cirrhosis portal hypertension, Budd-Chiari syndrome, portal vein thrombosis, veno-occlusive disease of the liver, congenital hepatitis fibrosis; intestinal disease and conditions including bowel fibrosis, colon fibrosis, small intestine fibrosis, inflammatory bowel disease, ulcerative colitis, Crohn's disease, infection with *Schistosoma mansoni*; kidney diseases and conditions, such as progressive kidney disease glomerulonephritis, glomerular disease, kidney fibrosis and diabetic nephropathy; eye diseases and conditions such as diabetic retinopathy, macular fibrosis, premacular fibrosis, retinal fibrosis, retinopathy, Diabetic Macular Edema, Proliferative Diabetic Retinopathy, fibrosis of the extraocular muscles, fibrovascular scarring, retina gliosis, Subretinal fibrosis, Epiretinal fibrosis; skin fibrotic diseases or subcutaneous scarring, such as keloids, adhesions, hypertrophic scarring or cosmetic scarring; nerve system related fibrosis; mediastinum related fibrosis; retroperitoneum related fibrosis; joint and tendon (arthrofibrosis); or as an adjuvant or anti-fibrotic in pancreatic diseases such to increase chemotherapeutic drug penetration by reducing the severity and/or progression the density of the connective tissue stroma.

In another aspect, the compounds can be used to prevent the onset and/or recurrence of fibrotic diseases.

The present disclosure is also directed to methods of treating fibrotic diseases of the skin, lung, liver, kidney, heart, muscular and eyes, comprising the step of administering a therapeutic amount of a compound described herein to a subject, preferably a human subject, in need of treatment thereof.

In some further embodiments, the compounds reduce the severity, progression of, or likelihood that a patient will develop clinical complications associated with the progression of a fibrosis-related disease by reducing the severity and/or progression of the fibrosis of one or more fibrotic patient organ(s), and or reducing the severity of the disease.

In another aspect, the compounds, or a pharmaceutical composition comprising a therapeutically effective amount of a compound is used to treat and/or decrease the severity and/or progression of fibrosis-related diseases.

In yet a further aspect, the compounds are used to treat, decrease the severity and/or progression of, or prevent a fibrosis-related disease.

In yet a further aspect, the compounds are used to treat, prevent, or decrease the severity and/or progression of a fibrosis-related disease. Representative diseases associated with organ fibrosis include, but are not limited to, organ fibrosis selected from the group consisting of pulmonary fibrosis, heart fibrosis, liver fibrosis, kidney fibrosis, eye fibrosis, intestinal fibrosis and scleroderma.

In a preferred embodiment, the fibrosis-related disease is the liver fibrosis, and the compounds are used to treat, decrease the severity and/or progression of, and/or prevent liver fibrosis. In some aspects of this embodiment, the liver fibrosis is associated with cirrhosis of the liver, hemochromatosis, hepatitis B virus infection, hepatitis C virus infection, hepatitis delta virus infection, Wilson's disease, alpha-1-antitrypsin deficiency, primary biliary cirrhosis, chlolangitis, primary sclerosing chlolangitis, autoimmune hepatitis, fibrosis of the liver, portal hypertension, focal fatty liver, liver cirrhosis, alcohol abuse, Non-alcoholic fatty liver disease (NAFLD) or Non-alcoholic steatohepatitis (NASH).

In another preferred embodiment, the fibrosis is lung fibrosis. In some aspects of this embodiment, the lung fibrosis is associated with idiopathic pulmonary fibrosis (IPF), nonidiopathic pulmonary fibrosis interstitial pneumonias, interstitial lung disease (ILD), idiopathic interstitial lung disease, pulmonary hypertension, chronic obstructive pulmonary disease (COPD) or sarcoidosis.

In some embodiments, the compounds are used to treat, decrease the severity and/or progression of, and/or prevent kidney fibrosis. In some aspects of this embodiment, the kidney fibrosis is associated with progressive kidney disease glomerulonephritis, glomerular disease, kidney fibrosis or diabetic nephropathy.

In some embodiments, the compounds are used to treat, decrease the severity and/or progression of, and/or prevent heart fibrosis. In some aspects of this embodiment, the heart fibrosis is associated with heart failure due to ischaemic heart disease, valvular heart disease and hypertensive heart disease, diabetic cardiomyopathy or hypertension.

In some embodiments, the compounds are used to treat, decrease the severity and/or progression of, and/or prevent skin fibrosis. In some aspects of this embodiment, the skin fibrosis is associated with keloids, adhesions, hypertrophic scarring or cosmetic scarring.

In some embodiments, the compounds are used to treat, decrease the severity and/or progression of, and/or prevent muscular fibrosis.

In some embodiments, the present disclosure provides compounds for use as a medicament to treat, decrease the severity and/or progression of, and/or prevent fibrosis in the eyes. In one aspect of this embodiment, the fibrosis of the eyes is associated with diabetic retinopathy.

In some embodiments, the compounds are used to treat, decrease the severity and/or progression of, and/or prevent intestinal fibrosis. In some aspects of this embodiment, the intestinal fibrosis is associated with bowel fibrosis, colon fibrosis, small intestine fibrosis, inflammatory bowel disease, ulcerative colitis, Crohn's disease, or infection with *Schistosoma mansoni*.

In some embodiments, the present disclosure provides compounds for use as a medicament to treat, decrease the severity and/or progression of, and/or prevent muscular fibrosis.

In some embodiments, the present disclosure provides compounds for use as a medicament to treat, decrease the severity and/or progression of, and/or prevent prostate fibrosis.

In some embodiments, the present disclosure provides compounds for use as a medicament to treat, decrease the severity and/or progression of, and/or prevent peritoneum membrane fibrosis.

In several embodiments, the present disclosure provides compounds which can be used to treat liver fibrosis, including reducing the severity and/or progression clinical liver fibrosis, reducing the severity and/or progression, or the likelihood that liver fibrosis will occur, and reducing the severity and/or progression of a parameter associated with liver fibrosis. Liver fibrosis is a precursor to the complications associated with the liver cirrhosis, such as portal hypertension, progressive liver insufficiency or other liver failures. A reduction in liver fibrosis therefore reduces the incidence of such clinical complications. Accordingly, the present disclosure provides compounds for use in reducing the severity and/or progression, or the likelihood that a patient will develop clinical complications associated with progression of the liver fibrosis and cirrhosis of the liver.

In another aspect, the compounds are used to treat, prevent, and/or reduce the severity and/or progression of a fibrosis-related disease, wherein the fibrosis level is reduced in severity as measured by standard scoring.

Whether treatment with a therapeutically effective amount of a compound or a pharmaceutical composition as described herein is effective in reducing the severity and/or progression the liver fibrosis, the level of the fibrosis is determined by any of a number of well-established techniques for measuring liver fibrosis and liver function.

In some embodiments, the degree of the fibrosis is determined by a biopsy.

In some other embodiments, the degree of the fibrosis is determined by noninvasive methods using biological tissue markers.

In some embodiments, the degree of the liver fibrosis is determined by pre-treatment and post-treatment staging of a liver biopsy or the stage of the liver fibrosis is estimated using noninvasive methods, as measured by standard scoring system.

In some other embodiments, the degree of the fibrosis is determined by noninvasive methods, as a standard scoring system.

In some other embodiments, the degree of the fibrosis is determined by noninvasive methods using biological markers.

In some other embodiments, the degree of the fibrosis is determined by noninvasive methods using biological serum markers.

In some other embodiments, the degree of the fibrosis is determined by noninvasive methods using biological plasma markers.

In some other embodiments, the degree of the fibrosis is determined by noninvasive methods using biochemical serum markers, wherein the markers can be direct marker (class 1 fibrosis markers) and/or an indirect marker (class 2 fibrosis marker) of the fibrosis.

In some other embodiments, the degree of the fibrosis is determined by noninvasive methods using biological markers (noninvasive biomarkers), wherein the markers is selected, but not limited to, Hyaluronan, Laminin, hydroxyproline, Chitinase-3-like protein 1 (YKL-40), Procollagen type I carboxy-terminal peptide (PI1CP), Procollagen type III amino-terminal peptide (PIIINP), type IV collagen, Metalloproteinase 1 (MMP-1), Metalloproteinase 2 (MMP-2), Metalloproteinase 3 (MMP-3), Metalloproteinase 7 (MMP-7), Metalloproteinase 8 (MMP-8), Metalloproteinase 9 (MMP-9), Tissue inhibitors of the metalloproteinases 1 (TIMP-1), Tissue inhibitors of the metalloproteinases 2 (TIMP-2), Tissue inhibitors of the metalloproteinases 4 (TIMP-4), Transforming growth factor-β1 (TGF-β1), Transforming growth factor-α (TGF-α), α-smooth muscle actin (α-SMA), 3-Platelet-derived growth factor (PDGF), MP3 score, Microfibril-associated glycoprotein 4 (MFAP-4), aspartate aminotransferase (AST) to alanine aminotransferase (ALT), platelet, albumin, α-2 macroglobulin, prothrombin time, γ-glutamyl transferase (γ-GT), apolipoprotein A1, prothrombin time plus γ-glutamyl transferase (γ-GT) and apolipoprotein A1 (PGA), PGA plus α-2 macroglobulin (PGAA), glucose, Aspartate aminotransferase-to-platelet ratio index (APRI), bilirubin, urea, serum haptoglobin, α2-macroglobulin, apolipoprotein-A, immunoglobulin G, hyaluronic acid, cholesterol (High-density lipoprotein cholesterol: HDL, Low density lipoprotein cholesterol: LDL), triglycerides, glycosylated hemoglobin (hba1c), Kreps von der Lungen-6 antigen (KL-6), Surfactant Protein A and D (SP-A, SP-D respectively), Lysyl oxidase-like 2 (LOXL-2), Periostin, CC Chemokine ligand 18 (CCL18), N-terminal pro-brain natriuretic peptide (NT-proBNP), Brain natriuretic peptide (BNP), Insulin-like Growth Factor 2 (IGFBP-2), Insulin-like growth factor-binding protein 1 (IGFBP-1), Intracellular adhesion molecule 1 and 2 (ICAM-1, ICAM-2), Vascular endothelial growth factor (VEGF), heat shock protein 70 (HSP 70), circulating level of CD45+Col-1$^+$ fibrocytes, circulating level of Sema7A$^+$ activated T cells, transforming growth factor-β1, Growth differentiation factor-15, connective tissue growth factor, osteopontin, osteoglycin, Syndecan-1, Syndecan-4, Galectin-3, cardiotrophin-1, interleukin 1 receptor-like 1 (IL1RL-1 also known as soluble ST-2), midregional pro-atrial natriuretic peptide, myostatin, creatinine, estimated glomerular filtration rate (eGFR), blood urea and proteinuria, cystatin C, Pentosidine, 8-hydroxy-2'-deoxyguanosine (8-OHdG), Uric acid, connective tissue growth factor (CTGF), Transforming growth factor β1 (TGF-β1), albuminuria, transferrin, Liver-type fatty acid binding protein (L-FABP), adipocyte-fatty acid binding protein (A-FABP), Neutrophil gelatinase-associated lipocalin (NGAL), Pigment epithelium-derived factor (PEDF), Kidney Injury Molecule-1 (KIM-1), Angiotensin-converting enzyme 2 (ACE2), Angiotensinogen, N-acetyl-beta-glucosamynidase (NAG), α1-microglobulin, fibroblast growth factor-21 (FGF21), fibroblast growth factor-23 (FGF23), pigment epithelium-derived factor (PEGF), Tumor necrosis factor (TNF-α), Tumor necrosis receptor 1 (TNFR1), Tumor necrosis receptor 2 (TNFR2), Tumor necrosis factor receptor superfamily member 1A (TNFRSA1F), monocyte chemoattractant protein-1 (MCP-1), chemokine (C-C motif) ligand 2 (CCL2), Interleukin-18 (IL-18), Interleukin-1 (IL-1), Interleukin-6 (IL-6), Interleukin-8 (IL-8), or using a scoring system (e.g. Forns index, FIB-4 score, Lok index, Fibrosis Probability Index, Goteborg University Cirrhosis Index (GUCI), Virahep-C model, SHASTA index, BAAT, NAFLD fibrosis score, BARD score, SHASTA index, Hepascore, European liver fibrosis panel (ELF) or using registred scoring index (e.g. Fibrotest®, Fibroindex®, Fibrosure®, Hepascore®, Fibrospect®, Fibrospect® II, FibroQ®, Enhanced Liver Fibrosis score (ELF®), Fibrometers®, ACTltest®), or using in the fibrosis assessment the age of the patient, patient gender, Body mass index (BMI).

In some other embodiments, the degree of the fibrosis is determined by noninvasive methods using an ultrasound imaging, ultrasonography technic or scoring techniques (e.g. echography, Transient Elastography (Fibroscan®), magnetic resonance elastography (MR-elastography), Acoustic radiation force impulses (ARFI), Fibro-CT).

In some other embodiments, the degree of the fibrosis is determined by noninvasive methods using an ultrasonography technique, computed tomography, magnetic resonance imaging (MRI).

In some embodiments, the liver fibrosis can be associated with emerging cirrhosis.

In some embodiments, the cirrhosis can be associated with alcohol damage.

In some embodiments, the liver fibrosis comprises non-cirrhotic hepatic fibrosis.

In some embodiments, the liver fibrosis can be associated with a hepatitis infection including but not limited to hepatitis B, hepatitis C and hepatitis delta.

In some embodiments, the liver fibrosis can be associated with one or more of emerging diseases such as for example cirrhosis, primary biliary cholangitis, primary sclerosing cholangitis, biliary atresia, cholestatic liver disease, chronic liver disease, alcoholic liver disease, hypercholesteremia and hyperlipidemia.

In some embodiments, the liver fibrosis can be associated with primary biliary cirrhosis (PBC), biliary atresia or primary sclerosing cholangitis.

In some embodiments, the liver fibrosis can be associated with primary biliary cholangitis, primary sclerosing cholangitis, biliary atresia or biliary obstruction.

In some further embodiments, the liver fibrosis can be associated with autoimmune hepatitis.

In some further embodiments, the liver fibrosis can be associated with hemochromatosis.

In some further embodiments, the liver fibrosis can be associated with alpha-1 antitrypsin deficiency, Wilson disease, Budd-Chiari syndrome.

In some further embodiments, the liver fibrosis can be associated with portal vein thrombosis, veno-occlusive disease of the liver, congenital hepatitis fibrosis.

In some further embodiments, the liver fibrosis can be associated with cirrhosis and non cirrhosis portal hypertension.

In some embodiments, the liver fibrosis can be associated with metabolic syndrome.

In some embodiments, the liver fibrosis can be associated with type 2 diabetes mellitus.

In some embodiments, the liver fibrosis can be associated with non-alcoholic fatty liver disease (NAFLD).

In some embodiments, the liver fibrosis is associated with Non-alcoholic steatohepatitis (NASH).

In some embodiments, the liver fibrosis is associated with alcoholic liver disease.

In some embodiments, the patient being treated is at risk of developing liver fibrosis or cirrhosis.

In yet another embodiment, the invention relates to the use of a compound of Formulas (I), (II), (III), (IV) and (V) or pharmaceutically acceptable salt thereof to treat liver diseases associated with fibrosis, including, but not limited to, cirrhosis of the liver, hemochromatosis, hepatitis B virus infection, hepatitis C virus infection, hepatitis delta virus infection, autoimmune hepatitis, drugs induced hepatitis, Wilson's disease, Budd-Chiari syndrome, alpha-1-antitrypsin deficiency, primary biliary cirrhosis, primary sclerosing chlolangitis, biliary atresia, biliary obstruction, cholestatic liver disease, chronic liver disease, alcoholic liver disease, hypercholesteremia, hyperlipidemia, fibrosis of the liver, Non-alcoholic fatty liver disease (NAFLD) and Non-alcoholic steatohepatitis (NASH), focal fatty liver, portal vein thrombosis, veno-occlusive disease of the liver, cirrhosis and non cirrhosis portal hypertension, heart failure, congenital hepatitis fibrosis, diabetes.

In another embodiment, the invention relates to the use of a compound of Formulas (I), (II), (III), (IV) and (V) or pharmaceutically acceptable salt thereof to treat liver diseases associated with fibrosis, including hepatitis B virus infection, hepatitis C virus infection, hepatitis delta virus infection, autoimmune hepatitis and drugs induced hepatitis.

In another embodiment, the invention relates to the use of a compound of Formulas (I), (II), (III), (IV) and (V) or pharmaceutically acceptable salt thereof to treat liver diseases associated with fibrosis, including primary biliary cirrhosis, primary sclerosing chlolangitis, biliary atresia, biliary obstruction.

In another embodiment, the invention relates to the use of a compound of Formulas (I), (II), (III), (IV) and (V) or pharmaceutically acceptable salt thereof to treat liver diseases associated with fibrosis, including Non-alcoholic fatty liver disease (NAFLD) and Non-alcoholic steatohepatitis (NASH), focal fatty liver, cholestatic liver disease.

In another embodiment, the invention relates to the use of a compound of Formulas (I), (II), (III), (IV) and (V) or pharmaceutically acceptable salt thereof to treat liver diseases associated with fibrosis, including Non-alcoholic fatty liver disease (NAFLD) and Non-alcoholic steatohepatitis (NASH).

In another embodiment, the invention relates to the use of a compound of Formulas (I), (II), (III), (IV) and (V) or pharmaceutically acceptable salt thereof to treat liver diseases associated with fibrosis, including portal vein thrombosis, veno-occlusive disease of the liver, cirrhosis and non cirrhosis portal hypertension, heart failure.

In another embodiment, the invention relates to the use of a compound of Formulas (I), (II), (III), (IV) and (V) or pharmaceutically acceptable salt thereof to treat liver diseases associated with fibrosis, including Wilson's disease, Budd-Chiari syndrome, alpha-1-antitrypsin deficiency.

In another embodiment, the invention relates to the use of a compound of Formulas (I), (II), (III), (IV) and (V) or pharmaceutically acceptable salt thereof to treat liver diseases associated with fibrosis, including heart failure, congenital hepatitis fibrosis, diabetes.

In another embodiment, the invention relates to the use of a compound of Formulas (I), (II), (III), (IV) and (V) or pharmaceutically acceptable salt thereof to treat liver diseases associated with fibrosis, including cirrhosis of the liver, hemochromatosis, diabetes.

In some other embodiments, the degree of the retinopathy is assessed by Multifocal electroretinography, spectral domain optical coherence tomography.

In yet another embodiment, the invention relates to the use of a compound of Formulas (I), (II), (III), (IV) and (V) or pharmaceutically acceptable salt thereof to treat kidney diseases associated with fibrosis, including, but not limited to, glomerulonephritis, glomerular disease, and diabetic nephropathy.

In another embodiment, the invention relates to the use of a compound of Formulas (I), (II), (III), (IV) or (V), or a pharmaceutically acceptable salt thereof, to treat heart diseases and conditions associated with fibrosis, including, but not limited to, heart failure due to ischaemic heart disease, valvular heart disease and hypertensive heart disease, diabetic cardiomyopathy and hypertension.

In some embodiments, the invention relates to the use of a compound of Formulas (I), (II), (III), (IV) and (V) or pharmaceutically acceptable salt thereof to treat lung diseases and conditions associated with fibrosis, including, but not limited to, pulmonary fibrosis including idiopathic pulmonary fibrosis (IPF), nonidiopathic pulmonary fibrosis interstitial pneumonias, interstitial lung disease (ILD), idiopathic interstitial lung disease and pulmonary hypertension.

In another embodiment, the invention relates to the use of a compound of Formulas (I), (II), (III), (IV) and (V) or pharmaceutically acceptable salt thereof to treat eye diseases and conditions associated with fibrosis, including, but not limited to, diabetic retinopathy, macular fibrosis, premacular fibrosis, retinal fibrosis, retinopathy, Diabetic Macular Edema, Proliferative Diabetic Retinopathy, fibrosis of the extraocular muscles, fibrovascular scarring, retina gliosis, Subretinal fibrosis, Epiretinal fibrosis.

The invention also relates to a compound of Formulas (I), (II), (III), (IV) and (V) or pharmaceutically acceptable salt thereof for its use in treating skin or subcutaneous scarring associated with fibrosis.

In some embodiments, the compounds of Formulas (I), (II), (III), (IV) and (V) or pharmaceutically acceptable salt thereof or pharmaceutical composition are co-administered together with one or more additional anti-fibrotic agents and/or more agents used to stabilize, to ameliorate, to palliate, to reverse, to decrease or to delay the progression of the fibrotic disease. The additional agent can be used in the therapy for fibrosis of specific organ(s). For example, for pulmonary fibrosis, such additional agents include corticosteroids such as prednisone or prednisolone, immunosuppressants such as cyclophosphamide, methotrexate, azathioprine, cyclosporine, mycophenolate mofetil, or N-acetylcysteine, or tyrosine kinase inhibitors such as vascular endothelial growth factor receptor (VEGFR), fibroblast growth factor receptor (FGFR) and platelet derived growth factor receptor (PDGFR) (e.g. nintedanib) or pirfenidone and the like. Other agents can be used in combination for fibrotic disease state such as idiopathic pulmonary fibrosis, nonidiopathic pulmonary fibrosis interstitial pneumonias, interstitial lung disease (ILD), diabetic nephropathy, myelofibrosis with a compound of Formulas (I), (II), (III), (IV) and (V) include NOX inhibitor (e.g. GKT-831), galectin-3 inhibitor (e.g. TD-139, Gal-300, Gal-400), LPA1 receptor antagonist (e.g. AM966, UD-009, BMS-986020); recombinant human PTX-2 (e.g. PRM-151); IL-3 antibodies (e.g. lebrikizumab, tralokinumab); LOXL2 inhibitor or antibodies (e.g. simtuzumab, PAT-1251); CTGF antibodies (e.g. FG-3019); IL-3/IL-4 antibodies (e.g. SAR156597); integrin αvβ6 (e.g. STX-100).

In another embodiment, present disclosure relates to the use of a compound of Formulas (I), (II), (III), (IV) or (V) or pharmaceutically acceptable salt, hydrates, solvate, prodrugs, polymorphs, tautomers, isotopic variants, isomers, stereoisomers or mixtures of stereoisomers thereof, to treat and/or decrease the severity and/or progression of and/or the prevent autophagy related diseases.

In one aspect of this embodiment, the compounds are used to treat, prevent, and/or ameliorate the symptoms and/or progression of hyperautophagy-related diseases characterized by an increased autophagy flux, including, but not limited to, hyper-chaperone mediated autophagy autoimmune related diseases or disorders.

In another aspect, the compounds are used to treat, or prevent, and/or ameliorate a disease state or condition in a patient in need thereof wherein said disease state or condition responds favorably to inhibition of autophagy.

In some further embodiments, the compounds are used to inhibit autophagy in a biological system in which inhibition of autophagy is desired.

The compounds are potent modulators of autophagy, and can be used to treat, prevent and/or ameliorate of the symptoms of diseases characterized by an increased autophagy flux, a hyperautophagy, an excessive or increased autophagy flux, wherein said excessive or increase autophagy is associated to chaperone-mediated autophagy (CMA).

The compounds can also be used to treat, prevent, and ameliorate the symptoms and/or progression of a hyper autophagy related immune system disease or disorder.

Some embodiments, the increased autophagy flux is associated with autoimmune disorders and related diseases, including those wherein said increased autophagy flux is associated with hyper chaperone mediated autophagy (CMA).

In a further embodiment, the compounds are used to treat, prevent, and/or ameliorate the symptoms and/or progression of an autoimmune disease or chronic inflammatory disease or disorder in a subject in need thereof, including those characterized by increased autophagy flux.

In another embodiment, the compounds are used to treat, prevent, and/or ameliorate a disease state or condition in a subject in need wherein said disease state or condition responds favorably to inhibition of autophagy, wherein said disease state or condition is selected from: rheumatoid arthritis, malaria, antiphospholipid antibody syndrome, lupus, chronic urticarial or Sjogren's disease.

In another embodiment, the compounds are used to treat, prevent, and/or ameliorate the symptoms and/or progression of diseases characterized by an increased autophagy flux, wherein said increased autophagy flux is a hyper autophagy-related autoimmune disorders.

In another embodiment, the compounds are used to treat, prevent, and/or ameliorate the symptoms and/or progression of a hyper autophagy-related disease or disorder.

In another embodiment, the present disclosure provides a compound of Formulas (I), (II), (III), (IV) or (V) or pharmaceutically acceptable salt, hydrates, solvate, prodrugs, polymorphs, tautomers, isotopic variants, isomers, stereoisomers or mixtures of stereoisomers thereof (i.e., "a compound") for use as a medicament to treat, prevent, and/or ameliorate the symptoms and/or progression of a hyper-chaperone mediated autophagy (CMA) related disease or disorder.

In another embodiment, the compounds are used to treat, prevent, and/or ameliorate the symptoms and/or progression of an autoimmune disease or disorder (e.g. hyper autophagy-related autoimmune disease or hyper-chaperone-mediated autophagy related autoimmune disease).

In another embodiment, the present disclosure provides a compound of Formulas (I), (II), (III), (IV) or (V) for use as a medicament to treat, prevent, and/or ameliorate the symptoms and/or progression of a disorder of a chronic inflammation-related disease.

In another embodiment, the present disclosure provides a compound of Formulas (I), (II), (III), (IV) or (V) for use as a medicament to treat, prevent, and/or ameliorate the symptoms and/or progression of a hyper autophagy-related immune disease or disorder.

In another embodiment, the present disclosure provides a compound of Formulas (I), (II), (III), (IV) or (V) for use as a medicament to treat, prevent, and/or ameliorate the symptoms and/or progression of a hyper-chaperone mediated autophagy (CMA) related disease or disorder. Representative disorders include, but are not limited to, rheumatoid arthritis (RA), multiple sclerosis (MS), muscular dystrophy (MD), asthma, chronic pulmonary obstructive disorder (COPD), Crohn's disease (CD), chronic inflammatory demyelinating polyradiculoneuropathy (CIDP), fibromyalgia, type I diabetes, polymyositis, pulmonary diseases, and chronic immune thrombocytopenia (ITP).

In another embodiment, the present disclosure provides a compound of Formulas (I), (II), (III), (IV) or (V) for use as a medicament to treat, prevent, and/or ameliorate the symptoms and/or progression of rheumatoid arthritis.

In another embodiment, the present disclosure provides a compound of Formulas (I), (II), (III), (IV) or (V) for use as a medicament to treat, prevent, and/or ameliorate the symptoms and/or progression of multiple sclerosis.

In another embodiment, the present disclosure provides a compound of Formulas (I), (II), (III), (IV) or (V) for use as a medicament to treat, prevent, and/or ameliorate the symptoms and/or progression of muscular dystrophy.

In another embodiment, the present disclosure provides a compound of Formulas (I), (II), (III), (IV) or (V) for use as a medicament to treat, prevent, and/or ameliorate the symptoms and/or progression of asthma.

In another embodiment, the present disclosure provides a compound of Formulas (I), (II), (III), (IV) or (V) for use as a medicament to treat, prevent, and/or ameliorate the symptoms and/or progression of chronic pulmonary obstructive disorder.

In another embodiment, the present disclosure provides a compound of Formulas (I), (II), (III), (IV) and (V) for use as a medicament to treat, prevent, and/or ameliorate the symptoms and/or progression of Crohn's disease.

In another embodiment, the present disclosure provides a compound of Formulas (I), (II), (III), (IV) and (V) for use as a medicament to treat, prevent, and/or ameliorate the symptoms and/or progression of chronic inflammatory demyelinating polyradiculoneuropathy.

In another embodiment, the present disclosure provides a compound of Formulas (I), (II), (III), (IV) and (V) for use as a medicament to treat, prevent, and/or ameliorate the symptoms and/or progression of fibromyalgia.

In another embodiment, the present disclosure provides a compound of Formulas (I), (II), (III), (IV) and (V) for use as a medicament to treat, prevent, and/or ameliorate the symptoms and/or progression of type I diabetes.

In another embodiment, the present disclosure provides a compound of Formulas (I), (II), (III), (IV) or (V) to treat, prevent, and/or ameliorate the symptoms and/or progression of type II diabetes.

In another embodiment, the present disclosure provides a compound of Formulas (I), (II), (III), (IV) and (V) or pharmaceutically acceptable salt, hydrates, solvate, prodrugs, polymorphs, tautomers, isotopic variants, isomers, stereoisomers or mixtures of stereoisomers thereof for use as a medicament to treat, prevent, and/or ameliorate the symptoms and/or progression of polymyositis.

In another embodiment, the present disclosure provides compound of Formulas (I), (II), (III), (IV) and (V) for use as a medicament to treat, prevent, and/or ameliorate the symptoms and/or progression of pulmonary diseases.

In another embodiment, the present disclosure provides a compound of Formulas (I), (II), (III), (IV) or (V) for use as a medicament to treat, prevent, and/or ameliorate the symptoms and/or progression of chronic immune thrombocytopenia.

In another embodiment, the present disclosure provides a compound of Formulas (I), (II), (III), (IV) or (V) for use as a medicament to treat, prevent, and/or ameliorate the symptoms and/or progression of chronic urticarial.

In another embodiment, the present disclosure provides a compound of Formulas (I), (II), (III), (IV) or (V) for use as a medicament to treat, prevent, and/or ameliorate the symptoms and/or progression of Sjorgen's disease.

In another embodiment, the present disclosure provides a compound of Formulas (I), (II), (III), (IV) or (V) for use as a medicament to treat, prevent, and/or ameliorate the symptoms and/or progression of antiphospholipid antibody syndrome.

In another embodiment, the present disclosure provides a compound of Formulas (I), (II), (III), (IV) or (V) for use as a medicament to treat, prevent, and/or ameliorate the symptoms and/or progression of ulcerative colitis.

In another embodiment, the present disclosure provides a compound of Formulas (I), (II), (III), (IV) or (V) for use as a medicament to treat, prevent, and/or ameliorate the symptoms and/or progression of irritable bowel syndrome.

In another embodiment, the present disclosure provides a compound of Formulas (I), (II), (III), (IV) or (V) for use as a medicament to treat or prevent the symptoms of psoriasis.

In another embodiment, the present disclosure provides a compound of Formulas (I), (II), (III), (IV) or (V) for use as a medicament to treat or prevent the symptoms of scleroderma.

In another embodiment, the present disclosure provides a compound of Formulas (I), (II), (III), (IV) or (V) for use as a medicament to treat or prevent the symptoms of lupus.

In another embodiment, the present disclosure provides a compound of Formulas (I), (II), (III), (IV) or (V) for use as a medicament to treat or prevent the symptoms of neuropsychiatric lupus.

In another embodiment, the present disclosure provides a compound of Formulas (I), (II), (III), (IV) or (V) for use as a medicament to treat or prevent the symptoms of chronic inflammatory demyelinating polyradiculoneuropathy.

Representative hyper autophagy-related diseases or disorders include, but are not limited to, rheumatoid arthritis (RA), multiple sclerosis (MS), myopathies, muscular dystrophy (MD), Crohn's disease (CD), Chronic obstructive pulmonary disease (COPD), fibromyalgia, polymyositis, pulmonary disease, chronic immune thrombocytopenia (ITP), neuropsychiatric lupus, Gougerot-Sjogren syndrome, rheumatoid arthritis, Guillain-Barre disease, Chronic inflammatory demyelinating polyneuropathy (CIDP), asthma (acute or chronic), eosinophilic airway inflammation, irritable bowel syndrome (IBS or IBD), chronic inflammatory demyelinating polyradiculoneuropathy (CIDP), type II diabetes, regeneration of fat tissue, scleroderma, psoriasis, Alzheimer's and Parkinson's diseases.

In some further embodiments, the autoimmune disease is an autoimmune pathology of the family of connective tissue diseases related to non-specific systemic organ diseases (e.g. systemic lupus erythematosus (SLE), rheumatoid arthritis, mixed connective tissue disease, Sjogren's syndrome, or chronic juvenile arthritis).

In other embodiments, the autoimmune disease is an autoimmune pathology of the family of connective tissue diseases related to organ-specific autoimmune pathologies including, but not limited to, multiple sclerosis, insulin-dependent diabetes, Crohn's disease, and bullous diseases.

In some further embodiments, the present disclosure provides a compound of Formulas (I), (II), (III), (IV) or (V) or pharmaceutically acceptable salt thereof which are inhibitors of autophagy, making them useful to treat, reduce the severity and/or progression of, and/or prevent diseases, conditions and disorders responsive to autophagy modulation where autophagy is dysregulated, and, more particularly, upregulated. Representative disorders include, but are not limited to, neurodegeneration, heart failure, obesity, sarcopenia, aging, inflammatory disorders including Crohns disease, ulcerative colitis, biliary cirrhosis, ischemia/reperfusion, inflammatory disorders, and lysosomal storage diseases, and infectious diseases associated with intracellular pathogens including viruses, bacteria, and parasites such as Trypanosomes and malaria. Further representative disorders include rheumatoid arthritis, malaria, antiphospholipid antibody syndrome, lupus, chronic urticarial and Sjogren's disease, and rheumatoid arthritis.

In some further embodiments, the present disclosure provides a compound of Formula (I), (II), (III), (IV) or (V) or a pharmaceutically acceptable salt, hydrate, solvate, prodrug, polymorph, tautomer, isotopic variant, isomer, stereoisomer or mixture of stereoisomers thereof, or a pharmaceutical composition comprising said compound for use as a medicament to treat a viral infection. Representative viruses which can be treated include influenza virus A, B and C, preferably influenza virus A, hepaciviruses, preferably hepacivirus C, more preferably, hepatitis C, hepadnaviruses, preferably hepatitis B, and flaviviruses, such as West Nile virus, dengue virus, tick-borne encephalitis virus, yellow fever virus, and Zika virus.

In some further embodiments, the compounds of the present disclosure are co-administered with an active agent able to inhibit or reduce the autophagy flux, or an immunomodulatory agent. The combination of the compound and further active agent can be present in the same pharmaceutical composition.

In some further embodiments, the present disclosure provides a compound of Formulas (I), (II), (III), (IV) or (V), or a pharmaceutical composition comprising said compound, for use in inhibiting autophagy and/or endosomal traffic.

In some other embodiments, the present disclosure provides a compound of Formulas (I), (II), (III), (IV) or (V), or a pharmaceutical composition comprising said compound, for use as a medicament in inhibiting the maturation of endosomes and lysosomes and contributes to increasing the lysosomal pH.

In a further aspect, the present disclosure provides a compound of Formulas (I), (II), (III), (IV) or (V), or a pharmaceutical composition comprising said compound, for use as a medicament in inhibiting autophagy by blocking the fusion between autophagosomes and lysosomes in mammalian cells, thereby leading to the accumulation of autophagosomes.

In some embodiments, the present disclosure provides a compound of Formulas (I), (II), (III), (IV) or (V), or a pharmaceutical composition comprising said compound, for use as a medicament in treating, preventing, or inhibiting malaria in a subject in need thereof. In some aspects of this embodiment, the compound can be co-administered with one or more additional anti-malaria agents. Representative agents include, but are not limited to, amodiaquine, amopyroquine, artemisinin, artemether, arteflene, arterolane, artesunate, atovaquone, clindamycin, chloroquine, chlorproguanil, dihydroartemisinin, doxycycline, ferroquine, halofantrine, quinacrine, quinidine quinine, lumefantrine, mefloquine, primaquine, piperaquine, proguanil, pyrimethamine-dap s one, pyrimethamine-sulfadoxine, pyronaridine, sulphonamides, tafenoquine and trimethoprim.

In another form, the present disclosure provides a compound of Formulas (I), (II), (III), (IV) or (V) as an inhibitor of the activity of cathepsins B, D and/or L.

In some embodiments, the present disclosure provides a compound of Formulas (I), (II), (III), (IV) or (V) as an inhibitor of the activity of cathepsin B.

In some embodiments, the present disclosure provides a compound of Formulas (I), (II), (III), (IV) or (V) as an inhibitor of the activity of cathepsin D.

In some embodiments, the present disclosure provides a compound of Formulas (I), (II), (III), (IV) or (V) as an inhibitor of the activity of cathepsin L.

In further embodiments, the present disclosure provides a compound of Formulas (I), (II), (III), (IV) or (V) as an inhibitor of cathepsins B, D and/or L, which is therefore useful to treat or prevent cathepsins B, D and/or L-dependent diseases or conditions in a subject.

In some embodiments, the present disclosure provides a compound of Formulas (I), (II), (III), (IV) or (V) for treating a disease state or condition in a patient in need thereof, wherein said disease state or condition responds favorably to inhibiting a cathepsin activity, preferentially cathepsins B, D and/or L.

In some further embodiments, the present disclosure provides a compound of Formulas (I), (II), (III), (IV) or (V) in the manufacture of a medicament for treating a disease state or condition in a patient in need thereof which inhibition of cathepsins B, D and/or L is desired.

In a further embodiment, the present disclosure provides a compound of Formulas (I), (II), (III), (IV) or (V) in the manufacture of a medicament for treating a disease state or condition in a subject in need wherein said disease state or condition responds favorably to inhibition of the activity of cathepsins B, D and/or L.

In a further embodiment, the present disclosure provides a compound of Formulas (I), (II), (III), (IV) or (V) which is a potent modulator of the activities of cathepsins B, D and/or L.

In a further embodiment, the present disclosure provides a compound of Formulas (I), (II), (III), (IV) or (V) or pharmaceutically acceptable salt thereof which are effective for treating, preventing and/or ameliorating the symptoms of diseases characterized by an increased cathepsins B, D and/or L activities.

In a further embodiment, the present disclosure provides a compound of Formulas (I), (II), (III), (IV) or (V) which is effective for treating, preventing and/or ameliorating the symptoms of diseases characterized by an upregulation and/or activities of cathepsins B, D and/or L.

In some embodiments, the compounds of the present disclosure are potent inhibitors of cysteine proteases in cellulo, wherein said cysteine proteases are preferentially cathepsin B and/or cathepsin L.

In some embodiments, the compounds of the present disclosure are potent inhibitors of aspartyl proteases in cellulo, wherein said aspartyl proteases are preferentially cathepsin D.

In a further embodiment, the compound of the present disclosure is an inhibitor of cathepsin B, and is effective for treating, preventing and/or ameliorating the symptoms and/or progression of Alzheimer's disease, rheumatism arthritis, inflammatory airway disease, chronic obstructive pulmonary disease, osteoarthritis, *Pneumocystis carinii*, acute pancreatitis, multiple sclerosis, bone and joint disease or disorder in a subject in need thereof.

In some further embodiments, the compounds described herein are inhibitors of Cathepsin B, a lysosomal cysteine protease, and are therefore useful in treating disease states associated with the normal activity or the increased expression of Cathepsin B, for example Alzheimer's Disease, arthritis, inflammatory diseases such as chronic and acute pancreatitis, inflammatory airway disease, and bone and joint disorders, including osteoporosis, osteoarthritis, rheumatoid arthritis, psoriasis, and other autoimmune disorders, liver fibrosis, including liver fibrosis associated with hepatitis B and/or C, all types of steatosis (including nonalcoholic steatohepatitis) and alcohol-associated steatohepatitis, non-alcoholic fatty liver disease, forms of pulmonary fibrosis including idiopathic pulmonary fibrosis, pathological diagnosis of interstitial pneumonia following lung biopsy, renal fibrosis, cardiac fibrosis, retinal angiogenesis and fibrosis/gliosis in the eye, schleroderma, and systemic sclerosis.

In still another aspect, the present disclosure provide a compound of Formulas (I), (II), (III), (IV) or (V) as cathepsin L inhibitor for treating a subject infected by or at risk of infection by a viral pathogen. The compounds described herein can be used alone, or optionally with one or more active agents, including antiviral agents.

In another aspect, the present disclosure provide a compound of Formulas (I), (II), (III), (IV) or (V) as cathepsin L inhibitor for treating a subject infected by a viral pathogen, or at risk of developing a viral infection, or for inhibiting the viral entry into mammalian cells.

In still another aspect, the present disclosure provide a compound of Formulas (I), (II), (III), (IV) or (V) as a cathepsin B inhibitor for treating a subject infected by a viral pathogen, or at risk of developing a viral infection, or for inhibiting the viral entry into mammalian cells.

Representative viral pathogens include, but are not limited to, Severe acute respiratory syndrome coronavirus (SARS), Ebola virus and Hendra virus (a henipavirus).

In another embodiment, the present disclosure provide a compound of Formulas (I), (II), (III), (IV) or (V) as a cathepsin B inhibitor for treating a subject infected by a non-viral pathogen infection, preferably a parasitic infection.

In another embodiment, the present disclosure provide a compound of Formulas (I), (II), (III), (IV) or (V) as a cathepsin L inhibitor for treating a subject infected by non-viral pathogen, wherein the non-viral pathogen infection is preferably parasitic.

In another embodiment, the present disclosure provide a compound of Formulas (I), (II), (III), (IV) or (V) as a cathepsin L inhibitor for treating a subject at risk of developing a non-viral pathogen infection, such as a parasitic infection.

In another aspect, the present disclosure provide a compound of Formulas (I), (II), (III), (IV) or (V) as cathepsin B inhibitor for treating a subject afflicted with or at risk of developing osteoporosis.

In still another embodiment, the present disclosure provide a compound of Formulas (I), (II), (III), (IV) or (V) as a cathepsin L inhibitor, for treating a subject afflicted with or at risk of a disease or disorder affecting bone and cartilage remodeling.

In still another embodiment, the present disclosure provide a compound of Formulas (I), (II), (III), (IV) or (V) as a cathepsin D inhibitor as effective for treating, preventing and/or ameliorating the symptoms of Alzheimer's disease in a subject in need thereof.

In still another embodiment, the present disclosure provide a compound of Formulas (I), (II), (III), (IV) or (V) as a cathepsin D inhibitor as effective for treating, preventing and/or ameliorating the symptoms of muscular dystrophy in a subject in need thereof.

In yet a further embodiment, the present disclosure provide a compound of Formulas (I), (II), (III), (IV) or (V) as a cathepsin D inhibitor as effective for treating, preventing, or reducing the severity and/or progression of physiological and/or pathophysiological states selected from the group consisting of Alzheimer's disease, Huntington's disease, mucolipidosis, contact dermatitis, late-onset hypersensitivity reaction, inflammation, endometriosis, scarring, benign prostate hyperplasia, rickets, skin diseases such as psoriasis, immunological diseases, autoimmune diseases and immunodeficiency diseases.

In a further embodiment, the compounds of the present disclosure are used to treat or prevent physiological and/or pathophysiological conditions selected from the group consisting of pain, allodynia and hyperalgesia.

In a further embodiment, the compounds of the present disclosure is used as a cathepsin D inhibitor as effective for treating and/or preventing physiological and/or pathophysiological conditions selected from the group consisting of arthrosis, traumatic cartilage injuries, arthritis, pain, allodynia and hyperalgesia.

Any combination of two or more of the embodiments described herein is considered within the scope of the present disclosure.

The compounds described herein can be formulated in compositions (see section "pharmaceutical compositions" below). Optionally, the pharmaceutical compositions can comprise one or more compounds according to the invention and/or one or more additional active substances (see section "Pharmaceutical combinations" below). The pharmaceutical compositions as well as the pharmaceutical combinations can be in any suitable form (depending upon the desired way of administration to an individual).

Pharmaceutical Compositions

Accordingly, in another aspect, the present disclosure also provides pharmaceutical compositions which can comprise as active ingredient one or more of the compounds described herein. Typically, the compounds described herein used as active ingredients can be formulated together with one or more pharmaceutically acceptable carriers (e.g. excipient, diluent or adjuvant). Generally, the compounds described herein, as active ingredients, can be present in a therapeutically-effective amount in the pharmaceutical compositions according to the invention.

As described in detail below, the pharmaceutical compositions described herein can be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin; intravaginally or intrarectally, for example, as a pessary, cream or foam; sublingually; ocularly; transdermally; nasally; pulmonary; or intrathecally.

The phrase "therapeutically-effective amount" as used herein means that amount of a compound, material, or composition comprising a compound described herein which is effective for producing some desired therapeutic effect in at least a sub-population of cells in an animal at a reasonable benefit/risk ratio applicable to any medical treatment.

Representative examples of materials which can serve as pharmaceutically-acceptable carriers include, without limitation: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oilglycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or poly anhydrides; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations can include those suitable for oral, nasal, topical (including buccal and sublingual), rectal, vaginal and/or parenteral administration. The formulations can conveniently be presented in unit dosage form and can be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Generally, out of one hundred percent, this amount will range from about 0.1% to about 99% of active ingredient, preferably from about 5% to about 70%, most preferably from about 10% to about 30%.

In certain embodiments, a formulation comprises an excipient selected from the group consisting of cyclodextrins, celluloses, liposomes, micelle forming agents, e.g., bile acids, and polymeric carriers, e.g., polyesters and poly anhydrides; and a compound described herein. In certain embodiments, an aforementioned formulation renders orally bioavailable a compound described herein.

Methods of preparing these formulations or compositions include the step of bringing into association a compound described herein with the carrier and, optionally, one or more accessory ingredients. In general, the formulations are prepared by uniformly and intimately bringing into association a compound described herein with liquid carriers, or finely divided solid carriers, or both, and then, if necessary, shaping the product.

Formulations suitable for oral administration can be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound described herein as an active ingredient. A compound described herein can also be administered as a bolus, electuary or paste.

In solid dosage forms for oral administration (capsules, tablets, pills, dragees, powders, granules, touches and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds and surfactants, such as poloxamer and sodium lauryl sulfate; wetting agents, such as, for example, cetyl alcohol, glycerol monostearate, and nonionic surfactants; absorbents, such as kaolin and bentonite clay; lubricants, such as talc, calcium stearate, magnesium stearate, solid polyethylene glycols, sodium lauryl sulfate, zinc stearate, sodium stearate, stearic acid, and mixtures thereof; coloring agents; and controlled release agents such as crospovidone or ethyl cellulose. In the case of capsules, tablets and pills, the pharmaceutical compositions can also comprise buffering agents. Solid compositions of a similar type can also be employed as fillers in soft and hard-shelled gelatin capsules using such excipients as lactose or milk sugars, as well as high molecular weight polyethylene glycols and the like.

A tablet can be made by compression or molding, optionally with one or more accessory ingredients. Compressed tablets can be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets can be made by molding in a suitable machine a mixture of the powdered compound moistened with an inert liquid diluent.

The tablets, and other solid dosage forms of the pharmaceutical compositions described herein, such as dragees, capsules, pills and granules, can optionally be scored or prepared with coatings and shells, such as enteric coatings and other coatings well known in the pharmaceutical-formulating art. They can also be formulated so as to provide slow or controlled release of the active ingredient therein using, for example, hydroxypropylmethyl cellulose in varying proportions to provide the desired release profile, other polymer matrices, liposomes and/or microspheres. They can be formulated for rapid release, e.g., freeze-dried. They can be sterilized by, for example, filtration through a bacteria-retaining filter, or by incorporating sterilizing agents in the form of sterile solid compositions which can be dissolved in sterile water, or some other sterile injectable medium immediately before use. These compositions can also optionally contain opacifying agents and can be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds described herein include pharmaceutically acceptable emulsions, microemulsions, solutions, suspensions, syrups and elixirs. In addition to the active ingredient, the liquid dosage forms can contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal or vaginal administration can be presented as a suppository, which can be prepared by mixing one or more compounds described herein with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound can be mixed under sterile conditions with a pharmaceutically-acceptable carrier, and with any preservatives, buffers, or propellants which can be required.

The ointments, pastes, creams and gels can contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound described herein to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds described herein in combination with one or more pharmaceutically-acceptable sterile isotonic aqueous or nonaqueous solutions, dispersions, suspensions or emulsions, or sterile powders which can be reconstituted into sterile injectable solutions or dispersions just prior to use, which can contain sugars, alcohols, antioxidants, buffers, bacteriostats, solutes which render the formulation isotonic with the blood of the intended recipient or suspending or thickening agents.

Examples of suitable aqueous and nonaqueous carriers which can be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of the action of microorganisms upon the subject compounds can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

In some cases, in order to prolong the effect of a drug, it is desirable to slow the absorption of the drug from subcutaneous or intramuscular injection. This can be accomplished by the use of a liquid suspension of crystalline or amorphous material having poor water solubility. The rate of absorption of the drug then depends upon its rate of dissolution which, in turn, can depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds described herein are administered as pharmaceuticals, to a subject in need thereof (e.g. humans or animals), they can be given per se or as a pharmaceutical composition containing, for example, 0.1 to 99% (preferably, 5 to 60%, more preferably 10 to 30%) of active ingredient in combination with a pharmaceutically acceptable carrier.

The preparations can be given orally, parenterally, topically, or rectally. They are of course given in forms suitable for each administration route. For example, they are administered in tablets or capsule form, by injection, inhalation, eye lotion, ointment, suppository, etc. . . . administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds can be administered to a subject in need (e.g. humans or animals), for therapy by any suitable route of administration, including orally, nasally (as by for example a spray), rectally, intravaginally, parenterally (e.g. subcutaneously, intracutaneously, intravenously, intramuscularly, intraarterially, intraarticularly, intrasynovially, intrasternally, intrathecally, intralesionally, by intracranial injection, by infusion techniques or by continuous infusion), intracisternally, via an implanted reservoir, by injection, subdermally, intraperitoneally, transmucosally, in an ophthalmic preparation and topically, as by powders, ointments or drops, including buccally and sublingually.

Regardless of the route of administration selected, the compounds, which can be used in a suitable hydrated form, and/or the pharmaceutical compositions described herein, are formulated into pharmaceutically-acceptable dosage forms by conventional methods known to those of skill in the art. Actual dosage levels of the active ingredients in the pharmaceutical compositions of this invention can be varied so as to obtain an amount of the active ingredient which is effective to achieve the desired therapeutic response for a particular patient, composition, and mode of administration, without being toxic to the patient.

The selected dosage level will firstly be dependent on the subject (human or animal) being treated and on the activity of the particular compound being employed, or the pharmaceutically acceptable salt, hydrate, solvate, prodrug, isotopic variant, tautomer or stereoisomer thereof. In the instances where pharmaceutical compositions are administered to a human individual, the daily dosage will normally be determined by the prescribing physician with the dosage generally varying according to the age, sex, diet, weight, general health and response of the individual, the severity of the individual's symptoms, the precise indication or condition being treated, the severity of the indication or condition being treated, time of administration, route of administration, the disposition of the composition, rate of excretion, drug combination, and the discretion of the prescribing physician. Also, the route of administration can vary depending on the condition and its severity. Preferably, the pharmaceutical composition is in unit dosage form. In such form, the preparation is subdivided into unit doses containing appropriate quantities of the active component, e.g., an effective amount to achieve the desired purpose. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage can be divided and administered in portions during the day if desired. The amount and frequency of administration of the compounds described herein, and if applicable other therapeutic agents and/or therapies, will be regulated according to the judgment of the attending clinician (physician) considering such factors as described above. Thus the amount of pharmaceutical composition to be administered can vary widely. Administration can occur in an amount of between about 0.001 mg/kg of body weight to about 100 mg/kg of body weight per day (administered in single or divided doses), more preferably at least about 0.1 mg/kg of body weight per day. A particular therapeutic dosage can include, e.g., from about 0.01 mg to about 7000 mg of compound, and preferably includes, e.g., from about 0.05 mg to about 2500 mg. More particularly, in the case of oral or parenteral administration to adult humans weighing approximately 70 kg, a daily dosage of 0.1 mg to 5 g, preferably from about 0.1 mg to 1 g, more preferably from 0.5 mg to 500 mg, and most preferably from about 1 mg to 300 mg, should be appropriate, although the upper limit can be exceeded when indicated. The quantity of active compound in a unit dose of preparation can be varied or adjusted from about 0.1 mg to 1000 mg, preferably from about 1 mg to 300 mg, more preferably 10 mg to 200 mg, according to the particular application. In some instances, dosage levels below the lower limit of the aforesaid range can be more than adequate, while in other cases still larger doses can be employed without causing any harmful side effect, e.g. by dividing such larger doses into several small doses for administration throughout the day. The amount administered will vary depending on the particular $IC_{50}$ or $EC_{50}$ value of the compound used. In combinational applications in which the compound is not the sole therapy, it can be possible to administer lesser amounts of compound and still have therapeutic or prophylactic effect. If desired, the effective daily dose of the active compound can be administered as two, three, four, five, six or more sub-doses administered separately at appropriate intervals throughout the day, optionally, in unit dosage forms or every 4 to 120 hours according to the requirements of the particular drug. Preferred dosing is one administration per day. In certain embodiments, the pharmaceutical compositions are administered by oral administration or by injection. The methods herein contemplate administration of an effective amount of compound or a pharmaceutical composition comprising one or more compounds to achieve the desired or stated effect.

Lower or higher doses than those recited above can be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, and the judgment of the treating physician.

Nevertheless, actual dosage levels and time course of administration of the ingredients in the pharmaceutical compositions described herein can be varied so as to obtain an amount of the active ingredient which is effective to achieve the desired therapeutic response for a particular patient, pharmaceutical composition and mode of administration, without being toxic to the patient. It can therefore be necessary where appropriate to deviate from the stated amounts, in particular as a function of age, gender, body weight, diet and general health status of the patient, route of administration, individual response to the active ingredient, nature of the preparation, and time or interval over which administration takes place. Thus, it can be satisfactory in some cases to manage with less than the aforementioned minimum amount, whereas in other cases the stated upper limit must be exceeded. It can in the event of administration of larger amounts be advisable to divide these into multiple individual doses spread over the day.

While it is possible for a compound described herein to be administered alone, it is preferable to administer the compound as a pharmaceutical formulation (composition). The compounds according to the invention can be formulated for administration in any convenient way for use in human or veterinary medicine, by analogy with other pharmaceuticals.

In another aspect, the present disclosure provides pharmaceutical compositions which comprise a therapeutically-effective amount of one or more of the subject compounds described herein, as described above, formulated together with one or more pharmaceutically acceptable carriers (additives) and/or diluents. As described in detail below, the pharmaceutical compositions described herein can be specially formulated for administration in solid or liquid form, including those adapted for the following: oral administration, for example, drenches (aqueous or non-aqueous solutions or suspensions), tablets, boluses, powders, granules, pastes for application to the tongue; parenteral administration, for example, by subcutaneous, intramuscular or intravenous injection as, for example, a sterile solution or suspension; topical application, for example, as a cream, ointment or spray applied to the skin, lungs, or mucous membranes; or intravaginally or intrarectally, for example, as a pessary, cream or foam; sublingually or buccally; ocularly; transdermally; or) nasally.

The compound can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Microemulsification technology can improve bioavailability of some lipophilic (water insoluble) pharmaceutical agents. Examples include Trimetrine (Dordunoo, S. K. et al. Drug Development and Industrial Pharmacy 1991 (17), 1685-1713) and REV 5901 (Sheen, P. C. et al. J. Pharm. Sci. 1991 (80), 712-714). Among other things, microemulsification provides enhanced bioavailability by preferentially directing absorption to the lymphatic system instead of the circulatory system, which thereby bypasses the liver, and prevents destruction of the compounds in the hepatobiliary circulation. While all suitable amphiphilic carriers are contemplated, the presently preferred carriers are generally those that have Generally-Recognized-as-Safe (GRAS) status, and that can both solubilize the compound and microemulsify it at a later stage when the solution comes into a contact with a complex water phase (such as one found in human gastrointestinal tract). Usually, amphiphilic ingredients that satisfy these requirements have HLB (hydrophilic to lipophilic balance) values of 2-20, and their structures contain linear chain aliphatic radicals in the range of $C_6$ to $C_{20}$. Examples are polyethylene-glycolized fatty glycerides and polyethylene glycols. Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide). Hydrophilic polymers suitable for use in the present disclosure are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG-750). Polymers can also be defined by the number of monomers therein; a preferred embodiment of the present disclosure utilizes polymers of at least about three monomers, such PEG polymers consisting of three monomers (approximately 150 daltons). Other hydrophilic polymers which can be suitable for use in the present disclosure include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and copolymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letter alpha, beta or gamma, respectively. Cyclodextrins with fewer than six glucose units are not known to exist. The glucose units are linked by alpha-1,4-glucosidic bonds. As a consequence of the chair conformation of the sugar units, all secondary hydroxyl groups (at $C_2$, $C_3$) are located on one side of the ring, while all the primary hydroxyl groups at $C_6$ are situated on the other side. As a result, the external faces are hydrophilic, making the cyclodextrins water-soluble. In contrast, the cavities of the cyclodextrins are hydrophobic, since they are lined by the hydrogen of atoms $C_3$ and $C_5$, and by ether-like oxygens. These matrices allow complexation with a variety of relatively hydrophobic compounds, including, for instance, steroid compounds such as 17.beta-estradiol (see, e.g., van Uden, W. et al. Plant Cell Tiss. Org. Cult. 1994 (38), 103-113). The complexation takes place by Van der Waals interactions and by hydrogen bond formation. For a general review of the chemistry of cyclodextrins, see, Wenz, G. Agnew. Chem. Int. Ed. Engl. 1994 (33) 803-822.

Liposomes consist of at least one lipid bilayer membrane enclosing an aqueous internal compartment. Liposomes can be characterized by membrane type and by size. Small unilamellar vesicles (SUVs) have a single membrane and typically range between 0.02 and 0.05 µm in diameter; large unilamellar vesicles (LUVS) are typically larger than 0.05 µm. Oligolamellar large vesicles and multilamellar vesicles have multiple, usually concentric, membrane layers and are typically larger than 0.1 µm. Liposomes with several non-concentric membranes, i.e., several smaller vesicles contained within a larger vesicle, are termed multivesicular vesicles.

One aspect of the present disclosure relates to formulations comprising liposomes containing a compound described herein, where the liposome membrane is formulated to provide a liposome with increased carrying capacity. Alternatively, or in addition, the compound can be contained within, or adsorbed onto, the liposome bilayer of the liposome. The compound can be aggregated with a lipid surfactant and carried within the liposome's internal space; in these cases, the liposome membrane is formulated to resist the disruptive effects of the active agent-surfactant aggregate.

According to one embodiment of the present disclosure, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment. Active agents contained within liposomes are in solubilized form. Aggregates of surfactant and active agent (such as emulsions or micelles containing the active agent of interest) can be entrapped within the interior space of liposomes according to the present disclosure. A surfactant acts to disperse and solubilize the active agent, and can be selected from any suitable aliphatic, cycloaliphatic or aromatic surfactant, including but not limited to biocompatible lysophosphatidylcholines (LPCs) of varying chain lengths (for example, from about $C_{14}$ to about $C_{20}$). Polymer-derivatized lipids such as PEG-lipids can also be utilized for micelle formation as they will act to inhibit micelle/membrane fusion, and as the addition of a polymer to surfactant molecules decreases the critical micellar concentration (CMC) of the surfactant and aids in micelle formation. Preferred are surfactants with CMCs in the micromolar range; higher CMC surfactants can be utilized to prepare micelles entrapped within liposomes, however, micelle surfactant monomers can affect liposome bilayer stability and would be a factor in designing a liposome of a desired stability.

Liposomes according to the present disclosure can be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic D D, Liposomes from physics to applications, Elsevier Science Publishers BV, Amsterdam, 1993.

For example, liposomes can be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In particular, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988). The release characteristics of a formulation described herein depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Enteric materials refer to polymers that are substantially insoluble in acidic environment of the stomach and that are predominantly soluble in intestinal fluids at specific pHs. The small intestine is the part of the gastrointestinal tract (gut) between the stomach and the large intestine (colon) and includes the duodenum; jejunum and lileum. The pH of the duodenum is about 5.5, the pH of the jejunum is about 6.5 and the pH of the distal ileum is about 7.5. Accordingly, enteric materials are not soluble until a pH, for example, of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2 or of about 9.4. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates). Example of enteric materials include cellulose acetate phatalate (CAP), hydroxypropyl methylcellulose phthalate (HPMPC), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophtalate, cellulose propionate phthalate, cellulose acetate maleate, cellulose acetate butyrate, cellulose acetate propionate, copolymer of methylmethacrylic and methyl methacryclate, copolymer of methyl acrylate, methyl methacrylate and methacrylic acid, copolymer of methyl vinyl ether and maleic anhydride, ethyl methylacrylate-methylmethacrylate chlorotrimethylammonium ethyl acrylate copolymer, natural resins such as zein, shellac and copal collophorium, and several commercially available enteric dispersion systems (e.g. Eudragit L30D55, Eudragit FS30D, Eudragit L100, Eudragit S100, Kollicoast EMM30D, Estacryl 30D, Coateric and Aquateric). The solubility of each of the above materials is either known or is readily determinable in vitro in the laboratory.

The foregoing is a list of possible materials, but one of skill in the art with the benefit of the disclosure would recognize that is not exhaustive and that there are other enteric materials that would meet the objectives of the present In addition, the compounds described herein can be used in combination with one or more other active agent (ingredients or drugs) in the treatment, prevention, suppression or amelioration of diseases or conditions for which compounds described herein or the other active agent have utility. The compounds or pharmaceutical compositions described herein can be co-formulated or co-administered with one or more additional anti-fibrotic agents, and/or more agents used to palliate, ameliorate, stabilize, reverse, slow or delay the progression of the fibrotic disease state. The particular additional agents can be used in the therapy for fibrosis of specific organ(s).

The compounds or pharmaceutical compositions described herein can be co-formulated or co-administered with one or more additional anti-autophagic agents, and/or more agents used to palliate, ameliorate, stabilize, reverse, slow or delay the progression of the autophagic disease state and/or or related diseases and for inhibiting the autophagy flux.

The compounds or pharmaceutical compositions described herein can be co-formulated or co-administered with one or more additional inhibitor(s) of cathepsins B (CTSB), L (CTSL) and/or D (CTSD) and/or agent(s) used to palliate, ameliorate, stabilize, reverse, slow or delay the progression of related diseases.

Typically the combination of the drugs is safer or more effective than either drug alone, or the combination is safer or more effective than would it be expected based on the additive properties of the individual drugs. Such other drug(s) can be administered, by a route and in an amount commonly used contemporaneously or sequentially with a compound. When a compound is used contemporaneously with one or more other drugs, a combination product containing such other drug(s) and the compound is preferred. However, combination therapy also includes therapies in which the compound and one or more other drugs can be administered on different overlapping schedules. It is contemplated that when used in combination with other active ingredients, the compound or the other active ingredient or both can be used effectively in lower doses than when each is used alone. Accordingly, the pharmaceutical compositions described herein can include those that contain one or more other active agents, in addition to a compound. When the pharmaceutical compositions described herein include a combination of a compound of the formulae described herein and one or more additional therapeutic or prophylactic agents, the compound and the additional agent(s) can be present at dosage levels of between about 1 to 100%, preferably between about 5 to 95% and more preferably between about 20 to 80% of the dosage normally administered in a monotherapy regimen.

In some specific embodiments, the active compound can be associated with at least one other compound and/or an other active agent, wherein the components constituting said combination can be for simultaneous, separate or sequential use in the treatment and/or decreasing the severity and/or progression and/or preventing fibrosis-related diseases and/or autophagic diseases and/or of cathepsins B (CTSB), L (CTSL) and/or D (CTSD) related diseases.

In some other specific embodiments, the pharmaceutical composition according to the present disclosure, can be administered to a human being or an animal in need thereof comprising at least one additional therapeutically active agent, said at least one additional therapeutically active agent being formulated in at least another one additional pharmaceutical composition, wherein the pharmaceutical compositions constituting said combination therapy can be for simultaneous, separate or sequential use in treatment and/or decreasing the severity and/or progression and/or prevention of fibrosis-related diseases and/or autophagic diseases and/or of cathepsins B (CTSB), L (CTSL) and/or D (CTSD) related diseases.

In some other specific embodiments of the pharmaceutical composition, the compound can be associated with at least one other additional therapeutically active agent. Specifically, the additional therapeutically active agent is for treating fibrosis-related diseases and/or autophagic related diseases and/or of cathepsins B (CTSB), L (CTSL) and/or D (CTSD) related diseases.

In some preferred embodiments, the additional active agent(s) that can be included in the pharmaceutical compositions described herein is for treating fibrosis-related diseases.

In some preferred embodiments, the additional active agent(s) that can be included in the pharmaceutical compositions described herein is for treating liver fibrosis-related diseases.

In some further preferred embodiments, the additional active agent(s) that can be included in the pharmaceutical compositions described herein is for treating non-alcoholic fatty liver disease (NAFLD), non-alcoholic steatohepatitis (NASH), focal fatty liver, alcoholic related liver disease, cirrhosis, primary biliary cholangitis, primary sclerosing cholangitis, biliary atresia, biliary obstruction, cholestatic liver disease, chronic liver disease, hypercholesteremia, hyperlipidemia, hepatitis B virus infection, hepatitis C virus infection, hepatitis delta virus infection, autoimmune hepatitis, drug induced hepatitis, portal hypertension, alcoholic hepatitis, Wilson's disease, alpha-1-antitrypsin deficiency, hemochromatosis, autoimmune hepatitis, bilifary obstruction, Budd-Chiari syndrome, portal vein thrombosis, veno-occlusive disease of the liver, congenital hepatitis fibrosis and diabetes.

In some further more preferred embodiments, the additional active agent(s) that can be included in the pharmaceutical compositions described herein is for treating hepatitis B virus infection, hepatitis C virus infection, hepatitis delta virus infection, autoimmune hepatitis.

In some further more preferred embodiments, the additional active agent(s) that can be included in the pharmaceutical compositions described herein is for treating focal fatty liver, alcoholic related liver disease, cirrhosis, cholestatic liver disease, chronic liver disease, hypercholesteremia, and hyperlipidemia.

In some further more preferred embodiments, the additional active agent(s) that can be included in the pharmaceutical compositions described herein is for treating heart failure, portal vein thrombosis, veno-occlusive disease of the liver, and portal hypertension.

In some further more preferred embodiments, the additional active agent(s) that can be included in the pharmaceutical compositions described herein is for treating nonalcoholic fatty liver disease (NAFLD), non-alcoholic steatohepatitis (NASH), primary biliary cholangitis, primary sclerosing cholangitis, biliary atresia, and biliary obstruction.

In some further more preferred embodiments, the additional active agent(s) that can be included in the pharmaceutical compositions described herein is for treating non-alcoholic fatty liver disease (NAFLD), non-alcoholic steatohepatitis (NASH).

In some further more preferred embodiments, the additional active agent(s) that can be included in the pharmaceutical compositions described herein is for treating primary biliary cholangitis, primary sclerosing cholangitis, biliary atresis, biliary obstruction.

In some further more preferred embodiments, the additional active agent(s) that can be included in the pharmaceutical compositions described herein is for treating hemochromatosis.

In some further preferred embodiments, the additional active agent(s) that can be included in the pharmaceutical compositions described herein is for treating type 1 diabetes.

In some further preferred embodiments, the additional active agent(s) that can be included in the pharmaceutical compositions described herein is for treating type 2 diabetes mellitus.

In some further preferred embodiments, the additional active agent(s) that can be included in the pharmaceutical compositions described herein is for treating heart failure, hypercholesteremia, and hyperlipidemia.

In a particular embodiment, the additional active agent(s) that can be included in the pharmaceutical compositions is for treating fibrosis-related diseases and/or autophagic related diseases and/or of cathepsins B (CTSB), L (CTSL) and/or D (CTSD) related diseases. Preferably, the additional active agent is selected from the following classes of drugs, such as:

A Tyrosine kinase inhibitor such as vascular endothelial growth factor receptor (VEGFR) inhibitor, a fibroblast growth factor receptor (FGFR) inhibitor (e.g. Nintedanib Esylate, IONIS-FGFR4Rx, RG-7992, Infigratinib, Erdafitinib), a platelet derived growth factor receptor (PDGFR) antagonist (e.g. Imatinib, BOT-191, Nilotinib, Dasatinib), an epidermal growth factor receptor (EGFR) antagonist or inhibitor (e.g. Sorafenib, Regorafenib, Erlotinib, Nintedanib or Pirfenidone and the like); a dual VEGFR/PDGFR antagonist (e.g. Nintedanib, Sorafenib, Regorafenib); a phosphatidylinositol 3-kinase (PI3K) inhibitor (e.g. Omipalisib); a MAP kinase activated kinase 2 (MAPKAPK2) inhibitor (e.g. MMI-0100); an apoptosis signal-regulating kinase 1 (ASK1) inhibitor (e.g. Selonsertib);

A mammalian target of rapamycin (mTOR) inhibitor (e.g. Everolimus); a mammalian target of rapamycin complex 1 mTOR1/2 inhibitor (e.g. Rapamycin, Palomid-529); a Janus kinase 1 (JAK1) and Janus kinase 2 (JAK2) inhibitor (e.g. Ruxolitinib, Baricitinib); a protein kinase B (PKB, also referred as to Akt) inhibitor (e.g. Omipalisib); a focal adhesion kinase 1 (FAK1) inhibitor (e.g. PF-562271); a c-Jun N-terminal kinase (JNK) inhibitor (e.g. Tanzisertib); a mitogen-activated protein kinase (MAPK) inhibitor (e.g. MMI-0100); an IκB kinase (IKK) inhibitor (e.g. IMD-1041, Bardoxolone methyl); a nuclear factor kappa-light-chain-enhancer of activated B cells (NF-Rho-associated protein kinase (ROCK) inhibitor (e.g. Y-27632); a 26S protease inhibitor (e.g. Bortezomib); a caspase inhibitor (e.g. Emricasan, VX-166, Z-VAD-fmk, Nivocam); a phosphodiesterase inhibitor (e.g. CTP-499); a catepsin B inhibitor (e.g. VBY-376, CA-074Me); a S100 calcium-binding protein A9 (S100A9, also referred to as migration inhibitory factor-related protein 14 (MRP14) or calgranulin B inhibitor (e.g. Paquinimod); a procollagen-proline dioxygenase (also referred to as prolyl hydroxylase) inhibitor (e.g. HOE-077); a mothers against decapentaplegic homolog 2 (SMAD2)/ Mothers against decapentaplegic homolog 3 (SMAD3) dual inhibitor (e.g. Pirfenidone); a mothers against decapentaplegic homolog 3 (SMAD3) and a mothers against decapentaplegic homolog 4 (SMAD3) dual inhibitor (e.g. Pentoxifylline); a mothers against decapentaplegic homolog 3 (SMAD3) inhibitor (e.g. SIS-3, Glycyrrhizin); a mi RNA 21 (mR-21) inhibitor (e.g. anti-miR-21 oligonucleotide), a transmethylation inhibitor (e.g. Ademetionine); a BMP binding endothelial regulator (BMPER) inhibitor (e.g. DNA methylation); a NADPH oxidase (NOX isoform 1 to 5) inhibitor (e.g. GKT-831, GTK-771, GM-CT-01, GR-MD-02, GCS-100), a reactive oxygen species (ROS) inhibitor (e.g. GKT137831, N-acetylcysteine, Mitoquinone, Salvianolic acid B, Resveratrol); a vitamin and vitamin derivatives with antioxidant properties (e.g. Pyridoxamine, α-tocopherol, β-tocopherol, γ-tocopherol, δ-tocopherol, vitamin E, a vitamin D analog, Seocalcitol); an antioxidant (e.g. Oltipraz, n-3 polyunsaturated fatty acids, eicosapentaenoic acid, S-adenosylmethionine, GC-4403, Hep-114, Lovaza); a galectin-3 inhibitor (e.g. GR-MD-02, GM-CT-01, TD139, Gal-300, Gal-200, TD139, RN1); an interferon-α (e.g. Sumiferon); a collagen derivative (e.g. IWO01); a galectin-3 inhibitor (e.g. TD-139, Gal-300, Gal-400), a Lysophosphatidic acid receptor 1 (LPA1) antagonist (e.g. AM966, UD-009, BMS-986020); a recombinant human PTX-2 (e.g. PRM-151); an IL-3 antibodies (e.g. lebrikizumab, tralokinumab); a LOXL2 inhibitor or antibodies (e.g. β-aminopropionitrile, Simtuzumab); a transforming growth factor-β (TGF-β) inhibitor (e.g. SHP-627, hydronidone, PXS-25, disitertide, fresolimumab, LY2382770, PXS-25, Pirfenidone); a transforming growth factor β type I receptor kinase (ALK5) inhibitor (e.g. SB-431542, ALK5 Inhibitor II, Galunisertib); a bone morphogenetic protein 7 (BMP7) agonist (e.g. THR-184); a hepatocyte growth factor receptor (c-Met/HGFR) stimulant (e.g. Refanalin); an IL-3/IL-4 antibodies (e.g. SAR156597); an IL-13 inhibitor (e.g. Dectrekumab, Tralokinumab); an IL-1R$_1$ antagonist (e.g. Anakinra); an IL-βR antagonist (e.g. Rilonacept); an IL-13/IL-4 dual inhibitor (e.g. SAR156597); a C-C motif chemiokine ligand 2 (CCL2) inhibitor (e.g. Carlumab, Bindarit); an integrin αvβ6 (e.g. STX-100, CWHM-12); an interferon-γ receptor stimulant (IFN-γR, e.g. Actimmune); an interferon-α (e.g. IFN-α Lozenges); a matrix metalloproteinase-2 (MMP-2) inhibitor (e.g. Batimastat); a matrix metalloproteinase-9 (MMP-9) inhibitor (e.g. Batimastat); a broad spectrum matrix metalloproteinase (MMPs) inhibitor (e.g. Marimastat); a lysophosphatidic acid receptors (LPAR) antagonist (e.g. BMS-986020); a protease-activated receptor 1 (PAR1) antagonist (e.g. PAR1 antagonism, FR-171113, Vorapaxar, Atopaxar); a prostacyclin receptor agonist (e.g. Beraprost, Iloprost, Treprostinil); a vasoactive intestinal peptide (VIP) receptor agonist (e.g. Aviptadil); a leukocyte elastase inhibitor (e.g. Sivelestat, CHF-6333); a thrombin-activable fibrinolysis inhibitor (TAFI, e.g. UK-396082); a relaxin receptor stimulant (e.g. Serelaxin); a serum amyloid protein (SAP) also referred to as Pentraxin-2 stimulant (e.g. PRM-151); an integrin-α5 (ITGA5) inhibitor (e.g. Dioscin); a transglutaminase 2 (TGM2) also referred to as glutamine gamma-glutamyltransferase 2 inhibitor (e.g. NTU281); a TNFα inhibitor (e.g. Pentoxifylline, Infliximab, Etanercept, Golimumab, Thalidomide, Pomalidomide, Belimumab), an anti-coagulant (e.g. Warfarin, Acetylsalicylic acid); a peroxisome proliferator-activated receptors (PPARs) agonist (PPARs: PPARα, PPARβ, PPARγ, PPARδ agonists e.g. Farglitazar, Docosahexaenoic, Saroglitazar, Elafibranor, GFT505, Rosiglitazone); a peroxisome proliferator-activated receptor gamma agonist (PPARγ, e.g. thiazolidinedione family drugs such as: rosiglitazone, pioglitazone, troglitazone, netoglitazone); an amine oxidase copper containing 3 inhibitor (AOC3 also known as vascular adhesion protein-1 (VAP-1) or semicarbazide-sensitive amine oxidase (SSAO), e.g. BI1467335, PXS-4728, SzV-1287, PXS-4728A, TERN-201, BTT-1023 also know as Timolumab, ASP-8232); a toll like receptor modulator (e.g. eritoran); a renin-Angiotensin System (RAS) blockade including inhibitors angiotensin I converting enzyme (ACE) (e.g. Losartan, Candesartan, Irbesartan, Moexipril); a calcium channel blocker (e.g. Amlodipine, Clevidipine, Diltiazem, Felodipine, Isradipine, Nicardipine, Nimodipine, Nisoldipine, Verapamil, Tetrandrine); an endothelin (ET-1) antagonist (e.g. Ambrisentan, Bosentan, Sitaxentan, Atrasentan, Sparsentan, Macitentan); a herbal medicine [e.g. *Phyllanthus urinaria*, Fuzheng Huayu (FZHY), Qishenyiqi (QSYQ), Qushi Huayu decoction (QHD), herbal compound 861 (Cpd 861), Xiao-Chai-Hu Tang (XCHT), Dahuangzhechong (DHZCP), Han-dan-gan-le, Qianggan-Rongxian decoction, Yi-gan-kang, *Ginkgo biloba* extract, *Rosa laevigata* Michx (RLTS), Liuweiwuling (LWWL), Xuefuzhuyu (XFZY), Diwu Yanggan (DWYG), *Ocimum gratissimum* extracts (OGEs), Yin-Chiao-San (YCS), Renshen pingfei decoction, Hu-qi-yin, Modified Kushen Gancao formula (mKG), Sho-seiryu-to (TJ-19), Hochu-ekki-to (TJ-41), Shenlong decoction, Yupingfeng, Danggui-Buxue-Tang (DBTG)]; a farnesoid X (FXR) ligand or agonist (e.g. INT-747, INT-767, Px-102, Px-104, Obeticholic acid, cholic acid, Turofexorate isopropyl, GW4064, fexaramine, TERN-101, LJN452, Tropifexor, Centatin, EDP-305, LY-2562175, EYP-001, GS-9674, Cilofexor, TPX-100, EDP-305, LMB-763, Apomine, Turofexorate, EYP-001); a endocannabinoid receptors 1 (CB1) antagonist (e.g. Curcumin); a endocannabinoid receptors 2 (CB2) agonist (e.g. β-caryophyllene); a μ-opioid receptor antagonist (e.g. Naltrexone, Naloxone, Nalmefene); a serotonin (5HT) antagonist (e.g. Methiothepin); a corticosteroid agents (e.g. Dexamethasone, prednisolone, prednisone, methylprednisolone, hydrocortisone, triamcinolone); an estrogen receptor beta (ERβ, also referred to as NR3A2) agonist (e.g. Genistein); a C-C chemokine receptor type 2 (CCR2) inhibitor (e.g. RS-504393, JNJ-41443532, CCX872, Plozalizumab, JNJ-17166864, PF-4136309, INCB-8696); a C-C chemokine receptor type 5 (CCR5) inhibitor (e.g. Maraviroc, AZD-5672, Vicriviroc); a CCR2 and/or CCR5 antagonist (e.g. Cenicriviroc, CCX872, CVC, PF-04634817, BMS-813160); a connective tissue growth factor (CTGF) inhibitor or antagonist (e.g. FG-3019, RXI-109, PF-06473871); a galecttin-3 inhibitor (e.g. GR-MD-02), a vascular adhesion protein-1 (VAP1) inhibitor or antagonist (e.g. BTT-1023); a lysyl oxidase-like-2 (LOXL2) inhibitor or antagonist (e.g. copper binding ligand: D-penicillamine, β-aminopropionitrile; an anti-LOXL2 antibodies (e.g. AB0023, Simtuzumab); a metal chelating agent, preferentially a zinc, a copper and iron chelating agent, more preferentially an iron chelating agent (e.g. Deferoxamine, Deferiprone, Deferasirox); an $\alpha_4\beta_7$ integrin antagonist (e.g. Vedolizumab, Natalizumab, MLN02); a methionine aminopeptidase 2 (MetAP2) inhibitor (e.g. ZGN-839, TNP-470, Fumagillin), a sodium-glucose co-transporter 2 (SGLT2) inhibitor (e.g. Empagliflozin, Canagliflozin, Dapagliflozin, Ipragliflozin, Remogliflozin); a glucagon-like peptide or pseudopeptide or peptidomimetic analog (GLP-1 analog, e.g. Liraglutide, Semaglutide), an ileal apical sodium-dependent bile acid transporter inhibitor (ASBT, e.g. LUM002, Aramchol, Volixibat, A-4250); a fatty acid-bile acid conjugates (FABAC e.g. Aramchol); an acetyl-CoA carboxylase (ACC) inhibitor (e.g. NDI-010976, GS-0976, PF-05175157); a FGF21 variant (e.g. BMS-986171, BMS-986036); a Cathepsin B inhibitor (e.g. VBY-376); a p38 MAPK inhibitor (e.g. Fluorofenidone); a lipid peroxidation inhibitor (e.g. HX-1171, Besigomsin); a c-Jun N-terminal kinase 1 (JNK1) inhibitor (e.g. CC-90001); a fibroblast growth factor (FGF) inhibitor (e.g. Hydronidone, NN-9499); MIRN103 microRNA modulator MIRN107 microRNA modulator (e.g. RG-125); a hepatoprotectant (e.g. Silibinin, Silicristin, Silidianin, Malotilate, Urazamide, ZSP-1601); a 5-lipoxygenase (5-LOX) inhibitor (e.g. Tipelukast); a retinoid X receptor (RXR) agonist (e.g. Peretinoin); a ketohexokinase (KHK, also known as fructokinase) inhibitor (e.g. PF-06835919); an eotaxin-1 (chemiokine CCL11) modulator (e.g. Bertilimumab); a nerve growth factor stimulant (e.g. Inosine); a sterol regulatory element binding protein inhibitor (e.g. MDV-4463); a leukotriene A4 hydrolase inhibitor (e.g. Acebilustat); a cystic fibrosis transmembrane conductance regulator (CFTR) stimulant (e.g. Tezacaftor, FDL-176, GLPG-2222, ABBV-974, ABBV-2451, VX-152, VX-440, VX-983, QR-010, Ivacaftor, Ivacaftor deutared, Lumacaftor, PTI-428, PTI-801, PTI-808, PTINC-733, GLPG-2737, GLP-3067, QBW-251); a fructose-bisphosphatase (FBP1) inhibitor (e.g. MB-07803); a collagen inhibitor (e.g. Deupirfenidone); a Wnt signaling pathway inhibitor (e.g. SM-04646); a S-nitrosoglutathione reductase (GSNOR) inhibitor (e.g. N-6022); an activin inhibitor and/or a follicle stimulating hormone inhibitor (e.g. PB-01); an integrin alpha(V) antagonist (GSK-3008348); a phosphodiesterase 3 (PDE3) inhibitor (e.g. RPL-554); a phosphodiesterase 4 (PDE4) inhibitor (e.g. Asp9831, RPL-554); an interleukin receptor antagonist (e.g. Elubrixin); an adenosine A2B receptor (ADORA2B) antagonist (e.g. GS-6201); an A3 adenosine receptor (A3AR) agonist (e.g. Namodenoson); a neutrophil elastase inhibitor (e.g. DMP-777); an interleukin 13 (IL-13) and/or interleukin 4 (IL-4) inhibitor or monoclonal antibody (e.g. SAR-156597); an interleukin 13 (IL-13) antagonist (e.g. Tralokinumab); a carboxypeptidase U inhibitor (e.g. UK-396082); an epithelial sodium channel antagonist (e.g. GS-9411, P-1037, SPX-101); a telomerase activator (e.g. Neumomir); a serotonin 2B receptor antagonist (e.g. Metadoxine); a diacylglycerol acyltransferase type 1 (AGAT-1, PF-06865571) inhibitor (e.g. GSK-3008356); a hepcidin stimulant (e.g. M-012); a thyroid hormone receptor beta (TRB) agonist (e.g. VIA-3196); a catecholamine transferase inhibitor (e.g. Trepibutone); a P2Y2 agonist (e.g. Denufosol); a prostaglandin D2 synthase (PTGDS) inhibitor (e.g. ZL-2102); a recombinant human serum amyloid P (e.g. PRM-151); a dipeptidyl peptidase (DPP4) inhibitor (e.g. Sitagliptina); an antiparasitic (e.g. nitazoxanide); a dual G Protein-Coupled Receptor 40 (GPR40, also known as free fatty acid receptor 1 [FFA1]) agonist and G Protein-Coupled Receptor 84 (GPR84) antagonist (e.g. PBI-4547; PBI-4050); a hyperimmune bovine colostrum (e.g. IMM-124E); Teroo hydrochloride, DUR-928, DS-102, ZSP-1603, Malotilate, 5-aminosalicylic acid; acetylcysteine, 6-thioguanine, 6-mercaptopurine, azathioprine; a recombinant IL-10, Insulin, ursodeoxycholic acid, a Sphingosine 1-Phosphate signaling modulator (e.g. a sphingosine kinase modulator or inhibitor), a sphingolipid synthesis modulator or Colchicine.

A compound of any of Formulas (I), (II), (III), (IV) and/or (V) can also be used in combination with the following adjunct therapies:

Anti-nausea: NK-1 receptor antagonists: Casopitant (sold under the tradenames Rezonic® and Zunrisa® by GlaxoSmithKline), Aprepitant, Rolapitant; 5-HT3 receptor antagonists: Dolasetron, Granisetron Mirtazapine, Ondansetron, Palonosetron, Tropisetron; Dopamine antagonists: Alizapride, Domperidone, Metoclopramide, Prochlorperazine; Antihistamines $H_1$ histamine receptor antagonists: Cyclizine, Diphenhydramine, Dimenhydrinate, Doxylamine, Hydroxyzine, Meclizine, promethazine; and Cytoprotective agents: Amifostine (sold under the tradename Ethyol®), leucovorin (also known as calcium leucovorin, citrovorum factor and folinic acid); and Proton pump inhibitors agents: omeprazole, lansoprazole, Dexlansoprazole, Esomeprazole, Pantoprazole, Rabeprazole, Ilaprazole; and Corticosteroid agents: Dexamethasone, prednisolone, prednisone, methylprednisolone, hydrocortisone, triamcinolone.

An antidiabetic agent: Insulin, metformin; a peroxisome proliferator-activated receptor gamma agonist (PPAR including thiazolidinedione family drugs such as: rosiglitazone, pioglitazone, troglitazone, netoglitazone; Lyn kinase activators (e.g. MLR1023), A secretagogue drugs including Sulfonylureas derivatives (e.g. Tolbutamide, Acetohexamide, Chlorpropamide, Tolazamide, Glipizide, Glibenclamide, Glimepiride, Gliclazide, Glyclopyramide, Gliquidone) and nonsulfonylurea derivatives (e.g. Repaglinide, Nateglinide).

A blood pressure lowering medication: an angiotension converting enzyme (ACE) inhibitor (e.g. Lisinopril, Benazepril, Moexipril, Perindopril, Quinapril, Ramipril, Trandolapril) an angiotensin II receptor antagonist (e.g. Losartan, Candesartan, Valsartan, Telmisartan, Fimasartan, Azilsartan, Eprosartan, Irbesartan), a β1 receptor blocker (e.g. acebutolol, Atenolol, Betaxolol, Bisoprolol, Carteolol, Carvedilol, Esmolol, Labetalol, Metoprolol, Nadolol, Nebivolol, Penbutolol, Pindolol, Propanolol, Sotalol, Timolol), a calcium channel blocker (e.g. Amlodipine, Clevidipine, Diltiazem, Felodipine, Isradipine, Nicardipine, Nimodipine, Nisoldipine, Verapamil), a Renin inhibitor (e.g. Aliskiren).

A diuretic, including carbonic anhydrase inbitors (e.g. Acetazolamide, Diclorphanamide, Methazolamide), loop diuretics (e.g. Bumetanide, Ethacrynic acid, Torsemide, Fursemide, Ethacrynic acid), potassium sparing diuretics (e.g. Eplerone, triamterene, Spironolactone, Amiloride, Spironolactone), a thiazide diuretics (e.g. Indapamide, hydrochlorothiazide, Chlorthalidone, Metolazone, Methylclothiazide, Hydrochlorothiazide, Chlorothiazide, Methylclothiazide, Bendroflumethiazide, Polythiazide, Hydroflumethiazide) an other diuretics drugs with for example: Pamabrom, Mannitol.

A cholesterol lowering medication including 3-hydroxy-3-methylglutaryl coenzyme A reductase (HMG-CoA reductase) inhibitors (e.g. Atorvastatin, Cerivastatin, Fluvastatin, Lovastatin, Pravastatin, Pivastatin, Rosuvastatin, Simvastatin or nicotinic acid (e.g. Niaspan, Nicoar), Cholesterol absorption inhibitors (e.g. Colestipol, Cholestyramine, Colesevelam, Ezetimibe), a fibrate drug (e.g. Fenofibrate, Gemfibrozil), a Proprotein convertase subtilisin/kexin type 9 (PCSK9) inhibitor (e.g. Alirocumab, Evolocumab), or norUrsodeoxycholic acid, Chenodeoxycholic acid (Chenodiol).

None of the quotations of references made within the present disclosure is to be understood as an admission that the references cited are prior art that would negatively affect the patentability of the present disclosure.

In another aspect, the present disclosure relates to a kit comprising (a) a compound of Formulas (I), (II), (III), (IV) or (V) according to the present disclosure; and (b) an additional active substance as a pharmaceutical combination for simultaneous, separate or sequential use, for treating fibrosis-related diseases and/or autophagic diseases and/or of cathepsins B (CTSB), L (CTSL) and/or D (CTSD) related diseases.

In another aspect, the present disclosure relates to a kit comprising (a) a compound of Formulas (I), (II), (III), (IV) or (V) according to the present disclosure; and (b) an additional active substance as a pharmaceutical combination for simultaneous, separate or sequential use, for treating fibrosis-related diseases.

In another aspect, the present disclosure also provides a method for treating fibrosis-related diseases and/or autophagic diseases and/or of cathepsins B (CTSB), L (CTSL) and/or D (CTSD) related diseases, comprising administering to a patient in need thereof a therapeutically effective amount of the compound of Formula (I), of Formula (II), of Formula (III), of Formula (IV) or Formula (V).

The present disclosure also provides a method for treating fibrosis-related diseases such as pulmonary fibrosis, heart fibrosis, liver fibrosis, kidney fibrosis, intestinal fibrosis, eye fibrosis, prostate fibrosis, peritoneum membrane fibrosis and scleroderma, comprising administering to a patient in need thereof a therapeutically effective amount of a compound according to present disclosure or a pharmaceutical composition according to the present disclosure.

In certain embodiments, the invention provides a method of treating and/or substantially preventing fatty liver disease and/or liver fibrosis, for example treating non-alcoholic steatohepatitis (NAFLD), nonalcoholic steatohepatitis (NASH) and/or associated hepatic fibrosis, cirrhosis, liver transplantation in a patient, liver failure, heart failure, chronic alcohol exposure, hepatitis B virus infection, hepatitis C virus infection, hepatitis delta virus infection, Wilson's disease, alpha-1-antitrypsin deficiency, hemochromatosis, primary biliary cirrhosis, primary sclerosing chlolangitis, autoimmune hepatitis, diabetes, cirrhosis and non cirrhosis portal hypertension, biliary obstruction, iron overload (hemochromatosis), Budd-Chiari syndrome, heart failure, portal vein thrombosis, veno-occlusive disease of the liver and congenital hepatitis fibrosis by administering to a patient in need thereof a therapeutically effective amount of a compound described herein.

The invention also features a methods of increasing the liver function in a patient suffering from liver fibrosis, comprising the administering a therapeutically effective amount of a compound described herein to increase the liver function. Liver function can be assessed by measuring a parameter selected from the group consisting of serum transaminase level, prothrombin time, serum bilirubin level, blood platelet count, serum albumin level, improvement in portal sedge pressure, reduction in degree of ascites, reduction in level of encephalopathy and reduction in a degree of internal varices.

In some embodiments, disclosed methods are directed to treating patients having a diabetic (e.g. type 1, type 2 diabetes) or pre-diabetic condition. Wherein the patients under treatment are not obese or alternatively are suffering from obesity.

In some embodiments, the invention provides methods and compositions that include a second active agent or administering a second active agent. For example, a patient with Non-alcoholic steatohepatitis (NASH) can also have other conditions, such as diabetes, high blood pressure, high cholesterol levels and high fatty glycerides levels. Thus, contemplated herein are disclosed compounds in combination with at least one other agent that can be used to treat one or more of these conditions. For example, the second active agent can be, for example, an antidiabetic medication (e.g. metformin, and/or a thiazolidinedione such as rosiglitazone, pioglitazone, troglitazone or netoglitazone), an antioxidant (e.g. vitamin E, selenium or betaine), a blood pressure lowering medication (e.g. Lisinopril, Irbesartan, propranolol) a cholesterol lowering medication (e.g. atorvastatin, rosuvastatin, nicotinic acid).

In other embodiments, contemplated methods further include administering to the patient an active agent such as one or more of: amiodarone, antiviral drugs such as nucleoside and nucleotide analogs, aspirin, corticosteroids, non-steroidal anti-inflammatory drugs (NSAIDs) drugs, methotrexate, tamoxifen or tetracycline.

The present disclosure will be better understood with reference to the following non-limiting examples.

EXAMPLES

In order that this invention can be better understood, figures are joined wherein FIG. 1 shows the inhibition, by compound 2-3, of cathepsin B (CTSB) in HepG2 cell line after 6 hours and 24 hours of treatment. The inhibition by compound 2-3 of cathepsin B (CTSB) was statistically significant compare to the control when dosed at 2 µM, 4 µM for 6 hours treatment and 2 µM for 24 hours treatment (p<0.05).

Figure 2:
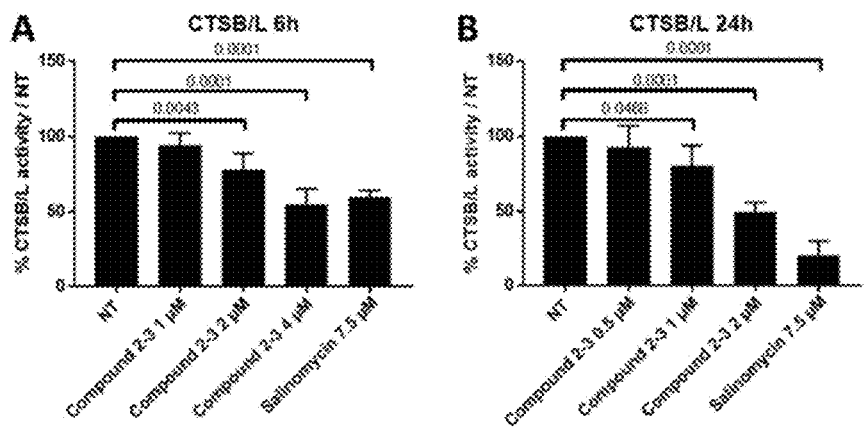
FIG. 2: describes the effect of compound 2-3 on cathepsins B and L (CTSB/L) activity (Mean±SD) after 6 hours and 24 hours of HepG2 cell line treatment.

FIG. 2 shows the inhibition, by compound 2-3, of cathepsins B and L (CTSB/L) in HepG2 cell line after 6 hours and 24 hours of treatment. The inhibition by compound 2-3 of cathepsins B and L (CTSB/L) was statistically significant compare to the control when dosed at 2 µM, 4 µM for 6 hours treatment and 1 µM, 2 µM for 24 hours treatment (p<0.05).

Figure 3:
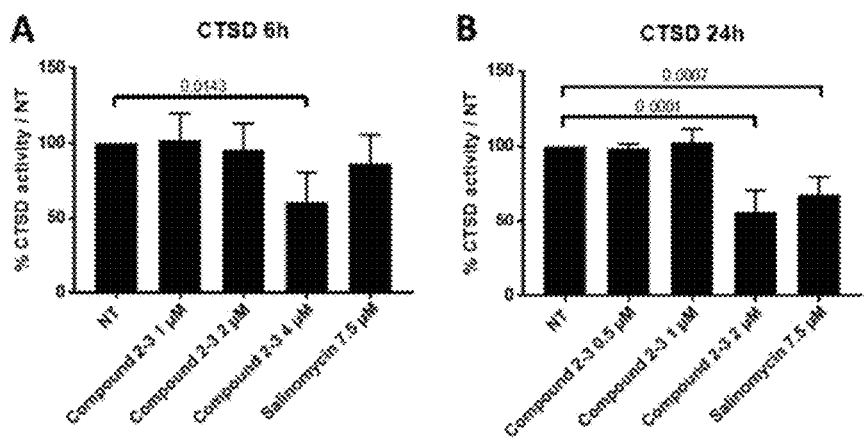
FIG. 3: describes the effect of compound 2-3 on cathepsin D (CTSD) activity after (Mean±SD) 6 hours and 24 hours of HepG2 cell line treatment.

FIG. 3 shows the inhibition, by compound 2-3, of cathepsin D (CTSD) in HepG2 cell line after 6 hours and 24 hours of treatment. The inhibition by compound 2-3 of cathepsin D (CTSD) was statistically significant compare to the control when dosed at 4 µM for 6 hours treatment and 2 µM for 24 hours treatment (p<0.05).

Figure 4:
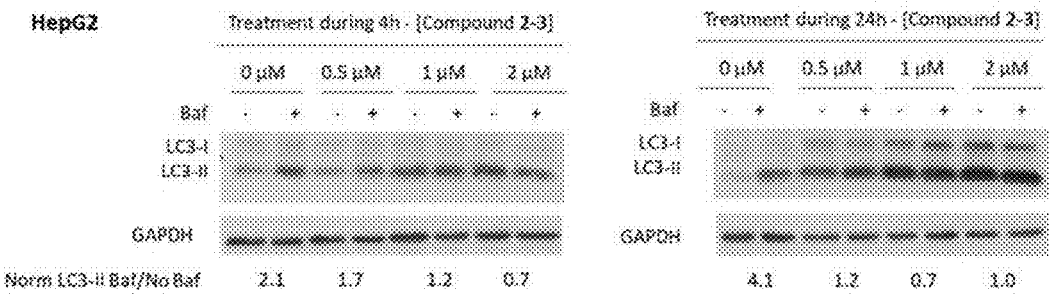
FIG. 4: Effect of compound 2-3 on the autophagy flux in two hepatocellular carcinoma cell lines, HepG2 and Huh7.
Figure 4:
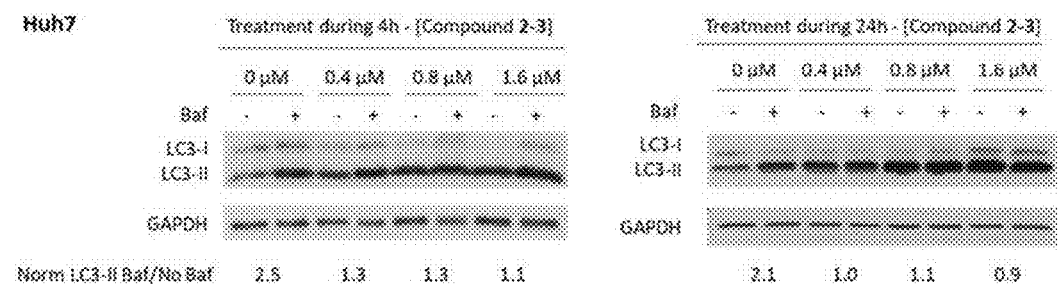

FIG. 4 shows an Immunoblot analysis of LC3-I and LC3-II levels in HepG2 (A) and Huh7 (B) cell lines incubated with control medium (0 µM of compound 2-3) or with indicated concentrations of compound 2-3 for 4 hours and 24 hours in the presence (Baf+) or absence (Baf−) of Bafilomycin. GAPDH immunoblotting was used as a loading control. The normalized LC3-II levels (ie. LC3-II signal/GAPDH signal ratios) were determined using the ImageJ software (NIH software, USA). As indicated below each lane, the autophagic flux was determined as the ratio between the normalized LC3-II levels with Bafilomycin (Baf+) and without Bafilomycin (Baf−) and was expressed in arbitrary units. Representative autoradiograms are shown.

This experiment shows the inhibition, by compound 2-3, of the autophagy flux in HepG2 and Huh7 cell lines after 4 hours and 24 hours of treatment. Accumulation of LC3-II being not enhanced in the presence of Bafilomycin (FIG. 4, comparison of lane with Bafilomycin (Baf+) with lane without Bafilomycin (Baf−)) supported that compound 2-3 inhibited the degradation of the cellular autophagic contents.

Figure 5:
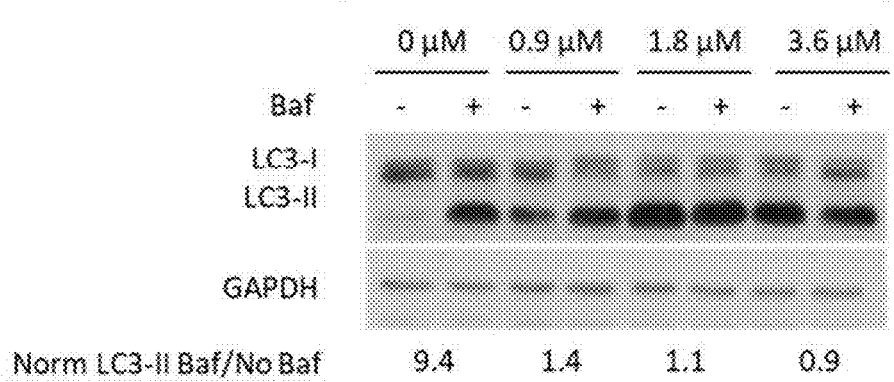
FIG. 5: Effect of compound 2-2 on the autophagy flux in RBE cell line (intrahepatic cholangiocarcinoma cell line).

FIG. 5 shows an Immunoblot analysis of LC3-I and LC3-II levels in RBE cell line incubated with control medium (0 µM of compound 2-2) or with indicated concentrations of compound 2-2 for 24 hours in the presence (Baf+) or absence (Baf−) of Bafilomycin. GAPDH immunoblotting was used as a loading control. The normalized LC3-II levels (ie LC3-II signal/GAPDH signal ratios) were determined using the ImageJ software (NIH software, USA). As indicated below each lane, the autophagic flux was determined as the ratio between the normalized LC3-II levels with Bafilomycin (Baf+) and without Bafilomycin (Baf−) and was expressed in arbitrary units. Representative autoradiogram is shown.

This experiment shows the inhibition, by compound 2-2, of the autophagy flux in RBE cell line after 24 hours of treatment. Accumulation of LC3-II being not enhanced in the presence of Bafilomycin (FIG. 5, comparison of lane without Bafilomycin (Baf−) with lane with Bafilomycin (Baf+)) supported that compound 2-2 inhibited the degradation of the cellular autophagic contents.

Figure 6:
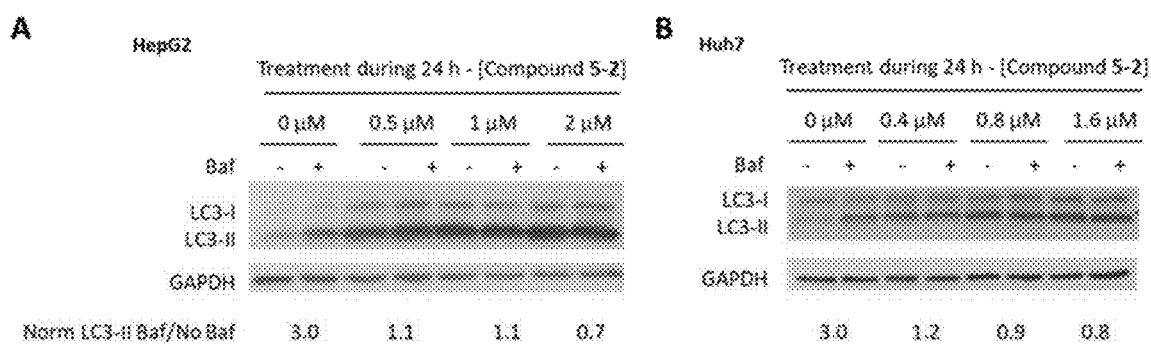
FIG. 6: Effect of compound 5-2 on the autophagy flux in two hepatocellular carcinoma cell lines, HepG2 and Huh7.

FIG. 6 shows Immunoblot analysis of LC3-I and LC3-II levels in HepG2 (A) and Huh7 (B) cell lines incubated with control medium (0 µM) or with indicated concentrations of compound 5-2 for 24 hours in the presence (Baf+) or absence (Baf−) of Bafilomycin. GAPDH immunoblotting was used as a loading control. The normalized LC3-II levels (ie. LC3-II signal/GAPDH signal ratios) were determined using the ImageJ software (NIH software, USA). As indicated below each lane, the autophagic flux was determined as the ratio between the normalized LC3-II levels with Bafilomycin (Baf+) and without Bafilomycin (Baf−) and was expressed in arbitrary units. Representative autoradiograms are shown.

This experiment shows the inhibition, by compound 5-2, of the autophagy flux in Huh7 and HepG2 cell lines after 24 hours of treatment. Accumulation of LC3-II being not enhanced in the presence of Bafilomycin (FIG. 6, comparison of lane with Bafilomycin (Baf+) with lane without Bafilomycin (Baf−)) supported that compound 5-2 inhibited the degradation of the cellular autophagic contents. Therefore, compound 5-2 is an inhibitor of the autophagy flux in HepG2 and Huh7 cellular environment.

Figure 7:
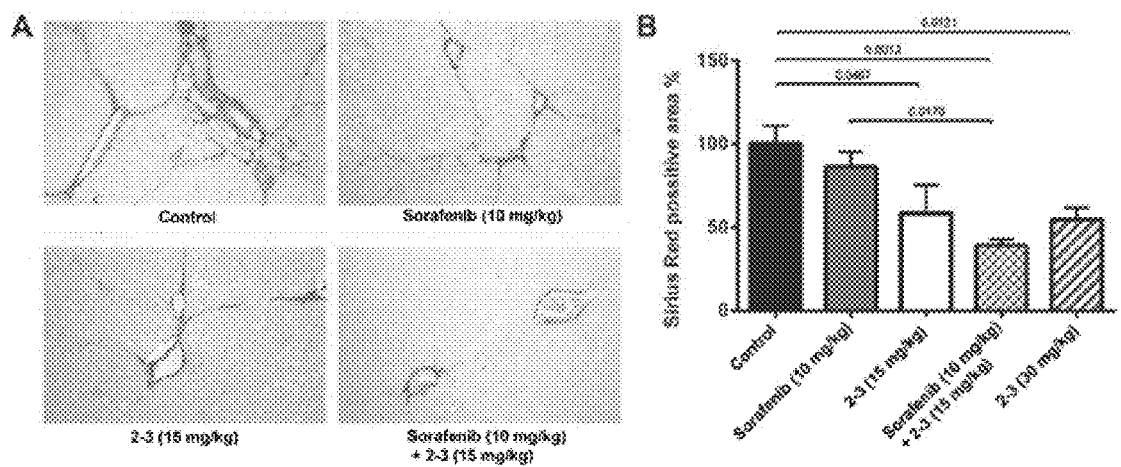
FIG. 7: Effect of compound 2-3 alone or in combination with Sorafenib on liver fibrosis in rats.

FIG. 7 shows in (A) Representative histological images of liver slices stained with Sirius red; and in (B) Quantification of Sirius red staining area per total area; control was set as 100%. Liver sections from rats receiving weekly intraperitoneal injections of DEN (50 mg/kg/week) for 14 weeks and then vehicle (group 1), Sorafenib 10 mg/kg/day (group 2), compound 2-3 15 mg/kg/day (group 3), Sorafenib 10 mg/kg/day+compound 2-3 15 mg/kg/day (group 4) and compound 2-3 15 mg/kg/day (group 5) during 6 weeks (FIG. 7A). These rat liver sections stained with Sirius red demonstrate that compound 2-3 alone or in combination with Sorafenib reduce significantly (p<0.05) and quantitatively (FIG. 7B) the liver fibrosis compared to the control group (group 1) or compared to the Sorafenib monotherapy group (group 2). The level of collagen fibers deposition in DEN cirrhotic rat model was reduced by 13.6% in the group 2 (Sorafenib, 10 mg/kg/day), by 41.0% (p<0.05) in the group 3 (compound 2-3, 15 mg/kg/day), by 60.7% (p=0.001) in group 4 (Sorafenib 10 mg/kg/day+compound 2-3 15 mg/kg/day) and by 45.3% (p=0.01) in group 5 (compound 2-3, 30 mg/kg/day), compared to the control group (group 1).

This experiment depicts clearly a strong reduction of the collagen fibers extracellular deposition in DEN induced cirrhosis rat animal model, when animals were dosed with compound 2-3 alone or in combination with Sorafenib a Raf-1, B-Raf, VEGFR-2, VEGFR3, PDGFRβ, Flt3 and c-Kit kinases inhibitor.

Figure 8:
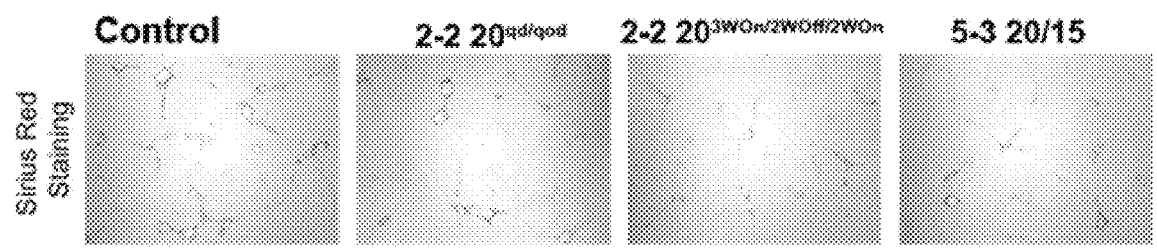
FIG. 8: Effect of compound 2-2 and compound 5-3 on liver fibrosis in rats.

FIG. 8 shows liver slices stained with Sirius red from rats receiving weekly intraperitoneal injections of DEN (50 mg/kg/week) during 13 weeks and then receiving during 7 weeks compound 2-2 according to two administration schedules (group 2 and group 3) and compound 5-3 according to one administration schedule (group 4). The group 2 received compound 2-2 from day 1 to 28 (4 weeks) 20 mg/kg/day via oral gavage administration (p.o.) and then at 20 mg/kg every 2 days from day 29 to 50 (3 weeks). The group 3 received compound 2-2 at 20 mg/kg/day during 3 weeks by oral gavage, followed by 2 weeks of washout and then received the compound 2-2 at 20 mg/kg/day during 3 weeks by oral gavage. The group 4 received compound 5-3 at 20 mg/kg/day from day 1 to 28 (4 weeks) by oral gavage and then from day 29 to 50 (3 weeks) at 15 mg/kg/day by oral gavage. At the end of the study, the Sirius red staining of liver slices demonstrated that the area of liver fibrosis (extracellular matrix proteins and collagen fibers deposition) was significantly reduced in groups treated by compound 2-3 (group 2, 3 and 4) compared to the control group (group 1).

The quantification of Sirius red staining showed that the area of fibrosis (collagen fibers deposition) was significantly (p<0.05) decreased in treated groups 2-2 $20^{qd/qod}$, 2-2 $20^{3WON/2WOFF/2WON}$ and 5-3 20/15 by 23%, 29% and 24%, respectively, compared to control group.

Figure 9:
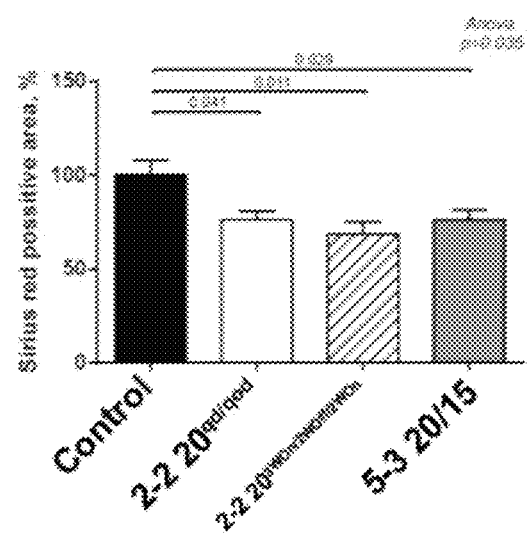
FIG. 9: Quantification by Sirius red staining of the effect of compound 2-2 and compound 5-3 on liver fibrosis in rats.

FIG. 9 shows the quantitative analysis of Sirius red staining of liver slices obtained from rats treated in group 1, 2, 3 and 4 (see FIG. 8). The decrease in deposition of extracellular matrix proteins including collagen fibers was quantitatively and significantly decreased in all 2-2 or 5-3 treated groups (group 2, 3 and 4) versus the control group (group 1). Compared to the control group (group 1), the level of collagen fibers deposition in DEN cirrhotic rat model was reduced by 23% (p=0.04) in the group 2 (compound 2-2), by 29% (p=0.01) in the group 3 (compound 2-2), and by 24% (p=0.03) in group 4 (compound 5-3). The decrease of collagen fibers deposition quantified in Sirius red staining was statistically significant (p<0.05) for all treated groups compared to the control group (see FIG. 9).

CONCLUSION

In cellulo data described firstly in examples 25, 26, 27 and 28 which showed that compounds described herein were potent inhibitors of the autophagy flux and cathepsins B, D and/or L proteolytic activity. In vivo studies (see example 29) demonstrated that compounds described herein are able to decrease in severity the liver cirrhosis or liver pre-cirrhosis lesion and allowed reduction in the rate of liver fibrosis progression and therefore reduce the risk of hepatocellular carcinoma, decompensated cirrhosis and/or improve liver function and morphology. As demonstrated herein, in subjects with liver cirrhosis or liver pre-cirrhosis lesions, administration of a therapeutically effective amount of a compound described herein and/or administration of a combination therapy including at least one compound described herein with at least one additional active agent results in decreases liver fibrosis and related diseases and progression.

Since the compounds described herein decrease the deposition rate of extracellular matrix components including collagen fibers, compounds described herein are claimed with anti-fibrotic activity in vivo including human being or animal in need thereof for treating and/or preventing pathological fibrosis of various organs and tissues including but not limited to pulmonary fibrosis, liver fibrosis, heart fibrosis, kidney fibrosis, eyes fibrosis, prostate fibrosis, peritoneum membrane fibrosis.

The following examples are set forth. These examples are for the purpose of illustration only, and are not to be construed as limiting the scope of the invention in any manner.

SYNTHETIC EXAMPLES

General Synthesis for Preparing the Compounds Described Herein

The invention further provides a general chemical process for preparing the compounds of Formula (I) as defined above.

The compounds of Formula (I) according to the invention can be prepared using various organic chemistry methods, including those known to those skilled in the art.

In some embodiments, synthesis of the a compound of Formula (I), (II), (III), (IV) or (V) according to the present disclosure can be carried out following the general synthesis procedure which comprises the following steps (see also scheme 1, 2, 3 and 4):

Step 1: Reacting of a compound of formula (I-a) having the following structure:

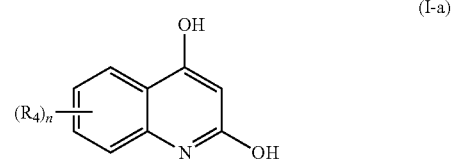

(I-a)

Wherein $R_4$ and n are as described under general Formula (I),

With a halogenating agent or halogenating or sulfonate esterification conditions in order to prepare the corresponding halogenated or pseudo-halogenated derivatives of general formula (I-b) having the following structure:

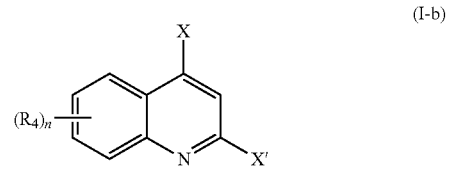

(I-b)

Wherein $R_4$ and n are as described under the general Formula (I)

and X, X' is a halogen atom as described above preferably a —Cl, —Br or —I and more preferably a —Br or —I, or a pseudohalides living group (e.g. preferentially a sulfonate ester, for example a trifluoromethanesulfonate and the like), Step 2: Reacting of the intermediate compound of formula (I-b) with an amino derivative of formula (I-c) having the following structure:

(I-c)

Wherein $L_1$, $R_1$ and $R_5$ are as described under the general Formula (I)

To form an intermediate compound of formula (I-d) having the following structure:

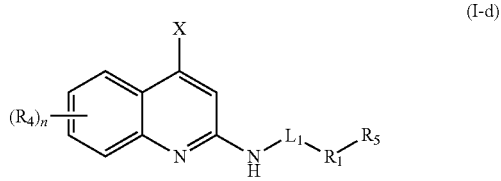
(I-d)

Wherein $R_4$, $L_1$, $R_1$ and $R_5$ and n are as described under the general Formula (I)

and X is a halogen atom as described above or a pseudohalides living group as described above.

Step 3: Reacting of the intermediate compound of formula (I-d) with a cyclic amino derivative of formula (I-e) having the following structure:

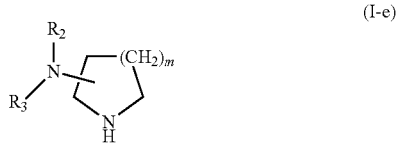
(I-e)

Wherein $R_2$, $R_3$ and m are as described under the general Formula (I)

To form the final compound of Formula (I) having the following structure:

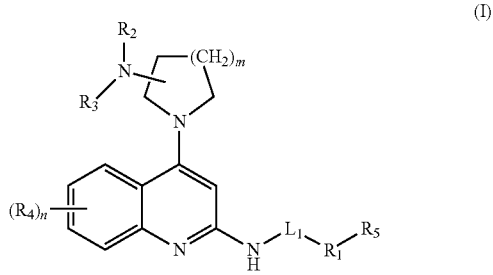
(I)

Wherein $L_1$, $R_1$, $R_2$, $R_3$, $R_4$ and $R_5$, n and m are as described under the general Formula (I)

Scheme 1

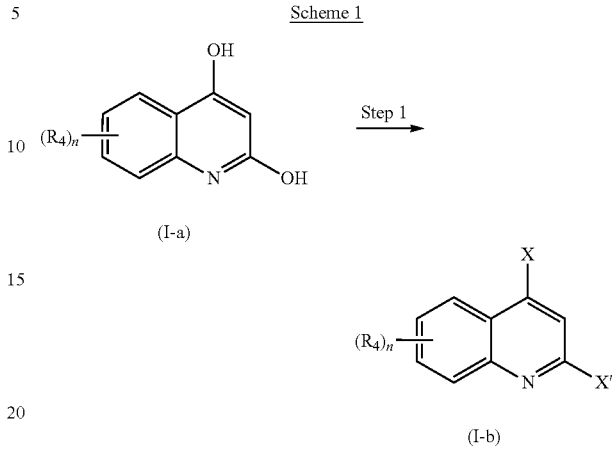

The step 1 of this general synthesis procedure can be carried out under various standard procedures, well known from the art, corresponding to the halogenation of hydroxyl substituted heteroaryl, wherein the OH is substituted by a halogen atom, preferably by —Cl, —Br or —I. In particular, Chloride derivatives can be obtained under standard halogenation conditions using $POCl_3$ neat (from 0.5 to 20 molar equivalents) under reflux until the consumption of the starting material. In some instance, the chlorination reaction can be done in an inert solvent (e.g. dichloromethane, chloroform, dichloroethane, toluene, chlorobenzene and the like) and $POCl_3$ is use as molar equivalent from 0.5 to 20 equivalents preferably from 0.5 to 10 equivalents. In such conditions, a proton sponge can be used such as dimethylaniline, pyridine or diisopropylethylamine and the like. The chlorination under $POCl_3$ conditions can be catalyzed using a disubstituted formamide, typically N,N-dimethylformamide (DMF), N-formylpiperidine, N-formylmorpholine and the like. $POCl_3$ can be substituted by $SOCl_2$ or oxalyl chloride using a catalytic quantity of a N,N-disubstituted formamide (e.g. dimethylformamide, N-formylpiperidine, N-formylmorpholine and the like) neat or in an inert solvent (e.g. dichloromethane, chloroform, dichloroethane, toluene, chlorobenzene and the like). The reactions can proceed from a temperature ranging from 30° C. to 110° C., more preferably from 40° C. to refluxing conditions. 2,4-dibromoquinoline derivatives can be obtained using a brominating agent such as $PBr_3$ neat or in an inert solvent (e.g. dichloromethane, chloroform, dichloroethane, toluene, chlorobenzene and the like) using a molar equivalent of $PBr_3$ from 0.5 to 20 equivalents preferably from 0.5 to 5 equivalents and at temperature of reaction conditions ranging from room temperature to reflux, preferably from 50° C. to refluxing conditions. The couple $PBr_3$—N,N-dimethylformamide can equally be advantageously used for such reaction. Selective bromination can proceed under more mild conditions using N-Bromosuccinimide and triphenylphosphine or using a water soluble phosphine and the like, using from 1 to 6 equivalents of the bromonating agent, preferably from 2 to 5 equivalents. The reaction can proceed in an inert solvent (e.g. tetrahydrofuran, 2-methyltetrahydrofuran, dioxane and the like). Using such bromination conditions, the reaction can proceed from a temperature ranging from 0° C. to refluxing conditions, preferably from 20° C. to 60° C. In some instance, N-Bromosuccinimide brominating agents can be substituted by N-Bromosaccharin, N-Bromophtalimide, 1,3-Dibromo-5,5-dimethylhydantoin and the like. Iodination can proceed using N-Iodosuccinimide and triphenylphosphine or with a water soluble phosphine and the like, using from 1 to 6 equivalents of the iodinating agent, preferably from 2 to 5 equivalents. In such conditions, other iodinating agents, such as N-Iodophtalimide, 1,3-Diiodo-5,5-dimethylhydantoin can be used. 2,4-dihalogenoquinoline of formula (I-b) can be equally obtained by halogen exchange for example from chloride to iodide derivatives using, for example but not limited to, NaI—AcCl in an inert solvent (e.g. $CH_2Cl_2$, $CHCl_3$, dichloroethane, acetonitrile and the like) or NaI in acetonitrile or acetone, or under phase transfer catalysis well known to those skilled in the art.

Sulfonic ester (pseudo-halide derivatives of formula I-b) can be obtained from the hydroxyquinoline by reaction with sulfonic chloride derivatives (e.g. methanesulfonyl chloride, ethanesulfonyl chloride, benzenesulfonyl chloride, para-toluenesulfonyl chloride and the like) or using sulfonic anhydride (e.g. methanesulfonic anhydride, trifluoromethanesulfonic anhydride, para-toluenesulfonic anhydride, 3-chloro-4-methylbenzenesulfonic anhydride, nonafluorobutansulfonic anhydride and the like) in presence of a non-nucleophile base (such as a proton sponge or substituted amine usually used in organic chemistry, e.g. 2,6-lutidine, collidine, N,N,N',N'-Tetramethyl-1,8-naphthalenediamine, triethylamine, N,N-Diisopropylethylamine and the like). In some instance, a catalytic pyridine analog can be used (e.g. pyridine, 4-(dimethylamino)pyridine and the like). The reaction can proceed in an inert solvent (e.g. $CH_2Cl_2$, $CHCl_3$, dichloroethane, tetrahydrofuran, 2-methyltetrahydrofuran, dioxane and the like) at a temperature ranging from −80° C. to refluxing conditions, preferably from 0° C. to 50° C. and more preferably for most reactive sulfonate from −80° C. to 30° C. Those skilled in the art will appreciate that other synthetic routes can be used to synthesize the compounds of formula (I-b). Although specific reagents are depicted and discussed in the Figures and general procedures, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

Notes: Compound of formula (I-a) (2,4-hydroxy-quinoline derivatives, eventually bearing one or more of the group $R_4$ can be either commercially available or prepared according to the methods known to those skilled in the art. In some instances, compounds of formula (I-a) can independently bear one or more particular chemically reactive functional groups (e.g. amine, hydroxy, thiol, carboxy, aldehyde, etc.) that can compete with the desired reaction and lead to undesired side-reaction products. In order to prevent the formation of undesired bonds and side reaction products, a functional group protection strategy can be used. This group protection strategy is well-known to those skilled in the art. Thus, protecting groups can be used to temporarily mask the particular chemically reactive functional group to allow the formation of the desired intermediate or the final compound. As used in the specification, the terms "protected," "protecting group" and "protective group" refer to the presence of a moiety (i.e., the protecting group) that prevents or blocks the reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any at all. Protecting groups known in the art can be found in Kocienski, P. PROTECTING GROUP $3^{rd}$ ed.; Georg Thieme Verlag (2003) or Greene, T. W., Wuts, P. G. M. PROTECTIVE GROUPS IN ORGANIC SYNTHESIS, $4^{st}$ ed., John Wiley & Sons, Inc., New York, N.Y. (2006).

Step 1 (See Scheme 1, Vide Supra), General Procedure for Synthesis of an Optionally Substituted 2,4-dichloroquinoline of Formula (I-b1):

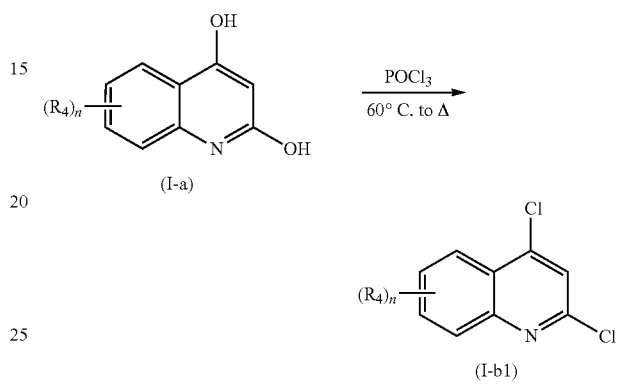

To a stirred solution of 2,4-dihydroxyquinoline derivative (I-a, 1.0 eq.) in an inert solvent (eg. dichloromethane, chloroform, dichloroethane, toluene, chlorobenzene and the like, preferably chloroform, dichloroethane, toluene from 1 to 10 volumes) was added dropwise Phosphoryl chloride (from 5 to 40 eq., preferably from 5 to 20 eq., the charging rate was controlled by the evolution of the internal reactor temperature). The resulting mixture was stirred between 60° C. to 110° C. (dependent of the substrate reactivity) until the reaction completion. Then, the reaction mixture was allowed to reach room temperature and poured into ice water and extracted with EtOAc. The combined organic layers were dried over $Na_2SO_4$, filtered and concentrated under reduced pressure to give a crude compound which was purified by flash chromatography. In some other conditions, the reaction can proceed in solvent free conditions, in such cases the quantity of $POCl_3$ will be adjusted in order to obtain a homogenous reaction mixture. In some other conditions, after reaction completion, the reaction mixture was allowed to reach room temperature and poured into ice water. The resulting cake was washed with water and with potentially additional washing using an organic solvent (e.g., methanol, ethanol, iso-propanol, butanol). The resulting solid was dried and used in the next step without further purification.

In some more specific conditions the reaction can be carried out as follow: To a 2,4-dihydroxyquinoline derivative (I-a, 1.0 eq.) was added dropwise under agitation $POCl_3$ (5 eq., charging rate was adjusted in order to maintain the interal reactor temperature <15° C.). The resulting mixture was stirred and heated under reflux until reaction completion. Then, the reaction mixture was cooled, concentrated under reduced pressure and co-evaporated twice times with toluene. The resulting residue was then taken up with an organic solvent (e.g. EtOAc, MeOAc, t-BuOMe, $CH_2Cl_2$), washed with a 1N NaOH aqueous solution, water, brine, was dried over $MgSO_4$, filtered and concentrated under reduced pressure the give the title compound corresponding to 2,4-dichloroquinoline derivatives (1-b1).

Scheme 2

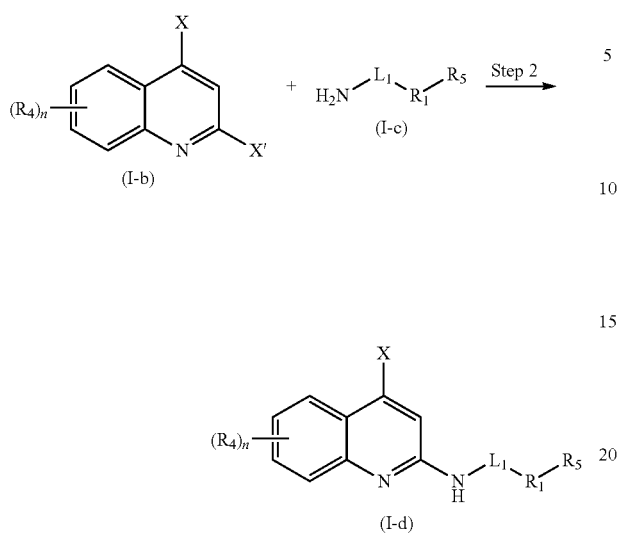

Step 2 (See Scheme 2, Vide Supra), General Procedure for Synthesis of a Substituted 2-Amino-4-dichloroquinoline of Formula (I-d1):

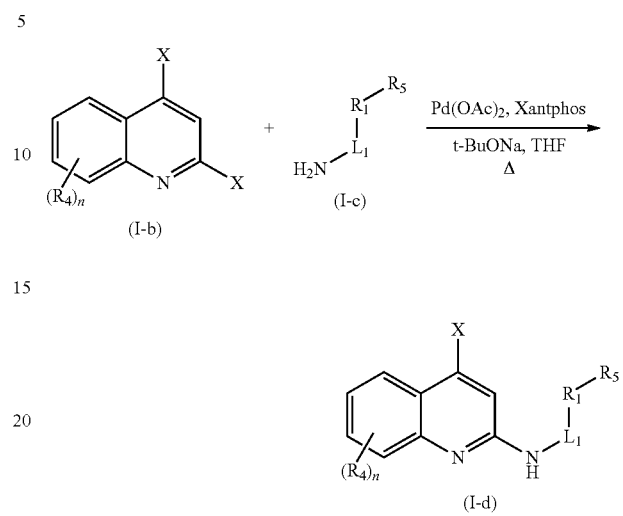

The step 2 of this general procedure can be carried out under various standard procedures, known to those skilled in the art, for hetero coupling between a substituted heteroaryl by a halogen or a pseudohalide (preferentially a sulfonate ester) of formula (I-b) with an amino derivative of formula (I-c). The chemical synthesis procedure can be carried out under standard Buchwald (or Buchwald-Hartwig) amination conditions (Ruiz-Castillo, P., Buchwald, S. L. Chem. Rev. 2016 (116), 12564-12649; or Ge, S. et al. J. Am. Chem. Soc. 2014 (136), 1617-1627; or Surry, D. S., Buchwald S. L. Chemical Science 2011 (2), 27-50), in particular in the presence of a palladium catalyst (e.g. palladium acetate (Pd(OAc)$_2$), Tris(dibenzylideneacetone)dipalladium(O) Pd$_2$(dba)$_3$, Allylpalladium(II) chloride dimer [(allyl)PdCl]$_2$ Crotylpalladium(II) chloride dimer [(crotyl)PdCl]$_2$ cinnamylpalladium(II) chloride dimer [(cinnamyl)PdCl]$_2$ and the like) of a ligand, preferably a bidentate organophosphorus ligand (e.g. Xantphos [161265-03-8], BINAP [98327-87-8], RuPhos [787618-22-8], SPhos [657408-07-6], XPhos [564483-18-7], BrettPhos [1070663-78-3] and the like, preferably a phosphine ligand having a wide bite angle) and of an organic or an inorganic base (e.g; sodium tert-butoxide, sodium ethoxide, sodium methoxide, potassium tert-butoxide, sodium acetate, cesium carbonate, sodium carbonate, potassium carbonate, potassium phosphate and the like), in an inert solvent (e.g. toluene, tetrahydrofuran (THF), dimethoxyethane (DME), N,N-dimethyl-formamide (DMF), dimethyl sulfoxide (DMSO), N-methyl-2-pyrrolidone (NMP), 1,4-dioxane, 2-Methyltetrahydrofuran (MTHF), ethanol, methanol, water and any mixtures thereof). The Step 2 can be carried out from room temperature up to a temperature of 150° C., preferably from 40° C. to 120° C., more preferably from 60° C. to 110° C. The step 2 can be carried out under microwave irradiation or not.

Note: Compound of formula (I-b) (2,4-dihalo-quinoline or 2,4-dipseudohalo-quinoline), eventually bearing the group R$_4$ and compound of formula (I-c) (amino derivative) can be either commercially available or prepared according to methods known to those skilled in the art.

To a solution under nitrogen or argon gas of starting material (I-b) (10 mmol) in dry MTHF (20 ml) (THF, Toluene, DMF, DME, NMP, Dioxane, water and any mixtures thereof can equally be used in such cross coupling reactions) was added amine derivative (I-c, from 1.1 to 5 eq. preferably 1.1 to 2.0) and a base such as t-BuONa (from 1.1 to 7 eq., preferably from 1.5 to 5 eq.). The resulting mixture was degassed 10 min with nitrogen or Argon, and then Xantphos or other bidentate phosphine ligand usually used in amino aryl or amino heteroaryl Pd assisted cross coupling reaction (e.g. 10 mmol, 0.1 eq.) and Pd(OAc)$_2$ (e.g. 5.0 mmol, 0.05 eq., Pd can be used from 0.001 eq. to 0.20 eq., preferably from 0.01 to 0.05 eq.) (preferably 0.5 eq. of "Pd" is used regarding bidentate phosphine ligand used such as Xantphos, BINAP, SPhos, XPhos or BrettPhos and other Pd(II) sources can be used, but preferentially Pd(OAc)$_2$) were added and the reaction mixture was heated under reflux until completion of the reaction. The reaction mixture was then cooled to room temperature and concentrated under reduced pressure or quenched and then partitioned with brine and water non miscible solvent such as EtOAc or DCM. The residue was partitioned between brine and EtOAc and the aqueous layer was extracted with EtOAc. The combined organic layers were dried over MgSO$_4$, filtered and concentrated under reduced pressure to give a crude mixture. The crude product was purified by flash chromatography to give the 2-(substituted amino)-4-chloroquinoline (I-d).

In some specific conditions the reaction can be carried out as follow:

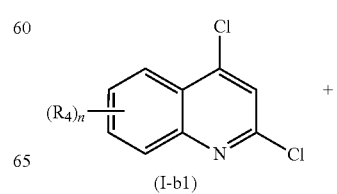

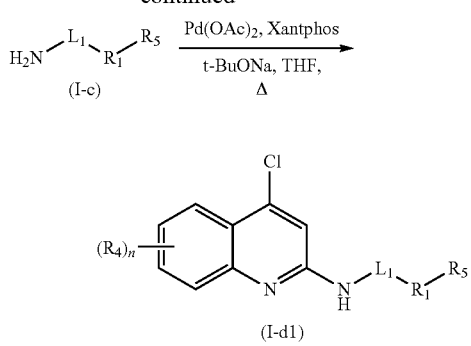

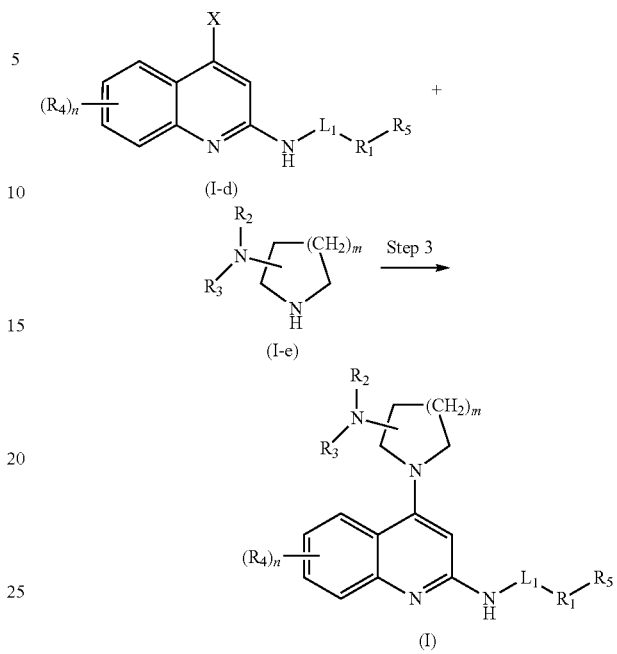

To a solution under nitrogen or argon gas of 2,4-dichloroquinoline derivative (I-b1, 1 eq.) in dry THF (from 2 to 10 ml per mmol of 2,4-dichloroquinoline I-b1) (Toluene and Dioxane solvents can equally be used in such reactions) was added amine derivative (I-c, from 1 to 3 eq. preferably from 1.05 to 1.5 eq.) and t-BuONa (from 1.1 to 5 eq. preferably from 1.5 to 3.0 eq.) (Other base sources can be used in such reaction like $K_2CO_3$, $K_3PO_4$). The resulting mixture was degassed 10 min with nitrogen or Argon, then Xantphos or other bidentate phosphine ligand usually used in amino aryl cross coupling or amino heteroaryl Pd assisted cross coupling reaction (from 0.005 to 0.3 eq. preferably from 0.02 to 0.2 eq.) and $Pd(OAc)_2$ (0.5 eq. of "Pd" was used regarding bidentate phosphine ligand used, other Pd(II) sources can be used see above, but preferentially $Pd(OAc)_2$) were added and the resulting reaction mixture was heated from 40° C. to reflux (preferably from 60° C. to reflux) until completion of the reaction. The reaction mixture was then cooled to room temperature and quenched with brine. Then, the resulting mixture was extracted with EtOAc and the combined organic layers were dried over $MgSO_4$, filtered and concentrated under reduced pressure to give a crude mixture. The crude product was purified by flash chromatography or preparative HPLC to give the 2-(substituted amino)-4-chloroquinoline (I-d1).

In some more specific conditions the reaction can be carried out as follow:

To a solution, under nitrogen or argon gas, of 2,4-dichloroquinoline derivative (I-b1, 1 eq.) in dry THF (2 ml per mmol of compound I-b1) were added amine derivative (I-c, 1.10 eq.) and $K_2CO_3$ (2.8 eq.). The resulting mixture was degassed 10 minutes with nitrogen gas or argon gas, then Xantphos (0.10 eq.) and $Pd(OAc)_2$ (0.05 eq.) were added and the resulting reaction mixture was heated under reflux for 2 hours. The reaction mixture was then cooled to room temperature and concentrated under reduced pressure. The residue was partitioned between water and EtOAc and the aqueous layer was extracted with EtOAc. The combined organic layers were washed with brine and dried over $MgSO_4$, filtered and concentrated under reduced pressure to give a residue. The crude product was purified by flash chromatography to give the title compound corresponding to 2-(substituted amino)-4-chloroquinoline (I-d1).

The amino substituent derivative (I-c) can be equally assembled and obtained using palladium assisted Aryl/Aryl coupling or palladium assisted Aryl/amino-aryl cross coupling reactions from methods known to those skilled in the art.

The step 3 of this general procedure can be carried out under various standard procedures, known to those skilled in the art. The hetero coupling between compounds of general formula (I-d) and amino substituted cyclic secondary amines of general formula (I-e) can be carried out under standard Buchwald methods (as described above) or under palladium free conditions. In particular, compound (I-d) which bears a living group in position 4 of the quinoline moiety (a halide or pseudo-halide, preferably a chlorine, bromine, triflate, tosylate or mesylate, more preferably a chlorine or bromine) can be subjected to a nucleophilic attack from cyclic secondary amines. Compounds of general formula (I-d) can undergoes a nucleophilic addition in position 4 of the quinoline moiety followed by the elimination of the leaving group (typically a nucleophilic substitution in aromatic system (SNAr)). The reaction can proceed with an excess of cyclic secondary amines of general formula (I-e) which can be used as nucleophilic agent and base, at the same time, since the reaction procession will generate $H^+$ as byproduct. Otherwise, an additional base can be used such as an organic base or an inorganic base. The organic base can be taken preferentially from the amino base family (e.g. triethylamine, N,N-Diisopropylethylamine, 1,4-diazabicyclo[2.2.2]octane, 1,4-diazabicyclo[2.2.2]octane, 1,5-Diazabicyclo[4.3.0] non-5-ene, 9-Azajulolidine and the like) or from an alkoxide (e.g. Lithium tert-butoxide, Lithium ethoxide, Lithium isopropoxide, Lithium methoxide or their sodium or potassium respective salt forms and the like). Moreover, an inorganic base can be used in such nuclephilic reaction, taken from carbonate or phosphate bases (e.g. lithium carbonate, sodium carbonate, potassium carbonate, cesium carbonate, lithium hydroxide, sodium hydroxide, potassium hydroxide, trilithium phosphate, trisodium phosphate, tripotassium phosphate and the like). The reaction can be carried out preferentially in an inert polar solvent (e.g. acetonitrile, tetrahydrofuran, N,N-dimethylformamide, N,N-dimethylacetamide, N-methyl-2-pyrrolidinone, dimethylsulfoxyde and the like) at a temperature ranging from 25° C. to 200° C.

(preferentially from 50° C. to 160° C.) and the coupling reaction can processed under microwaves irradiation or not.

Note: Compound of formula (I-e) (amino substituted cyclic secondary amines), eventually bearing the group $R_2$ and $R_3$ can be either commercially available or prepared according to methods known to those skilled in the art.

Step 3 (See Scheme 3, Vide Supra), General Procedure for Synthesis of a Substituted 2-substituted-amino-4-substituted amino-cycloaminoquinoline of Formula (I):

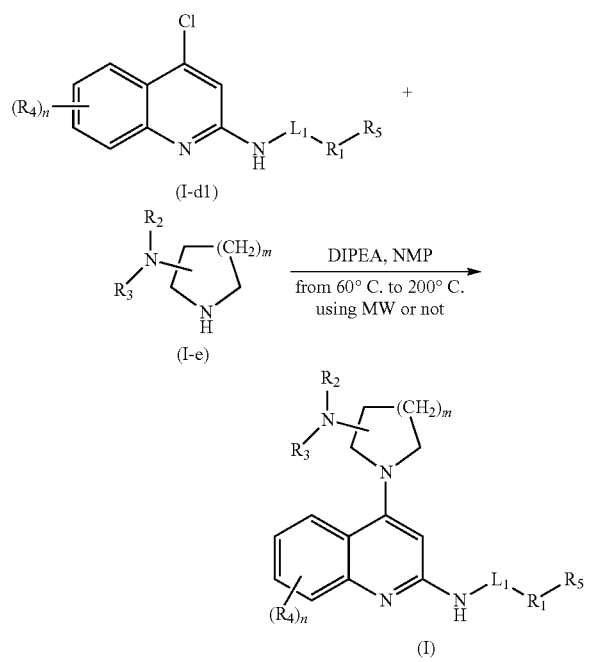

To a solution of 2-(substituted-amino)-4-chloroquinoline (I-d1, 1.0 eq.) and the aminosubstituted secondary cycloamine (I-e, from 1.0 to 3.0 eq. preferably from 1.02 to 2.0) in NMP (1 to 10 ml per mmol of I-d1, other solvents such as DMF can be used) was added N,N-Diisopropylethylamine (DiPEA, 1.1 to 5 eq. preferably from 1.2 to 2.5 eq. in some specific examples from 1.6 to 2.0 eq.). In some reaction and reactivity conditions other organic or mineral bases can be used (see above). Then, the resulting reaction mixture was heated until reaction completion at temperature ranging from 60° C. to 200° C., preferably from 80° C. to 160° C., dependent of the substrate reactivity. In some reaction and reactivity conditions, the reaction can be assisted with non-thermal microwave effect using a microwave oven. Then, the reaction mixture was cooled, diluted with a 1N NaOH aqueous solution and the resulting mixture was extracted with EtOAc. The combined organic layers were washed with brine, dried over $MgSO_4$, filtered and concentrated under reduced pressure to give a residue. Then, the crude product was purified by flash chromatography or preparative HPLC to give the substituted 2-substituted-amino-4-substituted amino-cycloaminoquinoline base form of general Formula (I).

In some more specific conditions the reaction can be carried out as follow:

To a solution of 2-(substituted-amino)-4-chloroquinoline (I-d1, 1.0 eq.) and the aminosubstituted secondary cycloamine (I-e, 1.2 eq.) in NMP (2 ml per mmol of I-d1) was added N,N-Diisopropylethylamine (DiPEA, 1.8 eq.). Then, the resulting reaction mixture was heated until reaction completion at 140° C. Then, the reaction mixture was cooled, diluted with a 1N NaOH aqueous solution and the resulting mixture was extracted with EtOAc. The combined organic layers were washed with brine, dried over $MgSO_4$, filtered and concentrated under reduced pressure to give a residue. Then, the crude product was purified by flash chromatography to give the title compound corresponding to the substituted 2-substituted-amino-4-substituted amino-cycloaminoquinoline base form of general Formula (I).

The compound can be converted into a hydrochloride salt by dilution in DCM and addition of a 2N HCl solution in $Et_2O$ or HCl solution in EtOH (from 1 to 4 eq.). The resulting solution was stirred for 15 min at room temperature and filtered off or concentrated under reduced pressure. The obtained hydrochloride salt was dissolved in $H_2O$ and was then freeze dried to give the title compound corresponding to the substituted 2-substituted-amino-4-substituted amino-cycloaminoquinoline hydrochloride salt form of general Formula (I).

Scheme 4

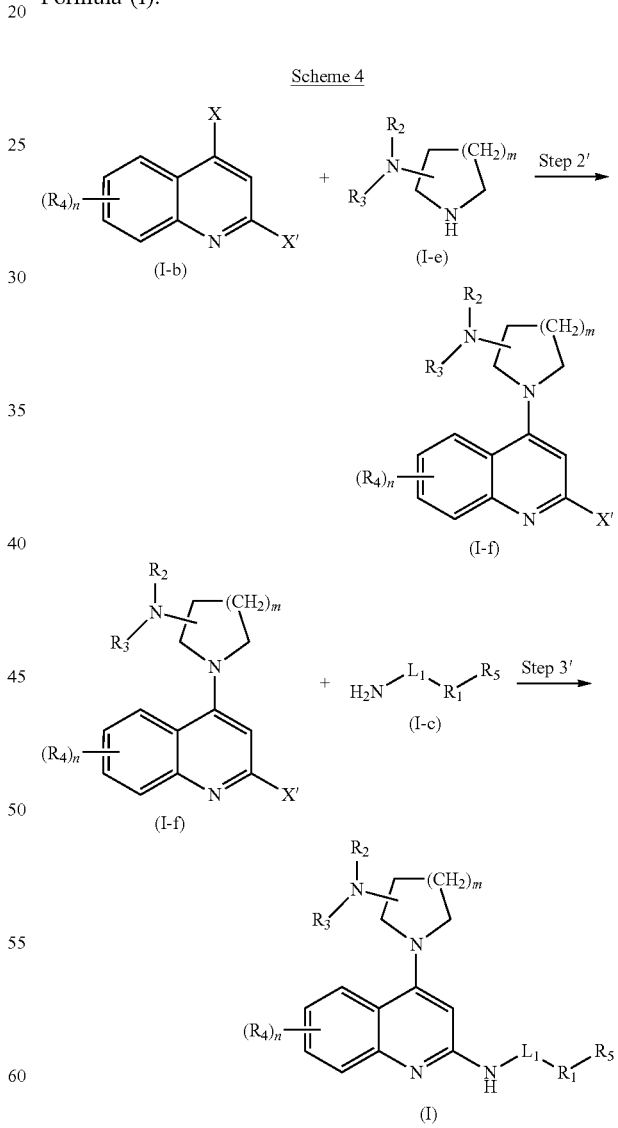

Dependent of the reactive groups bearing by compounds of general formula (I-e) and (I-c), the protection/deprotection strategy involved and their respective reactivity, the compounds of Formula (I) according to the invention, can also be synthesized according to the strategy of the chemical synthesis depicted in scheme 4 wherein the addition of the substituted cyclic secondary amines of general formula (I-e) occurs firstly and the coupling of the amino derivatives of formula (I-c) occurs secondly. The steps 2' and 3' can be carried out as previously described for respectively step 3 and step 2.

Notes: In some instances, compounds of formula (I-a) to (I-f) can independently bear one or more particular chemically reactive functional groups (e.g. amine, hydroxy, thiol, carboxy, aldehyde, etc.) that can compete with the desired reaction and lead to undesired side-reaction products. In order to prevent the formation of undesired bonds and side reaction products, a functional group protection strategy can be involved. This group protection strategy is well-known to those skilled in the art. Thus, protecting groups can be used to temporarily mask the particular chemically reactive functional group to allow the formation of the desired intermediate or the final compound. As used in the specification, the terms "protected," "protecting group" and "protective group" refer to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Kocienski, P. PROTECTING GROUP $3^{rd}$ ed.; Georg Thieme Verlag (2003) or Greene, T. W., Wuts, P. G. M. PROTECTIVE GROUPS IN ORGANIC SYNTHESIS, $4^{st}$ ed., John Wiley & Sons, Inc., New York, N.Y. (2006).

In the schemes 1, 2, 3 and 4 above, the starting compounds (e.g. compounds (I-a), (I-b), (I-b1), (I-c), (I-d), (I-d1), (I-e)) and the chemical intermediates, when their method of preparation is not described, are commercially available, or their chemical synthesis are described in the literature or else can be prepared according to methods which are described herein or which are known to those skilled in the art.

The Examples provide exemplary methods for preparing compounds of Formulas I, II, III, IV and V. Those skilled in the art will appreciate that other synthetic routes can be used to synthesize the compounds of Formulas I, II, III, IV and V. Although specific starting materials and reagents are depicted and discussed in the Figures and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

The invention includes compounds of the Formula (I) and the pharmaceutically acceptable salts thereof, wherein $L_1$ is any element in the $L_1$-Matrix (Table 5), $R_1$-$R_5$ is any element in the $R_1$-$R_5$-Matrix (Table 6), $R_2$-$R_3$ are any element in the $R_2$-$R_3$-Matrix (Table 7), $R_4$ is any element in the $R_4$-Matrix (Table 8).

The following compounds of general Formula (I) can be prepared according to the general procedures (vide supra) and the procedures (vide infra) disclosed in the and/or chemical procedures which are known to those skilled in the art.

provided that:

n can represent an equal integer which can have any one of the values 0, 1, 2, 3 or 4, preferably 0, 1, 2 or 3, more preferably 0, 1 or 2 still more preferably 0 or 1.

m can represent an equal integer which can have any one of the values 1, 2 or 3 preferably 1 or 2, more preferably 2.

p can represent an equal integer which can have any one of the values 1, 2, 3, 4 or 5, preferably 1, 2, 3 or 4, more preferably 1, 2 or 3, still more preferably 1 or 2.

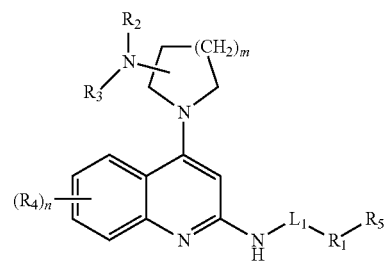

(I)

Matrix tables $L_1$, $R_1$-$R_5$, $R_2$, $R_3$ and $R_4$ thereafter (tables 5 to 8) define the substituents present on the general scaffold shown in Formula (I). A compound is defined by selecting any element from $L_1$, $R_1$-$R_5$, $R_2$-$R_3$, and $R_4$ matrices and positioned in their respective $L_1$, $R_1$, $R_2$, $R_3$, $R_4$ and $R_5$ position in the general Formula (I). Therefore, a compound is defined from any combination of m value and the $L_1$, $R_1$-$R_5$, $R_2$-$R_3$, and $R_4$ matrices. A compound can be identified from the combination of each m, $L_1$ and $R_1$ (wherein i is an integer from 1 to 5) substituents taken from the matrices described in tables 5 to 8.

For example, the compound 1-5 from example 1 can be defined as follow:

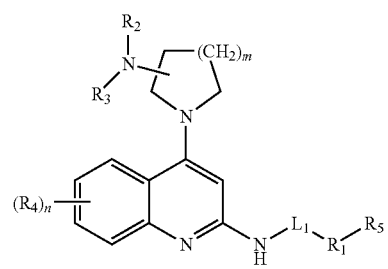

General formula (I)

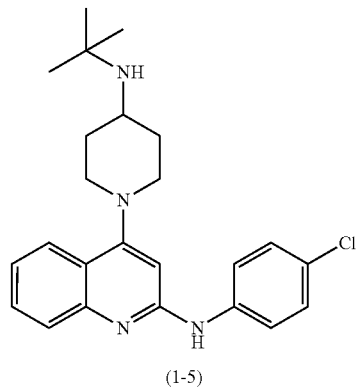

(1-5)

-continued $R_2$-$R_3$ matrix

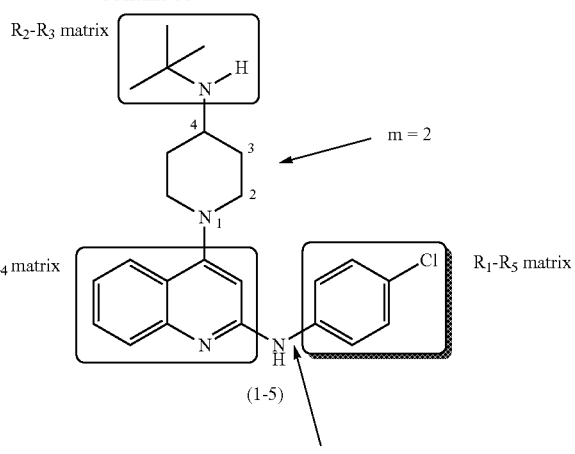

m = 2

$R_4$ matrix    $R_1$-$R_5$ matrix (1-5)

$L_1$ matrix

Matrix deconvolution

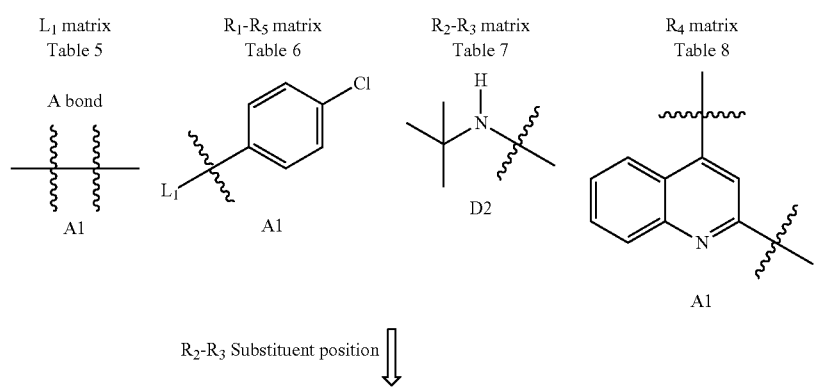

| $L_1$ matrix | $R_1$-$R_5$ matrix | $R_2$-$R_3$ matrix | $R_4$ matrix |
| Table 5 | Table 6 | Table 7 | Table 8 |
| A bond | | | |
| A1 | A1 | D2 | A1 |

$R_2$-$R_3$ Substituent position

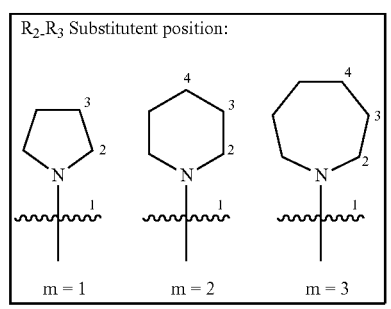

$R_2$_$R_3$ Substitutent position:

m = 1, m = 2, m = 3

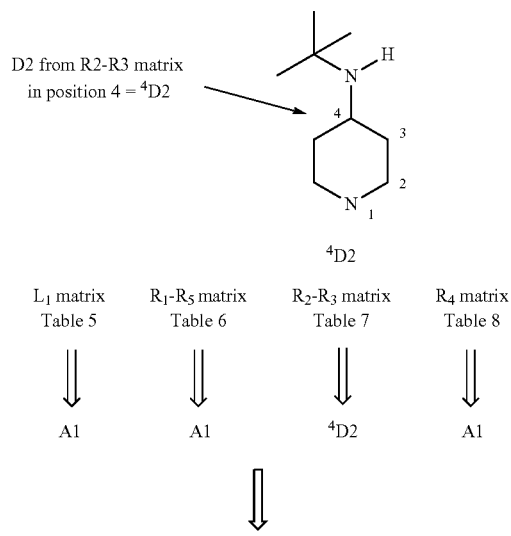

D2 from R2-R3 matrix in position 4 = $^4$D2

$^4$D2

| $L_1$ matrix | $R_1$-$R_5$ matrix | $R_2$-$R_3$ matrix | $R_4$ matrix |
| Table 5 | Table 6 | Table 7 | Table 8 |
| ⇓ | ⇓ | ⇓ | ⇓ |
| A1 | A1 | $^4$D2 | A1 |

Compound 1-5 can be identified as: $L_1$:A1_$R_1$-$R_5$:A1_m:2_$R_2$-$R_3$:$^4$D2_$R_4$:A1

Matrix definition of compound 1-5 therefore is:
L₁:A1_R₁-R₅:A1_R₂-R₃:D2_R₄:A1_m:2
TABLE 5
L₁-Matrix
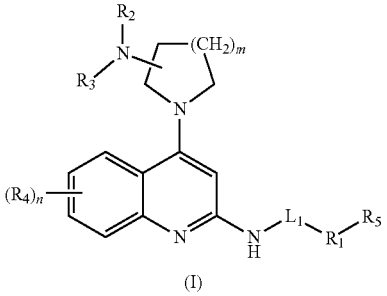

TABLE 6
$R_1$—$R_5$ Matrix
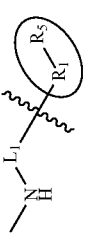
| | A | B | C | D | E |
|---|---|---|---|---|---|
| 1 | 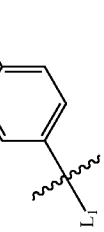 | 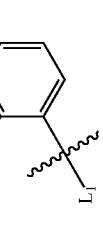 | 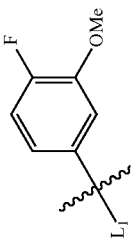 | 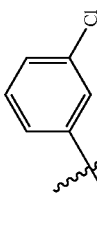 | 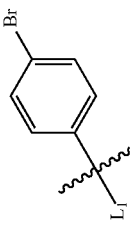 |
| 2 | 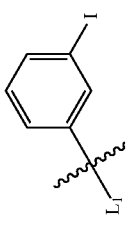 | 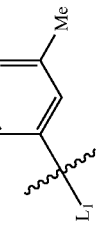 | 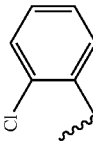 | 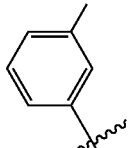 | 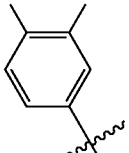 |
| 3 | 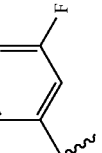 | 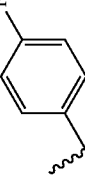 | 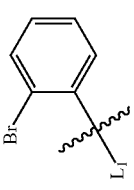 | 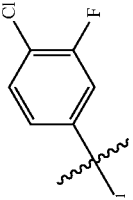 | 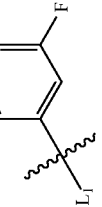 |
| 4 | 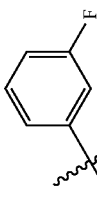 | 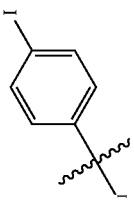 | 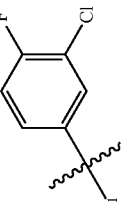 | 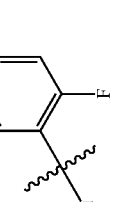 | |

TABLE 6-continued $R_1$—$R_5$ Matrix

| | A | B | C | D | E |
|---|---|---|---|---|---|
| 5 | 4-F, 2-Me phenyl | 2-COOH phenyl | 3-COOH phenyl | 4-COOH phenyl | 2-C(O)NH-iPr phenyl |
| 6 | 3-C(O)NH-iPr phenyl | 4-C(O)NH-iPr phenyl | 4-Me phenyl | 3-Me phenyl | 2-Me phenyl |
| 7 | 4-CF$_3$ phenyl | 3-CF$_3$ phenyl | 2-CF$_3$ phenyl | 4-cyclopropyl phenyl | 3-cyclopropyl phenyl |

TABLE 6-continued

R₁—R₅ Matrix

R₁—R₅ Matrix

| | A | B | C | D | E |
|---|---|---|---|---|---|
| 8 | 2-cyclopropylphenyl | 4-CN-phenyl | 3-CN-phenyl | 2-CN-phenyl | 4-N(Me)₂-phenyl |
| 9 | 3-N(Me)₂-phenyl | 2-N(Me)₂-phenyl | 4-OH-phenyl | 3-OH-phenyl | 2-OH-phenyl |
| 10 | 4-OMe-phenyl | 3-OMe-phenyl | 2-OMe-phenyl | 4-(2-methoxyethoxy)-phenyl | 3-(2-methoxyethoxy)-phenyl |
| 11 | 4-(propargyloxy)-phenyl | 3-(propargyloxy)-phenyl | 2-(propargyloxy)-phenyl | 4-(but-3-ynyloxy)-phenyl | 3-(but-3-ynyloxy)-phenyl |

TABLE 6-continued

R₁—R₅ Matrix

TABLE 6-continued

TABLE 6-continued
R₁—R₅ Matrix
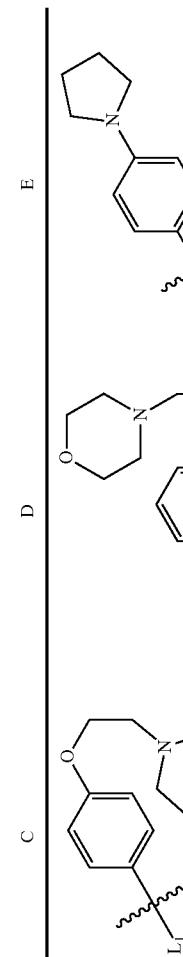
| | A | B | C | D | E |
|---|---|---|---|---|---|
| 18 | 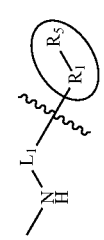 | 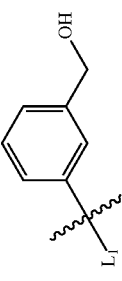 | 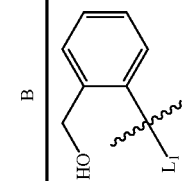 | 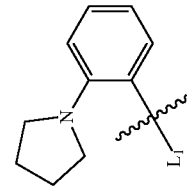 | 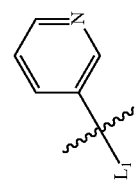 |
| 19 | | | | | |
| 20 | | | | | |

TABLE 6-continued $R_1$—$R_5$ Matrix

TABLE 6-continued

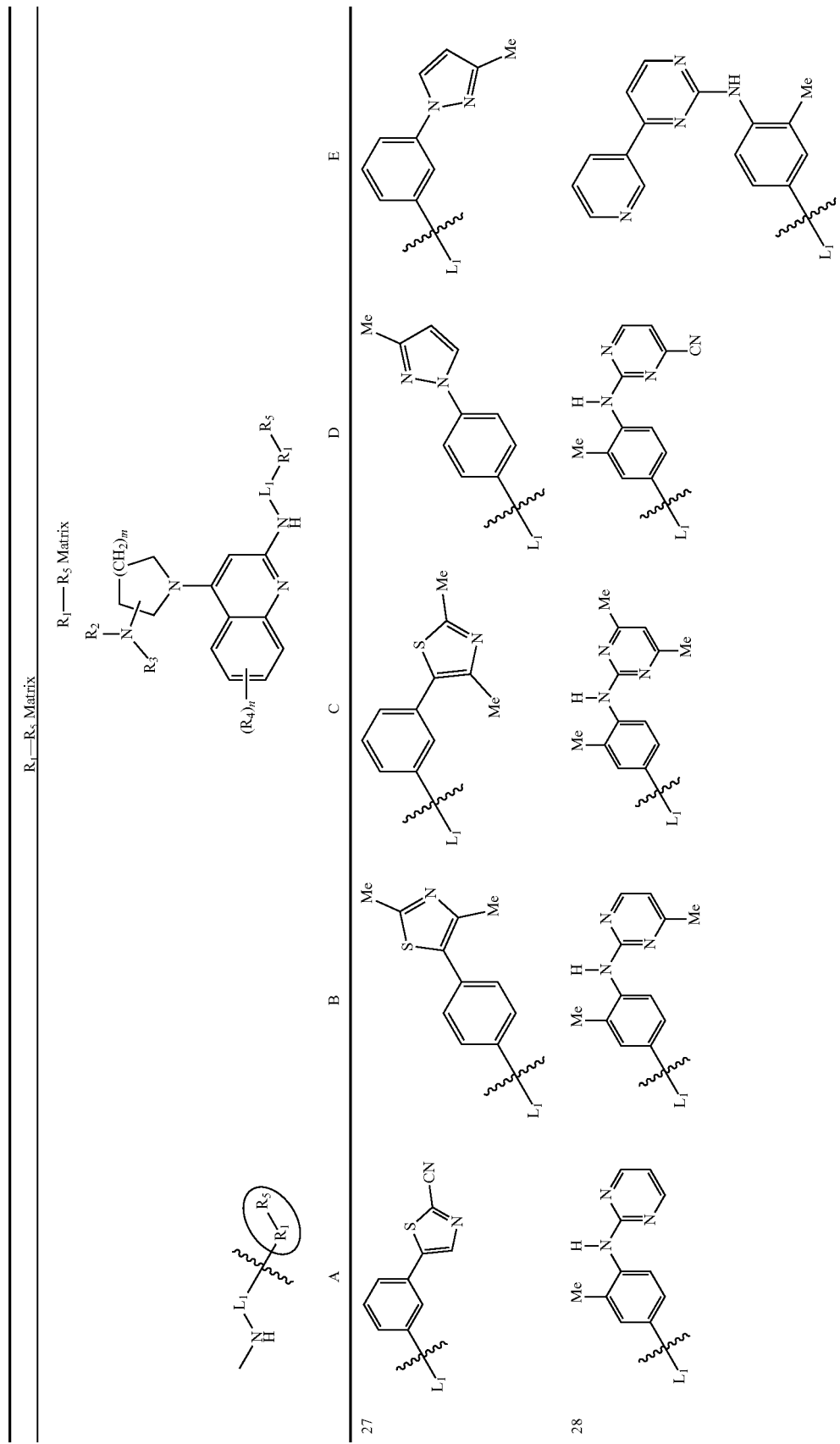

TABLE 6-continued

R₁—R₅ Matrix

TABLE 6-continued $R_1$—$R_5$ Matrix

TABLE 6-continued
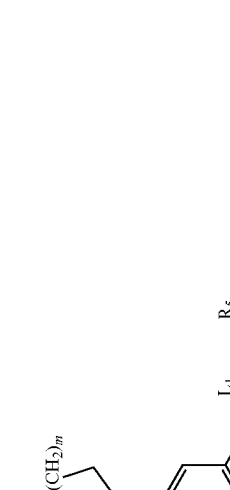

TABLE 7

$R_2$, $R_3$ Matrix (I)

[Structure showing pyrrolidine with (CH₂)ₘ, N-methyl, with R₂, R₃ circled on nitrogen]

$R_2$, $R_3$ Matrix

[Structure of quinoline core with (CH₂)ₘ pyrrolidine bearing NR₂R₃, (R₄)ₙ substituents, and 2-amino substituted with L₁-R₁ and R₅]

| | A | B | C | D | E |
|---|---|---|---|---|---|
| 1 | H–NH– | Me–NH– | Et–NH– | Et(n-Pr)N– | i-Pr–NH– |
| 2 | n-Pr–NH– | i-Bu–NH– | i-Pr–NH– | t-Bu–NH– | n-Bu–NH– |
| 3 | i-Bu–NH– | Me₂N– | Et₂N– | i-Pr(Me)N– | i-Pr(Et)N– |

TABLE 7-continued

R₂, R₃ Matrix

TABLE 7-continued

R₂, R₃ Matrix

TABLE 7-continued

R₂, R₃ Matrix

TABLE 7-continued

R₂, R₃ Matrix

TABLE 7-continued

R₂, R₃ Matrix (I)

R₂, R₃ Matrix

| | A | B | C | D | E |
|---|---|---|---|---|---|
| 14 | H-N-cyclobutyl | Me-N(Me)-cyclobutyl | MeOCH₂-cyclobutyl-N(H)- | NC-cyclobutyl-N(H)- | Me-N-cyclobutyl |
| 15 | Me-N-(3-methylcyclobutyl) | H-N-cyclopentyl | Me-N-cyclopentyl | Et-N-cyclopentyl | HO-cyclopentyl-N(H)- (trans) |
| 16 | HO-cyclopentyl-N(H)- (trans) | cyclopentyl-N-CH₂-(4-pyridyl) | H-N-cyclohexyl | Me-N-cyclohexyl | Et-N-cyclohexyl |

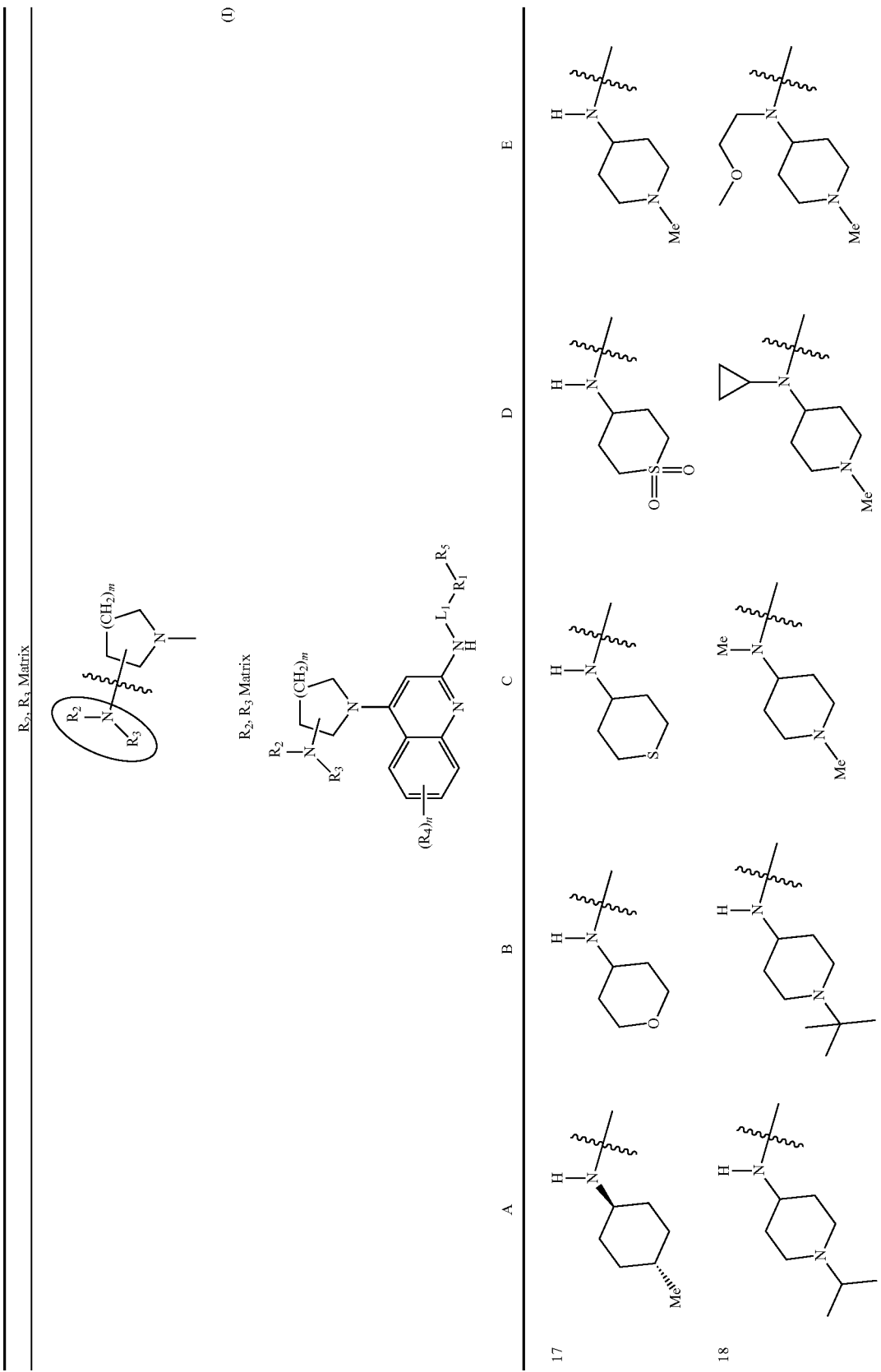

TABLE 7-continued

R₂, R₃ Matrix (I)

| | A | B | C | D | E |
|---|---|---|---|---|---|
| 19 | NH-piperidine-Boc | NH-piperidine-tetrahydropyran | NH-piperidine-cyclopropyl | NH-(S)-tetrahydrofuran-3-yl | NH-(R)-tetrahydrofuran-3-yl |
| 20 | N(Me)-tetrahydrofuran-3-yl | NH-pyrrolidine-N-Me | NH-pyrrolidine-N-iPr | NH-pyrrolidine-N-tBu | NH-pyrrolidine-N-C(O)Me |

TABLE 7-continued

R₂, R₃ Matrix (I)

| | A | B | C | D | E |
|---|---|---|---|---|---|
| 21 | 3-oxopyrrolidin-3-yl-NH- (HN, O) | 3-oxopyrrolidin-3-yl-NH- (HN, O) | 1-methyl-2-oxopyrrolidin-3-yl-NH- | 1-methyl-2-oxopyrrolidin-3-yl-NH- | 1-methyl-5-oxopyrrolidin-3-yl-NH- |
| 22 | PhNH- | 4-F-C₆H₄-NH- | 3-Cl-4-F-C₆H₃-NH- | pyridin-2-yl-NH- | pyridin-3-yl-NH- |

TABLE 7-continued
R₂, R₃ Matrix
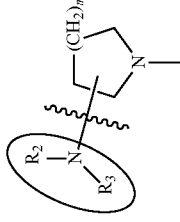
R₂, R₃ Matrix
| | A | B | C | D | E |
|---|---|---|---|---|---|
| 23 | | | | | |
| 24 | | | | | |

TABLE 7-continued
R₂, R₃ Matrix
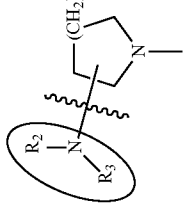
R₂, R₃ Matrix
| | A | B | C | D | E |
|---|---|---|---|---|---|
| 25 | 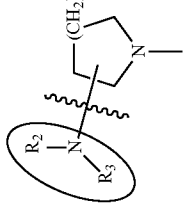 | 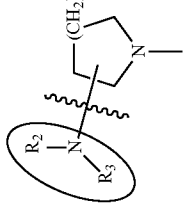 | 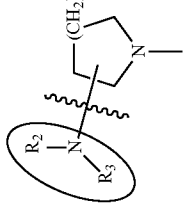 | 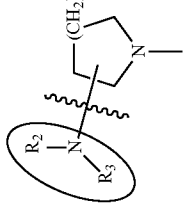 | 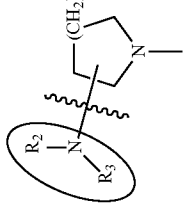 |
| 26 | 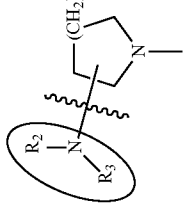 | 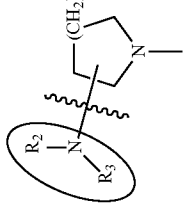 | 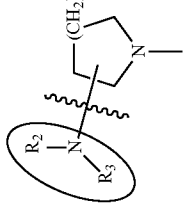 | 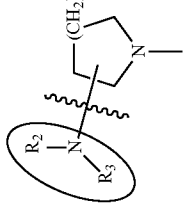 | |
R₂ and R₃ are linked together with the nitrogen atom to which they are covalently linked to form a heterocyclyl TABLE 7-continued
$R_2$, $R_3$ Matrix
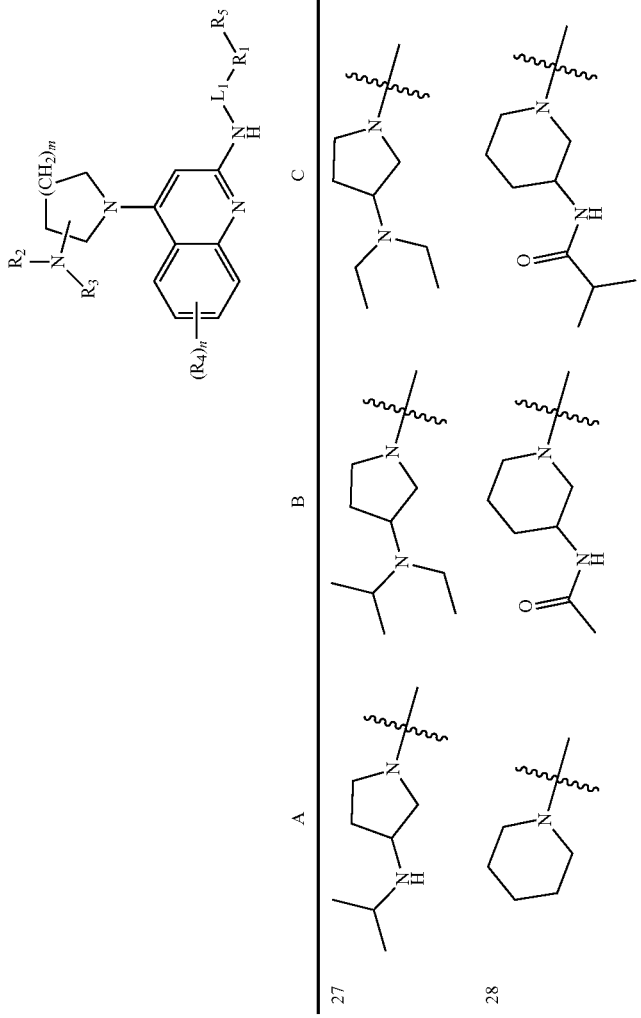

TABLE 7-continued
R₂, R₃ Matrix
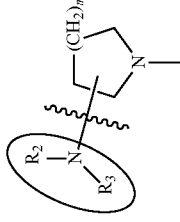
R₂, R₃ Matrix
| | A | B | C | D | E |
|---|---|---|---|---|---|
| 29 | 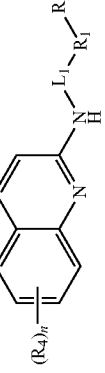 | 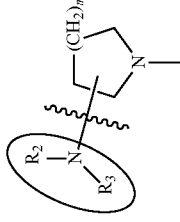 | 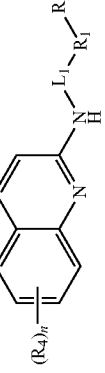 | 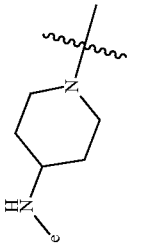 | 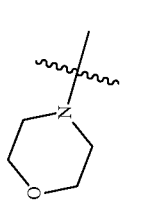 |
| 30 | | | | | |

TABLE 7-continued
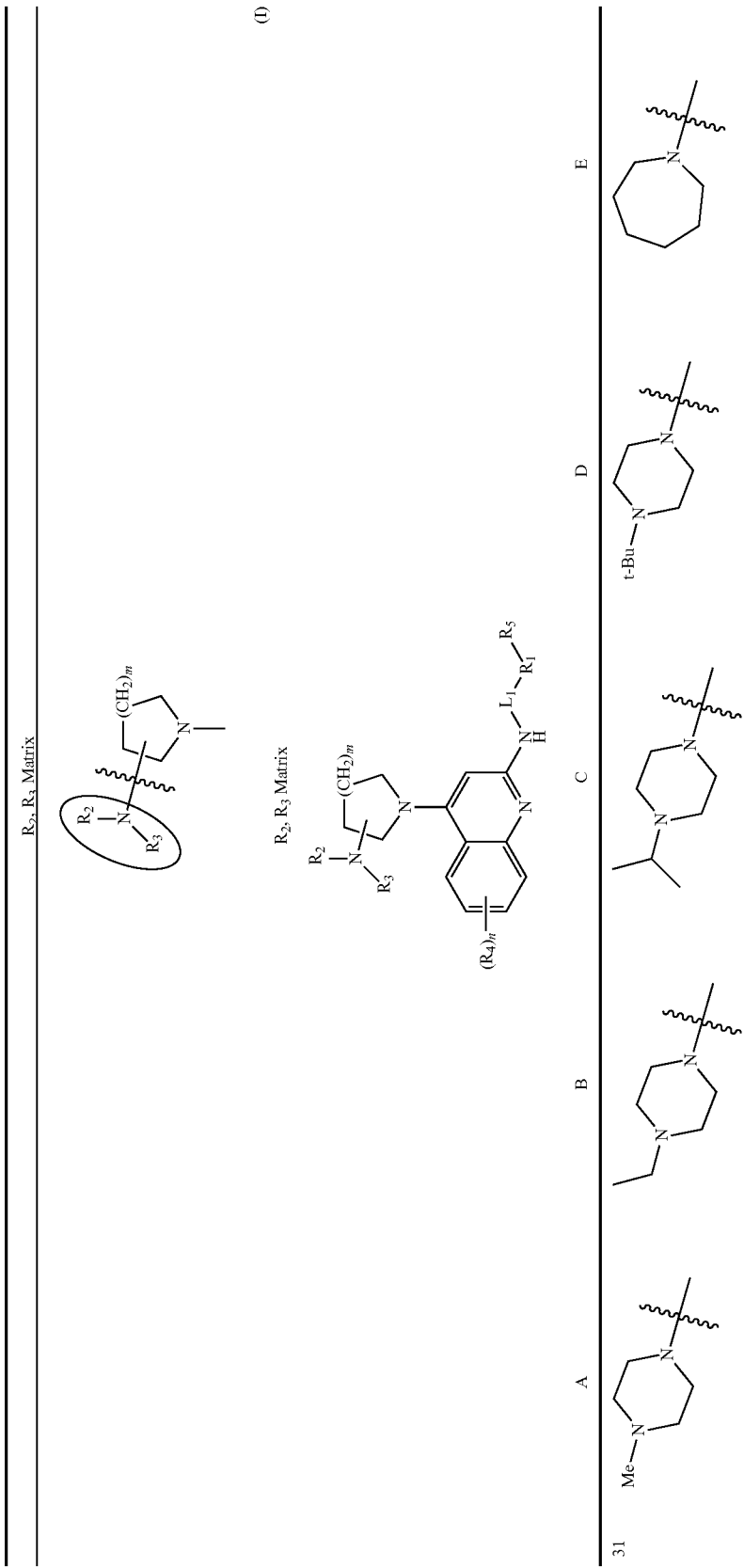

TABLE 8

R4-Matrix (structure I)

R4-Matrix

| | A | B | C | D |
|---|---|---|---|---|
| 1 | quinoline | 8-OMe quinoline | 7-MeO quinoline | 6-MeO quinoline |

TABLE 8-continued
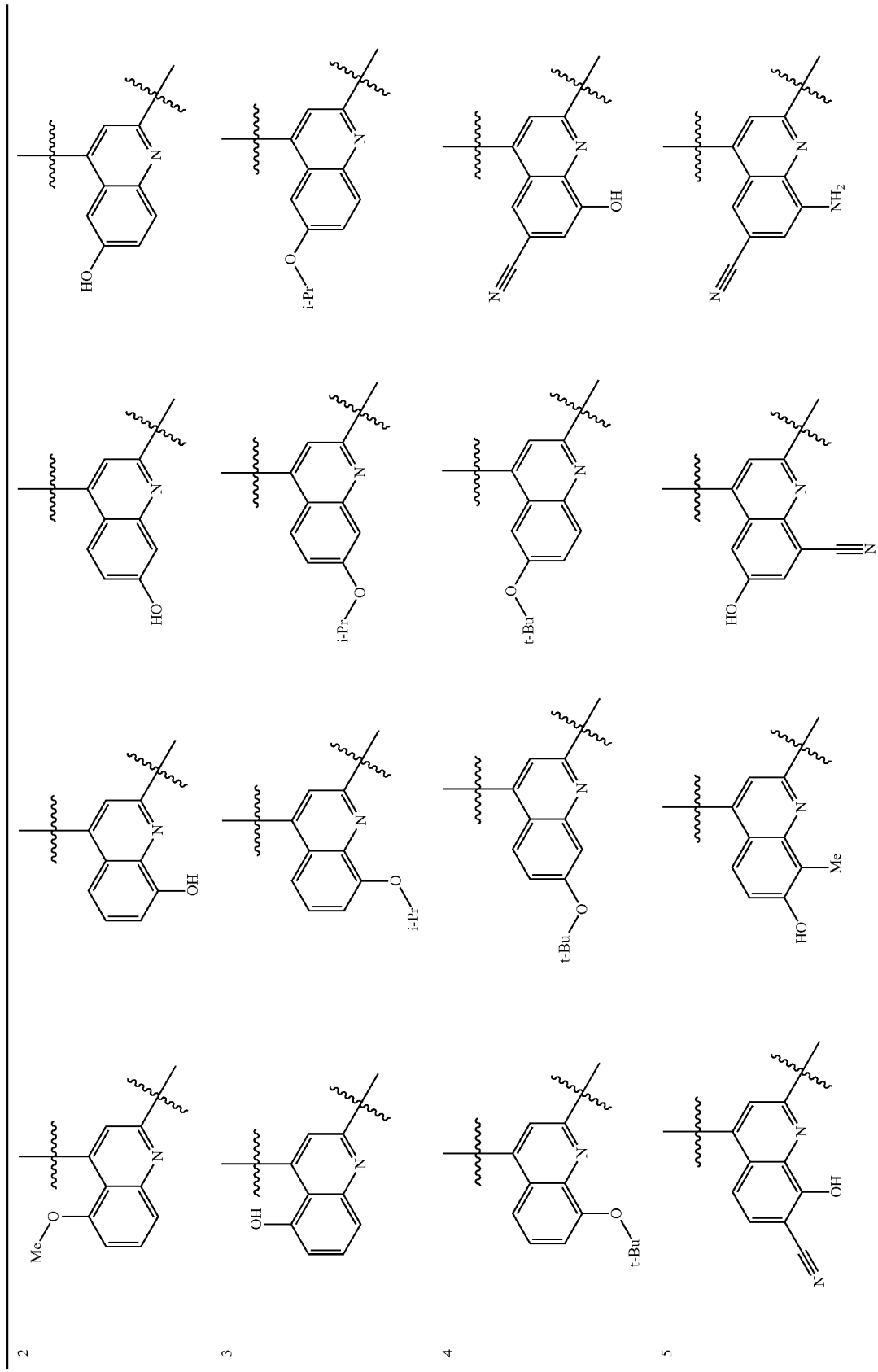

TABLE 8-continued
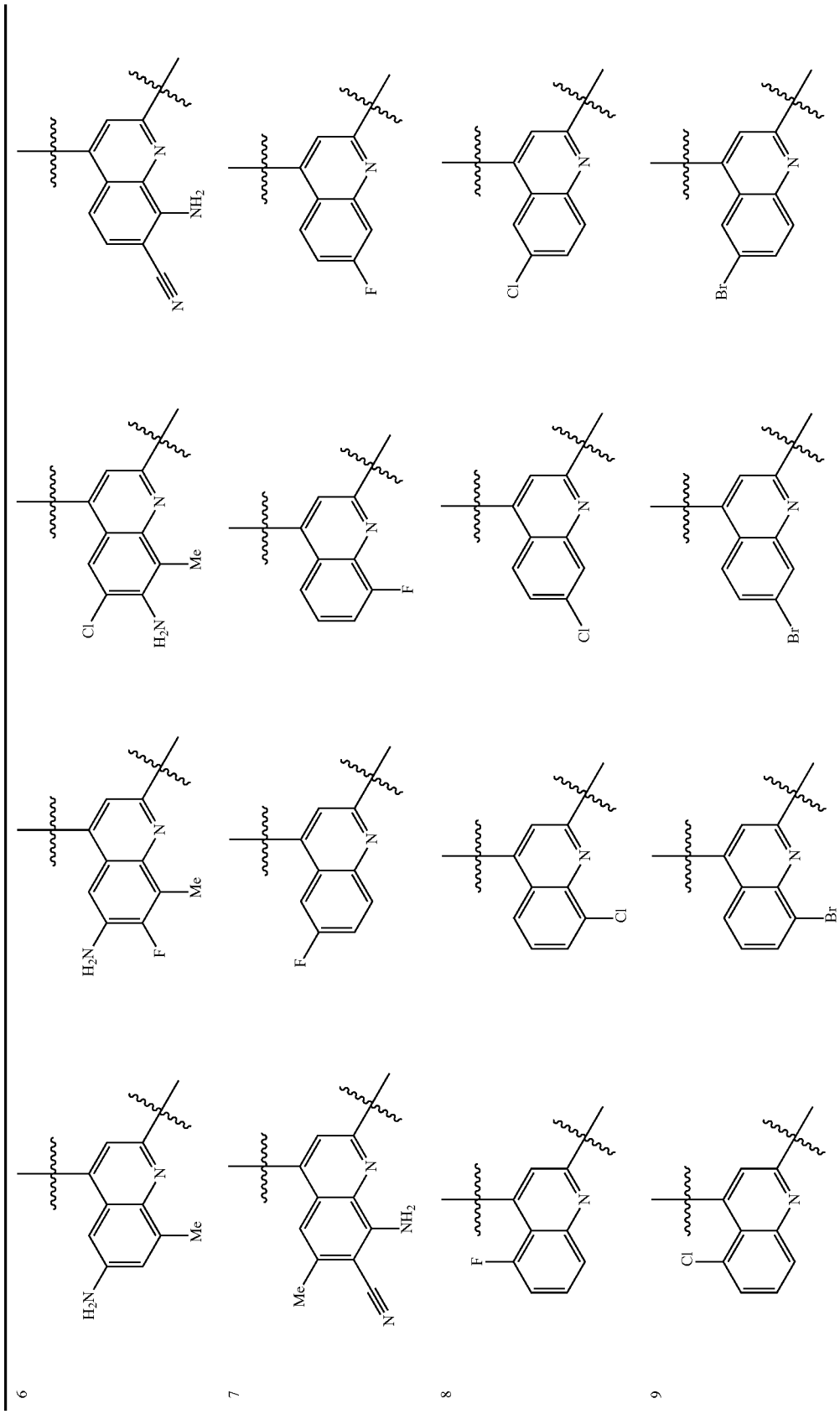

TABLE 8-continued
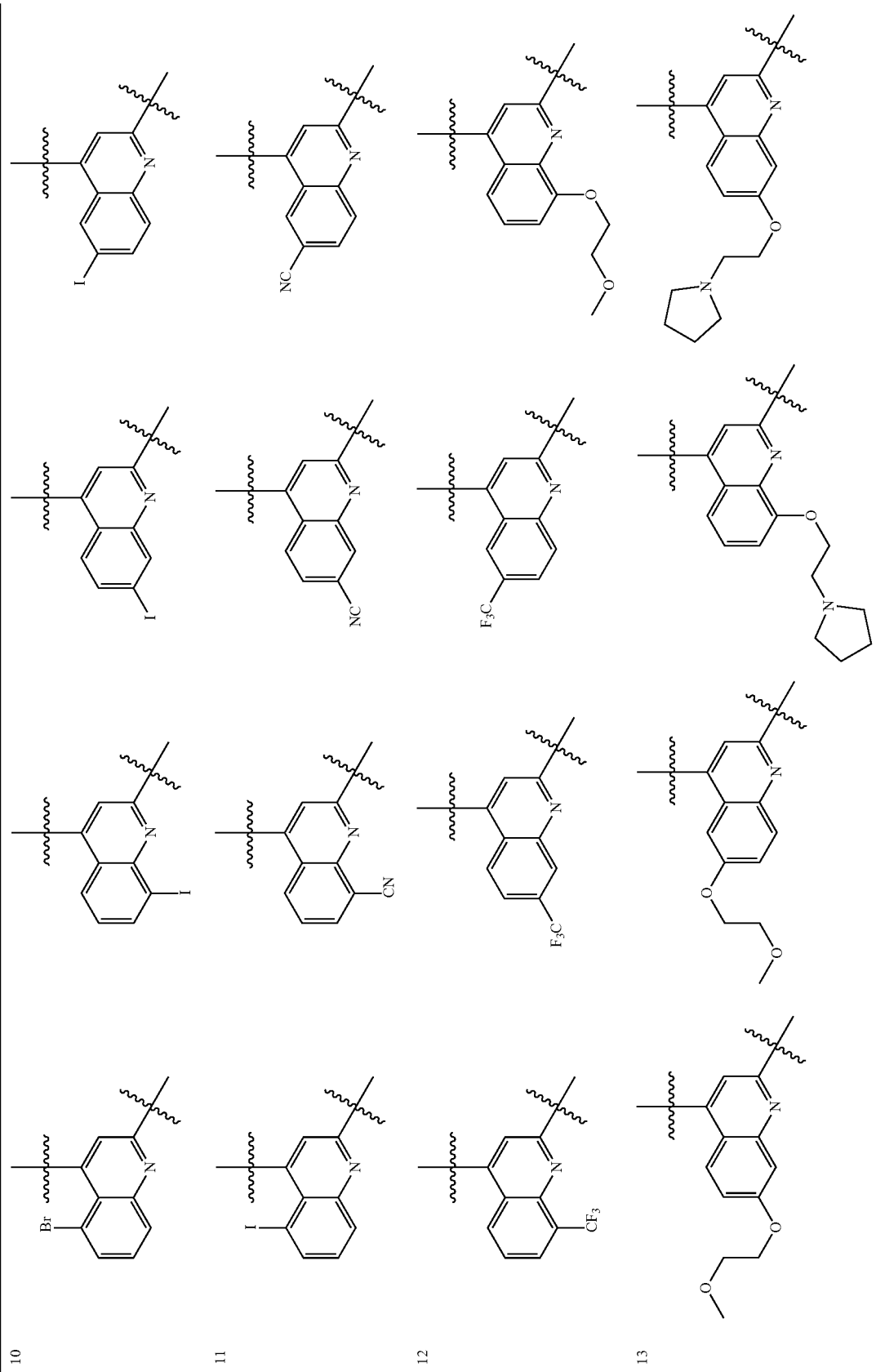

TABLE 8-continued
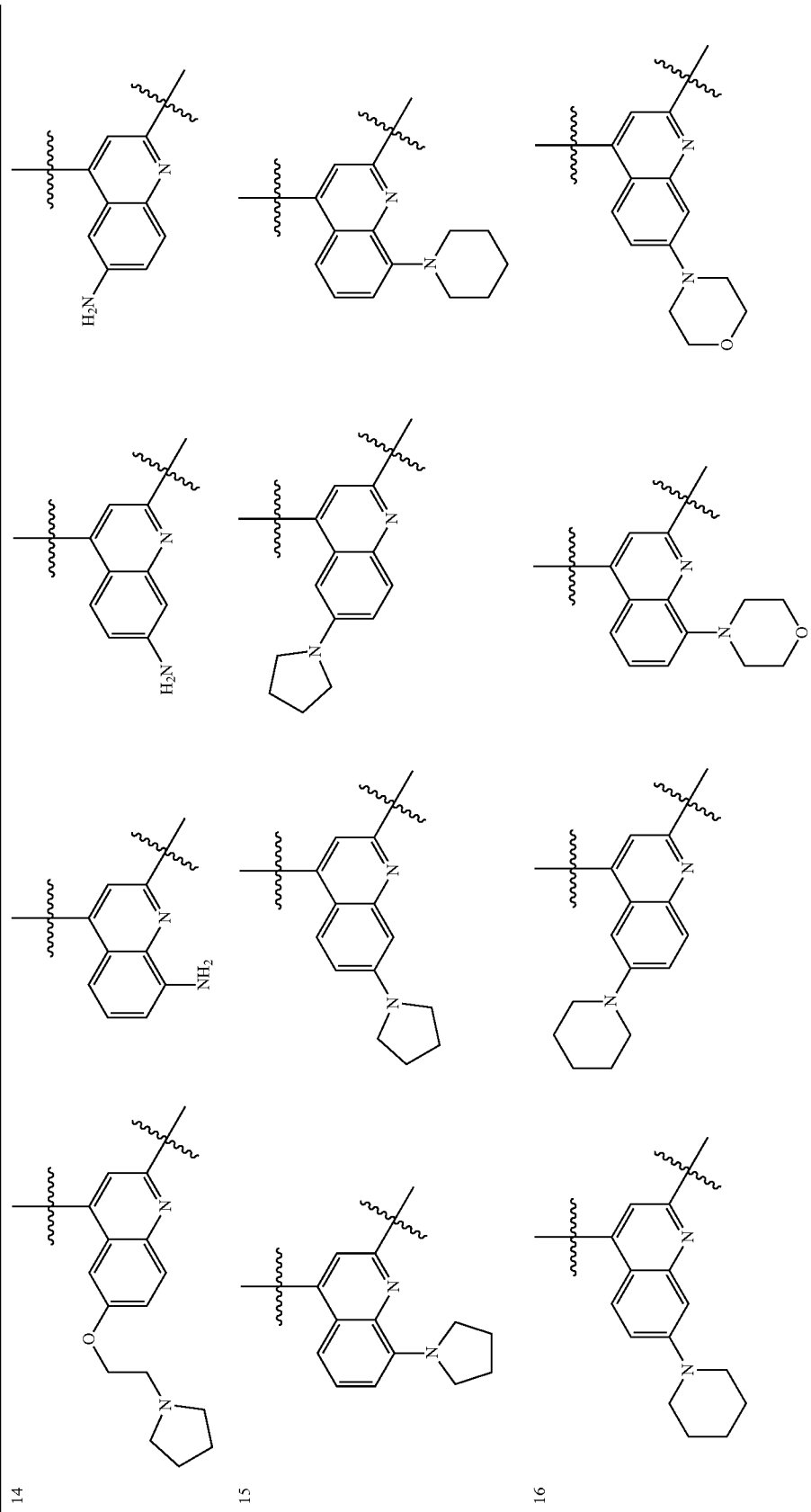
14
15
16

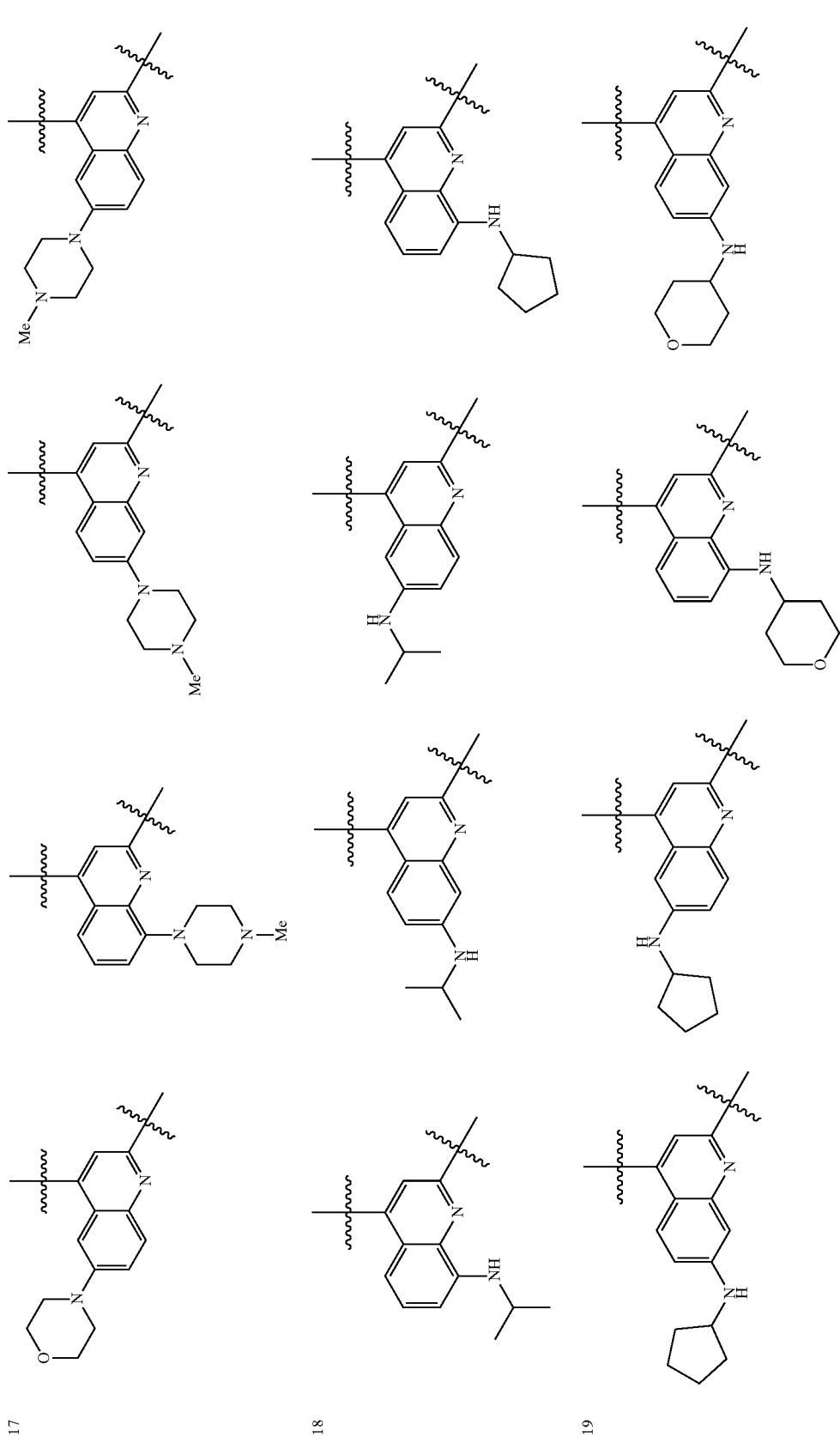

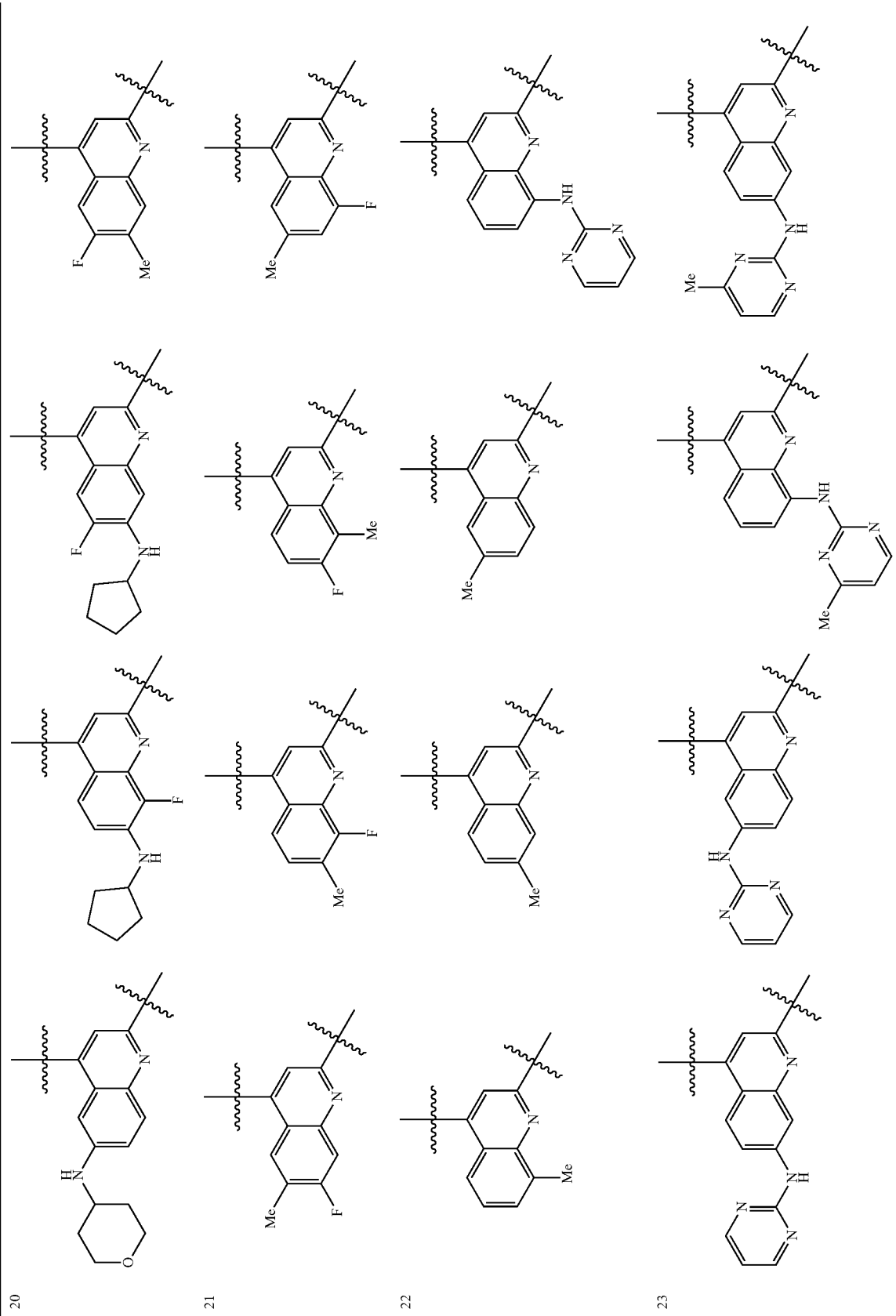

TABLE 8-continued
| | | | |
|---|---|---|---|
| 24 | 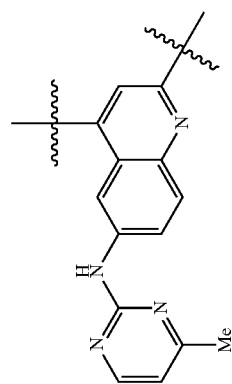 | 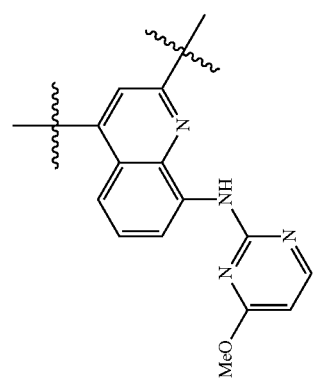 | 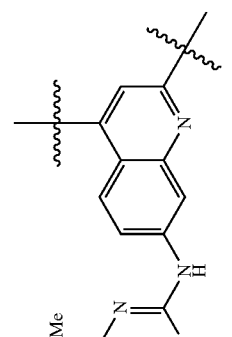 | 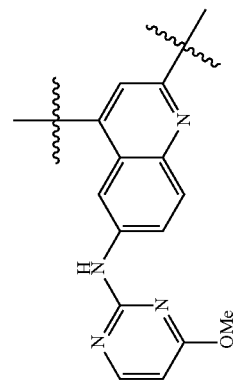 |
| 25 | 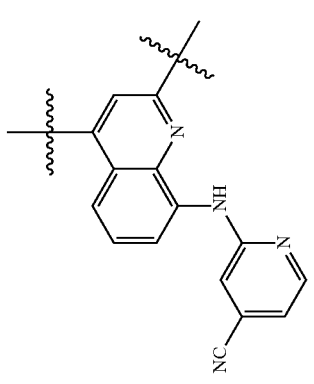 | 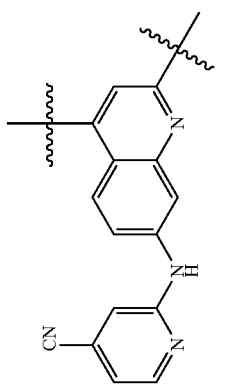 | 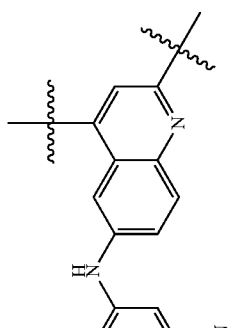 | 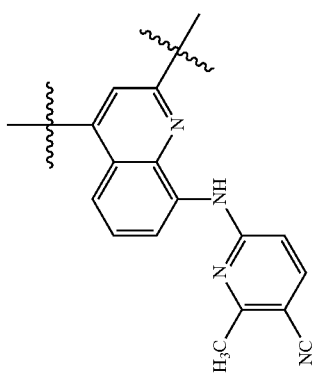 |
| 26 | 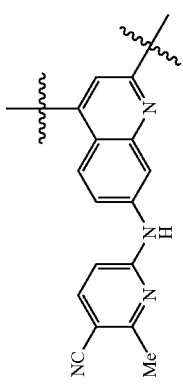 | 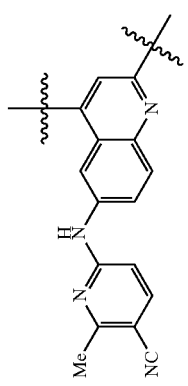 | 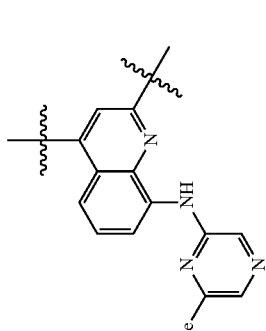 | 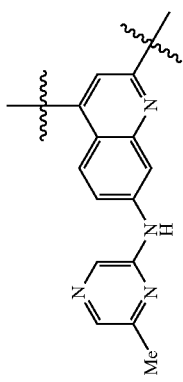 |

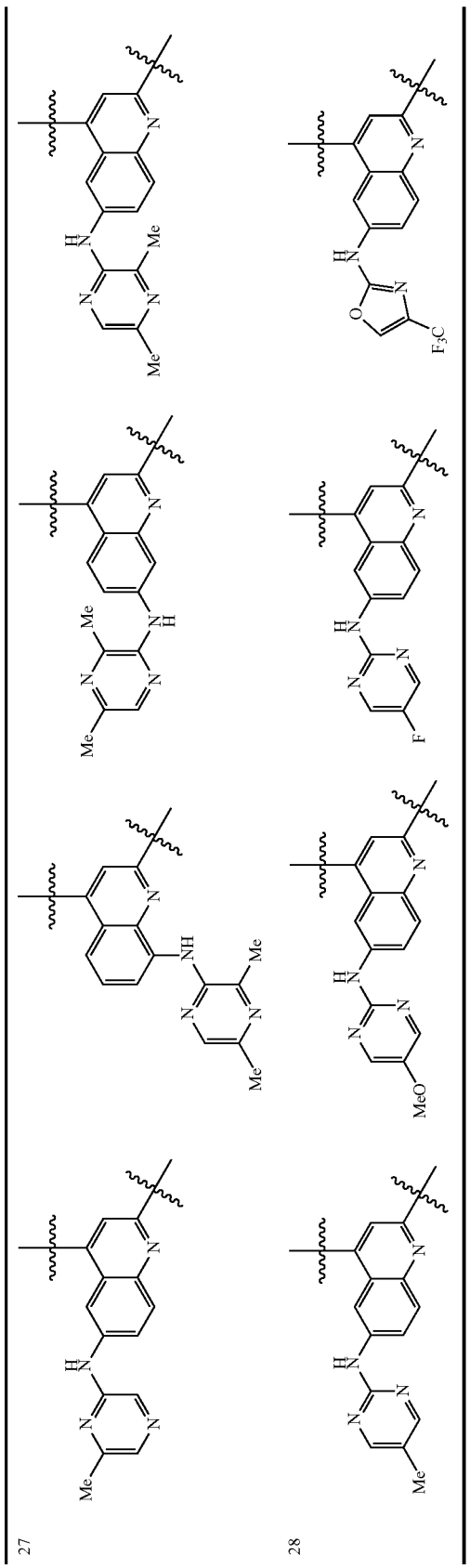

Material and Methods Relative to the Examples 1, 2, 3 and 4

Abbreviations and Acronyms

A comprehensive list of the abbreviations used by organic chemists of ordinary skill in the art appears in The ACS Style Guide *Effective Communication of Scientific Information* (third edition, June 2006, Editors A. M. Coghill and L. R. Garson) or the Guidelines for Authors for the Journal of Organic Chemistry. The abbreviations contained in said lists, and all abbreviations utilized by organic chemists of ordinary skill in the art are hereby incorporated by reference. For purposes of this invention, the chemical elements are identified in accordance with the Periodic Table of the Elements, CAS version, Handbook of Chemistry and Physics, 67$^{th}$ Ed., 1986-87.

More specifically, when the following abbreviations are used throughout this disclosure, they have the following meanings:

EtOAc: Ethyl acetate
$CH_2Cl_2$: Dichloromethane
DCM: Dichloromethane
DiPEA: N,N-Diisopropylethylamine
DME: Dimethoxyethane
DMF: N,N-Dimethylformamide
$Et_2O$: Diethylether
ES+: Electrospray Ionisation in positive mode
HCl: Hydrochloric acid
HMBC: Heteronuclear Multiple Bond Correlation, nuclear magnetic resonance
HPLC: High Performance Liquid Chromatography
MeCN: acetonitrile
MS: Mass spectrum, Mass spectrometry
MTBE: Methyl tert-Butyl ether
NMP: N-Methyl-2-Pyrrolidinone
NMR: Nuclear Magnetic Resonance experiment
RT: Room Temperature
UPLC: Ultra Performance Liquid Chromatography
THF: Tetrahydrofuran
MTHF: 2-methyltetrahydrofuran
TLC: Thin Layer Chromatography
$^1$H NMR: Proton Nuclear Magnetic Resonance
$^{13}$C NMR: Carbon Nuclear Magnetic Resonance
Δ: heating under reflux
g: gram
h: hour, hours
M: mol·L$^{-1}$ (molar)
m: multiplet
MHz: megahertz
min: minute, minutes
ml milliliter
μM: micromolar
mol: mole
mmol: milimole
MW: microwave
m/z: mass-to-charge ratio
q: quartet
$t_r$: retention time (HPLC)
rt: room temperature
s: singlet
t: triplet
TPP: triphenylphosphine Since the compounds described herein can contain more than one basic amine function, the salt form of the compounds can contain more than one acid addition (e.g. HCl). For example for HCl as acid addition, the stoichiometry of the hydrochloride salts can be variable and dependent of the compound's pKa and HCl's equivalent used for salification. Therefore, the hydrochloride salt form is presented as x.HCl, wherein x is ≥1 and is an integer or as HCl salt.

Reagents and solvents were obtained from commercial suppliers and were used without further purification if not otherwise stated. Dry Methylene chloride was dried and distilled over $CaCl_2$ and stored over molecular sieves 4 Å under argon. Anhydrous tetrahydrofuran was dried over sodium/benzophenone ketyl under argon and distilled prior to use. Flash chromatography purifications were performed on Merck silica gel ($SiO_2$ 40-63 μM or 15-40 μM) as the stationary phase.

At least some of the compounds identified as "intermediates" herein are contemplated as compounds described herein.

NMR spectra were recorded on Bruker Avance 300 MHz, Bruker Avance 400 MHz or on a Bruker Avance 500 MHz Analytical Ultra High Performance Liquid Chromatography-mass analysis (UHPLC-MS): UPLC Waters Acquity, UV DAD, coupled to a mass spectrometer.

HPLC-MS, Method A: Column Acquity UPLC BEH C18 (2.1×50 mm, 1.7 μm), mobile phase: A: $H_2O$+0.1% $HCO_2H$, B: MeCN+0.1% $HCO_2H$. Eluting conditions comprised a linear gradient (minute/% B): from 0 min/5% B to 4 min/98% B, flow rate 0.6 ml/min. Column Temp: 40° C. Mass: tandem quadrupole Waters Quattro Premier XE.

HPLC-MS, Method B: Column Supelco Titan C18 (2.1×50 mm, 1.9 μm), mobile phase: A: $H_2O$+0.1% $HCO_2H$, B: MeCN+0.1% $HCO_2H$. Eluting conditions comprised a linear gradient (minute/% B): from 0 min/5% B to 4 min/98% B, flow rate 0.6 ml/min. Column Temp: 40° C. Mass: tandem quadrupole Waters Quattro Premier XE.

HPLC-MS, Method C: Column Acquity UPLC BEH C18 (2.1×50 mm, 1.7 μm), mobile phase: A: $H_2O$+0.1% $HCO_2H$, B: MeCN+0.1% $HCO_2H$. Eluting conditions comprised a linear gradient (minute/% B): from 0 min/2% B to 0.2 min/2% B to 1.5 min/98% B, flow rate: 0.8 ml/min. Column Temp: 45° C. Mass: Agilent 6150 quadrupole.

HPLC-MS, Method D: Column Acquity UPLC BEH C18 (2.1×50 mm, 1.7 μm), mobile phase: A: $H_2O$+0.1% $HCO_2H$, B: MeCN+0.1% $HCO_2H$. Eluting conditions comprised a linear gradient (minute/% B): from 0 min/3% B to 0.4 min/3% B to 2.2 min/98% B, flow rate: 0.8 ml/min. Column Temp: 45° C. Mass: Agilent 6150 quadrupole.

HPLC-MS, Method E: Column Acquity UPLC BEH C18 (2.1×50 mm, 1.7 μm), mobile phase: A: $H_2O$+0.1% $HCO_2H$, B: MeCN+0.1% $HCO_2H$. Eluting conditions comprised a linear gradient (minute/% B): from 0 min/3% B to 0.2 min/3% B to 1.5 min/95% B, flow rate: 0.8 ml/min. Column Temp: 60° C. Mass: Agilent 6150 quadrupole.

HPLC-MS, Method F: Column Atlantis HPLC T3 C18 (4.6×250 mm, 5.0 μm), mobile phase: A: $H_2O$+10 mM ammonium acetate, B: MeCN. Eluting conditions comprised a linear gradient (minute/% B): from 0 min/2% B to 2.0 min/2% B to 10.0 min/98% B, flow rate: 1.0 ml/min. Column Temp: room temperature. Mass: Agilent 6150 quadrupole.

HPLC-MS, Method G: Column Acquity UPLC BEH C18 (2.1×50 mm, 1.7 μm), mobile phase: A: $H_2O$+0.1% TFA, B: MeCN+0.1% TFA. Eluting conditions comprised a linear gradient (minute/% B): from 0 min/2% B to 0.3 min/2% B to 2.3 min/98% B, flow rate: 0.8 ml/min. Column Temp: 60° C. Mass: Agilent 6150 quadrupole.

HPLC-MS, Method H: Column X-bridge C18 (4.6×75 mm, 3.5 μm), mobile phase: A: $H_2O$+10 mM ammonium acetate, B: MeCN. Eluting conditions comprised a linear gradient (minute/% B): from 0 min/10% B to 0.2 min/10% B to 2.5 min/75% B to 3.0 min/100% B, flow rate: 2.0 ml/min. Column Temp: ambient temperature. Mass: Agilent 6150 quadrupole.

HPLC-MS, Method I: Column Proshell 120 SB-C18 (4.6×75 mm, 2.7 μm), mobile phase: A: $H_2O+0.1\%$ $HCO_2H$, B: MeOH. Eluting conditions comprised a linear gradient (minute/% B): from 0 min/5% B to 0.5 min/5% B to 4.0 min/90% B, flow rate: 2.0 ml/min. Column Temp: 35° C. Mass: Agilent 6150 quadrupole.

Example 1: Preparation of 2-(4-chlorophenylamino)-4-(4-tert-butylaminopiperidin-1-yl)-quinoline Hydrochloride Salt (1-6)

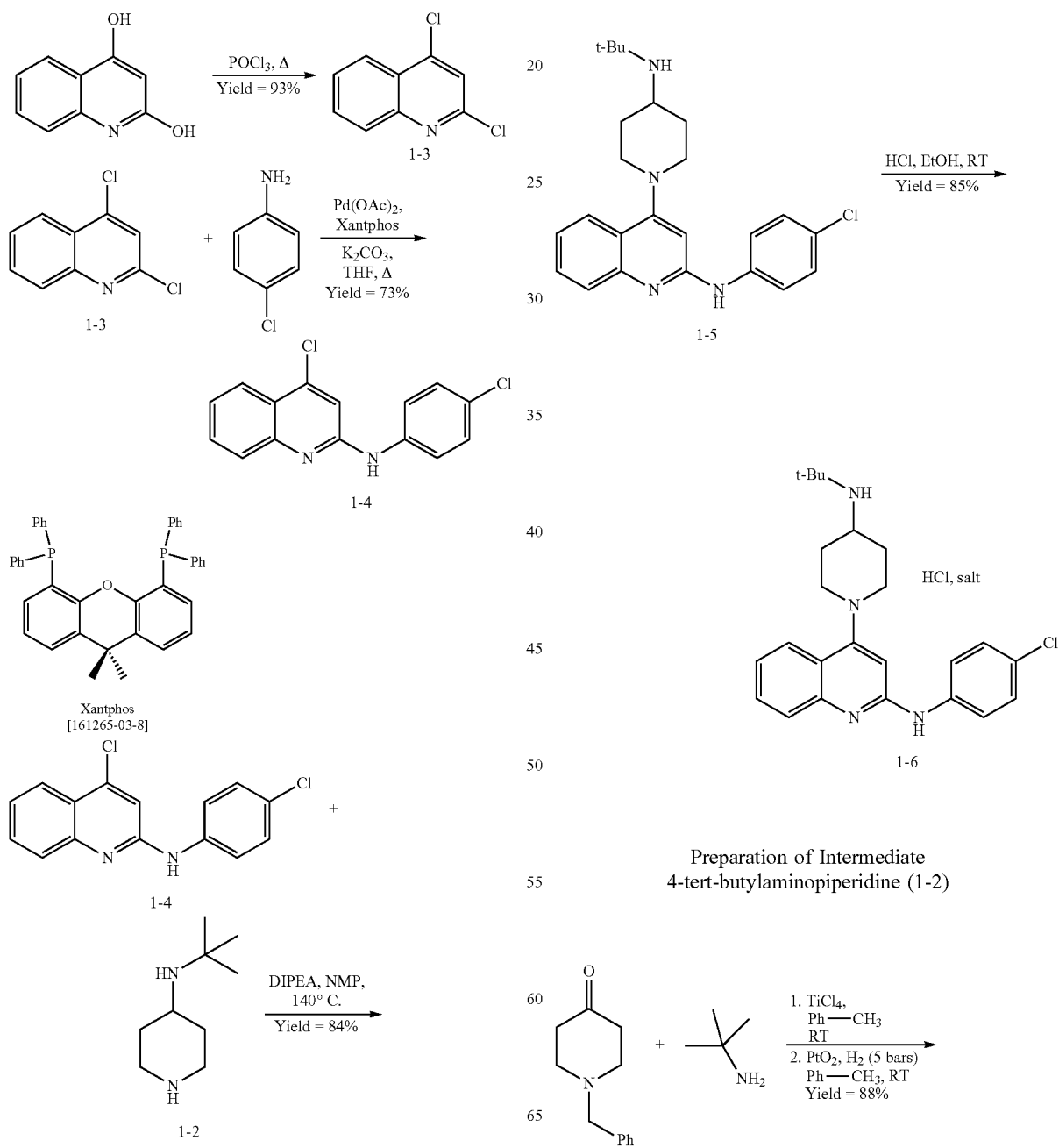

Preparation of Intermediate 4-tert-butylaminopiperidine (1-2)

(yield 88%) of an orange oil corresponding to N-Benzyl-4-tert-butylaminopiperidine (1-1).

Mass, Method A: (ES+) $C_{16}H_{26}N_2$ required 246; found 247 [M+H]

$^1$H NMR (300 MHz, CDCl$_3$)

1.2. Synthesis of 4-tert-butylaminopiperidine (1-2)

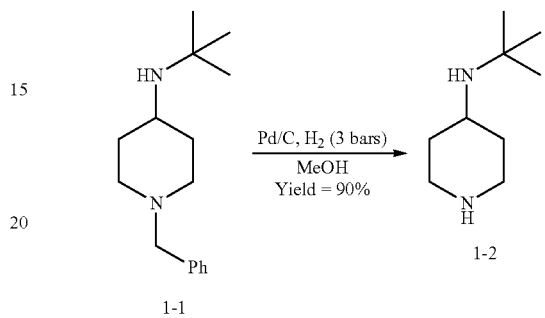

In a hydrogen chemical reactor and to a nitrogen degased solution of N-Benzyl-4-tert-butylaminopiperidine 1-1 (68.05 g, 276 mmol) in 700 ml of methanol was added under nitrogen Palladium on carbon powder 10 wt %, 50% wet (29.40 g, 13.81 mmol, 5 mol %). Hydrogen was then introduced to the reactor at a pressure of 3 bars and the reaction proceeded at room temperature during 2 days. Then, the resulting mixture was filter through a Celite® pad and the filtrate was concentrated under reduced pressure to give 38.86 g (yield 90%) of a yellow solid corresponding to 4-tert-butylaminopiperidine (1-2).

Mass, Method A: (ES+) $C_9H_{20}N_2$ required 156; found 157 [M+H]

$^1$H NMR (300 MHz, CDCl$_3$)

1.3. Synthesis of 2,4-dichloroquinoline (1-3)

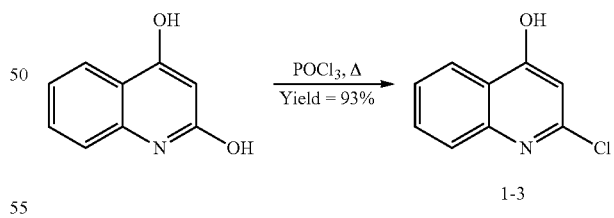

To quinoline-2,4-diol (50.0 g, 310 mmol) was added dropwise at 0° C. Phosphoryl chloride (250 ml, 2682 mmol). The resulting mixture was stirred and heated under reflux overnight. Then, the reaction mixture was cooled, concentrated under reduced pressure and co-evaporated twice with 500 ml of toluene. The residue was then taken up with CH$_2$Cl$_2$ (500 ml) and washed with cold water. The aqueous layer was extracted with CH$_2$Cl$_2$ and the combined organic layers were dried over MgSO$_4$, filtered and concentrated

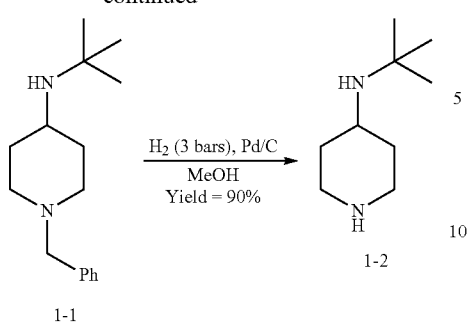

1.1. Synthesis of 1-Benzyl-4-tert-butylaminopiperidine (1-1)

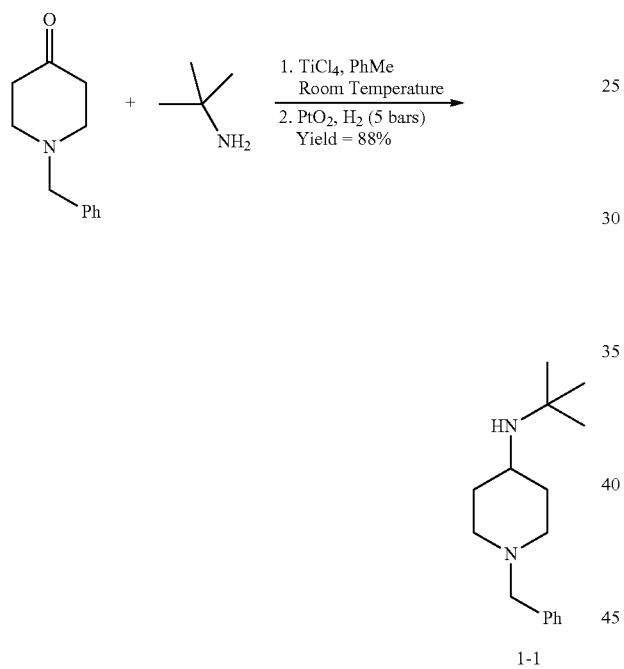

To a solution of N-Benzyl-4-piperidinone (60.0 g, 314 mmol) in 500 ml of dry toluene and tert-Butylamine (135 ml, 1280 mmol) was added dropwise at a temperature maintained below +15° C., a solution of Titanium tetrachloride (23.0 ml, 210 mmol) in 250 ml of dry toluene. The resulting mixture was stirred at room temperature during 20 h and then filtered trough a Celite® pad. The toluene solution was transferred to a high pressure hydrogenation reactor and the catalyst Platinum dioxide (160 mg, 0.70 mmol) was added. Hydrogen was introduced to the reactor at a pressure of 5 bars and the reaction proceeded at room temperature during 2 days. Then, the resulting mixture was diluted with a 2 M NaOH aqueous solution (400 ml) and filtered through a Celite® pad. The layers were separated and the aqueous layer was extracted with toluene. The combined organic layers were dried over Na$_2$SO$_4$ filtered and concentrated under reduced pressure to give 68.05 g under reduced pressure to give a brown solid (57.0 g, yield 93%) corresponding to 2,4-dichloroquinoline (1-3).

Mass, Method A: (ES+) C$_9$H$_5$Cl$_2$N required 197; found 198 [M+H]

$^1$H NMR (300 MHz, CDCl$_3$)

1.4. Synthesis of 2-(4-chlorophenylamino)-4-chloroquinoline (1-4)

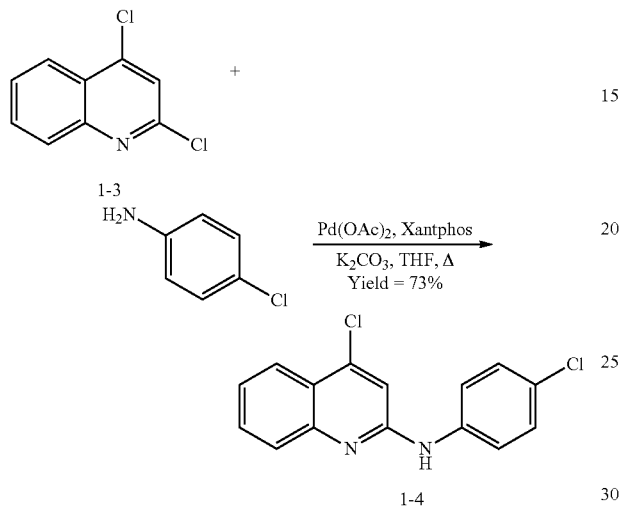

To a solution, under nitrogen gas, of 2,4-dichloroquinoline 1-3 (2.00 g, 10.1 mmol) in dry THF (20 ml) were added 4-chloroaniline (1.45 g, 11.1 mmol) and K$_2$CO$_3$ (3.91 g, 28.3 mmol). The resulting mixture was degassed 5 min with nitrogen, then Xantphos (590 mg, 1.01 mmol) and Pd(OAc)$_2$ (120 mg, 0.5 mmol) were added and the reaction mixture was heated under reflux for 2 hours. The reaction mixture was then cooled to room temperature and concentrated under reduced pressure. The residue was partitioned between water and EtOAc and the aqueous layer was extracted with EtOAc. The combined organic layers were dried over Na$_2$SO$_4$, filtered and concentrated under reduced pressure to give a yellow oil. The crude product was purified by flash chromatography (gradient cyclohexane/EtOAc from 7/3 to 0/10) to give 2.13 g (yield 73%) of a yellow solid corresponding to 2-(4-chlorophenylamino)-4-chloroquinoline (1-4).

Mass, Method A: (ES+) C$_{15}$H$_{10}$Cl$_2$N$_2$ required 288; found 289 [M+H]

$^1$H NMR (300 MHz, CDCl$_3$)

1.5. Synthesis of 2-(4-chlorophenylamino)-4-(4-tert-butylaminopiperidin-1-yl)-quinoline (1-5)

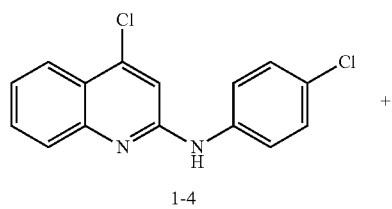

+

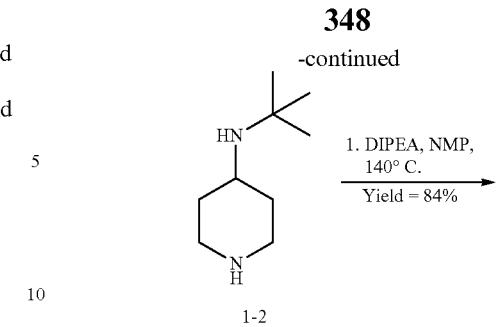

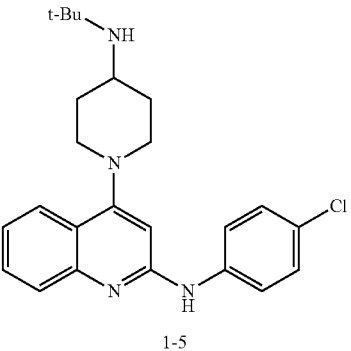

To a solution of 2-(4-chlorophenylamino)-4-chloroquinoline 1-4 (1.00 g, 3.46 mmol) and 4-(tert-butylamino)piperidine (684 mg, 4.38 mmol) in 5 ml of NMP was added N,N-Diisopropylethylamine (0.947 ml, 5.47 mmol) and the mixture was heated at 140° C. during 24 hours. Then, the reaction mixture was cooled, diluted with a 1N NaOH aqueous solution and the resulting mixture was extracted with EtOAc. The combined organic layers were dried over Na$_2$SO$_4$, filtered and concentrated under reduced pressure to give a brown liquid. The crude product was purified by flash chromatography (gradient cyclohexane/EtOAc from 8/2 to 2/8) to give a yellowish solid. This solid was recrystallized from MeCN to give 1.19 g (yield 84%) of a white solid corresponding to 2-(4-chlorophenylamino)-4-(4-tert-butylaminopiperidin-1-yl)-quinoline (1-5).

HPLC-MS, Method A: t$_r$=1.24 min, (ES+) C$_{24}$H$_{29}$ClN$_4$ required 408; found 409 [M+H], 353 [M-tBu+H]

$^1$H NMR (300 MHz, CDCl$_3$)

1.6. Preparation of 2-(4-chlorophenylamino)-4-(4-tert-butylaminopiperidin-1-yl)-quinoline Hydrochloride Salt (1-6)

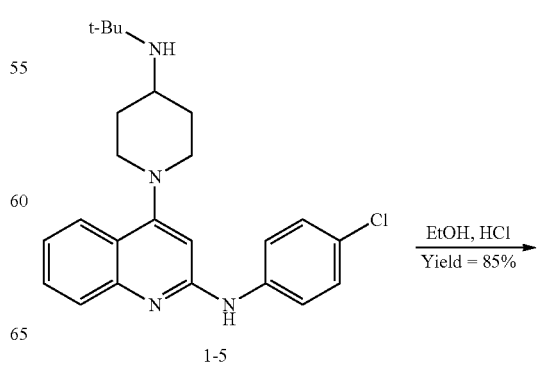

349
-continued

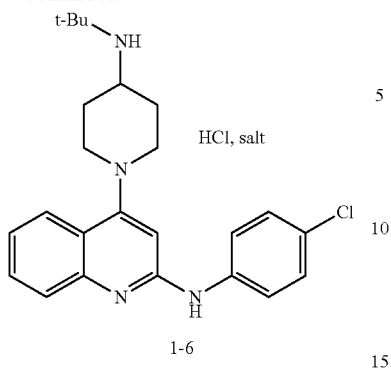

1-6

To a suspension of 2-(4-chlorophenylamino)-4-(4-tert-butylaminopiperidin-1-yl)-quinoline 1-5 (440 mg, 1.1 mmol) in 4 ml of EtOH was added dropwise 371 µL of a 7.25 M solution of HCl in EtOH. After dissolution of the solid, the mixture was stirred 20 minutes at room temperature. Then, the resulting solution was concentrated to about the half volume under reduced pressure and 6 ml of ether were added. The resulting mixture was stirred 1 hour at room temperature to obtain a white solid which was filtered off, rinsed with ether and dried under vacuum at 45° C. to give 401 mg (yield 85%) of a white solid corresponding to 2-(4-chlorophenylamino)-4-(4-tert-butylaminopiperidin-1-yl)-quinoline hydrochloride salt (1-6).

HPLC-MS, Method A: $t_r$=1.21 min, (ES+) $C_{24}H_{29}ClN_4$ required 408; found 409 [M+H], 353 [M-tBu+H]

$^1$H NMR (300 MHz, CD$_3$OD)

$^{13}$C NMR (75 MHz, CD$_3$OD)

Example 2: Preparation of 2-(4-chlorobenzylamino)-4-(4-tert-butylaminopiperidin-1-yl)-quinoline Hydrochloride Salt (2-3)

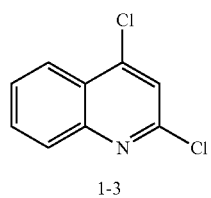

1-3

+

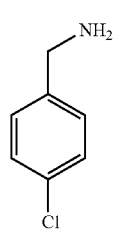

Pd(OAc)$_2$,
Xantphos
[161265-03-8]
t-BuONa,
THF, Δ
Yield = 59%

350
-continued

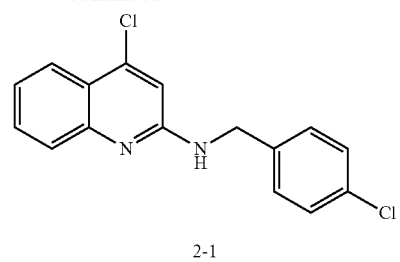

2-1

2-1 + 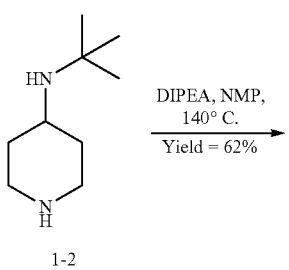

1-2

DIPEA, NMP,
140° C.
Yield = 62%

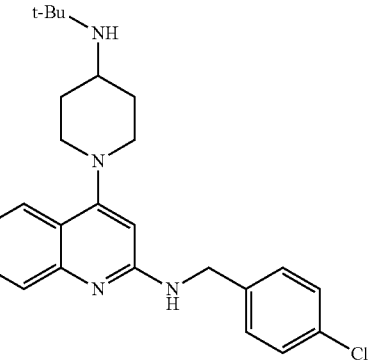

2-2

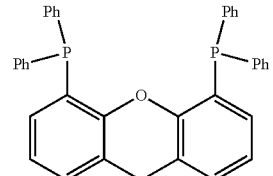

2-2

HCl, EtOH,
RT
Yield = 94%

-continued

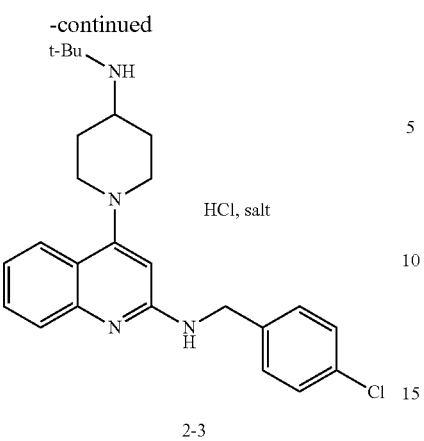

2-3

2.1 Synthesis of 2-(4-chlorobenzylamino)-4-chloroquinoline (2-1)

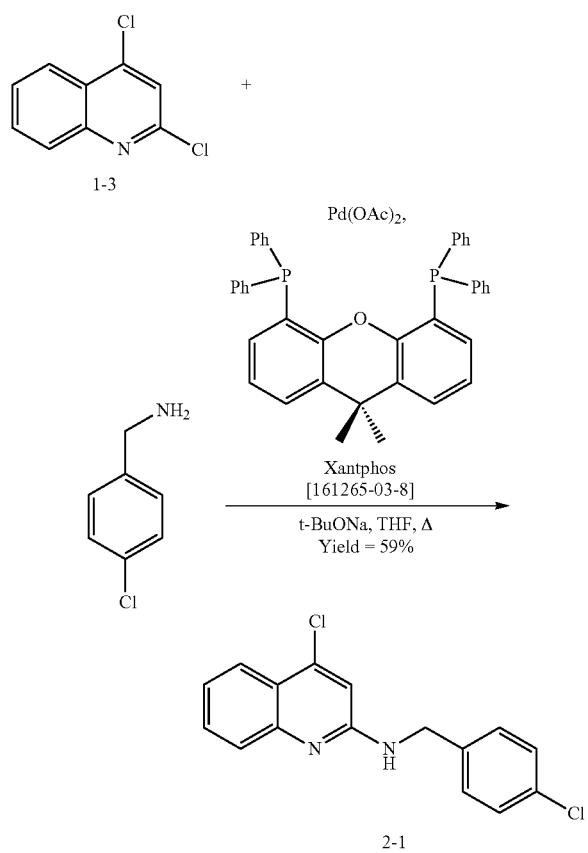

To a solution under nitrogen gas of 2,4-dichloroquinoline 1-3 (1.00 g, 5.05 mmol) in dry THF (10 ml) was added 4-chlorobenzylamine (1.46 g, 10.1 mmol) and t-BuONa (1.36 g, 14.1 mmol). The resulting mixture was degassed 5 min with nitrogen, then Xantphos (295 mg, 0.51 mmol) and Pd(OAc)$_2$ (58 mg, 0.25 mmol) were added and the reaction mixture was heated under reflux for 2 hours. The reaction mixture was then cooled to room temperature and concentrated under reduced pressure. The residue was partitioned between brine and EtOAc and the aqueous layer was extracted with EtOAc. The combined organic layers were dried over Na$_2$SO$_4$, filtered and concentrated under reduced pressure to give a brown oil. The crude product was purified by flash chromatography (gradient cyclohexane/DCM from 5/5 to 0/10) to give 897 mg (yield 59%) of a brown solid corresponding to 2-(4-chlorobenzylamino)-4-chloroquinoline (2-1).

Mass, Method A: (ES+) C$_{16}$H$_{12}$Cl$_2$N$_2$ required 302; found 303 [M+H]

$^1$H NMR (300 MHz, CDCl$_3$)

2.2 Synthesis of 2-(4-chlorobenzylamino)-4-(4-tert-butylaminopiperidin-1-yl)-quinoline (2-2)

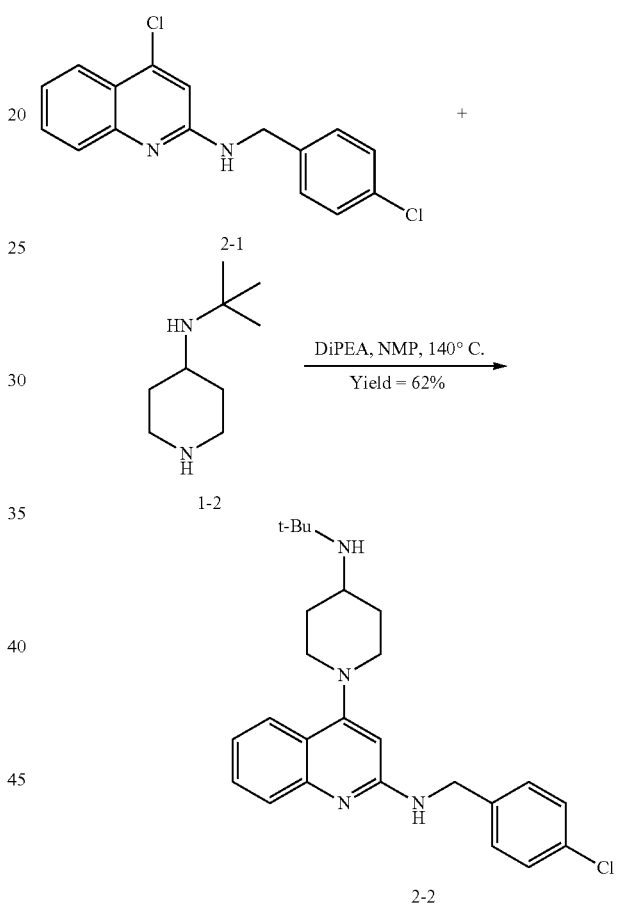

To a solution of 2-(4-chlorobenzylamino)-4-chloroquinoline 2-1 (1.05 g, 3.46 mmol) and 4-(tert-butylamino)-piperidine 1-2 (0.684 g, 4.38 mmol) in 5 ml of NMP was added N,N-Diisopropylethylamine (0.947 ml, 5.47 mmol) and the mixture was heated for 22 hours at 140° C. Then, the reaction mixture was cooled to room temperature, diluted with a 1N NaOH aqueous solution and the resulting mixture was extracted with EtOAc. The combined organic layers were dried over Na$_2$SO$_4$, filtered and concentrated under reduced pressure to give a yellow oil. The crude product was purified by flash chromatography (gradient cyclohexane/EtOAc from 8/2 to 0/10) to give a yellow solid. This solid was then recrystallized from MeCN to give 904 mg (yield 62%) of a white solid corresponding to 2-(4-chlorobenzylamino)-4-(4-tert-butylaminopiperidin-1-yl)-quinoline (2-2).

HPLC-MS, Method A: $t_r$=1.30 min, (ES+) $C_{25}H_{31}ClN_4$ required 422; found 423 [M+H], 368 [M-tBu+H]

$^1$H NMR (300 MHz, CDCl$_3$)

2.3 Preparation of 2-(4-chlorobenzylamino)-4-(4-tert-butylaminopiperidin-1-yl)-quinoline Hydrochloride Salt (2-3)

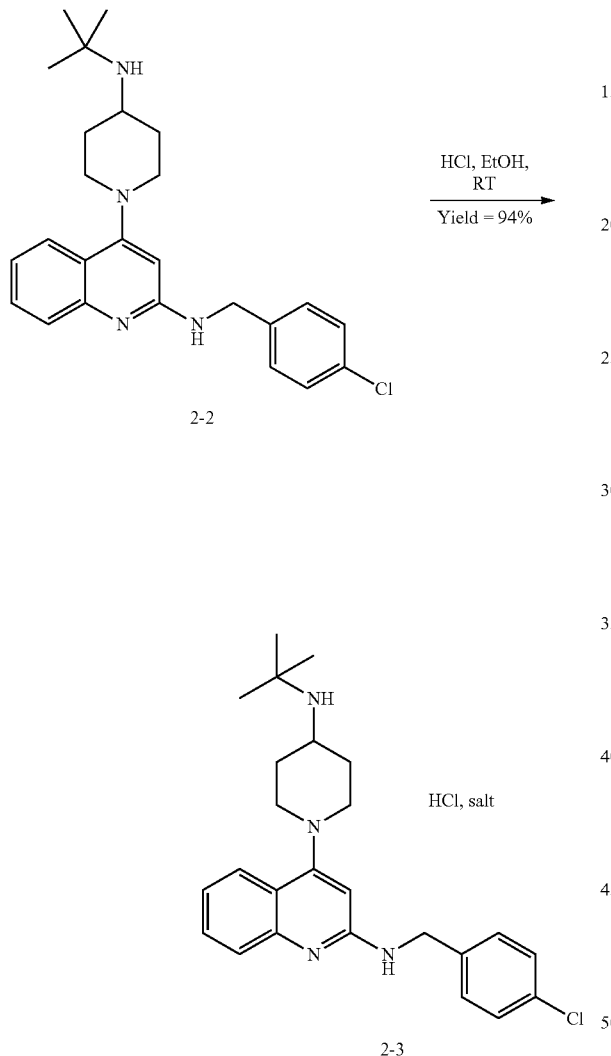

To a suspension of 2-(4-chlorobenzylamino)-4-(4-tert-butylaminopiperidin-1-yl)-quinoline 2-2 (450 mg, 1.06 mmol) in 2.5 ml of EtOH was added dropwise 400 µL of a 7 M solution of HCl in EtOH. After dissolution of the solid, the resulting mixture was stirred for 3 hours at room temperature. Then, the resulting solution was concentrated under reduced pressure and diethyl ether were added. The resulting mixture was stirred and triturated at room temperature to obtain a yellowish solid which was filtered off, rinsed with ether and dried under vacuum. The yellowish solid was dissolved in pure water and was then freeze-dried to give 401 mg (yield 94%) of a white solid corresponding to 2-(4-chlorobenzylamino)-4-(4-tert-butylaminopiperidin-1-yl)-quinoline hydrochloride salt (2-3).

HPLC-MS, Method A: $t_r$=1.31 min, (ES+) $C_{25}H_{31}ClN_4$ required 422; found 423 [M+H], 369 [M-tBu+H]

$^1$H NMR (300 MHz, DMSO-d$_6$)

Example 3: Preparation of 2-[3-methyl-4-(pyrimidin-2-ylamino)phenylamino]-4-(4-tert-butylaminopiperidin-1-yl)-quinoline Hydrochloride Salt (3-5)

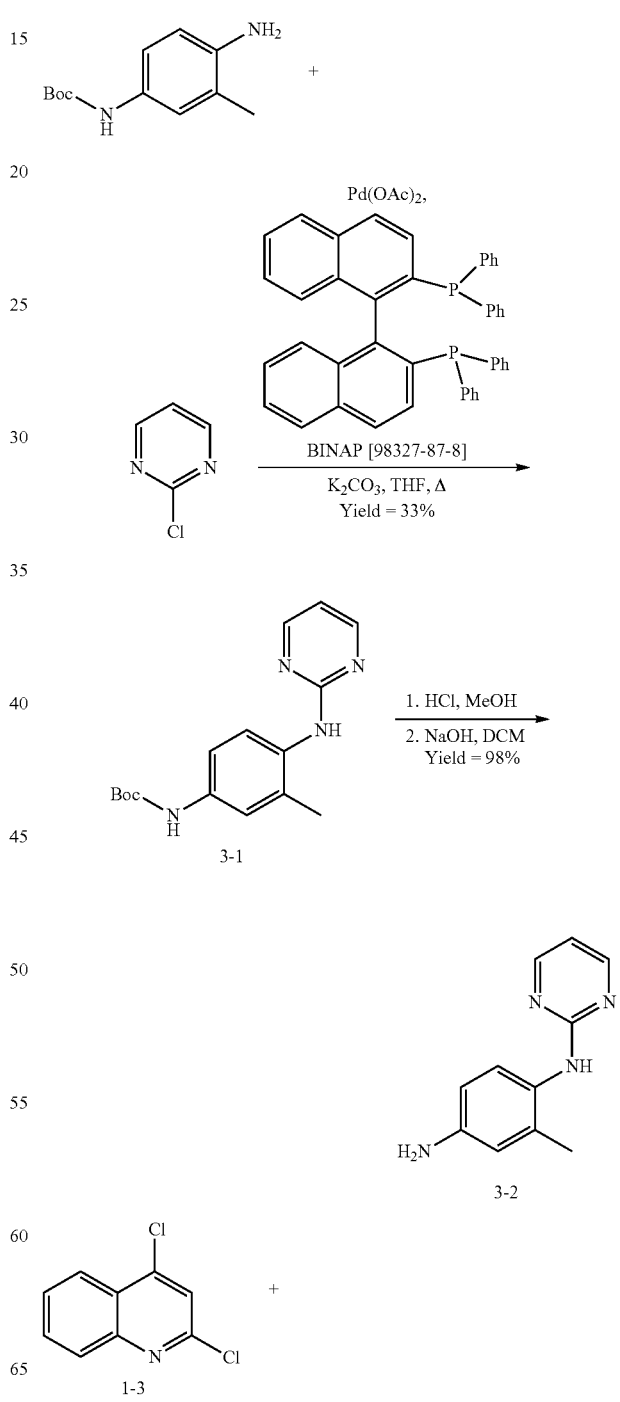

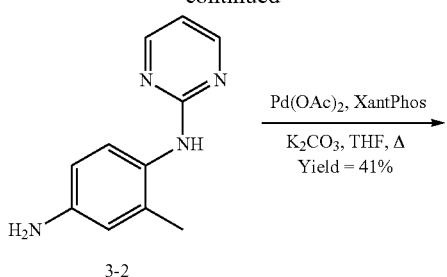
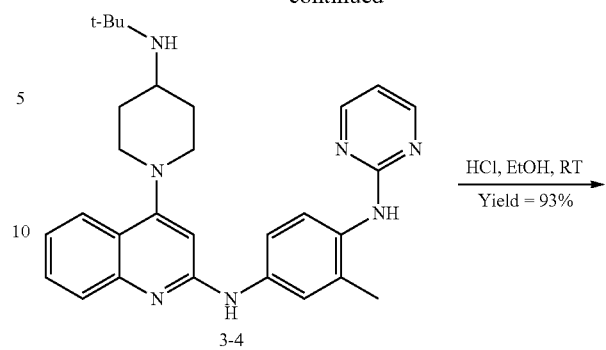

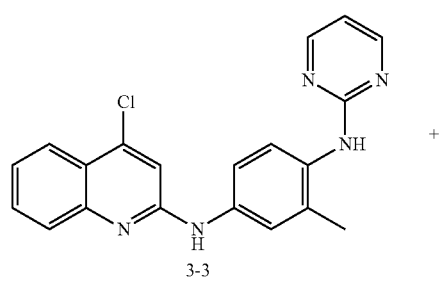

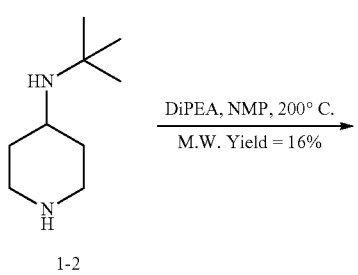

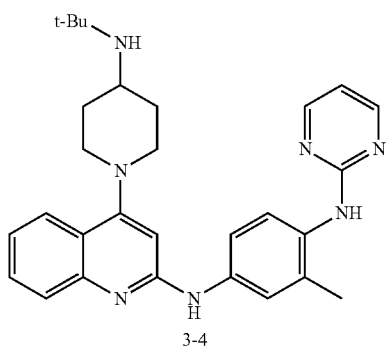

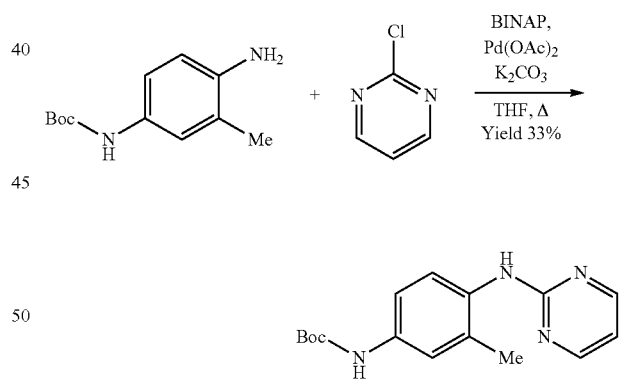

3.1 Synthesis of 2-methyl-$N^1$-(pyrimidin-2-yl)-$N^4$-(tert-butyloxycarbonyl)-benzene-1,4-diamine (3-1)

A solution of 2-methyl-$N^4$-(tert-butyloxycarbonyl)-benzene-1,4-diamine (2.40 g, 10.8 mmol), 2-chloropyrimidine (0.78 g, 6.5 mmol) and K$_2$CO$_3$ (2.24 g, 16.2 mmol) in dry THF (48 ml) was degassed with nitrogen during 15 minutes. Then, Pd(OAc)$_2$ (58 mg, 0.26 mmol) and BINAP ligand (320 mg, 0.52 mmol) were added and the reaction mixture was degassed a second time during 20 minutes. The reaction mixture was finally heated under reflux for 1 hour. The reaction mixture was then cooled to room temperature and concentrated under reduced pressure. The residue was partitioned between water and EtOAc and the aqueous layer was extracted with EtOAc. The combined organic layers were dried over Na₂SO₄, filtered and concentrated under reduced pressure. The crude product was purified by flash chromatography (gradient cyclohexane/EtOAc from 10/0 to 7/3) to give 650 mg (yield 33%) of a brown solid corresponding to 2-methyl-$N^1$-(pyrimidin-2-yl)-$N^4$-(tert-butyloxycarbonyl)-benzene-1,4-diamine (3-1).

HPLC-MS, Method A: $t_r$=2.06 min, (ES+) $C_{16}H_{20}N_4O_2$ required 300; found 301 [M+H]

$^1$H NMR (300 MHz, CD₃OD)

3.2 Synthesis of 2-methyl-N1-(pyrimidin-2-yl)-benzene-1,4-diamine (3-2)

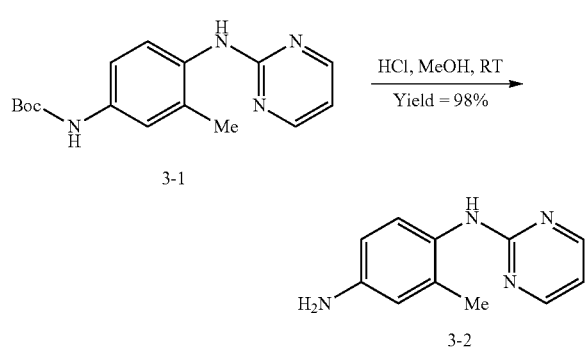

To 2-methyl-$N^1$-(pyrimidin-2-yl)-$N_4$-(tert-butyloxycarbonyl)-benzene-1,4-diamine 3-1 (1.18 g, 3.93 mmol) was added dropwise at room temperature a 3M HCl solution in methanol (15 ml). Then, the reaction mixture was stirred at room temperature during 1 hour. The reaction was then concentrated under reduced pressure and the residue was partitioned between DCM and a 1M NaOH aqueous solution. The resulting aqueous layer was extracted with CH₂Cl₂. The combined organic layers were dried over Na₂SO₄, filtered and concentrated under reduced pressure to give 787 mg (yield 98%) of a yellow oil corresponding to 2-methyl-$N_1$-(pyrimidin-2-yl)benzene-1,4-diamine (3-2).

Mass, Method A: (ES+) $C_{11}H_{12}N_4$ required 200; found 201 [M+H]

$^1$H NMR (300 MHz, CD₃OD)

3.3 Synthesis of 2-[4-(2-pyrimidinylamino)-3-methyl-phenylamino]-4-chloroquinoline (3-3)

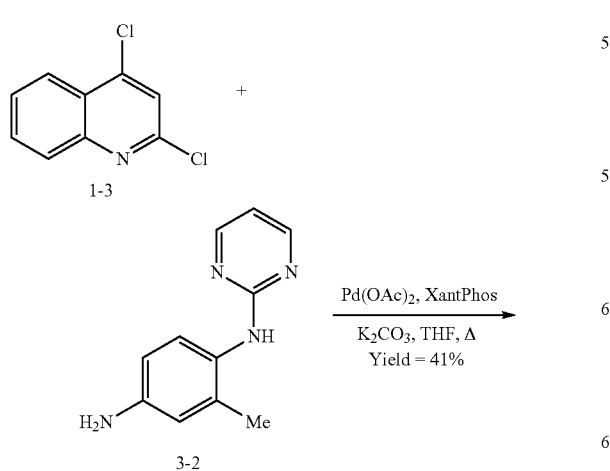

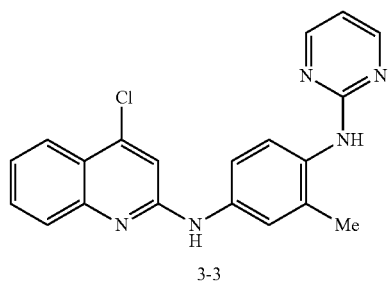

A solution of 2-methyl-$N^1$-(pyrimidin-2-yl)benzene-1,4-diamine 3-2 (771 mg, 3.85 mmol), 2,4-dichloroquinoline 1-3 (693 mg, 3.5 mmol) and K₂CO₃ (1.35 g, 9.80 mmol) in dry THF (7 ml) was degassed with nitrogen during 20 minutes. Then, Pd(OAc)₂ (47 mg, 0.21 mmol) and XantPhos ligand (61 mg, 0.10 mmol) were added and the reaction mixture was degassed a second time during 20 minutes. The reaction mixture was finally heated under reflux during 4 hours. The reaction mixture was then cooled to room temperature and concentrated under reduced pressure. The residue was partitioned between water and EtOAc and the aqueous layer was extracted with EtOAc. The combined organic layers were dried over Na₂SO₄, filtered and concentrated under reduced pressure. The crude product was purified by flash chromatography (gradient cyclohexane/EtOAc from 10/0 to 5/5) to give 520 mg (yield 41%) of a yellow solid corresponding to 2-[4-(2-pyrimidinylamino)-3-methyl-phenylamino]-4-chloroquinoline (3-3).

Mass, Method A: (ES+) $C_{20}H_{16}ClN_5$ required 361; found 362 [M+H]

3.4 Synthesis of 2-[4-(2-pyrimidinylamino)-3-methyl-phenylamino]-4-(4-tert-butylaminopiperidin-1-yl)-quinoline (3-4)

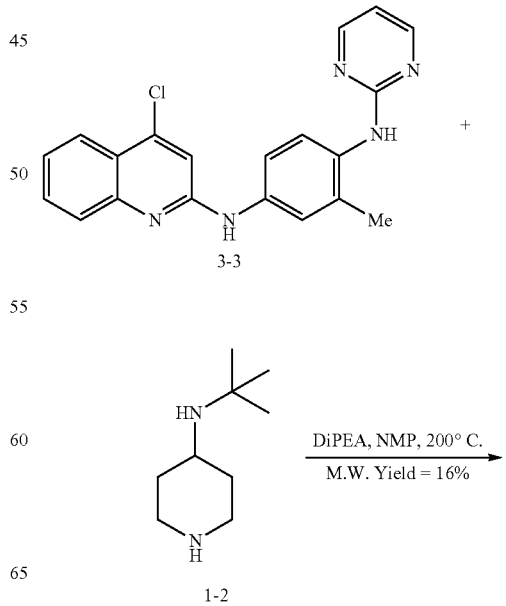

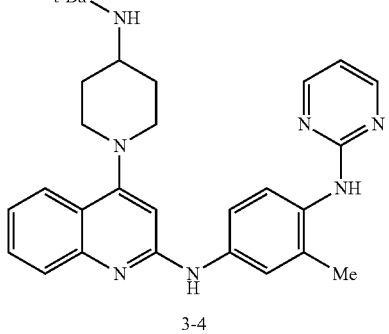

3-4

To a solution of 2-[4-(2-pyrimidinylamino)-3-methyl-phenylamino]-4-chloroquinoline 3-3 (350 mg, 0.97 mmol) in NMP (1.5 ml) was added 4-tert-butylaminopiperidine 1-2 (760 mg, 4.80 mmol). The resulting solution was heated for 30 minutes at 200° C. in a laboratory microwave oven. Then, the resulting reaction mixture was cooled and partitioned between water and EtOAc and the aqueous layer was extracted with EtOAc. The combined organic layers were dried over Na$_2$SO$_4$, filtered and concentrated under reduced pressure. The crude product was purified by flash chromatography (gradient cyclohexane/EtOAc from 10/0 to 5/5) to give 75 mg (yield 16%) of a brown solid corresponding to 2-[4-(2-pyrimidinylamino)-3-methyl-phenylamino]-4-(4-tert-butylaminopiperidin-1-yl)-quinoline 3-4.

HPLC-MS, Method A: t$_r$=1.15 min, (ES+) C$_{29}$H$_{35}$N$_7$ required 481; found 482 [M+H], 426 [M-tBu+H]

3.5 Preparation of 2-[4-(2-pyrimidinylamino)-3-methyl-phenylamino]-4-(4-tert-butylaminopiperidin-1-yl)-quinoline Hydrochloride Salt (3-5)

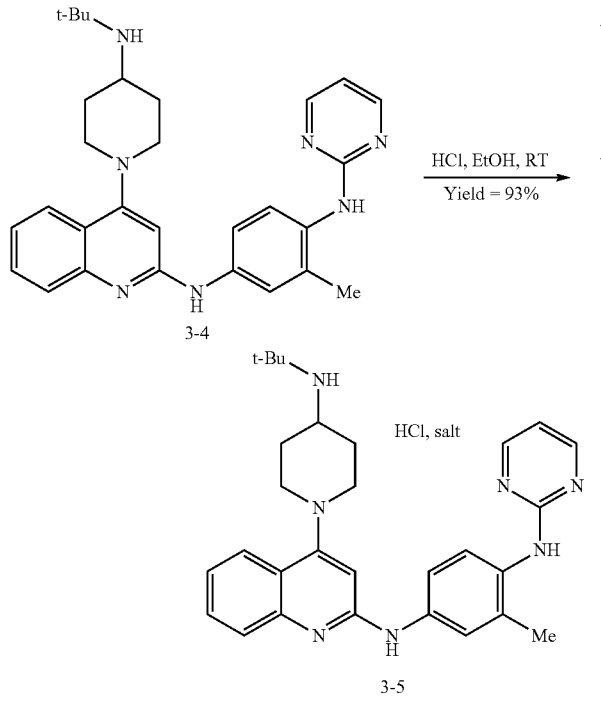

A 3.0 M solution of HCl in EtOH (290 µL) was added dropwise to 2-[4-(2-pyrimidinylamino)-3-methyl-phenylamino]-4-(4-tert-butylaminopiperidin-1-yl)-quinoline 3-4 (75 mg, 0.16 mmol). The resulting mixture was stirred for 1 hour at room temperature. The resulting mixture was filtered and evaporated under reduced pressure to give 80 mg (yield 93%) of a yellowish solid corresponding to 2-[4-(2-pyrimidinylamino)-3-methyl-phenylamino]-4-(4-tert-butylaminopiperidin-1-yl)-quinoline hydrochloride salt (3-5).

HPLC-MS, Method A: t$_r$=1.14 min, (ES+) C$_{29}$H$_{35}$N$_7$ required 481; found 482 [M+H], 426 [M-tBu+H]

$^1$H NMR (300 MHz, CD$_3$OD+few drops of DMSO-d$_6$)

Example 4: Preparation of 2-{4-[4-(pyridin-3-yl)-2-pyrimidinamino]-3-methyl-phenylamino}-4-(4-tert-butylaminopiperidin-1-yl)-quinoline Hydrochloride Salt (4-3)

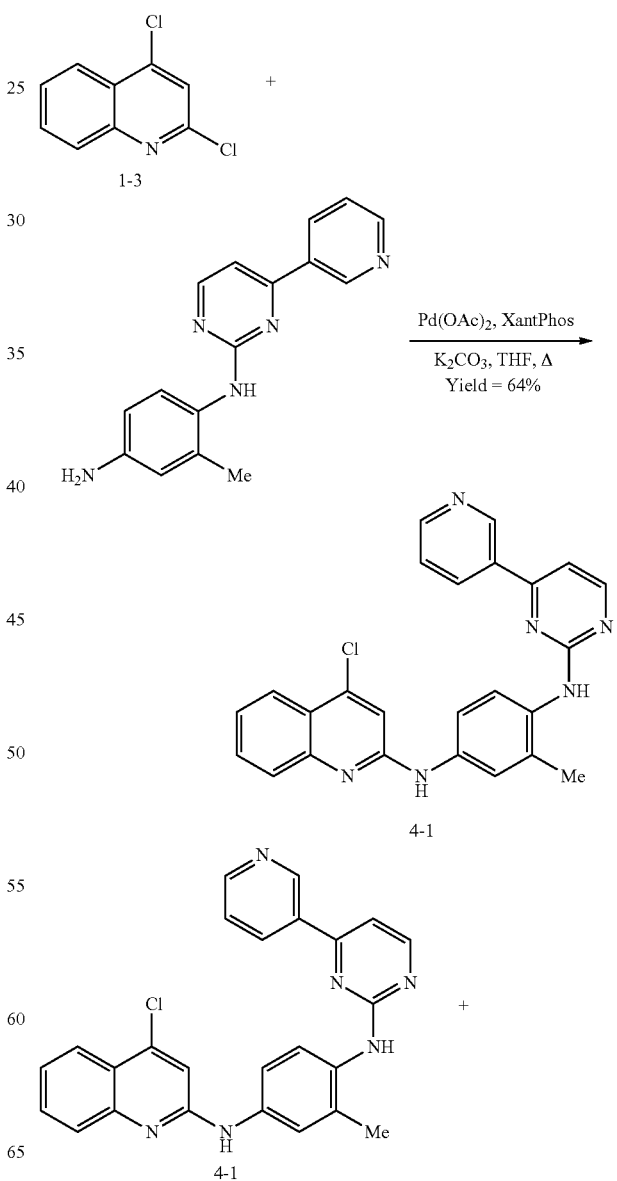

-continued

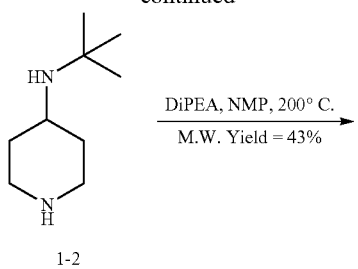
1-2

4.1 Synthesis of 2-{4-[4-(pyridin-3-yl)-2-pyrimidinamino]-3-methyl-phenylamino}-4-chloroquinoline (4-1)

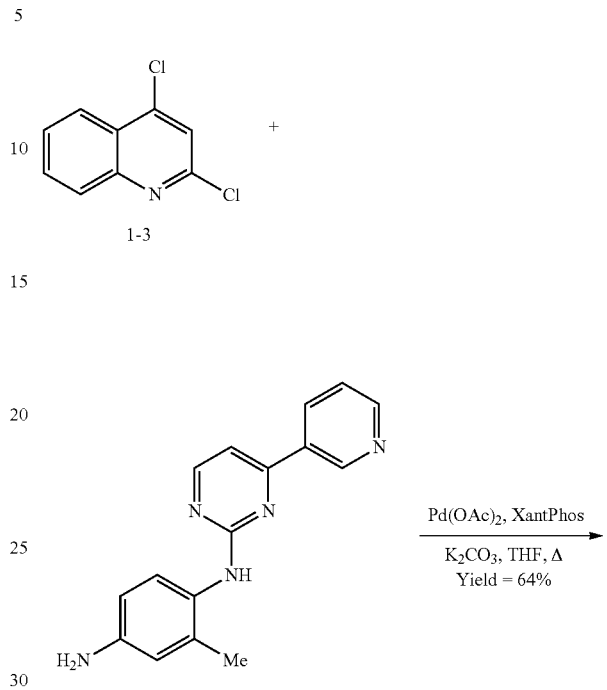

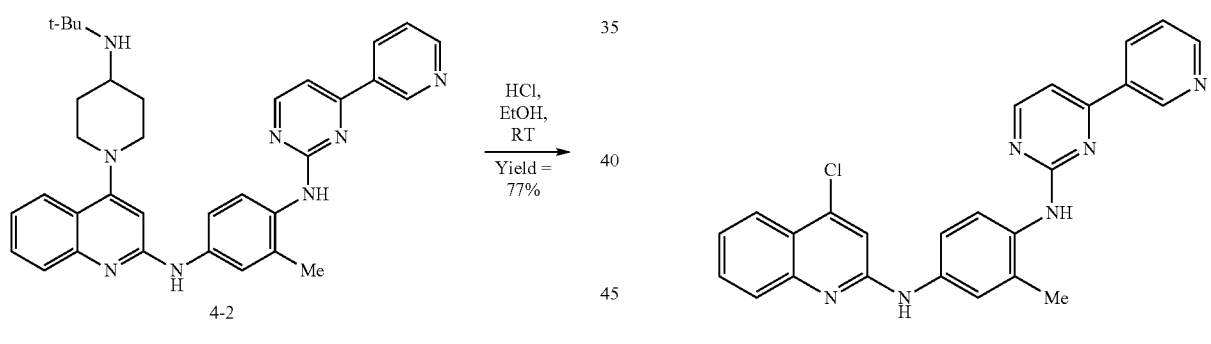

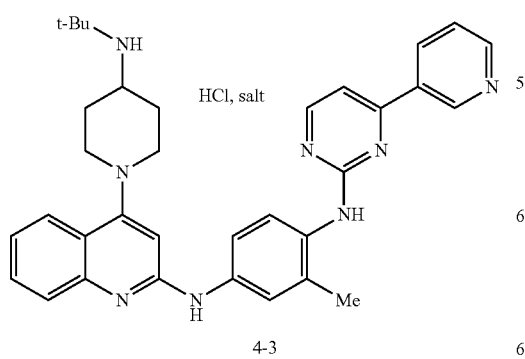

To a solution of 2-methyl-$N^1$-[4-(pyridine-3-yl)-pyrimidin-2-yl]benzene-1,4-diamine (1.18 g, 4.26 mmol), 2,4-dichloroquinoline 1-3 (767 mg, 3.87 mmol) in dry THF (11.9 ml) was added $K_2CO_3$ (2.7 g, 19.0 mmol) and the reaction mixture was degassed with nitrogen during 15 minutes. Then, XantPhos ligand (226 mg, 0.387 mmol) and Pd(OAc)$_2$ (44 mg, 0.19 mmol) were added and the reaction mixture was degassed a second time during 15 minutes. Then, the resulting reaction mixture was finally heated under reflux overnight. The reaction mixture was then cooled to room temperature and concentrated under reduced pressure. The residue was partitioned between water and EtOAc and the aqueous layer was extracted with EtOAc. The combined organic layers were dried over $Na_2SO_4$, filtered and concentrated under reduced pressure. The crude product was purified by flash chromatography (gradient cyclohexane/EtOAc from 10/0 to 0/10) to give 1.08 g (yield 64%) of a brown solid corresponding to 2-{4-[4-(pyridin-3-yl)-2-pyrimidinamino]-3-methyl-phenylamino}-4-chloroquinoline (4-1).

Mass, Method A: (ES+) $C_{25}H_{19}ClN_6$ required 438; found 439 [M+H]

$^1$H NMR (300 MHz, CD$_3$OD)

4.2 Synthesis of 2-{4-[4-(pyridin-3-yl)-2-pyrimidinamino]-3-methyl-phenylamino}-4-(4-tert-butylaminopiperidin-1-yl)-quinoline (4-2)

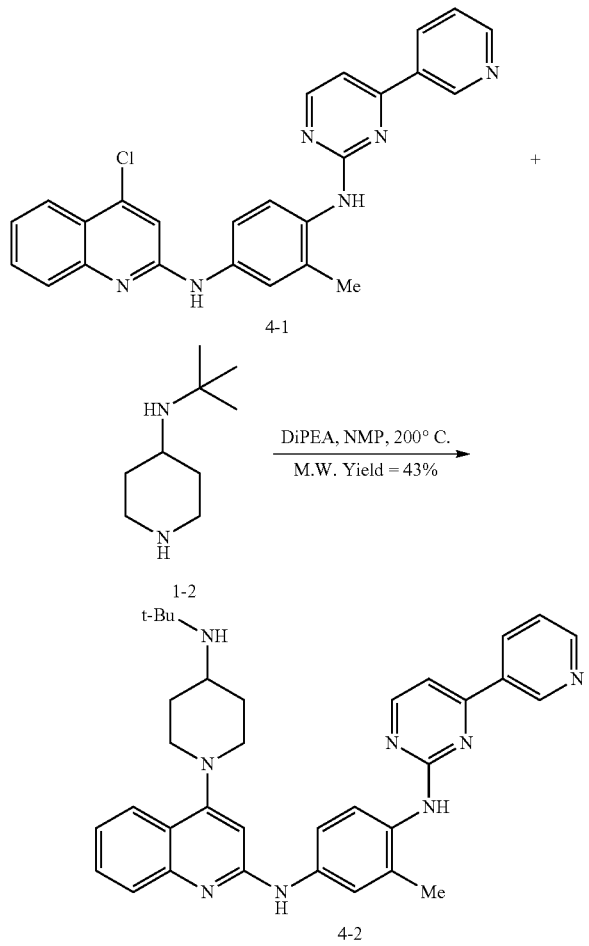 [SMILES: Cc1cc(Nc2cc(Cl)c3ccccc3n2)ccc1Nc1nccc(-c2cccnc2)n1 ; CC(C)(C)NC1CCNCC1 ; Cc1cc(Nc2cc(N3CCC(NC(C)(C)C)CC3)c3ccccc3n2)ccc1Nc1nccc(-c2cccnc2)n1]

To a solution of 2-{4-[4-(pyridin-3-yl)-2-pyrimidinamino]-3-methyl-phenylamino}-4-chloroquinoline 4-1 (1.0 g, 2.28 mmol) in NMP (10 ml) was added 4-tert-butylaminopiperidine 1-2 (1.8 g, 11.0 mmol). Then, the reaction mixture was heated for 90 minutes at 200° C. in a laboratory microwave oven. The resulting mixture was partitioned between water and EtOAc and the aqueous layer was extracted with EtOAc. The combined organic layers were dried over Na$_2$SO$_4$, filtered and concentrated under reduced pressure. The crude product was purified by flash chromatography (from EtOAc/DCM 3/2 then DCM/MeOH 9/1) to give 1.01 g of a yellow solid which was recrystallized from EtOH to give 550 mg (yield 43%) of a white solid corresponding to 2-{4-[4-(pyridin-3-yl)-2-pyrimidinamino]-3-methyl-phenylamino}-4-(4-tert-butylaminopiperidin-1-yl)-quinoline (4-2).

HPLC-MS, Method A: $t_r$=1.20 min, (ES+) $C_{34}H_{38}N_8$ required 558; found 559 [M+H], 503 [M-tBu+H]

$^1$H NMR (300 MHz, DMSO-d$_6$)

4.3 Preparation of 2-{4-[4-(pyridin-3-yl)-2-pyrimidinamino]-3-methyl-phenylamino}-4-(4-tert-butylaminopiperidin-1-yl)-quinoline Hydrochloride Salt (4-3)

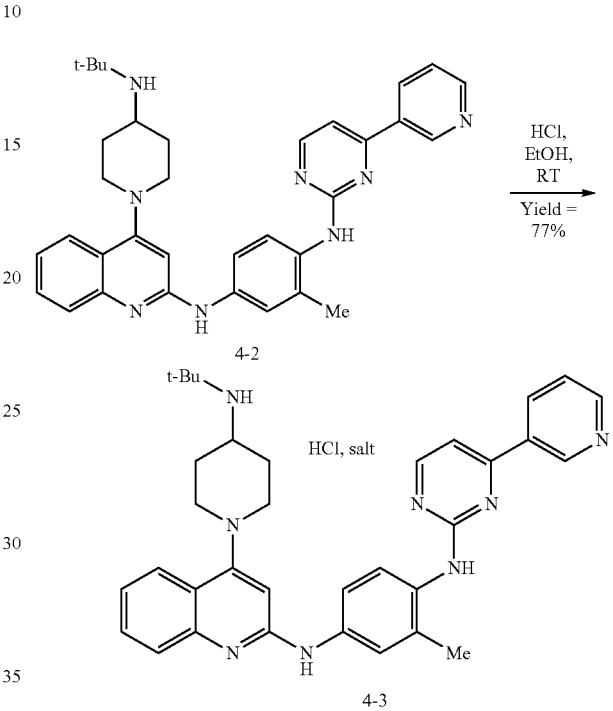

To a suspension of 2-{4-[4-(pyridin-3-yl)-2-pyrimidinamino]-3-methyl-phenylamino}-4-(4-tert-butylaminopiperidin-1-yl)-quinoline 4-2 in EtOH (5.5 ml) was added dropwise a 3.0 M solution of HCl in EtOH (4 ml). The formed yellow solid was filtered off and then triturated with cyclohexane. The suspension was filtered off to give 505 mg (yield 77%) of a white solid corresponding to 2-{4-[4-(pyridin-3-yl)-2-pyrimidinamino]-3-methyl-phenylamino}-4-(4-tert-butylaminopiperidin-1-yl)-quinoline hydrochloride salt (4-3).

HPLC-MS, Method A: $t_r$=1.22 min, (ES+) $C_{34}H_{38}N_8$ required 558; found 559 [M+H], 503 [M-tBu+H]

$^1$H NMR (300 MHz, CD$_3$OD+few drops of DMSO-d$_6$)
$^{13}$C NMR (125 MHz, CD$_3$OD)

Example 5: Preparation of 2-(4-fluorobenzylamino)-4-(4-tert-butylaminopiperidin-1-yl)-quinoline Hydrochloride Salt (5-2) and Base Form (5-3)

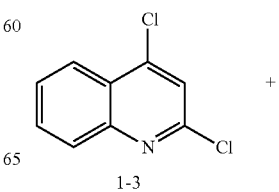

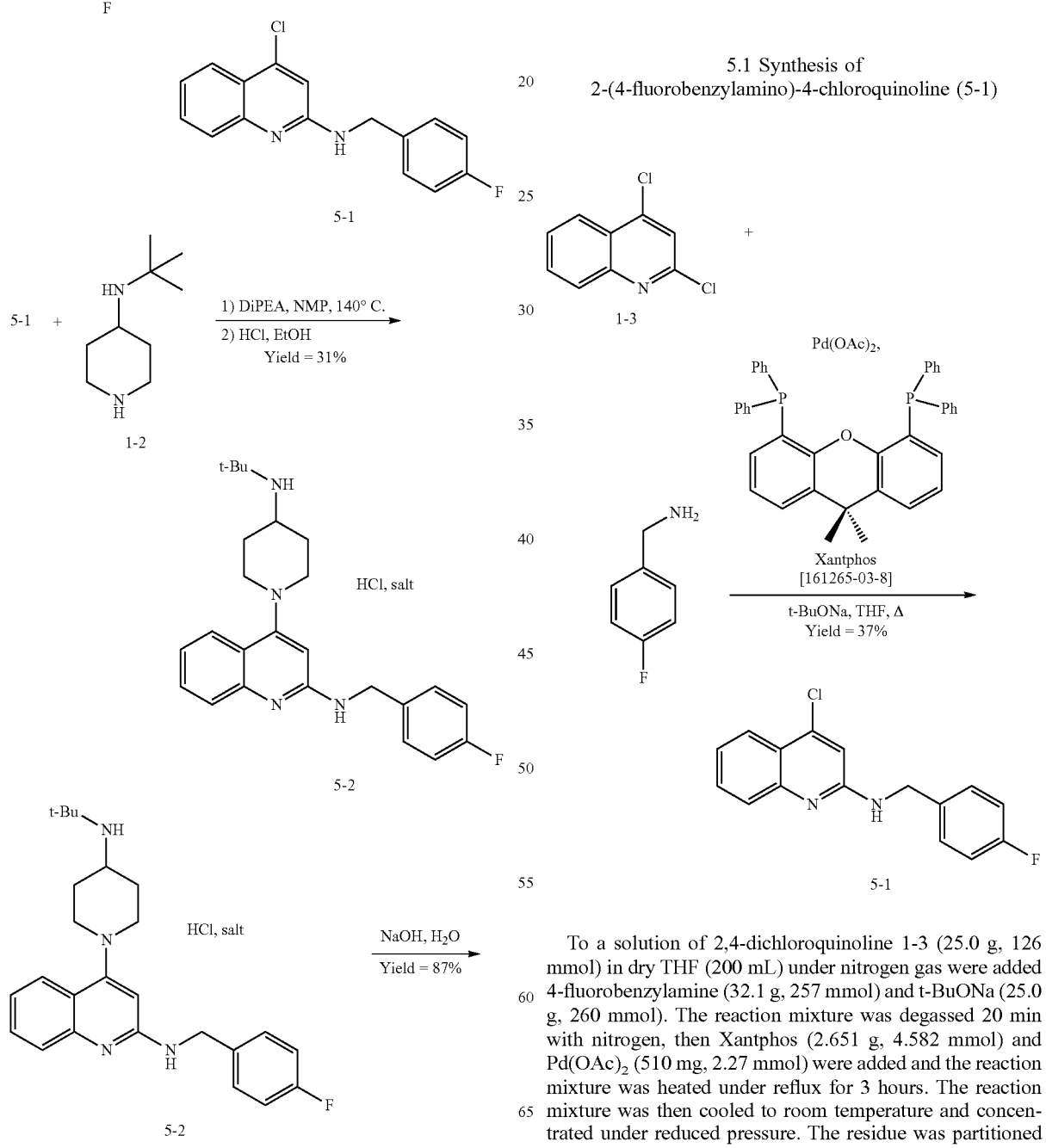

5.1 Synthesis of 2-(4-fluorobenzylamino)-4-chloroquinoline (5-1)

To a solution of 2,4-dichloroquinoline 1-3 (25.0 g, 126 mmol) in dry THF (200 mL) under nitrogen gas were added 4-fluorobenzylamine (32.1 g, 257 mmol) and t-BuONa (25.0 g, 260 mmol). The reaction mixture was degassed 20 min with nitrogen, then Xantphos (2.651 g, 4.582 mmol) and Pd(OAc)₂ (510 mg, 2.27 mmol) were added and the reaction mixture was heated under reflux for 3 hours. The reaction mixture was then cooled to room temperature and concentrated under reduced pressure. The residue was partitioned between brine and EtOAc and the aqueous layer was extracted with EtOAc. The combined organic layers were dried over $Na_2SO_4$, filtered and concentrated under reduced pressure to give a brown oil. The crude product was purified by flash chromatography (gradient cyclohexane/EtOAc from 100:0 to 70:30) to give 13.6 g (yield 37%) of a brown solid corresponding to 2-(4-fluorobenzylamino)-4-chloroquinoline (5-1).

HPLC-MS, Method B: $t_r$=1.79 min, (ES+) $C_{16}H_{12}ClFN_2$ required 286; found 287 [M+H]

5.2 Synthesis of 2-(4-fluorobenzylamino)-4-(4-tert-butylaminopiperidin-1-yl)-quinoline Hydrochloride Salt (5-2)

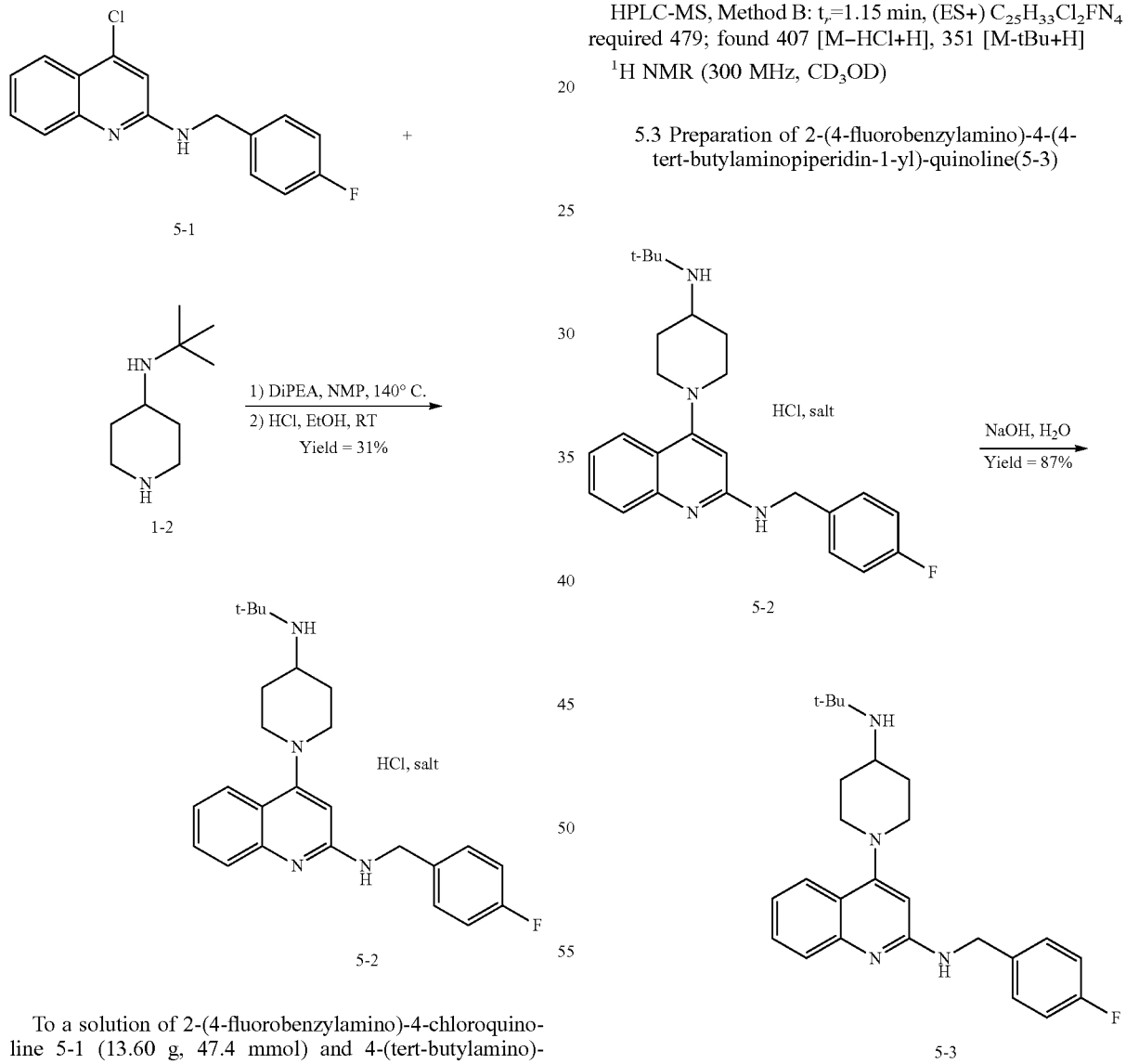

To a solution of 2-(4-fluorobenzylamino)-4-chloroquinoline 5-1 (13.60 g, 47.4 mmol) and 4-(tert-butylamino)-piperidine 1-2 (9.64 g, 61.7 mmol) in NMP (68 mL) was added N,N-Diisopropylethylamine (13.2 mL, 75.8 mmol) and the reaction mixture was heated for 18 hours at 140° C. The solution was then cooled to room temperature, diluted with 1N NaOH aqueous solution and the resulting mixture was extracted with EtOAc. The combined organic layers were washed with brine, dried over $Na_2SO_4$, filtered and concentrated under reduced pressure to give a yellow oil. The crude product was purified by flash chromatography (gradient EtOAc/MeOH from 100:0 to 80:20) to give a yellow solid. This solid was then recrystallized from Cyclohexane to give 10.1 g of a yellow solid. The yellow solid was then dissolved in EtOH (90 mL) and 10.9 mL of a 5.25M solution of HCl in EtOH was added dropwise. The reaction mixture was then concentrated under reduced pressure. The obtained residue was dissolved in acetone (85 mL) and iPrOH (25 mL) and the mixture was heated under reflux for 30 min, cooled to room temperature and filtered under nitrogen to give a yellow solid. The solid was washed with acetone and dried under vacuum to provide 7.1 g (yield 31%) of a beige solid corresponding to 2-(4-fluorobenzylamino)-4-(4-tert-butylaminopiperidin-1-yl)-quinoline hydrochloride salt (5-2).

HPLC-MS, Method B: $t_r$=1.15 min, (ES+) $C_{25}H_{33}Cl_2FN_4$ required 479; found 407 [M−HCl+H], 351 [M-tBu+H]

$^1$H NMR (300 MHz, $CD_3OD$)

5.3 Preparation of 2-(4-fluorobenzylamino)-4-(4-tert-butylaminopiperidin-1-yl)-quinoline(5-3)

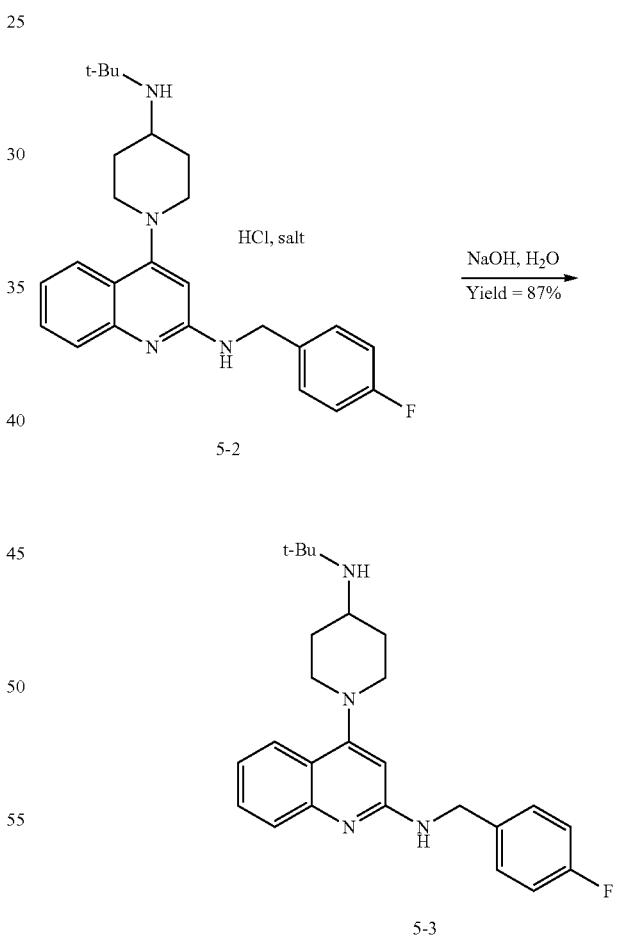

To a solution of 2-(4-fluorobenzylamino)-4-(4-tert-butylaminopiperidin-1-yl)-quinoline hydrochloride salt (2.10 g) in EtOAc (300 mL) was added dropwise a 1N NaOH aqueous solution (150 mL), and the resulting reaction mixture was stirred at room temperature for 1 hour. Layers were separated and the aqueous layer was extracted with EtOAc.

The combined organic layers were washed with H$_2$O, dried over MgSO$_4$, filtered and concentrated under reduced pressure to give 1.55 g (yield 87%) of a yellow solid corresponding to 2-(4-fluorobenzylamino)-4-(4-tert-butylaminopiperidin-1-yl)-quinoline (5-3).

HPLC-MS, Method B: t$_r$=1.16 min, (ES+) C$_{25}$H$_{33}$Cl$_2$FN$_4$ required 479; found 407 [M−HCl+H], 351 [M−tBu+H]

$^1$H NMR (300 MHz, CD$_3$OD)

Example 6: Preparation of 2-(4-chlorophenylamino)-4-(4-tert-butylaminopiperidin-1-yl)-8-methoxyquinoline Hydrochloride Salt (6-4)

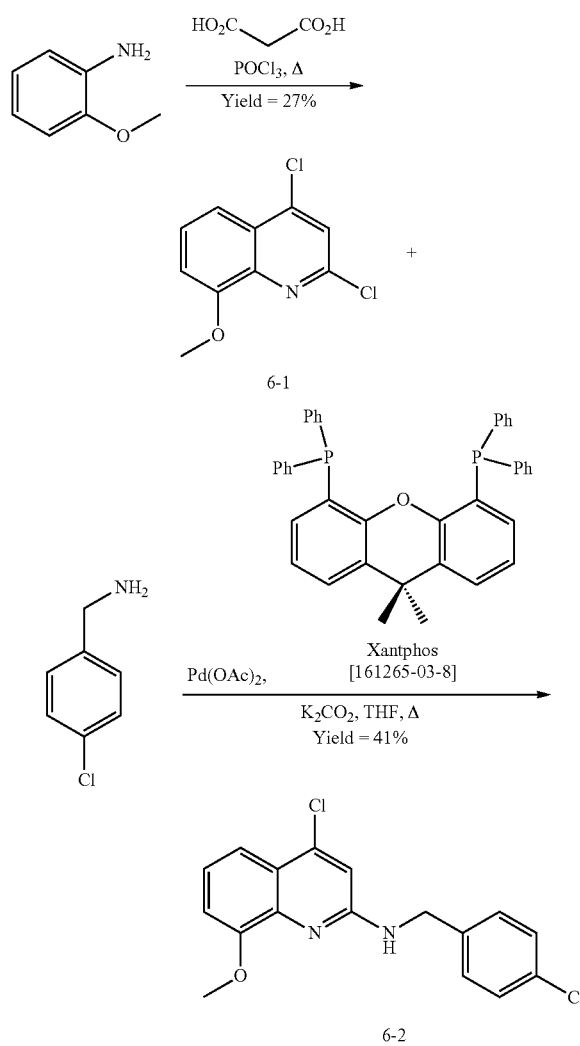

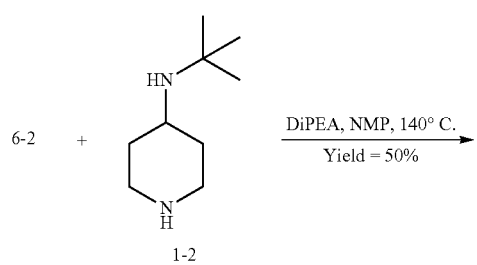

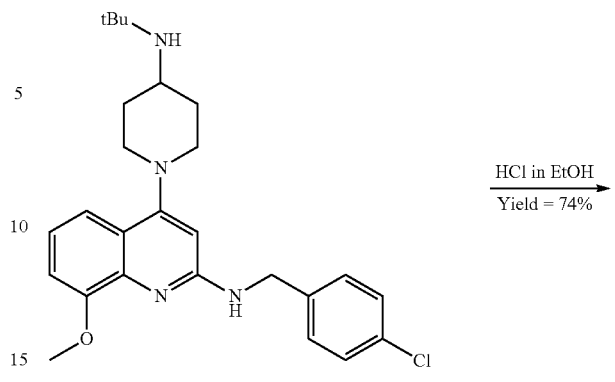

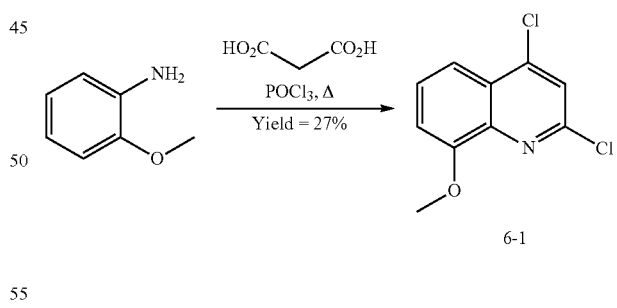

6.1 Synthesis of 2,4-chloro-8-methoxyquinoline (6-1)

To 2-methoxyaniline (5.0 g, 40.6 mmol) and Malonic acid (6.34 g, 60.97 mmol) was added dropwise at 0° C. phosphoryl chloride (50 ml). The resulting mixture was stirred and heated under reflux overnight. Then, the mixture was cooled, concentrated under reduced pressure and co-evaporated twice with toluene. The residue was then taken up with DCM and washed with cold water. The aqueous layer was extracted with DCM and the combined organic layers were dried over Na$_2$SO$_4$, filtered and concentrated under reduced pressure to give a brown-solid. The crude product was purified by flash chromatography (gradient Petroleum ether/EtOAC from 8/2 to 5/10) to give 2.5 g (yield 27%) of a yellowish solid corresponding to 2, 4-dichloro-8-methoxyquinoline (6-1).

HPLC-MS, Method C: $t_r$=2.02 min, (ES+) $C_{10}H_7Cl_2NO$ required 227; found 228 [M+H].

$^1$H NMR (500 MHz, CDCl$_3$)

6.2 Synthesis of 2-(4-chlorobenzylamino)-4-chloro-8-methoxyquinoline (6-2)

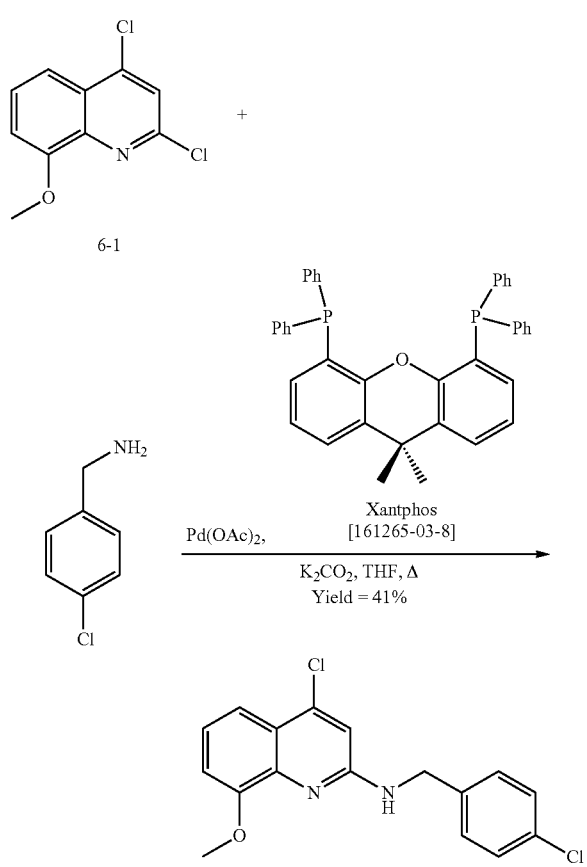

To a solution under nitrogen gas of 2,4-dichloro-8-methoxyquinoline (6-1, 2.0 g, 8.81 mmol) in dry THF (20 ml) was added 4-chlorobenzylamine (1.86 g, 13.21 mmol) and K$_2$CO$_3$ (2.43 g, 17.6 mmol). The resulting mixture was degassed 5 min with nitrogen, then Xantphos (509 mg, 0.81 mmol) and Pd(OAc)$_2$ (98 mg, 0.44 mmol) were added and the reaction mixture was heated under reflux for 16 hours. The reaction mixture was then cooled to room temperature and concentrated under reduced pressure. The residue was partitioned between brine and EtOAC and the aqueous layer was extracted with EtOAC. The combined organic layers were dried over Na$_2$SO$_4$, filtered and concentrated under reduced pressure to give a light brown solid. The crude product was purified by flash chromatography (gradient petroleum ether/EtOAC from 09/01 to 04/06) to give 1.2 g (yield 41%) of a brown solid corresponding to 2-(4-chlorobenzylamino)-4-chloro-8-methoxyquinoline (6-2).

HPLC-MS, Method D: $t_r$=1.30 min, (ES+) $C_{17}H_{14}Cl_2N_2O$ required 332; found 333 [M+H]

$^1$H NMR (400 MHz, CDCl$_3$)

6.3 Synthesis of 2-(4-chlorobenzylamino)-4-(4-tert-butylaminopiperidin-1-yl)-8-methoxy Quinoline (6-3)

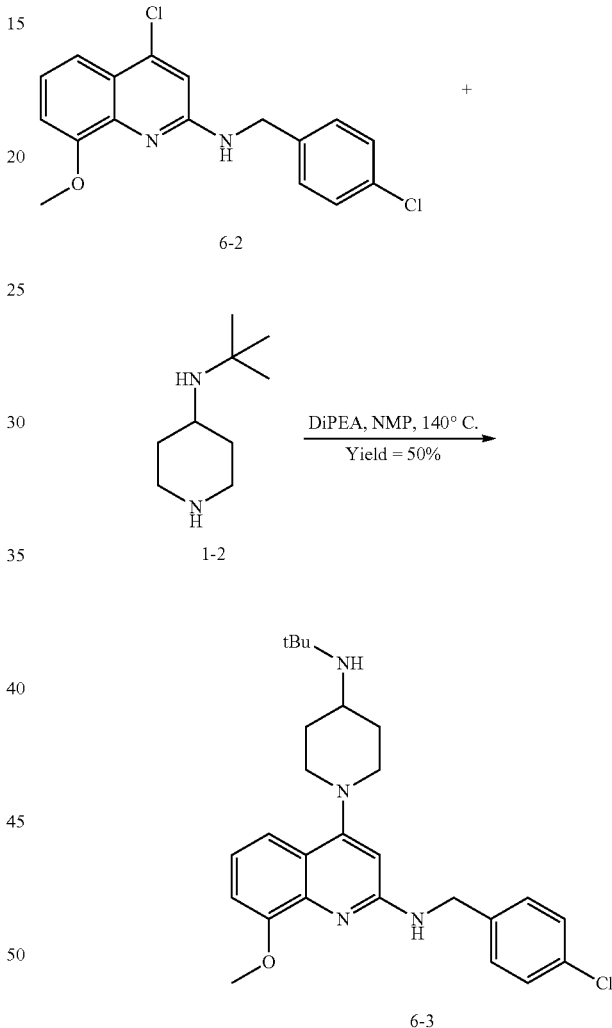

To a solution of 2-(4-chlorobenzylamino)-4-chloro-8-methoxyquinoline (6-2, 1.2 g, 3.61 mmol) and 4-tert-butylaminopiperidine (1-2, 0.563 g, 3.61 mmol) in 10 ml of NMP was added N,N-diisopropylethylamine (2.3 ml, 7.22 mmol) and the mixture was heated for 48 hours at 140° C. in a sealed tube. Then, the reaction mixture was cooled, diluted with water and the resulting mixture was extracted with EtOAC. The combined organic layers were dried over Na$_2$SO$_4$, filtered and concentrated under reduced pressure to give a light brown solid. The crude product was purified by flash chromatography (gradient Petroleum ether/EtOAc from 8/2 to 0/10) to give 800 mg (yield 50%) of a yellowish solid corresponding to 2-(4-chlorobenzylamino)-4-(4-tert-butylaminopiperidin-1-yl)-8-methoxyquinoline (6-3).

HPLC-MS, Method D: $t_r$=0.99 min, (ES+) $C_{26}H_{33}ClN_4O$ required 452; found 453 [M+H]

¹H NMR (500 MHz, DMSO-d6)

6.4 Synthesis of 2-(4-chlorobenzylamino)-4-(4-tert-butylaminopiperidin-1-yl)-8-methoxy Quinoline Hydrochloride Salt (6-4)

solid corresponding to 2-(4-chlorobenzylamino)-4-(4-tert-butylaminopiperidin-1-yl)-8-methoxyquinoline hydrochloride salt (6-4).

HPLC-MS, Method C: $t_r$=1.55 min, (ES+) $C_{26}H_{33}ClN_4O$ required 452; found 453 [M+H]

¹H NMR (400 MHz, DMSO-d6)

Example 7: Preparation of 2-(4-chlorophenylamino)-4-(4-tert-butylaminopiperidin-1-yl)-8-hydroxyquinoline Hydrochloride Salt (7-2)

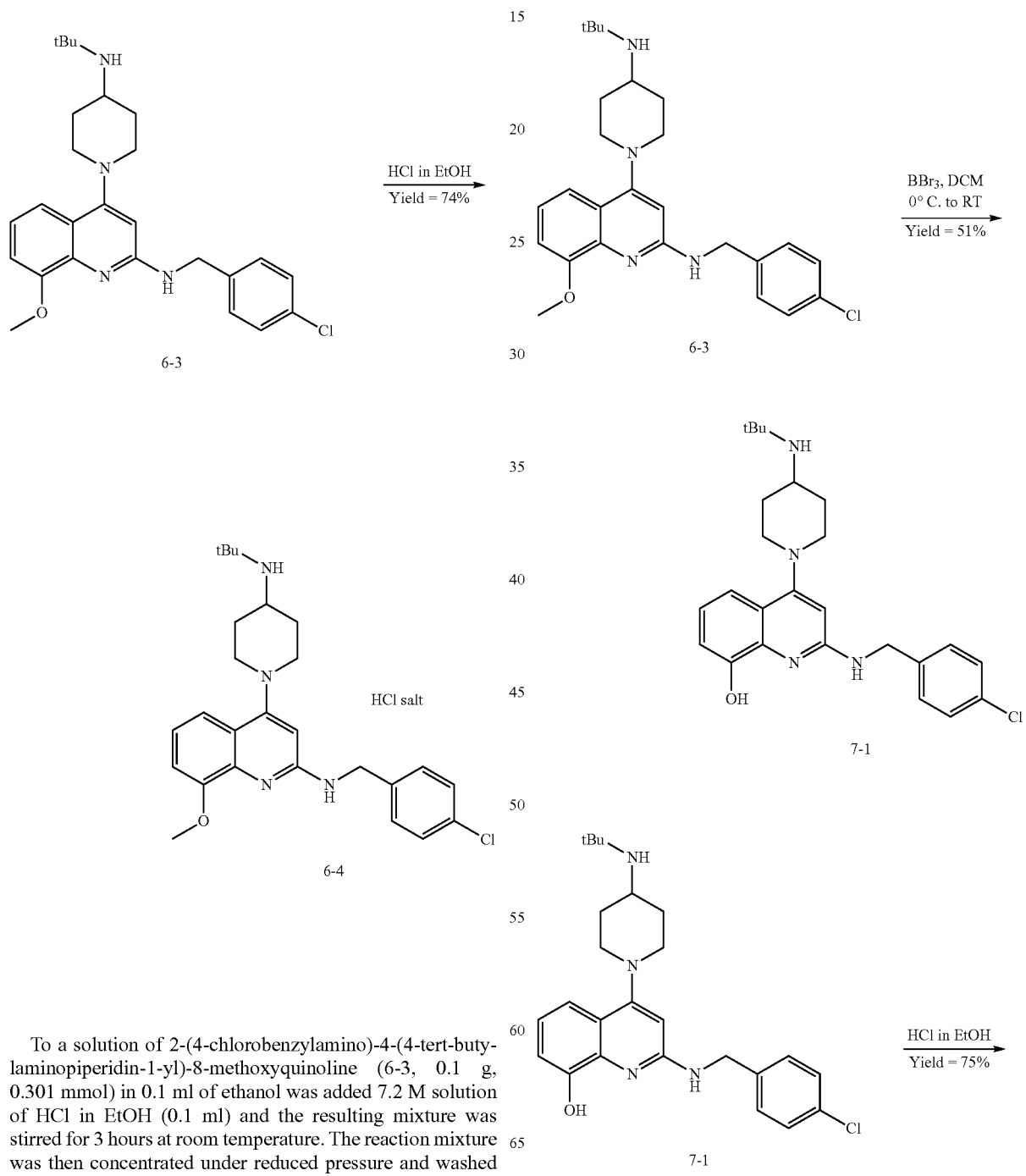

To a solution of 2-(4-chlorobenzylamino)-4-(4-tert-butylaminopiperidin-1-yl)-8-methoxyquinoline (6-3, 0.1 g, 0.301 mmol) in 0.1 ml of ethanol was added 7.2 M solution of HCl in EtOH (0.1 ml) and the resulting mixture was stirred for 3 hours at room temperature. The reaction mixture was then concentrated under reduced pressure and washed with diethyl ether to give 75 mg (yield 74%) of an off-white -continued

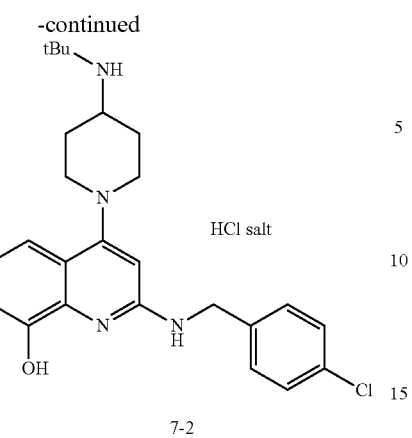

7-2

7.1 Synthesis of 2-(4-chlorobenzylamino)-4-(4-tert-butylaminopiperidin-1-yl)-8-hydroxyquinoline (7-1)

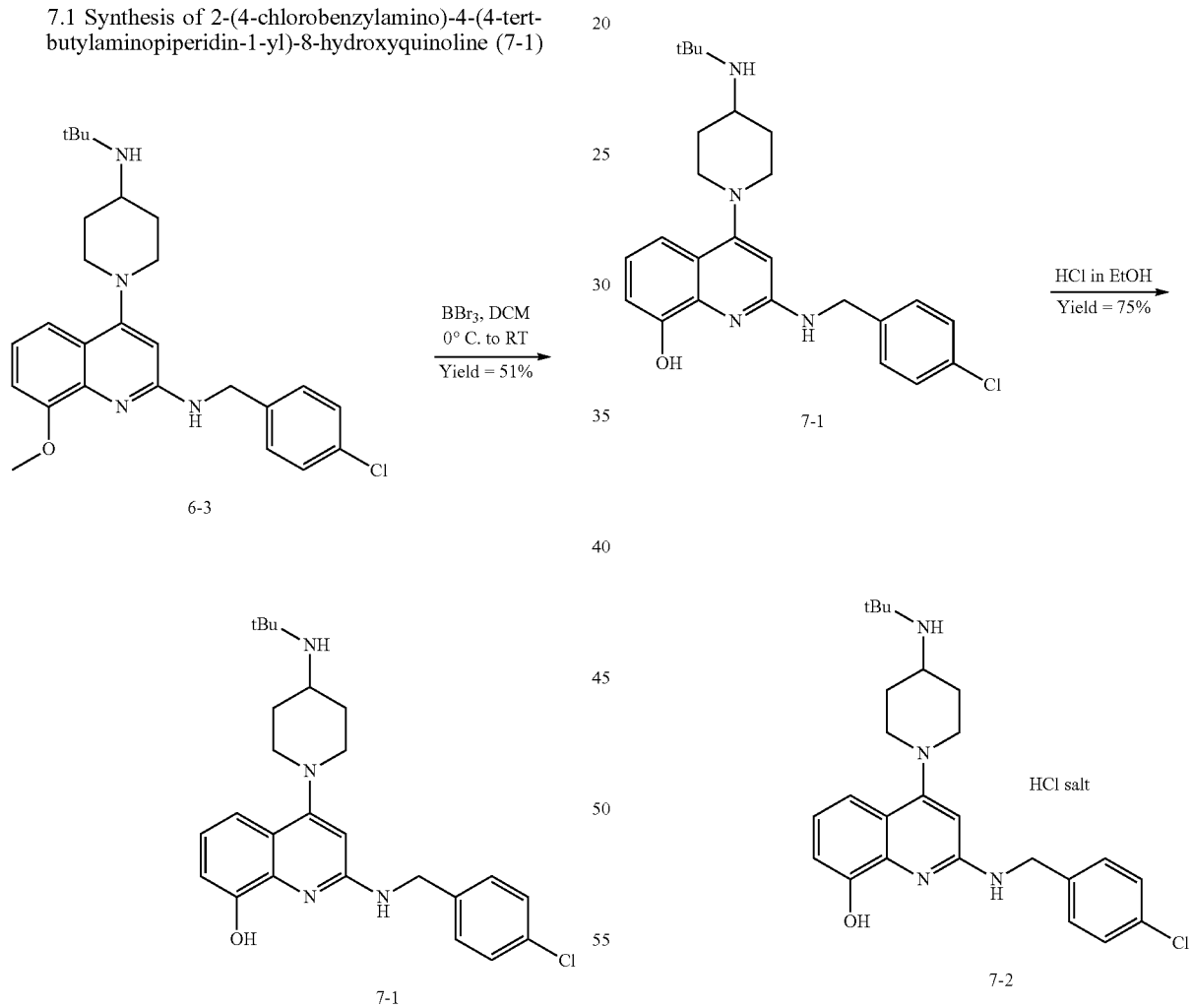

To a solution of 2-(4-chlorobenzylamino)-4-(4-tert-butylaminopiperidin-1-yl)-8-methoxyquinoline (6-3, 0.8 g, 1.76 mmol) in 10 ml of DCM was added dropwise at 0° C. BBr₃ (0.83 ml, 8.84 mmol). The resulting mixture was allowed to stir for 48 hours at room temperature. Then, the reaction mixture was cooled, diluted with ice-water and the resulting mixture was extracted with 10% MeOH/DCM and washed with saturated NaHCO₃ solution. The combined organic layers were dried over Na₂SO₄, filtered and concentrated under reduced pressure to give a light brown solid. The crude product was purified by preparative HPLC to give 400 mg (yield 51%) off-white solid corresponding to 2-(4-chlorobenzylamino)-4-(4-tert-butylaminopiperidin-1-yl)-8-hydroxyquinoline (7-1).

HPLC-MS, Method C: $t_r$=1.51 min, (ES+) $C_{25}H_{31}ClN_4O$ required 438; found 439 [M+H]

¹H NMR (400 MHz, DMSO-d6)

7.2 Preparation of 2-(4-chlorobenzylamino)-4-(4-tert-butylaminopiperidin-1-yl)-8-hydroxyquinoline Hydrochloride Salt (7-2)

To a solution of 2-(4-chlorobenzylamino)-4-(4-tert-butylaminopiperidin-1-yl)-8-hydroxyquinoline (7-1, 0.4 g, 0.913 mmol) in 4 ml of ethanol was added 7.2 M solution of HCl in EtOH (1.0 ml) and the resulting mixture was stirred for 3 hours at room temperature. The resulting reaction mixture was concentrated under reduced pressure and washed with diethyl ether to give 323 mg (yield 75%) of an off-white solid corresponding to (4-chlorobenzylamino)-4-(4-tert-butylaminopiperidin-1-yl)-8-hydroxyquinoline hydrochloride salt (7-2).

HPLC-MS, Method E: $t_r$=0.95 min, (ES+) $C_{25}H_{31}ClN_4O$ required 438; found 439 [M+H]

$^1$H NMR (400 MHz, DMSO-d6)

Example 8: Preparation of 2-(4-chlorophenylamino)-4-(4-tert-butylaminopiperidin-1-yl)-7-methoxyquinoline Hydrochloride Salt (8-3)

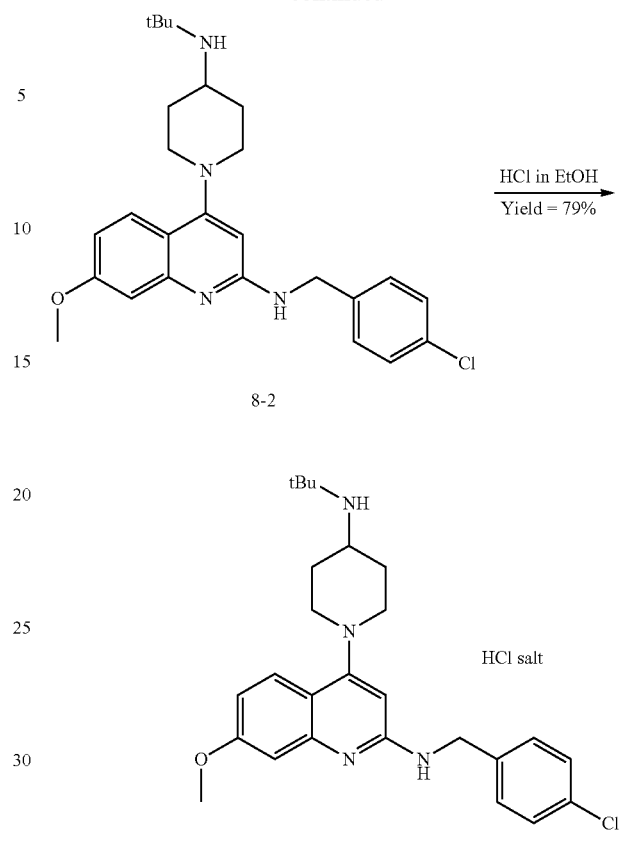

8-2

8-3

8.1 Synthesis of 2-(4-chlorobenzylamino)-4-chloro-7-methoxyquinoline (8-1)

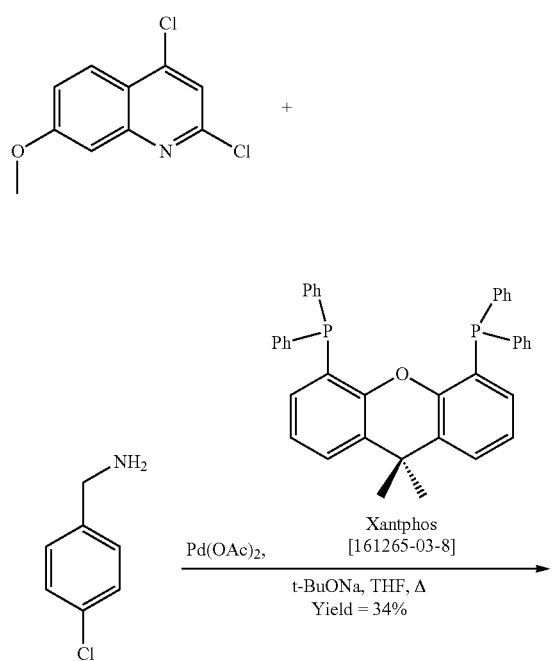

8-1

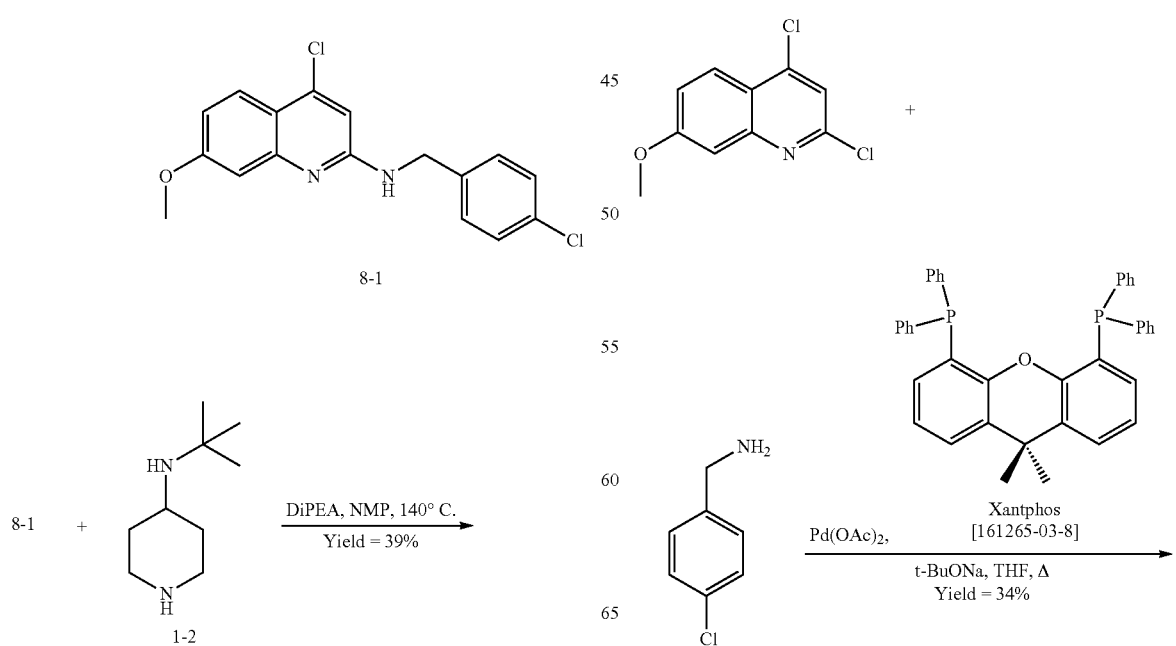

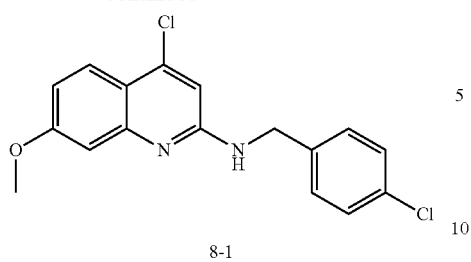

8-1

To a solution under nitrogen gas of 2,4-dichloro-7-methoxyquinoline (3.0 g, 13.21 mmol) in dry THF (30 ml) was added 4-chlorobenzylamine (2.79 g, 19.82 mmol) and t-BuONa (2.53 g, 26.42 mmol). The resulting mixture was degassed 5 min with nitrogen, then Xantphos (764 mg, 1.32 mmol) and Pd(OAc)$_2$ (148 mg, 0.66 mmol) were added and the reaction mixture was heated for 3 hours under reflux. The reaction mixture was then cooled to room temperature and concentrated under reduced pressure. The residue was partitioned between brine and EtOAc and the aqueous layer was extracted with EtOAc. The combined organic layers were dried over Na$_2$SO$_4$, filtered and concentrated under reduced pressure to give a brown solid. The crude product was purified by flash chromatography (gradient Petroleum ether/EtOAC from 9/1 to 6/4) to give 1.5 g (yield 34%) of an off-white solid corresponding to 4-(4-chlorobenzylamino)-4-chloro-7-methoxyquinoline (8-1).

HPLC-MS, Method B: $t_r$=1.86 min, (ES+) C$_{17}$H$_{14}$Cl$_2$N$_2$O required 332; found 333 [M+H]

$^1$H NMR (300 MHz, DMSO-d6)

8.2 Synthesis of 2-(4-chlorobenzylamino)-4-(4-tert-butylaminopiperidin-1-yl)-7-methoxyquinoline (8-2)

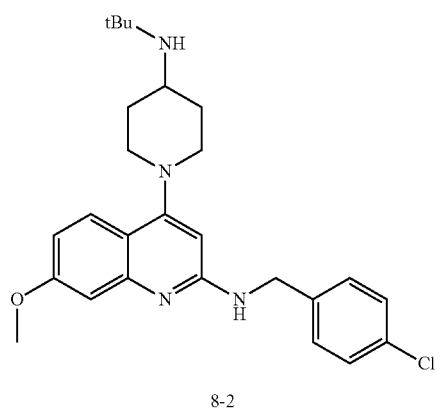

8-2

To a solution of 2-(4-chlorobenzylamino)-4-chloro-7-methoxyquinoline (8-1, 1.5 g, 4.51 mmol) and 4-tert-butylaminopiperidine (1-2, 0.775 g, 4.96 mmol) in 10 ml of NMP was added N,N-Diisopropylethylamine (1.6 ml, 9.03 mmol) and the mixture was heated for 72 hours at 140° C. in a sealed tube. Then, the reaction mixture was cooled, diluted with water and the resulting mixture was extracted with EtOAC. The combined organic layers were dried over Na$_2$SO$_4$, filtered and concentrated under reduced pressure to give a light brown solid. The crude product was purified by flash chromatography (gradient Petroleum ether/EtOAC from 8/2 to 0/10) to give 800 mg (yield 39%) of an off-white solid corresponding to 2-(4-chlorobenzylamino)-4-(4-tert-butylaminopiperidin-1-yl)-7-methoxyquinoline (8-2).

HPLC-MS, Method C: $t_r$=1.56 min, (ES+) C$_{26}$H$_{33}$ClN$_4$O required 452; found 453 [M+H]

$^1$H NMR (400 MHz, DMSO-d6)

8.3 Preparation of 2-(4-chlorobenzylamino)-4-(4-tert-butylaminopiperidin-1-yl)-7-methoxyquinoline Hydrochloride Salt (8-3)

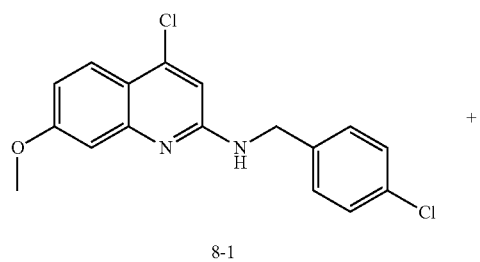

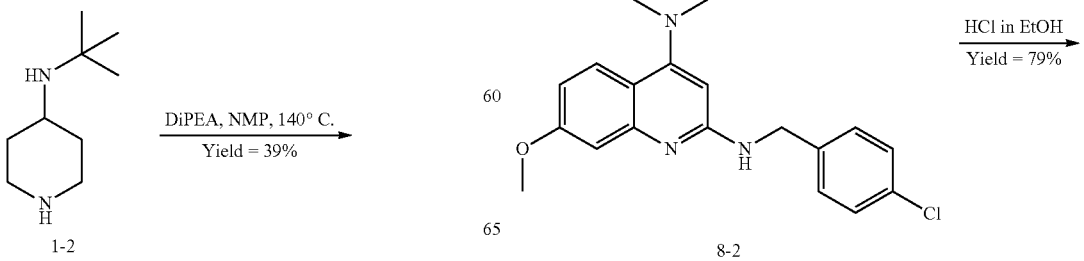

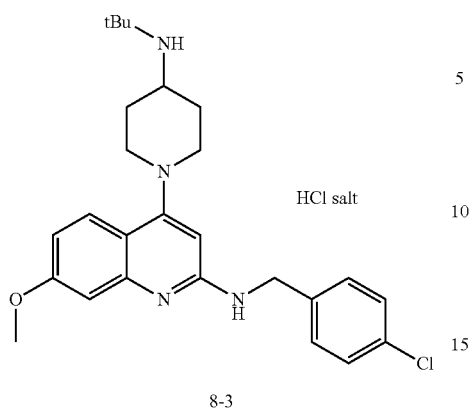

8-3

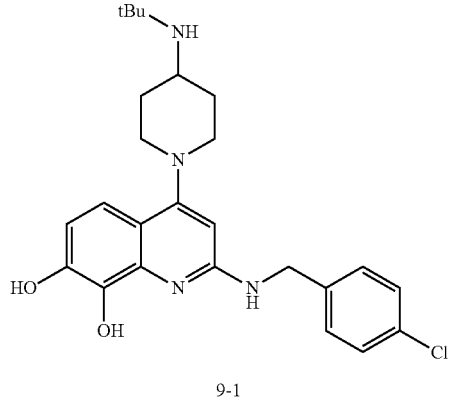

9-1

To a solution of 2-(4-chlorobenzylamino)-4-(4-tert-butylaminopiperidin-1-yl)-7-methoxyquinoline (8-2, 0.1 g, 0.301 mmol) in 0.1 ml of ethanol was added a 7.2M solution of HCl in ethanol (0.1 ml) and the mixture was stirred for 3 hours at room temperature. The resulting reaction mixture was concentrated under reduced pressure and the residue was washed with diethyl ether to give 85 mg (yield 79%) of an off-white solid corresponding to 2-(4-chlorobenzylamino)-4-(4-tert-butylaminopiperidin-1-yl)-7-methoxyquinoline hydrochloride salt (8-3).

HPLC-MS, Method E: $t_r$=0.99 min, (ES+) $C_{26}H_{33}ClN_4O$ required 452; found 453 [M+H]

$^1$H NMR (400 MHz, DMSO-d6)

Example 9: Preparation of 2-(4-chlorophenylamino)-4-(4-tert-butylaminopiperidin-1-yl)-7-hydroxyquinoline Hydrochloride Salt (9-2)

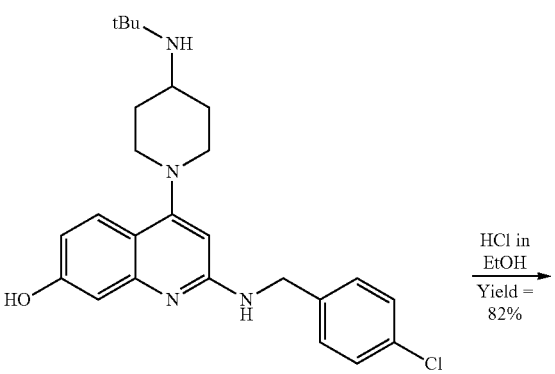

9-1

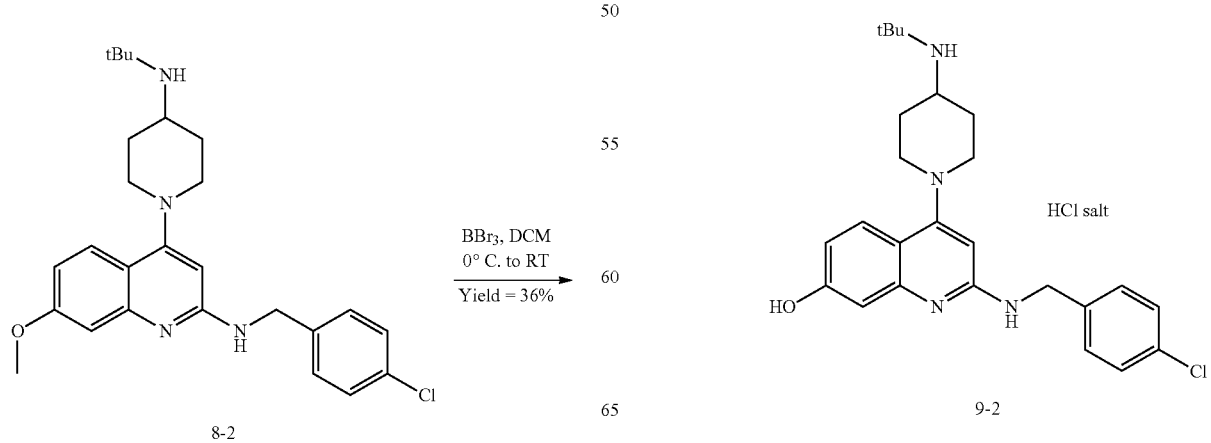

8-2             9-2

9.1 Synthesis of 2-(4-chlorobenzylamino)-4-(4-tert-butylaminopiperidin-1-yl)-7-hydroxyquinoline (9-1)

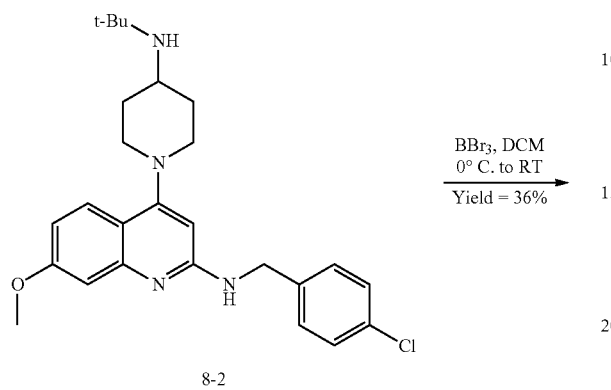

9.2 Preparation of 2-(4-chlorobenzylamino)-4-(4-tert-butylaminopiperidin-1-yl)-7-hydroxyquinoline Hydrochloride Salt (9-2)

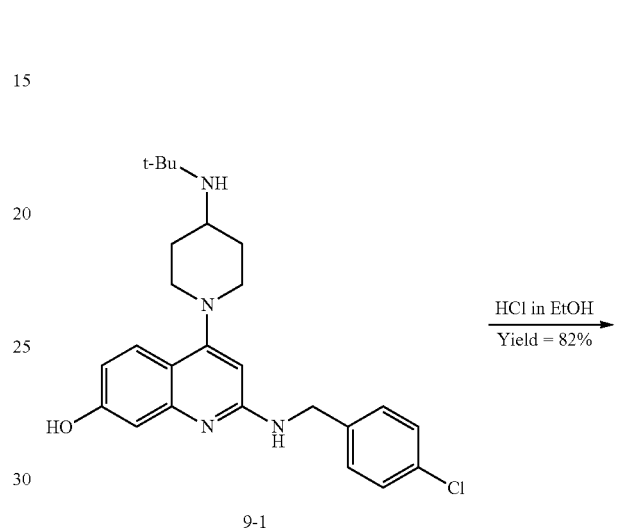

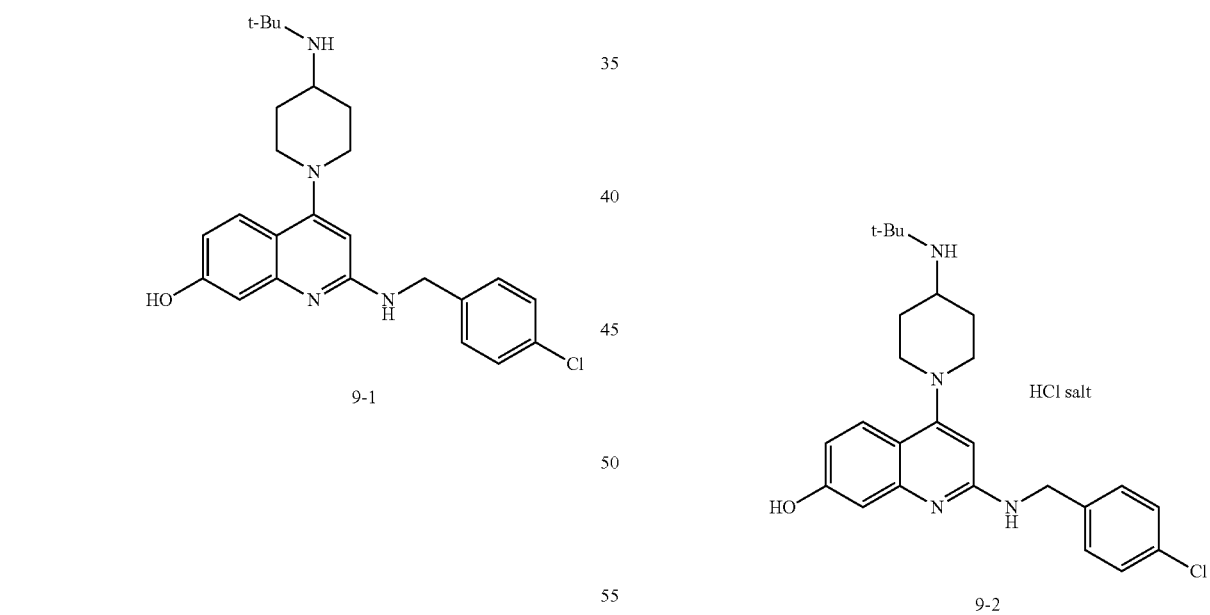

To a solution of 2-(4-chlorobenzylamino)-4-(4-tert-butylaminopiperidin-1-yl)-7-methoxyquinoline (8-2, 0.8 g, 1.76 mmol) in 10 ml of DCM was added dropwise at 0° C. BBr$_3$ (0.83 mL, 8.84 mmol). The resulting reaction was allowed to stir for 48 hours at room temperature. Then, the reaction mixture was cooled, diluted with ice-water and the resulting mixture was extracted with 10% MeOH/DCM. The combined organic layers were washed with a saturated NaHCO$_3$ aqueous solution, dried over Na$_2$SO$_4$, filtered and concentrated under reduced pressure to give a light brown solid. The crude product was purified by Prep-HPLC to give 280 mg (yield 36%) corresponding to 2-(4-chlorobenzylamino)-4-(4-tert-butylaminopiperidin-1-yl)-7-hydroxyquinoline (9-1).

HPLC-MS, Method C: t$_r$=1.51 min, (ES+) C$_{25}$H$_{31}$ClN$_4$O required 438; found 439 [M+H]

$^1$H NMR (400 MHz, DMSO-d6)

To a solution of 2-(4-chlorobenzylamino)-4-(4-tert-butylaminopiperidin-1-yl)-'7-hydroxyquinoline (9-1, 0.250 g, 0.570 mmol) in 3 ml of ethanol was added a 7.2M HCl solution in ethanol (1.0 ml) and the resulting mixture was stirred for 3 hours at room temperature. Then, the reaction mixture was concentrated under reduced pressure and the residue was washed with diethyl ether to give 240 mg (yield 82%) of an off-white solid corresponding to 2-(4-chlorobenzylamino)-4-(4-tert-butylaminopiperidin-1-yl)-7-hydroxyquinoline hydrochloride salt (9-2).

HPLC-MS, Method E: $t_r$=0.95 min, (ES+) $C_{25}H_{31}ClN_4O$ required 438; found 439 [M+H]

$^1$H NMR (400 MHz, DMSO-d6)

Example 10: Preparation of 2-(4-chlorophenylamino)-4-(4-tert-butylaminopiperidin-1-yl)-6-methoxyquinoline Hydrochloride Salt (10-3)

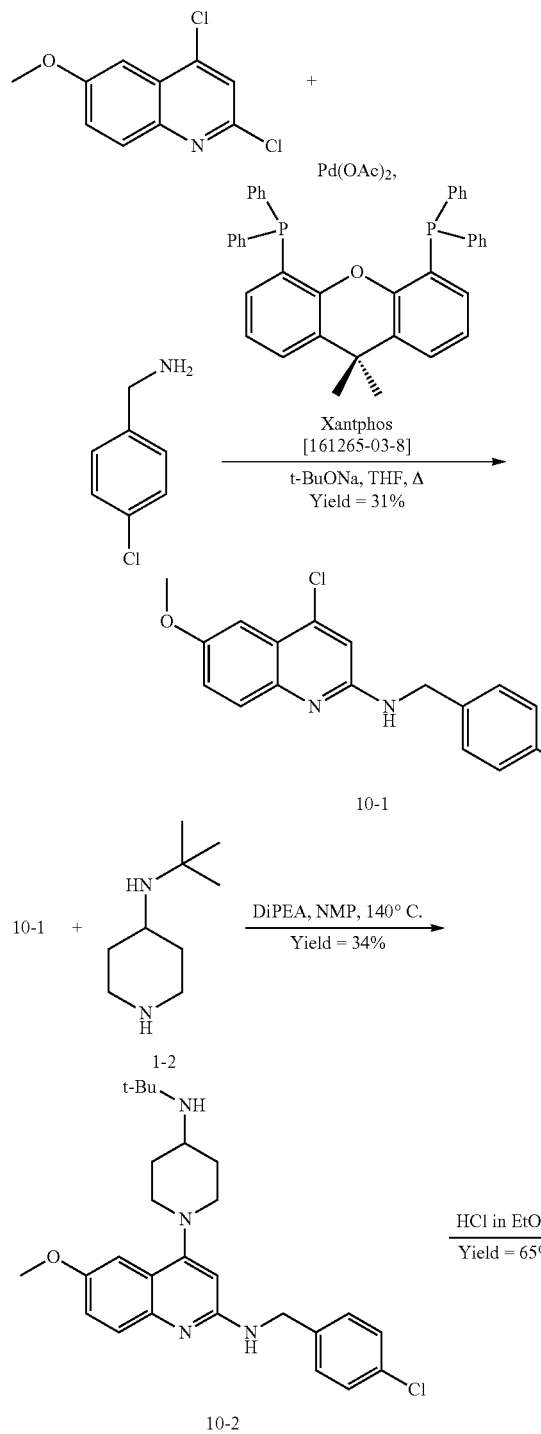

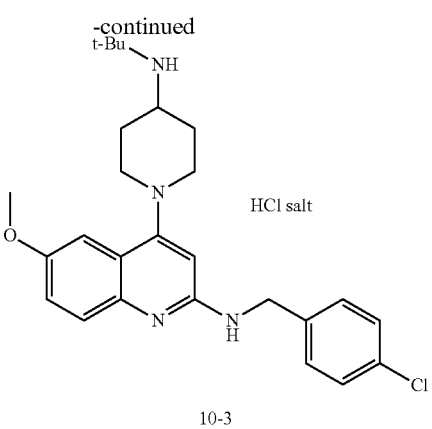

10.1 Synthesis of 2-(4-chlorobenzylamino)-4-chloro-6-methoxyquinoline (10-1)

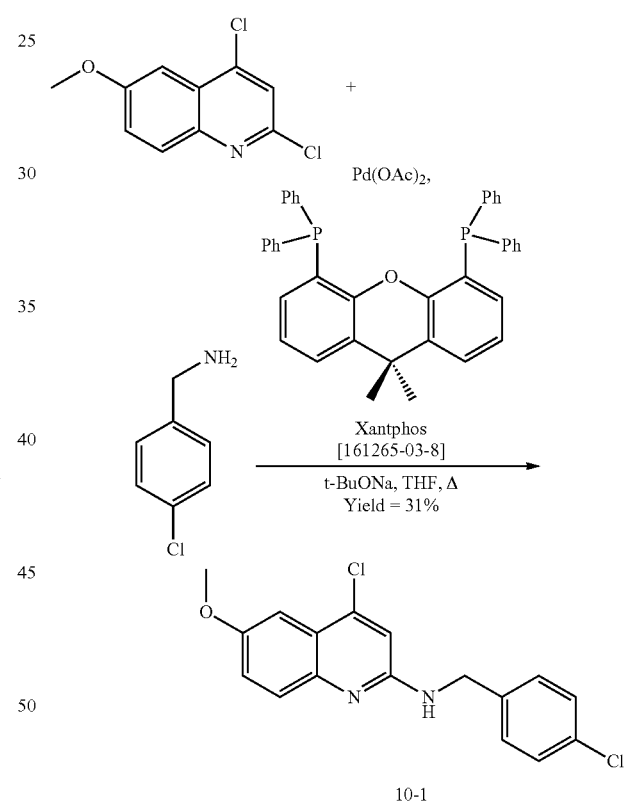

To a solution under nitrogen gas of 2,4-dichloro-6-methoxyquinoline (5.00 g, 21.92 mmol) in dry THF (50 ml) was added 4-chlorobenzylamine (4.67 g, 32.89 mmol) and t-BuONa (4.2 g, 43.85 mmol). The resulting mixture was degassed 5 min with nitrogen, then Xantphos (1.26 g, 2.19 mmol) and Pd(OAc)$_2$ (0.24 g, 1.09 mmol) were added and the reaction mixture was heated under reflux for 3 hours. The reaction mixture was then cooled to room temperature and concentrated under reduced pressure. The residue was partitioned between brine and EtOAc and the aqueous layer was extracted with EtOAc. The combined organic layers were dried over Na$_2$SO$_4$, filtered and concentrated under reduced pressure to give brown oil. The crude product was purified by flash chromatography (gradient ethyl acetate/petroleum ether from 1/10 to 3/10) to give 2.3 g (yield 31%) of a yellow solid corresponding to 2-(4-chlorobenzylamino)-4-chloro-6-methoxyquinoline (10-1)

HPLC-MS, Method C: $t_r$=1.88 min, (ES+) $C_{17}H_{14}Cl_2N_2O$ required 332; found 333 [M+H]

$^1$H NMR (400 MHz, CDCl$_3$)

10.2 Synthesis of 2-(4-chlorobenzylamino)-4-(4-tert-butylaminopiperidin-1-yl)-6-methoxyquinoline (10-2)

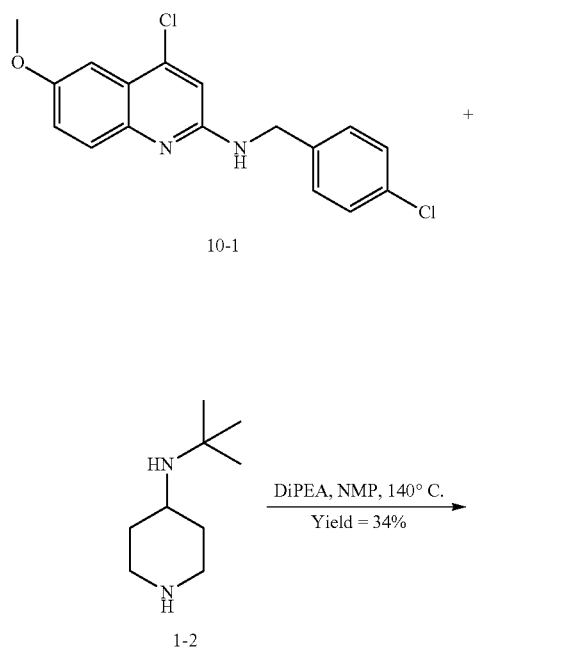

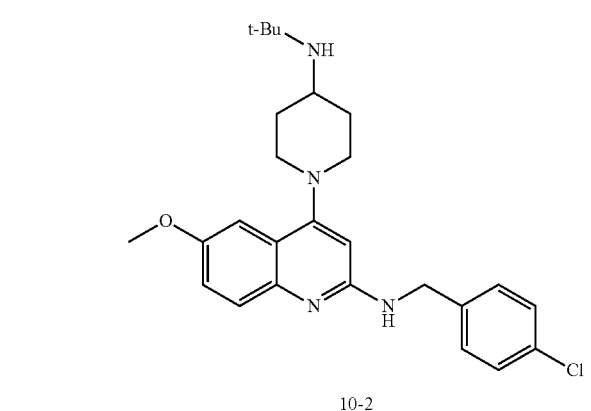

To a solution of 2-(4-chlorobenzylamino)-4-chloro-6-methoxyquinoline (10-1, 1.5 g, 4.50 mmol) and 4-(tert-butylamino)-piperidine (0.84 g, 5.40 mmol) in 10 ml of NMP was added N,N-Diisopropylethylamine (3.9 ml, 22.52 mmol) and the mixture was heated at 140° C. for 72 hours in sealed tube. Then, the reaction mixture was cooled, diluted with water, filtered and concentrated under reduced pressure. The crude product was purified by flash chromatography (gradient petroleum ether/EtOAc from 2/8 to 0/10) to give 850 mg (yield 34%) of an off-white solid corresponding to 2-(4-chlorobenzylamino)-4-(4-tert-butylaminopiperidin-1-yl)-6-methoxyquinoline (10-2).

HPLC-MS, Method E: $t_r$=0.97 min, (ES+) $C_{26}H_{33}ClN_4O$ required 452; found 453 [M+H].

$^1$H NMR (400 MHz, CDCl$_3$)

10.3 Preparation of 2-(4-chlorobenzylamino)-4-(4-tert-butylaminopiperidin-1-yl)-6-methoxyquinoline Hydrochloride Salt (10-3)

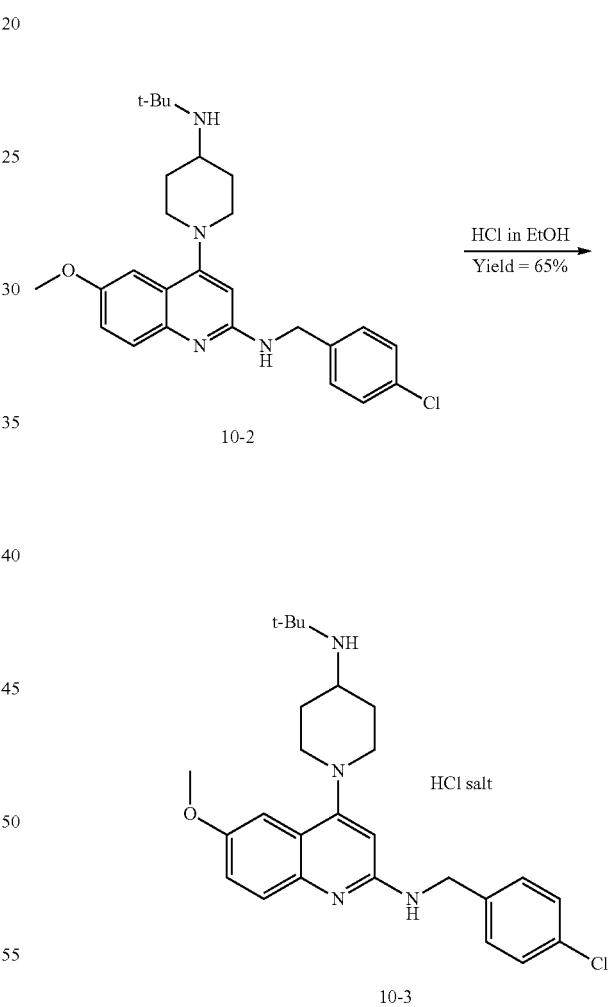

To a solution of 2-(4-chlorobenzylamino)-4-(4-tert-butylaminopiperidin-1-yl)-6-methoxyquinoline (10-2, 0.1 g, 0.22 mmol) in 3 ml of ethanol was added a 7.2M HCl solution in ethanol (1.0 ml). The resulting reaction mixture was stirred at room temperature four 1 hour. Then, the reaction mixture was concentrated under reduced pressure and the residue was washed with diethyl ether to give 0.07 mg (yield 65%) of an off-white solid corresponding to 2-(4-chlorobenzylamino)-4-(4-tert-butylaminopiperidin-1-yl)-6-methoxyquinoline (10-3).

HPLC-MS, Method E: $t_r$=0.96 min, (ES+) $C_{26}H_{33}ClN_4O$ required 452; found 453 [M+H].

$^1$H NMR (400 MHz, DMSO-d6)

Example 11: Preparation of 2-(4-chlorophenylamino)-4-(4-tert-butylaminopiperidin-1-yl)-6-hydroxyquinoline Hydrochloride Salt (11-2)

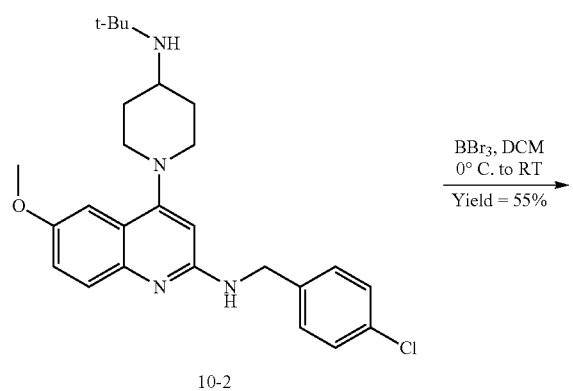

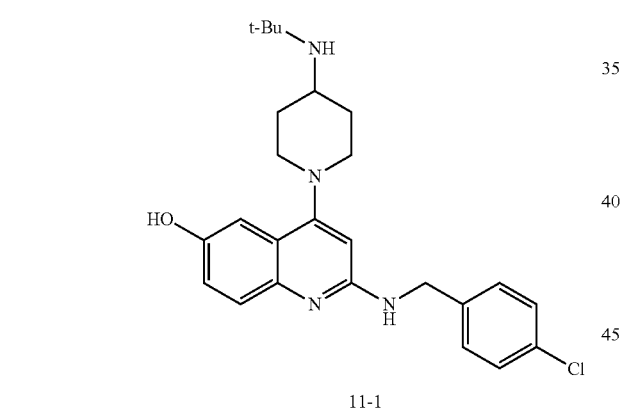

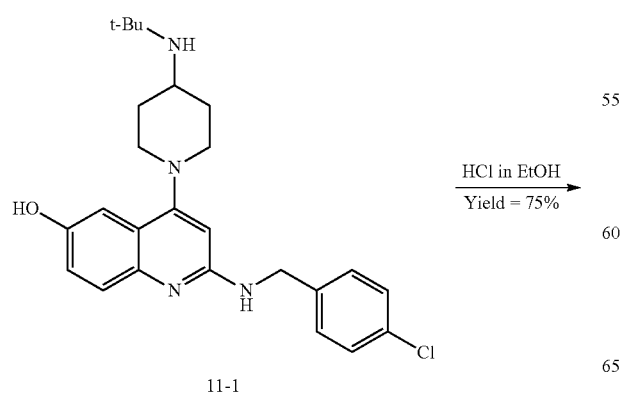

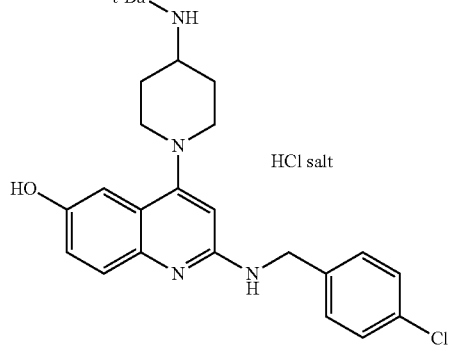

11.1 Synthesis of 2-(4-chlorobenzylamino)-4-(4-tert-butylaminopiperidin-1-yl)-6-hydroxyquinoline (11-1)

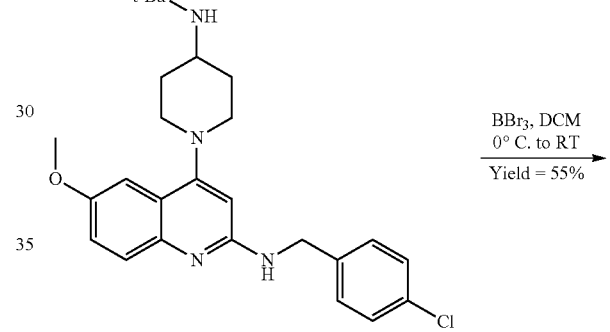

To a solution of 2-(4-chlorobenzylamino)-4-(4-tert-butylaminopiperidin-1-yl)-6-methoxyquinoline (10-2, 750 mg, 1.65 mmol) in 10 ml of DCM at 0° C. was added BBr$_3$ (0.91 ml, 8.25 mmol) and the resulting reaction mixture was stirred at room temperature for 12 hours. Then, the reaction mixture was cooled, quenched with a 1N NaHCO$_3$ aqueous solution and the resulting mixture was extracted with 10% MeOH/DCM. The combined organic layers were dried over Na$_2$SO$_4$, filtered and concentrated under reduced pressure to give a brown solid. The crude product was purified by Prep-HPLC to give 400 mg (yield 55%) of an off-white solid corresponding to 2-(4-chlorobenzylamino)-4-(4-tert-butylaminopiperidin-1-yl)-6-hydroxyquinoline (11-1).

HPLC-MS, Method E: $t_r$=0.95 min, (ES+) $C_{25}H_{31}ClN_4O$ required 438; found 439 [M+H].

$^1$H NMR (400 MHz, DMSO-d6)

11.2 Preparation of 2-(4-chlorobenzylamino)-4-(4-tert-butylaminopiperidin-1-yl)-6-hydroxyquinoline Hydrochloride Salt (11-2)

75%) of an off-white solid corresponding to 2-(4-chlorobenzylamino)-4-(4-tert-butylaminopiperidin-1-yl)-6-hydroxyquinoline hydrochloride salt (11-2).

HPLC-MS, Method F: $t_r$=9.47 min, (ES+) $C_{25}H_{31}ClN_4O$ required 438; found 439 [M+H].

$^1$H NMR (500 MHz, DMSO-d6)

Example 12: Preparation of 2-(4-chlorophenylamino)-4-(4-tert-butylaminopiperidin-1-yl)-5-methoxyquinoline Hydrochloride Salt (12-5)

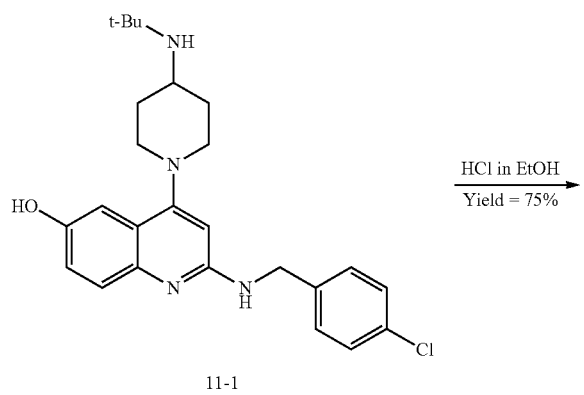

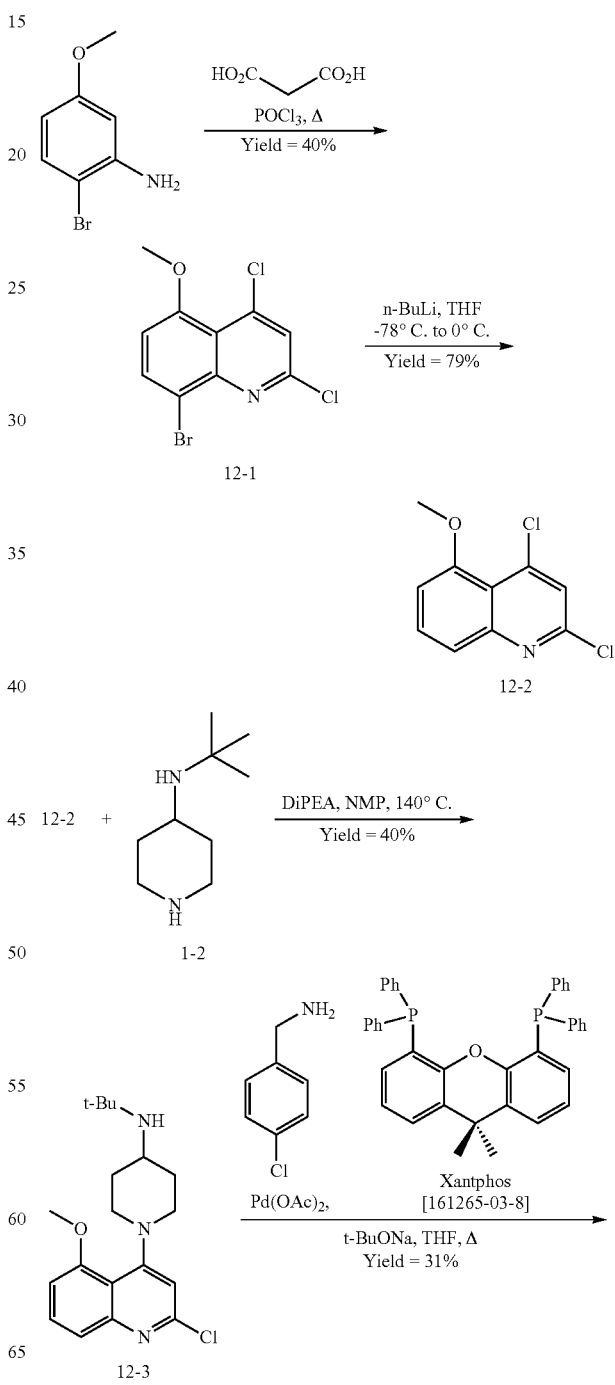

To a solution of 2-(4-chlorobenzylamino)-4-(4-tert-butylaminopiperidin-1-yl)-6-hydroxyquinoline (11-1, 0.4 g, 0.913 mmol) in 3 ml of ethanol was added a 7.2M HCl solution in ethanol (1.0 ml) and the resulting mixture was stirred at room temperature for 3 hours. Then, the reaction mixture was concentrated under reduced pressure and the residue was washed with diethyl ether to give 323 mg (yield

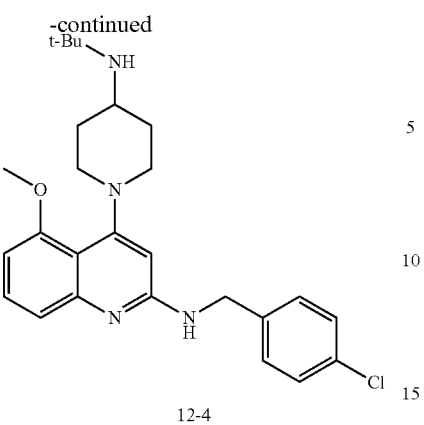

12-4

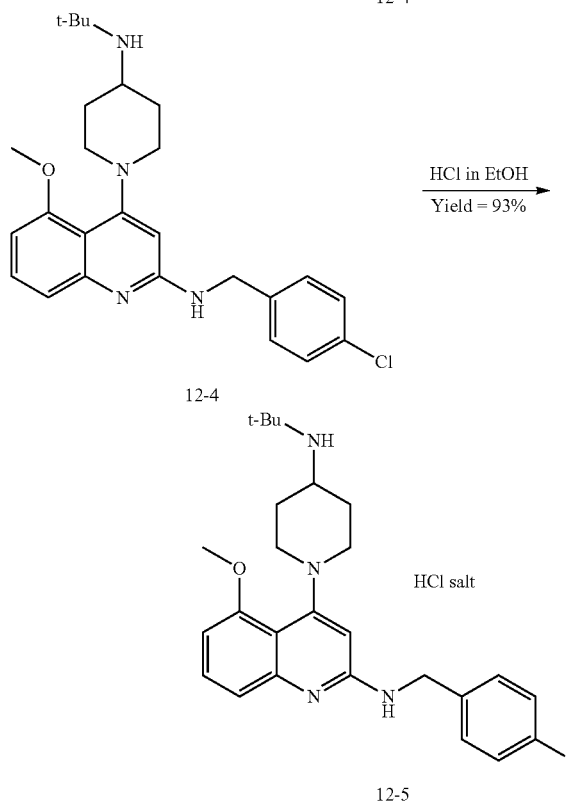

12.1 Synthesis of
2,4-dichloro-5-methoxy-8-bromoquinoline (12-1)

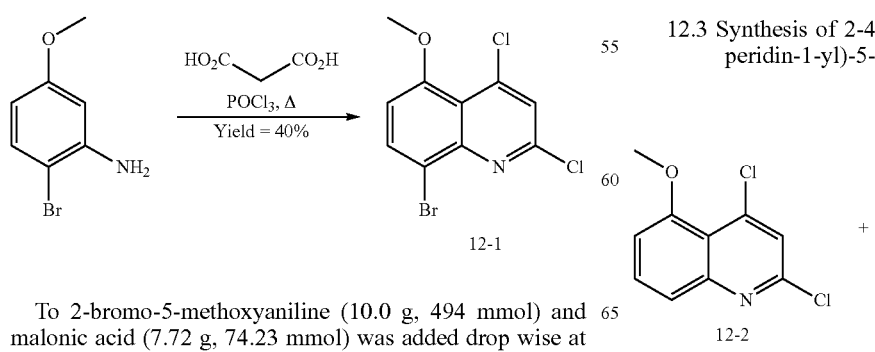

To 2-bromo-5-methoxyaniline (10.0 g, 494 mmol) and malonic acid (7.72 g, 74.23 mmol) was added drop wise at 0° C. POCl₃ (100 ml). The resulting mixture was stirred under reflux overnight. Then, the reaction mixture was cooled, concentrated under reduced pressure and co-evaporated twice with toluene (500 ml). The residue was then taken up with DCM (500 ml) and washed with cold water. The aqueous layer was extracted with DCM and the combined organic layers were dried over Na₂SO₄, filtered and concentrated under reduced pressure to give a brown solid (6.0 g, yield: 40%) corresponding to 2,4-dichloro-5-methoxy-8-bromoquinoline (12-1).

HPLC-MS, Method C: $t_r$=2.21 min, (ES+) $C_{10}H_6BrCl_2NO$ found 306 [M+required 305; H].

¹H NMR (400 MHz, CDCl₃)

12.2 Synthesis of 2,4-dichloro-5-methoxyquinoline (12-2)

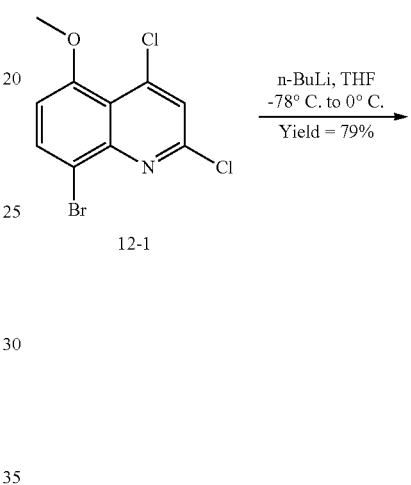

To a stirred solution of 2,4-dichloro-5-methoxy-8-bromoquinoline (12-1, 6.0 g, 19.54 mmol) in THF (60 ml), n-BuLi (29.31 mmol, 2.5 M in n-hexane, 11.7 mL) was added dropwise at −78° C. The resulting mixture was stirred at −78° C. for 1 hour, and MeOH (5 mL) was added dropwise at −78° C. Then, the mixture was allowed to reach 0° C. and stirred for 1 hour. Then, the reaction was quenched by the addition of water (20 ml) and dichloromethane (20 ml). The two layers were separated, and the aqueous layer was extracted with dichloromethane. The combined organic layers were washed with brine, dried over Na₂SO₄, filtered, and concentrated under reduced pressure to give 3.0 g (yield=79%) of a yellow solid corresponding to 2,4-dichloro-5-methoxyquinoline (12-2).

HPLC-MS, Method C: $t_r$=2.10 min, (ES+) $C_{10}H_7Cl_2NO$ required 227; found 228 [M+H].

¹H NMR (400 MHz, CDCl₃)

12.3 Synthesis of 2-4-chloro-4-(4-tert-butylaminopiperidin-1-yl)-5-methoxyquinoline (12-3)

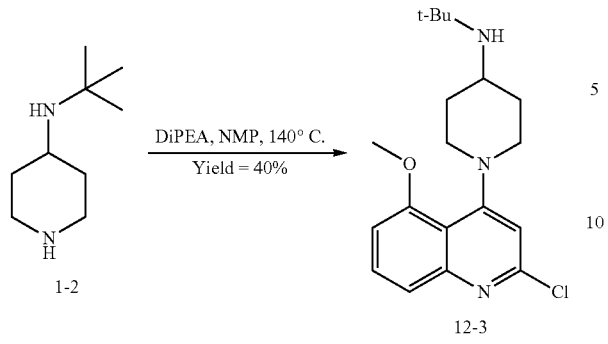

To a solution of 2,4-dichloro-5-methoxyquinoline (12-2, 1.0 g, 4.38 mmol) and 4-(tert-butylamino)-piperidine (1-2, 0.68 g, 4.38 mmol) in 5 ml of NMP was added N,N-Diisopropylethylamine (0.91 ml, 5.25 mmol) and the reaction mixture was heated at 140° C. for 5 hours. Then, the reaction mixture was cooled, diluted with a 1N NaOH aqueous solution and the resulting mixture was extracted with EtOAc. The combined organic layers were dried over $Na_2SO_4$, filtered and concentrated under reduced pressure to give a yellow oil. The crude product was purified by flash chromatography (gradient petroleum ether/EtOAc from 8/2 to 0/10) to give a yellow solid 600 mg (yield 40%) of a white solid corresponding to 2-chloro-4-(4-tert-butylaminopiperidin-1-yl)-5-methoxyquinoline (12-3).

HPLC-MS, Method B: $t_r$=1.55 min, (ES+) $C_{19}H_{26}ClN_3O$ required 347; found 348 [M+H].

$^1$H NMR (400 MHz, DMSO-d6)

12.4 Synthesis of 2-(4-chlorobenzylamino)-4-(4-tert-butylaminopiperidin-1-yl)-5-methoxyquinoline (12-4)

To a solution under nitrogen gas of 2-chloro-4-(4-tert-butylaminopiperidin-1-yl)-5-methoxyquinoline (12-3, 0.6 g, 1.72 mmol) in dry THF (10 ml) was added 4-chlorobenzylamine (0.36 g, 2.58 mmol) and t-BuONa (0.248 g, 2.58 mmol). The resulting mixture was degassed 5 minutes with nitrogen, then Xantphos (100 mg, 0.17 mmol) and Pd(OAc)$_2$ (19 mg, 0.08 mmol) were added and the reaction mixture was heated under reflux for 3 hours. Then, the reaction mixture was cooled to room temperature and concentrated under reduced pressure. The residue was partitioned between brine and EtOAc and the aqueous layer was extracted with EtOAc. The combined organic layers were dried over $Na_2SO_4$, filtered and concentrated under reduced pressure to give a brown oil. The crude product was purified by flash chromatography (gradient petroleum ether/DCM from 5/5 to 0/10) to give 240 mg (yield 31%) of a brown solid corresponding to 2-(4-chlorobenzylamino)-4-(4-tert-butylaminopiperidin-1-yl)-5-methoxyquinoline (12-4).

HPLC-MS, Method E: $t_r$=0.97 min, (ES+) $C_{26}H_{33}ClN_4O$ required 452; found 453 [M+H].

$^1$H NMR (300 MHz, DMSO-d6)

12.5 Preparation of 2-(4-chlorobenzylamino)-4-(4-tert-butylaminopiperidin-1-yl)-5-methoxyquinoline Hydrochloride Salt (12-5)

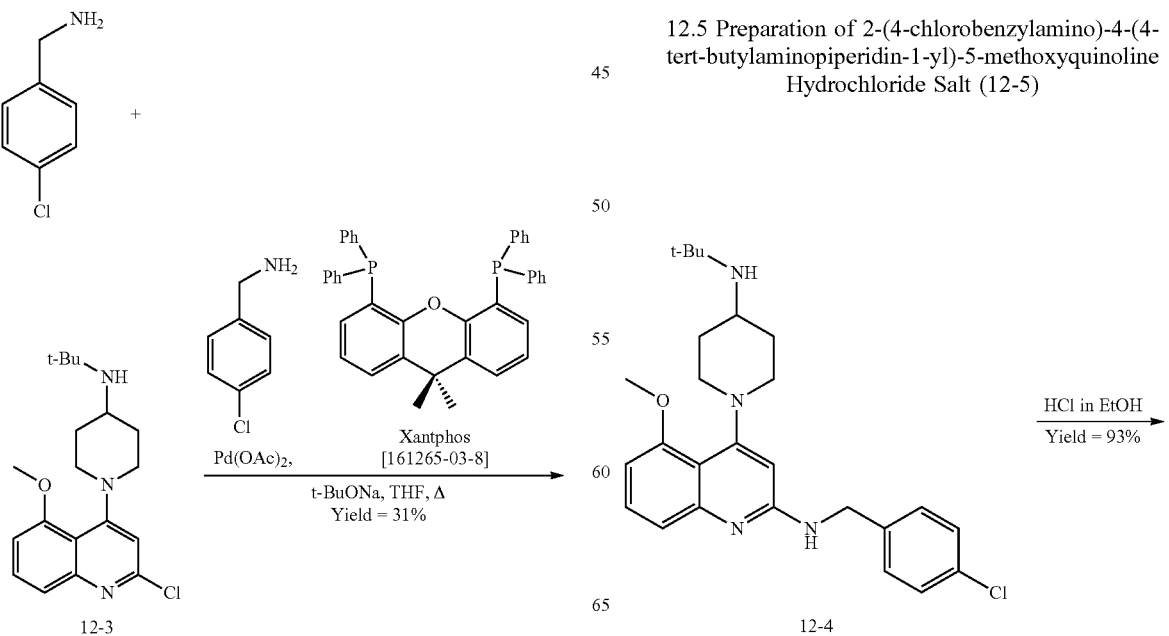

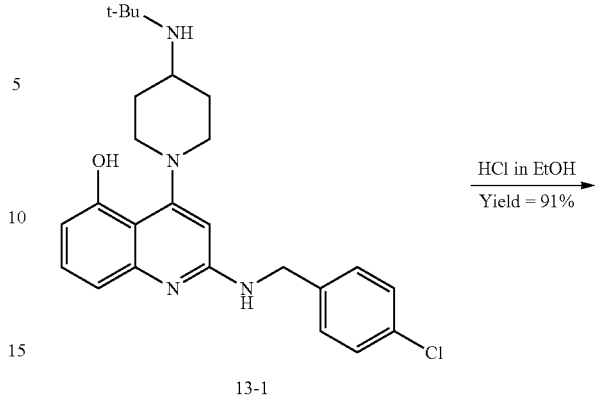

12-5

To a solution of 2-(4-chlorobenzylamino)-4-(4-tert-butylaminopiperidin-1-yl)-5-methoxyquinoline (12-4, 0.06 g, 0.13 mmol) in 3 ml of ethanol was added a 7.2M HCl solution in ethanol (0.5 ml) and the resulting mixture was stirred at room temperature for 3 hours. The resulting mixture was concentrated under reduced pressure and the residue was washed with diethyl ether to give 60 mg (yield 93%) of an off-white solid corresponding to 2-(4-chlorobenzylamino)-4-(4-tert-butylaminopiperidin-1-yl)-5-methoxyquinoline hydrochloride salt (12-5).

HPLC-MS, Method E: $t_r$=0.98 min, (ES+) $C_{26}H_{33}ClN_4O$ required 452; found 453 [M+H].

$^1$H NMR (400 MHz, DMSO-d6)

Example 13: Preparation of 2-(4-chlorophenylamino)-4-(4-tert-butylaminopiperidin-1-yl)-5-hydroxyquinoline (13-2)

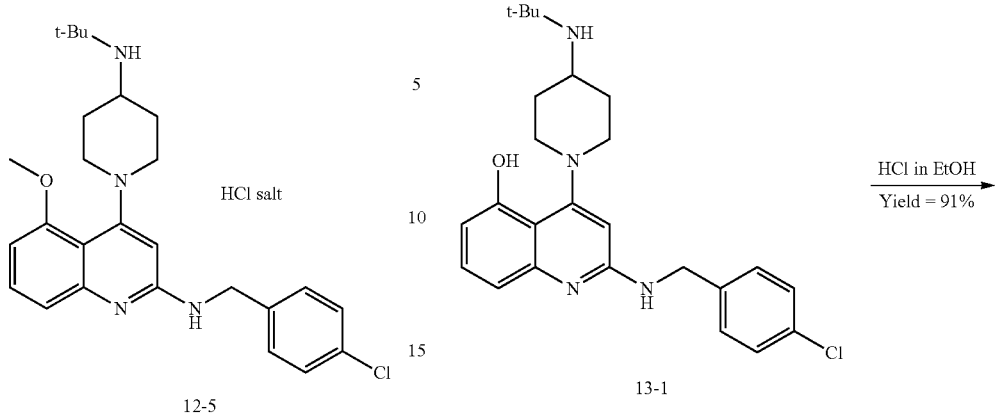

13-1

13-2

13.1 Synthesis of 2-(4-chlorobenzylamino)-4-(4-tert-butylaminopiperidin-1-yl)-5-hydroxyquinoline (13-1)

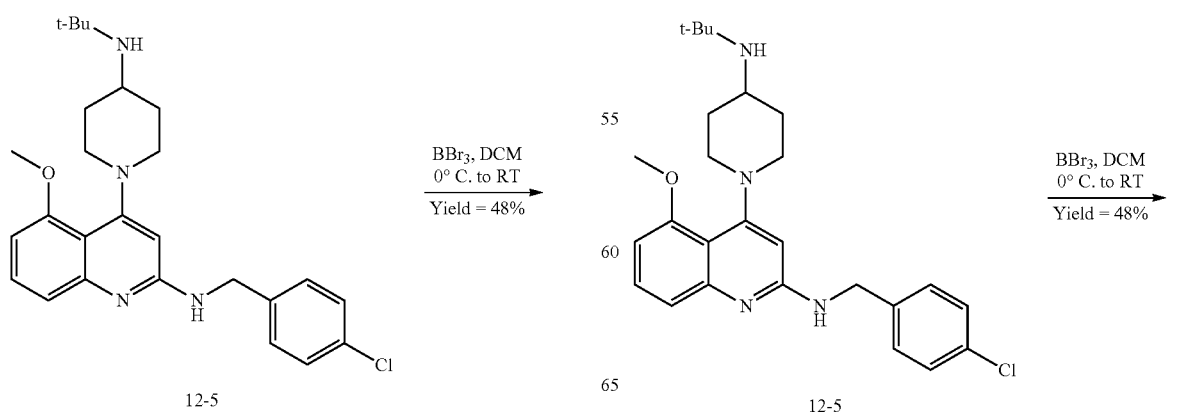

12-5

12-5

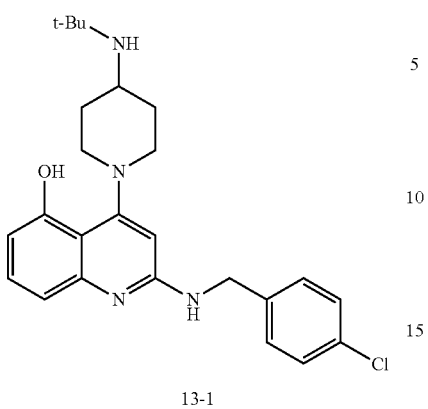

13-1

To a solution of 2-(4-chlorobenzylamino)-4-(4-tert-butylaminopiperidin-1-yl)-5-methoxyquinoline (12-5, 150 mg, 0.331 mmol) in 4 ml of DCM at 0° C. was added BBr₃ (183 μl, 1.656 mmol) and the resulting reaction mixture was stirred at room temperature for 12 hours. Then, the reaction mixture was cooled, quenched with a 1N NaHCO₃ aqueous solution and the resulting mixture was extracted with 10% MeOH/DCM. The combined organic layers were dried over Na₂SO₄, filtered and concentrated under reduced pressure to give a brown solid. The crude product was purified by Prep-HPLC to give 70 mg (yield 48%) of an off-white solid corresponding to 2-(4-chlorobenzylamino)-4-(4-tert-butylaminopiperidin-1-yl)-5-hydroxyquinoline (13-1).

¹H NMR (400 MHz, DMSO-d6)

13.2 Preparation of 2-(4-chlorobenzylamino)-4-(4-tert-butylaminopiperidin-1-yl)-5-hydroxyquinoline Hydrochloride Salt (13-2)

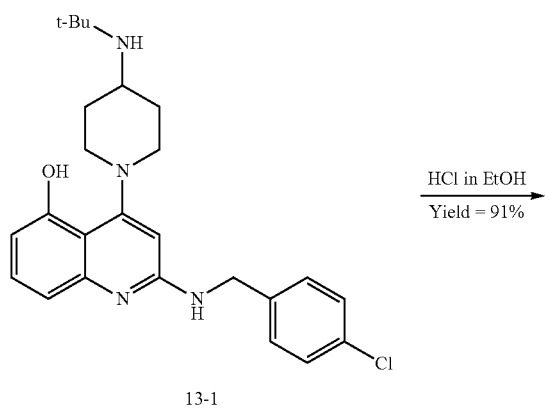

13-1

HCl in EtOH
Yield = 91%

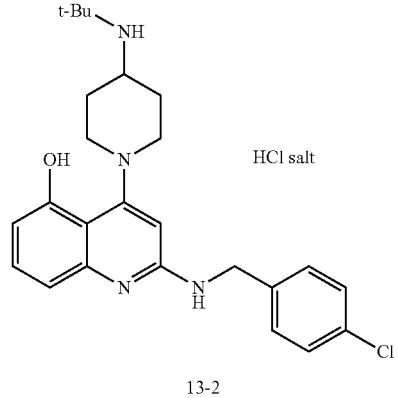

13-2

To a solution of 2-(4-chlorobenzylamino)-4-(4-tert-butylaminopiperidin-1-yl)-5-hydroxyquinoline (13-1, 60 mg, 0.132 mmol) in 3 ml of ethanol was added a 7.2M HCl solution in ethanol (0.5 ml) and the resulting mixture was stirred at room temperature for 1 hour. Then, the resulting mixture was concentrated under reduced pressure and the residue was washed with diethyl ether to give 57 mg (yield 91%) of an off-white solid corresponding to 2-(4-chlorobenzylamino)-4-(4-tert-butylaminopiperidin-1-yl)-5-hydroxyquinoline hydrochloride salt (13-2).

¹H NMR (400 MHz, DMSO-d6)

Example 14: Preparation of 2-(2-methoxy-4-chlorophenylamino)-4-(4-tert-butylaminopiperidin-1-yl)quinoline (14-5)

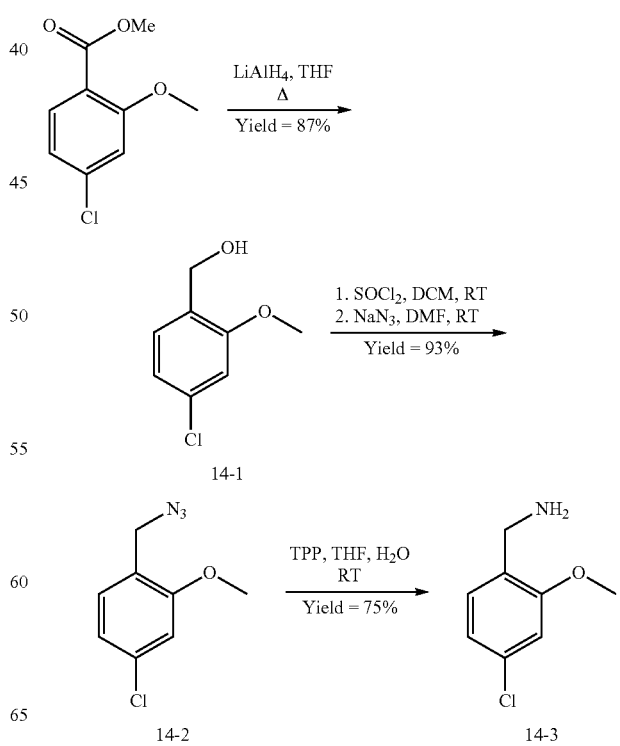

-continued

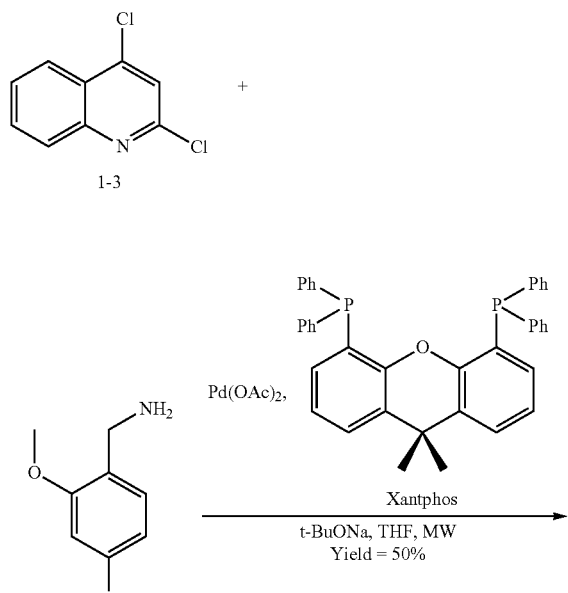

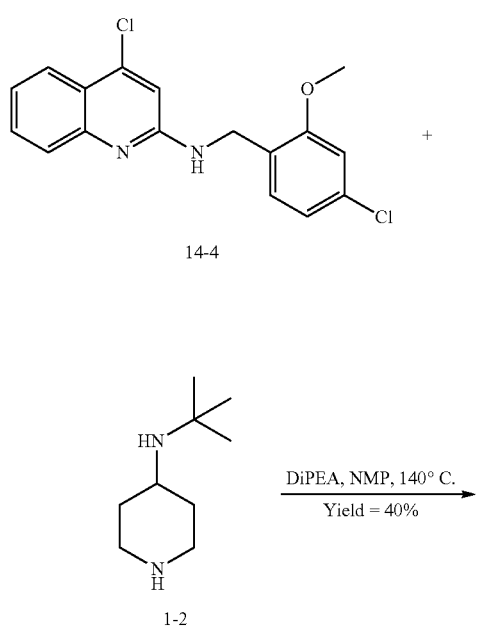

-continued

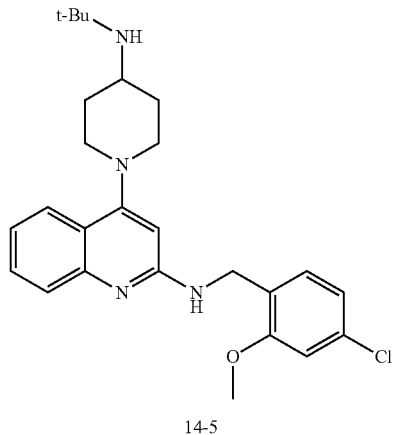

14.1 Synthesis of 2-methoxy-4-chlorobenzyl Alcohol (14-1)

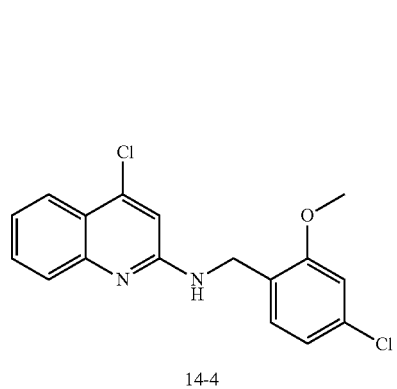

To a solution under nitrogen gas of methyl 2-methoxy-4-chlorobenzoate (10.0 g, 50 mmol) in THF (100 mL) was added at 0° C. a 1.0 M LiAlH₄ solution in THF (75 mL, 75 mmol). The resulting reaction mixture was stirred at room temperature for 3 hours. Then, the solvent was removed under vacuum and the residue was stirred in a 5% aqueous acetic acid solution (pH 6) for 15 minutes. The aqueous layer was extracted with EtOAc, then the combined organic layers were washed with brine, dried over Na₂SO₄, filtered, and concentrated under reduced pressure to give the crude product as a tan oil. The crude product was purified by flash chromatography (gradient petroleum ether/EtOAc 100/5) to give 7.5 g (yield=87%) of white solid corresponding to 2-methoxy-4-chlorobenzyl alcohol (14-1).

¹H NMR (400 MHz, CDCl₃)

14.2 Synthesis of 1-(azidomethyl)-4-chloro-2-methoxybenzene (14-2)

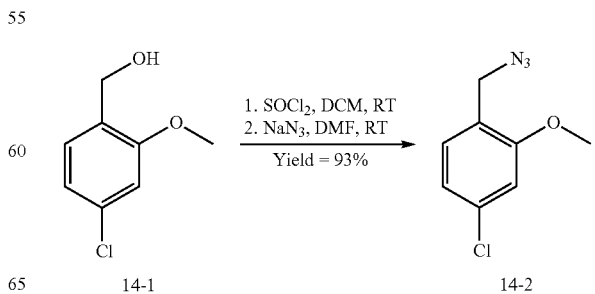

To a stirred solution under nitrogen gas of 2-methoxy-4-chlorobenzyl alcohol (14-1, 7.5 g, 43.45 mmol) in DCM (100 mL) was added dropwise under nitrogen at room temperature SOCl₂ (6.1 mL, 86.90 mmol). The resulting reaction mixture was stirred at room temperature for 6 hours. Then, the reaction mixture was poured into ice water (100 mL) and extracted with dichloromethane. The combinated organic layers were dried over Na₂SO₄, filtered, concentrated under reduced pressure to give 4-chloro-1-(chloromethyl)-2-methoxybenzene which was used in the next step without further purification.

4-chloro-1-(chloromethyl)-2-methoxybenzene (7.5 g, 39.25 mmol) was dissolved in DMF (70 mL) and NaN₃ (7.6 g, 117.77 mmol) was added followed by a few drops of water and the resulting reaction mixture was stirred at room temperature for 20 hours. Then, the reaction mixture was poured into cold water and extracted with ether. The combined organic layers were washed with water, dried over Na₂SO₄, filtered and concentrated under reduced pressure to give 1-(azidomethyl)-4-chloro-2-methoxybenzene (7.5 g, crude) which was used in the next step without further purification. 2-methoxy-4-chlorobenzylamine (14-2)

¹H NMR (400 MHz, CDCl₃)

14.3 Synthesis of 2-methoxy-4-chlorobenzylamine (14-3)

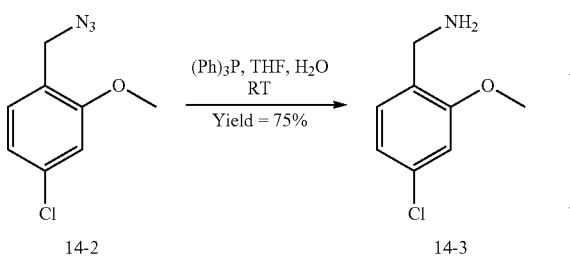

To a stirred solution of 1-(azidomethyl)-4-chloro-2-methoxybenzene (14-2, 7.5 g, 38.07 mmol) in THF (70 ml) was added subsequently triphenylphosphine (29.94 g, 114.21 mmol) and water (2.0 mL). The resulting reaction mixture was stirred at room temperature for 3 days. Then, the reaction mixture was poured over a 1 M HCl aqueous solution and was extracted with EtOAc. The combinated organic layers were washed with a 1 M HCl aqueous solution. The combined aqueous phases were basified to pH 10 with a saturated Na₂CO₃ aqueous solution and extracted with DCM. The combined organic layers were dried over Na₂SO₄, filtered and concentrated under reduced pressure to give 5.2 g (yield=75%) corresponding to 2-methoxy-4-chlorobenzylamine (14-3) which was used in the next step without further purification.

HPLC-MS, Method E: t$_r$=0.82 min, (ES+) C₈H₁₀ClNO (ES+) required 171; found 172[M+H].

¹H NMR (400 MHz, CDCl₃)

14.4 Synthesis of 2-(2-methoxy-4-chlorobenzylamino)-4-chloroquinoline (14-4)

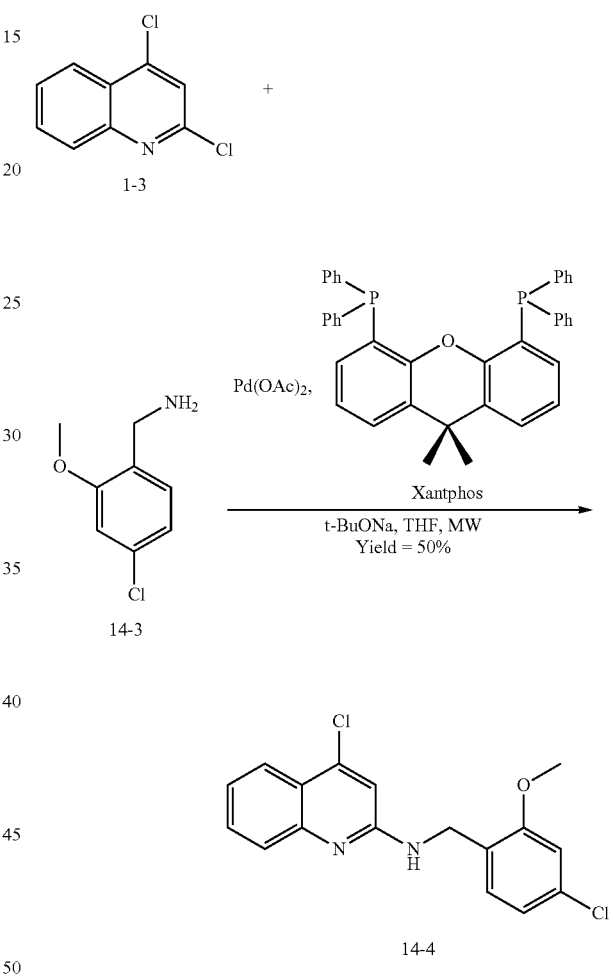

To a solution under nitrogen gas of 2,4-dichloroquinoline (1-3, 3.0 g, 15.15 mmol) in dry THF (50 ml) was added (4-chloro-2-methoxyphenyl) methanamine (14-3, 3.9 g, 22.72 mmol) and t-BuONa (2.9 g, 30.30 mmol). The resulting mixture was degassed 5 min with nitrogen, then Xantphos (0.87 g, 1.5 mmol) and Pd(OAc)₂ (170 mg, 0.75 mmol) were added and the resulting reaction mixture was heated to 100° C. under micro wave conditions for 30 minutes. The reaction mixture was then cooled to room temperature and concentrated under reduced pressure. The residue was partitioned between brine and EtOAc and the aqueous layer was extracted with EtOAc. The combined organic layers were dried over Na₂SO₄, filtered and concentrated under reduced pressure to give a brown oil. The crude product was purified by flash chromatography (gradient petroleum ether/DCM from 5/5 to 0/10) to give 2.1 g (yield 50%) corresponding to 2-(2-methoxy-4-chlorobenzylamino)-4-chloroquinoline (14-4) as a brown solid.

HPLC-MS, Method E: $t_r$=1.31 min, (ES+) $C_{17}H_{14}Cl_2N_2O$ required 332; found 333 [M+H].

$^1$H NMR (500 MHz, DMSO-d6)

14.5 Synthesis of 2-(2-methoxy-4-chlorobenzylamino)-4-(4-tert-butylaminopiperidin-1-yl)quinoline (14-5)

solid corresponding to 2-(2-methoxy-4-chlorobenzylamino)-4-(4-tert-butylaminopiperidin-1-yl)quinoline (14-5).

HPLC-MS, Method C: $t_r$=1.54 min, (ES+) $C_{26}H_{33}ClN_4O$ required 452; found 453 [M+H]

$^1$H NMR (400 MHz, DMSO-d6)

Example 15: Preparation of 2-(2-hydroxy-4-chlorophenylamino)-4-(4-tert-butylaminopiperidin-1-yl)quinoline Hydrochloride Salt (15-2)

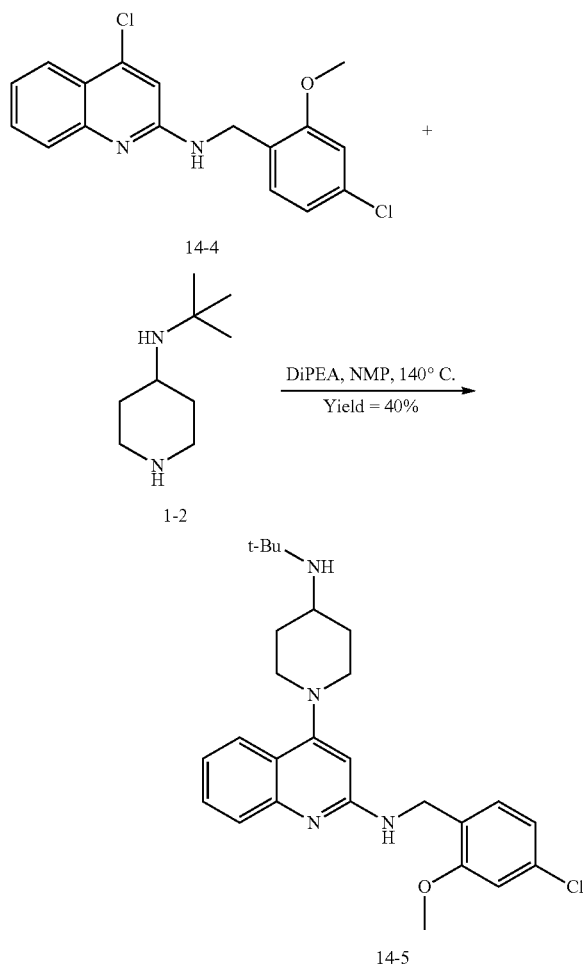

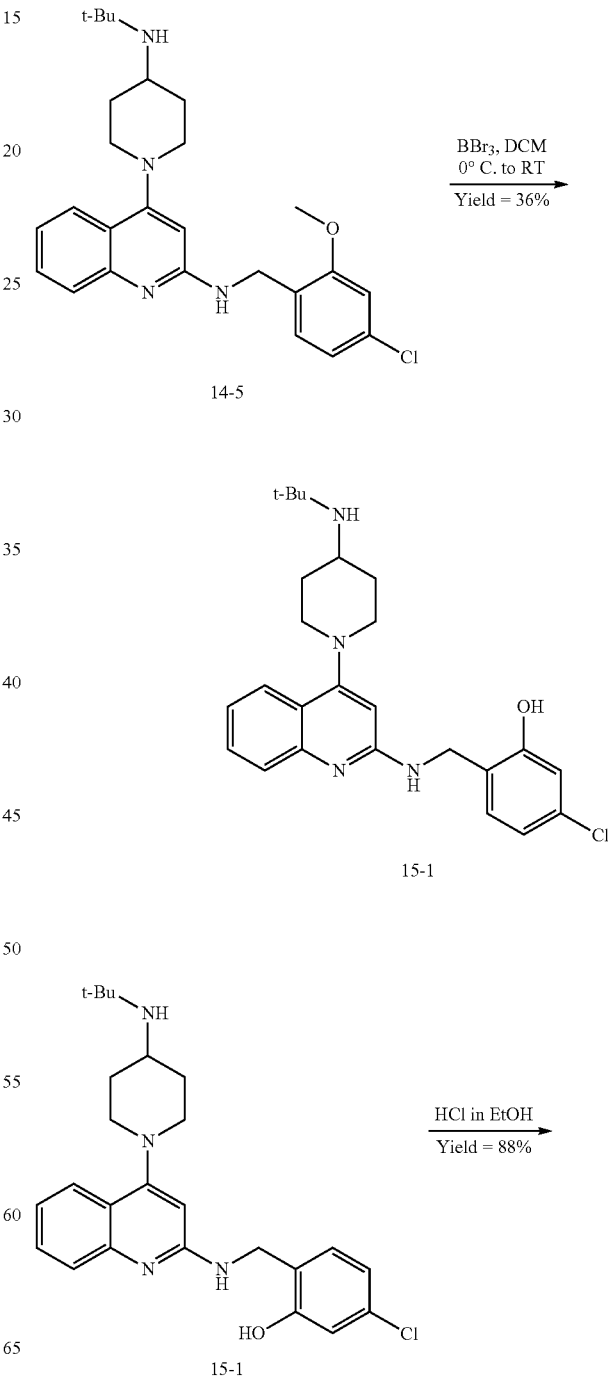

To a solution of 2-(2-methoxy-4-chlorobenzylamino)-4-chloroquinoline (14-4, 1.5 g, 4.5 mmol) and 4-(tert-butylamino)piperidine (1-2, 0.84 g, 5.40 mmol) in NMP (5 ml) was added N,N-Diisopropylethylamine (3.9 ml, 22.52 mmol) and the resulting reaction mixture was heated at 140° C. for 5 hours. Then, the reaction mixture was cooled, diluted with a 1N NaOH aqueous solution and extracted with EtOAc. The combined organic layers were dried over Na$_2$SO$_4$, filtered and concentrated under reduced pressure to give a yellow oil. The crude product was purified by flash chromatography (gradient petroleum ether/EtOAc from 8/2 to 0/10) to give a yellow solid. This solid was then recrystallized from MeCN to give 800 mg (yield 40%) of a white

15.1 Synthesis of 2-(2-hydroxy-4-chlorobenzylamino)-4-(4-tert-butylaminopiperidin-1-yl)quinoline (15-1)

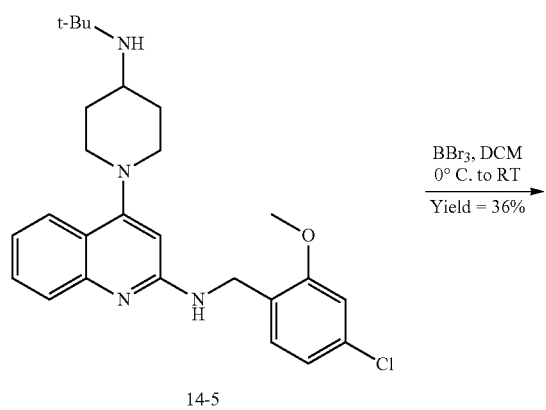

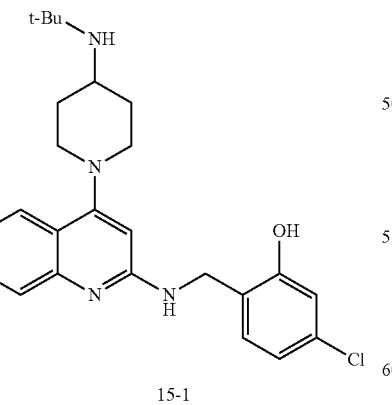

To a solution of (2-methoxy-4-chlorobenzylamino)-4-(4-tert-butylaminopiperidin-1-yl)quinoline (14-5, 0.7 g, 1.54 mmol) in 10 ml of DCM was added at 0° C. BBr$_3$ (0.85 mL, 7.7 mmol) and the resulting reaction mixture was stirred at room temperature for 48 hours. Then, the reaction mixture was cooled, diluted with ice-water and the resulting mixture was extracted with 10% MeOH/DCM. The combinated organic layers were washed with a saturated NaHCO$_3$ aqueous solution, dried over Na$_2$SO$_4$, filtered and concentrated under reduced pressure to give a light brown solid. The crude product was purified by Prep-HPLC to give 250 mg (yield 36%) of a yellowish solid corresponding to (2-hydroxy-4-chlorobenzylamino)-4-(4-tert-butylaminopiperidin-1-yl)quinoline (15-1).

HPLC-MS, Method E: t$_r$=0.94 min, (ES+) C$_{25}$H$_{31}$ClN$_4$O required 438; found 439 [M+H].

15.2 Preparation of 2-(2-hydroxy-4-chlorobenzylamino)-4-(4-tert-butylaminopiperidin-1-yl)quinoline Hydrochloride Salt (15-2)

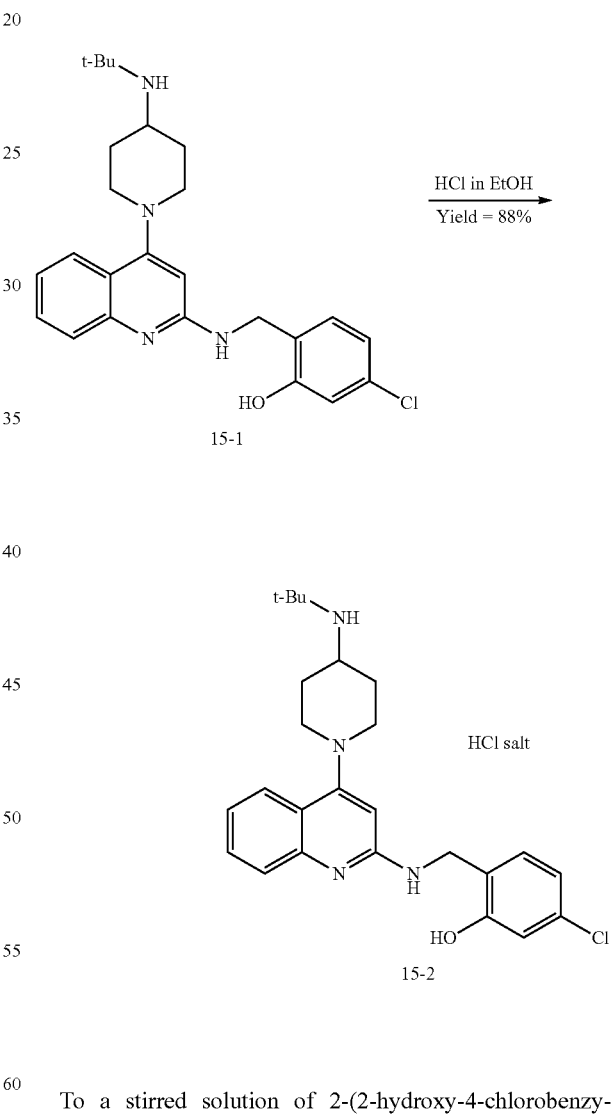

To a stirred solution of 2-(2-hydroxy-4-chlorobenzylamino)-4-(4-tert-butylaminopiperidin-1-yl)quinoline (15-1, 0.25 g, 0.569 mmol) in 3 ml of ethanol was added a 7.2M HCl solution in ethanol (1.0 ml) and the resulting mixture was stirred at room temperature for 3 hours. The resulting mixture was concentrated under reduced pressure and the residue was washed with diethyl ether to give 280 mg (yield 88%) of an off-white solid corresponding (2-hydroxy-4-chlorobenzylamino)-4-(4-tert-butylaminopiperidin-1-yl)quinoline hydrochloride salt (15-2).

HPLC-MS, Method F: $t_r$=10.80 min, (ES+) $C_{25}H_{32}Cl_2N_4O$ required 438; found 439 [M+H].

$^1$H NMR (500 MHz, DMSO-d6)

Example 16: Preparation of 2-(3-methoxy-4-chloro-phenylamino)-4-(4-tert-butylaminopiperidin-1-yl)quinoline (16-6)

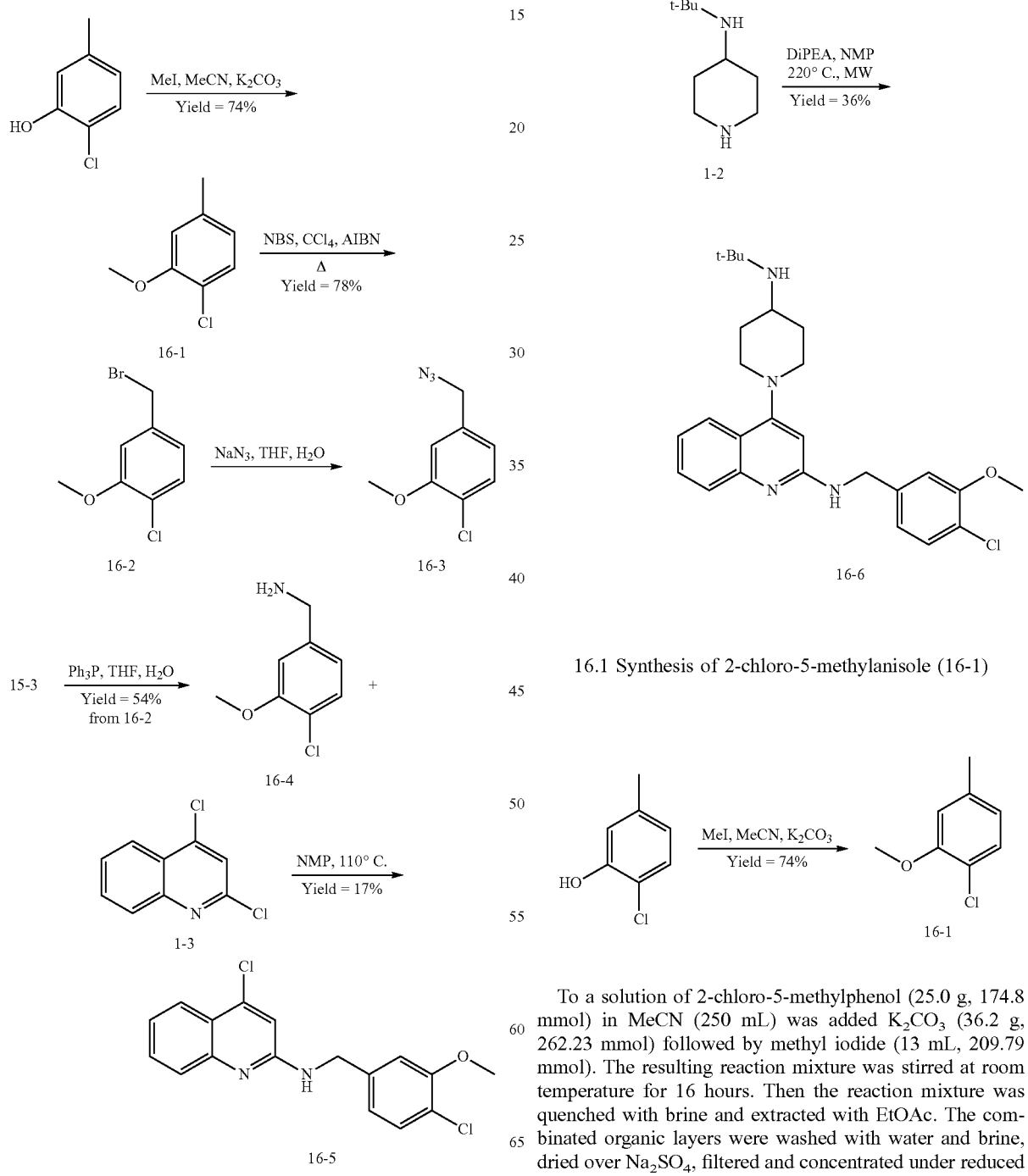

16.1 Synthesis of 2-chloro-5-methylanisole (16-1)

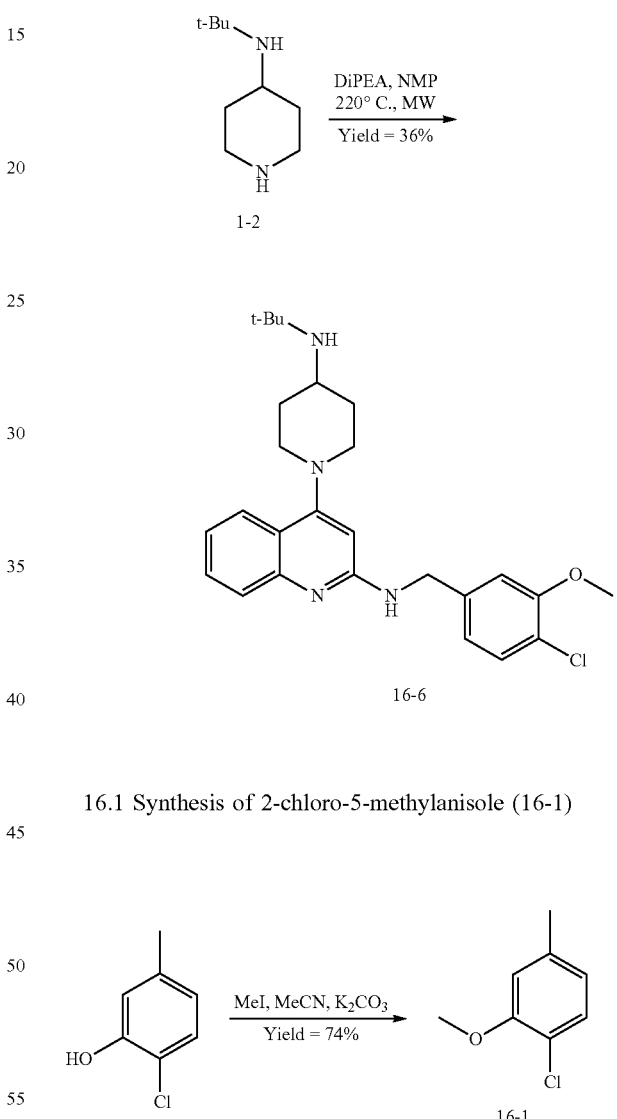

To a solution of 2-chloro-5-methylphenol (25.0 g, 174.8 mmol) in MeCN (250 mL) was added $K_2CO_3$ (36.2 g, 262.23 mmol) followed by methyl iodide (13 mL, 209.79 mmol). The resulting reaction mixture was stirred at room temperature for 16 hours. Then the reaction mixture was quenched with brine and extracted with EtOAc. The combinated organic layers were washed with water and brine, dried over $Na_2SO_4$, filtered and concentrated under reduced pressure to give a yellowish solid. The crude product was purified by flash chromatography (eluent: petroleum ether/ EtOAc 100/5) to give 20.0 g (yield=74%) of a white solid corresponding to 2-chloro-5-methylanisole (16-1).

HPLC-MS, Method G: $t_r$=1.74 min, (ES+) $C_8H_9C_1O$ required 156; found 157[M+H].

$^1$H NMR (400 MHz, CDCl$_3$)

16.2 Synthesis of 4-(bromomethyl)-1-chloro-2-methoxybenzene (16-2)

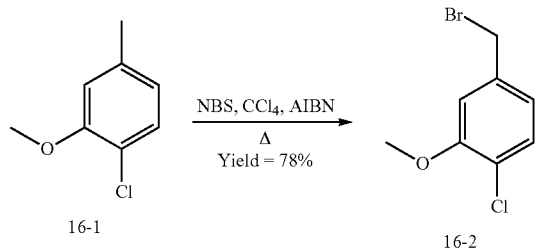

To a stirred solution of 2-chloro-5-methylanisole (16-1, 20.0 g, 127.71 mol) in CCl$_4$ (200 mL) was added AIBN (4.19 g, 25.54 mol) and NBS (22.7 g, 127.7 mol). The resulting reaction mixture was heated under reflux for 3 hours. Then, the reaction mixture was cooled, washed with a 1N HCl aqueous solution, NaHCO$_3$ saturated aqueous solution and brine. The organic layer was dried over Na$_2$SO$_4$, filtered and concentrated under reduced pressure to give 22 g (yield=78%) of a light yellow solid corresponding to 2-chloro-5-(bromomethyl)anisole (16-2).

$^1$H NMR (400 MHz, CDCl$_3$)

16.3 Synthesis of 2-chloro-5-(azidomethyl)anisole (16-3)

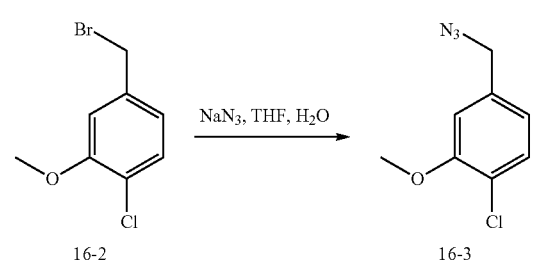

To a stirred solution of 2-chloro-5-(bromomethyl)anisole (16-2, 20.0 g, 84.92 mmol) in DMF (150 mL) was added NaN$_3$ (16.5 g, 254.76 mmol) followed by a few drops of water. The resulting reaction was stirred at room temperature for 24 hours. Then, the reaction mixture was poured on to water and extracted with ether. The combined organic layers were washed with water, dried with Na$_2$SO$_4$ and concentrated under reduced pressure to give 15.6 g (crude product) of a yellowish solid corresponding to 2-chloro-5-(azidomethyl)anisole (16-3) which was used in the next step without further purification.

16.4 Synthesis of 3-methoxy-4-chlorobenzyl Amine (16-4)

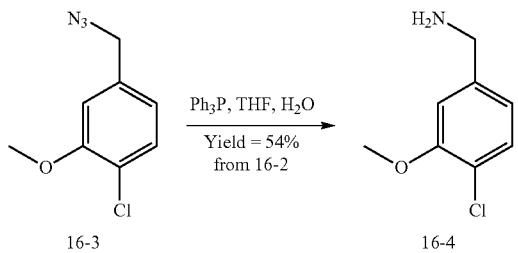

To a stirred solution of 2-chloro-5-(azidomethyl)anisole (16-3, 15.0 g, 75.91 mmol) in THF (150 ml) was added subsequently triphenylphosphine (59.71 g, 227.7 mmol) and water (5.0 mL). The resulting reaction mixture was then stirred at room temperature for 48 hours. The reaction mixture was then poured over a 1 M HCl aqueous solution and extracted with EtOAc. The combined organic layers were washed with a 1 M HCl aqueous solution and the combined aqueous phases were basified to pH 10 with a saturated Na$_2$CO$_3$ aqueous solution and then extracted with DCM. The combined DCM organic layers were dried with Na$_2$SO$_4$, filtered and concentrated under reduced pressure to give 7.0 g (yield=54%) of a yellowish oil corresponding to 3-methoxy-4-chlorobenzyl amine (16-4).

HPLC-MS, Method E: $t_r$=0.76 min, (ES+) $C_8H_{10}ClNO$ required 171; found 172[M+H]

$^1$H NMR (400 MHz, DMSO-d6)

16.5 Synthesis of 2-(3-methoxy-4-chlorobenzylamino)-4-chloroquinoline (16-5)

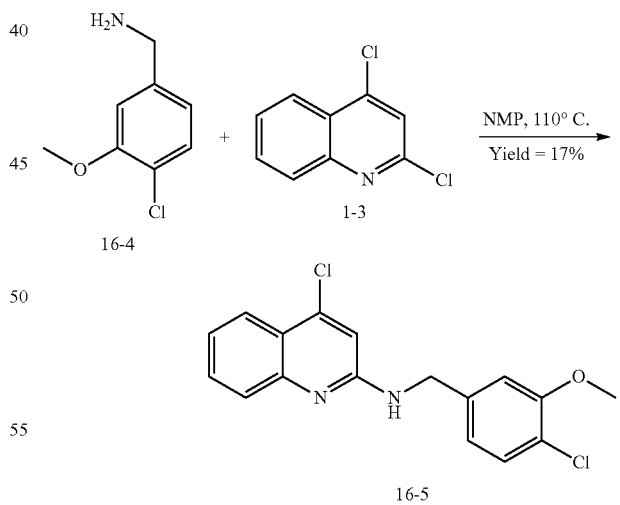

To a stirred solution under nitrogen gas of 2, 4-dichloroquinoline (1-3, 5.0 g, 25.38 mmol) in NMP (25 ml) was added 3-methoxy-4-chlorobenzyl amine (16-4, 4.30 g, 25.38 mmol) and the resulting reaction mixture was heated at 110° C. for 3 hours. Then, the reaction mixture was cooled, diluted with a 1N NaOH aqueous solution and the resulting mixture was extracted with EtOAc. The combined organic layers were dried over Na$_2$SO$_4$, filtered and concentrated under reduced pressure to give a yellow oil. The crude product was purified by flash chromatography (gradient petroleum ether/EtOAc from 8/2 to 0/10) to give 1.5 g (yield 17%) of a yellow solid corresponding to 2-(3-methoxy-4-chlorobenzylamino)-4-chloroquinoline (16-5).

HPLC-MS, Method C: $t_r$=1.85 min, (ES+) $C_{17}H_{14}Cl_2N_2O$ required 332; found 333 [M+H]

16.6 Synthesis of 2-(3-methoxy-4-chlorobenzylamino)-4-(4-tert-butylaminopiperidin-1-yl)quinoline (16-6)

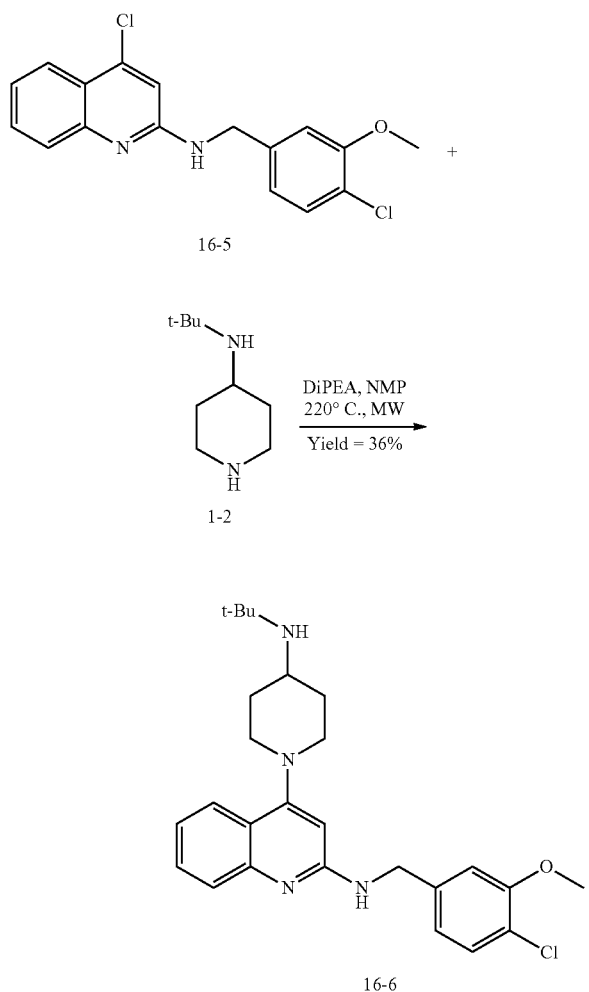

To a solution of 2-(3-methoxy-4-chlorobenzylamino)-4-chloroquinoline (16-5, 1.5 g, 4.51 mmol) and 4-(tert-butylamino)piperidine (1-2, 1.0 g, 6.77 mmol) in NMP (10 ml) was added N,N-Diisopropylethylamine (1.1 ml, 6.77 mmol) and the resulting reaction mixture was heated at 220° C. under micro wave conditions for 40 minutes. Then, the reaction mixture was cooled, diluted with water and the resulting mixture was extracted with EtOAc. The combined organic layers were dried over $Na_2SO_4$, filtered and concentrated under reduced pressure to give a light brown solid. The crude product was purified by flash chromatography (gradient Petroleum ether/EtOAc from 8/2 to 0/10) to give 0.70 g (yield 36%) of a yellowish solid corresponding to 2-(3-methoxy-4-chlorobenzylamino)-4-(4-tert-butylaminopiperidin-1-yl)quinoline (16-6).

HPLC-MS, Method E: $t_r$=0.95 min, (ES+) $C_{26}H_{33}ClN_4O$ required 452; found 453 [M+H]

$^1$H NMR (400 MHz, DMSO-d6)

Example 17: Preparation of 2-(3-hydroxy-4-chlorobenzylamino)-4-(4-tert-butylaminopiperidin-1-yl)quinoline (17-2)

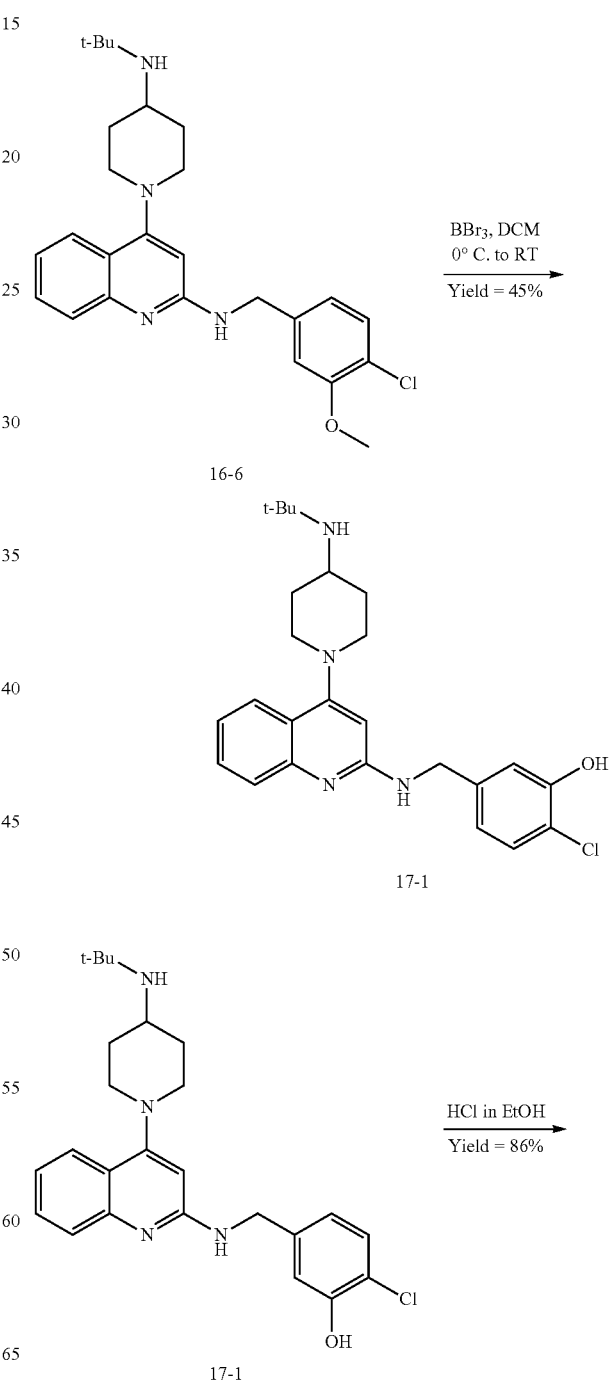

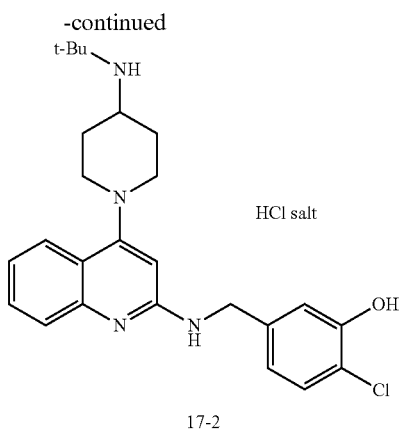

17.1 Synthesis of 2-(3-hydroxy-4-chlorobenzylamino)-4-(4-tert-butylaminopiperidin-1-yl)quinoline (17-1)

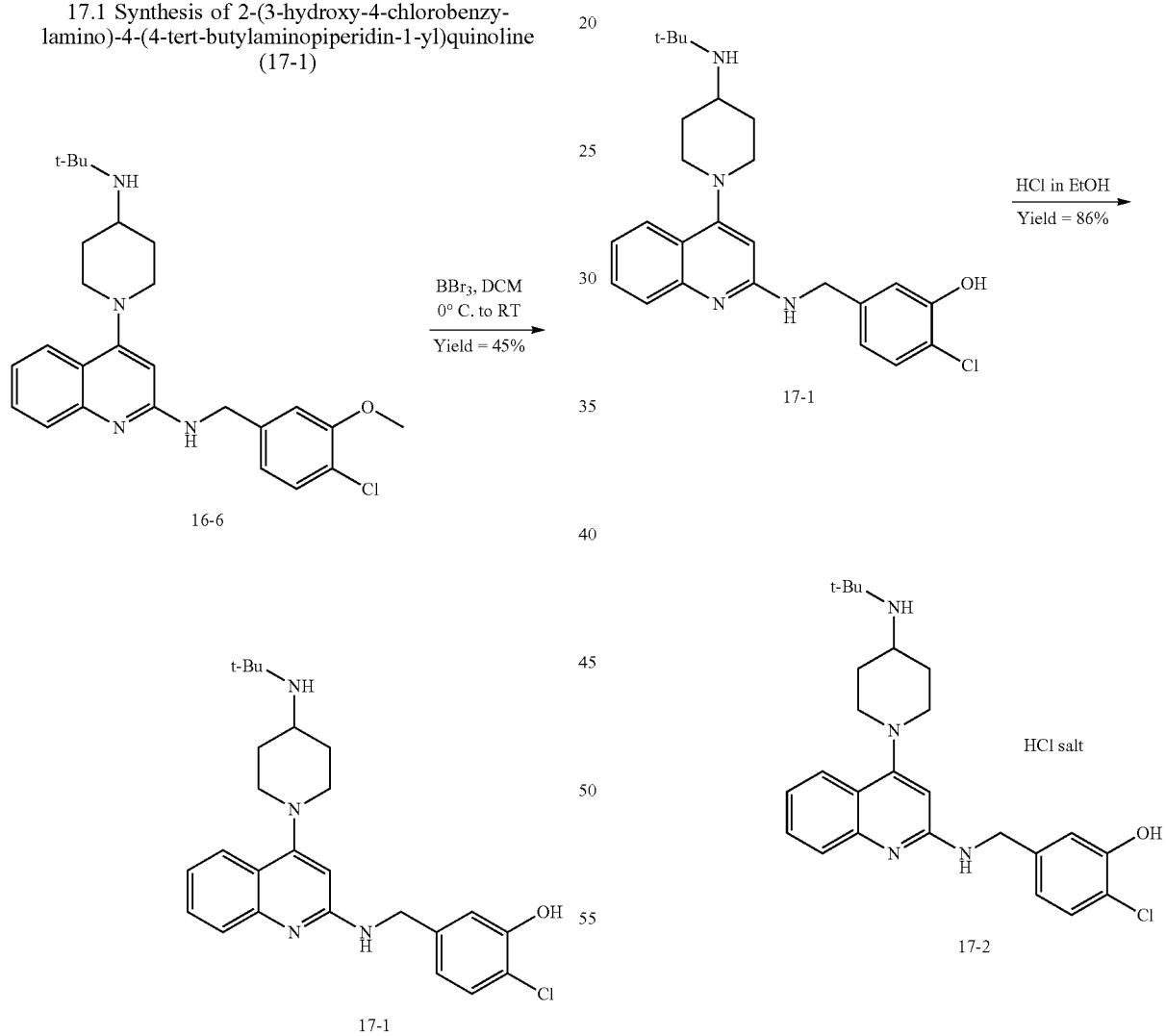

To a stirred solution of 2-(3-methoxy-4-chlorobenzylamino)-4-(4-tert-butylaminopiperidin-1-yl)quinoline (16-6, 0.7 g, 1.54 mmol) in DCM was added at 0° C. BBr$_3$ (0.85 mL, 7.70 mmol) and the resulting reaction mixture was stirred at room temperature for 12 hours. Then, the reaction mixture was cooled in an ice batch, diluted with ice-water and the resulting mixture was extracted with 10% MeOH/DCM. The combined organic layers were washed with a saturated NaHCO$_3$ aqueous solution, dried over Na$_2$SO$_4$, filtered and concentrated under reduced pressure to give a light brown solid. The crude product was purified by Prep-HPLC to give 280 mg (yield 45%) off-white solid corresponding to 2-(3-hydroxy-4-chlorobenzylamino)-4-(4-tert-butylaminopiperidin-1-yl)quinoline (17-1).

HPLC-MS, Method C: t$_r$=1.52 min, (ES+) C$_{25}$H$_{31}$ClN$_4$O required 438; found 439 [M+1-1]

17.2 Preparation of 2-(3-hydroxy-4-chlorobenzylamino)-4-(4-tert-butylaminopiperidin-1-yl)quinoline Hydrochloride Salt (17-2)

To a solution of 2-(3-hydroxy-4-chlorobenzylamino)-4-(4-tert-butylaminopiperidin-1-yl)quinoline (17-1, 0.28 g, 0.63 mmol) in ethanol (3 ml) was added a 7.2M HCl solution in ethanol (1.0 ml) and the resulting mixture was stirred at room temperature for 3 hours. Then, the reaction mixture was concentrated under reduced pressure and the residue was washed with diethyl ether to give 260 mg (yield 86%)

of an off-white solid corresponding to 2-(3-hydroxy-4-chlorobenzylamino)-4-(4-tert-butylaminopiperidin-1-yl)quinoline hydrochloride salt (17-2).

HPLC-MS, Method E: $t_r$=0.89 min, (ES+) $C_{25}H_{31}ClN_4O$ required 438; found 439[M+H].

$^1$H NMR (500 MHz, DMSO-d6)

Example 18: Preparation of 2-(4-chlorobenzamido)-4-(4-tert-butylaminopiperidin-1-yl)-quinoline Hydrochloride Salt (18-4)

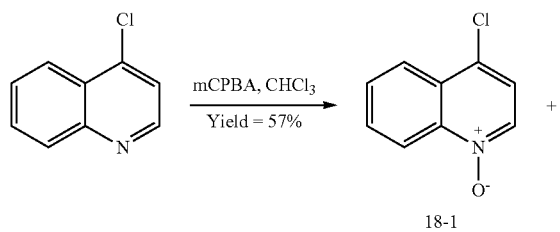

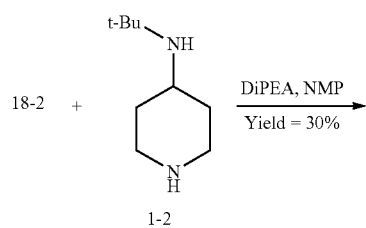

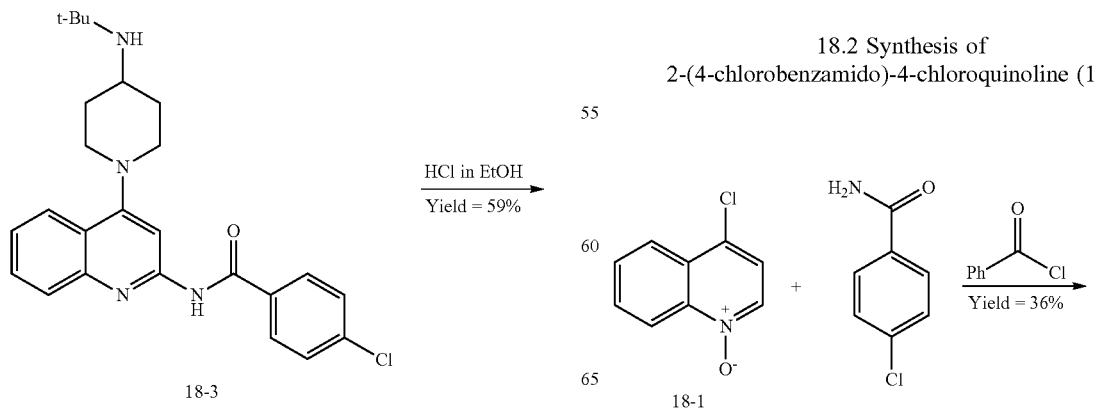

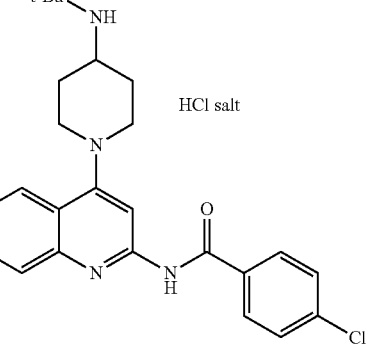

18.1 Synthesis of 4-chloroquinoline N-Oxide (18-1)

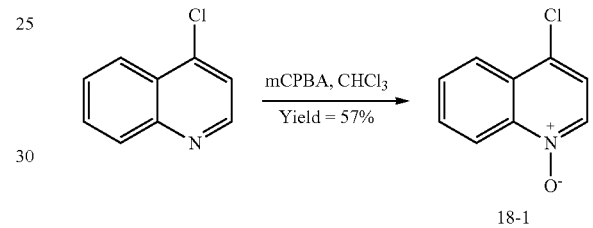

To a stirred solution of 4-chloroquinoline (3.0 g, 18.40 mmol) in chloroform was added at 0° C. m-chloroperbenzoic acid (16.29 g, 94.39 mmol) and the resulting mixture was stirred at room temperature for 2 hours. Then, the reaction mixture was basified with a saturated NaHCO$_3$ aqueous solution. The organic layer was washed with water, brine, dried over MgSO$_4$, filtered and concentrated under reduced pressure to give a yellow solid. The residue was washed with diethylether to give 1.9 g (yield=57%) of a yellowish solid corresponding 4-chloroquinoline N-oxide (18-1).

HPLC-MS, Method E: $t_r$=1.01 min, (ES+) $C_9H_6ClNO$ required 179.01; found 180 [M+H]

$^1$H NMR (400 MHz, CDCl$_3$)

18.2 Synthesis of 2-(4-chlorobenzamido)-4-chloroquinoline (18-2)

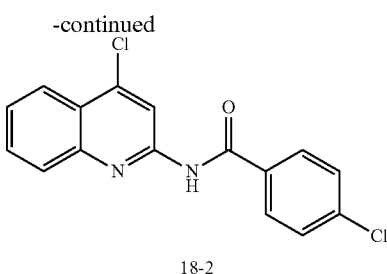

18-2

A mixture of 4-chloroquinoline N-oxide (18-1, 1.50 g, 8.379 mmol), benzoyl chloride (4.69 g, 33.52 mmol) and 4-chlorobenzamide (1.55 g, 10.055 mmol) was heated under agitation at 160° C. for 30 minutes. Then, the reaction mixture was cooled to room temperature, diluted with EtOAc and filtered. The solid residue was washed with methanol and dried under vacuum to give 0.95 g (yield=36%) of a yellowish solid corresponding to 2-(4-chlorobenzamido)-4-chloroquinoline (18-2).

HPLC-MS, Method H: $t_r$=3.29 min, (ES+) $C_{16}H_{10}Cl_2N_2O$ required 316; found 317 [M+H].

$^1$H NMR (400 MHz, DMSO-d6)

18.3 Synthesis of 2-(4-chlorobenzamido)-4-(4-tert-butylaminopiperidin-1-yl)-quinoline (18-3)

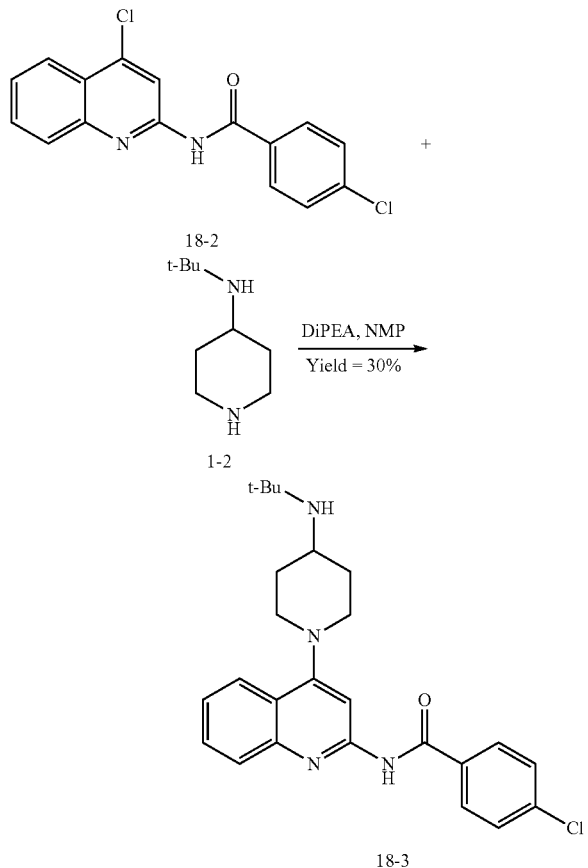

To a solution of 2-(4-chlorobenzamido)-4-chloroquinoline (18-2, 1.3 g, 4.113 mmol) and 4-(tert-butylamino)piperidine (1-2, 0.770 g, 4.9375 mmol) in NMP (13 ml) was added N,N-Diisopropylethylamine (1.4 ml, 7.59 mmol) and the resulting reaction mixture was heated at 160° C. for 4 hours. Then, the reaction mixture was cooled, diluted with a 1N NaOH aqueous solution and the resulting mixture was extracted with EtOAc. The combined organic layers were dried over $Na_2SO_4$, filtered and concentrated under reduced pressure to give a yellow oil. The crude product was purified by flash chromatography (gradient cyclohexane/EtOAc from 8/2 to 0/10) to give an off-white solid. This solid was recrystallized from MeCN to give 0.55 g (yield 30%) of a white solid corresponding to 2-(4-chlorobenzamido)-4-(4-tert-butylaminopiperidin-1-yl)-quinoline (18-3).

HPLC-MS, Method E: $t_r$=1.05 min, (ES+) $C_{25}H_{29}ClN_4O$ required 436; found 437 [M+H].

$^1$H NMR (500 MHz, DMSO-d6)

18.4 Preparation of 2-(4-chlorobenzamido)-4-(4-tert-butylaminopiperidin-1-yl)-quinoline Hydrochloride Salt (18-4)

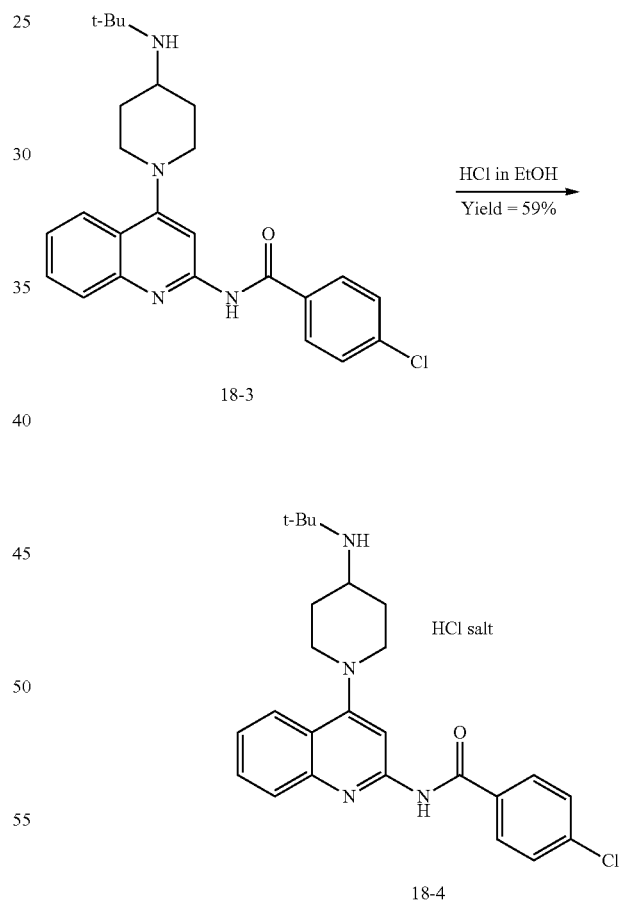

To a solution of 2-(4-chlorobenzamido)-4-(4-tert-butylaminopiperidin-1-yl)-quinoline (18-3, 0.55 g, 1.26 mmol) in ethanol (4 ml) was added a 7.2M HCl solution in ethanol (1.0 ml) and the resulting mixture was stirred at room temperature for 3 hours. Then, the reaction mixture was concentrated under reduced pressure and the residue was washed with diethyl ether to give 350 mg (yield 59%) of an off-white solid corresponding to 2-(4-chlorobenzamido)-4-(4-tert-butylaminopiperidin-1-yl)-quinoline hydrochloride salt (18-4).
HPLC-MS, Method H: $t_r$=2.33 min, (ES+) $C_{25}H_{29}ClN_4O$ required 436; found 437 [M+H].
$^1$H NMR (500 MHz, DMSO-d6)
Example 19: Preparation of 2-(4-chlorobenzylamino)-4-[4-(pyrrolidin-1-yl)piperidin-1-yl]quinoline (19-2)
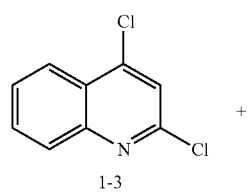
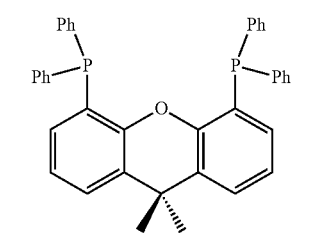
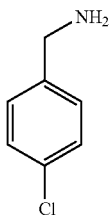
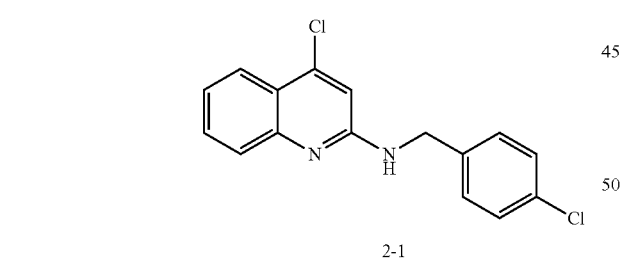
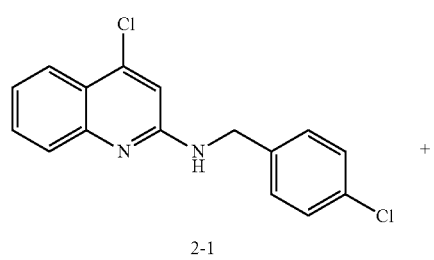
-continued
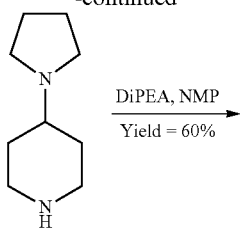
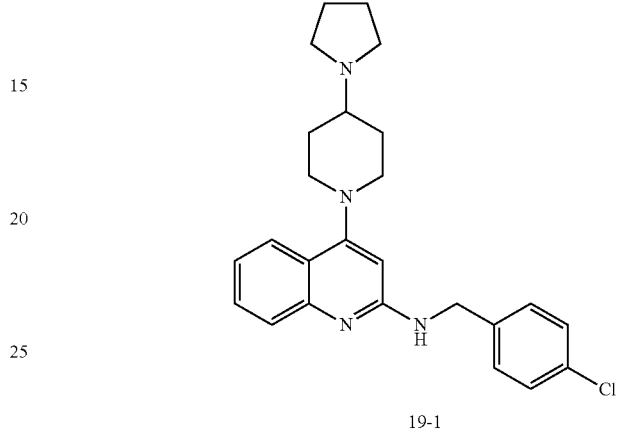
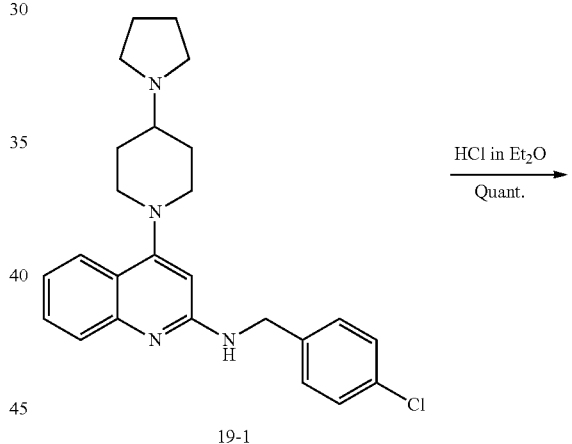
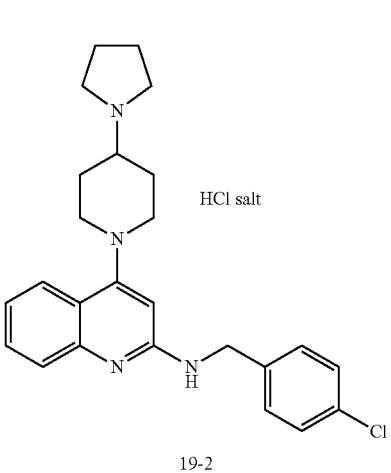

19.1 Synthesis of 2-(4-chlorobenzylamino)-4-chloroquinoline (2-1)

Synthesis of intermediate 2-(4-chlorobenzylamino)-4-chloroquinoline (2-1) can be carried out equally with the following procedure:

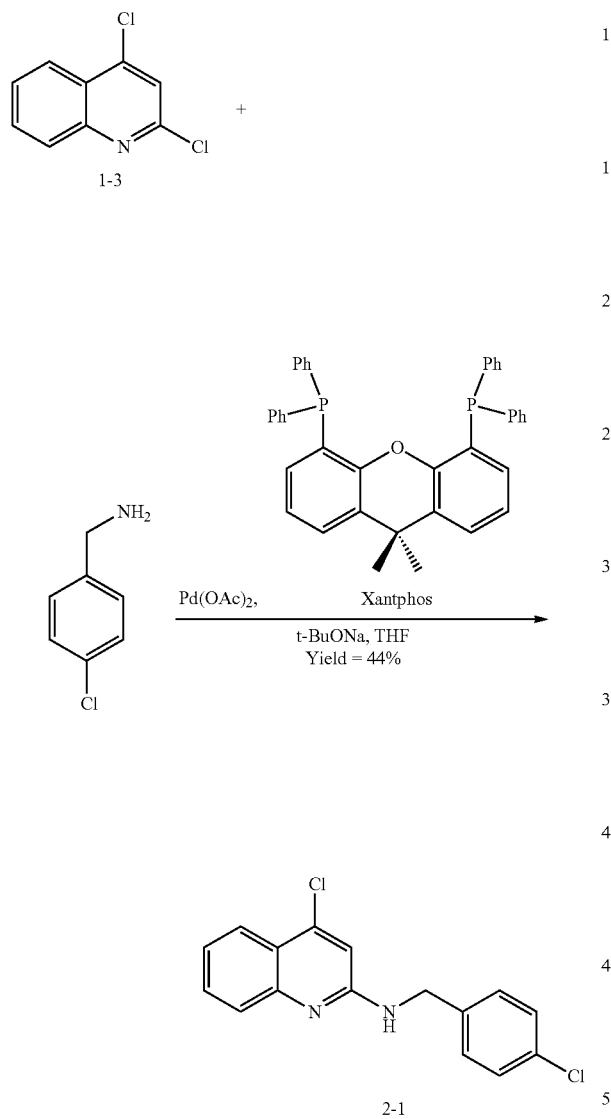

To a solution under nitrogen gas of 2,4-dichloroquinoline (1-3, 20.0 g, 101 mmol) in dry THF (200 ml) was added 4-chlorobenzylamine (24.7 mL, 202 mmol) and t-BuONa (27.2 g, 283 mmol). The resulting mixture was degassed 10 min with nitrogen, then Xantphos (5.8 g, 10.1 mmol) and Pd(OAc)$_2$ (1.1 g, 5.0 mmol) were added and the reaction mixture was heated under reflux for 3 hours. The resulting reaction mixture was then cooled to room temperature and concentrated under reduced pressure. The residue was partitioned between brine and EtOAc and the aqueous layer was extracted with EtOAc. The combined organic layers were dried over MgSO$_4$, filtered and concentrated under reduced pressure to give a brown oil. The crude product was purified by flash chromatography (gradient Petroleum ether/DCM from 5/5 to 0/10) to give 13.5 g (yield 44%) of a brown solid corresponding to 2-(4-chlorobenzylamino)-4-chloroquinoline (2-1).

$^1$H NMR (300 MHz, CDCl$_3$)

19.2 Synthesis of 2-(4-chlorobenzylamino)-4-[4-(pyrrolidin-1-yl)piperidin-1-yl]quinoline (19-1)

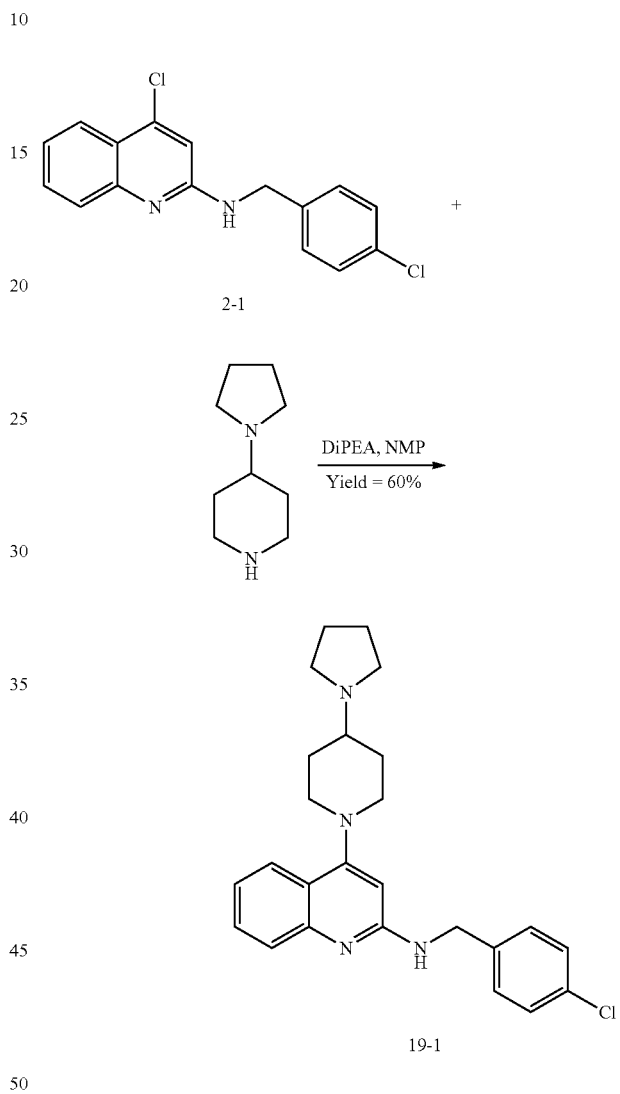

The synthesis 2-(4-chlorobenzylamino)-4-[4-(pyrrolidin-1-yl)piperidin-1-yl]quinoline (19-1) was carried out using the following general procedure.

To a solution of 2-substituted amino-4-chloroquinoline (1.0 eq., e.g. 2-(4-chlorobenzylamino)-4-chloroquinoline 2-1) and the cyclic secondary amine (1.25 eq., e.g. 4-(pyrrolidin-1-yl)piperidine) in NMP (2 ml) was added N,N-Diisopropylethylamine (1.6 eq.) and the resulting reaction mixture was heated at 140° C. for 24 hours. Then, the reaction mixture was cooled, diluted with a 1N NaOH aqueous solution (25 mL) and the resulting mixture was extracted with EtOAc. The combined organic layers were washed with brine, dried over MgSO$_4$, filtered and concentrated under reduced pressure to give a residue. The crude product was purified by flash chromatography (gradient DCM/EtOAc from 10/0 to 0/10) to give a brown solid (yield 60%) corresponding to 2-(4-chlorobenzylamino)-4-[4-(pyrrolidin-1-yl)piperidin-1-yl]quinoline (19-1).

$^{1}$H NMR (300 MHz, CDCl$_{3}$)

19.3 Preparation of 2-(4-chlorobenzylamino)-4-[4-(pyrrolidin-1-yl)piperidin-1-yl]quinoline Hydrochloride Salt (19-2)

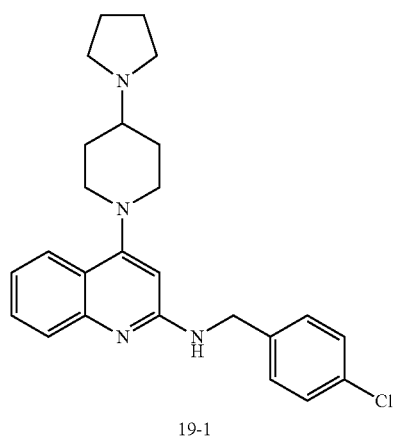

To a solution of 2-(4-chlorobenzylamino)-4-[4-(pyrrolidin-1-yl)piperidin-1-yl]quinoline (19-1, 210 mg, 0.499 mmol) in DCM (4 ml) was added a 2 N HCl solution in Et$_{2}$O (1 ml, 4 eq.). The resulting mixture was stirred at room temperature for 15 minutes and was then concentrated under reduced pressure. The obtained salt was dissolved in H$_{2}$O and was then freeze dried to give 254 mg (yield=quantitative) a yellowish solid in (yield=88%) corresponding to 2-(4-chlorobenzylamino)-4-[4-(pyrrolidin-1-yl)piperidin-1-yl]quinoline hydrochloride salt (19-2).

HPLC-MS, Method I: t$_{r}$=3.02 min, (ES+) C$_{25}$H$_{29}$ClN$_{4}$ required 420; found 421 [M+H].

$^{1}$H NMR (300 MHz, DMSO-d6)

Example 20: Preparation of 2-(4-chlorobenzylamino)-4-{4-[(1-methylpiperidin-4-yl)amino]piperidin-1-yl}quinoline Hydrochloride Salt (20-2)

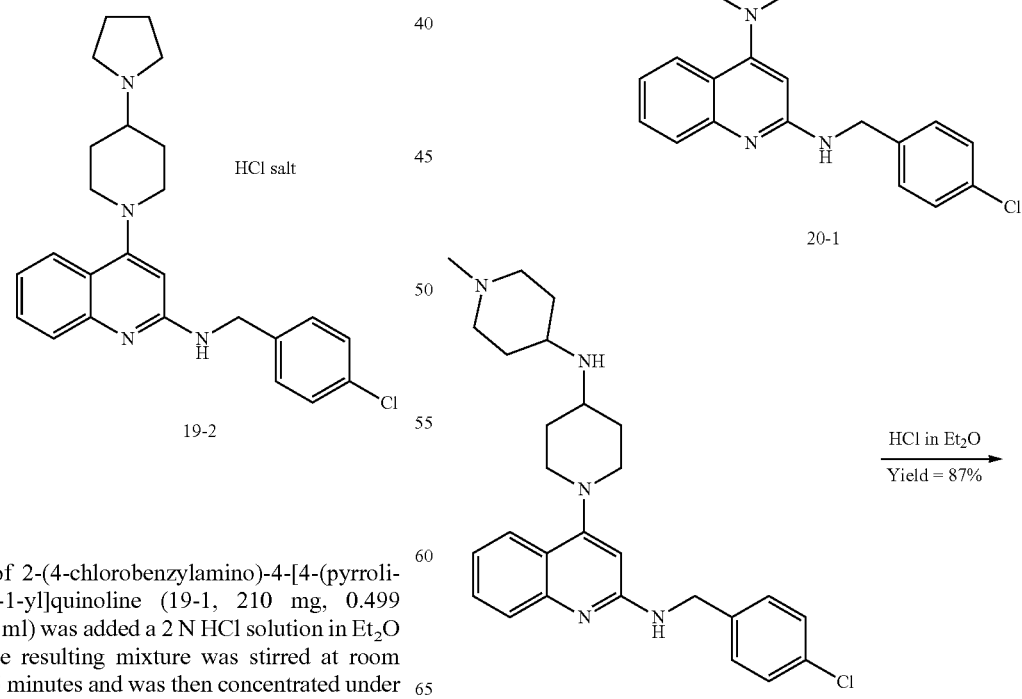

-continued

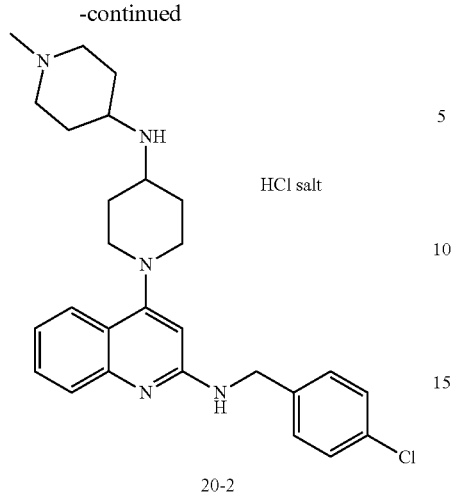
20-2

20.1 Synthesis of 2-(4-chlorobenzylamino)-4-{4-[(1-methylpiperidin-4-yl)amino]piperidin-1-yl}quinoline (20-1)

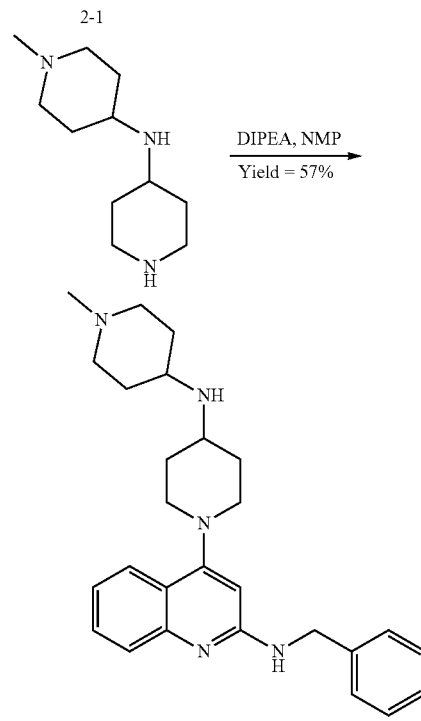

The synthesis 2-(4-chlorobenzylamino)-4-{4-[(1-methylpiperidin-4-yl)amino]piperidin-1-yl}quinoline (20-1) was carried out using the general procedure described in example 19-2. The compound corresponding to 2-(4-chlorobenzylamino)-4-{4-[(1-methylpiperidin-4-yl)amino]piperidin-1-yl}quinoline (20-1) was obtained as an off-white solid in 57% yield.

$^1$H NMR (300 MHz, DMSO-d6)

20.2 Preparation of 2-(4-chlorobenzylamino)-4-{4-[(1-methylpiperidin-4-yl)amino]piperidin-1-yl}quinoline Hydrochloride Salt (20-2)

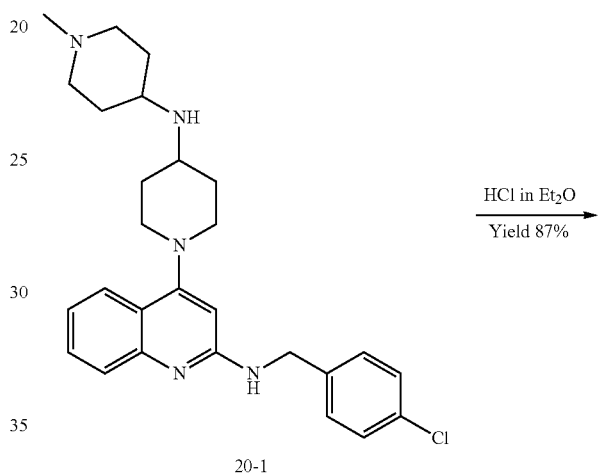

The preparation of 2-(4-chlorobenzylamino)-4-{4-[(1-methylpiperidin-4-yl)amino]piperidin-1-yl}quinoline hydrochloride salt (20-2) was carried out using the same procedure as described in example 19-3. The compound corresponding to 2-(4-chlorobenzylamino)-4-{4-[(1-methylpiperidin-4-yl)amino]piperidin-1-yl}quinoline hydrochloride salt (20-2) was obtained as an off-white solid in 87% yield.

$^1$H NMR (300 MHz, DMSO-d6)

Example 21: Preparation of 2-(4-methoxybenzylamino)-4-(4-tert-butylaminopiperidin-1-yl)quinoline (21-2)

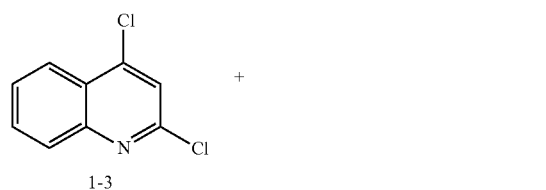

1-3

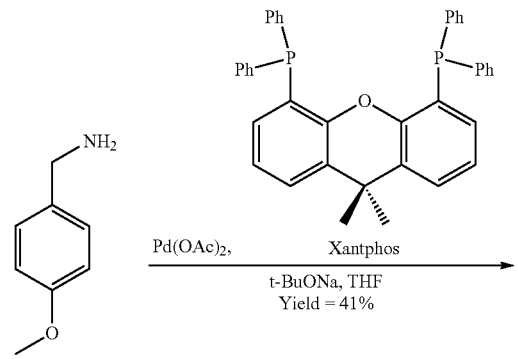

Pd(OAc)₂, Xantphos
t-BuONa, THF
Yield = 41%

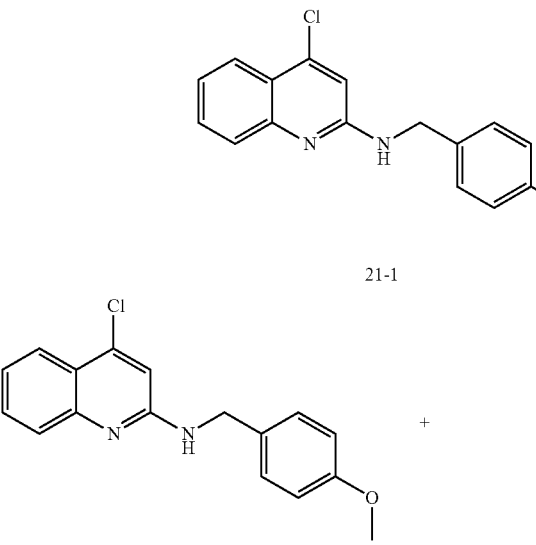

21-1

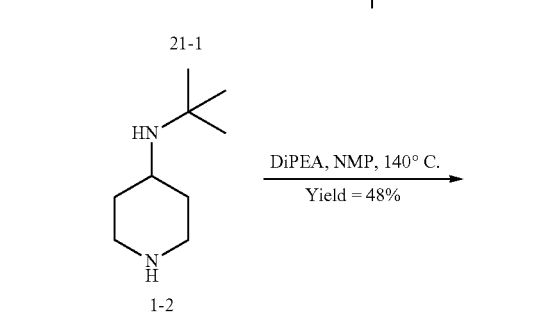

1-2

DiPEA, NMP, 140° C.
Yield = 48%

-continued

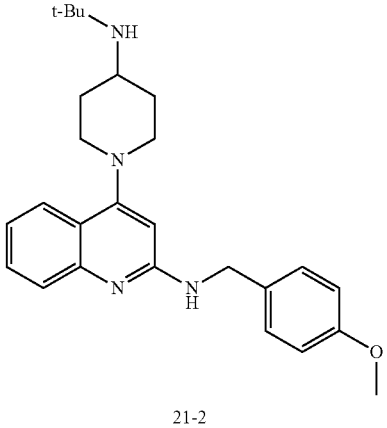

21-2

21.1 Synthesis of 2-(4-methoxybenzylamino)-4-chloroquinoline (21-1)

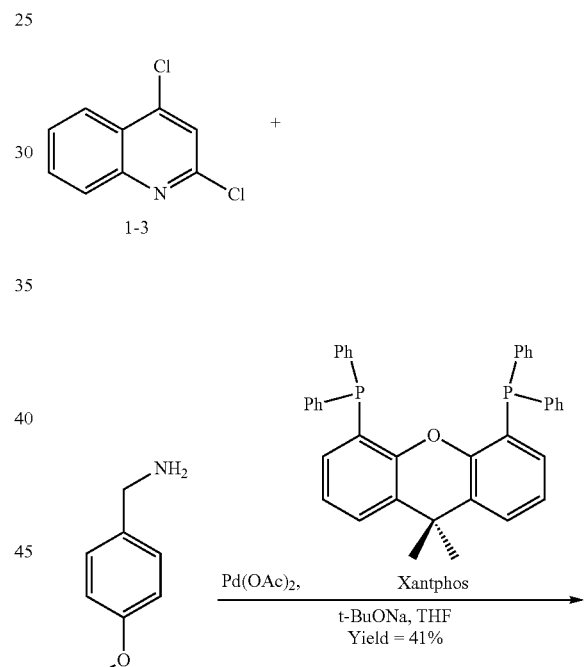

1-3

Pd(OAc)₂, Xantphos
t-BuONa, THF
Yield = 41%

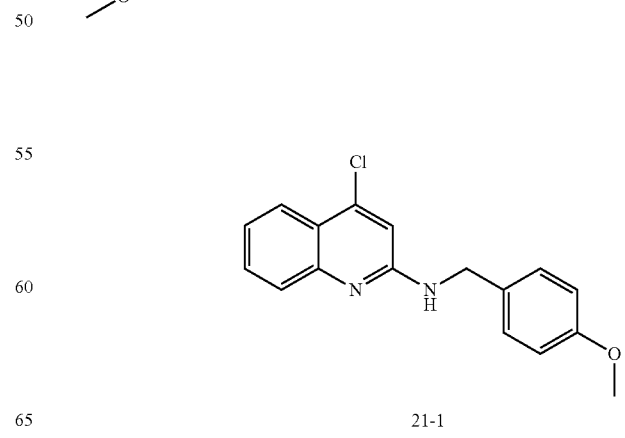

21-1

The synthesis 2-(4-methoxybenzylamino)-4-chloroquinoline (21-1) was carried out using the general procedure described in example 19-1. The compound corresponding to 2-(4-methoxybenzylamino)-4-chloroquinoline (21-1) was obtained as a yellow solid in 41% yield.

$^1$H NMR (300 MHz, DMSO-d6)

21.2 Synthesis of 2-(4-methoxybenzylamino)-4-(4-tert-butylaminopiperidin-1-yl)quinoline (21-2)

The synthesis 2-(4-methoxybenzylamino)-4-(4-tert-butylaminopiperidin-1-yl)quinoline (21-2) was carried out using the general procedure described in example 19-2. The compound corresponding to 2-(4-methoxybenzylamino)-4-(4-tert-butylaminopiperidin-1-yl)quinoline (21-2) was obtained as a yellowish solid in 48% yield.

$^1$H NMR (300 MHz, DMSO-d6)

Example 22: Synthesis of 2-(4-hydroxybenzylamino)-4-(4-tert-butylaminopiperidin-1-yl)quinoline (22-1)

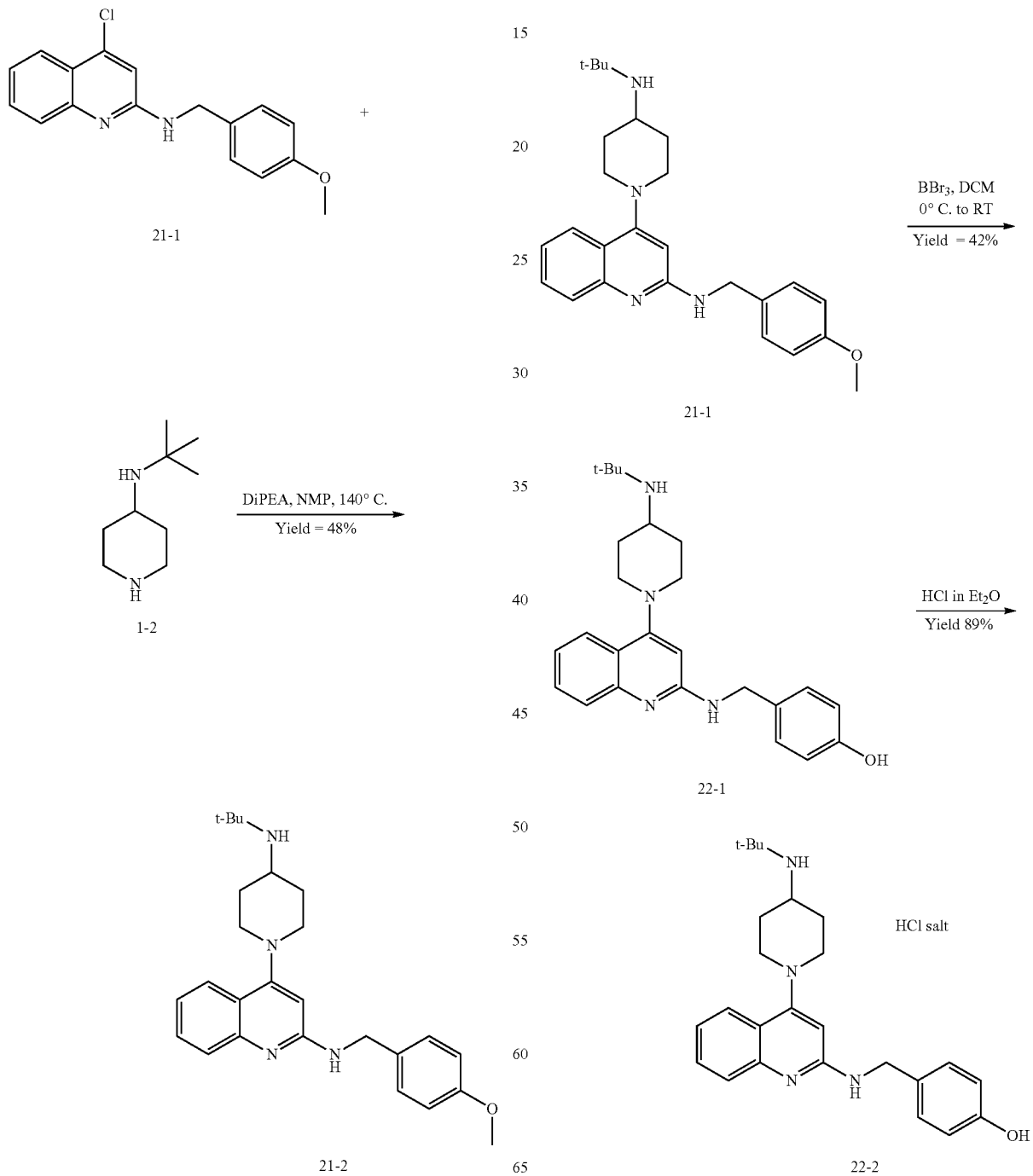

22.1 Synthesis of 2-(4-hydroxybenzylamino)-4-(4-tert-butylaminopiperidin-1-yl)quinoline (22-1)

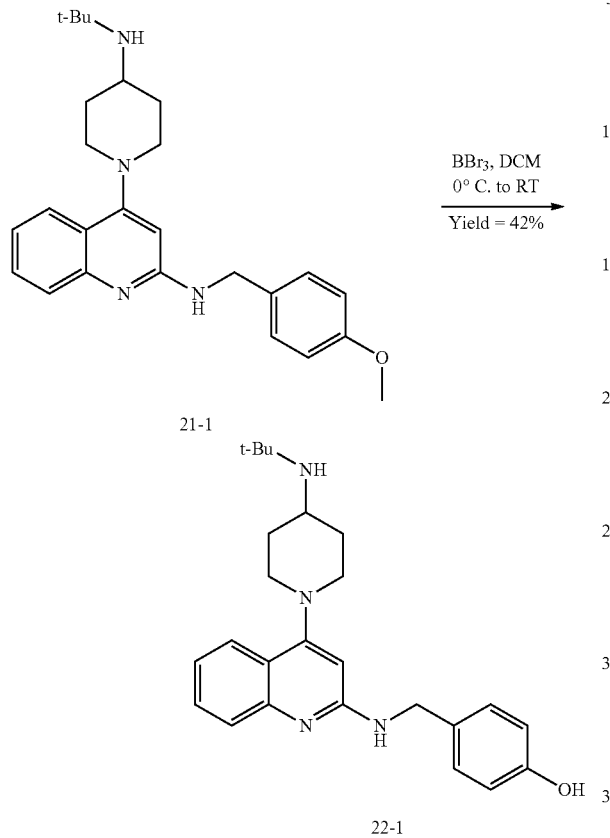

The synthesis 2-(4-hydroxybenzylamino)-4-(4-tert-butylaminopiperidin-1-yl)quinoline (22-1) was carried out using the general procedure described in example 17-1. The compound corresponding to 2-(4-hydroxybenzylamino)-4-(4-tert-butylaminopiperidin-1-yl)quinoline (22-1) was obtained as a yellowish solid in 42% yield.

$^1$H NMR (300 MHz, DMSO-d6)

22.2 Synthesis of 2-(4-hydroxybenzylamino)-4-(4-tert-butylaminopiperidin-1-yl)quinoline Hydrochloride Salt (22-2)

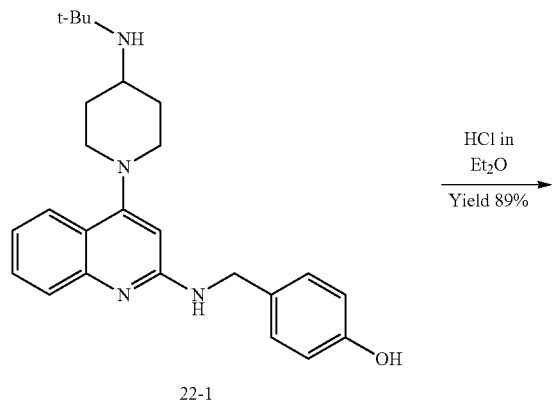

The preparation of 2-(4-hydroxybenzylamino)-4-(4-tert-butylaminopiperidin-1-yl)quinoline hydrochloride salt (22-2) was carried out using the same procedure as described in example 19-3. The compound corresponding to 2-(4-hydroxybenzylamino)-4-(4-tert-butylaminopiperidin-1-yl)quinoline hydrochloride salt (22-2) was obtained as an off-white solid in 89% yield.

$^1$H NMR (300 MHz, DMSO-d6)

Example 23: Synthesis of 2-benzylamino-4-(4-tert-butylaminopiperidin-1-yl)quinoline Hydrochloride Salt (23-3)

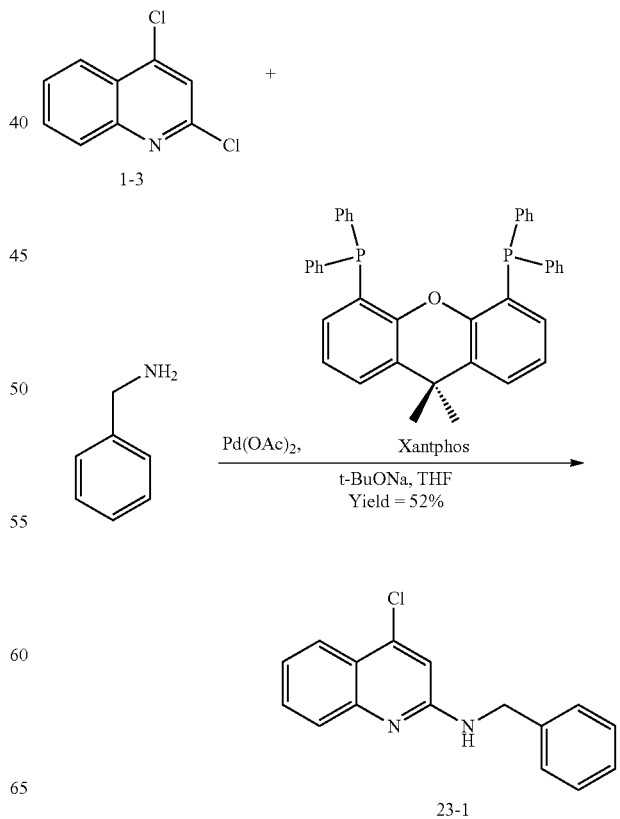

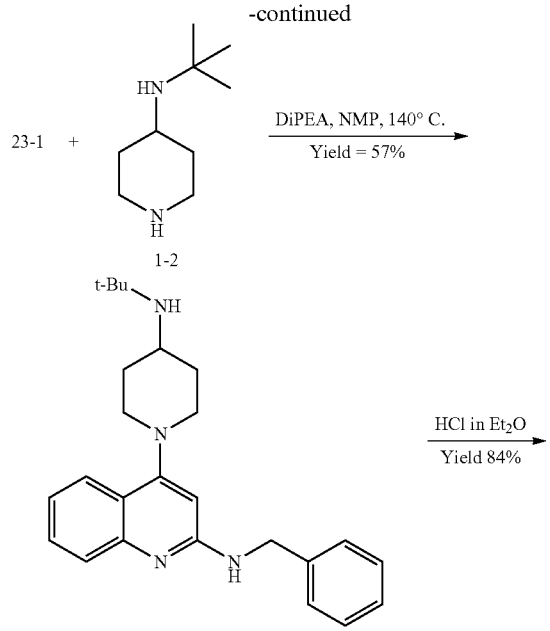
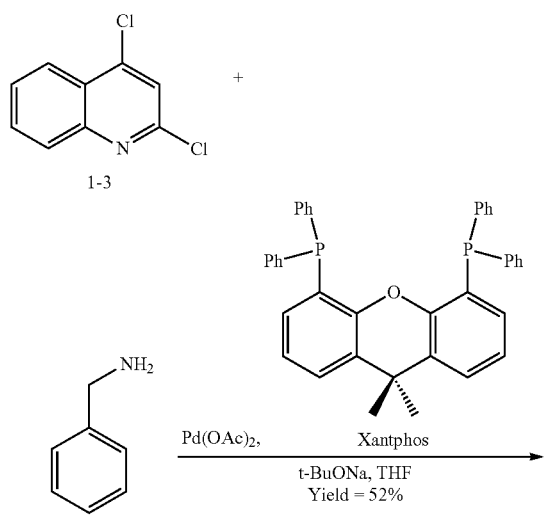
23.1 Synthesis of 2-benzylamino-4-chloroquinoline (23-1)
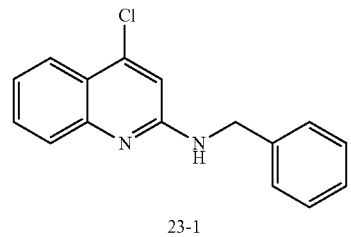
The synthesis of 2-benzylamino-4-chloroquinoline (23-1) was carried out using the general procedure described in example 19-1. The compound corresponding to 2-benzylamino-4-chloroquinoline (23-1) was obtained as a yellow solid in 52% yield.
$^1$H NMR (300 MHz, DMSO-d6)
23.2 Synthesis of 2-benzylamino-4-(4-tert-butylaminopiperidin-1-yl)quinoline (23-2)
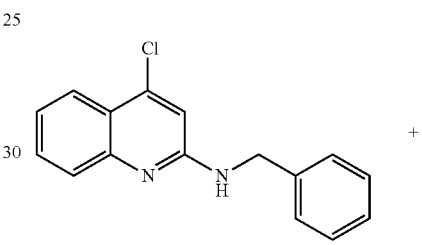
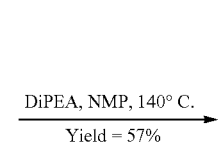
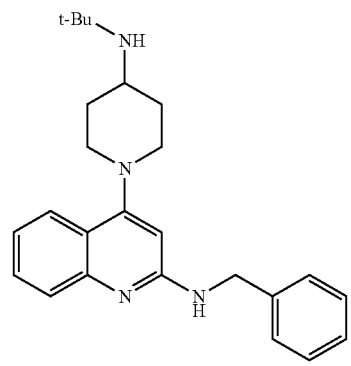

The synthesis 2-benzylamino-4-(4-tert-butylaminopiperidin-1-yl)quinoline (23-2) was carried out using the general procedure described in example 19-2. The compound corresponding to 2-benzylamino-4-(4-tert-butylaminopiperidin-1-yl)quinoline (23-2) was obtained as a yellowish solid in 57% yield.

$^1$H NMR (300 MHz, DMSO-d6)

23.3 Synthesis of 2-benzylamino-4-(4-tert-butylaminopiperidin-1-yl)quinoline Hydrochloride Salt (23-3)

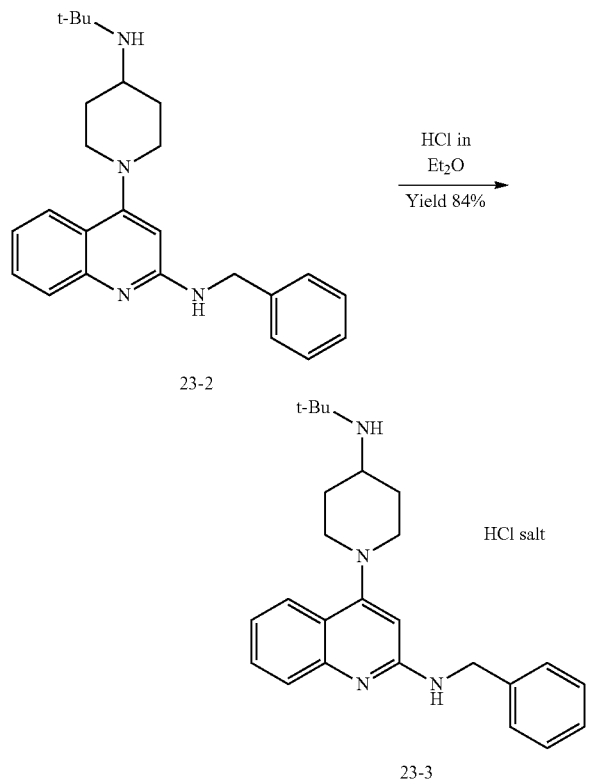

The preparation of 2-benzylamino-4-(4-tert-butylaminopiperidin-1-yl)quinoline hydrochloride salt (23-3) was carried out using the same procedure as described in example 19-3. The compound corresponding to 2-benzylamino-4-(4-tert-butylaminopiperidin-1-yl)quinoline hydrochloride salt (23-3) was obtained as an off-white solid in 84% yield.

$^1$H NMR (300 MHz, DMSO-d6)

Example 24: Preparation Pharmaceutical Formulation Containing a Compound Described Herein Formulation A: Liquid Oral Administration
Compound: 50-500 mg
Citric acid monohydrate: 210 mg
Sodium hydroxide: 36 mg
Flavoring
Water: quantum satis (q.s.) to 100 ml
Formulation B: Intravenous Administration
Compound: 0.1-10 mg
Citric acid monohydrate: 105 mg
Sodium hydroxide: 18 mg
Dextrose monohydrate: quantum satis (q.s.) to make isotonic preparation
Water intravenous administration: quantum satis (q.s.) to 100 ml
Formulation B: Tablet Formulation
Compound: 1%
Stearic acid: 25%
Microcrystalline cellulose: 73%
Colloidal silica: 1%
Biological Data

Example 25: Inhibition of Cathepsin B, D and L in HepG2 Cell Line by Compound 2-3

Lysosomal functions was investigated in a hepatocellular carcinoma (HCC) cell line HepG2 after 6 hours and 24 hours of treatment with compound 2-3 (the hydrochloride salt form of compound 2-2) using functional assays of some lysosomal enzymes activity: two cysteine proteinases: cathepsin B (CTSB) and cathepsin L (CTSL), and one aspartic proteinase: cathepsin D (CTSD). Two sets of three concentrations of compound 2-3 (1 µM, 2 µM, and 4 µM for 6 hours, and 0.5 µM, 1 µM and 2 µM for 24 hours) were tested at least in triplicate and four independent experiments were performed. Salinomycin (7.5 µM for 6 hours and 24 hours) was used as a positive control.

Methods:
Cell Culture:
The HepG2 cell line was maintained in DMEM (Dulbecco's Modified Eagle Media) high glucose (Cat #L0103-500, Dutscher) containing 1% penicillin-streptomycin (Cat #P06-07100, Dutscher) and 10% FBS (Fetal Bovine Serum) (Cat #11543407, Life Technologies). Cells were cultured at 37° C. with 5% $CO_2$.

Cell Plating:
The day before the experiment, 6-well plates (Cat #353046, Dutscher) with 250,000 cells in 2.7 mL of medium per well were prepared.

Test Items Preparation:
Compound 2-3 was dissolved with filtrated $H_2O$ mQ to make a 10 mM stock solution and serial working solutions (10× solutions) were prepared with the diluent (=culture medium with 0.4% $H_2O$ mQ) at 5 µM, 10 µM, 20 µM and 40 µM: the "dilution 1" is made from the 10 mM stock solution in the culture medium and the following serial dilutions were made in the diluent to maintain a constant percentage of $H_2O$.

Salinomycin [CAS 53003-10-4] was used as positive control and was dissolved with methanol to make a 10 mM stock solution and a 10× solution at 75 µM was prepared with the culture medium.

Treatment with Test Items:
300 µL of compound 2-3 10× solutions (solutions at 10 µM, 20 µM and 40 µM for 6 hours of treatment and solutions at 5 µM, 10 µM and 20 µM for 24 hours of treatment) or 300 µL of diluent (=non-treated (NT) condition) or 300 µL of Salinomycin 10× solution were dispensed in the appropriate wells (4 wells/condition). After cells treatment, 6-well plates were returned to incubator for 6 hours or 24 hours.

Preparation of Cell Extracts:
After 6 hours or 24 hours of cells treatment, the medium was removed from each well. The cells were carefully rinsed with PBS (phosphate-buffered saline, Cat #L0615-500, Dutscher) and detached with 500 µL per well of a trypsin solution. After 5 min of trypsin (Cat #L0930-100, Dutscher) incubation at 37° C., 800 µL of medium was added per well and transferred to a 1.5 mL tube. Then, 800 μL of PBS was used to rinse each well and the corresponding solution was pooled in each corresponding 1.5 mL tube. Cell suspensions were centrifuged 5 min at 2,500 rpm at 4° C. At this time, for each condition of treatment, cell pellets were pooled in a 1.5 mL tube and centrifuged 5 min at 2500 rpm at 4° C. Cell pellets were resuspended in 900 μL of PBS with a protease inhibitor cocktail (one tablet per 50 mL PBS, Cat #4693132001, Sigma) and splited in 2 conditions (300 μL for CTSD assay and 600 μL for CTSB and both cathepsin B and cathepsin L (CTSB/L) assays). Cell suspensions were centrifuged 5 min at 2,500 rpm at 4° C. Then, cell pellets were lysed in 50 μL of acetate buffer (sodium acetate 0.1 M, pH 5.5, Cat #EU0310, Euromedex) with a cocktail of protease inhibitors/cathepsin assay (0.5 mM PMSF, Cat #78830-5 g, Sigma; 1 mM MMTS, Cat #64306-1 mL, Fluka; 0.5 mM EDTA, Cat #P10-15100, Dutscher) and 0.04 mM Pepastin A (Cat #sc-45036A, Santa Cruz Biotechnologies) for CTSB/L and CTSB and 0.5 mM PMSF, 1 mM MMTS, 0.5 mM EDTA for CTSD). Then, three freeze-thawing cycles were done to lyse cells. Cell lysates were then centrifuged 10 min at 12,000 rpm at 4° C. Total protein concentration was assessed using the Bradford reagent (Cat #B6916-500ML, Sigma-Aldrich) and cellular lysates were stored at −80° C. until catalytic activity measurement.

Determination of Catalytic Activity:

The overall peptidase activity of CTSB/L was determined fluorometrically using the synthetic substrate Z-Phe-Arg-7-amido-4-methylcoumarin (Z-FR-AMC, release of the fluorescent coumaryl moiety, Cat #03-32-1501, Calbiochem) while the catalytic activity of CTSB was measured by using the selective substrate Z-Arg-Arg-7-amido-4-methylcoumarin (Z-RR-AMC, Cat #219392, Calbiochem). Alternatively the peptidase activity of CTSD was measured in the presence of methoxycoumarin-4-acetyl-Gly-Lys-Pro-Ile-Leu-Phe-Phe-Arg-Leu-Lys(Dnp)-D-Arg-NH$_2$ (MOCAc-GKPILF~FRLK(Dnp)-D-R—NH$_2$, a selective intramolecularly quenched fluorogenic substrate of CTSD, Cat #219360-1MG, Merck).

Cell lysates (1 μg of total proteins) were pre-incubated with acetate buffer (0.1 M sodium acetate) pH 5.5 (Cat #EU0310, Euromedex), 10 mM DTT (Cat #233155, Calbiochem), 2 mM EDTA (Cat #108418, Merck), and 0.01% Brij®35 (Cat #B0217, BIO BASIC CANADA INC) during 10 minutes at 30° C. prior measurement of CTSB/L and CTSB activities. Alternatively cell lysates (1 μg of total proteins) were pre-incubated with citrate buffer pH 4.0 (0.1 M sodium citrate Cat #C-3674 Sigma, 2 mM EDTA Cat #108418 Merck, containing 0.01% Brij®35 Cat #B0217 BIO BASIC CANADA INC) during 10 minutes at 30° C. prior measurement of CTSD activity. Finally, the respective final concentration of substrates for monitoring peptidase activities were 50 μM for Z-FR-AMC and Z-RR-AMC (excitation wavelength: 350 nm; emission wavelength: 460 nm) and 20 μM for MOCAc-GKPILF~FRLK(Dnp)-D-R-NH$_2$ (excitation wavelength: 325 nm; emission wavelength: 390 nm). The released fluorescence was continuously recorded at 37° C. under gentle agitation with a fluorescence reader (Gemini spectrofluorimeter, Molecular Devices). Synthetic protease inhibitors E-64 [CAS: 66701-25-5] (inhibitor of both CTSB/L, 100 μM), CA-074 [CAS: 134448-10-5] (specific inhibitor of CTSB, 50 μM) and Pepstatin A [CAS: 6305-03-3] (inhibitor of CTSD, 50 μM) were used as control to confirm the detection of specific activities and inhibition. Samples were measured in triplicate. Slopes of the enzymatic activity were calculated with the software Softmaxpro (Molecular Devices).

Data Analysis:

Four independent experiments were performed. The data are presented as the mean value+standard deviation (SD).

For each experiment and each tested condition, percentage of activity of each cathepsin were determined by comparing the slope of the enzymatic activity in treated conditions to the slope of the enzymatic activity in non-treated condition (NT) as described below:

$$\% \text{ Cat} = \frac{(\text{slope of the enzymatic activity in treated condition})}{(\text{slope of the enzymatic activity in } NT)} \times 100$$

The data were displayed graphically using GraphPad Prism 7 (GraphPad Software, Inc. La Jolla, Calif.).

Statistical Analysis:

Comparisons of means were calculated using Dunnett's multiple comparisons test. Statistical analyses were performed using GraphPad Prism 7 (GraphPad Software, Inc. La Jolla, Calif.).

Results:

After 6 hours of treatment, compound 2-3 decreased the proteolytic activity of cathepsins B, D and/or L in a dose-response manner (FIG. 1, FIG. 2 and FIG. 3). The highest compound 2-3 concentrations (2 μM and 4 μM) significantly decreased the activity of CTSB and CTSB/L (75.4% and 54.0% of CTSB activity versus NT, 78.0% and 55.3% of CTSB/L activity versus NT) and 4 μM of compound 2-3 induced a significant decrease of CTSD activity (60.6% of CTSD activity versus NT).

After 24 hours of treatment, this functional inhibition was persistent after compound 2-3 treatment.

The positive control (Salynomycin), significantly decreased the proteolytic activity of cathepsins B, D and/or L after 6 hours and 24 hours of treatment, as described in bibliography (Yue, W. et al. Autophagy 2013 (9), 714-729).

These results showed in FIGS. 1, 2 and 3 indicated that compound 2-3 induced an inhibition of the proteolytic activity of cathepsins B, D and/or L in HepG2 cell line supporting that compound 2-3 induced an inhibition of some lysosomal functions in cellulo.

Example 26: Inhibition of the Autophagy Flux in HepG2 and Huh7 Cell Lines by Compound 2-3

Since compound 2-3 induced an inhibition of the proteolytic activity of cathepsins B, D and/or L (see example 1) supporting an inhibition of some lysosomal functions which can affect the cellular autophagy flux, the capacity of compound 2-3 to modulate the cellular autophagy processes and functions was evaluated in two Hepatocellular carcinoma (HCC) cell lines: Huh7 and HepG2. For this purpose, the accumulation of LC3-II (Light Chain 3 phosphatidylethanolamine conjugate) in presence or absence of compound 2-3 was analyzed using immunoblot analysis of LC3-II.

Methods:

Cell Culture:

The HepG2 cell line was maintained in DMEM low glucose (Cat #21885025, ThermoFischer) containing 1% penicillin-streptomycin (Cat #P06-07100, Dutscher) and 10% FBS (Cat #SV30160.03C, Dutscher). The Huh7 cell line was maintained in DMEM high glucose (Cat #L0103-500, Dutscher) containing 1% penicillin-streptomycin (Cat #P06-07100, Dutscher) and 10% SVF (Cat #SV30160.03C, Dutscher). Cells lines were cultured at 37° C. with 5% CO$_2$.

Cell Plating:

The day before the experiment, 6-well plates with 250,000 cells for HepG2 and 310,000 cells for Huh7 in 1.8 mL of medium per well were prepared.

Test Items Preparation:

Compound 2-3 was dissolved with filtrated $H_2O$ mQ to make a 10 mM stock solution and serial working solutions (10× solutions) at 5 µM, 10 µM and 20 µM for HepG2 and at 4 µM, 8 µM and 16 µM for Huh7 were prepared with the diluent (=culture medium with 1.0% $H_2O$ mQ for HepG2 and with 1.6% for Huh7) to maintain a constant percentage of $H_2O$. Bafilomycin (CAS [88899-55-2], Cat #B1793-10UG, Sigma) was dissolved with DMSO to make a 160.6 µM stock solution and a working solution (200× solution) was prepared with the culture medium at 20.1 µM. A "Baf diluent" solution corresponding to the dilution of DMSO in the Bafilomycin 200× solution (culture medium with 12.5% DMSO) was also prepared.

Treatment with Test Items:

200 µL of compound 2-3 10× solutions (solutions at 5 µM, 10 µM, 20 µM for HepG2 treatments and at 4 µM, 8 µM and 16 µM for Huh7 treatments) or 200 µL of diluent (=0 µM condition) were dispensed in the appropriate wells (6 wells/condition). After cells treatment, 6-well plates were returned to incubator for 24 hours. Two hours before the end of incubation period, 10 µL of the Bafilomycin 200× solution or 10 µL of the "Baf diluent" solution were added for each condition of compound 2-3: 3 wells with Bafilomycin (Baf+) and 3 wells with the "Baf diluent" (Baf−).

Preparation of Cell Extracts:

After 4 hours and 24 hours of cells treatment, the medium was removed from each well. The cells were carefully rinsed with PBS (Cat #L0615-500, Dutscher) and detached with 500 µL per well of a trypsin solution. After 8 min of trypsin (Cat #L0930-100, Dutscher) at 37° C., 500 µL of medium was added per well and transferred to a 1.5 mL tube. Then, 1 mL of PBS was used to rinse each well and the corresponding solution was pooled in each corresponding 1.5 mL tube. Cell suspensions were centrifuged 5 min at 2,500 rpm at 4° C. At this time, for each condition of treatment, cell pellets were pooled in a 1.5 mL tube and centrifuged 5 min at 2,500 rpm at 4° C. Cell pellets were resuspended in 500 µL of PBS with a protease inhibitor cocktail (one tablet per 50 mL PBS) (Cat #4693132001, Sigma). Cell suspensions were centrifuged 5 min at 2,500 rpm at 4° C. Cell pellets were lysed with Mammalian Protein Extraction Buffer (Cat #28941279, GE Healtcare) with a protease inhibitor cocktail (Cat #4693132001, Sigma). Total protein concentration was assessed using the BCA reagent (Cat #23227, ThermoFischer) and cellular lysates were stored at −80° C. until western-blot analysis.

LC3-II Immunoblotting:

Proteins in cell lysates (10 µg of total proteins) prepared with 4× loading buffer were separated using 15% SDS-PAGE gel. LC3-II immunoblotting analysis was realized using rabbit anti-LC3B (1/3000, Cat #L7543, Sigma-Aldrich) and goat anti-rabbit (1/40,000, Cat #111-035-003 Jackson Immunoresearch) antibodies. GAPDH (Glyceraldehyde-3-Phosphate Dehydrogenase) immunoblotting (mouse anti-GAPDH (1/5000, H00002597-M01, Abnova) and goat anti-mouse (1/40,000, Cat #115-035-003, Jackson Immunoresearch) was used as a loading control. The normalized LC3-II levels (LC3-II signal/GAPDH signal ratios) were determined using ImageJ software (NIH software, USA). The cellular autophagic flux was determined as the ratio between the normalized LC3-II levels with Bafilomycin (Baf+) and without Bafilomycin (Baf−) and was expressed in an arbitrary unit. The experiment was repeated at least twice and representative autoradiograms are shown in FIG. 4.

Results:

The results showed in FIG. 4 demonstrate that compound 2-3 significantly induced, in a dose-dependent manner, an accumulation of the LC3-II form in both treated cell lines (HepG2 and Huh7) after 4 hours and 24 hours of treatment (FIG. 4). Enhanced LC3-II levels can be associated either with increased autophagosome synthesis or with decreased autophagosome turnover. However, compound 2-3-induced accumulation of LC3-II being not enhanced in the presence of Bafilomycin, a late stage autophagy inhibitor, (FIG. 4, comparison of lane with Bafilomycin (Baf+) with lane without Bafilomycin (Baf−)), supported that compound 2-3 inhibited the degradation of the cellular autophagic contents, which means that compound 2-3 is an inhibitor of the autophagy flux in cellulo in the HepG2 and Huh7 cell lines.

Example 27: Inhibition of the Autophagy Flux in RBE Cell Line by Compound 2-2

The capacity of compound 2-2 to modulate the cellular autophagy processes was also evaluated in the intrahepatic cholangiocarcinoma cell line RBE.

Methods:

Cell Culture:

The RBE cell line was maintained in RPMI (Roswell Park Memorial Institute) 1640 (Cat #L0498-500, Dutscher) containing 1% penicillin-streptomycin (Cat #P06-07100, Dutscher) and 10% FBS (Cat #SV30160.03C, Dutscher). RBE Cells line were cultured at 37° C. with 5% $CO_2$.

Cell Plating:

The day before the experiment, 6-well plates with 125,000 cells in 1.8 mL of medium per well were prepared.

Test Items Preparation:

Compound 2-2 was dissolved with filtrated DMSO to make a 10 mM stock solution and serial working solutions (10× solutions) at 9 µM, 18 µM and 36 µM were prepared with the diluent (=culture medium with 0.12% DMSO) to maintain a constant percentage of DMSO. Bafilomycin [CAS 88899-55-2] (Cat #B1793-10UG, Sigma) was dissolved with DMSO to make a 160.6 µM stock solution and a working solution (200× solution) was prepared with the culture medium at 20.1 µM. A "Baf diluent" solution corresponding to the dilution of DMSO in the Bafilomycin 200× solution (culture medium with 12.5% DMSO) is also prepared.

Treatment with Test Items

200 µL of compound 2-2 10× solutions (solutions at 9, 18 and 36 µM for 24 hours of treatment) or 200 µL of diluent (=0 µM condition) were dispensed in the appropriate wells (6 wells/condition). After cells treatment, 6-well plates were returned to incubator for 24 hours. Two hours before the end of incubation period, 10 µL of the Bafilomycin 200× solution or 10 µL of the "Baf diluent" solution were added for each condition of compound 2-2: 3 wells with Bafilomycin (Baf+) and 3 wells with the "Baf diluent" (Baf−).

Preparation of Cell Extracts:

After 24 hours of cell line treatment, the medium was removed from each well. The cells were carefully rinsed with PBS (Cat #L0615-500, Dutscher) and detached with 500 µL per well of a trypsin solution. After 8 min of trypsin (Cat #L0930-100, Dutscher) at 37° C., 500 µL of medium was added per well and transferred to a 1.5 mL tube. Then, 1 mL of PBS was used to rinse each well and the resulting solution was pooled in each corresponding 1.5 mL tube. Cell suspensions were centrifuged 5 min at 2,500 rpm at 4° C. At this time, for each condition of treatment, cell pellets were pooled in a 1.5 mL tube and centrifuged 5 min at 2,500 rpm at 4° C. Pellets were resuspended in 500 μL of PBS with a protease inhibitor cocktail (one tablet per 50 mL PBS, Cat #4693132001, Sigma). Cell suspensions were centrifuged 5 min at 2,500 rpm at 4° C. Then, cell pellets were lysed with Mammalian Protein Extraction Buffer (Cat #28941279, GE Healtcare) with a protease inhibitor cocktail (Cat #4693132001, Sigma). Total protein concentration was assessed using the BCA reagent (Cat #23227, ThermoFischer) and cellular lysates were stored at −80° C. until western-blot analysis.

LC3-II Immunoblotting:

Proteins in cell lysates (10 μg of total proteins) prepared with 4× loading buffer were separated using 15% SDS-PAGE gel. LC3-II immunoblotting analysis was realized using rabbit anti-LC3B (1/3000, Cat #L7543, Sigma-Aldrich) and goat anti-rabbit (1/40,000, Cat #111-035-003 Jackson Immunoresearch) antibodies. GAPDH immunoblotting (mouse anti-GAPDH (1/5000, H00002597-M01, Abnova) and goat anti-mouse (1/40,000, Cat #115-035-003, Jackson Immunoresearch) was used as a loading control. The normalized LC3-II levels (LC3-II signal/GAPDH signal ratios) were determined using ImageJ software (NIH software, USA). The cellular autophagic flux was determined as the ratio between the normalized LC3-II levels with Bafilomycin (Baf+) and without Bafilomycin (Baf−) and was expressed in an arbitrary unit. The experiment was repeated at least twice and the representative autoradiogram is presented in FIG. 5.

Results:

The results showed in FIG. 5 demonstrate that compound 2-2 significantly induced a dose-dependent accumulation of the LC3-II form after 24 hours of RBE cell line treatment. As demonstrated with Huh7 and HepG2 cell lines (example 25), compound 2-2 induced an accumulation of LC3-II in RBE cell line which was not enhanced in the presence of Bafilomycin (FIG. 5, comparison of lane with Bafilomycin (Baf+) with lane without Bafilomycin (Baf−)), supporting that compound 2-2 inhibited the degradation of the autophagic contents in RBE cell line. These results demonstrate that compound 2-2 induced an inhibition of the autophagic flux in cellulo in RBE cell line.

Example 28: Inhibition of the Autophagy Flux in HepG2 and Huh7 Cell Lines by Compound 5-2

The inhibition of the autophagic flux was also investigated with compound 5-2 in HepG2 and Huh7 cell lines. The general procedures were the same as previously described in Example 25.

Methods:

Cell Culture:

The HepG2 cell line was maintained in DMEM low glucose (Cat #21885025, ThermoFischer) containing 1% penicillin-streptomycin (Cat #P06-07100, Dutscher) and 10% FBS (Cat #SV30160.03C, Dutscher). The Huh7 cell line was maintained in DMEM high glucose (Cat #L0103-500, Dutscher) containing 1% penicillin-streptomycin (Cat #P06-07100, Dutscher) and 10% SVF (Cat #SV30160.03C, Dutscher). Cells were cultured at 37° C. with 5% $CO_2$.

Cell Plating:

The day before the experiment, 6-well plates with 250,000 cells for HepG2 and 310,000 cells for Huh7 in 1.8 mL of medium per well were prepared.

Test Items Preparation:

Compound 5-2 was dissolved with filtrated $H_2O$ mQ to make a 10 mM stock solution and serial working solutions (10× solutions) at 5 μM, 10 μM and 20 μM for HepG2 and at 4 μM, 8 μM and 16 μM for Huh7 were prepared with the diluent (=culture medium with 1% $H_2O$ mQ for HepG2 and with 1.6% $H_2O$ mQ for Huh7) to maintain a constant percentage of $H_2O$. Bafilomycin (Cat #B1793-10UG, Sigma) was dissolved with DMSO to make a 160.6 μM stock solution and a working solution (200× solution) was prepared with the culture medium at 20.1 μM. A "Baf diluent" solution corresponding to the dilution of DMSO in the Bafilomycin 200× solution (culture medium with 12.5% DMSO) was also prepared.

Treatment with Test Items:

200 μL of compound 5-2 10× solutions (solutions at 5 μM, 10 μM, 20 μM for HepG2 and at 4 μM, 8 μM and 16 μM for Huh7) or 200 μL of diluent (=0 μM condition) were dispensed in the appropriate wells (6 wells/condition). After treatment, 6-well plates were returned to incubator for 24 hours. Two hours before the end of incubation period, 10 μL of the Bafilomycin 200× solution or 10 μL of the "Baf diluent" solution were added for each condition of compound 5-2: 3 wells with Bafilomycin (Baf+) and 3 wells with the "Baf diluent" (Baf−).

Preparation of Cell Extracts:

After 24 hours of cells treatment, the medium was removed from each well. The cells were carefully rinsed with PBS (Cat #L0615-500, Dutscher) and detached with 500 μL per well of a trypsin solution. After 8 min of trypsin (Cat #L0930-100, Dutscher) at 37° C., 500 μL of medium was added per well and transferred to a 1.5 mL tube. Then, 1 mL of PBS was used to rinse each well and the resulting solution was pooled in each corresponding 1.5 mL tube. Cell suspensions were centrifuged 5 min at 2,500 rpm at 4° C. At this time, for each condition of treatment, cell pellets were pooled in a 1.5 mL tube and centrifuged 5 min at 2,500 rpm at 4° C. Pellets were resuspended in 500 μL of PBS with a protease inhibitor cocktail (one tablet per 50 mL PBS, Cat #4693132001, Sigma). Cell suspensions were centrifuged 5 min at 2,500 rpm at 4° C. Cell pellets were then lysed with Mammalian Protein Extraction Buffer (Cat #28941279, GE Healtcare) with a protease inhibitor cocktail. Total protein concentration was assessed using the BCA reagent (Cat #23227, ThermoFischer) and cellular lysates were stored at −80° C. until western-blot analysis.

LC3-II Immunoblotting:

Proteins in cell lysates (10 μg of total proteins) prepared with 4× loading buffer were separated using 15% SDS-PAGE gel. LC3-II immunoblotting analysis was realized using rabbit anti-LC3B (1/3000, Cat #L7543, Sigma-Aldrich) and goat anti-rabbit (1/40,000, Cat #111-035-003 Jackson Immunoresearch) antibodies. GAPDH immunoblotting (mouse anti-GAPDH 1/5000, Cat #H00002597-M01, Abnova and goat anti-mouse 1/40,000, Cat #115-035-003, Jackson Immunoresearch) was used as a loading control. The normalized LC3-II levels (LC3-II signal/GAPDH signal ratios) were determined using ImageJ software (NIH software, USA). The cellular autophagic flux was determined as the ratio between the normalized LC3-II levels with Bafilomycin (Baf+) and without Bafilomycin (Baf−) and was expressed in an arbitrary unit. The experiment was repeated at least twice and representative autoradiograms are presented in FIG. 6.

Results:

The results shown in FIG. 6 demonstrate that compound 5-2 significantly induced, in a dose-dependent manner, an accumulation of the LC3-II form in both treated cell lines (HepG2 and Huh7) after 24 hours of treatment (FIG. 6). Enhanced LC3-II levels can be associated either with increased autophagosome synthesis or with decreased autophagosome turnover. However, compound 5-2 induced accumulation of LC3-II being not enhanced in the presence of Bafilomycin (FIG. 6, comparison of lane without Bafilomycin (Baf−) with lane with Bafilomycin (Baf+)) supported that compound 5-2 inhibited the degradation of the cellular autophagic contents. Therefore, these data demonstrate that compound 5-2 is an inhibitor of the autophagy flux in cellulo in HepG2 and Huh7 cellular environment.

Example 29: In Vivo Anti-Fibrotic Activity of Compounds 2-2, 2-3 and 5-3 Using Diethyl Nitrosamine (DEN) Induced Cirrhosis in Rat Animal Model In vivo, compound 5-3, compound 2-2 and compound 2-3 (hydrochloride salt form of compound 2-2) demonstrated an liver anti-fibrotic activity as demonstrated in a diethyl nitrosamine (DEN) cirrhotic rat model of liver fibrosis. This animal model allows developing an extensive liver fibrosis, leading to a compensated liver cirrhosis with a multifocal hepatocarcinoma (HCC) after 14 weeks of induction (Schiffer, E. et al. *Hepatology* 2005 (41), 307-314). The DEN cirrhotic rat animal model was used here as a specific animal model of liver fibrosis.

In Vivo Assessment of Anti-Fibrotic Activity of Compound 2-3 Alone or in Combination with Sorafenib:
Methods:
Forty two Fisher 344 male rat (obtained from Charles River Laboratories France, including spare animals), weighting approximately 280 g at the start of the study, were randomized in 5 groups of 8 (groups 1, 2, 3 and 5) or 6 (group 4) animals and housed with 3 animals per cage, given free access to food and water and allowed to acclimate for at least 5 days prior to test initiation.

The DEN cirrhotic rat model was obtained after 14 weekly intraperitoneal injections of DEN (intra-peritoneal injections (i.p.) of DEN at 50 mg/kg/week). The animals were then treated according to Table 9 during 6 weeks. In this in vivo experiment, the anti-fibrotic activity of compound 2-3 was evaluated in liver fibrosis animal model, alone or in combination with Sorafenib (a multikinase inhibitor of Raf-1, B-Raf, VEGFR-2, VEGFR3, PDGFRβ, Flt3 and c-Kit). After 6 weeks of treatment, all animals were sacrificed using $CO_2$ and rat livers were collected for analysis. The quantification of the liver fibrotic tissue was evaluated by Sirius red staining of rat liver sections.

Study Design:
The study design is described in table 1, briefly:
Group 1 contained 8 animals which were daily dosed (q.d.) by oral gavage (per os, p.o.) with the vehicle during 6 weeks.

Group 2 contained 8 animals which were daily dosed (q.d.) by oral gavage (per os, p.o.) with Sorafenib at 10 mg/kg/day during 6 weeks.

Group 3 contained 8 animals which were daily dosed (q.d.) by oral gavage (per os, p.o.) with compound 2-3 at 15 mg/kg/day during 6 weeks.

Group 4 contained 6 animals which were daily dosed (q.d.) by oral gavage (per os, p.o.) with compound 2-3 at 15 mg/kg/day in combination with Sorafenib at 10 mg/kg/day during 6 weeks.

Group 5 contained 8 animals which were daily dosed (q.d.) by oral gavage (per os, p.o.) with compound 2-3 at 30 mg/kg/day during 6 weeks.

TABLE 9

Study 1, Design of DEN-induced cirrhosis in rats

| Group | Treatment[a] | Number of animals | Route[b] |
|---|---|---|---|
| 1 | Vehicle | 8 | p.o |
| 2 | Sorafenib 10 mg/kg/day | 8 | p.o. |
| 3 | Compound 2-3 15 mg/kg/day | 8 | p.o. |
| 4 | Compound 2-3 15 mg/kg/day + Sorafenib 10 mg/kg/day | 6 | p.o. |
| 5 | Compound 2-3 30 mg/kg/day | 8 | p.o. |

[a]all animals from groups 1, 2, 3, 4 and 5 were treated once daily (q.d.) during 6 weeks.
[b]p.o. per os (gavage).

Oral Formulation:
Sorafenib and compound 2-3 were administered p.o. (gavage) once daily. Sorafenib was formulated by dissolving the sugar coating of the 200 mg tablet in DMSO (200 mg Sorafenib tosylate tablet, Nexavar®). A sorafenib emulsion was prepared by mixing with 1 mL of poly-oxyl castor oil (Cremophor® EL, Sigma-Aldrich) and 1 mL of 95% ethanol per tablet. The resulting emulsion was diluted in purified water to obtain a solution of Sorafenib suitable for oral gavage. Compound 2-3 (group 3 and 5) were formulated in water for injection. Combination of compound 2-3+Sorafenib (group 4) was prepared by mixing the same volume of single drug formulation just before oral gavage. The vehicle for the control group (group 1) was water for injection.

Results: (See FIG. 7)
The quantification of the liver fibrotic tissue, by Sirius red staining, showed that the area of liver fibrosis (collagen fibers) was significantly reduced in groups 3 and 5 (p=0.0467 and 0.0121, respectively) compared to the control group (group 1). The strongest effect was observed in the combination therapy group (group 4), where the compound 2-3 was administered in combination with Sorafenib. The combination therapy administered in group 4 (compound 2-3+Sorafenib) showed a liver fibrosis reduction significantly higher than those observed in the control group (group 1), or when Sorafenib (group 2) was administered in monotherapy (p=0.0013 and 0.0170, respectively, (FIG. 7). Quantitatively compared to the control group (group 1), the level of collagen fibers deposition in DEN cirrhotic rat model was reduced by 13.6% in the group 2 (Sorafenib), by 41.0% (p<0.05) in the group 3 (compound 2-3), by 60.7% (p=0.001) in group 4 (Sorafenib+compound 2-3) and by 45.3% (p=0.01) in group 5 (compound 2-3, 30 mg/kg).

In Vivo Assessment of Anti-Fibrotic Activity of Compounds 2-2 and 5-3:
Methods:
A second in vivo experiment, with the same diethyl nitrosamine (DEN) cirrhotic rat animal model of liver fibrosis, was performed including compound 2-2 (base form of compound 2-3) with discontinued oral dosing schedule and compound 5-3 with daily oral exposure. Compounds 2-2 and 5-3 were administered p.o. by gavage (oral gavage) once daily during 7 weeks.

Rats were treated with DEN for 13 weeks (intra-peritoneal injections (i.p.) of 50 mg/kg/week) and then treated according to the Table 10 dosage schedule during 7 weeks. At the end of the study, all animals were sacrificed using $CO_2$ and rat livers were collected for analysis. The quantification of the liver fibrotic tissue was evaluated by Sirius red staining of rat liver sections.

Study Design:

The study design is described in table 2, briefly:

Group 1 contained 6 animals which were daily dosed (q.d.) by oral gavage (per os, p.o.) with the vehicle during 7 weeks.

Group 2 contained 8 animals and the corresponding animals were daily dosed (q.d.) by oral gavage (per os, p.o.) with compound 2-2 during 4 weeks at 20 mg/kg/day and then during 3 weeks at 20 mg/kg every 2 days (q.o.d.: quaque altera die, one day treated, on day untreated).

Group 3 contained 8 animals and the corresponding animals were daily dosed (q.d.) by oral gavage (per os, p.o.) with compound 2-2 during 3 weeks at 20 mg/kg/day, then 2 weeks of treatment free period, and were then daily dosed (q.d.) by oral gavage (per os, p.o.) with compound 2-2 during 2 weeks at 20 mg/kg/day.

Group 4 contained 8 animals and the corresponding animals were daily dosed (q.d.) by oral gavage (per os, p.o.) with compound 5-3 during 4 weeks at 20 mg/kg/day, and were then daily dosed (q.d.) by oral gavage (per os, p.o.) with compound 5-3 during 3 weeks at 15 mg/kg/day.

was statistically significant ($p<0.05$) for all treated groups compared to the control group (see FIG. 9).

CONCLUSION

These in vivo studies (described in example 29) performed with diethyl nitrosamine (DEN) cirrhotic rat animal model of liver fibrosis, allowed to demonstrate that compounds 2-2 and 2-3 (hydrochloride salt form of compound 2-2) and compound 5-3 reduced significantly in vivo the liver fibrosis. These anti-fibrotic in vivo data validated the rational of this disclosure based on in cellulo data described firstly in examples 25, 26, 27 and 28 which showed that compounds described herein were potent inhibitors of the autophagy flux and cathepsins B, D and/or L proteolytic activity.

These in vivo studies demonstrated that compounds described herein are able to decrease in severity the liver cirrhosis or liver pre-cirrhosis lesion and allowed reduction in the rate of liver fibrosis progression and therefore reduce the risk of hepatocellular carcinoma, decompensated cirrhosis and/or improve liver function and morphology. As demonstrated herein, in subjects with liver cirrhosis or liver

TABLE 10

Study 2, Design of DEN-induced cirrhotic rats

| Group | Group Name[a] | N | Test Item | Route[b] | Dose level (mg/kg) | Remark |
|---|---|---|---|---|---|---|
| 1 | Control | 6 | Vehicle | p.o. | 0 | q.d. administration |
| 2 | 2-2 $20^{qd/qod}$ | 8 | Compound 2-2 | p.o. | 20 | On the 29th day of treatment, switch q.d. to q.o.d schedule |
| 3 | 2-2 $20^{3WON/2WOFF/2WON}$ | 8 | Compound 2-2 | p.o. | 20 | q.d. for 3 weeks, then 2 weeks off then q.d. for 2 weeks |
| 4 | 5-3 20/15 | 8 | Compound 5-3 | p.o. | 20 then 15 from day 29 to the end of the study | On the 29th day of treatment 25% decrease in dose |

[a]Group 1 "Control" rats were treated once daily (q.d.: quaque die) with vehicle. Group 2 "2-2 $20^{qd/qod}$" rats were treated with compound 2-2 from day 1 to 28 (4 weeks) by daily oral gavage (q.d.) at 20 mg/kg and then at 20 mg/kg every 2 days (q.o.d.: quaque altera die, one day treated, on day untreated) during 3 weeks. Group 3 "2-2 $20^{3WON/2WOFF/2WON}$" rats were treated with compound 2-2 at 20 mg/kg for 3 weeks by daily oral gavage (q.d.), followed by 2 weeks of treatment free period and then treated with compound 2-2 at 20 mg/kg for 2 weeks by daily oral gavage (q.d.). Group 4 "5-3 20/15" rats were treated with compound 5-3 at 20 mg/kg from day 1 to 28 (4 weeks) by p.o. (gavage) q.d. and then from day 29 to the end of the study (3 weeks) by daily oral gavage (q.d.) at 15 mg/kg.
[b]p.o. per os.

Oral Formulation:

Compound 2-2 and 5-3 were formulated in water for injection acidified with hydrochloric acid to pH 4.

Results:

As shown in FIG. 8, fibrotic area was significantly reduced in groups treated by compounds 2-2 and 5-3: Group 2: 2-2 $20^{qd/qod}$, Group 3: 2-2 $20^{3WON/2WOFF/2WON}$ and Group 4: 5-3 20/15 compared to the control group (Group 1). In the groups treated with compounds 2-2 and 5-3 (group 2, 3, and 4), the liver slices showed that the area of fibrosis was significantly reduced compare to the control group (see FIG. 8).

FIG. 9 shows the quantitative analysis of Sirius red staining of liver slices obtained from rats treated in group 1, 2, 3 and 4 (see FIG. 8). The decrease in deposition of extracellular matrix proteins including collagen fibers was quantitatively and significantly decreased in all 2-2 or 5-3 treated groups (group 2, 3 and 4) versus the control group (group 1). Compared to the control group (group 1), the level of collagen fibers deposition in DEN cirrhotic rat model was reduced by 23% (p=0.04) in the group 2 (compound 2-2), by 29% (p=0.01) in the group 3 (compound 2-2), and by 24% (p=0.03) in group 4 (compound 5-3). The decrease of collagen fibers deposition quantified in Sirius red staining pre-cirrhosis lesions, administration of a therapeutically effective amount of a compound described herein and/or administration of a combination therapy including at least one compound described herein with at least one additional active agent results in decreases liver fibrosis and related diseases and progression.

Since the compounds described herein decrease the deposition rate of extracellular matrix components including collagen fibers, compounds described herein are claimed with anti-fibrotic activity in vivo including human being or animal in need thereof for treating and/or preventing pathological fibrosis of various organs and tissues including but not limited to pulmonary fibrosis, liver fibrosis, heart fibrosis, kidney fibrosis, eyes fibrosis, prostate fibrosis and peritoneum membrane fibrosis.

While the foregoing specification teaches the principles of the present disclosure, with examples provided for the purpose of illustration, it will be understood that the practice of the invention encompasses all of the usual variations, adaptations and/or modifications as come within the scope of the following claims and their equivalents. All references cited herein are incorporated by reference in their entirety for all purposes.

The invention claimed is:
1. A method for treating, decreasing the severity and/or progression of fibrosis, or treating, decreasing the severity and/or progression of autophagy, comprising administering to a patient in need of treatment thereof an effective amount of a compound of Formula (I), with the proviso that the method is not treating any form of cancer

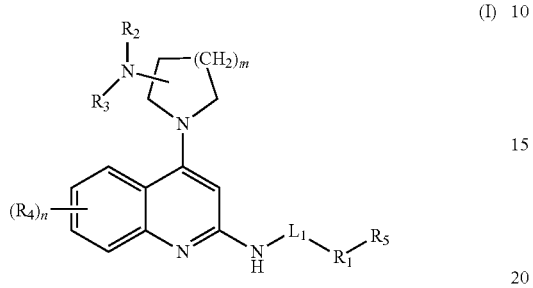

(I)

wherein
$L_1$ is selected from the group consisting of a single bond; optionally substituted alkyl, said optionally substituted alkyl being or not further substituted by at least one $R_6$; optionally substituted cycloalkyl; optionally substituted alkenyl; optionally substituted cycloalkenyl; optionally substituted alkynyl; optionally substituted cycloalkynyl; —C=O; —SO; —SO$_2$; —(C=O)—NR$_8$; —(C=O)—O; —(C=O)—O-alkyl; —SO$_2$—NR$_8$; and —NR$_8$, $R_1$ is an optionally substituted aryl, said optionally substituted aryl being or not further substituted by at least one $R_9$; or an optionally substituted heteroaryl, said optionally substituted heteroaryl being or not further substituted by at least one $R_9$, $R_2$ and $R_3$ are independently selected from the group consisting of hydrogen; —(CO)—R$_7$; —(CO)—O—R$_7$; —(CO)—NR$_8$OH; —(CO)—NR$_{12}$OH; —(CO)—NR$_8$R$_{8'}$; —(CO)—NR$_{12}$R$_{13}$; —SO$_2$—R$_7$; —SO$_2$—NR$_8$R$_{8'}$; —SO$_2$—NR$_{12}$R$_{13}$; optionally substituted alkyl; optionally substituted cycloalkyl; optionally substituted alkenyl; optionally substituted alkynyl; optionally substituted cycloalkenyl; optionally substituted cycloalkynyl; optionally substituted aryl; optionally substituted benzyl; optionally substituted heteroaryl; optionally substituted heterocyclyl; or $R_2$ and $R_3$ can be linked together with nitrogen to which they are covalently linked to form an optionally substituted heterocyclyl, $R_2'$ is selected from the group consisting of hydrogen; optionally substituted alkyl; optionally substituted alkenyl; optionally substituted alkynyl; optionally substituted cycloalkyl; optionally substituted cycloalkenyl; and optionally substituted cycloalkynyl; optionally substituted heterocyclyl, $R_4$ is, alone or simultaneously or independently when n>1, selected from the group consisting of hydrogen; halogen; optionally substituted alkyl; optionally substituted alkenyl; optionally substituted alkynyl; optionally substituted cycloalkyl; optionally substituted cycloalkenyl; optionally substituted cycloalkynyl; optionally substituted alkoxy; hydroxyl; nitro; azido; cyano; —NR$_{12}$R$_{13}$; —NR$_8$R$_{8'}$; —O—(R$_7$); —(CO)—R$_7$; —(CO)—O—R$_7$; —(CO)—NR$_{12}$OH; —(CO)—NR$_8$OH; —(CO)—NR$_{12}$R$_{13}$; —(CO)—NR$_8$R$_{8'}$; —O—(CO)—R$_7$; —O—(CO)—NR$_{12}$R$_{13}$; —O—(CO)—NR$_8$R$_{8'}$; —NR$_8$—(CO)—R$_7$; —NR$_{12}$—(CO)—R$_7$; —NR$_{12}$—(CO)—OR$_7$; —NR$_8$—(CO)—OR$_7$; —O—(CO)—OR$_7$; —NR$_{12}$—(CO)—NR$_{12}$R$_{13}$; —NR$_8$—(CO)—NR$_8$R$_{8'}$; —(O—CH$_2$CH$_2$)$_p$—OR$_{12}$; —(O—CH$_2$CH$_2$)$_p$—OR$_7$; —(O—CH$_2$CH$_2$)$_p$—NR$_{12}$R$_{13}$; —(O—CH$_2$CH$_2$)$_p$—NR$_8$R$_{8'}$; —NR$_{12}$—(CH$_2$CH$_2$—O)$_p$—R$_{13}$; —NR$_8$—(CH$_2$CH$_2$—O)$_p$—R$_7$; —SO$_2$—R$_7$; —NR$_{12}$—SO$_2$—R$_7$; —NR$_8$—SO$_2$—R$_7$; —SO$_2$—NR$_{12}$R$_{13}$; —SO$_2$—NR$_8$R$_{8'}$; —NR$_{12}$—SO$_2$—NR$_{12}$R$_{13}$; —NR$_8$—SO$_2$—NR$_8$R$_{8'}$; —NR$_{12}$—(C$_2$-C$_8$)-alkyl-NR$_{12}$R$_{13}$; —NR$_8$—(C$_2$-C$_8$)-alkyl-NR$_8$R$_{8'}$; —NR$_{12}$—(C$_2$-C$_8$)-alkyl-OR$_{13}$; —NR$_8$—(C$_2$-C$_8$)-alkyl-OR$_7$, optionally substituted aryl; optionally substituted heteroaryl; and optionally substituted heterocyclyl, $R_5$ is selected from the group consisting of hydrogen; halogen; hydroxyl; optionally substituted alkoxy; —NR$_2'$R$_{10}$; —O—R$_{10}$; nitro; azido; cyano; —NR$_{12}$R$_{13}$; —NR$_8$R$_{8'}$; —(CO)—R$_7$; —(CO)—O—R$_7$; —(CO)—NR$_{12}$OH; —(CO)—NR$_8$OH; —(CO)—NR$_{12}$R$_{13}$; —(CO)—NR$_8$R$_{8'}$; —O—(CO)—R$_7$; —O—(CO)—NR$_{12}$R$_{13}$; —O—(CO)—NR$_8$R$_{8'}$; —NR$_{12}$—(CO)—R$_7$; —NR$_8$—(CO)—R$_7$; —NR$_{12}$—(CO)—OR$_7$; —NR$_8$—(CO)—OR$_7$; —O—(CO)—OR$_7$; —NR$_{12}$—(CO)—NR$_{12}$R$_{13}$; —NR$_8$—(CO)—NR$_8$R$_{8'}$; —SO$_2$—R$_7$; —NR$_{12}$—SO$_2$—R$_7$; —NR$_8$—SO$_2$—R$_7$; —SO$_2$—NR$_{12}$R$_{13}$; —SO$_2$—NR$_8$R$_{8'}$; —NR$_{12}$—SO$_2$—NR$_{12}$R$_{13}$; —NR$_8$—SO$_2$—NR$_8$R$_{8'}$; —NR$_{12}$—(C$_2$-C$_{10}$)-alkyl-NR$_{12}$R$_{13}$; —NR$_8$—(C$_2$-C$_{10}$)-alkyl-NR$_8$R$_{8'}$; —NR$_{12}$—(C$_2$-C$_{10}$)-alkyl-OR$_{13}$; —NR$_8$—(C$_2$-C$_{10}$)-alkyl-OR$_7$; —O(R$_7$); —(O—CH$_2$CH$_2$)$_p$—OR$_{12}$; —(O—CH$_2$CH$_2$)$_p$—OR$_7$; —(O—CH$_2$CH$_2$)$_p$—NR$_{12}$R$_{13}$; —(O—CH$_2$CH$_2$)$_p$—NR$_8$R$_{8'}$; —NR$_{12}$—(CH$_2$CH$_2$—O)$_p$—R$_{13}$; —NR$_8$—(CH$_2$CH$_2$—O)$_p$—R$_7$; optionally substituted alkyl; optionally substituted alkenyl; optionally substituted alkynyl; optionally substituted cycloalkyl; optionally substituted cycloalkenyl; optionally substituted cycloalkynyl; optionally substituted alkoxy; optionally substituted aryl; optionally substituted heteroaryl; and optionally substituted heterocyclyl, $R_6$ is simultaneously or independently selected from the group consisting of hydrogen atom; optionally substituted alkyl; optionally substituted alkenyl; optionally substituted alkynyl; optionally substituted cycloalkyl; optionally substituted cycloalkenyl; optionally substituted cycloalkynyl; optionally substituted aryl; optionally substituted heteroaryl; optionally substituted heterocyclyl; and optionally substituted alkoxy, $R_7$ is selected from the group consisting of hydrogen; optionally substituted alkyl; optionally substituted alkenyl; optionally substituted alkynyl; optionally substituted cycloalkyl; optionally substituted cycloalkenyl; optionally substituted cycloalkynyl; optionally substituted aryl; optionally substituted heteroaryl; and optionally substituted heterocyclyl, $R_8$ and $R_{8'}$ are simultaneously or independently selected from the group consisting of hydrogen; optionally substituted alkyl; optionally substituted alkenyl; optionally substituted alkynyl; optionally substituted cycloalkyl; optionally substituted cycloalkenyl; optionally substituted cycloalkynyl; optionally substituted heterocyclyl; optionally substituted aryl; and optionally substituted heteroaryl; or $R_8$ and $R_{8'}$ are linked together with nitrogen to which they are covalently linked to form an optionally substituted heterocyclyl group, $R_9$ is simultaneously or independently selected from the group consisting of hydrogen; halogen; hydroxyl; —$NR_2'R_{10}$; —O—$R_{10}$; nitro; azido; cyano; —$NR_{12}R_{13}$; —$NR_8R_{8'}$; —(CO)—$R_7$; —(CO)—O—$R_7$; —(CO)—$NR_{12}$OH; —(CO)—$NR_8$OH; —(CO)—$NR_{12}R_{13}$; —(CO)—$NR_8R_{8'}$; —O—(CO)—$R_7$; —O—(CO)—$NR_{12}R_{13}$; —O—(CO)—$NR_8R_{8'}$; —$NR_{12}$—(CO)—$R_7$; —$NR_8$—(CO)—$R_7$; —$NR_{12}$—(CO)—$OR_7$; —$NR_8$—(CO)—$OR_7$; —O—(CO)—$OR_7$; —$NR_{12}$—(CO)—$NR_{12}R_{13}$; —$NR_8$—(CO)—$NR_8R_{8'}$; —$SO_2$—$R_7$; —$NR_{12}$—$SO_2$—$R_7$; —$NR_8$—$SO_2$—$R_7$; —$SO_2$—$NR_{12}R_{13}$; —$SO_2$—$NR_8R_{8'}$; —$NR_{12}$—$SO_2$—$NR_{12}R_{13}$; —$NR_8$—$SO_2$—$NR_8R_{8'}$; —$NR_{12}$—($C_2$-$C_{10}$)-alkyl-$NR_{12}R_{13}$; —$NR_8$—($C_2$-$C_{10}$)-alkyl-$NR_8R_{8'}$; —$NR_{12}$—($C_2$-$C_{10}$)-alkyl-$OR_{13}$; —$NR_8$—($C_2$-$C_{10}$)-alkyl-$OR_7$; —$O(R_7)$; —(O—$CH_2CH_2$)$_p$—$OR_{12}$; —(O—$CH_2CH_2$)$_p$—$OR_7$; —(O—$CH_2CH_2$)$_p$—$NR_{12}R_{13}$; —(O—$CH_2CH_2$)$_p$—$NR_8R_{8'}$; —$NR_{12}$—($CH_2CH_2$—O)$_p$—$R_{13}$; —$NR_8$—($CH_2CH_2$—O)$_p$—$R_7$; optionally substituted alkyl; optionally substituted alkenyl; optionally substituted alkynyl; optionally substituted cycloalkyl; optionally substituted cycloalkenyl; optionally substituted cycloalkynyl; optionally substituted alkoxy; optionally substituted aryl; optionally substituted heteroaryl; and optionally substituted heterocyclyl, $R_{10}$ is selected from the group consisting of hydrogen; optionally substituted aryl said optionally substituted aryl being or not further substituted by one or more $R_{11}$; optionally substituted heteroaryl said optionally substituted heteroaryl being or not further substituted by one or more $R_{11}$; optionally substituted heterocyclyl, said optionally substituted heterocyclyl group being or not further substituted by one or more $R_{11}$, $R_{11}$ is simultaneously or independently selected from the group consisting of hydrogen; halogen; optionally substituted alkoxy; hydroxyl; nitro; cyano; azido; —$NR_{12}R_{13}$; —$NR_8R_{8'}$; —O—$(R_8)$; —(CO)—$R_8$; —(CO)—O—$R_8$; —(CO)—$NR_{12}$OH; —(CO)—$NR_8$OH; —(CO)—$NR_{12}R_{13}$; —(CO)—$NR_8R_{8'}$; —O—(CO)—$R_8$; —O—(CO)—$NR_{12}R_{13}$; —O—(CO)—$NR_8R_{8'}$; —$NR_{12}$—(CO)—$R_8$; —$NR_8$—(CO)—$R_8$; —$NR_{12}$—(CO)—$OR_8$; —$NR_8$—(CO)—$OR_8$; —O—(CO)—$OR_8$; —$NR_{12}$—(CO)—$NR_{12}R_{13}$; —$NR_8$—(CO)—$NR_8R_{8'}$; —(O—$CH_2CH_2$)$_p$—$OR_{12}$; —(O—$CH_2CH_2$)$_p$—$OR_8$; —(O—$CH_2CH_2$)$_p$—$NR_{12}R_{13}$; —(O—$CH_2CH_2$)$_p$—$NR_8R_{8'}$; —$NR_{12}$(—$CH_2CH_2$—O)$_p$—$R_{13}$; —$NR_8$(—$CH_2CH_2$—O)$_p$—$R_8$; —$SO_2$—$R_8$; —$NR_{12}$—$SO_2$—$R_8$; —$NR_8$—$SO_2$—$R_8$; —$SO_2$—$NR_{12}R_{13}$; —$SO_2$—$NR_8R_{8'}$; —$NR_{12}$—$SO_2$—$NR_{12}R_{13}$; —$NR_8$—$SO_2$—$NR_8R_{8'}$; —$NR_{12}$—($C_2$-$C_8$)-alkyl-$NR_{12}R_{13}$; —$NR_8$—($C_2$-$C_8$)-alkyl-$NR_8R_{8'}$; —$NR_{12}$—($C_2$-$C_8$)-alkyl-$OR_{13}$; —$NR_8$—($C_2$-$C_8$)-alkyl-$OR_8$; optionally substituted alkyl; optionally substituted alkenyl; optionally substituted alkynyl; optionally substituted cycloalkyl; optionally substituted cycloalkenyl; optionally substituted cycloalkynyl; optionally substituted aryl; optionally substituted heteroaryl; and optionally substituted heterocyclyl, $R_{12}$ and $R_{13}$ are simultaneously or independently selected from the group consisting of hydrogen; —(CO)—$R_7$; —(CO)—O—$R_7$; —(CO)—$NR_8$OH; —(CO)—$NR_8R_{8'}$; —$SO_2$—$R_7$; —$SO_2$—$NR_8R_{8'}$; optionally substituted alkyl; optionally substituted alkenyl; optionally substituted alkynyl; optionally substituted cycloalkenyl; optionally substituted cycloalkynyl; optionally substituted aryl; optionally substituted heteroaryl; and optionally substituted heterocyclyl; or $R_{12}$ and $R_{13}$ are linked together with the nitrogen atom to which they are covalently linked to form an optionally substituted heterocyclyl, n is 0, 1, 2, 3 or 4, m is 1, 2 or 3, p is 1, 2, 3, 4 or 5, and pharmaceutically acceptable salts, tautomers, isotopic variants, isomers, stereoisomers or mixtures of stereoisomers thereof.

2. The method of claim 1, wherein the compound is selected from the group consisting of 2-(4-chlorophenylamino)-4-(4-tert-butylaminopiperidin-1-yl)-quinoline (1-5) of formula (I-a); 2-(4-chlorobenzylamino)-4-(4-tert-butylaminopiperidin-1-yl)-quinoline (2-2) of formula (I-b); 2-[3-methyl-4-(pyrimidin-2-ylamino)phenylamino]-4-(4-tert-butylaminopiperidin-1-yl)-quinoline (3-4) of formula (I-c); 2-{4-[4-(pyridin-3-yl)-2-pyrimidinamino]-3-methylphenylamino}-4-(4-tert-butylaminopiperidin-1-yl)-quinoline (4-2) of formula (I-d); 2-(4-fluorobenzylamino)-4-(4-tert-butylaminopiperidin-1-yl)-quinoline (5-3) of formula (I-e); 2-(4-chlorobenzylamino)-4-(4-tert-butylaminopiperidin-1-yl)-8-methoxyquinoline (6-3) of formula (I-f); 2-(4-chlorobenzylamino)-4-(4-tert-butylaminopiperidin-1-yl)-8-hydroxyquinoline (7-1) of formula (I-g); 2-(4-chlorobenzylamino)-4-(4-tert-butylaminopiperidin-1-yl)-7-methoxyquinoline (8-2) of formula (I-h); 2-(4-chlorobenzylamino)-4-(4-tert-butylaminopiperidin-1-yl)-7-hydroxyquinoline (9-1) of formula (I-i); 2-(4-chlorobenzylamino)-4-(4-tert-butylaminopiperidin-1-yl)-6-methoxyquinoline (10-2) of formula (I-j); 2-(4-chlorobenzylamino)-4-(4-tert-butylaminopiperidin-1-yl)-6-hydroxyquinoline (11-1) of formula (I-k); 2-(4-chlorobenzylamino)-4-(4-tert-butylaminopiperidin-1-yl)-5-methoxyquinoline (12-4) of formula (I-l); 2-(4-chlorobenzylamino)-4-(4-tert-butylaminopiperidin-1-yl)-5-hydroxyquinoline (13-1) of formula (I-m); 2-(2-methoxy-4-chlorobenzylamino)-4-(4-tert-butylaminopiperidin-1-yl)quinoline (14-5) of formula (I-n); 2-(2-hydroxy-4-chlorobenzylamino)-4-(4-tert-butylaminopiperidin-1-yl)quinoline (15-1) of formula (I-o); 2-(3-methoxy-4-chlorobenzylamino)-4-(4-tert-butylaminopiperidin-1-yl)quinoline (16-6) of formula (I-p); 2-(3-hydroxy-4-chlorobenzylamino)-4-(4-tert-butylaminopiperidin-1-yl)quinoline (17-1) of formula (I-q); 2-(4-chlorobenzamido)-4-(4-tert-butylaminopiperidin-1-yl)quinoline (18-3) of formula (I-r); 2-(4-chlorobenzylamino)-4-[4-(pyrrolidin-1-yl)piperidin-1-yl]quinoline (19-1) of formula (I-s); 2-(4-chlorobenzylamino)-4-{4-[(1-methylpiperidin-4-yl)amino]piperidin-1-yl}quinoline (20-1) of formula (I-t); 2-(4-methoxybenzylamino)-4-(4-tert-butylaminopiperidin-1-yl)quinoline (21-2) of formula (I-u); 2-(4-hydroxybenzylamino)-4-(4-tert-butylaminopiperidin-1-yl)quinoline (22-1) of formula (I-v); and 2-benzylamino-4-(4-tert-butylaminopiperidin-1-yl)quinoline (23-2) of formula (I-w); and any pharmaceutically acceptable salt, tautomers, isotopic variants, isomers, stereoisomers or mixtures of stereoisomers thereof.

3. The method of claim 1, wherein the compound is selected from the group consisting of 2-(4-chlorophenylamino)-4-(4-tert-butylaminopiperidin-1-yl)-quinoline hydrochloride salt (1-6); 2-(4-chlorobenzylamino)-4-(4-tert-butylaminopiperidin-1-yl)-quinoline hydrochloride salt (2-3); 2-[3-methyl-4-(pyrimidin-2-ylamino)phenylamino]-4-(4-tert-butylaminopiperidin-1-yl)-quinoline hydrochloride salt (3-5); 2-{4-[4-(pyridin-3-yl)-2-pyrimidinamino]-3-methyl-phenylamino}-4-(4-tert-butylaminopiperidin-1-yl)-quinoline hydrochloride salt (4-3); 2-(4-fluorobenzylamino)-4-(4-tert-butylaminopiperidin-1-yl)-quinoline hydrochloride salt (5-2); 2-(4-fluorobenzylamino)-4-(4-tert-butylaminopiperidin-1-yl)-quinoline hydrochloride salt (5-2); 2-(4-chlorobenzylamino)-4-(4-tert-butylaminopiperidin-1-yl)-8-methoxyquinoline hydrochloride salt (6-4); 2-(4-chlorobenzylamino)-4-(4-tert-butylaminopiperidin-1-yl)-8-hydroxyquinoline hydrochloride salt (7-2); 2-(4-chlorobenzylamino)-4-(4-tert-butylaminopiperidin-1-yl)-7-methoxyquinoline hydrochloride salt (8-3); 2-(4-chlorobenzylamino)-4-(4-tert-butylaminopiperidin-1-yl)-7-hydroxyquinoline hydrochloride salt (9-2); 2-(4-chlorobenzylamino)-4-(4-tert-butylaminopiperidin-1-yl)-6-methoxyquinoline hydrochloride salt (10-3); 2-(4-chlorobenzylamino)-4-(4-tert-butylaminopiperidin-1-yl)-6-hydroxyquinoline hydrochloride salt (11-2); 2-(4-chlorobenzylamino)-4-(4-tert-butylaminopiperidin-1-yl)-5-methoxyquinoline hydrochloride salt (12-5); 2-(4-chlorobenzylamino)-4-(4-tert-butylaminopiperidin-1-yl)-5-hydroxyquinoline hydrochloride salt (13-2); 2-(2-hydroxy-4-chlorobenzylamino)-4-(4-tert-butylaminopiperidin-1-yl) quinoline hydrochloride salt (15-2); 2-(3-hydroxy-4-chlorobenzylamino)-4-(4-tert-butylaminopiperidin-1-yl) quinoline hydrochloride salt (17-2); 2-(4-chlorobenzamido)-4-(4-tert-butylaminopiperidin-1-yl)quinoline hydrochloride salt (18-4); 2-(4-chlorobenzylamino)-4-[4-(pyrrolidin-1-yl)piperidin-1-yl]quinoline hydrochloride salt (19-2); 2-(4-chlorobenzylamino)-4-{4-[(1-methylpiperidin-4-yl)amino]piperidin-1-yl}quinoline hydrochloride salt (20-2); 2-(4-methoxybenzylamino)-4-(4-tert-butylaminopiperidin-1-yl) quinoline hydrochloride salt (21-2); 2-(4-hydroxybenzylamino)-4-(4-tert-butylaminopiperidin-1-yl) quinoline hydrochloride salt (22-2); and 2-benzylamino-4-(4-tert-butylaminopiperidin-1-yl)quinoline hydrochloride salt (23-3); and pharmaceutically acceptable salts, tautomers, isotopic variants, isomers, stereoisomers or mixtures of stereoisomers thereof.

4. The method of claim 1, wherein the compound administered to the patient in need thereof has the structure of Formula (II)

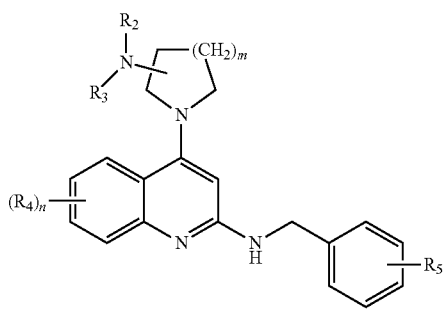

(II)

wherein, $R_2$ and $R_3$ are simultaneously or independently selected from the group consisting of hydrogen; —(CO)—$R_7$; —(CO)—O—$R_7$; —(CO)—NR$_8$OH; —(CO)— NR$_8$R$_{8'}$; —SO$_2$—R$_7$; —SO$_2$—NR$_8$R$_{8'}$; optionally substituted alkyl; optionally substituted cycloalkyl; optionally substituted alkenyl; optionally substituted alkynyl; optionally substituted cycloalkenyl; optionally substituted cycloalkynyl; optionally substituted aryl; optionally substituted heteroaryl; optionally substituted heterocyclyl group; or $R_2$ and $R_3$ are linked together with the nitrogen atom to which they are covalently linked to form an optionally substituted heterocyclyl group, $R_4$ is, alone or simultaneously or independently when n>1, chosen from hydrogen atom; halogen atom; optionally substituted alkyl; optionally substituted alkenyl; optionally substituted alkynyl; optionally substituted cycloalkyl; optionally substituted cycloalkenyl; optionally substituted cycloalkynyl; optionally substituted alkoxy; hydroxyl; nitro; azido; cyano; —NR$_{12}$R$_{13}$; —NR$_8$R$_{8'}$; —O—(R$_7$); —(CO)—R$_7$; —(CO)—O—R$_7$; —(CO)—NR$_{12}$OH; —(CO)—NR$_8$OH; —(CO)—NR$_{12}$R$_{13}$; —(CO)—NR$_8$R$_{8'}$; —O—(CO)—R$_7$; —O—(CO)—NR$_{12}$R$_{13}$; —O—(CO)—NR$_8$R$_{8'}$; —NR$_{12}$—(CO)—R$_7$; —NR$_8$—(CO)—R$_7$; —NR$_{12}$—(CO)—OR$_7$; —NR$_8$—(CO)—OR$_7$; —O—(CO)—OR$_7$; —NR$_{12}$—(CO)—NR$_{12}$R$_{13}$; —NR$_8$—(CO)—NR$_8$R$_{8'}$; —(O—CH$_2$CH$_2$)$_p$—OR$_{12}$; —(O—CH$_2$CH$_2$)$_p$—OR$_7$; —(O—CH$_2$CH$_2$)$_p$—NR$_{12}$R$_{13}$; —(O—CH$_2$CH$_2$)$_p$—NR$_8$R$_{8'}$; —NR$_{12}$(—CH$_2$CH$_2$—O)$_p$—R$_{13}$; —NR$_8$(—CH$_2$CH$_2$—O)$_p$—R$_7$; —SO$_2$—R$_7$; —NR$_{12}$—SO$_2$—R$_7$; —NR$_8$—SO$_2$—R$_7$; —SO$_2$—NR$_{12}$R$_{13}$; —SO$_2$—NR$_8$R$_{8'}$; —NR$_{12}$—SO$_2$—NR$_{12}$R$_{13}$; —NR$_8$—SO$_2$—NR$_8$R$_{8'}$; —NR$_{12}$—(C$_2$-C$_8$)-alkyl-NR$_{12}$R$_{13}$; —NR$_8$—(C$_2$-C$_8$)-alkyl-NR$_8$R$_{8'}$; —NR$_{12}$—(C$_2$-C$_8$)-alkyl-OR$_{12}$; —NR$_8$—(C$_2$-C$_8$)-alkyl-OR$_7$; optionally substituted aryl; an optionally substituted heteroaryl; an optionally substituted heterocyclyl group, $R_5$ is selected from a group consisting of hydrogen; halogen; hydroxyl; nitro; azido; cyano; —NR$_{12}$R$_{13}$; —NR$_8$R$_{8'}$; —O—(R$_7$); —(CO)—R$_7$; —(CO)—O—R$_7$; —(CO)—NR$_{12}$OH; —(CO)—NR$_8$OH; —(CO)—NR$_{12}$R$_{13}$; —(CO)—NR$_8$R$_{8'}$; —O—(CO)—R$_7$; —NR$_{12}$—(CO)—R$_7$; —NR$_8$—(CO)—R$_7$; —O—(CO)—NR$_{12}$; —O—(CO)—NR$_8$; —NR$_{12}$—(CO)—OR$_7$; —NR$_8$—(CO)—OR$_7$; —O—(CO)—OR$_7$; —NR$_{12}$—(CO)—NR$_{12}$R$_{13}$; —NR$_8$—(CO)—NR$_8$R$_{8'}$; —NR$_{12}$—SO$_2$—R$_7$; —NR$_8$—SO$_2$—R$_7$; —SO$_2$—NR$_{12}$R$_{13}$; —SO$_2$—NR$_8$R$_{8'}$; —NR$_{12}$—SO$_2$—NR$_{12}$R$_{13}$; —NR$_8$—SO$_2$—NR$_8$R$_{8'}$; —NR$_{12}$—(C$_2$-C$_{10}$)-alkyl-NR$_{12}$R$_{13}$; —NR$_8$—(C$_2$-C$_{10}$)-alkyl-NR$_8$R$_{8'}$; —NR$_{12}$—(C$_2$-C$_{10}$)-alkyl-OR$_{13}$; —NR$_8$—(C$_2$-C$_{10}$)-alkyl-OR$_7$; —(O—CH$_2$CH$_2$)$_p$—OR$_{12}$; —(O—CH$_2$CH$_2$)$_p$—OR$_7$; —(O—CH$_2$CH$_2$)$_p$—NR$_{12}$R$_{13}$; —(O—CH$_2$CH$_2$)$_p$—NR$_8$R$_{8'}$; —NR$_{12}$(—CH$_2$CH$_2$—O)$_p$—R$_{13}$; —NR$_8$(—CH$_2$CH$_2$—O)$_p$—R$_7$; optionally substituted alkyl; optionally substituted alkenyl; optionally substituted alkynyl; optionally substituted cycloalkyl; optionally substituted cycloalkenyl; optionally substituted cycloalkynyl; optionally substituted alkoxy; optionally substituted heterocyclyl group, $R_7$ is selected from the group consisting of hydrogen; optionally substituted alkyl; optionally substituted alkenyl; optionally substituted alkynyl; optionally substituted cycloalkyl; optionally substituted cycloalkenyl; optionally substituted cycloalkynyl; optionally substituted aryl; optionally substituted heteroaryl; optionally substituted heterocyclyl group, $R_8$ and $R_{8'}$ are simultaneously or independently selected from the group consisting of hydrogen; optionally substituted alkyl; optionally substituted alkenyl; optionally substituted alkynyl; optionally substituted cycloalkyl; optionally substituted cycloalkenyl; optionally substituted cycloalkynyl; and optionally substituted heterocyclyl group; optionally substituted aryl; optionally substituted heteroaryl or $R_8$ and $R_{8'}$ can be linked together with nitrogen to which they are covalently linked to form optionally substituted heterocyclyl, $R_{12}$ and $R_{13}$ are simultaneously or independently hydrogen; —(CO)—$R_7$; —(CO)—O—$R_7$; —(CO)—$NR_8OH$; —(CO)—$NR_8R_{8'}$; —$SO_2$—$R_7$; —$SO_2$—$NR_8R_{8'}$; optionally substituted alkyl; optionally substituted cycloalkyl; optionally substituted alkenyl; optionally substituted alkynyl; optionally substituted cycloalkenyl; optionally substituted cycloalkynyl; optionally substituted aryl; optionally substituted heteroaryl; and optionally substituted heterocyclyl group; or $R_{12}$ and $R_{13}$ can be linked together with nitrogen to which they are covalently linked to form optionally substituted heterocyclyl, n is 0, 1, 2, 3 or 4, m is 1, 2 or 3, p is 1, 2, 3, 4 or 5, and any pharmaceutically acceptable salt, tautomers, isotopic variants, isomers, stereoisomers or mixtures of stereoisomers thereof.

5. The method of claim 1, wherein the compound administered to the patient in need thereof has the structure of Formula (III)

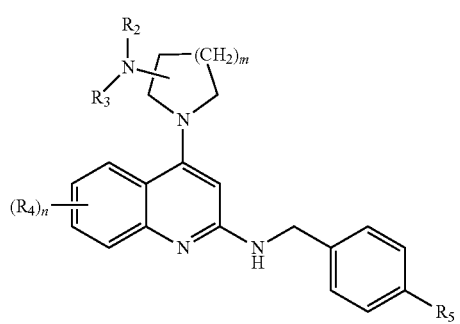

(III)

wherein, $R_2$ and $R_3$ are simultaneously or independently selected from the group consisting of hydrogen; —(CO)—$R_7$; —(CO)—O—$R_7$; —(CO)—$NR_8OH$; —(CO)—$NR_8R_{8'}$; —$SO_2$—$R_7$; —$SO_2$—$NR_8R_{8'}$; optionally substituted alkyl; optionally substituted cycloalkyl; optionally substituted alkenyl; optionally substituted alkynyl; optionally substituted cycloalkenyl; optionally substituted cycloalkynyl; optionally substituted aryl; optionally substituted heteroaryl; optionally substituted heterocyclyl group; or $R_2$ and $R_3$ can be linked together with nitrogen to which they are covalently linked to form an optionally substituted heterocyclyl group, $R_4$ is, alone or simultaneously or independently when n>1, chosen from hydrogen; halogen atom; optionally substituted alkyl; optionally substituted alkenyl; optionally substituted alkynyl; optionally substituted cycloalkyl; optionally substituted cycloalkenyl; optionally substituted cycloalkynyl; optionally substituted alkoxy; hydroxyl; nitro; azido; cyano; —$NR_{12}R_{13}$; —$NR_8R_{8'}$; —O—($R_7$); —(CO)—$R_7$; —(CO)—O—$R_7$; —(CO)—$NR_{12}OH$; —(CO)—$NR_8OH$; —(CO)—$NR_{12}R_{13}$; —(CO)—$NR_8R_{8'}$; —O—(CO)—$R_7$; —O—(CO)—$NR_{12}R_{13}$; —O—(CO)—$NR_8R_{8'}$; —$NR_{12}$—(CO)—$R_7$; —$NR_8$—(CO)—$R_7$; —$NR_{12}$—(CO)—$OR_7$; —$NR_8$—(CO)—$OR_7$; —O—(CO)—$OR_7$; —$NR_{12}$—(CO)—$NR_{12}R_{13}$; —$NR_8$—(CO)—$NR_8R_{8'}$; —(O—$CH_2CH_2$)$_p$—$OR_{12}$; —(O—$CH_2CH_2$)$_p$—$OR_7$; —(O—$CH_2CH_2$)$_p$—$NR_{12}R_{13}$; —(O—$CH_2CH_2$)$_p$—$NR_8R_{8'}$; —$NR_{12}$(—$CH_2CH_2$—O)$_p$—$R_{13}$; —$NR_8$(—$CH_2CH_2$—O)$_p$—$R_7$; —$SO_2$—$R_7$; —$NR_{12}$—$SO_2$—$R_7$; —$NR_8$—$SO_2$—$R_7$; —$SO_2$—$NR_{12}R_{13}$; —$SO_2$—$NR_8R_{8'}$; —$NR_{12}$—$SO_2$—$NR_{12}R_{13}$; —$NR_8$—$SO_2$—$NR_8R_{8'}$; —$NR_{12}$—($C_2$-$C_8$)-alkyl- $NR_{12}R_{13}$; —$NR_8$—($C_2$-$C_8$)-alkyl-$NR_8R_{8'}$; —$NR_{12}$—($C_2$-$C_8$)-alkyl-$OR_{13}$; —$NR_8$—($C_2$-$C_8$)-alkyl-$OR_7$; optionally substituted aryl; optionally substituted heteroaryl; and optionally substituted heterocyclyl, $R_5$ is selected from a group consisting of hydrogen; fluorine; chlorine; —$CF_3$; methyl; hydroxyl; optionally substituted alkoxy; cyano; azido; and carboxyl, $R_7$ is selected from a group consisting of hydrogen; optionally substituted alkyl; optionally substituted alkenyl; optionally substituted alkynyl; optionally substituted cycloalkyl; optionally substituted cycloalkenyl; optionally substituted cycloalkynyl; optionally substituted aryl; optionally substituted heteroaryl; and optionally substituted heterocyclyl, $R_8$ and $R_{8'}$ are simultaneously or independently selected from the group consisting of hydrogen; optionally substituted alkyl; optionally substituted alkenyl; optionally substituted alkynyl; optionally substituted cycloalkyl; optionally substituted cycloalkenyl; optionally substituted cycloalkynyl; optionally substituted heterocyclyl group; optionally substituted aryl; optionally substituted heteroaryl; or $R_8$ and $R_{8'}$ can be linked together with nitrogen to which they are covalently linked to form optionally substituted heterocyclyl, $R_{12}$ and $R_{13}$ are simultaneously or independently selected from a group consisting of hydrogen; —(CO)—$R_7$; —(CO)—O—$R_7$; —(CO)—$NR_8OH$; —(CO)—$NR_8R_{8'}$; —$SO_2$—$R_7$; —$SO_2$—$NR_8R_{8'}$; optionally substituted alkyl; optionally substituted cycloalkyl; optionally substituted alkenyl; optionally substituted alkynyl; optionally substituted cycloalkenyl; optionally substituted cycloalkynyl; optionally substituted aryl; optionally substituted heteroaryl; optionally substituted heterocyclyl group; or $R_{12}$ and $R_{13}$ can be linked together with nitrogen to which they are covalently linked to form optionally substituted heterocyclyl, n is 0, 1, 2, 3 or 4, m is 1, 2 or 3, p is 1, 2, 3, 4 or 5, and pharmaceutically acceptable salts, tautomers, isotopic variants, isomers, stereoisomers or mixtures of stereoisomers thereof.

6. The method of claim 1, wherein the compound administered to the patient in need thereof has the structure of Formula (IV):

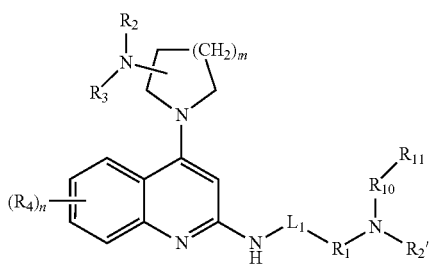

wherein,

L$_1$ is a single bond; optionally substituted alkyl; and carbonyl,

R$_1$ is chosen from optionally substituted aryl, or an optionally substituted heteroaryl, R$_2$ and R$_3$ are simultaneously or independently selected from the group consisting of hydrogen; optionally substituted alkyl; optionally substituted alkenyl; optionally substituted alkynyl; optionally substituted cycloalkyl; optionally substituted cycloalkenyl; optionally substituted cycloalkynyl; —(CO)—R$_7$; —(CO)—O—R$_7$; —(CO)—NR$_8$OH; —(CO)—NR$_8$R$_{8'}$; —SO$_2$—R$_7$; —SO$_2$—NR$_8$R$_{8'}$; optionally substituted aryl; optionally substituted heteroaryl; optionally substituted heterocyclyl group; or R$_2$ and R$_3$ can be linked together with nitrogen to which they are covalently linked to form optionally substituted heterocyclyl, R$_2$' is selected from the group consisting of hydrogen; optionally substituted alkyl; optionally substituted alkenyl; optionally substituted alkynyl; optionally substituted cycloalkyl; optionally substituted cycloalkenyl; optionally substituted cycloalkynyl; and optionally substituted heterocyclyl, R$_4$ is, alone or simultaneously or independently when n>1, selected from the group consisting of hydrogen; halogen atom; optionally substituted alkyl; optionally substituted alkenyl; optionally substituted alkynyl; optionally substituted cycloalkyl; optionally substituted cycloalkenyl; optionally substituted cycloalkynyl; optionally substituted alkoxy; hydroxyl; nitro; azido; cyano; —NR$_{12}$R$_{13}$; —NR$_8$R$_{8'}$; —O—(R$_7$); —(CO)—R$_7$; —(CO)—O—R$_7$; —(CO)—NR$_{12}$OH; —(CO)—NR$_8$OH; —(CO)—NR$_{12}$R$_{13}$; —(CO)—NR$_8$R$_{8'}$; —O—(CO)—R$_7$; —O—(CO)—NR$_{12}$R$_{13}$; —O—(CO)—NR$_8$R$_{8'}$; —NR$_{12}$—(CO)—R$_7$; —NR$_8$—(CO)—R$_7$; —NR$_{12}$—(CO)—OR$_7$; —NR$_8$—(CO)—OR$_7$; —O—(CO)—OR$_7$; —NR$_{12}$—(CO)—NR$_{12}$R$_{13}$; —NR$_8$—(CO)—NR$_8$R$_{8'}$; —(O—CH$_2$CH$_2$)$_p$—OR$_{12}$; —(O—CH$_2$CH$_2$)$_p$—OR$_8$; —(O—CH$_2$CH$_2$)$_p$—NR$_{12}$R$_{13}$; —(O—CH$_2$CH$_2$)$_p$—NR$_8$R$_{8'}$; —NR$_{12}$—(CH$_2$CH$_2$—O)$_p$—R$_{13}$; —NR$_8$—(CH$_2$CH$_2$—O)$_p$—R$_{8'}$; —SO$_2$—R$_7$; —NR$_{12}$—SO$_2$—R$_7$; —NR$_8$—SO$_2$—R$_7$; —SO$_2$—NR$_{12}$R$_{13}$; —SO$_2$—NR$_8$R$_{8'}$; —NR$_{12}$—SO$_2$—NR$_{12}$R$_{13}$; —NR$_8$—SO$_2$—NR$_8$R$_{8'}$; —NR$_{12}$—(C$_2$-C$_8$)-alkyl-NR$_{12}$R$_{13}$; —NR$_8$—(C$_2$-C$_8$)-alkyl-NR$_8$R$_{8'}$; —NR$_{12}$—(C$_2$-C$_8$)-alkyl-OR$_{13}$; —NR$_8$—(C$_2$-C$_8$)-alkyl-OR$_7$; optionally substituted aryl; optionally substituted heteroaryl; and optionally substituted heterocyclyl, R$_8$ and R$_{8'}$ are simultaneously or independently selected from the group consisting of hydrogen; optionally substituted alkyl; optionally substituted alkenyl; optionally substituted alkynyl; optionally substituted cycloalkyl; optionally substituted cycloalkenyl; optionally substituted cycloalkynyl; optionally substituted heterocyclyl; optionally substituted aryl; optionally substituted heteroaryl; or R$_8$ and R$_{8'}$ can be linked together with nitrogen to which they are covalently linked to form an optionally substituted heterocyclyl, R$_{10}$ is selected from the group consisting of optionally substituted aryl; optionally substituted heteroaryl, R$_{11}$ is selected from the group consisting of hydrogen; halogen; optionally substituted alkoxy; hydroxyl; nitro; cyano; azido; —NR$_{12}$R$_{13}$; —NR$_8$R$_{8'}$; —O—(R$_8$); —(CO)—R$_8$; —(CO)—O—R$_8$; —(CO)—NR$_{12}$OH; —(CO)—NR$_8$OH; —(CO)—NR$_{12}$R$_{13}$; —(CO)—NR$_8$R$_{8'}$; —O—(CO)—R$_8$; —O—(CO)—NR$_{12}$R$_{13}$; —O—(CO)—NR$_8$R$_{8'}$; —NR$_{12}$—(CO)—R$_8$; —NR$_8$—(CO)—R$_{8'}$; —NR$_{12}$—(CO)—OR$_8$; —NR$_8$—(CO)—OR$_{8'}$; —O—(CO)—OR$_8$; —NR$_{12}$—(CO)—NR$_{12}$R$_{13}$; —NR$_8$—(CO)—NR$_8$R$_{8'}$; —(O—CH$_2$CH$_2$)$_p$—OR$_{12}$; —(O—CH$_2$CH$_2$)$_p$—OR$_8$; —(O—CH$_2$CH$_2$)$_p$—NR$_{12}$R$_{13}$; —(O—CH$_2$CH$_2$)$_p$—NR$_8$R$_{8'}$; —NR$_{12}$—(CH$_2$CH$_2$—O)$_p$—R$_{13}$; —NR$_8$—(CH$_2$CH$_2$—O)$_p$—R$_{8'}$; —SO$_2$—R$_8$; —NR$_{12}$—SO$_2$—R$_8$; —NR$_8$—SO$_2$—R$_{8'}$; —SO$_2$—NR$_{12}$R$_{13}$; —SO$_2$—NR$_8$R$_{8'}$; —NR$_{12}$—SO$_2$—NR$_{12}$R$_{13}$; —NR$_8$—SO$_2$—NR$_8$R$_{8'}$; —NR$_{12}$—(C$_2$-C$_8$)-alkyl-NR$_{12}$R$_{13}$; —NR$_8$—(C$_2$-C$_8$)-alkyl-NR$_8$R$_{8'}$; —NR$_{12}$—(C$_2$-C$_8$)-alkyl-OR$_{13}$; —NR$_8$—(C$_2$-C$_8$)-alkyl-OR$_{8'}$; optionally substituted alkyl; optionally substituted alkenyl; optionally substituted alkynyl; optionally substituted cycloalkyl; optionally substituted cycloalkenyl; optionally substituted cycloalkynyl; optionally substituted aryl; optionally substituted heteroaryl; and optionally substituted heterocyclyl, R$_{12}$ and R$_{13}$ are simultaneously or independently selected from the group consisting of hydrogen; —(CO)—R$_7$; —(CO)—O—R$_7$; —(CO)—NR$_8$OH; —(CO)—NR$_8$R$_{8'}$; —SO$_2$—R$_7$; —SO$_2$—NR$_8$R$_{8'}$; optionally substituted alkyl; optionally substituted cycloalkyl; optionally substituted alkenyl; optionally substituted alkynyl; optionally substituted cycloalkenyl; optionally substituted cycloalkynyl; optionally substituted aryl; optionally substituted heteroaryl; optionally substituted heterocyclyl; or R$_{12}$ and R$_{13}$ can be linked together with nitrogen to which they are covalently linked to form optionally substituted heterocyclyl, n is 0, 1, 2, 3 or 4, m is 1, 2 or 3, p is 1, 2, 3, 4 or 5, and pharmaceutically acceptable salts, tautomers, isotopic variants, isomers, stereoisomers or mixtures of stereoisomers thereof.

7. The method of claim 1, wherein the compound administered to the patient in need thereof has the structure of Formula (V):

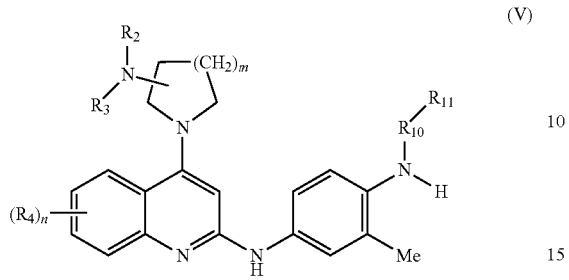

wherein $R_2$ and $R_3$ are simultaneously or independently chosen from hydrogen; optionally substituted alkyl; optionally substituted alkenyl; optionally substituted alkynyl; optionally substituted cycloalkyl; optionally substituted cycloalkenyl; optionally substituted cycloalkynyl; —(CO)—$R_7$; —(CO)—O—$R_7$; —(CO)—$NR_8OH$; —(CO)—$NR_8R_{8'}$; —$SO_2$—$R_7$; —$SO_2$—$NR_8R_{8'}$; optionally substituted aryl; optionally substituted heteroaryl; optionally substituted heterocyclyl; or $R_2$ and $R_3$ can be linked together with nitrogen to which they are covalently linked to form optionally substituted heterocyclyl, $R_4$ is, alone or simultaneously or independently when n>1, selected from the group consisting of hydrogen; halogen atom; optionally substituted alkyl; optionally substituted alkenyl; optionally substituted alkynyl; optionally substituted cycloalkyl; optionally substituted cycloalkenyl; optionally substituted cycloalkynyl; optionally substituted alkoxy; hydroxyl; nitro; azido; cyano; —$NR_{12}R_{13}$; —$NR_8R_{8'}$; —O—($R_7$); —(CO)—$R_7$; —(CO)—O—$R_7$; —(CO)—$NR_{12}OH$; —(CO)—$NR_8OH$; —(CO)—$NR_{12}R_{13}$; —(CO)—$NR_8R_{8'}$; —O—(CO)—$R_7$; —O—(CO)—$NR_{12}R_{13}$; —O—(CO)—$NR_8R_{8'}$; —$NR_{12}$—(CO)—$R_7$; —$NR_8$—(CO)—$R_7$; —$NR_{12}$—(CO)—$OR_7$; —$NR_8$—(CO)—$OR_7$; —O—(CO)—$OR_7$; —$NR_{12}$—(CO)—$NR_{12}R_{13}$;—$NR_8$—(CO)—$NR_8R_{8'}$; —(O—$CH_2CH_2$—)$_p$—$OR_{12}$; —(O—$CH_2CH_2$)$_p$—$OR_7$; —(O—$CH_2CH_2$—)$_p$—$NR_{12}R_{13}$; —(O—$CH_2CH_2$)$_p$—$NR_8R_{8'}$; —$NR_{12}$—($CH_2CH_2$—O)$_p$—$R_{13}$; —$NR_8$—($CH_2CH_2$—O)$_p$—$R_7$; —$SO_2$—$R_7$; —$NR_{12}$—$SO_2$—$R_7$; —$NR_8$—$SO_2$—$R_7$; —$SO_2$—$NR_{12}R_{13}$; —$SO_2$—$NR_8R_{8'}$; —$NR_{12}$—$SO_2$—$NR_{12}R_{13}$; —$NR_8$—$SO_2$—$NR_8R_{8'}$; —$NR_{12}$—($C_2$-$C_8$)-alkyl-$NR_{12}R_{13}$; —$NR_8$—($C_2$-$C_8$)-alkyl-$NR_8R_{8'}$; —$NR_{12}$—($C_2$-$C_8$)-alkyl-$OR_{13}$; —$NR_8$—($C_2$-$C_8$)-alkyl-$OR_7$; optionally substituted aryl; optionally substituted heteroaryl; and optionally substituted heterocyclyl, $R_7$ is selected from the group consisting of hydrogen; optionally substituted alkyl; optionally substituted alkenyl; optionally substituted alkynyl; optionally substituted cycloalkyl; optionally substituted cycloalkenyl; optionally substituted cycloalkynyl; optionally substituted aryl; optionally substituted heteroaryl; and optionally substituted heterocyclyl, $R_8$ and $R_{8'}$ are simultaneously or independently selected from the group consisting of hydrogen; optionally substituted alkyl; optionally substituted alkenyl; optionally substituted alkynyl; optionally substituted cycloalkyl; optionally substituted cycloalkenyl; optionally substituted cycloalkynyl; optionally substituted heterocyclyl group; optionally substituted aryl; optionally substituted heteroaryl; or $R_8$ and $R_{8'}$ can be linked together with nitrogen to which they are covalently linked to form optionally substituted heterocyclyl, $R_{10}$ is selected from the group consisting of optionally substituted aryl; optionally substituted heteroaryl, $R_{11}$ is selected from the group consisting of hydrogen; halogen; optionally substituted alkoxy; hydroxyl; nitro; cyano; azido; —$NR_{12}R_{13}$; —$NR_8R_{8'}$; —O—($R_8$); —(CO)—$R_8$; —(CO)—O—$R_8$; —(CO)—$NR_{12}OH$; —(CO)—$NR_8OH$; —(CO)—$NR_{12}R_{13}$; —(CO)—$NR_8R_{8'}$; —O—(CO)—$R_8$; —O—(CO)—$NR_{12}R_{13}$; —O—(CO)—$NR_8R_{8'}$; —$NR_{12}$—(CO)—$R_8$; —$NR_8$—(CO)—$R_8$; —$NR_{12}$—(CO)—$OR_8$; —$NR_8$—(CO)—$OR_{8'}$; —O—(CO)—$OR_8$; —$NR_{12}$—(CO)—$NR_{12}R_{13}$; —$NR_8$—(CO)—$NR_8R_{8'}$; —(O—$CH_2CH_2$—)$_p$—$OR_{12}$; —(O—$CH_2CH_2$—)$_p$—$OR_8$; —(O—$CH_2CH_2$—)$_p$—$NR_{12}R_{13}$; —(O—$CH_2CH_2$—)$_p$—$NR_8R_{8'}$; —$NR_{12}$—($CH_2CH_2$—O)$_p$—$R_{13}$; —$NR_8$—($CH_2CH_2$—O)$_p$—$R_8$; —$SO_2$—$R_8$; —$NR_{12}$—$SO_2$—$R_8$; —$NR_8$—$SO_2$—$R_{8'}$; —$SO_2$—$NR_{12}R_{13}$; —$SO_2$—$NR_8R_{8'}$; —$NR_{12}$—$SO_2$—$NR_{12}R_{13}$; —$NR_8$—$SO_2$—$NR_8R_{8'}$; —$NR_{12}$—($C_2$-$C_8$)-alkyl-$NR_{12}R_{13}$; —$NR_8$—($C_2$-$C_8$)-alkyl-$NR_8R_{8'}$; —$NR_{12}$—($C_2$-$C_8$)-alkyl-$OR_{13}$; —$NR_8$—($C_2$-$C_8$)-alkyl-$OR_8$; optionally substituted alkyl; optionally substituted alkenyl; optionally substituted alkynyl; optionally substituted cycloalkyl; optionally substituted cycloalkenyl; optionally substituted cycloalkynyl; optionally substituted aryl; optionally substituted heteroaryl; and optionally substituted heterocyclyl, $R_{12}$ and $R_{13}$ are simultaneously or independently selected from the group consisting of hydrogen; —(CO)—$R_7$; —(CO)—O—$R_7$; —(CO)—$NR_8OH$; —(CO)—$NR_8R_{8'}$; —$SO_2$—$R_7$; —$SO_2$—$NR_8R_{8'}$; optionally substituted alkyl; optionally substituted cycloalkyl; optionally substituted alkenyl; optionally substituted alkynyl; optionally substituted cycloalkenyl; optionally substituted cycloalkynyl; optionally substituted aryl; optionally substituted heteroaryl; optionally substituted heterocyclyl; or $R_{12}$ and $R_{13}$ can be linked together with nitrogen to which they are covalently linked to form optionally substituted heterocyclyl, n is 0, 1, 2, 3 or 4, m is 1, 2 or 3, p is 1, 2, 3, 4 or 5, and pharmaceutically acceptable salts, tautomers, isotopic variants, isomers, stereoisomers or mixtures of stereoisomers thereof.

8. The method of claim 1, wherein $L_1$ is alkyl substituted with at least one $R_6$.

9. The method of claim 1, wherein $R_1$ is aryl substituted with at least one $R_9$.

10. The method of claim 1, wherein $R_2$ is hydrogen.

11. The method of claim 1, wherein $R_3$ is alkyl, cycloalkyl, or heterocyclyl.

12. The method of claim 1, wherein $R_2$ and $R_3$ is linked together with nitrogen to which they are covalently linked to form heterocyclyl.

13. The method of claim 1, wherein $R_4$ is hydrogen, hydroxyl, or methoxy.

14. The method of claim 1, wherein $R_5$ is hydrogen, fluorine, chlorine, hydroxyl, or methoxy.

15. The method of claim 1, wherein m is 2.

16. The method of claim 1, wherein $R_{10}$ is heterocyclyl, aryl, or heteraryl, substituted with at least one $R_{11}$.

17. The method of claim 1, wherein fibrosis is present in a tissue or organ selected from the group consisting of skin, lung, liver, kidney, heart, muscular, prostate, peritoneum, nervous system, and eyes.

18. The method of claim 17, wherein fibrosis is present in a tissue or organ as a fibrotic skin disease or condition selected from the group consisting of scleroderma, subcutaneous scarring, keloids, adhesions, hypertrophic scarring and cosmetic scarring.

19. The method of claim 17, wherein fibrosis is present in a tissue or organ as a fibrotic lung disease or condition selected from the group consisting of idiopathic pulmonary fibrosis (IPF), nonidiopathic pulmonary fibrosis interstitial pneumonias, interstitial lung disease (ILD), idiopathic interstitial lung disease, pulmonary hypertension, chronic obstructive pulmonary disease (COPD) and sarcoidosis.

20. The method of claim 17, wherein fibrosis is present in a tissue or organ as a fibrotic liver disease or condition selected from the group consisting of cirrhosis of the liver, hemochromatosis, hepatitis B virus infection, hepatitis C virus infection, hepatitis delta virus infection, Wilson's disease, alpha-1-antitrypsin deficiency, primary biliary cirrhosis, primary sclerosing chlolangitis, autoimmune hepatitis, drug induced hepatitis, fibrosis of the liver, cirrhosis and non cirrhosis portal hypertension, Non-alcoholic fatty liver disease (NAFLD) and Non-alcoholic steatohepatitis (NASH), focal fatty liver, fatty liver diseases, biliary obstruction, Budd-Chiari syndrome, portal vein thrombosis, liver veno-occlusive disease, congenital hepatitis fibrosis, alcoholism, alcohol-associated steatohepatitis, and diabetes.

21. The method of claim 17, wherein fibrosis is present in a tissue or organ as a fibrotic kidney disease or condition selected from the group consisting of progressive kidney disease glomerulonephritis, glomerular disease, kidney fibrosis and diabetic nephropathy.

22. The method of claim 17, wherein fibrosis is present in a tissue or organ as a fibrotic heart disease or condition selected from the group consisting of heart failure due to ischaemic heart disease, valvular heart disease, hypertensive heart disease, diabetic cardiomyopathy and hypertension.

23. The method of claim 1, wherein fibrosis is present in a tissue or organ as a fibrotic intestinal disease or condition selected from the group consisting of bowel fibrosis, colon fibrosis, small intestine fibrosis, inflammatory bowel disease, ulcerative colitis, Crohn's disease, and infection with *Schistosoma mansoni*.

24. The method of claim 17, wherein fibrosis is present in a tissue or organ as a fibrotic eye disease selected from the group consisting of macular fibrosis, premacular fibrosis, retinal fibrosis, retinopathy, diabetic retinopathy, Diabetic Macular Edema, Proliferative Diabetic Retinopathy, fibrosis of the extraocular muscles, fibrovascular scarring, retina gliosis, Subretinal fibrosis, and Epiretinal fibrosis.

25. The method of claim 17, wherein fibrosis is present in a tissue or organ as a fibrotic nerve system disease or condition selected from the group consisting of nerve system related fibrosis; mediastinum related fibrosis; retroperitoneum related fibrosis; and joint and tendon fibrosis (arthrofibrosis).

26. The method of claim 1, wherein the compound is used as an adjuvant or anti-fibrotic agent in the treatment of pancreatic diseases to increase chemotherapeutic drug penetration by reducing the severity and/or progression of the density of the connective tissue stroma.

27. The method of claim 1, wherein the compound is used to treat or ameliorate the symptoms or progression of autophagy a disease selected from the group consisting of rheumatoid arthritis (RA), malaria, antiphospholipid antibody syndrome, lupus, chronic urticarial, Gougerot-Sjogren syndrome, Guillain-Barre disease, Alzheimer's or Parkinson's diseases, eosinophilic airway inflammation, regeneration of fat tissue, psoriasis, multiple sclerosis (MS), muscular dystrophy (MD), myopathies, asthma, chronic pulmonary obstructive disorder (COPD), Crohn's disease (CD), chronic inflammatory demyelinating polyradiculoneuropathy (CIDP), fibromyalgia, diabetes, polymyositis, pulmonary diseases, chronic immune thrombocytopenia (ITP), ulcerative colitis, irritable bowel syndrome, scleroderma, neurodegeneration, heart failure, obesity, sarcopenia, aging, inflammatory disorders, ischemia/reperfusion, lysosomal storage diseases, and infectious diseases associated with intracellular pathogens including viruses, bacteria, and parasites such as Trypanosomes.

28. The method of claim 27, wherein the infectious disease is malaria, and the compound is administered with a further anti-malarial agent selected from the group consisting of amodiaquine, amopyroquine, artemisinin, artemether, arteflene, arterolane, artesunate, atovaquone, clindamycin, chloroquine, chlorproguanil, dihydroartemisinin, doxycycline, ferroquine, halofantrine, quinacrine, quinidine quinine, lumefantrine, mefloquine, primaquine, piperaquine, proguanil, pyrimethamine-dapsone, pyrimethamine-sulfadoxine, pyronaridine, sulphonamides, tafenoquine and trimethoprim.

29. The method of claim 1, wherein the step of administering to the patient in need thereof administers a pharmaceutical composition comprising a therapeutically effective amount of at least one compound of Formula (I), or a pharmaceutically acceptable salt, tautomer, isotopic variant, isomer, stereoisomer or mixture of stereoisomers thereof, and a pharmaceutically acceptable adjuvant, diluent or carrier.

30. The method of claim 29, wherein the compound is administered in combination with another active agent.

31. The method of claim 30, wherein the additional active agent is a further anti-fibrotic agent.

32. The method of claim 30, wherein the additional active agent is selected from the group consisting of a Tyrosine kinase inhibitor, a fibroblast growth factor receptor (FGFR) inhibitor, a platelet derived growth factor receptor (PDGFR) antagonist, an epidermal growth factor receptor (EGFR) antagonist or inhibitor; a dual VEGFR/PDGFR antagonist; a phosphatidylinositol 3-kinase (PI3K) inhibitor; a MAP kinase activated kinase 2 (MAPKAPK2) inhibitor; an apoptosis signal-regulating kinase 1 (ASK1) inhibitor; a mammalian target of rapamycin (mTOR) inhibitor; a mammalian target of rapamycin complex 1 mTOR1/2 inhibitor; a Janus kinase 1 (JAK1) and Janus kinase 2 (JAK2) inhibitor; a protein kinase B (PKB, also referred as to Akt) inhibitor; a focal adhesion kinase 1 (FAK1) inhibitor; a c-Jun N-terminal kinase (JNK) inhibitor; a mitogen-activated protein kinase (MAPK) inhibitor; an IκB kinase (IKK) inhibitor; a nuclear factor kappa-light-chain-enhancer of activated B cells (NF-Rho-associated protein kinase (ROCK) inhibitor; a 26S protease inhibitor; a caspase inhibitor; a phosphodiesterase inhibitor; a catepsin B inhibitor; a S100 calcium-binding protein A9 (S100A9, also referred to as migration inhibitory factor-related protein 14 (MRP14) or calgranulin B inhibitor; a procollagen-proline dioxygenase (also referred to as prolyl hydroxylase) inhibitor; a mothers against decapentaplegic homolog 2 (SMAD2)/Mothers against decapentaplegic homolog 3 (SMAD3) dual inhibitor; a mothers against decapentaplegic homolog 3 (SMAD3) and a mothers against decapentaplegic homolog 4 (SMAD4) dual inhibitor; a mothers against decapentaplegic homolog 3 (SMAD3) inhibitor; a mi RNA 21 (mR-21) inhibitor, a transmethylation inhibitor; a BMP binding endothelial regulator (BMPER) inhibitor; a NADPH oxidase (NOX isoform 1 to 5) inhibitor; a reactive oxygen species (ROS) inhibitor; a vitamin and vitamin derivatives with antioxidant properties; an antioxidant; a galectin-3 inhibitor; an interferon-α; a collagen derivative; a galectin-3 inhibitor, a Lysophosphatidic acid receptor 1 (LPA1) antagonist; a recombinant human PTX-2; an IL-3 antibodies; a LOXL2 inhibitor or antibodies; a transforming growth factor-β (TGF-β) inhibitor; a transforming growth factor β type I receptor kinase (ALK5) inhibitor; a bone morphogenetic protein 7 (BMP7) agonist; a hepatocyte growth factor receptor (c-Met/HGFR) stimulant; an IL-3/IL-4 antibodies; an IL-13 inhibitor; an IL-1R1 antagonist; an IL-1βR antagonist; an IL-13/IL-4 dual inhibitor; a C-C motif chemokine ligand 2 (CCL2); an integrin αvβ6 inhibitor; an interferon-γ receptor stimulant (IFN-γR); an interferon-α; a matrix metalloproteinase-2 (MMP-2) inhibitor; a matrix metalloproteinase-9 (MMP-9) inhibitor; a broad spectrum matrix metalloproteinase (MMPs) inhibitor; a lysophosphatidic acid receptors (LPAR) antagonist; a protease-activated receptor 1 (PAR1) antagonist; a prostacyclin receptor agonist; a vasoactive intestinal peptide (VIP) receptor agonist; a leukocyte elastase inhibitor; a thrombin-activable fibrinolysis inhibitor; a relaxin receptor stimulant; a serum amyloid protein (SAP) also referred to as Pentraxin-2 stimulant; an integrin-α5 (ITGA5) inhibitor; a transglutaminase 2 (TGM2) also referred to as glutamine gamma-glutamyltransferase 2 inhibitor; a TNFα inhibitor; an anti-coagulant; a peroxisome proliferator-activated receptors (PPARs) agonist (PPARs: PPARα, PPARβ, PPARγ; PPARδ agonists; a peroxisome proliferator-activated receptor gamma (PPARγ) agonist; an amine oxidase copper containing 3 inhibitor (AOC3 also known as vascular adhesion protein-1 (VAP-1) or semicarbazide-sensitive amine oxidase (SSAO); a toll like receptor modulator; a renin-Angiotensin System (RAS) blockade including inhibitors angiotensin I converting enzyme (ACE); a calcium channel blocker; an endothelin (ET-1) antagonist; a herbal medicine; a farnesoid X (FXR) ligand or agonist; an endocannabinoid receptors 1 (CB1) antagonist; an endocannabinoid receptors 2 (CB2) agonist; a μ-opioid receptor antagonist; a serotonin (5HT) antagonist; a corticosteroid agents; an estrogen receptor beta (ER β, also referred to as NR3A2) agonist; a C-C chemokine receptor type 2 (CCR2) inhibitor; a C-C chemokine receptor type 5 (CCR5) inhibitor; a CCR2 and/or CCR5 antagonist; a connective tissue growth factor (CTGF) inhibitor or antagonist; a galecttin-3 inhibitor; a vascular adhesion protein-1 (VAP1) inhibitor or antagonist; a lysyl oxidase-like-2 (LOXL2) inhibitor or antagonist; an anti-LOXL2 antibody; a metal chelating agent; an $\alpha_4\beta_7$ integrin antagonist; a methionine aminopeptidase 2 (MetAP2) inhibitor; a sodium-glucose co-transporter 2 (SGLT2) inhibitor; a glucagon-like peptide or pseudopeptide or peptidomimetic analog; an ileal apical sodium-dependent bile acid transporter inhibitor; a fatty acid-bile acid conjugates (FABAC); an acetyl-CoA carboxylase (ACC) inhibitor; a FGF21 variant; a Cathepsin B inhibitor; a p38 MAPK inhibitor; a lipid peroxidation inhibitor; a c-Jun N-terminal kinase 1 (JNK1) inhibitor; a fibroblast growth factor (FGF) inhibitor; MIRN103 microRNA modulator MIRN107 microRNA modulator; a hepatoprotectant; a 5-lipoxygenase (5-LOX) inhibitor; a retinoid X receptor (RXR) agonist; a ketohexokinase (KHK, also known as fructokinase) inhibitor; an eotaxin-1 (chemokine CCL11) modulator; a nerve growth factor stimulant; a sterol regulatory element binding protein inhibitor; a leukotriene A4 hydrolase inhibitor; a cystic fibrosis transmembrane conductance regulator (CFTR) stimulant; a fructose-bisphosphatase (FBP1) inhibitor; a collagen inhibitor; a Wnt signaling pathway inhibitor; a S-nitrosoglutathione reductase (GSNOR) inhibitor; an activin inhibitor and/or a follicle stimulating hormone inhibitor; an integrin alpha(V) antagonist; a phosphodiesterase 3 (PDE3) inhibitor; a phosphodiesterase 4 (PDE4) inhibitor; an interleukin receptor antagonist; an adenosine A2B receptor (ADORA2B) antagonist; an A3 adenosine receptor (A3AR) agonist; a neutrophil elastase inhibitor; an interleukin 13 (IL-13) and/or interleukin 4 (IL-4) inhibitor or monoclonal antibody; an interleukin 13 (IL-13) antagonist; a carboxypeptidase U inhibitor; an epithelial sodium channel antagonist; a telomerase activator; a serotonin 2B receptor antagonist; a diacylglycerol acyltransferase type 1 (AGAT-1, PF-06865571) inhibitor; a hepcidin stimulant; a thyroid hormone receptor beta (TRB) agonist; a catecholamine transferase inhibitor; a P2Y2 agonist; a prostaglandin D2 synthase (PTGDS) inhibitor; a recombinant human serum amyloid P; a dipeptidyl peptidase (DPP4) inhibitor; an antiparasitic; a dual G Protein-Coupled Receptor 40 (GPR40, also known as free fatty acid receptor 1 [FFA1]) agonist and G Protein-Coupled Receptor 84 (GPR84) antagonist; a hyperimmune bovine colostrum; Teroo hydrochloride; DUR-928; DS-102; ZSP-1603; Malotilate; 5-aminosalicylic acid; acethylcysteine; 6-thioguanine; 6-mercaptopurine; azathioprine; a recombinant IL-10; Insulin; ursodeoxycholic acid; a Sphingosine 1-Phosphate signaling modulator; a sphingolipid synthesis modulator and Colchicine.

33. The method of claim 30, wherein the additional active agent is selected from the group consisting of an NK-1 receptor antagonist, 5-HT3 receptor antagonist, Dopamine antagonist, $H_1$ histamine receptor antagonist, cytoprotective agent, proton pump inhibitor, corticosteroid, antidiabetic agent, peroxisome proliferator-activated receptor gamma agonist (PPARγ), Lyn kinase activator, secretagogue, angiotensin converting enzyme (ACE) inhibitor, angiotensin II receptor antagonist, β1 receptor blocker, calcium channel blocker, Renin inhibitor, diuretic, cholesterol lowering medication, and a hyperlipidemia lowering medication.

34. The method of claim 1, wherein the step of administering to a subject in need of treatment thereof administers a therapeutically effective amount of at least one compound of Formula (I), or a pharmaceutically acceptable salt, tautomers, isotopic variant, isomer, stereoisomer or mixtures of stereoisomers thereof.

35. The method of claim 1, wherein the compound has one of the following formulas:

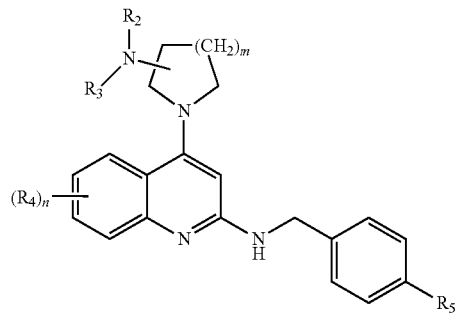

(III)

| ID | R₂ | R₃ | R₄ | n | R₅ | R₅ | m |
|---|---|---|---|---|---|---|---|
| 5-3 | H— | t-Bu— | 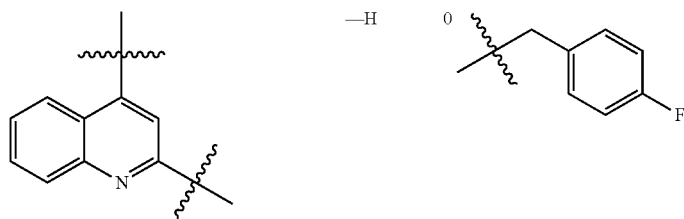 | —H | 0 | | —F | 2 |
| 6-3 | H— | t-Bu— | 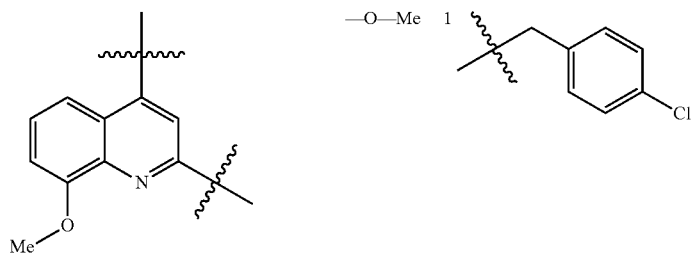 | —O—Me | 1 | | —Cl | 2 |
| 7-1 | H— | t-Bu— | 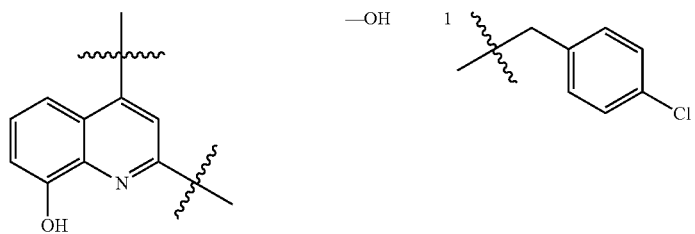 | —OH | 1 | | —Cl | 2 |

-continued
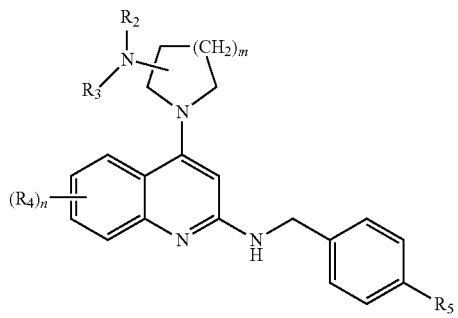
(III)
| ID | R$_2$ | R$_3$ | | R$_4$ | n | | R$_5$ | m |
|---|---|---|---|---|---|---|---|---|
| 8-2 | H— | t-Bu— | 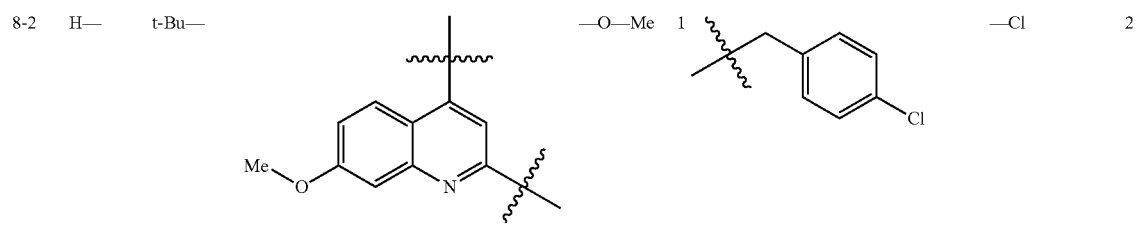 | —O—Me | 1 | | —Cl | 2 |
| 9-1 | H— | t-Bu— | 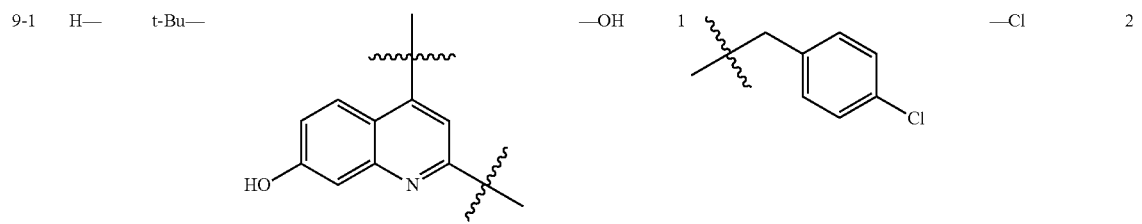 | —OH | 1 | | —Cl | 2 |
| 10-2 | H— | t-Bu— | 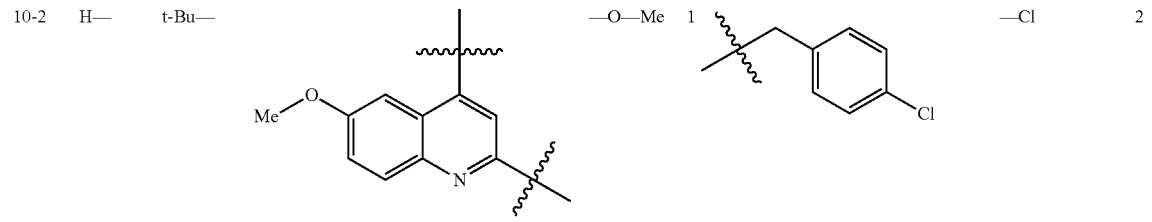 | —O—Me | 1 | | —Cl | 2 |
| 11-1 | H— | t-Bu— | 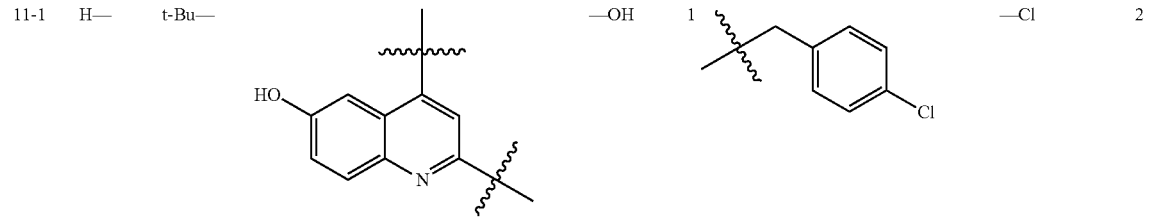 | —OH | 1 | | —Cl | 2 |

-continued
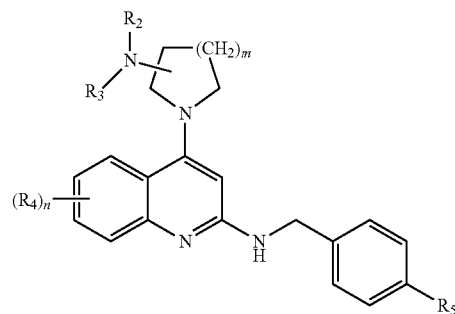
| ID | R$_2$ | R$_3$ | R$_4$ | n | R$_5$ | m |
|---|---|---|---|---|---|---|
| 12-4 | H— | t-Bu— | 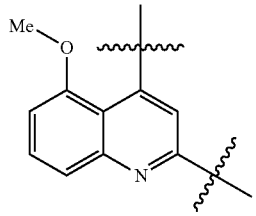 [SMILES: *c1cc(*)c2c(OC)cccc2n1] —O—Me | 1 | 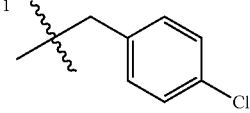 —Cl | 2 |
| 13-1 | H— | t-Bu— | 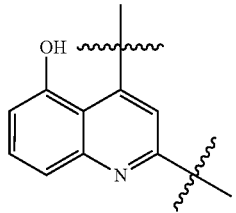 [SMILES: *c1cc(*)c2c(O)cccc2n1] —OH | 1 | 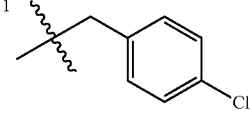 —Cl | 2 |
| 19-1 | 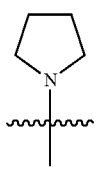 | | 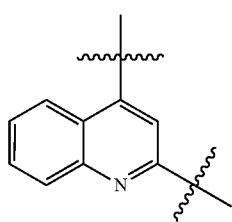 [SMILES: *c1cc(*)c2ccccc2n1] —H | 0 | 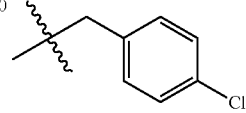 —Cl | 2 |

-continued
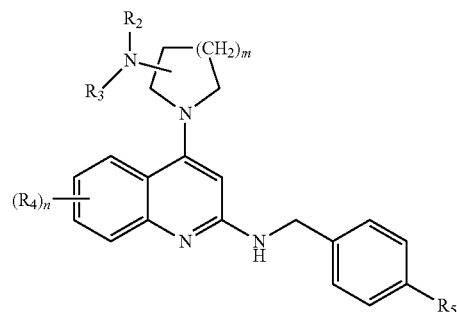
(III)
| ID | R<sub>2</sub> | R<sub>3</sub> | | R<sub>4</sub> | n | | R<sub>5</sub> | m |
|---|---|---|---|---|---|---|---|---|
| 20-1 | H— | Me- $N$-piperidine | 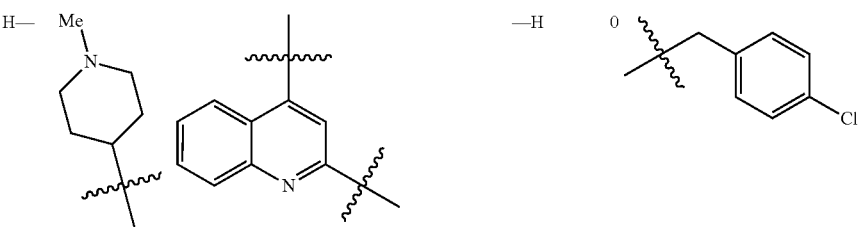 | —H | 0 | 4-Cl-benzyl | —Cl | 2 |
| 21-2 | H— | t-Bu— | 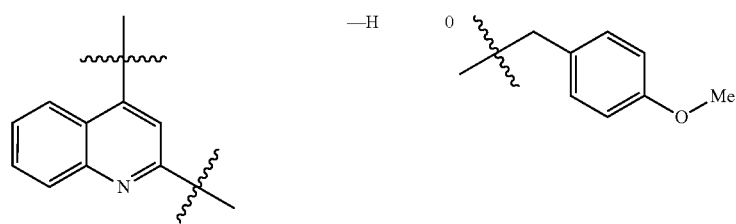 | —H | 0 | 4-OMe-benzyl | —O—Me | 2 |
| 22-1 | H— | t-Bu— | 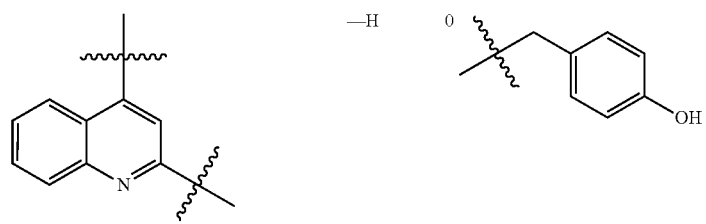 | —H | 0 | 4-OH-benzyl | —OH | 2 |
| 23-1 | H— | t-Bu— | 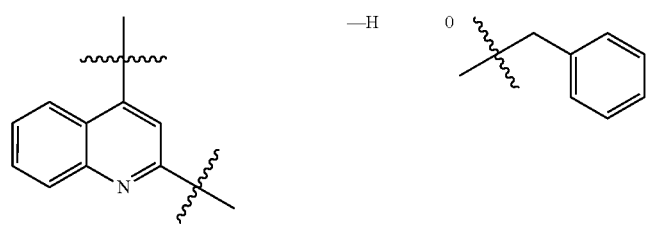 | —H | 0 | benzyl | —H | 2 |

36. The method of claim 1, wherein the compound has one of the following formulas:
(I-n)
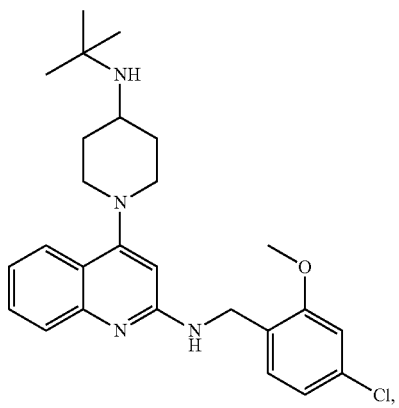
(I-o)
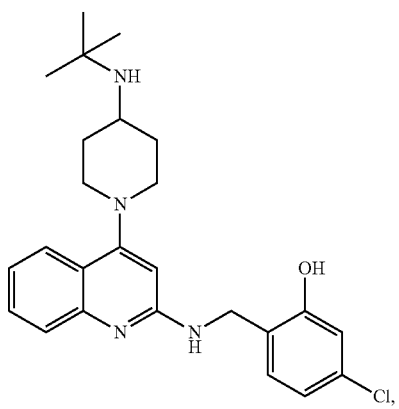
(I-p)
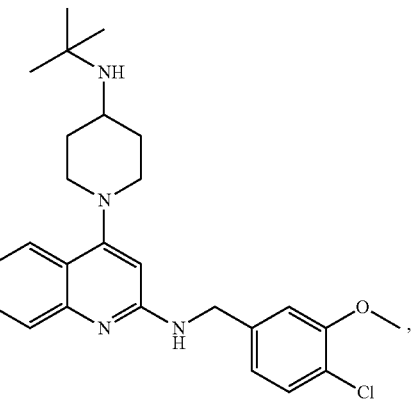
(I-q)
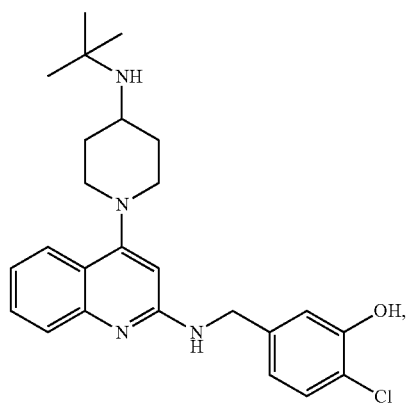
(I-r)
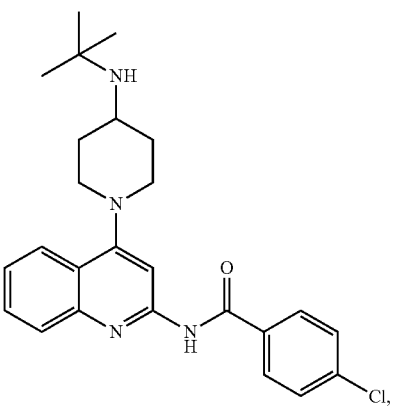
(I-s)
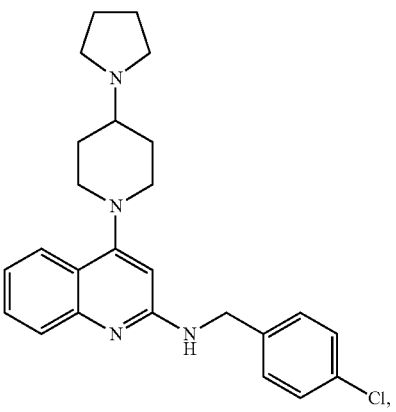

475
-continued
(I-t)
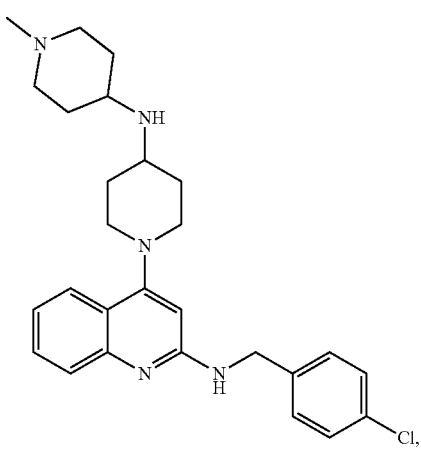
(I-u)
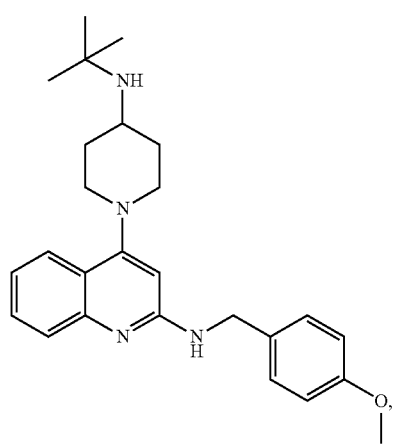
476
-continued
(I-v)
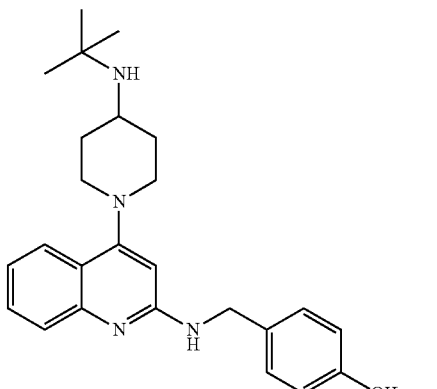
OH, and
(I-w)
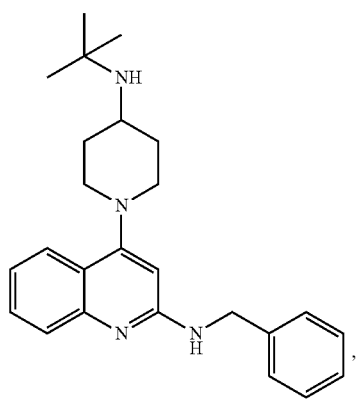
as well as their pharmaceutically acceptable salts, tautomers, isotopic variants, and stereoisomers thereof.
* * * * *